United States Patent
De Man et al.

(10) Patent No.: US 9,718,828 B2
(45) Date of Patent: Aug. 1, 2017

(54) BTK INHIBITORS

(71) Applicants: MERCK SHARP & DOHME CORP., Rahway, NJ (US); MERCK SHARP & DOHME B.V., Haarlem (NL)

(72) Inventors: Adrianus Petrus Antonius De Man, Hurwenen (NL); Jan-Gerard Sterrenburg, Renkum (NL); Hans C. A. Raaijmakers, Eindhoven (NL); Allard Kaptein, Zaltbommel (NL); Arthur A. Oubrie, Wijchen (NL); Johannes Bernardus Maria Rewinkel, Berghem (NL); Christiaan Gerardus Johannes Maria Jans, Cuijk (NL); Jacobus C. H. M. Wijkmans, Oss (NL); Tjeerd A. Barf, Ravenstein (NL); Alan B. Cooper, West Caldwell, NJ (US); Ronald M. Kim, Summit, NJ (US); Sobhana Babu Boga, Scotch Plains, NJ (US); Hugh Y. Zhu, Warren, NJ (US); Xiaolei Gao, Bridgewater, NJ (US); Xin Yao, Westfield, NJ (US); Rajan Anand, Fanwood, NJ (US); Hao Wu, Shanghai (CN); Shilan Liu, Shanghai (CN); Chundao Yang, Shanghai (CN); Abdul-Basit Alhassan, Scotch Plains, NJ (US); James Wang, Westfield, NJ (US); Younong Yu, East Brunswick, NJ (US); Jian Liu, Edison, NJ (US); Henry M. Vaccaro, South Plainfield, NJ (US)

(73) Assignees: MERCK SHARP & DOHME CORP., Rahway, NJ (US); MERCK SHARP & DOHME B.V., Haarlem (NL)

( * ) Notice: Subject to any disclaimer, the term of this patent is extended or adjusted under 35 U.S.C. 154(b) by 0 days.

(21) Appl. No.: 15/250,978

(22) Filed: Aug. 30, 2016

(65) Prior Publication Data
US 2017/0008899 A1    Jan. 12, 2017

Related U.S. Application Data

(63) Continuation of application No. 14/233,478, filed as application No. PCT/CN2012/000971 on Jul. 19, 2012, now abandoned.
(Continued)

(30) Foreign Application Priority Data
Jul. 19, 2011    (EP) .................................... 11174570

(51) Int. Cl.
C07D 487/04    (2006.01)
C07D 497/02    (2006.01)
(Continued)

(52) U.S. Cl.
CPC ........ *C07D 487/04* (2013.01); *A61K 31/4985* (2013.01); *A61K 31/53* (2013.01);
(Continued)

(58) Field of Classification Search
CPC .. C07D 487/04; C07D 497/02; C07D 401/04; C07D 401/14; C07D 403/04;
(Continued)

(56) References Cited

U.S. PATENT DOCUMENTS 6,660,744 B1 * 12/2003 Hirst ..................... C07F 9/6561
                                                                        514/210.21
6,921,763 B2 * 7/2005 Hirst ..................... C07F 9/6561
                                                                        514/262.1
(Continued)

FOREIGN PATENT DOCUMENTS

EP    0429257 A2    5/1991
EP    2181710 A1    5/2010
(Continued)

OTHER PUBLICATIONS

Hirst et al. WO 2002080926, Oct. 17, 2002; CA 137: 310925, 2002. CAPLUS Abstract provided.*
(Continued)

*Primary Examiner* — Venkataraman Balasubramanian
(74) *Attorney, Agent, or Firm* — Matthew A. Leff; John C. Todaro

(57) ABSTRACT

Provided are 6-5 membered fused pyridine ring compounds according to Formula (I) or pharmaceutically acceptable salts thereof, pharmaceutical compositions comprising these compounds and their use in therapy. In particular, provided is the use of 6-5 membered fused pyridine ring compounds in the treatment of Bruton's Tyrosine Kinase (Btk) mediated disorders.

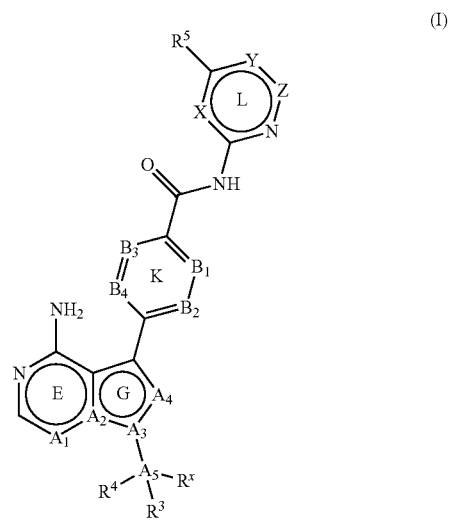

15 Claims, No Drawings

Related U.S. Application Data

(60) Provisional application No. 61/509,446, filed on Jul. 19, 2011.

(51) Int. Cl.

| | |
|---|---|
| *C07D 401/04* | (2006.01) |
| *C07D 401/14* | (2006.01) |
| *C07D 403/04* | (2006.01) |
| *C07D 403/14* | (2006.01) |
| *A61K 31/437* | (2006.01) |
| *A61K 31/4985* | (2006.01) |
| *A61K 31/519* | (2006.01) |
| *A61K 31/52* | (2006.01) |
| *A61K 31/53* | (2006.01) |
| *A61P 19/02* | (2006.01) |
| *C07D 519/00* | (2006.01) |
| *A61K 45/06* | (2006.01) |
| *A61K 31/5377* | (2006.01) |
| *A61K 31/541* | (2006.01) |
| *A61K 31/55* | (2006.01) |
| *C07D 513/04* | (2006.01) |
| *C07D 471/04* | (2006.01) |

(52) U.S. Cl.
CPC ........ *A61K 31/5377* (2013.01); *A61K 31/541* (2013.01); *A61K 31/55* (2013.01); *A61K 45/06* (2013.01); *C07D 471/04* (2013.01); *C07D 513/04* (2013.01); *C07D 519/00* (2013.01)

(58) Field of Classification Search
CPC ................ C07D 403/14; A61K 31/437; A61K 31/4987; A61K 31/519; A61K 31/52; A61K 31/53
USPC ........ 544/183, 184, 256, 280, 350; 546/112, 546/119; 514/243, 249, 258.1, 262.1, 514/265.1
See application file for complete search history.

(56) References Cited

U.S. PATENT DOCUMENTS

| | | | |
|---|---|---|---|
| 7,825,118 | B2 | 11/2010 | Honigberg et al. |
| 7,960,396 | B2 | 6/2011 | Honigberg et al. |
| 8,377,946 | B1 | 2/2013 | Chen et al. |
| 8,658,794 | B2 | 2/2014 | de Man et al. |
| 2002/0156081 | A1* | 10/2002 | Hirst ................ C07F 9/6561 514/247 |
| 2006/0084654 | A1 | 4/2006 | Beck et al. |
| 2008/0076921 | A1 | 3/2008 | Honigberg et al. |
| 2011/0257203 | A1 | 10/2011 | Honigberg et al. |
| 2012/0053189 | A1 | 3/2012 | Loury |
| 2012/0095026 | A1 | 4/2012 | Honigberg et al. |
| 2012/0129821 | A1 | 5/2012 | Honigberg et al. |
| 2012/0135944 | A1 | 5/2012 | Honigberg et al. |
| 2012/0165328 | A1 | 6/2012 | Honigberg et al. |
| 2013/0018032 | A1 | 1/2013 | Chen et al. |
| 2013/0079327 | A1 | 3/2013 | Yamamoto et al. |
| 2014/0073593 | A1 | 3/2014 | Conklin et al. |
| 2014/0206681 | A1 | 7/2014 | Kim et al. |
| 2014/0212425 | A1 | 7/2014 | Chang et al. |

FOREIGN PATENT DOCUMENTS

| | | |
|---|---|---|
| EP | 2548877 | 1/2013 |
| JP | 2007238463 | 9/2007 |
| WO | WO0119828 A2 | 3/2001 |
| WO | WO02080926 | 10/2002 |
| WO | WO03065995 | 8/2003 |
| WO | WO2005037836 A2 | 4/2005 |
| WO | WO2005097800 | 10/2005 |
| WO | WO2006063167 A1 | 5/2006 |
| WO | WO2007061737 | 5/2007 |
| WO | WO2007064883 A2 | 6/2007 |
| WO | WO2007064993 A2 | 6/2007 |
| WO | WO2007106503 | 9/2007 |
| WO | WO2008039218 | 4/2008 |
| WO | WO2008121742 | 10/2008 |
| WO | WO2009076170 | 6/2009 |
| WO | WO2010126960 | 11/2010 |
| WO | WO2010126960 A1 | 11/2010 |
| WO | WO2011095556 A1 | 8/2011 |
| WO | WO2011119663 | 9/2011 |
| WO | WO2011153514 A1 | 12/2011 |
| WO | WO2012158843 | 11/2012 |
| WO | WO2013003629 | 1/2013 |
| WO | WO2013010380 A1 | 1/2013 |
| WO | WO2013010868 | 1/2013 |
| WO | WO2013010869 | 1/2013 |
| WO | WO2013059738 | 4/2013 |
| WO | WO2014143807 | 9/2014 |
| WO | WO2014159745 | 10/2014 |
| WO | WO2014168975 | 10/2014 |
| WO | WO2015018522 | 2/2015 |

OTHER PUBLICATIONS

Akinleye et al, Ibrutinib and novel BTK inhibitors in clinical development, Journal of Hematology & Oncology, 2013, 1-9, 6:59.

Berge et al., Pharmaceutical Salts, J. Pharm Sci., 1977, pp. 1-19, 66(1).

Bingham et al., Over one hundred solvates of sulfathiazole, Chem. Commun., 2001, 603-604.

Caira et al., Preparation and Crystal Characterization of a Polymorph, a Monohydrate, and an Ethyl Acetate Solvate of the Antifungal Fluconazole, J. Pharmaceutical Sci, 2004, 601-611, 93(3).

Chakravarty et al, Kinase inhibitors: A new tool for the treatment of rheumatoid arthritis, Clinical Immunology, 2013, 66-78, 148.

Davis et al, Chronic Active B-Cell-Receptor Signaling in Diffuse Large B-Cell Lymphoma, Nature, 2010, 88-92, 463.

Dhar et al, Synthesis and SAR of p38alpha Map Kinase Inhibitors Based on Heterobicyclic Scaffolds, Bioorganic & Medicinal Chemistry Letters, 2007, 5019-5024, 17.

Gaudet et al, A Homogenous Fluorescence Polarization Assay Adaptable for a Range of Protein Serine/Threonine and Tyrosine Kinases, Biomol. Screening, 2003, 164-175, 8(2).

Gennaro (Ed.), Remington: The Science and Practice of Pharmacy, 20 Edition, 2000, Part—Final.

Gennaro (Ed.), Remington: The Science and Practice of Pharmacy, 20th Edition, 2000, Part 1.

Gennaro (Ed.), Remington: The Science and Practice of Pharmacy, 20th Edition, 2000, Part 2.

Gennaro (Ed.), Remington: The Science and Practice of Pharmacy, 20th Edition, 2000, Part 3.

Gennaro (Ed.), Remington: The Science and Practice of Pharmacy, 20th Edition, 2000, Part 6.

Gennaro (Ed.), Remington: The Science and Practice of Pharmacy, 20th Edition, 2000, Part 7.

Gennaro (Ed.), Remington: The Science and Practice of Pharmacy, 20th Edition, 2000, Part 8.

Gennaro (Ed.), Remington: The Science and Practice of Pharmacy, 20th Edition, 2000, Parts 4 & 5.

Gennaro (Ed.), Remington: The Science and Practice of Pharmacy, 20th Edition, 2000, Preface.

Gilfillan et al, The Tyrosine Kinase Network Regulating Mast Cell Activation, Immun. Rev., 2009, 149-69, 288.

Gould, Salt selection for basic drugs, International J. of Pharmaceutics, 1986, 201-217, 33.

Green & Wuts, Protective Groups in Organic Synthesis, 2nd Edition, 1991, -, -.

Harder et al, Gain and Loss of Function Lyn Mutant Mice Define a Critical Inhibitory Role for Lyn in the Myeloid Lineage, Immunity, 2001, 603-615, 15.

(56) References Cited

OTHER PUBLICATIONS

Hartz et al, Synthesis and Evaluation Ofimidazo[1,5-a]pYRAZINES as Corticotropin Releasing Hormone Receptor Ligands, Bioorg. Med. Chem. Letter, 2002, 291-294, 12.

Higuchi et al (Eds.), Pro Drugs as Novel Delivery Systems, ACS Symposium Series, 1975, 14.

Ji et al, A Novel, Potent, and Selective Insulin-Like Growth Factor-I Receptor Kinase Inhibitor Blocks Insulin-Like Growth Factor-I Receptor Signaling in Vitro and Inhibits Insulin-Like Growth Factor-I Receptor-Dependent Tumor Growth in Vivo, Mol Cancer Ther, 2007, 2158-2167, 6(8).

King et al, Nucleofugality Effects in the Pyridine Promoted Formation of Esters From 2-Substituted Ethanesulfonyl Chlorides, Can. J. Chem., 1988, 1109-1116, 66.

Klinghoffer et al, SRC Family Kinases are Required for Integrin But Not PDGFR Signal Transduction, EMBO J., 1999, 2459-2471, 18(9).

Lim et al, Anti CD20 Monoclonal Antibodies; Historical and Future Perspectives, Haematologica, 2010, 135-143, 95(1).

Lowell et al, Deficiency of the HCK and SRC Tyrosine Kinases Results in Extreme Levels of Extramedullary Hematopoiesis, Blood, 1996, 1780-1792, 87(5).

Mitchell et al, Synthesis of C-Nucleoside Isosteres of 9-(2-Hydroxyethoxymethyl)Guanine (Acyclovir), J. Heterocyclic Chem., 1984, 697-699, 21(3).

Mukaiyama et al, Synthesis and C-SRC Inhibitory Activity of Imidazo[1,5-alpha]Pyrazine Derivatives as an Agent for Treatment of Acute Ischemic Stroke, Bioorganic & Medicinal Chemistry, 2007, 868-885, 15.

Mulvihill et al, 1,3-Disubstituted-Imidazo[1,5-a]Pyrazines as Insulin-Like Growth-Factor-I Receptor (IGF-IR) Inhibitors, Bioorganic & Medicinal Chemistry Letters, 2007, 1091-1097, 17.

Mulvihill et al, Novel 2-Phenylquinolin-7-YL-Derived Imidazo[1,5-a]Pyrazines as Potent Insulin-Like Growth Factor-I Receptor (IGF-IR) Inhibitors, Bioorganic & Medicinal Chemstry, 2008, 1359-1375, 16.

Odom et al, Negative Regulation of Immunoglobulin E Dependent Allergic Responses by Lyn Kinases, J. Exp. Med., 2004, 1491-1502, 199(11).

Pan et al, Discovery of Selective Irreversible Inhibitors for Bruton's Tyrosine Kinase, Chem Med Chem, 2007, 58-61, 2.

Roby et al, Alterations in Reproductive Function in SRC Tyrosine Kinase Knockout Mice, Endocrine, 2005, 169-176, 26.

Roche (Ed.), Bioreversible Carriers in Drug Design, Pergamon Press, 1987.

Shinohara et al, Tyrosine Kinases BTK and TEC Regulate Osteoclast Differentiation by Linking Rank and Itam Signals, Cell, 2008, 794-806, 132.

Van Tonder, et al, Preparation and Physicochemical Characterization of 5 Niclosamide Solvates and 1 Hemisolvate, AAPS Pharmscitech, 2004, pp. 1-10, 5(1), US.

Wang, Yongjun et al, Identification of SR1078, a Synthetic Agonist for the Orphan Nuclear Receptors RORalpha and RORgamma, ACS Chemical Biology, 2010, 1029-1034, 5/11, ACS Chemical Biology.

Wang, Yongjun et al, Modulation of Retinoic Acid Receptor-related Orphan Receptor alpha and gamma Activity by 7-Oxygenated Sterol Ligands, Journal of Biological Chemistry, 2010, 5013-5025, 285/7.

Whang et al, Bruton's tyrosine kinase inhibitors for the treatment of rheumatoid arthritis, Drug Discovery Today, 2014, 1-5, 00-00.

\* cited by examiner

BTK INHIBITORS

FIELD OF THE INVENTION

The present invention relates to 6-5 membered fused pyridine ring compounds, to pharmaceutical compositions comprising these compounds and to their use in therapy. In particular, the present invention relates to the use of 6-5 membered fused pyridine ring compounds in the treatment of Bruton's Tyrosine Kinase (Btk) mediated disorders.

BACKGROUND OF THE INVENTION

B lymphocyte activation is key in the generation of adaptive immune responses. Derailed B lymphocyte activation is a hallmark of many autoimmune diseases and modulation of this immune response is therefore of therapeutic interest. Recently the success of B cell therapies in autoimmune diseases has been established. Treatment of rheumatoid arthritis (RA) patients with Rituximab (anti-CD20 therapy) is an accepted clinical therapy by now. More recent clinical trial studies show that treatment with Rituximab also ameliorates disease symptoms in relapsing remitting multiple sclerosis (RRMS) and systemic lupus erythematosus (SLE) patients. This success supports the potential for future therapies in autoimmune diseases targeting B cell immunity.

Bruton tyrosine kinase (Btk) is a Tec family non-receptor protein kinase, expressed in B cells and myeloid cells. The function of Btk in signaling pathways activated by the engagement of the B cell receptor (BCR) and FcεR1 on mast cells is well established. In addition, a function for Btk as a downstream target in Toll like receptor signaling was suggested. Functional mutations in Btk in human results in the primary immunodeficiency disease called XLA which is characterized by a defect in B cell development with a block between pro- and pre-B cell stage. This results in an almost complete absence of B lymphocytes in human causing a pronounced reduction of serum immunoglobulin of all classes. These finding support the key role for Btk in the regulation of the production of auto-antibodies in autoimmune diseases. In addition, regulation of Btk may affect BCR-induced production of pro-inflammatory cytokines and chemokines by B cells, indicating a broad potential for Btk in the treatment of autoimmune diseases.

With the regulatory role reported for Btk in FcεR-mediated mast cell activation, Btk inhibitors may also show potential in the treatment of allergic responses [Gilfillan et al, Immunological Reviews 288 (2009) pp 149-169]. Furthermore, Btk is also reported to be implicated in RANKL-induced osteoclast differentiation [Shinohara et al, Cell 132 (2008) pp 794-806] and therefore may also be of interest for the treatment of bone resorption disorders.

Other diseases with an important role for dysfunctional B cells are B cell malignancies. Indeed anti-CD20 therapy is used effectively in the clinic for the treatment of follicular lymphoma, diffuse large B-cell lymphoma and chronic lymphocytic leukemia [Lim et al, Haematologica, 95 (2010) pp 135-143]. The reported role for Btk in the regulation of proliferation and apoptosis of B cells indicates there is potential for Btk inhibitors in the treatment of B cell lymphomas as well. Inhibition of Btk seems to be relevant in particular for B cell lymphomas due to chronic active BCR signaling [Davis et al, Nature, 463 (2010) pp 88-94].

Some classes of 6-5 membered fused pyridine ring compounds have been described as kinase inhibitors e.g. Imidazo[1,5-f][1,2,4]triazine compounds have been described in WO2005097800 and WO2007064993; Imidazo[1,5-a]pyrazine compounds have been described in WO2005037836 and WO2001019828 as IGF-1R enzyme inhibitors.

Some of the Btk inhibitors reported are not selective over Src-family kinases. With dramatic adverse effects reported for knockouts of Src-family kinases, especially for double and triple knockouts, this is seen as prohibitive for the development of Btk inhibitors that are not selective over the Src-family kinases.

Both Lyn-deficient and Fyn-deficient mice exhibit autoimmunity mimicking the phenotype of human lupus nephritis. In addition, Fyn-deficient mice also show pronounced neurological defects. Lyn knockout mice also show an allergic-like phenotype, indicating Lyn as a broad negative regulator of the IgE-mediated allergic response by controlling mast cell responsiveness and allergy-associated traits [Odom et al, J. Exp. Med., 199 (2004) pp 1491-1502]. Furthermore, aged Lyn knock-out mice develop severe splenomegaly (myeloid expansion) and disseminated monocyte/macrophage tumors [Harder et al, Immunity, 15 (2001) pp 603-615]. These observations are in line with hyperresponsive B cells, mast cells and myeloid cells, and increased Ig levels observed in Lyn-deficient mice. Female Src knockout mice are infertile due to reduced follicle development and ovulation [Roby et al, Endocrine, 26 (2005) pp 169-176]. The double knockouts Src$^{-/-}$Fyn$^{-/-}$ and Src$^{-/-}$Yes$^{-/-}$ show a severe phenotype with effects on movement and breathing. The triple knockouts Src$^{-/-}$Fyn$^{-/-}$Yes$^{-/-}$ die at day 9.5 [Klinghoffer et al, EMBO J., 18 (1999) pp 2459-2471]. For the double knockout Src$^{-/-}$Hck$^{-/-}$, two thirds of the mice die at birth, with surviving mice developing osteopetrosis, extramedullary hematopoiseis, anemia, leukopenia [Lowell et al, Blood, 87 (1996) pp 1780-1'792].

Hence, an inhibitor that inhibits multiple or all kinases of the Src-family kinases simultaneously may cause serious adverse effects.

SUMMARY OF THE INVENTION

The present invention provides compounds which inhibit Btk activity, their use for treatment of Btk mediated diseases and disorders, in particular autoimmune diseases and inflammatory diseases, as well as pharmaceutical compositions comprising such compounds and pharmaceutical carriers.

DETAILED DESCRIPTION

The object of the present invention is to provide 6-5 membered fused pyridine ring compounds, to pharmaceutical compositions comprising these compounds and to their use in therapy. In particular, the present invention relates to the use of 6-5 membered fused pyridine ring compounds in the treatment of Bruton's Tyrosine Kinase (Btk) mediated disorders.

More specifically, the present invention provides 6-5 membered fused pyridine ring compounds according to Formula I or pharmaceutically acceptable salts thereof

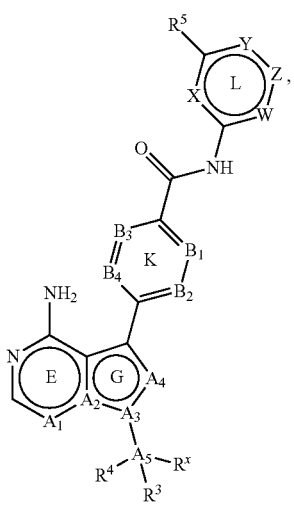

Formula I wherein:
A₁, A₂, A₃, and A₄ are independently C, CH, $CR^{11}$ or N and bicyclic ring system E-G is selected from the group consisting of:

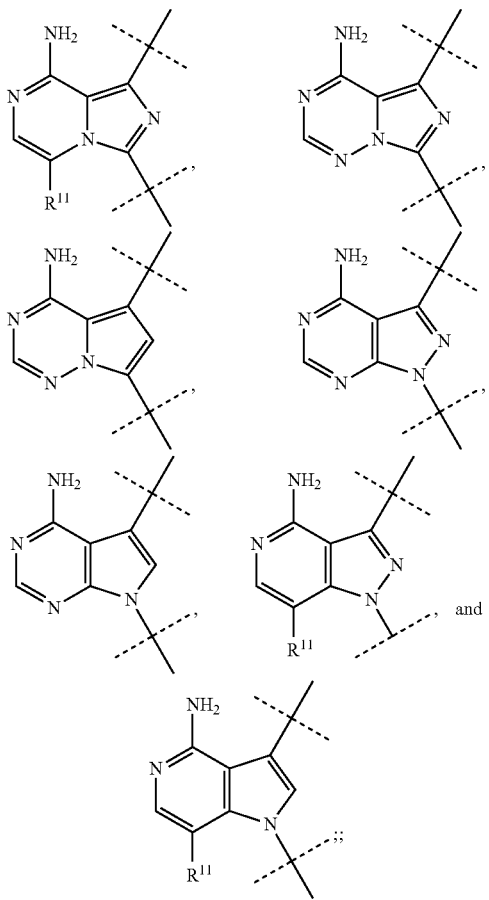

and

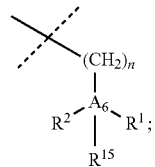

;

$R^{11}$ is independently selected from the group consisting of:
a) deuterium,
b) H,
c) halogen,
d) Si(CH₃)₃,
e) cyano,
f) C²H₃,
g) COOH,
h) CO₂(1-6C)alkyl,
i) CO(1-6C)alkyl,
j) CONH(1-6C)alkoxy,
k) CONH(1-6C)alkyl,
l) CONHdi(1-6C)alkyl,
m) CONHheterocycloalkyl,
n) CONHheteroaryl(1-6C)alkyl,
o) (1-6C)alkyl,
p) (3-7C)cycloalkyl,
q) (6-10C)aryl,
r) (1-5C)heteroaryl,
s) (2-6C)alkenyl,
t) (2-6C)alkynyl,
u) (6-10C)aryl(2-6C)alkenyl,
v) (3-7C)heterocycloalkyl, and
w) (3-7C)heterocycloalkenyl;

$R^{11}$ is optionally substituted with one or more groups selected from: halogen, (1-6C)alkyl, (1-5C)alkoxy, hydroxyl, oxo, (6-10C)aryl or $R^{16}$(CO);

wherein in aromatic ring K
B₁ is N or C(R⁷);
B₂ is N or C(R⁸);
B₃ is N or C(R⁹);
B₄ is N or C(R¹⁰);
$R^7$ is H, halogen, OH, CF₃, (1-3C)alkyl, (1-3C)alkoxy or halo(1-3C)alkyl;
$R^8$ is H, halogen, OH, CF₃, (1-3C)alkyl, (1-3C)alkoxy or halo(1-3C)alkyl; or
$R^7$ and $R^8$ together with ring K they are attached to, form (6-10C)aryl or (1-9C)heteroaryl;
$R^9$ is H, halogen, OH, CF3, (1-3C)alkyl, (1-3C)alkoxy or halo(1-3C)alkyl;
$R^{10}$ is H, halogen, OH, CF3, (1-3C)alkyl, (1-3C)alkoxy or halo(1-3C)alkyl;

wherein in heteroaromatic ring L
X is CH, N, O or S;
Y is C(R⁶), N, O or S;
Z is CH, N or bond;
$R^5$ is H, halogen, cyano, (1-4C)alkyl, (1-5C)alkoxy, (3-6C)cycloalkyl or (3-6C)cycloalkoxy; any alkyl group of R⁵ may optionally be substituted with one, two or three halogen; or $R^5$ is (6-10C)aryl, (1-5C)heteroaryl or (2-6C)heterocycloalkyl; the aryl or heterocycloalkyl of which may optionally be substituted with halogen, (1-6C)alkyl, (1-3C)alkoxy;
$R^6$ is H, halogen, (1-3C)alkyl, cyano, (1-6C)alkyl, or (1-6C)alkoxy; $R^6$ may optionally be substituted with one, two or three halogen or cyano; or
$R^5$ and $R^6$ together form a (3-7C)cycloalkenyl or (2-6C) heterocycloalkenyl; each optionally substituted with (1-3C)alkyl or with one or more halogen;
A₅ is C or N;
$R^x$ is selected from the group consisting of H, (1-6C)alkyl, (1-5C)heteroalkyl, and n is 1 or 2;
A₆ is C, N or O;
R¹ is
  a) $R^{21}C(O)$,
  b) $R^{22}NHC(O)$,
  c) $R^{23}C(O)NH$,
  d) $R^{24}S(O)$,
  e) $R^{25}SO_2$,
  f) $NH_2$,
  g) H,
  h) (3-7C)cycloalkyl(1-4C)alkyl,
  i) (1-6C)alkoxycarbonyl(3-7C)cycloalkyl(1-4C)alkyl,
  j) (6-10C)aryl(1-4C)alkyl,
  k) (1-6C)alkyl,
  l) (1-5C)heteroaryl(1-4C)alkyl, wherein the (1-5C)heteroaryl is optionally substituted with one or two (1-4C)alkyl, hydroxyl or halogen,
  m) (1-5C)heterocycloalkyl(1-4C)alkyl, wherein the (1-5C)heterocycloalkyl is optionally substituted with one or two (1-4C)alkyl, hydroxyl or halogen,
  n) Cyano(1-6C)alkyl,
  o) halo(1-6C)alkyl,
  p) hydroxy(1-6C)alkyl,
  q) (1-4C)alkoxy(1-6C)alkyl, or
  r) (1-6C)alkoxyl;
$R^2$ is H, (1-3C)alkyl or (3-7C)cycloalkyl;
$R^3$ is H, (1-6C)alkyl or (3-7C)cycloalkyl; or
$R^2$ and $R^3$ may form, together with the N or C atom to which they are attached, to form a (3-7C)heterocycloalkyl or (3-7C)cycloalkyl, both optionally substituted with one or two $R^{13}$;
$R^2$ and $R^3$ may form a cyclohexyl ring with the $A_5$=C and $A_6$=C to which they are attached, and when substituted with $R^{13}$ on the carbon one removed from the carbon adjacent to the $A_5$=C, such that the $R^{13}$ and $R^{15}$ can join to form a fused (2-5C)heteroaryl ring, optionally substituted with one or two $R^a$ selected from (1-3C)alkyl, hydroxy(1-3C)alkyl, hydroxyl(1-3C)alkyl, (3-6C)cycloalkyl, or (1-3C)alkoxy(1-3C)alkyl;
$R^2$ and $R^3$ may form a cyclohexyl ring with the $A_5$=C and $A_6$=C to which they are attached, and when substituted with two $R^{13}$ groups on the carbon adjacent to the $A_5$=C and the carbon one removed from the $A_5$=C, such that the two $R^{13}$ groups join together to form a fused (2-5C)heteroaryl ring, optionally substituted with one or two $R^a$ selected from (1-3C)alkyl, hydroxy(1-3C)alkyl, (3-6C)cycloalkyl, or (1-3C)alkoxy(1-3C)alkyl;
$A_5$, $R^3$, $R^4$ and $R^x$ may combine to form the following ring:

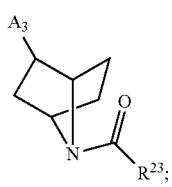

$R^3$ and $R^4$ may join to form a (3-6C)cycloalkyl ring with the $A_5$=C and $R^x$=H to which they are attached said ring being substituted with a spiro-linked piperidine ring at the 4-position of the piperidine ring and the nitrogen atom of the piperidine ring being substituted with $C(O)R^{21}$. An example of such a ring is

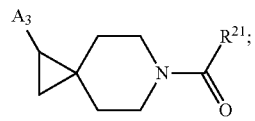

$R^4$ is H, OH, (1-3C)alkyl, hydroxy, (1-3C)alkoxy;
$R^{13}$ is independently selected from the group consisting of: (1-3C)alkoxy, (2-5C)heterocycloalkyl, (1-6C)alkyl, halo(1-6C)alkyl, hydroxy(1-6C)alkyl, (1-6C)alkoxy(1-6C)alkyl, hydrogen, hydroxyl, (1-3C)alkylcarbonyloxy, one or more halogen, halo(1-3C)alkyl, and oxo;
$R^{15}$ is H or (1-4C)alkyl;
$R^{16}$ is
  a) (1-6C)alkyl,
  b) (3-7C)cycloalkyl,
  c) (6-10C)aryl,
  d) (1-9C)heteroaryl,
  e) (1-4C)alkoxy(1-6C)alkyl,
  f) (6-10C)aryl(1-6C)alkyl,
  g) (1-5C)heteroaryl(1-6C)alkyl,
  h) di[(1-6C)alkyl]amino,
  i) (3-7C)heterocycloalkyl;
$R^{21}$ is selected from the group consisting of:
  a) H,
  b) trifluoromethylcarbonyl,
  c) hydroxy(1-6C)alkyl,
  d) di[hydroxy](1-6C)alkyl,
  e) di[(1-6C)alkyl]amino(1-6C)alkyl,
  f) $CF_3$,
  g) $CCl_3$,
  h) amino(3-7C)cycloalkyl,
  i) (6-10C)aryloxy,
  j) (6-10C)arylcarbonyl(2-5C)heterocycloalkyl,
  k) (6-10C)arylcarbonyl,
  l) (6-10C)aryl(1-6C)alkoxy,
  m) (3-7C)cycloalkylcarbonyl(1-5C)heterocycloalkyl,
  n) (3-7C)cycloalkyl(1-4C)alkyl,
  o) (3-7C)cycloalkyl,
  p) (3-10C)cycloalkylamino,
  q) (3-10C)cycloalkyl,
  r) (3-10C)cycloalkylcarbonyl,
  s) (4-10C)bicycloalkyl,
  t) (1-6C)heterocycloalkyl,
  u) (1-6C)alkylsulfonyl(2-5C)heterocycloalkyl,
  v) (1-6C)alkylcarbonyl(2-5C)heterocycloalkyl,
  w) (1-6C)alkylcarbonyl,
  x) (1-6C)alkylaminocarbonyl,
  y) (6-10C)arylaminocarbonyl,
  z) (1-6C)alkylamino,
  aa) (1-6C)alkoxycarbonyl,
  bb) (1-6C)alkoxycarbonyl(1-4C)alkylamino(3-7C)cycloalkyl,
  cc) (1-6C)alkoxycarbonyl(1-4C)alkyl,
  dd) (1-6C)alkoxycarbonyl(3-7C)cycloalkyl (1-4C)alkyl,
  ee) (1-6C)alkoxy,
  ff) (6-10C)aryl(1-6C)alkoxy,
  gg) (1-5C)heteroarylcarbonyl,
  hh) (1-5C)heteroaryl(1-4C)alkyl,
  ii) (1-5C)heteroaryl(3-7C)cycloalkyl,
  jj) (1-5C)heterocycloalkyl,
  kk) (1-4C)thioalkyl(1-6C)alkyl,
  ll) di[(1-4C)alkyl]aminocarbonyl,
  mm) (1-4C)alkylsulfonyl(1-6C)alkyl,
  nn) (1-4C)alkylaminocarbonyl, oo) (1-4C)alkoxy(1-6C)alkyl,
pp) (1-8C)alkoxy(1-16C)alkyl,
qq) cyano(1-6C)alkyl,
rr) amino(1-6C)alkyl,
ss) (6-10C)arylamino,
tt) (3-7C)cycloalkoxy,
uu) (1-6C)alkyl,
vv) (1-5C)heteroaryl,
ww) (1-4C)alkoxy[(2-4C)alkoxy]$_m$(1-6C)alkyl, and
xx) amino(1-4C)alkoxy[(2-4C)alkoxy]$_m$ (1-6C)alkyl;

$R^{21}$ may optionally be substituted with one, two or three $R^{211}$ substituents;

m is 1-10;

$R^{22}$ is selected from the group consisting of:
  a) (3-7C)cycloalkyl(1-4C)alkyl,
  b) (3-7C)cycloalkyl,
  c) (4-10C)bicycloalkyl,
  d) (3-7C)cycloalkoxy(1-4C)alkyl,
  e) (3-6C)cycloalkoxy,
  f) (1-5C)heterocycloalkyl,
  g) (1-5C)heterocycloalkyl(1-6C)alkyl,
  h) (6-10C)aryl,
  i) (1-6C)alkyl,
  j) (1-6C)alkoxy,
  k) (1-4C)thioalkyl(1-6C)alkyl,
  l) (1-4C)alkylsulfonyl(1-6C)alkyl, and
  m) (1-4C)alkoxy(1-6C)alkyl;

$R^{22}$ may optionally be substituted with one, two or three $R^{221}$ substituents;

$R^{23}$ is selected from the group consisting of:
  a) (6-10C)aryl(1-6C)alkoxy,
  b) (3-7C)cycloalkyl,
  c) (3-7C)cycloalkoxy,
  d) (1-6C)alkylamino,
  e) (1-6C)alkyl, and
  f) (1-4C)alkoxy(1-6C)alkyl;

$R^{23}$ may optionally be substituted with one, two or three $R^{231}$ substituents;

$R^{24}$ is selected from the group consisting of:
  a) (3-7C)cycloalkyl,
  b) (1-6C)alkyl,
  c) (6-10C)aryl, and
  d) (2-5C)heteroaryl;

$R^{24}$ may optionally be substituted with one, two or three $R^{241}$ substituents;

$R^{25}$ is independently selected from the group consisting of:
  a) (3-7C)cycloalkyl,
  b) (1-6C)alkyl,
  c) (6-10C)aryl, and
  d) (2-5C)heteroaryl;

$R^{25}$ may optionally be substituted with one, two or three $R^{251}$ substituents;

$R^{211}$, $R^{221}$, $R^{231}$, $R^{241}$, and $R^{251}$ are independently selected from the group consisting of:
  a) one or more halogen,
  b) $CF_3$,
  c) $OCF_3$,
  d) oxo,
  e) hydroxyl,
  f) cyano,
  g) amino,
  h) (1-6C)alkyl,
  i) (1-4C)alkoxyl,
  j) (3-7C)cycloalkyl,
  k) (3-7C)cycloalkoxy,
  l) di[(1-6C)alkyl]amino,
  m) (1-4C)alkoxy(1-6C)alkyl,
  n) (1-5C)heteroaryl, and
  o) (2-5C)heterocycloalkyl;

with the proviso that:
  1) 0 to 2 atoms of X, Y, Z can simultaneously be a heteroatom;
  2) when one atom selected from X, Y is O or S, then Z is a bond and the other atom selected from X, Y cannot be O or S;
  3) when Z is C or N then Y is C($R^6$) or N and X is C, N or a bond;
  4) when $A_3$ is N then $A_5$ is C;
  5) in ring K, 0 to 2 atoms of $B_1$, $B_2$, $B_3$ and $B_4$ are N;
  6) when $A_5$ is N then $R^4$ is absent;
  7) when $A_6$ is N then $R^{15}$ is absent;
  8) when $A_6$ is O then $R^1$ and $R^{15}$ are absent;
  9) when X is a bond, then Y is O or S and Z is CH; and
  10) when W is CH, then X is a bond, Y is S and Z is N.

The terms as used herein refer to the following:

Halogen means fluorine, chlorine, bromine or iodine, fluorine, chlorine or bromine being preferred halogens, fluorine or chlorine being more preferred.

(1-2C)Alkyl means an alkyl group having 1 to 2 carbon atoms, being methyl or ethyl. A methyl group may be indicated as Me or $CH_3$.

(1-3C)Alkyl means a branched or unbranched alkyl group having 1-3 carbon atoms, being methyl, ethyl, propyl or isopropyl.

(1-4C)Alkyl means a branched or unbranched alkyl group having 1-4 carbon atoms, being methyl, ethyl, propyl, isopropyl, butyl, isobutyl, sec-butyl or tert-butyl, (1-3C) alkyl groups being preferred.

(1-5C)Alkyl means a branched or unbranched alkyl group having 1-5 carbon atoms, for example methyl, ethyl, propyl, isopropyl, butyl, isobutyl, sec-butyl, tert-butyl, pentyl and isopentyl, (1-4C)alkyl groups being preferred.

(1-6C)Alkyl means a branched or unbranched alkyl group having 1-6 carbon atoms, for example methyl, ethyl, propyl, isopropyl, butyl, tert-butyl, n-pentyl and n-hexyl. (1-5C)alkyl groups are preferred, (1-4C)alkyl being more preferred.

Halo(1-6C)alkyl means a branched or unbranched alkyl group having 1-6 carbon atoms, in which one and up to all hydrogen atoms are replaced by a halogen; halogen is as defined herein. Examples of such branched or straight chained haloalkyl groups useful in the present invention include, but are not limited to, methyl, ethyl, propyl, isopropyl, isobutyl and n-butyl substituted independently with one or more halos, e.g., fluoro, chloro, bromo and iodo. Examples of "haloalkyl" include, but are not limited to, fluoromethyl, difluoromethyl, trifluoromethyl, 1-fluoroethyl, 2-fluoroethyl, 2,2-difluoroethyl, 2,2,2-trifluoroethyl, and perfluoro-n-propyl.

(1-2C)Alkoxy means an alkoxy group having 1-2 carbon atoms, the alkyl moiety having the same meaning as previously defined.

(2-4C)Alkoxy means an alkoxy group having 2-4 carbon atoms, for example ethoxy, propyloxy, butyloxy, isopropyloxy, isobutyloxy, and tertbutyloxy. ethyloxy and propyloxy being preferred. ethyloxy groups being more preferred.

(1-3C)Alkoxy means an alkoxy group having 1-3 carbon atoms, the alkyl moiety having the same meaning as previously defined. (1-2C)alkoxy groups are preferred.

(1-4C)Alkoxy means an alkoxy group having 1-4 carbon atoms, the alkyl moiety having the same meaning as previously defined. (1-3C)alkoxy groups are preferred, (1-2C)alkoxy groups being most preferred.

(1-5C)Alkoxy means an alkoxy group having 1-5 carbon atoms, the alkyl moiety having the same meaning as previously defined. (1-4C)alkoxy groups are preferred, (1-3C)alkoxy groups being more preferred.

(1-6C)Alkoxy means an alkoxy group having 1-6 carbon atoms, the alkyl moiety having the same meaning as previously defined. (1-5C)alkoxy groups are preferred, (1-4C)alkoxy groups being more preferred.

(2-4C)Alkenyl means a branched or unbranched alkenyl group having 2-4 carbon atoms, such as ethenyl, 2-propenyl, isobutenyl or 2-butenyl.

(2-6C)Alkenyl means a branched or unbranched alkenyl group having 2-6 carbon atoms, such as ethenyl, 2-butenyl, and n-pentenyl. (2-4C)alkenyl groups are preferred.

(2-4C)Alkynyl means a branched or unbranched alkynyl group having 2-4 carbon atoms, such as ethynyl, 2-propynyl or 2-butynyl.

(2-6C)Alkynyl means a branched or unbranched alkynyl group having 2-6 carbon atoms, such as ethynyl, propynyl, n-butynyl, n-pentynyl, isopentynyl, isohexynyl or n-hexynyl. (2-4C)alkynyl groups are preferred.

(3-6C)Cycloalkyl means a cycloalkyl group having 3-6 carbon atoms, being cyclopropyl, cyclobutyl, cyclopentyl or cyclohexyl. cyclopropyl, cyclobutyl, cyclopentyl being preferred.

(3-7C)Cycloalkyl means a cycloalkyl group having 3-7 carbon atoms, being cyclopropyl, cyclobutyl, cyclopentyl, cyclohexyl or cycloheptyl. Cyclopropyl, cyclobutyl, cyclopentyl being more preferred.

(3-10C)Cycloalkyl means a cycloalkyl group having 3-10 carbon atoms, being cyclopropyl, cyclobutyl, cyclopentyl, cyclohexyl, cycloheptyl, cyclooctyl, cyclononyl or cyclodecyl. (3-7C)Cycloalkyl groups are preferred. Cyclopropyl, cyclobutyl, cyclopentyl being more preferred.

(1-5C)Heterocycloalkyl means a heterocycloalkyl group having 1-5 carbon atoms, preferably 2-5 carbon atoms, more preferably 3-5 carbon atoms; and one or two heteroatoms selected from N, O and/or S, which may be attached via a heteroatom if feasible, or a carbon atom. Preferred heteroatoms are N or O. Preferred are piperidine, morpholine, pyrrolidine and piperazine. Most preferred (1-5C)heterocycloalkyl is pyrrolidine.

(1-6C)Heterocycloalkyl means a heterocycloalkyl group having 1-6 carbon atoms, preferably 2-6 carbon atoms, more preferably 3-5 carbon atoms; and one or two heteroatoms selected from N, O and/or S, which may be attached via a heteroatom if feasible, or a carbon atom. Preferred heteroatoms are N or O. Preferred are piperidine, morpholine, pyrrolidine and piperazine. Most preferred (1-6C)heterocycloalkyl is pyrrolidine.

(2-5C)Heterocycloalkyl means a heterocycloalkyl group having 2-5 carbon atoms, preferably 3-5 carbon atoms; and one or two heteroatoms selected from N, O and/or S, which may be attached via a heteroatom if feasible, or a carbon atom. Preferred heteroatoms are N or O. Preferred are piperidine, morpholine, pyrrolidine and piperazine. Most preferred (2-5C)heterocycloalkyl is piperidine.

(2-6C)Heterocycloalkyl means a heterocycloalkyl group having 2-6 carbon atoms, preferably 3-5 carbon atoms, and one or two heteroatoms selected from N, O and/or S, which may be attached via a heteroatom if feasible, or a carbon atom. Preferred heteroatoms are N or O. Preferred are piperidine, morpholine, pyrrolidine and piperazine.

Most preferred (2-6C)heterocycloalkyl is pyrrolidine. The heterocycloalkyl group may be attached via a heteroatom if feasible.

(3-7C)Heterocycloalkyl means a heterocycloalkyl group having 3-7 carbon atoms, preferably 3-5 carbon atoms, and one or two heteroatoms selected from N, O and/or S. Preferred heteroatoms are N or O. Preferred (3-7C)heterocycloalkyl groups are azetidinyl, pyrrolidinyl, piperidinyl, homopiperidinyl or morpholinyl. More preferred (3-7C)heterocycloalkyl groups are piperidinyl, morpholinyl and pyrrolidinyl. The heterocycloalkyl group may be attached via a heteroatom if feasible.

(3-6C)Cycloalkoxy means a cycloalkyl group having 3-6 carbon atoms, with the same meaning as previously defined, attached via a ring carbon atom to an exocyclic oxygen atom.

(3-7C)Cycloalkoxy means a cycloalkyl group having 3-7 carbon atoms, with the same meaning as previously defined, attached via a ring carbon atom to an exocyclic oxygen atom.

(6-10C)Aryl means an aromatic hydrocarbon group having 6-10 carbon atoms, such as phenyl, naphthyl, tetrahydronaphthyl or indenyl. The preferred (6-10C)aryl group is phenyl.

(1-5C)Heteroaryl means a substituted or unsubstituted aromatic group having 1-5 carbon atoms and 1-4 heteroatoms selected from N, O and/or S. The (1-5C)heteroaryl may optionally be substituted. Preferred (1-5C)heteroaryl groups are tetrazolyl, imidazolyl, thiadiazolyl, pyridyl, pyrimidyl, triazinyl, thienyl or furyl, more preferred (1-5C)heteroaryl is pyrimidyl.

(1-9C)Heteroaryl means a substituted or unsubstituted aromatic group having 1-9 carbon atoms and 1-4 heteroatoms selected from N, O and/or S. The (1-9C)heteroaryl may optionally be substituted. Preferred (1-9C)heteroaryl groups are quinoline, isoquinoline and indole.

(6-10C)Aryloxy means a (6-10C)aryl group with the same meaning as previously defined, attached via a ring carbon to an exocyclic oxygen atom.

(6-10C)Arylcarbonyl means a carbonyl group substituted with a (6-10C)aryl group having the same meaning as previously defined.

(3-10C)Cycloalkylamino means an amino group, monosubstituted with an cycloalkyl group containing 3-10 carbon atoms having the same meaning as previously defined.

(1-6C)Alkylamino means an amino group, monosubstituted with an alkyl group containing 1-6 carbon atoms having the same meaning as previously defined. Preferred (1-6C)alkylamino group is methylamino.

Di[(1-6C)alkyl]amino means an amino group, disubstituted with alkyl group(s), each independently containing 1-6 carbon atoms and having the same meaning as previously defined. Preferred di[(1-6C)alkyl]amino group is dimethylamino.

Di[(1-6C)alkyl]amino(1-6C)alkyl means an alkyl group with 1-6 carbon atoms and having the same meaning as previously defined, substituted with a di[(1-6C)alkyl]amino group having the same meaning as previously defined.

(6-10C)Arylamino means an amino group, monosubstituted with an aryl group containing 6-10 carbon atoms having the same meaning as previously defined. Preferred (6-10C)arylamino group is phenylamino.

Hydroxy(1-6C)alkyl means an (1-6C)alkyl group as previously defined, substituted with a primary hydroxyl group.

Amino(1-6C)alkyl means an (1-6C)alkyl group as previously defined, substituted with an amino group.

Amino(3-7C)cycloalkyl means a (3-7C)cycloalkyl group with the same meaning as previously defined substituted with an amino group.

Trifluoromethylcarbonyl means a carbonyl groups substituted with a trifluoromethyl group.

(1-3C)Alkylcarbonyl means a carbonyl group substituted with an alkyl group having 1-3 carbon atoms and having the same meaning as previously defined.

(1-6C)Alkylcarbonyl means a carbonyl group substituted with an alkyl group having 1-6 carbon atoms and having the same meaning as previously defined.

(1-3C)Alkylcarbonyloxy means an oxy-group substituted with an (1-3C)alkylcarbonyl group with the same meaning as previously defined.

(1-5C)Heteroarylcarbonyl means a carbonyl group substituted with an heteroaryl group having 1-5 carbon atoms and having the same meaning as previously defined.

(1-6C)alkylaminocarbonyl means a carbonyl group substituted with an (1-6C)alkylamino group as previously defined.

(1-4C)Alkylaminocarbonyl means a carbonyl group substituted with an amino group. Said amino group being monosubstituted with an alkyl group having 1-4 carbon atoms and having the same meaning as previously defined.

Di[(1-4C)alkyl]aminocarbonyl means a carbonyl group substituted with an amino group. Said amino group being disubstituted with an alkyl group each independently having 1-4 carbon atoms and having the same meaning as previously defined.

(1-6C)Alkoxycarbonyl means a carbonyl group substituted with an alkoxy group the alkyl moiety of which having 1-6 carbon atoms as previously defined.

(1-6C)Alkoxycarbonyl(1-4C)alkyl means an alkyl group with 1-4 carbon atoms as previously defined, substituted with an (1-6C)alkoxycarbonyl group as previously defined.

(1-6C)Alkoxydicarbonyl(1-4C)alkyl means an alkyl group with 1-4 carbon atoms as previously defined, substituted with carbonyl group, said carbonyl group being substituted with an (1-6C)alkoxycarbonyl group.

(1-6C)Alkylcarbonyl(2-5C)heterocycloalkyl means a (2-5C)heterocycloalkyl group as previously defined substituted with an (1-6C)alkylcarbonyl group as previously defined.

(6-10C)Arylcarbonyl(2-5C)heterocycloalkyl means a (2-5C)heterocycloalkyl group as previously defined substituted with an arylcarbonyl group, the aryl moiety of which having 6-10 carbon atoms, as previously defined.

(1-6C)alkylsulfonyl(2-5C)heterocycloalkyl means a (2-5C)heterocycloalkyl group as previously defined substituted with an alkylsulphonyl group, the alkyl moiety of which having 1-6 carbon atoms, as previously defined.

(3-7C)Cycloalkylcarbonyl means a carbonyl group substituted with a cycloakyl group with 3-7 carbon atoms as previously defined.

(3-7C)Cycloalkylcarbonyl(1-5C)heterocycloalkyl means a (1-5C)heterocycloalkyl group substituted with (3-7C)cycloalkylcarbonyl as previously defined.

(1-6C)Alkoxycarbonyl(1-4C)alkylamino(3-7C)cycloalkyl means a cycloalkyl group with 3-7 carbon atoms as previously defined substituted with an amino group. Said amino group being monosubstituted with an (1-6C) alkoxycarbonyl(1-4C)alkyl group as previously defined.

(3-7C)Cycloalkenyl means a cycloalkenyl group having 3-7 carbon atoms, preferably 5-7 carbon atoms. Preferred (3-7C)cycloalkenyl groups are cyclopentenyl or cyclohexenyl. Cyclohexenyl groups are most preferred.

(2-6C)Heterocycloalkenyl means a heterocycloalkenyl group having 2-6 carbon atoms, preferably 3-5 carbon atoms; and 1 heteroatom selected from N, O and/or S. Preferred (2-6C)heterocycloalkenyl groups are oxycyclohexenyl and azacyclohexenyl group.

(3-7C)Heterocycloalkenyl means a heterocycloalkenyl group having 3-7 carbon atoms, preferably 3-6 carbon atoms, more preferably 3-5 carbon atoms; and 1 heteroatom selected from N, O and/or S. Preferred (3-7C)heterocycloalkenyl groups are oxycyclohexenyl and azacyclohexenyl group.

(1-4C)Thioalkyl(1-6C)alkyl means an alkyl group having 1-6 carbon atoms with the same meaning as previously defined, substituted with a thioalkyl group the alkyl moiety of which having 1-4 carbon atoms as previously defined.

(1-4C)Alkylsulfonyl(1-6C)alkyl means an alkyl group having 1-6 carbon atoms with the same meaning as previously defined, substituted with a alkylsulphonyl group the alkyl moiety of which having 1-4 carbon atoms as previously defined.

(3-7C)Cycloalkyl(1-4C)alkyl means an alkyl group having 1-4 carbon atoms with the same meaning as previously defined, substituted with a cycloalkyl group having 3-7 carbon atoms as previously defined.

(3-7C)cycloalkoxy(1-4C)alkyl means an alkyl group having 1-4 carbon atoms with the same meaning as previously defined, substituted with a cycloalkoxy group having 3-7 carbon atoms as previously defined. The cycloalkoxy group is linked via the exocyclic oxygen to the alkyl group.

(6-10C)Aryl(1-4C)alkyl means an alkyl group having 1-4 carbon atoms with the same meaning as previously defined, substituted with a aryl group having 6-10 carbon atoms as previously defined. Preferred (6-10C)Aryl(1-4C)alkyl is phenyl-methylene.

(6-10C)Aryl(1-6C)alkyl means an alkyl group having 1-6 carbon atoms with the same meaning as previously defined, substituted with a aryl group having 6-10 carbon atoms as previously defined.

(6-10C)Aryl(1-6C)alkoxy means an alkoxy group the alkyl moiety of which having 1-6 carbon atoms with the same meaning as previously defined, substituted with a aryl group having 6-10 carbon atoms as previously defined.

(1-5C)Heteroaryl(1-4C)alkyl means an alkyl group having 1-4 carbon atoms with the same meaning as previously defined, substituted with a heteroaryl group having 1-5 carbon atoms as previously defined. Preferred (1-5C)heteroaryl(1-4C)alkyl is pyrazol-methylene.

(1-5C)Heteroaryl(1-6C)alkyl means an alkyl group having 1-6 carbon atoms with the same meaning as previously defined, substituted with a heteroaryl group having 1-5 carbon atoms as previously defined.

(2-5C)Heterocycloalkyl(1-6C)alkyl means an alkyl group having 1-6 carbon atoms with the same meaning as previously defined, substituted with a heterocycloalkyl group having 2-5 carbon atoms as previously defined.

(1-4C)Alkoxy(1-6C)alkyl means an alkyl group having 1-6 carbon atoms with the same meaning as previously defined, substituted with an alkoxy group the alkyl moiety of which having 1-4 carbon atoms as previously defined. Examples of "alkoxyalkyl" include, but are not limited to, methoxymethyl, 1-methoxyethyl, 2-ethoxyethyl, and 1,1-dimethoxyethyl.

(1-4C)Alkoxy[(2-4C)alkoxy]$_m$(1-6C)alkyl means a (1-6C) alkyl group having 1-6 carbon atoms with the same meaning as previously defined, substituted with one or more (2-4C)alkyloxy groups, i.e. m is an integer greater than or equal to 1, the alkoxy groups being linearly connected one to another. The last (2-4C)alkyloxy group being substituted with an (1-4C)alkyloxy group. In the (1-4C)alkoxy[(2-4C)alkoxy]$_m$(1-6C)alkyl group, the preferred (1-4C)alkoxy group is methoxy, the preferred (2-4C)alkoxy is ethoxy, and the preferred (1-6C)alkyl is ethyl, preferably m is 1, 2, 3, 4, 5, 6, 7, 8, 9, or 10, m is 1, 3 or 7 being more preferred. (1-4C)alkoxy[(2-4C)alkoxy]$_m$(1-6C)alkyl includes an (1-6C)alkyl group substituted with polyethylene glycol.

Amino(1-4C)alkoxy[(2-4C)alkoxy]$_m$(1-6C)alkyl means an (1-4C)alkoxy[(2-4C)alkoxy]$_m$(1-6C)alkyl group, the (1-4C)alkoxy group of which being substituted with an amino group.

Hydroxy(1-6C)alkyl means a branched or unbranched alkyl group having 1-6 carbon atoms, in which one, two or three hydrogen atoms are replaced by a hydroxyl group. Examples of "hydroxyalkyl" include, but are not limited to, hydroxymethyl, 1-hydroxyethyl, 2-hydroxyethyl, and 1,2-dihydroxyethyl.

Di[hydroxy](1-6C)alkyl means an alkyl group with 1-6 carbon atoms as previously defined substituted with two hydroxyl groups.

In the above definitions with multifunctional groups, the attachment point is at the last group.

When, in the definition of a substituent, is indicated that "all of the alkyl groups" of said substituent are optionally substituted, this also includes the alkyl moiety of an alkoxy group.

A circle in a ring of Formula I indicates that the ring is aromatic.

Depending on the ring formed, the nitrogen, if present in W, X, Y or Z, may carry a hydrogen.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent.

The term "optionally substituted" means optional substitution with the specified groups, radicals or moieties.

The term pharmaceutically acceptable salt is well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

Aspects of the Invention

In one aspect the invention relates to a compound according to Formula I wherein:

$B_1$ is $C(R^7)$, $B_2$ is $C(R^8)$, $B_3$ is $C(R^9)$, and $B_4$ is $C(R^{10})$; or
$B_1$ is N, $B_2$ is N, $B_3$ is $C(R^9)$, and $B_4$ is $C(R^{10})$; or
$B_1$ is N, $B_2$ is $C(R^8)$, $B_3$ is N, and $B_4$ is $C(R^{10})$; or
$B_1$ is N, $B_2$ is $C(R^8)$, $B_3$ is $C(R^9)$, and $B_4$ is N; or
$B_1$ is $C(R^7)$, $B_2$ is $C(R^8)$, $B_3$ is N, and $B_4$ is N; or
$B_1$ is $C(R^7)$, $B_2$ is N, $B_3$ is $C(R^9)$, and $B_4$ is N.

In another aspect the invention relates to a compound of Formula I wherein ring K is defined as: $B_1$ is $C(R^7)$, $B_2$ is $C(R^8)$, $B_3$ is $C(R^9)$, and $B_4$ is $C(R^{10})$ and wherein $R^7$, $R^8$, $R^9$ and $R^{10}$ each are H or halogen.

In yet another aspect the invention relates to a compound according to Formula I wherein ring L is selected from the group consisting of pyridyl, pyrimidyl, pyridazyl, triazinyl, thiazolyl, oxazolyl, isoxazolyl, pyrazolyl, thiadiazolyl, and isothiazolyl.

In yet another aspect the invention relates to a compound according to Formula I wherein ring L is selected from the group consisting of pyridyl, pyrimidyl, and thiazolyl.

In another aspect the invention relates to a compound according to Formula I wherein $R^5$ is selected from the group consisting of hydrogen, fluorine, chlorine, CN, cyclopropyl, (1-3C)alkyl and (1-2C) alkoxy; the (1-3C)alkyl group of which is optionally substituted with one or more halogen.

In another aspect the invention relates to a compound according to Formula I wherein $R^5$ is selected from the group consisting of hydrogen, fluorine, methyl, ethyl, propyl, cyclopropyl, methoxy and trifluoromethyl.

In another aspect the invention relates to a compound according to Formula I wherein $R^1$ is selected from the group consisting of $R^{21}C(O)$, $R^{22}NHC(O)$, $R^{23}C(O)NH$, $R^{25}SO2$, (3-7C)cycloalkyl(1-4C)alkyl, (6-10C)aryl(1-4C)alkyl, (1-6C)alkyl, (1-5C)heteroaryl(1-4C)alkyl, halo(1-6C)alkyl, hydroxy(1-6C)alkyl, (1-4C)alkoxy(1-6C)alkyl, and (1-6C)alkoxyl.

In yet another aspect the invention relates to a compound according to Formula I wherein $R^1$ is selected from the group consisting of $R^{21}C(O)$, $R^{22}NHC(O)$, $R^{23}C(O)NH$, (6-10C)aryl(1-4C)alkyl, (1-5C)heteroaryl(1-4C)alkyl, halo (1-6C)alkyl, hydroxy(1-6C)alkyl, (1-4C)alkoxy(1-6C)alkyl, and (1-6C)alkoxyl.

In $R^1$, the preferred (6-10C)aryl(1-4C)alkyl is phenylmethylene and the preferred (1-5C)heteroaryl(1-4C)alkyl is pyrazol-methylene.

In another aspect the invention relates to a compound according to Formula I wherein $R^1$ is selected from the group consisting of $R^{21}C(O)$, $R^{22}NHC(O)$, and $R^{23}C(O)NH$.

In another aspect the invention relates to a compound according to Formula I wherein

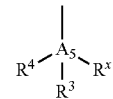

is selected from the group consisting of

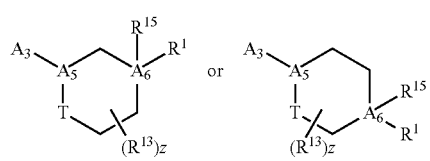

wherein:
T is O, S or CH2; and
A₆ is C or N; and
z is 0, 1 or 2.
In yet another aspect the invention relates to a compound according to Formula I wherein
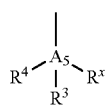
is selected from the group consisting of
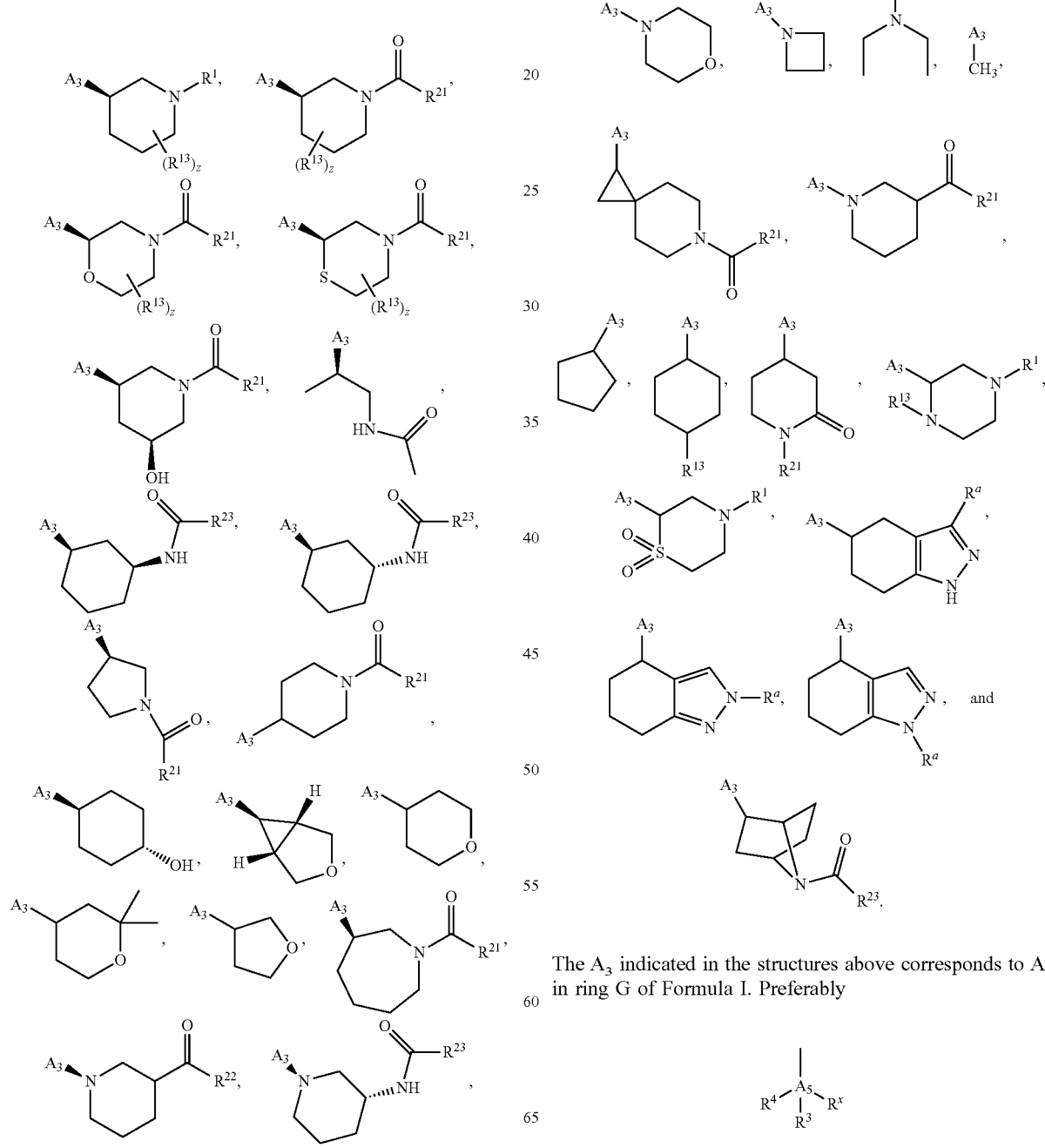
The A₃ indicated in the structures above corresponds to A₃ in ring G of Formula I. Preferably
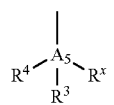

is selected from the group consisting of

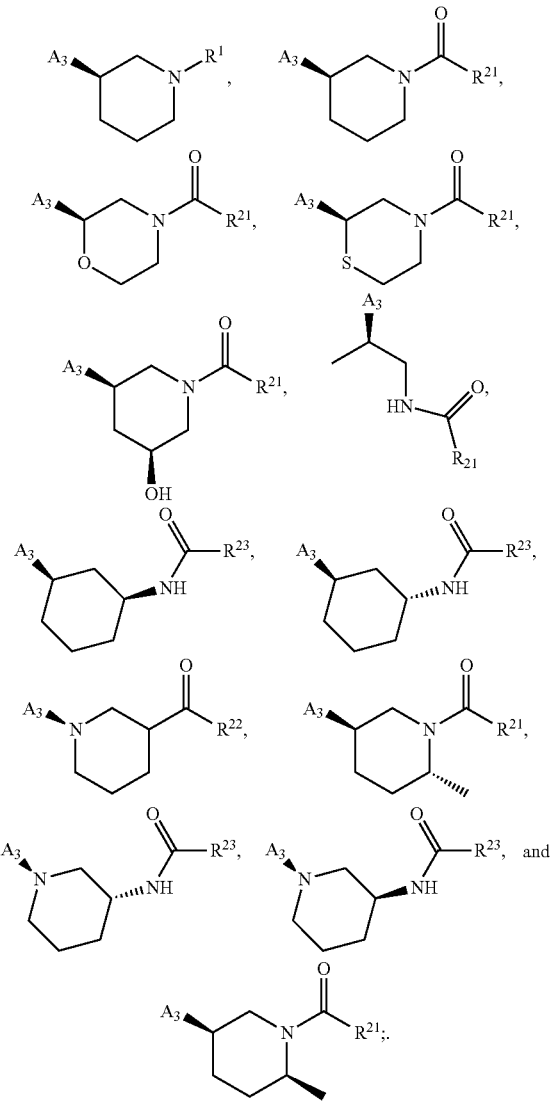

More preferred,

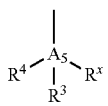

is selected from the group consisting of

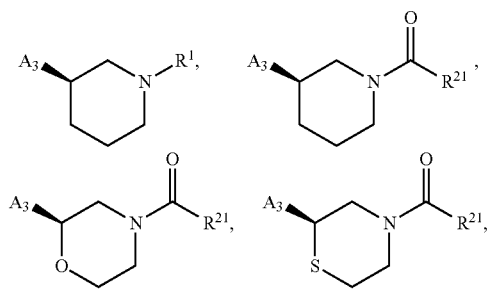

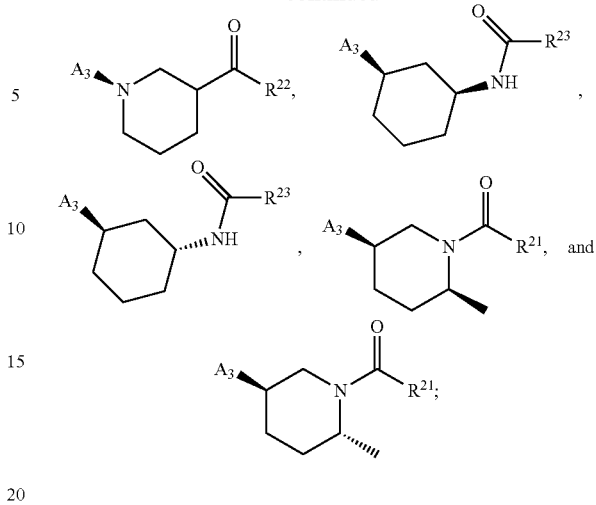

Again, as indicated above, the $A_3$ indicated in the structures corresponds to $A_3$ in ring G of Formula I.

In yet another aspect the invention relates to a compound according to Formula I wherein $R^{21}$ is selected from the group consisting of di[hydroxy](1-6C)alkyl, di[(1-6C)alkyl]amino(1-6C)alkyl, amino(3-7C)cycloalkyl, (6-10C)aryloxy, (6-10C)arylcarbonyl(2-5C)heterocycloalkyl, (3-7C)cycloalkylcarbonyl(1-5C)heterocycloalkyl, (3-7C)cycloalkyl, (3-6C)cycloalkoxy, (3-10C)cycloalkylamino, (3-10C)cycloalkyl, (1-6C)alkylsulfonyl(2-5C)heterocycloalkyl, (1-6C)alkylcarbonyl(2-5C)heterocycloalkyl, (1-6C)alkylamino, (1-6C)alkoxy, (1-5C)heteroarylcarbonyl, (1-5C)heteroaryl(1-4C)alkyl, (1-5C)heterocycloalkyl, (1-4C)thioalkyl(1-6C)alkyl, di[(1-4C)alkyl]aminocarbonyl, (1-4C)alkylsulfonyl(1-6C)alkyl, (1-4C)alkylaminocarbonyl, (1-4C)alkoxy(1-6C)alkyl, (1-6C)alkoxy, amino(1-6C)alkyl, (6-10C)arylamino, (3-7C)cycloalkoxy, (2-5C)heterocycloalkyl, (1-6C)cycloalkyl, (1-6C)alkyl, (1-6C)alkoxycarbonyl(1-4C)alkyl, (1-5C)heteroaryl, (1-4C)alkoxy[(2-4C)alkoxy]$_m$(1-6C)alkyl, and amino(1-4C)alkoxy[(2-4C)alkoxy]$_m$(1-6C)alkyl. $R^{21}$ may optionally be substituted with $R^{211}$.

Preferably, $R^{21}$ is selected from the group consisting of (3-7C)cycloalkylcarbonyl(1-5C)heterocycloalkyl, (3-7C)cycloalkyl, (3-6C)cycloalkoxy, (3-10C)cycloalkylamino, (3-10C)cycloalkyl, (1-6C)alkylsulfonyl(2-5C)heterocycloalkyl, (1-6C)alkylcarbonyl(2-5C)heterocycloalkyl, (1-6C)alkylamino, (1-6C)alkoxy, (1-5C)heteroarylcarbonyl, (1-5C)heteroaryl(1-4C)alkyl, (1-5C)heterocycloalkyl, (1-4C)thioalkyl(1-6C)alkyl, di[(1-4C)alkyl]aminocarbonyl, (1-4C)alkoxy[(2-4C)alkoxy]$_m$(1-6C)alkyl, (1-4C)alkylsulfonyl(1-6C)alkyl, (1-4C)alkylaminocarbonyl, (1-4C)alkoxy(1-6C)alkyl, (1-6C)alkoxy, amino(1-6C)alkyl, (6-10C)arylamino, (3-7C)cycloalkoxy, (2-5C)heterocycloalkyl, (1-6C)cycloalkyl, (1-6C)alkyl, (1-6C)alkoxycarbonyl(1-4C)alkyl, and (1-5C)heteroaryl. $R^{21}$ may optionally be substituted with $R^{211}$.

More preferred, $R^{21}$ is selected from the group consisting of (3-7C)cycloalkyl, (3-6C)cycloalkoxy, (1-6C)alkylsulfonyl(2-5C)heterocycloalkyl, (1-4C)thioalkyl(1-6C)alkyl, (1-4C)alkylsulfonyl(1-6C)alkyl, (1-4C)alkoxy(1-6C)alkyl, (3-7C)cycloalkoxy, (1-6C)alkyl, and (1-5C)heteroaryl. R21 may optionally be substituted with $R^{211}$.

Most preferred, $R^{21}$ may optionally be substituted with $R^{211}$ and substituted $R^{21}$ is selected from the group consisting of

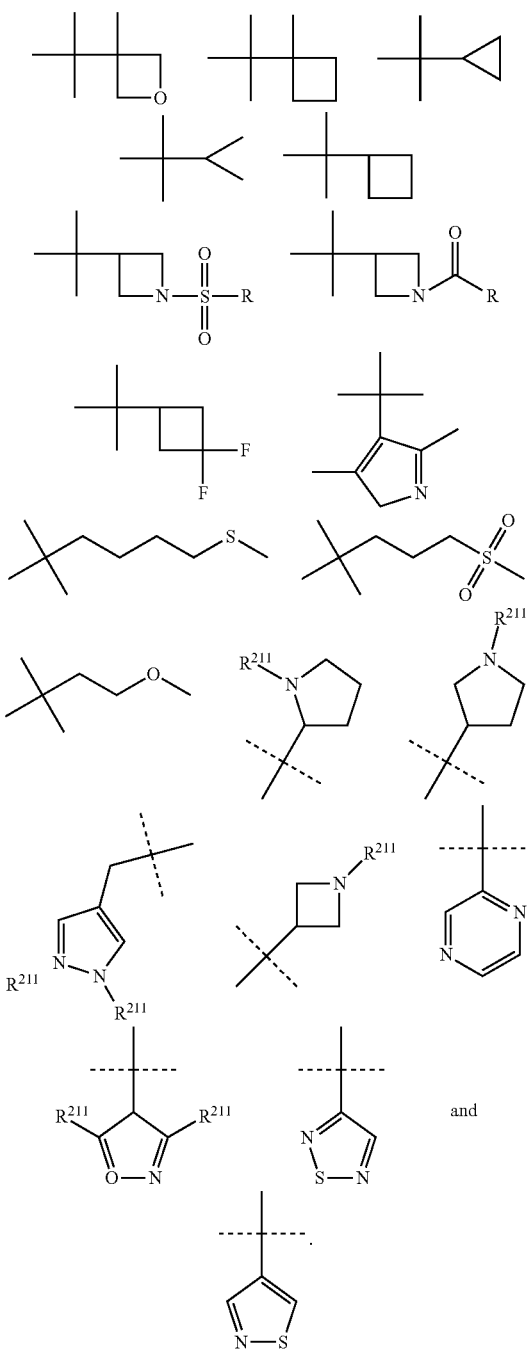

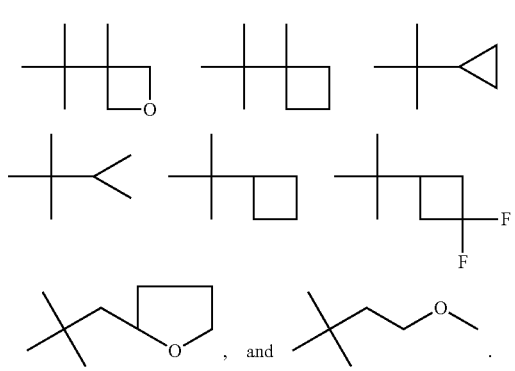

In another aspect the invention relates to a compound according to Formula I wherein $R^{23}$ is selected from the group consisting of (6-10C)aryl(1-6C)alkoxy, (3-7C)cycloalkyl, (3-7C)cycloalkoxy, (1-6C)alkylamino, (1-6C)alkyl, and (1-4C)alkoxy(1-6C)alkyl. $R^{23}$ may optionally be substituted with $R^{231}$.

Preferably, $R^{23}$ is selected from the group consisting of (3-7C)cycloalkyl, (3-7C)cycloalkoxy, and (1-4C)alkoxy(1-6C)alkyl and $R^{23}$ may optionally be substituted with $R^{231}$.

Most preferred, $R^{23}$ is selected from the group consisting of

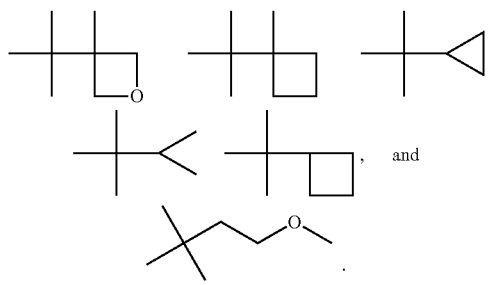

and $R^{23}$ may optionally be substituted with $R^{231}$.

In yet another aspect the invention relates to a compound according to Formula I wherein $R^{24}$ is selected from the group consisting of (3-7C)cycloalkyl and (1-6C)alkyl and $R^{24}$ may optionally be substituted with $R^{241}$.

Most preferred, $R^{24}$ is selected from the group consisting of

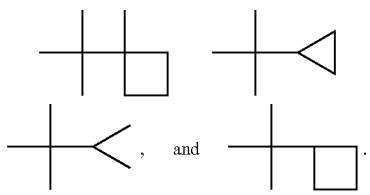

and $R^{24}$ may optionally be substituted with $R^{241}$.

In still another aspect the invention relates to a compound according to Formula I wherein $R^{25}$ is selected from the group consisting of (3-7C)cycloalkyl and (1-6C)alkyl and $R^{25}$ may optionally be substituted with $R^{251}$.

In another aspect the invention relates to a compound according to Formula I wherein $R^{22}$ is selected from the group consisting of (3-7C)cycloalkyl(1-4C)alkyl, (3-7C)cycloalkyl, (3-7C)cycloalkoxy(1-4C)alkyl, (3-6C)cycloalkoxy, (1-6C)alkyl, (1-6C)alkoxy, (1-4C)thioalkyl(1-6C)alkyl, (1-4C)alkylsulfonyl(1-6C)alkyl, and (1-4C)alkoxy(1-6C)alkyl. $R^{22}$ may optionally be substituted with $R^{221}$. Preferrably, $R^{22}$ is selected from the group consisting of (3-7C)cycloalkyl, (3-7C)cycloalkoxy(1-4C)alkyl, (3-6C)cycloalkoxy, (1-6C)alkyl, and (1-4C)alkoxy(1-6C)alkyl. $R^{22}$ may optionally be substituted with $R^{221}$.

Most preferred, $R^{22}$ may optionally be substituted with $R^{221}$ and $R^{22}$ is selected from the group consisting of Preferably, $R^{25}$ is selected from the group consisting of

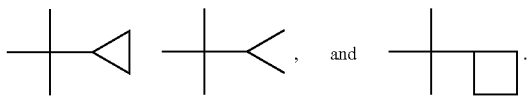

and $R^{25}$ may optionally be substituted with $R^{251}$.

In yet another aspect the invention relates to a compound according to Formula I wherein optional substituents $R^{211}$, $R^{221}$, $R^{231}$, $R^{241}$, and $R^{251}$ are independently selected from the group consisting of: one or more halogen, $CF_3$, $OCF_3$, oxo, hydroxy, cyano, (1-6C)alkyl, (3-7C)cycloalkoxy, di[(1-6C)alkyl]amino, (1-4C)akoxy(1-6C)alkyl, (1-5C)heteroaryl, and (2-5C)heterocycloalkyl and $R^{21}$, $R^{22}$, $R^{23}$, $R^{24}$, and $R^{25}$ may optionally be substituted with one to four substituents $R^{211}$, $R^{221}$, $R^{231}$, $R^{241}$, and $R^{251}$ respectively.

Preferably, optional substituents $R^{211}$, $R^{221}$, $R^{231}$, $R^{241}$, and $R^{251}$ are independently selected from the group consisting of F, hydroxyl, (1-3C)alkyl, and dimethylamino.

In yet another aspect the invention relates to a compound according to Formula I wherein $R^{11}$ is selected from the group consisting of H, $^2H$, F, Cl, Br, Me, $C^2H_3$, ethyl, cyclopropyl and vinyl. Preferably, $R^{11}$ is H.

In yet another aspect the invention relates to a compound according to Formula I wherein $A_1$-$A_4$ are C or N and bicyclic ring system E-G is selected from the group consisting of

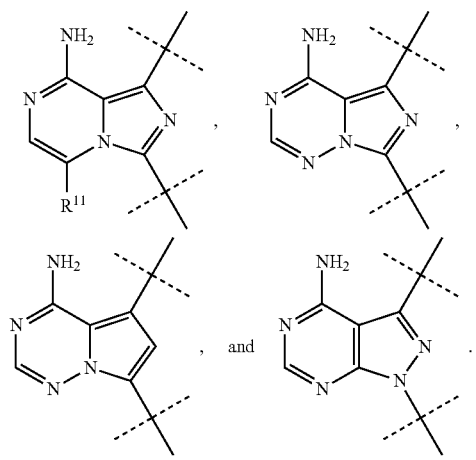

In yet another aspect the invention relates to a compound according to Formula I wherein $A_1$-$A_4$ are C or N and bicyclic ring system E-G is

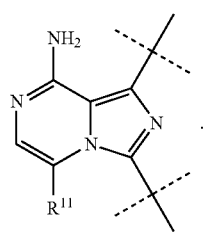

In one aspect the invention relates to a compound having Formula Ia

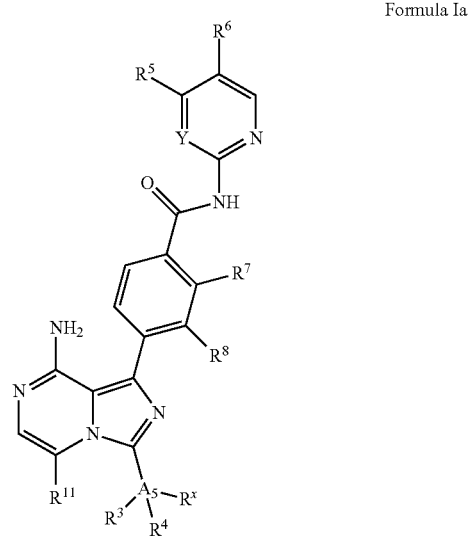

Formula Ia or a pharmaceutically acceptable salt or solvate thereof.

In another aspect the invention relates to a compound having Formula Ib

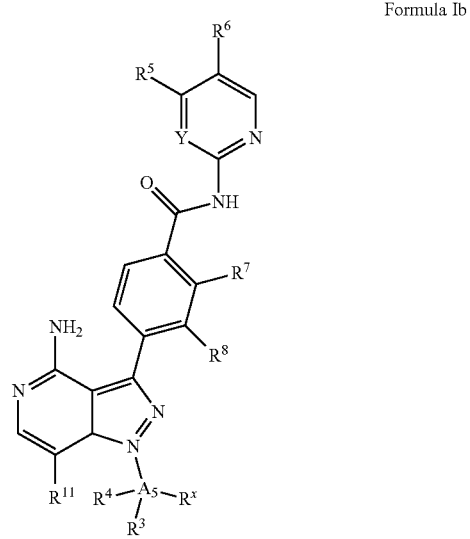

Formula Ib or a pharmaceutically acceptable salt or solvate thereof.

In another aspect the invention relates to a compound having Formula Ic

Formula Ic

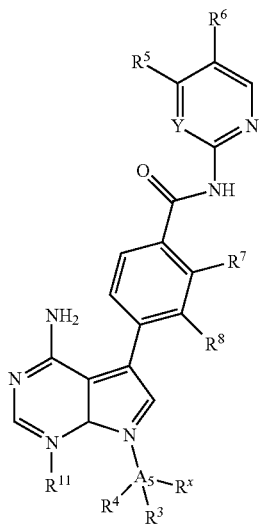

or a pharmaceutically acceptable salt or solvate thereof.

In yet another aspect the invention relates to a compound having Formula Id

Formula Id

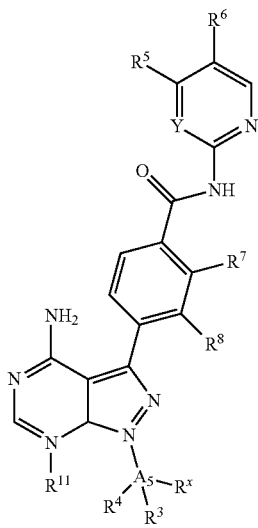

or a pharmaceutically acceptable salt or solvate thereof.

The invention also relates to those compounds wherein all specific definitions for $A_1$-$A_6$, $B_1$-$B_4$, X, Y, Z, $R^3$, $R^4$, $R^5$ and $R^x$, and all substituent groups in the various aspects of the inventions defined here above occur in any combination within the definition of the 6-5 membered fused pyridine ring compounds of Formula I or pharmaceutically acceptable salts thereof.

In still another aspect the invention relates to a compound according to Formula I or a pharmaceutically acceptable salt or solvate thereof selected from the group consisting of:

4-(8-amino-3-((trans)-4-hydroxycyclohexyl)imidazo[1,5-a]pyrazin-1-yl)-N-(pyridin-2-yl)benzamide;
4-(8-amino-3-((trans)-4-hydroxycyclohexyl)imidazo[1,5-a]pyrazin-1-yl)-N-(4-(trifluoromethyl)pyridin-2-yl)benzamide;
4-(8-amino-3-((trans)-4-hydroxycyclohexyl)imidazo[1,5-a]pyrazin-1-yl)-N-(4-propylpyridin-2-yl)benzamide;
4-(8-amino-3-((trans)-4-hydroxycyclohexyl)imidazo[1,5-a]pyrazin-1-yl)-N-(5-ethylthiazol-2-yl)benzamide;
4-(8-amino-3-((trans)-4-hydroxycyclohexyl)imidazo[1,5-a]pyrazin-1-yl)-N-(4-methylpyridin-2-yl)benzamide;
4-(8-amino-3-((trans)-4-hydroxycyclohexyl)imidazo[1,5-a]pyrazin-1-yl)-N-(4-isopropylpyridin-2-yl)benzamide;
4-(8-amino-3-((trans)-4-hydroxycyclohexyl)imidazo[1,5-a]pyrazin-1-yl)-N-(4-cyclopropylppidin-2-yl)benzamide;
4-(8-amino-3-((trans)-4-hydroxycyclohexyl)imidazo[1,5-a]pyrazin-1-yl)-N-(4,5,6,7-tetrahydrobenzo[d]thiazol-2-yl)benzamide;
4-(8-amino-3-((trans)-4-hydroxycyclohexyl)imidazo[1,5-a]pyrazin-1-yl)-2-methoxy-N-(pyridin-2-yl)benzamide;
4-(8-amino-3-((trans)-4-hydroxycyclohexyl)imidazo[1,5-a]pyrazin-1-yl)-3-methyl-N-(4-propylpyridin-2-yl)benzamide;
4-(8-amino-3-((trans)-4-hydroxycyclohexyl)imidazo[1,5-a]pyrazin-1-yl)-2-methoxy-N-(4-propylpyridin-2-yl)benzamide;
4-(8-amino-3-((trans)-4-hydroxycyclohexyl)imidazo[1,5-a]pyrazin-1-yl)-2-fluoro-N-(pyridin-2-yl)benzamide;
4-(8-amino-3-((trans)-4-hydroxycyclohexyl)imidazo[1,5-a]pyrazin-1-yl)-2-fluoro-N-(4-propylpyridin-2-yl)benzamide;
4-(8-amino-3-((trans)-4-hydroxycyclohexyl)imidazo[1,5-a]pyrazin-1-yl)-N-(6-methyl-4,5,6,7-tetrahydrobenzo[d]thiazol-2-yl)benzamide;
4-(8-amino-3-((trans)-4-hydroxycyclohexyl)imidazo[1,5-a]pyrazin-1-yl)-N-(6,7-dihydro-4H-pyrano[4,3-d]thiazol-2-yl)benzamide;
4-(8-amino-3-((trans)-4-hydroxycyclohexyl)imidazo[1,5-a]pyrazin-1-yl)-3-methyl-N-(pyridin-2-yl)benzamide;
4-(8-amino-3-((trans)-4-hydroxycyclohexyl)imidazo[1,5-a]pyrazin-1-yl)-N-(4,5,6,7-tetrahydrothiazolo[5,4-c]pyridin-2-yl)benzamide;
4-(8-amino-3-((trans)-4-hydroxycyclohexyl)imidazo[1,5-a]pyrazin-1-yl)-N-(5-methyl-4,5,6,7-tetrahydrothiazolo[5,4-c]pyridin-2-yl)benzamide;
4-(8-amino-3-((trans)-4-hydroxycyclohexyl)imidazo[1,5-a]pyrazin-1-yl)-N-(4-ethylpyridin-2-yl)benzamide;
4-(8-amino-3-((trans)-4-hydroxycyclohexyl)imidazo[1,5-a]pyrazin-1-yl)-N-(4-phenylpyridin-2-yl)benzamide;
4-(8-amino-3-((trans)-4-hydroxycyclohexyl)imidazo[1,5-a]pyrazin-1-yl)-N-(4-(pyrrolidin-1-yl)pyridin-2-yl)benzamide;
4-(8-amino-3-((trans)-4-hydroxycyclohexyl)imidazo[1,5-a]pyrazin-1-yl)-N-(pyridin-2-yl)-1-naphthamide;
4-(8-amino-3-((trans)-4-hydroxycyclohexyl)imidazo[1,5-a]pyrazin-1-yl)-2-chloro-N-(pyridin-2-yl)benzamide;
4-(8-amino-3-(tetrahydro-2H-pyran-4-yl)imidazo[1,5-a]pyrazin-1-yl)-N-(4-propylpyridin-2-yl)benzamide;
4-(8-amino-3-(tetrahydro-2H-pyran-4-yl)imidazo[1,5-a]pyrazin-1-yl)-N-(4-(trifluoromethyl)pyridin-2-yl)benzamide;
4-(8-amino-3-(tetrahydro-2H-pyran-4-yl)imidazo[1,5-a]pyrazin-1-yl)-N-(4-cyanopyridin-2-yl)benzamide;
4-(8-amino-3-(tetrahydro-2H-pyran-4-yl)imidazo[1,5-a]pyrazin-1-yl)-N-(pyridin-2-yl)benzamide
4-(8-amino-3-(tetrahydro-2H-pyran-4-yl)imidazo[1,5-a]pyrazin-1-yl)-N-(5-ethylthiazol-2-yl)benzamide;
4-(8-amino-3-(tetrahydro-2H-pyran-4-yl)imidazo[1,5-a]pyrazin-1-yl)-N-(thiazol-2-yl)benzamide
4-(8-amino-3-((1R,5S,6S)-3-oxabicyclo[3.1.0]hexan-6-yl)imidazo[1,5-a]pyrazin-1-yl)-N-(4-propylpyridin-2-yl)benzamide;

4-(8-amino-3-((1R,5S,6S)-3-oxabicyclo[3.1.0]hexan-6-yl)imidazo[1,5-a]pyrazin-1-yl)-N-(4-(trifluoromethyl)pyridin-2-yl)benzamide;

4-(8-amino-3-((1R,5S,6S)-3-oxabicyclo[3.1.0]hexan-6-yl)imidazo[1,5-a]pyrazin-1-yl)-N-(6-methyl-4,5,6,7-tetrahydrobenzo[d]thiazol-2-yl)benzamide;

4-(8-amino-3-(tetrahydrofuran-3-yl)imidazo[1,5-a]pyrazin-1-yl)-N-(4-cyanopyridin-2-yl)benzamide;

4-(8-amino-3-(2,2-dimethyltetrahydro-2H-pyran-4-yl)imidazo[1,5-a]pyrazin-1-yl)-N-(4-(trifluoromethyl)pyridin-2-yl)benzamide;

4-(8-amino-3-(2,2-dimethyltetrahydro-2H-pyran-4-yl)imidazo[1,5-a]pyrazin-1-yl)-N-(pyridin-2-yl)benzamide;

4-(8-amino-3-(2,2-dimethyltetrahydro-2H-pyran-4-yl)imidazo[1,5-a]pyrazin-1-yl)-N-(4-propylpyridin-2-yl)benzamide;

4-(8-amino-3-(2,2-dimethyltetrahydro-2H-pyran-4-yl)imidazo[1,5-a]pyrazin-1-yl)-N-(4-cyanopyridin-2-yl)benzamide;

(trans)-4-(8-amino-1-(4-(5-ethylthiazol-2-ylcarbamoyl)phenyl)imidazo[1,5-a]pyrazin-3-yl)cyclohexyl acetate;

4-(8-amino-3-((cis)-4-methoxycyclohexyl)imidazo[1,5-a]pyrazin-1-yl)-N-(5-ethylthiazol-2-yl)benzamide;

4-(8-amino-3-((cis)-4-methoxycyclohexyl)imidazo[1,5-a]pyrazin-1-yl)-N-(4-(trifluoromethyl)pyridin-2-yl)benzamide;

4-(8-amino-3-((cis)-4-methoxycyclohexyl)imidazo[1,5-a]pyrazin-1-yl)-N-(4-cyanopyridin-2-yl)benzamide;

4-(8-amino-3-((cis)-4-methoxycyclohexyl)imidazo[1,5-a]pyrazin-1-yl)-N-(4-propylpyridin-2-yl)benzamide;

4-(8-amino-3-cyclopentylimidazo[1,5-a]pyrazin-1-yl)-N-(4-(trifluoromethyl)pyridin-2-yl)benzamide;

4-(8-amino-3-cyclopentylimidazo[1,5-a]pyrazin-1-yl)-N-(4-cyanopyridin-2-yl)benzamide;

4-(8-amino-3-cyclopentylimidazo[1,5-a]pyrazin-1-yl)-N-(pyridin-2-yl)benzamide;

(R)-4-(8-amino-3-(1-propionylpiperidin-3-yl)imidazo[1,5-a]pyrazin-1-yl)-N-(pyridin-2-yl)benzamide;

(R)-ethyl 3-(8-amino-1-(4-(pyridin-2-ylcarbamoyl)phenyl)imidazo[1,5-a]pyrazin-3-yl)piperidine-1-carboxylate;

(R)-3-(8-amino-1-(4-(pyridin-2-ylcarbamoyl)phenyl)imidazo[1,5-a]pyrazin-3-yl)-N-ethylpiperidine-1-carboxamide;

(R)-4-(8-amino-3-(1-(methylsulfonyl)piperidin-3-yl)imidazo[1,5-a]pyrazin-1-yl)-N-(pyridin-2-yl)benzamide;

(R)-4-(8-amino-3-(1-(3-methoxypropanoyl)piperidin-3-yl)imidazo[1,5-a]pyrazin-1-yl)-N-(pyridin-2-yl)benzamide;

(R)-4-(8-amino-3-(1-(4-(dimethylamino)butanoyl)piperidin-3-yl)imidazo[1,5-a]pyrazin-1-yl)-N-(pyridin-2-yl)benzamide;

(R)-4-(8-amino-3-(1-(cyclopropanecarbonyl)piperidin-3-yl)imidazo[1,5-a]pyrazin-1-yl)-N-(pyridin-2-yl)benzamide;

(R)-4-(8-amino-3-(1-(2-hydroxyacetyl)piperidin-3-yl)imidazo[1,5-a]pyrazin-1-yl)-N-(pyridin-2-yl)benzamide;

(R)-4-(8-amino-3-(1-(5-aminopentanoyl)piperidin-3-yl)imidazo[1,5-a]pyrazin-1-yl)-N-(pyridin-2-yl)benzamide;

4-(8-amino-3-((R)-1-((trans)-4-aminocyclohexanecarbonyl)piperidin-3-yl)imidazo[1,5-a]pyrazin-1-yl)-N-(pyridin-2-yl)benzamide;

4-(8-amino-3-((3R)-1-(tetrahydrofuran-3-carbonyl)piperidin-3-yl)imidazo[1,5-a]pyrazin-1-yl)-N-(pyridin-2-yl)benzamide;

4-(8-amino-3-((R)-1-((S)-2-methoxypropanoyl)piperidin-3-yl)imidazo[1,5-a]pyrazin-1-yl)-N-(pyridin-2-yl)benzamide;

4-(8-amino-3-((R)-1-((S)-2-methylbutanoyl)piperidin-3-yl)imidazo[1,5-a]pyrazin-1-yl)-N-(pyridin-2-yl)benzamide;

(R)-4-(8-amino-3-(1-(cyclobutanecarbonyl)piperidin-3-yl)imidazo[1,5-a]pyrazin-1-yl)-N-(4-cyclopropylpyridin-2-yl)benzamide;

(R)-4-(8-amino-3-(1-propionylpiperidin-3-yl)imidazo[1,5-a]pyrazin-1-yl)-N-(4-cyclopropylpyridin-2-yl)benzamide;

(R)-4-(8-amino-3-(1-(3-methoxypropanoyl)piperidin-3-yl)imidazo[1,5-a]pyrazin-1-yl)-N-(4-cyclopropylpyridin-2-yl)benzamide;

4-(8-amino-3-((3R)-1-(2-methylcyclopropanecarbonyl)piperidin-3-yl)imidazo[1,5-a]pyrazin-1-yl)-N-(4-cyclopropylpyridin-2-yl)benzamide;

(R)-3-(8-amino-1-(4-(4-cyclopropylpyridin-2-ylcarbamoyl)phenyl)imidazo[1,5-a]pyrazin-3-yl)-N-ethylpiperidine-1-carboxamide;

(R)-4-(8-amino-3-(1-(2-fluoro-2-methylpropanoyl)piperidin-3-yl)imidazo[1,5-a]pyrazin-1-yl)-N-(4-cyclopropylpyridin-2-yl)benzamide;

(R)-4-(8-amino-3-(1-propionylpiperidin-3-yl)imidazo[1,5-a]pyrazin-1-yl)-N-(6-methyl-4,5,6,7-tetrahydrobenzo[d]thiazol-2-yl)benzamide;

(R)-4-(8-amino-3-(1-(1-(methoxymethyl)cyclobutanecarbonyl)piperidin-3-yl)imidazo[1,5-a]pyrazin-1-yl)-N-(4-(trifluoromethyl)pyridin-2-yl)benzamide;

(R)-4-(8-amino-3-(1-(3-methyloxetane-3-carbonyl)piperidin-3-yl)imidazo[1,5-a]pyrazin-1-yl)-N-(4-(trifluoromethyl)pyridin-2-yl)benzamide;

(R)-4-(8-amino-3-(1-(3-(2-methoxyethoxy)propanoyl)piperidin-3-yl)imidazo[1,5-a]pyrazin-1-yl)-N-(4-(trifluoromethyl)pyridin-2-yl)benzamide;

(R)-4-(8-amino-3-(1-(3-(methylthio)propanoyl)piperidin-3-yl)imidazo[1,5-a]pyrazin-1-yl)-N-(4-(trifluoromethyl)pyridin-2-yl)benzamide;

(R)-4-(8-amino-3-(1-(1-methylcyclobutanecarbonyl)piperidin-3-yl)imidazo[1,5-a]pyrazin-1-yl)-N-(4-(trifluoromethyl)pyridin-2-yl)benzamide;

(R)-4-(8-amino-3-(1-(3-hydroxy-3-methylbutanoyl)piperidin-3-yl)imidazo[1,5-a]pyrazin-1-yl)-N-(4-(trifluoromethyl)pyridin-2-yl)benzamide;

(R)-4-(8-amino-3-(1-(2,2,2-trifluoroacetyl)piperidin-3-yl)imidazo[1,5-a]pyrazin-1-yl)-N-(4-(trifluoromethyl)pyridin-2-yl)benzamide;

(R)-4-(8-amino-3-(1-(1-(methylsulfonyl)azetidine-3-carbonyl)piperidin-3-yl)imidazo[1,5-a]pyrazin-1-yl)-N-(4-(trifluoromethyl)pyridin-2-yl)benzamide;

(R)-4-(8-amino-3-(1-(3,5-dimethylisoxazole-4-carbonyl)piperidin-3-yl)imidazo[1,5-a]pyrazin-1-yl)-N-(4-(trifluoromethyl)pyridin-2-yl)benzamide;

(R)-4-(8-amino-3-(1-(cyclopropylsulfonyl)piperidin-3-yl)imidazo[1,5-a]pyrazin-1-yl)-N-(4-(trifluoromethyl)pyridin-2-yl)benzamide;

(R)-4-(8-amino-3-(1-pivaloylpiperidin-3-yl)imidazo[1,5-a]pyrazin-1-yl)-N-(4-(trifluoromethyl)pyridin-2-yl)benzamide;

(R)-4-(8-amino-3-(1-(3-(methylsulfonyl)propanoyl)piperidin-3-yl)imidazo[1,5-a]pyrazin-1-yl)-N-(4-(trifluoromethyl)pyridin-2-yl)benzamide;

(R)-4-(8-amino-3-(1-(3-hydroxy-2,2-dimethylpropanoyl)piperidin-3-yl)imidazo[1,5-a]pyrazin-1-yl)-N-(4-(trifluoromethyl)pyridin-2-yl)benzamide;

(R)-4-(8-amino-3-(1-(1-(dimethylamino)cyclobutanecarbonyl)piperidin-3-yl)imidazo[1,5-a]pyrazin-1-yl)-N-(4-(trifluoromethyl)pyridin-2-yl)benzamide;

(R)-4-(3-(1-2,5,8,11,14,17,20,23-octaoxahexacosanepiperidin-3-yl)-8-aminoimidazo[1,5-a]pyrazin-1-yl)-N-(4-(trifluoromethyl)pyridin-2-yl)benzamide;

(R)-4-(8-amino-3-(1-(1-hydroxycyclobutanecarbonyl)piperidin-3-yl)imidazo[1,5-a]pyrazin-1-yl)-N-(4-(trifluoromethyl)pyridin-2-yl)benzamide;

4-(8-amino-3-((R)-1-((1S,2S)-2-(3-methyl-1,2,4-oxadiazol-5-yl)cyclopropanecarbonyl)piperidin-3-yl)imidazo[1,5-a]pyrazin-1-yl)-N-(4-(trifluoromethyl)pyridin-2-yl)benzamide;

(R)-4-(8-amino-3-((R)-1-(3,3-difluorocyclobutanecarbonyl)piperidin-3-yl)imidazo[1,5-a]pyrazin-1-yl)-N-(4-(trifluoromethyl)pyridin-2-yl)benzamide;

(R)-4-(8-amino-3-(1-(1-benzoylazetidine-3-carbonyl)piperidin-3-yl)imidazo[1,5-a]pyrazin-1-yl)-N-(4-(trifluoromethyl)pyridin-2-yl)benzamide;

(R)-4-(8-amino-3-(1-(1-amino-3,6,9,12-tetraoxapentadecane)piperidin-3-yl)imidazo[1,5-a]pyrazin-1-yl)-N-(4-(trifluoromethyl)pyridin-2-yl)benzamide;

(R)-4-(8-amino-3-(1-(thietane-3-carbonyl)piperidin-3-yl)imidazo[1,5-a]pyrazin-1-yl)-N-(4-(trifluoromethyl)pyridin-2-yl)benzamide;

4-(8-amino-3-((R)-1-((R)-4-oxoazetidine-2-carbonyl)piperidin-3-yl)imidazo[1,5-a]pyrazin-1-yl)-N-(4-(trifluoromethyl)pyridin-2-yl)benzamide;

(R)-4-(8-amino-3-(1-(1-(dimethylamino)cyclopropanecarbonyl)piperidin-3-yl)imidazo[1,5-a]pyrazin-1-yl)-N-(4-(trifluoromethyl)pyridin-2-yl)benzamide;

(R)-4-(8-amino-3-(1-(3-isopropylcyclobutanecarbonyl)piperidin-3-yl)imidazo[1,5-a]pyrazin-1-yl)-N-(4-(trifluoromethyl)pyridin-2-yl)benzamide;

(R)-4-(8-amino-3-(1-(bicyclo[1.1.1]pentane-1-carbonyl)piperidin-3-yl)imidazo[1,5-a]pyrazin-1-yl)-N-(4-(trifluoromethyl)pyridin-2-yl)benzamide;

(R)-4-(8-amino-3-(1-(3-vinyloxetane-3-carbonyl)piperidin-3-yl)imidazo[1,5-a]pyrazin-1-yl)-N-(4-(trifluoromethyl)pyridin-2-yl)benzamide;

(R)-4-(8-amino-3-(1-(2-cyclopropylacetyl)piperidin-3-yl)imidazo[1,5-a]pyrazin-1-yl)-N-(pyridin-2-yl)benzamide;

(R)-4-(8-amino-3-(1-(2,2-difluorobutanoyl)piperidin-3-yl)imidazo[1,5-a]pyrazin-1-yl)-N-(pyridin-2-yl)benzamide;

(R)-4-(8-amino-3-(1-(1-hydroxycyclopropanecarbonyl)piperidin-3-yl)imidazo[1,5-a]pyrazin-1-yl)-N-(pyridin-2-yl)benzamide;

(R)-4-(8-amino-3-(1-formylpiperidin-3-yl)imidazo[1,5-a]pyrazin-1-yl)-N-(pyridin-2-yl)benzamide;

(R)-4-(8-amino-3-(1-propionylpiperidin-3-yl)imidazo[1,5-a]pyrazin-1-yl)-N-(4-cyanopyridin-2-yl)benzamide;

(R)-4-(8-amino-3-(1-(3-methoxypropanoyl)piperidin-3-yl)imidazo[1,5-a]pyrazin-1-yl)-N-(4-cyanopyridin-2-yl)benzamide;

(R)-4-(8-amino-3-(1-(cyclopropanecarbonyl)piperidin-3-yl)imidazo[1,5-a]pyrazin-1-yl)-N-(4-cyanopyridin-2-yl)benzamide;

(R)-4-(8-amino-3-(1-(3-methyloxetane-3-carbonyl)piperidin-3-yl)imidazo[1,5-a]pyrazin-1-yl)-N-(4-cyanopyridin-2-yl)benzamide;

(R)-4-(8-amino-3-(1-isobutyrylpiperidin-3-yl)imidazo[1,5-a]pyrazin-1-yl)-N-(4-cyanopyridin-2-yl)benzamide;

(R)-3-(8-amino-1-(4-(4-cyanopyridin-2-ylcarbamoyl)phenyl)imidazo[1,5-a]pyrazin-3-yl)-N-ethylpiperidine-1-carboxamide;

(R)-4-(8-amino-3-(1-(3-methoxypropanoyl)piperidin-3-yl)imidazo[1,5-a]pyrazin-1-yl)-N-(4-(trifluoromethyl)pyridin-2-yl)benzamide;

(R)-4-(8-amino-3-(1-(cyclopropanecarbonyl)piperidin-3-yl)imidazo[1,5-a]pyrazin-1-yl)-N-(4-(trifluoromethyl)pyridin-2-yl)benzamide;

(R)-4-(8-amino-3-(1-isobutyrylpiperidin-3-yl)imidazo[1,5-a]pyrazin-1-yl)-N-(4-(trifluoromethyl)pyridin-2-yl)benzamide;

(R)-4-(8-amino-3-(1-(3-hydroxy-2-(hydroxymethyl)-2-methylpropanoyl)piperidin-3-yl)imidazo[1,5-a]pyrazin-1-yl)-N-(4-(trifluoromethyl)pyridin-2-yl)benzamide;

(R)-4-(8-amino-3-(piperidin-3-yl)imidazo[1,5-a]pyrazin-1-yl)-N-(4-(trifluoromethyl)pyridin-2-yl)benzamide;

(R)-benzyl 3-(8-amino-1-(4-(4-(trifluoromethyl)pyridin-2-ylcarbamoyl)phenyl)imidazo[1,5-a]pyrazin-3-yl)piperidine-1-carboxylate;

(R)-4-(8-amino-3-(1-(2-cyano-2-methylpropanoyl)piperidin-3-yl)imidazo[1,5-a]pyrazin-1-yl)-N-(pyridin-2-yl)benzamide;

(R)-4-(8-amino-3-(1-(3,3-difluorocyclobutanecarbonyl)piperidin-3-yl)imidazo[1,5-a]pyrazin-1-yl)-N-(4-cyclopropylpyridin-2-yl)benzamide;

(R)-4-(8-amino-3-(1-(2-(2-oxooxazolidin-3-yl)acetyl)piperidin-3-yl)imidazo[1,5-a]pyrazin-1-yl)-N-(4-cyclopropylpyridin-2-yl)benzamide;

(R)-4-(8-amino-3-(1-(2-(dimethylamino)-2-oxoacetyl)piperidin-3-yl)imidazo[1,5-a]pyrazin-1-yl)-N-(4-cyclopropylpyridin-2-yl)benzamide;

(R)-4-(8-amino-3-(1-(2-(isobutylamino)-2-oxoacetyl)piperidin-3-yl)imidazo[1,5-a]pyrazin-1-yl)-N-(4-cyclopropylpyridin-2-yl)benzamide;

(R)-4-(8-amino-3-(1-(2-(3,4-dimethylphenylamino)-2-oxoacetyl)piperidin-3-yl)imidazo[1,5-a]pyrazin-1-yl)-N-(4-cyclopropylpyridin-2-yl)benzamide;

(R)-4-(8-amino-3-(1-(2-oxobutanoyl)piperidin-3-yl)imidazo[1,5-a]pyrazin-1-yl)-N-(4-cyclopropylpyridin-2-yl)benzamide;

(R)-4-(8-amino-3-(1-(3,3,3-trifluoro-2-oxopropanoyl)piperidin-3-yl)imidazo[1,5-a]pyrazin-1-yl)-N-(4-cyclopropylpyridin-2-yl)benzamide;

(R)-4-(8-amino-3-(1-(5-methyl-1,3,4-oxadiazole-2-carbonyl)piperidin-3-yl)imidazo[1,5-a]pyrazin-1-yl)-N-(4-cyclopropylpyridin-2-yl)benzamide;

(R)-4-(8-amino-3-(1-(6-cyanonicotinoyl)piperidin-3-yl)imidazo[1,5-a]pyrazin-1-yl)-N-(4-cyclopropylpyridin-2-yl)benzamide;

(R)-4-(8-amino-3-(1-(4-cyanothiophene-2-carbonyl)piperidin-3-yl)imidazo[1,5-a]pyrazin-1-yl)-N-(4-cyclopropylpyridin-2-yl)benzamide;

(R)-4-(8-amino-3-(1-(pyrrolidine-1-carbonyl)piperidin-3-yl)imidazo[1,5-a]pyrazin-1-yl)-N-(4-cyclopropylpyridin-2-yl)benzamide;

(R)-3-(8-amino-1-(4-(4-cyclopropylpyridin-2-ylcarbamoyl)phenyl)imidazo[1,5-a]pyrazin-3-yl)-N-(2-chlorophenyl)piperidine-1-carboxamide;

(R)-4-(8-amino-3-(1-(adamantyl-1-carbonyl)piperidin-3-yl)imidazo[1,5-a]pyrazin-1-yl)-N-(4-cyclopropylpyridin-2-yl)benzamide;

(R)-phenyl 3-(8-amino-1-(4-(4-cyclopropylpyridin-2-ylcarbamoyl)phenyl)imidazo[1,5-a]pyrazin-3-yl)piperidine-1-carboxylate;

(R)-4-(8-amino-3-(1-(2-(furan-2-yl)-2-oxoacetyl)piperidin-3-yl)imidazo[1,5-a]pyrazin-1-yl)-N-(4-cyclopropylpyridin-2-yl)benzamide;

(R)-4-(8-amino-3-(1-(4-(dimethylamino)butanoyl)pyrrolidin-3-yl)imidazo[1,5-a]pyrazin-1-yl)-N-(pyridin-2-yl)benzamide;

(R)-4-(8-amino-3-(1-(3-methoxypropanoyl)pyrrolidin-3-yl)imidazo[1,5-a]pyrazin-1-yl)-N-(pyridin-2-yl)benzamide;

(R)-4-(8-amino-3-(1-(3-methyloxetane-3-carbonyl)pyrrolidin-3-yl)imidazo[1,5-a]pyrazin-1-yl)-N-(pyridin-2-yl)benzamide;

(R)-4-(8-amino-3-(1-isobutyrylpyrrolidin-3-yl)imidazo[1,5-a]pyrazin-1-yl)-N-(pyridin-2-yl)benzamide;
(R)-4-(8-amino-3-(1-(tetrahydrofuran-3-carbonyl)pyrrolidin-3-yl)imidazo[1,5-a]pyrazin-1-yl)-N-(pyridin-2-yl)benzamide;
4-(8-amino-3-(1-isobutyrylpiperidin-4-yl)imidazo[1,5-a]pyrazin-1-yl)-N-(pyridin-2-yl)benzamide
4-(8-amino-3-(1-propionamidopropan-2-yl)imidazo[1,5-a]pyrazin-1-yl)-N-(4-(trifluoromethyl)pyridin-2-yl)benzamide;
N-(2-(8-amino-1-(4-(4-(trifluoromethyl)pyridin-2-ylcarbamoyl)phenyl)imidazo[1,5-a]pyrazin-3-yl)propyl)-3-methyloxetane-3-carboxamide;
benzyl 2-(8-amino-1-(4-(4-(trifluoromethyl)pyridin-2-ylcarbamoyl)phenyl)imidazo[1,5-a]pyrazin-3-yl)propylcarbamate;
(R)-4-(8-amino-3-(1-benzylpiperidin-3-yl)imidazo[1,5-a]pyrazin-1-yl)-N-(pyridin-2-yl)benzamide
(R)-4-(8-amino-3-(1-phenethylpiperidin-3-yl)imidazo[1,5-a]pyrazin-1-yl)-N-(pyridin-2-yl)benzamide;
(R)-4-(8-amino-3-(1-((1-methyl-1H-pyrazol-4-yl)methyl)piperidin-3-yl)imidazo[1,5-a]pyrazin-1-yl)-N-(pyridin-2-yl)benzamide;
(R)-4-(8-amino-3-(1-(3,3,3-trifluoropropyl)piperidin-3-yl)imidazo[1,5-a]pyrazin-1-yl)-N-(pyridin-2-yl)benzamide;
ethyl 2-(((R)-3-(8-amino-1-(4-(pyridin-2-ylcarbamoyl)phenyl)imidazo[1,5-a]pyrazin-3-yl)piperidin-1-yl)methyl)cyclopropanecarboxylate;
(R)-4-(8-amino-3-(1-ethylpiperidin-3-yl)imidazo[1,5-a]pyrazin-1-yl)-N-(4-(trifluoromethyl)pyridin-2-yl)benzamide;
4-(8-amino-3-((3R)-1-(2,3-dihydroxypropyl)piperidin-3-yl)imidazo[1,5-a]pyrazin-1-yl)-N-(4-(trifluoromethyl)pyridin-2-yl)benzamide;
(R)-4-(8-amino-3-(1-(cyclopropylmethyl)piperidin-3-yl)imidazo[1,5-a]pyrazin-1-yl)-N-(4-(trifluoromethyl)pyridin-2-yl)benzamide;
(R)-4-(8-amino-3-(1-(pyridin-4-ylmethyl)piperidin-3-yl)imidazo[1,5-a]pyrazin-1-yl)-N-(4-(trifluoromethyl)pyridin-2-yl)benzamide;
4-(8-amino-3-((3R)-1-((tetrahydrofuran-3-yl)methyl)piperidin-3-yl)imidazo[1,5-a]pyrazin-1-yl)-N-(4-(trifluoromethyl)pyridin-2-yl)benzamide;
(R)-4-(8-amino-3-(1-(cyclopentylmethyl)piperidin-3-yl)imidazo[1,5-a]pyrazin-1-yl)-N-(4-cyclopropylpyridin-2-yl)benzamide;
(R)-4-(3-(1-((1H-pyrrol-2-yl)methyl)piperidin-3-yl)-8-aminoimidazo[1,5-a]pyrazin-1-yl)-N-(4-cyclopropylpyridin-2-yl)benzamide;
4-(8-amino-3-((3R)-1-((tetrahydrofuran-3-yl)methyl)piperidin-3-yl)imidazo[1,5-a]pyrazin-1-yl)-N-(4-cyclopropylpyridin-2-yl)benzamide;
4-(8-amino-3-(7-(tetrahydrofuran-2-carbonyl)-7-azabicyclo[2.2.1]heptan-2-yl)imidazo[1,5-a]pyrazin-1-yl)-N-(pyridin-2-yl)benzamide;
4-(8-amino-3-(7-propionyl-7-azabicyclo[2.2.1]heptan-2-yl)imidazo[1,5-a]pyrazin-1-yl)-N-(pyridin-2-yl)benzamide;
4-(8-amino-3-(7-(3-methoxypropanoyl)-7-azabicyclo[2.2.1]heptan-2-yl)imidazo[1,5-a]pyrazin-1-yl)-N-(pyridin-2-yl)benzamide;
benzyl 2-(8-amino-1-(4-(pyridin-2-ylcarbamoyl)phenyl)imidazo[1,5-a]pyrazin-3-yl)-7-azabicyclo[2.2.1]heptane-7-carboxylate;
4-(8-amino-3-(6-isobutyryl-6-azaspiro[2.5]octan-1-yl)imidazo[1,5-a]pyrazin-1-yl)-N-(pyridin-2-yl)benzamide;
4-(8-amino-3-(6-(3-methoxypropanoyl)-6-azaspiro[2.5]octan-1-yl)imidazo[1,5-a]pyrazin-1-yl)-N-(pyridin-2-yl)benzamide;
4-(8-amino-3-(6-(2-hydroxyacetyl)-6-azaspiro[2.5]octan-1-yl)imidazo[1,5-a]pyrazin-1-yl)-N-(pyridin-2-yl)benzamide;
4-(8-amino-3-(6-propionyl-6-azaspiro[2.5]octan-1-yl)imidazo[1,5-a]pyrazin-1-yl)-N-(pyridin-2-yl)benzamide;
benzyl (cis)-3-(8-amino-1-(4-(4-(trifluoromethyl)pyridin-2-ylcarbamoyl)phenyl)imidazo[1,5-a]pyrazin-3-yl)cyclohexylcarbamate;
4-(8-amino-3-((cis)-3-(3-ethylureido)cyclohexyl)imidazo[1,5-a]pyrazin-1-yl)-N-(4-(trifluoromethyl)pyridin-2-yl)benzamide;
4-(8-amino-3-((cis)-3-(cyclopropanecarboxamido)cyclohexyl)imidazo[1,5-a]pyrazin-1-yl)-N-(4-(trifluoromethyl)pyridin-2-yl)benzamide;
4-(8-amino-3-((cis)-3-aminocyclohexyl)imidazo[1,5-a]pyrazin-1-yl)-N-(4-(trifluoromethyl)pyridin-2-yl)benzamide;
4-(8-amino-3-((cis)-3-(3-methoxypropanamido)cyclohexyl)imidazo[1,5-a]pyrazin-1-yl)-N-(4-(trifluoromethyl)pyridin-2-yl)benzamide;
4-(8-amino-3-((cis)-3-isobutyramidocyclohexyl)imidazo[1,5-a]pyrazin-1-yl)-N-(4-(trifluoromethyl)pyridin-2-yl)benzamide;
N-((cis)-3-(8-amino-1-(4-(4-(trifluoromethyl)pyridin-2-ylcarbamoyl)phenyl)imidazo[1,5-a]pyrazin-3-yl)cyclohexyl)-3-methyloxetane-3-carboxamide;
4-(8-amino-3-((cis)-3-propionamidocyclohexyl)imidazo[1,5-a]pyrazin-1-yl)-N-(4-(trifluoromethyl)pyridin-2-yl)benzamide;
4-(8-amino-3-((trans)-3-(2-cyano-2-methylpropanamido)cyclohexyl)imidazo[1,5-a]pyrazin-1-yl)-N-(4-(trifluoromethyl)pyridin-2-yl)benzamide;
4-(8-amino-3-((trans)-3-(2-fluoro-2-methylpropanamido)cyclohexyl)imidazo[1,5-a]pyrazin-1-yl)-N-(4-(trifluoromethyl)pyridin-2-yl)benzamide;
4-(8-amino-3-((trans)-3-(cyclopropanecarboxamido)cyclohexyl)imidazo[1,5-a]pyrazin-1-yl)-N-(4-(trifluoromethyl)pyridin-2-yl)benzamide;
4-(8-amino-3-((trans)-3-aminocyclohexyl)imidazo[1,5-a]pyrazin-1-yl)-N-(4-(trifluoromethyl)pyridin-2-yl)benzamide;
4-(8-amino-3-((trans)-3-(3-methoxypropanamido)cyclohexyl)imidazo[1,5-a]pyrazin-1-yl)-N-(4-(trifluoromethyl)pyridin-2-yl)benzamide;
4-(8-amino-3-((trans)-3-isobutyramidocyclohexyl)imidazo[1,5-a]pyrazin-1-yl)-N-(4-(trifluoromethyl)pyridin-2-yl)benzamide;
N-((trans)-3-(8-amino-1-(4-(4-(trifluoromethyl)pyridin-2-ylcarbamoyl)phenyl)imidazo[1,5-a]pyrazin-3-yl)cyclohexyl)-3-methyloxetane-3-carboxamide;
N-((trans)-3-(8-amino-1-(4-(4-(trifluoromethyl)pyridin-2-ylcarbamoyl)phenyl)imidazo[1,5-a]pyrazin-3-yl)cyclohexyl)tetrahydrofuran-2-carboxamide;
4-(8-amino-3-((trans)-3-propionamidocyclohexyl)imidazo[1,5-a]pyrazin-1-yl)-N-(4-(trifluoromethyl)pyridin-2-yl)benzamide;
4-(8-amino-3-((trans)-3-(cyclobutanecarboxamido)cyclohexyl)imidazo[1,5-a]pyrazin-1-yl)-N-(4-(trifluoromethyl)pyridin-2-yl)benzamide;
4-(8-amino-3-(4-propionylthiomorpholin-2-yl)imidazo[1,5-a]pyrazin-1-yl)-N-(4-(trifluoromethyl)pyridin-2-yl)benzamide;

4-(8-amino-3-(4-isobutyrylmorpholin-2-yl)imidazo[1,5-a]pyrazin-1-yl)-N-(4-(trifluoromethyl)pyridin-2-yl)benzamide;
4-(8-amino-3-(4-(2-fluoro-2-methylpropanoyl)morpholin-2-yl)imidazo[1,5-a]pyrazin-1-yl)-N-(4-(trifluoromethyl)pyridin-2-yl)benzamide;
4-(8-amino-3-(4-(3-methoxypropanoyl)morpholin-2-yl)imidazo[1,5-a]pyrazin-1-yl)-N-(4-(trifluoromethyl)pyridin-2-yl)benzamide;
4-(8-amino-3-(4-(cyclopropanecarbonyl)morpholin-2-yl)imidazo[1,5-a]pyrazin-1-yl)-N-(4-(trifluoromethyl)pyridin-2-yl)benzamide;
4-(8-amino-3-(4-(3-methyloxetane-3-carbonyl)morpholin-2-yl)imidazo[1,5-a]pyrazin-1-yl)-N-(4-(trifluoromethyl)pyridin-2-yl)benzamide;
2-(8-amino-1-(4-(4-(trifluoromethyl)pyridin-2-ylcarbamoyl)phenyl)imidazo[1,5-a]pyrazin-3-yl)-N-ethylmorpholine-4-carboxamide;
4-(8-amino-3-((cis)-5-hydroxy-1-(3-methyloxetane-3-carbonyl)piperidin-3-yl)imidazo[1,5-a]pyrazin-1-yl)-N-(4-(trifluoromethyl)pyridin-2-yl)benzamide;
4-(8-amino-3-((cis)-1-(cyclopropanecarbonyl)-5-hydroxypiperidin-3-yl)imidazo[1,5-a]pyrazin-1-yl)-N-(4-(trifluoromethyl)pyridin-2-yl)benzamide;
4-(8-amino-3-((cis)-5-hydroxy-1-(3-methoxypropanoyl)piperidin-3-yl)imidazo[1,5-a]pyrazin-1-yl)-N-(4-(trifluoromethyl)pyridin-2-yl)benzamide;
(trans)-ethyl 5-(8-amino-1-(4-(4-(trifluoromethyl)pyridin-2-ylcarbamoyl)phenyl)imidazo[1,5-a]pyrazin-3-yl)-2-methylpiperidine-1-carboxylate;
4-(8-amino-3-((cis)-1-(3-methoxypropanoyl)-6-methylpiperidin-3-yl)imidazo[1,5-a]pyrazin-1-yl)-N-(4-cyclopropylpyridin-2-yl)benzamide;
4-(8-amino-3-((cis)-6-methyl-1-(piperidine-1-carbonyl)piperidin-3-yl)imidazo[1,5-a]pyrazin-1-yl)-N-(4-cyclopropylpyridin-2-yl)benzamide;
4-(8-amino-3-((trans)-6-methyl-1-(tetrahydrofuran-2-carbonyl)piperidin-3-yl)imidazo[1,5-a]pyrazin-1-yl)-N-(4-(trifluoromethyl)pyridin-2-yl)benzamide;
(trans)-5-(8-amino-1-(4-(4-(trifluoromethyl)pyridin-2-ylcarbamoyl)phenyl)imidazo[1,5-a]pyrazin-3-yl)-N-ethyl-2-methylpiperidine-1-carboxamide;
4-(8-amino-3-((trans)-6-methyl-1-(3-(methylthio)propanoyl)piperidin-3-yl)imidazo[1,5-a]pyrazin-1-yl)-N-(4-(trifluoromethyl)pyridin-2-yl)benzamide;
4-(8-amino-3-((trans)-1-(cyclopropanecarbonyl)-6-methylpiperidin-3-yl)imidazo[1,5-a]pyrazin-1-yl)-N-(4-(trifluoromethyl)pyridin-2-yl)benzamide;
4-(8-amino-3-((cis)-1-(3-ethoxypropanoyl)-6-methylpiperidin-3-yl)imidazo[1,5-a]pyrazin-1-yl)-N-(4-(trifluoromethyl)pyridin-2-yl)benzamide;
4-(8-amino-3-((cis)-1-(2,2-difluorocyclobutanecarbonyl)-6-methylpiperidin-3-yl)imidazo[1,5-a]pyrazin-1-yl)-N-(4-(trifluoromethyl)pyridin-2-yl)benzamide;
4-(8-amino-3-((cis)-1-(2-cyclopropylacetyl)-6-methylpiperidin-3-yl)imidazo[1,5-a]pyrazin-1-yl)-N-(pyridin-2-yl)benzamide;
4-(8-amino-3-((cis)-1-(cyclopropanecarbonyl)-6-methylpiperidin-3-yl)imidazo[1,5-a]pyrazin-1-yl)-N-(pyridin-2-yl)benzamide;
(cis)-5-(8-amino-1-(4-(pyridin-2-ylcarbamoyl)phenyl)imidazo[1,5-a]pyrazin-3-yl)-N-ethyl-2-methylpiperidine-1-carboxamide;
4-(8-amino-3-((cis)-6-methyl-1-(tetrahydrofuran-2-carbonyl)piperidin-3-yl)imidazo[1,5-a]pyrazin-1-yl)-N-(4-(trifluoromethyl)pyridin-2-yl)benzamide;
4-(8-amino-3-((cis)-6-methyl-1-(3-(methylthio)propanoyl)piperidin-3-yl)imidazo[1,5-a]pyrazin-1-yl)-N-(4-(trifluoromethyl)pyridin-2-yl)benzamide;
4-(8-amino-3-((cis)-6-methyl-1-(2-(2-oxooxazolidin-3-yl)acetyl)piperidin-3-yl)imidazo[1,5-a]pyrazin-1-yl)-N-(4-cyclopropylpyridin-2-yl)benzamide;
4-(8-amino-3-((cis)-1-(cyclobutanecarbonyl)-6-methylpiperidin-3-yl)imidazo[1,5-a]pyrazin-1-yl)-N-(4-cyclopropylpyridin-2-yl)benzamide;
4-(8-amino-3-((cis)-6-methyl-1-(3-(methylthio)propanoyl)piperidin-3-yl)imidazo[1,5-a]pyrazin-1-yl)-N-(4-cyclopropylpyridin-2-yl)benzamide;
(cis)-ethyl 5-(8-amino-1-(4-(4-cyclopropylpyridin-2-ylcarbamoyl)phenyl)imidazo[1,5-a]pyrazin-3-yl)-2-methylpiperidine-1-carboxylate;
4-(8-amino-3-((cis)-6-methyl-1-(2-oxobutanoyl)piperidin-3-yl)imidazo[1,5-a]pyrazin-1-yl)-N-(4-(trifluoromethyl)pyridin-2-yl)benzamide;
(cis)-5-(8-amino-1-(4-(4-(trifluoromethyl)pyridin-2-ylcarbamoyl)phenyl)imidazo[1,5-a]pyrazin-3-yl)-N-ethyl-2-methylpiperidine-1-carboxamide;
4-(8-amino-3-((cis)-1-(cyclopropanecarbonyl)-6-methylpiperidin-3-yl)imidazo[1,5-a]pyrazin-1-yl)-N-(4-(trifluoromethyl)pyridin-2-yl)benzamide;
4-(8-amino-3-((cis)-1-(3,3-difluorocyclobutanecarbonyl)-6-methylpiperidin-3-yl)imidazo[1,5-a]pyrazin-1-yl)-N-(pyridin-2-yl)benzamide;
4-(8-amino-3-((cis)-1-(cyclobutanecarbonyl)-6-methylpiperidin-3-yl)imidazo[1,5-a]pyrazin-1-yl)-N-(pyridin-2-yl)benzamide;
4-(8-amino-3-((cis)-1-isobutyryl-6-methylpiperidin-3-yl)imidazo[1,5-a]pyrazin-1-yl)-N-(pyridin-2-yl)benzamide;
4-(8-amino-3-((cis)-1-(3-ethoxypropanoyl)-6-methylpiperidin-3-yl)imidazo[1,5-a]pyrazin-1-yl)-N-(pyridin-2-yl)benzamide;
4-(8-amino-3-((cis)-6-methyl-1-propionylpiperidin-3-yl)imidazo[1,5-a]pyrazin-1-yl)-N-(pyridin-2-yl)benzamide;
4-(8-amino-3-(azetidin-1-yl)imidazo[1,5-a]pyrazin-1-yl)-N-(4-propylpyridin-2-yl)benzamide;
4-(8-amino-3-(azetidin-1-yl)imidazo[1,5-a]pyrazin-1-yl)-N-(4-cyanopyridin-2-yl)benzamide;
4-(8-amino-3-(azetidin-1-yl)imidazo[1,5-a]pyrazin-1-yl)-N-(4-(trifluoromethyl)pyridin-2-yl)benzamide;
4-(8-amino-3-morpholinoimidazo[1,5-a]pyrazin-1-yl)-N-(4-(trifluoromethyl)pyridin-2-yl)benzamide;
4-(8-amino-3-morpholinoimidazo[1,5-a]pyrazin-1-yl)-N-(4-propylpyridin-2-yl)benzamide;
4-(8-amino-3-(diethylamino)imidazo[1,5-a]pyrazin-1-yl)-N-(pyridin-2-yl)benzamide;
4-(8-amino-3-(diethylamino)imidazo[1,5-a]pyrazin-1-yl)-N-(4-propylpyridin-2-yl)benzamide;
4-(8-amino-3-(diethylamino)imidazo[1,5-a]pyrazin-1-yl)-N-(4-cyanopyridin-2-yl)benzamide;
4-(8-amino-3-(diethylamino)imidazo[1,5-a]pyrazin-1-yl)-N-(4-(trifluoromethyl)pyridin-2-yl)benzamide;
4-(8-amino-3-(3-methoxyazetidin-1-yl)imidazo[1,5-a]pyrazin-1-yl)-N-(pyridin-2-yl)benzamide;
(S)-N-(1-(8-amino-1-(4-(4-(trifluoromethyl)pyridin-2-ylcarbamoyl)phenyl)imidazo[1,5-a]pyrazin-3-yl)piperidin-3-yl)-3-methyloxetane-3-carboxamide;
(R)-4-(8-amino-3-(3-(3-methoxypropanamido)piperidin-1-yl)imidazo[1,5-a]pyrazin-1-yl)-N-(4-(trifluoromethyl)pyridin-2-yl)benzamide;
(R)-4-(8-amino-3-(3-(cyclopropanecarboxamido)piperidin-1-yl)imidazo[1,5-a]pyrazin-1-yl)-N-(4-(trifluoromethyl)pyridin-2-yl)benzamide;

(R)-4-(8-amino-3-(3-(3-ethylureido)piperidin-1-yl)imidazo[1,5-a]pyrazin-1-yl)-N-(4-(trifluoromethyl)pyridin-2-yl)benzamide;

(S)-4-(8-amino-3-(3-(cyclopropanecarboxamido)piperidin-1-yl)imidazo[1,5-a]pyrazin-1-yl)-N-(4-(trifluoromethyl)pyridin-2-yl)benzamide;

(S)-4-(8-amino-3-(3-(cyclobutanecarboxamido)piperidin-1-yl)imidazo[1,5-a]pyrazin-1-yl)-N-(4-(trifluoromethyl)pyridin-2-yl)benzamide;

1-(8-amino-1-(4-(4-(trifluoromethyl)pyridin-2-ylcarbamoyl)phenyl)imidazo[1,5-a]pyrazin-3-yl)-N-isopropylpiperidine-3-carboxamide;

1-(8-amino-1-(4-(pyridin-2-ylcarbamoyl)phenyl)imidazo[1,5-a]pyrazin-3-yl)-N-(cyclopropylmethyl)piperidine-3-carboxamide;

1-(8-amino-1-(4-(4-(trifluoromethyl)pyridin-2-ylcarbamoyl)phenyl)imidazo[1,5-a]pyrazin-3-yl)-N-(3,3-difluorocyclobutyl)piperidine-3-carboxamide;

1-(8-amino-1-(4-(pyridin-2-ylcarbamoyl)phenyl)imidazo[1,5-a]pyrazin-3-yl)-N—(((S)-tetrahydrofuran-2-yl)methyl)piperidine-3-carboxamide;

1-(8-amino-1-(4-(pyridin-2-ylcarbamoyl)phenyl)imidazo[1,5-a]pyrazin-3-yl)-N-tert-butylpiperidine-3-carboxamide;

4-(8-amino-3-(3-(morpholine-4-carbonyl)piperidin-1-yl)imidazo[1,5-a]pyrazin-1-yl)-N-(pyridin-2-yl)benzamide;

1-(8-amino-1-(4-(pyridin-2-ylcarbamoyl)phenyl)imidazo[1,5-a]pyrazin-3-yl)-N,N-diethylpiperidine-3-carboxamide;

1-(8-amino-1-(4-(4-(trifluoromethyl)pyridin-2-ylcarbamoyl)phenyl)imidazo[1,5-a]pyrazin-3-yl)-N—(((S)-tetrahydrofuran-2-yl)methyl)piperidine-3-carboxamide;

1-(8-amino-1-(4-(4-(trifluoromethyl)pyridin-2-ylcarbamoyl)phenyl)imidazo[1,5-a]pyrazin-3-yl)-N-(2-methoxyethyl)piperidine-3-carboxamide;

1-(8-amino-1-(4-(4-(trifluoromethyl)pyridin-2-ylcarbamoyl)phenyl)imidazo[1,5-a]pyrazin-3-yl)-N-(cyclopropylmethyl)piperidine-3-carboxamide;

4-(8-amino-3-(3-(morpholine-4-carbonyl)piperidin-1-yl)imidazo[1,5-a]pyrazin-1-yl)-N-(4-(trifluoromethyl)pyridin-2-yl)benzamide;

1-(8-amino-1-(4-(pyridin-2-ylcarbamoyl)phenyl)imidazo[1,5-a]pyrazin-3-yl)-N-((S)-1-methoxypropan-2-yl)piperidine-3-carboxamide;

1-(8-amino-1-(4-(4-(trifluoromethyl)pyridin-2-ylcarbamoyl)phenyl)imidazo[1,5-a]pyrazin-3-yl)-N-ethylpiperidine-3-carboxamide;

1-(8-amino-1-(4-(4-(trifluoromethyl)pyridin-2-ylcarbamoyl)phenyl)imidazo[1,5-a]pyrazin-3-yl)-N-((S)-tetrahydrofuran-3-yl)piperidine-3-carboxamide;

1-(8-amino-1-(4-(4-(trifluoromethyl)pyridin-2-ylcarbamoyl)phenyl)imidazo[1,5-a]pyrazin-3-yl)-N-((R)-tetrahydrofuran-3-yl piperidine-3-carboxamide;

1-(8-amino-1-(4-(4-(trifluoromethyl)pyridin-2-ylcarbamoyl)phenyl)imidazo[1,5-a]pyrazin-3-yl)-N-(2-(methylthio)ethyl)piperidine-3-carboxamide;

1-(8-amino-1-(4-(4-(trifluoromethyl)pyridin-2-ylcarbamoyl)phenyl)imidazo[1,5-a]pyrazin-3-yl)-N-(2-(methylsulfonyl)ethyl)piperidine-3-carboxamide;

1-(8-amino-1-(4-(4-cyclopropylpyridin-2-ylcarbamoyl)phenyl)imidazo[1,5-a]pyrazin-3-yl)-N-((S)-1-methoxypropan-2-yl)piperidine-3-carboxamide;

1-(8-amino-1-(4-(4-(trifluoromethyl)pyridin-2-ylcarbamoyl)phenyl)imidazo[1,5-a]pyrazin-3-yl)-N-methoxypiperidine-3-carboxamide;

4-(8-amino-3-(3-(3,3-difluoropiperidine-1-carbonyl)piperidin-1-yl)imidazo[1,5-a]pyrazin-1-yl)-N-(4-(trifluoromethyl)pyridin-2-yl)benzamide;

1-(8-amino-1-(4-(4-cyclopropylpyridin-2-ylcarbamoyl)phenyl)imidazo[1,5-a]pyrazin-3-yl)-N-methoxypiperidine-3-carboxamide;

1-(8-amino-1-(4-(4-cyclopropylpyridin-2-ylcarbamoyl)phenyl)imidazo[1,5-a]pyrazin-3-yl)-N-(cyclopropylmethyl)piperidine-3-carboxamide;

1-(8-amino-1-(4-(4-cyclopropylpyridin-2-ylcarbamoyl)phenyl)imidazo[1,5-a]pyrazin-3-yl)-N,N-diethylpiperidine-3-carboxamide;

4-(8-amino-3-(3-(pyrrolidine-1-carbonyl)piperidin-1-yl)imidazo[1,5-a]pyrazin-1-yl)-N-(4-cyclopropylpyridin-2-yl)benzamide;

4-(8-amino-3-(3-cyclopropyl-4,5,6,7-tetrahydro-1H-indazol-5-yl)imidazo[1,5-a]pyrazin-1-yl)-N-(4-(trifluoromethyl)pyridin-2-yl)benzamide;

4-(8-amino-3-(3-cyclopropyl-4,5,6,7-tetrahydro-1H-indazol-5-yl)imidazo[1,5-a]pyrazin-1-yl)-N-(4-cyanopyridin-2-yl)benzamide;

4-(8-amino-3-(3-(methoxymethyl)-4,5,6,7-tetrahydro-1H-indazol-5-yl)imidazo[1,5-a]pyrazin-1-yl)-N-(4-(trifluoromethyl)pyridin-2-yl)benzamide;

ethyl 3-(4-amino-5-(4-(4-(trifluoromethyl)pyridin-2-ylcarbamoyl)phenyl)pyrrolo[1,2-f][1,2,4]triazin-7-yl)piperidine-1-carboxylate;

3-(4-amino-5-(4-(4-(trifluoromethyl)pyridin-2-ylcarbamoyl)phenyl)pyrrolo[1,2-f][1,2,4]triazin-7-yl)-N-ethylpiperidine-1-carboxamide;

4-(4-amino-7-(1-(3-methyloxetane-3-carbonyl)piperidin-3-yl)pyrrolo[1,2-f][1,2,4]triazin-5-yl)-N-(4-(trifluoromethyl)pyridin-2-yl)benzamide;

(R)-4-(4-amino-7-(1-(1-methylcyclobutanecarbonyl)piperidin-3-yl)imidazo[1,5-f][1,2,4]triazin-5-yl)-N-(4-(trifluoromethyl)pyridin-2-yl)benzamide;

(R)-ethyl 3-(4-amino-5-(4-(4-(trifluoromethyl)pyridin-2-ylcarbamoyl)phenyl)imidazo[1,5-f][1,2,4]triazin-7-yl)piperidine-1-carboxylate;

(R)-3-(4-amino-5-(4-(4-(trifluoromethyl)pyridin-2-ylcarbamoyl)phenyl)imidazo[1,5-f][1,2,4]triazin-7-yl)-N-ethylpiperidine-1-carboxamide;

(R)-4-(4-amino-7-(1-(2-fluoro-2-methylpropanoyl)piperidin-3-yl)imidazo[1,5-f][1,2,4]triazin-5-yl)-N-(4-(trifluoromethyl)pyridin-2-yl)benzamide;

(R)-4-(4-amino-7-(piperidin-3-yl)imidazo[1,5-f][1,2,4]triazin-5-yl)-N-(4-(trifluoromethyl)pyridin-2-yl)benzamide;

(R)-4-(4-amino-7-(1-(3-ethoxypropanoyl)piperidin-3-yl)imidazo[1,5-f][1,2,4]triazin-5-yl)-N-(4-(trifluoromethyl)pyridin-2-yl)benzamide;

(R)-4-(4-amino-7-(1-(3,3-difluorocyclobutanecarbonyl)piperidin-3-yl)imidazo[1,5-f][1,2,4]triazin-5-yl)-N-(4-(trifluoromethyl)pyridin-2-yl)benzamide;

(R)-4-(4-amino-7-(1-(3-methyloxetane-3-carbonyl)piperidin-3-yl)imidazo[1,5-f][1,2,4]triazin-5-yl)-N-(4-(trifluoromethyl)pyridin-2-yl)benzamide;

4-(4-amino-1-((R)-1-((R)-tetrahydrofuran-2-carbonyl)piperidin-3-yl)-1H-pyrazolo[3,4-d]pyrimidin-3-yl)-N-(4-(trifluoromethyl)pyridin-2-yl)benzamide;

(R)-4-(4-amino-1-(1-(2-cyano-2-methylpropanoyl)piperidin-3-yl)-1H-pyrazolo[3,4-d]pyrimidin-3-yl)-N-(4-(trifluoromethyl)pyridin-2-yl)benzamide;

(R)-4-(1-(1-2,5,8,11-tetraoxatetradecanepiperidin-3-yl)-4-amino-1H-pyrazolo[3,4-d]pyrimidin-3-yl)-N-(4-(trifluoromethyl)pyridin-2-yl)benzamide;

(R)-4-(4-amino-1-(1-(2,2,2-trichloroacetyl)piperidin-3-yl)-1H-pyrazolo[3,4-d]pyrimidin-3-yl)-N-(4-(trifluoromethyl)pyridin-2-yl)benzamide;

(R)-4-(4-amino-1-(1-(1-methylcyclobutanecarbonyl)piperidin-3-yl)-1H-pyrazolo[3,4-d]pyrimidin-3-yl)-N-(4-(trifluoromethyl)pyridin-2-yl)benzamide;
(R)-4-(4-amino-1-(1-(3-methyloxetane-3-carbonyl)piperidin-3-yl)-1H-pyrazolo[3,4-d]pyrimidin-3-yl)-N-(4-(trifluoromethyl)pyridin-2-yl)benzamide;
(R)-3-(4-amino-3-(4-(4-(trifluoromethyl)pyridin-2-ylcarbamoyl)phenyl)-1H-pyrazolo[3,4-d]pyrimidin-1-yl)-N-ethylpiperidine-1-carboxamide;
(R)-4-(4-amino-1-(1-(cyclopropanecarbonyl)piperidin-3-yl)-1H-pyrazolo[3,4-d]pyrimidin-3-yl)-N-(4-(trifluoromethyl)pyridin-2-yl)benzamide;
(R)-4-(4-amino-1-(1-(2-fluoro-2-methylpropanoyl)piperidin-3-yl)-1H-pyrazolo[3,4-d]pyrimidin-3-yl)-N-(4-(trifluoromethyl)pyridin-2-yl)benzamide;
(R)-4-(4-amino-1-(1-propionylpiperidin-3-yl)-1H-pyrazolo[3,4-d]pyrimidin-3-yl)-N-(4-(trifluoromethyl)pyridin-2-yl)benzamide;
(R)-4-(4-amino-1-(1-(1-(methoxymethyl)cyclobutanecarbonyl)piperidin-3-yl)-1H-pyrazolo[3,4-d]pyrimidin-3-yl)-N-(4-(trifluoromethyl)pyridin-2-yl)benzamide;
(R)-ethyl 3-(4-amino-3-(4-(4-(trifluoromethyl)pyridin-2-ylcarbamoyl)phenyl)-1H-pyrazolo[3,4-d]pyrimidin-1-yl)piperidine-1-carboxylate;
(R)-4-(4-amino-1-(1-(2,2,2-trifluoroacetyl)piperidin-3-yl)-1H-pyrazolo[3,4-d]pyrimidin-3-yl)-N-(4-(trifluoromethyl)pyridin-2-yl)benzamide;
(R)-4-(4-amino-1-(1-(3-(2-methoxyethoxy)propanoyl)piperidin-3-yl)-1H-pyrazolo[3,4-d]pyrimidin-3-yl)-N-(4-(trifluoromethyl)pyridin-2-yl)benzamide;
(R)-4-(4-amino-1-(1-(3-(methylthio)propanoyl)piperidin-3-yl)-1H-pyrazolo[3,4-d]pyrimidin-3-yl)-N-(4-(trifluoromethyl)pyridin-2-yl)benzamide;
(R)-4-(4-amino-1-(1-(cyclobutanecarbonyl)piperidin-3-yl)-1H-pyrazolo[3,4-d]pyrimidin-3-yl)-N-(4-(trifluoromethyl)pyridin-2-yl)benzamide;
(R)-4-(4-amino-1-(1-(3,3-difluorocyclobutanecarbonyl)piperidin-3-yl)-1H-pyrazolo[3,4-d]pyrimidin-3-yl)-N-(4-(trifluoromethyl)pyridin-2-yl)benzamide
(R)-4-(4-amino-1-(1-isobutyrylpiperidin-3-yl)-1H-pyrazolo[3,4-d]pyrimidin-3-yl)-N-(4-(trifluoromethyl)pyridin-2-yl)benzamide;
(R)-4-(4-amino-1-(1-(3-methoxypropanoyl)piperidin-3-yl)-1H-pyrazolo[3,4-d]pyrimidin-3-yl)-N-(4-(trifluoromethyl)pyridin-2-yl)benzamide;
(R)-4-(4-amino-1-(1-(3-ethoxypropanoyl)piperidin-3-yl)-1H-pyrazolo[3,4-d]pyrimidin-3-yl)-N-(4-(trifluoromethyl)pyridin-2-yl)benzamide;
(R)-4-(8-amino-3-(1-(3-methoxypropanoyl)piperidin-3-yl)imidazo[1,5-a]pyrazin-1-yl)-2-fluoro-N-(pyridin-2-yl)benzamide;
4-(8-amino-3-((R)-1-(3-methoxypropanoyl)piperidin-3-yl)imidazo[1,5-a]pyrazin-1-yl)-N-(pyridin-2-yl)-3-(trifluoromethyl)benzamide;
4-(8-amino-3-((R)-1-(3-methoxypropanoyl)piperidin-3-yl)imidazo[1,5-a]pyrazin-1-yl)-3-fluoro-N-(pyridin-2-yl)benzamide;
4-(8-amino-3-((R)-1-(3-methoxypropanoyl)piperidin-3-yl)imidazo[1,5-a]pyrazin-1-yl)-3-methyl-N-(pyridin-2-yl)benzamide;
(R)-4-(8-amino-3-(1-(3-methoxypropanoyl)piperidin-3-yl)imidazo[1,5-a]pyrazin-1-yl)-2-methyl-N-(pyridin-2-yl)benzamide;
(R)-5-(8-amino-3-(1-(3-methoxypropanoyl)piperidin-3-yl)imidazo[1,5-a]pyrazin-1-yl)-N-(pyridin-2-yl)picolinamide;
(R)-6-(8-amino-3-(1-(3-methoxypropanoyl)piperidin-3-yl)imidazo[1,5-a]pyrazin-1-yl)-N-(pyridin-2-yl)nicotinamide;
4-(8-amino-3-((R)-1-((R)-2,3-dihydroxypropanoyl)piperidin-3-yl)imidazo[1,5-a]pyrazin-1-yl)-N-(4-cyclopropylpyridin-2-yl)benzamide;
(R)-4-(8-amino-3-(1-(3-methyloxetane-3-carbonyl)piperidin-3-yl)imidazo[1,5-a]pyrazin-1-yl)-N-(pyrazin-2-yl)benzamide;
8-amino-N-(3-methoxypropyl)-3-methyl-1-(4-(4-(trifluoromethyl)pyridin-2-ylcarbamoyl)phenyl)imidazo[1,5-a]pyrazine-5-carboxamide;
8-amino-N-benzyl-3-methyl-1-(4-(4-(trifluoromethyl)pyridin-2-ylcarbamoyl)phenyl)imidazo[1,5-a]pyrazine-5-carboxamide;
8-amino-N,N,3-trimethyl-1-(4-(4-(trifluoromethyl)pyridin-2-ylcarbamoyl)phenyl)imidazo[1,5-a]pyrazine-5-carboxamide;
8-amino-N-(3-methoxypropyl)-3-methyl-1-(4-(4-propylpyridin-2-ylcarbamoyl)phenyl)imidazo[1,5-a]pyrazine-5-carboxamide;
8-amino-3-methyl-N-(1-methylpiperidin-4-yl)-1-(4-(4-(trifluoromethyl)pyridin-2-ylcarbamoyl)phenyl)imidazo[1,5-a]pyrazine-5-carboxamide;
8-amino-3-methyl-N-(pyridin-3-ylmethyl)-1-(4-(4-(trifluoromethyl)pyridin-2-ylcarbamoyl)phenyl)imidazo[1,5-a]pyrazine-5-carboxamide;
8-amino-3-methyl-N-(oxazol-5-ylmethyl)-1-(4-(4-(trifluoromethyl)pyridin-2-ylcarbamoyl)phenyl)imidazo[1,5-a]pyrazine-5-carboxamide;
4-(8-amino-5-chloro-3-(tetrahydro-2H-pyran-4-yl)imidazo[1,5-a]pyrazin-1-yl)-N-(4-propylpyridin-2-yl)benzamide;
(R)-ethyl 8-amino-3-(1-(3-methyloxetane-3-carbonyl)piperidin-3-yl)-1-(4-(4-(trifluoromethyl)pyridine-2-ylcarbamoyl)phenyl)imidazo[1,5-a]pyrazine-5-carboxylate;
(R)-8-amino-3-(1-(3-methyloxetane-3-carbonyl)piperidin-3-yl)-1-(4-(4-(trifluoromethyl)pyridin-2-ylcarbamoyl)phenyl)imidazo[1,5-a]pyrazine-5-carboxylic acid;
(R)-4-(8-amino-5-chloro-3-(1-(3-methyloxetane-3-carbonyl)piperidin-3-yl)imidazo[1,5-a]pyrazin-1-yl)-N-(4-(trifluoromethyl)pyridin-2-yl)benzamide;
(R)-4-(8-amino-3-(1-(3-methyloxetane-3-carbonyl)piperidin-3-yl)-5-vinylimidazo[1,5-a]pyrazin-1-yl)-N-(4-(trifluoromethyl)pyridin-2-yl)benzamide;
(R)-4-(8-amino-5-cyclopropyl-3-(1-(3-methyloxetane-3-carbonyl)piperidin-3-yl)imidazo[1,5-a]pyrazin-1-yl)-N-(4-(trifluoromethyl)pyridin-2-yl)benzamide;
(R)-4-(8-amino-5-deutero-3-(1-(3-methoxypropanoyl)piperidin-3-yl)imidazo[1,5-a]pyrazin-1-yl)-N-(4-(trifluoromethyl)pyridin-2-yl)benzamide;
(R)-4-(8-amino-5-deutero-3-(1-(3-methyloxetane-3-carbonyl)piperidin-3-yl)imidazo[1,5-a]pyrazin-1-yl)-N-(4-(trifluoromethyl)pyridin-2-yl)benzamide;
(R)-4-(8-amino-5-methyl-3-(1-(3-methyloxetane-3-carbonyl)piperidin-3-yl)imidazo[1,5-a]pyrazin-1-yl)-N-(4-(trifluoromethyl)pyridin-2-yl)benzamide;
(R)-4-(8-amino-3-(piperidin-3-yl)imidazo[1,5-a]pyrazin-1-yl)-N-(4-(trifluoromethyl)pyridin-2-yl)benzamide;
(R)-4-(8-amino-5-ethyl-3-(1-(3-methyloxetane-3-carbonyl)piperidin-3-yl)imidazo[1,5-a]pyrazin-1-yl)-N-(4-(trifluoromethyl)pyridin-2-yl)benzamide;
(R,E)-4-(8-amino-3-(1-(3-methyloxetane-3-carbonyl)piperidin-3-yl)-5-styrylimidazo[1,5-a]pyrazin-1-yl)-N-(4-(trifluoromethyl)pyridin-2-yl)benzamide;
(R,E)-4-(8-amino-3-(1-(3-methoxypropanoyl)piperidin-3-yl)-5-styrylimidazo[1,5-a]pyrazin-1-yl)-N-(4-(trifluoromethyl)pyridin-2-yl)benzamide;

(R)-4-(8-amino-5-(furan-2-yl)-3-(1-(3-methyloxetane-3-carbonyl)piperidin-3-yl)imidazo[1,5-a]pyrazin-1-yl)-N-(4-(trifluoromethyl)pyridin-2-yl)benzamide;

methyl 8-amino-3-methyl-1-(4-(4-(trifluoromethyl)pyridin-2-ylcarbamoyl)phenyl)imidazo[1,5-a]pyrazine-5-carboxylate;

(E)-4-(8-amino-5-styryl-3-(tetrahydro-2H-pyran-4-yl)imidazo[1,5-a]pyrazin-1-yl)-N-(pyridin-2-yl)benzamide;

4-(8-amino-5-chloro-3-(4-(3-methoxypropanoyl)morpholin-2-yl)imidazo[1,5-a]pyrazin-1-yl)-N-(4-(trifluoromethyl)pyridin-2-yl)benzamide;

4-(8-amino-5-chloro-3-(4-(3-methyloxetane-3-carbonyl)morpholin-2-yl)imidazo[1,5-a]pyrazin-1-yl)-N-(4-(trifluoromethyl)pyridin-2-yl)benzamide;

4-(8-amino-5-chloro-3-(4-(1-hydroxycyclobutanecarbonyl)morpholin-2-yl)imidazo[1,5-a]pyrazin-1-yl)-N-(4-(trifluoromethyl)pyridin-2-yl)benzamide;

(R)-4-(8-amino-5-deuteromethyl-3-(1-(3-methyloxetane-3-carbonyl)piperidin-3-yl)imidazo[1,5-a]pyrazin-1-yl)-N-(4-(trifluoromethyl)pyridin-2-yl)benzamide;

(R,E)-4-(8-amino-5-(4-fluorostyryl)-3-(1-(3-methyloxetane-3-carbonyl)piperidin-3-yl)imidazo[1,5-a]pyrazin-1-yl)-N-(4-(trifluoromethyl)pyridin-2-yl)benzamide;

(R)-4-(8-amino-3-(1-(3-methyloxetane-3-carbonyl)piperidin-3-yl)-5-phenethylimidazo[1,5-a]pyrazin-1-yl)-N-(4-(trifluoromethyl)pyridin-2-yl)benzamide;

(R)-4-(8-amino-5-(3-methoxyphenyl)-3-(1-(3-methyloxetane-3-carbonyl)piperidin-3-yl)imidazo[1,5-a]pyrazin-1-yl)-N-(4-(trifluoromethyl)pyridin-2-yl)benzamide;

(R)-4-(8-amino-3-(1-(3-methyloxetane-3-carbonyl)piperidin-3-yl)-5-phenylimidazo[1,5-a]pyrazin-1-yl)-N-(4-(trifluoromethyl)pyridin-2-yl)benzamide;

4-(8-amino-5-(1-hydroxy-3-methylbutyl)-3-methylimidazo[1,5-a]pyrazin-1-yl)-N-(4-(trifluoromethyl)pyridin-2-yl)benzamide;

(R)-4-(8-amino-5-(3,6-dihydro-2H-pyran-4-yl)-3-(1-(3-methyloxetane-3-carbonyl)piperidin-3-yl)imidazo[1,5-a]pyrazin-1-yl)-N-(4-(trifluoromethyl)pyridin-2-yl)benzamide;

4-(8-amino-3-{(3R)-1-[(3-methyloxetan-3-yl)carbonyl]piperidin-3-yl}imidazo[1,5-a]pyrazin-1-yl)-3-fluoro-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-N-(5-methoxypyridin-2-yl)benzamide;

4-{3-[(3R)-1-acetylpiperidin-3-yl]-8-aminoimidazo[1,5-a]pyrazin-1-yl}-N-(4-methylpyridin-2-yl)benzamide;

4-(8-amino-3-{(3R)-1-[(3-methyloxetan-3-yl)carbonyl]piperidin-3-yl}imidazo[1,5-a]pyrazin-1-yl)-N-(5-cyanopyridin-2-yl)benzamide;

4-(8-amino-3-{(3R)-1-[(3,5-dimethylisoxazol-4-yl)carbonyl]piperidin-3-yl}imidazo[1,5-a]pyrazin-1-yl)-N-[4-(trifluoromethyl)pyridin-2-yl]benzamide;

4-{8-amino-3-[(3R)-1-{[1-(1-methylethyl)azetidin-3-yl]carbonyl}piperidin-3-yl]imidazo[1,5-a]pyrazin-1-yl}-N-[4-(trifluoromethyl)pyridin-2-yl]benzamide;

4-{8-amino-3-[(3R)-1-(1,2,5-thiadiazol-3-ylcarbonyl)piperidin-3-yl]imidazo[1,5-a]pyrazin-1-yl}-N-[4-(trifluoromethyl)pyridin-2-yl]benzamide;

4-{8-amino-3-[(3R)-1-(4,4,4-trifluorobutanoyl)piperidin-3-yl]imidazo[1,5-a]pyrazin-1-yl}-N-[4-(trifluoromethyl)pyridin-2-yl]benzamide;

4-{8-amino-3-[(3R)-1-(3,3,3-trifluoropropanoyl)piperidin-3-yl]imidazo[1,5-a]pyrazin-1-yl}-N-[4-(trifluoromethyl)pyridin-2-yl]benzamide;

4-{8-amino-3-[(3R)-1-(isothiazol-4-ylcarbonyl)piperidin-3-yl]imidazo[1,5-a]pyrazin-1-yl}-N-[4-(trifluoromethyl)pyridin-2-yl]benzamide;

4-{8-amino-3-[(3R)-1-{[1-(methoxymethyl)cyclopropyl]carbonyl}piperidin-3-yl]imidazo[1,5-a]pyrazin-1-yl}-N-[4-(trifluoromethyl)pyridin-2-yl]benzamide;

4-(8-amino-3-{(3R)-1-[(1-cyanocyclopropyl)carbonyl]piperidin-3-yl}[1,5-a]pyrazin-1-yl)-N-[4-(trifluoromethyl)pyridin-2-yl]benzamide;

4-{8-amino-3-[(3R)-1-(pyrazin-2-ylcarbonyl)piperidin-3-yl]imidazo[1,5-a]pyrazin-1-yl}-N-[4-(trifluoromethyl)pyridin-2-yl]benzamide;

4-{8-amino-3-[(3R)-1-(4,4-difluoro-L-prolyl)piperidin-3-yl]imidazo[1,5-a]pyrazin-1-yl}-N-[4-(trifluoromethyl)pyridin-2-yl]benzamide;

4-(8-amino-3-{(3R)-1-[(3-methyloxetan-3-yl)methyl]piperidin-3-yl}imidazo[1,5-a]pyrazin-1-yl)-N-[4-(trifluoromethyl)pyridin-2-yl]benzamide;

4-{8-amino-3-[(3R)-1-(ethoxyacetyl)piperidin-3-yl]imidazo[1,5-a]pyrazin-1-yl}-N-[4-(trifluoromethyl)pyridin-2-yl]benzamide;

4-{8-amino-3-[(3R)-1-(methoxyacetyl)piperidin-3-yl]imidazo[1,5-a]pyrazin-1-yl}-N-[4-(trifluoromethyl)pyridin-2-yl]benzamide;

4-{8-amino-3-[(3R)-1-(1-methyl-L-prolyl)piperidin-3-yl]imidazo[1,5-a]pyrazin-1-yl}-N-[4-(trifluoromethyl)pyridin-2-yl]benzamide;

4-(8-amino-3-{(3R)-1-[(1-hydroxycyclopropyl)carbonyl]piperidin-3-yl}imidazo[1,5-a]pyrazin-1-yl)-N-[4-(trifluoromethyl)pyridin-2-yl]benzamide;

4-{8-amino-3-[(3R)-1-(2-hydroxybutanoyl)piperidin-3-yl]imidazo[1,5-a]pyrazin-1-yl}-N-[4-(trifluoromethyl)pyridin-2-yl]benzamide;

4-(8-amino-3-{(3R)-1-[(2,2-difluorocyclopropyl)carbonyl]piperidin-3-yl}imidazo[1,5-a]pyrazin-1-yl)-N-[4-(trifluoromethyl)pyridin-2-yl]benzamide;

4-(8-amino-3-{(3R)-1-[(2S)-2-hydroxypropanoyl]piperidin-3-yl}imidazo[1,5-a]pyrazin-1-yl)-N-[4-(trifluoromethyl)pyridin-2-yl]benzamide;

4-(8-amino-3-{(3R)-1-[(2R)-2-hydroxypropanoyl]piperidin-3-yl}imidazo[1,5-a]pyrazin-1-yl)-N-[4-(trifluoromethyl)pyridin-2-yl]benzamide;

4-{8-amino-3-[(3R)-1-(N,N-dimethylglycyl)piperidin-3-yl]imidazo[1,5-a]pyrazin-1-yl}-N-[4-(trifluoromethyl)pyridin-2-yl]benzamide;

4-{8-amino-3-[(3R)-1-{[(3R)-1-methylpyrrolidin-3-yl]carbonyl}piperidin-3-yl]imidazo[1,5-a]pyrazin-1-yl}-N-[4-(trifluoromethyl)pyridin-2-yl]benzamide formate salt;

4-(8-amino-3-{(3R)-1-[(methylsulfonyl)acetyl]piperidin-3-yl}imidazo[1,5-a]pyrazin-1-yl)-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-N-1,3-thiazol-4-ylbenzamide;

4-(8-amino-3-{(3R)-1-[(3-methyloxetan-3-yl)carbonyl]piperidin-3-yl}imidazo[1,5-a]pyrazin-1-yl)-N-(5-fluoropyridin-2-yl)benzamide;

4-(8-amino-3-{(3R)-1-[(3-methyloxetan-3-yl)carbonyl]piperidin-3-yl}imidazo[1,5-a]pyrazin-1-yl)-N-(4-methylpyridin-2-yl)benzamide;

4-(8-amino-3-{(3R)-1-[(3-methyloxetan-3-yl)carbonyl]piperidin-3-yl}imidazo[1,5-a]pyrazin-1-yl)-N-(5-methylisoxazol-3-yl)benzamide;

4-(8-amino-3-{(3R)-1-[(3-methyloxetan-3-yl)carbonyl]piperidin-3-yl}imidazo[1,5-a]pyrazin-1-yl)-N-(4-cyclobutylpyridin-2-yl)benzamide;

4-(8-amino-3-{(3R)-1-[(3-methyloxetan-3-yl)carbonyl]piperidin-3-yl}imidazo[1,5-a]pyrazin-1-yl)-N-[5-(difluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-N-(5-methylpyridin-2-yl)benzamide;

4-(8-amino-3-{(3R)-1-[(3-methyloxetan-3-yl)carbonyl]piperidin-3-yl}imidazo[1,5-a]pyrazin-1-yl)-N-pyridazin-3-ylbenzamide 4-(8-amino-3-{(3R)-1-[(3-methyloxetan-3-yl)carbonyl]piperidin-3-yl}imidazo[1,5-a]pyrazin-1-yl)-N-(5-chloropyridin-2-yl)benzamide;

4-(8-amino-3-{(3R)-1-[(3-methyloxetan-3-yl)carbonyl]piperidin-3-yl}imidazo[1,5-a]pyrazin-1-yl)-N-[5-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-N-(5-fluoro-4-methylpyridin-2-yl)benzamide;

4-(8-amino-3-{(3R)-1-[(3-methyloxetan-3-yl)carbonyl]piperidin-3-yl}imidazo[1,5-a]pyrazin-1-yl)-N-(4-methoxypyrimidin-2-yl)benzamide;

4-(8-amino-3-{(3R)-1-[(3-methyloxetan-3-yl)carbonyl]piperidin-3-yl}imidazo[1,5-a]pyrazin-1-yl)-N-(4-ethylpyridin-2-yl)benzamide;

4-(8-amino-3-{(3R)-1-[(3-methyloxetan-3-yl)carbonyl]piperidin-3-yl}imidazo[1,5-a]pyrazin-1-yl)-N-(5-methylpyridin-2-yl)benzamide;

4-(8-amino-3-{(3R)-1-[(3-methyloxetan-3-yl)carbonyl]piperidin-3-yl}imidazo[1,5-a]pyrazin-1-yl)-N-(6,7-dihydro-5H-cyclopenta[d]pyrimidin-2-yl)benzamide;

4-(8-amino-3-{(3R)-1-[(3-methyloxetan-3-yl)carbonyl]piperidin-3-yl}imidazo[1,5-a]pyrazin-1-yl)-N-(1-methyl-1H-pyrazol-3-yl)benzamide;

4-(8-amino-3-{(3R)-1-[(3-methyloxetan-3-yl)carbonyl]piperidin-3-yl}imidazo[1,5-a]pyrazin-1-yl)-N-(5-methyl-1,3-thiazol-2-yl)benzamide;

4-(8-amino-3-{(3R)-1-[(3-methyloxetan-3-yl)carbonyl]piperidin-3-yl}imidazo[1,5-a]pyrazin-1-yl)-N-(4,5-dimethyl-1,3-thiazol-2-yl)benzamide;

4-(8-amino-3-{(3R)-1-[(3-methyloxetan-3-yl)carbonyl]piperidin-3-yl}imidazo[1,5-a]pyrazin-1-yl)-N-1,2,4-thiadiazol-5-ylbenzamide;

4-(8-amino-3-{(3R)-1-[(3-methyloxetan-3-yl)carbonyl]piperidin-3-yl}imidazo[1,5-a]pyrazin-1-yl)-N-(5-tert-butyl-1,3-thiazol-2-yl)benzamide;

4-(8-amino-3-{(3R)-1-[(3-methyloxetan-3-yl)carbonyl]piperidin-3-yl}imidazo[1,5-a]pyrazin-1-yl)-N-isothiazol-4-ylbenzamide;

4-(8-amino-3-{(3R)-1-[(1-hydroxycyclopropyl)carbonyl]piperidin-3-yl}imidazo[1,5-a]pyrazin-1-yl)-N-(4-ethylpyridin-2-yl)benzamide;

4-{8-amino-3-[(3R)-1-propanoylpiperidin-3-yl]imidazo[1,5-a]pyrazin-1-yl}-N-(4-methoxypyridin-2-yl)benzamide;

4-(8-amino-5-cyano-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(3R,5S)-5-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(3R,5R)-5-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{5,5-difluoro-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-(3R,4R)-4-methyl-1-[(3-methyloxetan-3-yl)carbonyl]piperidin-3-yl 1 imidazo[1,5-a]pyrazin-1-yl)-N-[4-(trifluoromethyl)pyridin-2-yl]benzamide;

4-(8-amino-3-{(3R,4S)-4-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(2R,3R)-2-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(2S,3R)-2-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(4-amino-1-{(3R)-1-[(3-methyloxetan-3-yl)carbonyl]piperidin-3-yl}-1H-pyrazolo[4,3-c]pyridin-3-yl)-N-[4-(trifluoromethyl)pyridin-2-yl]benzamide;

4-(4-amino-7-chloro-1-{(3R)-1-[(3-methyloxetan-3-yl)carbonyl]piperidin-3-yl}-1H-pyrazolo[4,3-c]pyridin-3-yl)-N-[4-(trifluoromethyl)pyridin-2-yl]benzamide;

4-{4-amino-1-[(3R)-1-(methoxyacetyl)piperidin-3-yl]-1H-pyrazolo[4,3-c]pyridin-3-yl}-N-[4-(trifluoromethyl)pyridin-2-yl]benzamide;

4-{4-amino-1-[(3R)-1-(cyclopropylcarbonyl)piperidin-3-yl]-1H-pyrazolo[4,3-c]pyridin-3-yl}-N-[4-(trifluoromethyl)pyridin-2-yl]benzamide;

4-{1-[(3R)-1-acetylpiperidin-3-yl]-4-amino-1H-pyrazolo[4,3-c]pyridin-3-yl}-N-[4-(trifluoromethyl)pyridin-2-yl]benzamide;

4-(4-amino-1-{(3R)-1-[(3-methyloxetan-3-yl)carbonyl]piperidin-3-yl}-1H-pyrazolo[4,3-c]pyridin-3-yl)-N-(4-ethylpyridin-2-yl)benzamide;

4-(4-amino-1-{(3R)-1-[(3-methyloxetan-3-yl)carbonyl]piperidin-3-yl}-1H-pyrazolo[4,3-c]pyridin-3-yl)-N-(4-methylpyridin-2-yl)benzamide;

4-(4-amino-1-{(3R)-1-[(3-methyloxetan-3-yl)carbonyl]piperidin-3-yl}-1H-pyrazolo[4,3-c]pyridin-3-yl)-N-(4-methoxypyridin-2-yl)benzamide;

4-(4-amino-7-{(3R)-1-[(3-methyloxetan-3-yl)carbonyl]piperidin-3-yl}-7H-pyrrolo[2,3-d]pyrimidin-5-yl)-N-[4-(trifluoromethyl)pyridin-2-yl]benzamide;

4-(4-amino-7-{(3R)-1-[(3-methyloxetan-3-yl)carbonyl]piperidin-3-yl}-7H-pyrrolo[2,3-d]pyrimidin-5-yl)-N-(4-cyanopyridin-2-yl)benzamide;

4-(4-amino-7-{(3R)-1-[(3-methyloxetan-3-yl)carbonyl]piperidin-3-yl}-7H-pyrrolo[2,3-d]pyrimidin-5-yl)-N-(4-ethylpyridin-2-yl)benzamide;

4-{8-amino-3-[(3R,6S)-1-(3-methoxypropanoyl)-6-methylpiperidin-3-yl]imidazo[1,5-a]pyrazin-1-yl}-2-fluoro-N-[4-(trifluoromethyl)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-{8-amino-3-[(3R,6S)-1-(cyclopropylcarbonyl)-6-methylpiperidin-3-yl]imidazo[1,5-a]pyrazin-1-yl}-N-pyridin-2-ylbenzamide;

4-(8-amino-3-{(3R,6S)-6-methyl-1-[(3-methyloxetan-3-yl)carbonyl]piperidin-3-yl}imidazo[1,5-a]pyrazin-1-yl)-3-fluoro-N-[4-(trifluoromethyl)pyridin-2-yl]benzamide;

4-{8-amino-3-[(3R,6S)-1-(cyclopropylcarbonyl)-6-methylpiperidin-3-yl]imidazo[1,5-a]pyrazin-1-yl}-3-fluoro-N-[4-(trifluoromethyl)pyridin-2-yl]benzamide;

4-{8-amino-3-[(3R,6S)-6-methyl-1-propanoylpiperidin-3-yl]imidazo[1,5-a]pyrazin-1-yl}-3-fluoro-N-[4-(trifluoromethyl)pyridin-2-yl]benzamide;

4-{8-amino-3-[(3R,6S)-1-(3-methoxypropanoyl)-6-methylpiperidin-3-yl]imidazo[1,5-a]pyrazin-1-yl}-3-fluoro-N-[4-(trifluoromethyl)pyridin-2-yl]benzamide;

4-{8-amino-3-[1-(cyclopropylcarbonyl)-6-(trifluoromethyl)piperidin-3-yl]imidazo[1,5-a]pyrazin-1-yl}-3-fluoro-N-[4-(trifluoromethyl)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-2-chloro-N-[4-(trifluoromethyl)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-3-methoxy-N-[4-(trifluoromethyl)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-N-(4-methylpyridin-2-yl)benzamide;

4-(8-amino-3-{(3R,6S)-6-methyl-1-[(3-methyloxetan-3-yl)carbonyl]piperidin-3-yl}imidazo[1,5-a]pyrazin-1-yl)-N-(4-methoxypyridin-2-yl)benzamide;

4-(8-amino-3-{(3R,6S)-6-methyl-1-[(3-methyloxetan-3-yl)carbonyl]piperidin-3-yl}imidazo[1,5-a]pyrazin-1-yl)-N-(4-ethoxypyridin-2-yl)benzamide;

4-(8-amino-3-{(3R,6R)-6-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-{8-amino-3-[(3S,6R)-1-ethyl-6-(trifluoromethyl)piperidin-3-yl]imidazo[1,5-a]pyrazin-1-yl}-N-[4-(trifluoromethyl)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-{8-amino-3-[(3S,6R)-1-ethyl-6-(trifluoromethyl)piperidin-3-yl]imidazo[1,5-a]pyrazin-1-yl}-N-pyridin-2-ylbenzamide;

4-(8-amino-3-{(3R,6S)-6-methyl-1-[(3-methyloxetan-3-yl)carbonyl]piperidin-3-yl}imidazo[1,5-a]pyrazin-1-yl)-N-[4-(cyclopropyloxy)pyridin-2-yl]benzamide;

4-{8-amino-3-[(3S,6R)-1-methyl-6-(trifluoromethyl)piperidin-3-yl]imidazo[1,5-a]pyrazin-1-yl}-N-[4-(trifluoromethyl)pyridin-2-yl]benzamide;

4-{8-amino-3-[(3S,6R)-1-methyl-6-(trifluoromethyl)piperidin-3-yl]imidazo[1,5-a]pyrazin-1-yl}-3-fluoro-N-[4-(trifluoromethyl)pyridin-2-yl]benzamide;

(2R,5S)-5-[8-amino-1-(4-{[4-(trifluoromethyl)pyridin-2-yl]carbamoyl}-phenyl)imidazo[1,5-a]pyrazin-3-yl]-N-methyl-2-(trifluoromethyl)piperidine-1-carboxamide;

4-(8-amino-3-{(3R,6S)-6-methyl-1-[(3-methyloxetan-3-yl)carbonyl]piperidin-3-yl}imidazo[1,5-a]pyrazin-1-yl)-N-[4-(1,1-difluoroethyl)pyridin-2-yl]benzamide;

4-{8-amino-3-[(3S,6S)-1-methyl-6-(trifluoromethyl)piperidin-3-yl]imidazo[1,5-a]pyrazin-1-yl}-N-[4-(trifluoromethyl)pyridin-2-yl]benzamide;

4-{8-amino-3-[(3S,6R)-1-propanoyl-6-(trifluoromethyl)piperidin-3-yl]imidazo[1,5-a]pyrazin-1-yl}-N-[4-(trifluoromethyl)pyridin-2-yl]benzamide;

4-(8-amino-3-{(3R,6R)-6-(difluoromethyl)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-N-[4-(2-methylpropoxy)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-N-[4-(2,2,2-trifluoroethoxy)pyridin-2-yl]benzamide;

4-{8-amino-3-[(3S,6S)-1-(cyclopropylcarbonyl)-6-(hydroxymethyl)piperidin-3-yl]imidazo[1,5-a]pyrazin-1-yl}-N-[4-(trifluoromethyl)pyridin-2-yl]benzamide;

4-{8-amino-3-[(3S,6R)-1-(cyclopropylcarbonyl)-6-(trifluoromethyl)piperidin-3-yl]imidazo[1,5-a]pyrazin-1-yl}-N-(4-fluoropyridin-2-yl)benzamide;

4-{8-amino-3-[(3S,6R)-1-(cyclopropylcarbonyl)-6-(trifluoromethyl)piperidin-3-yl]imidazo[1,5-a]pyrazin-1-yl}-N-(4-methylpyridin-2-yl)benzamide;

(2R,5S)-5-[8-amino-1-(4-{[4-(trifluoromethyl)pyridin-2-yl]carbamoyl}-phenyl)imidazo[1,5-a]pyrazin-3-yl]-N,N-dimethyl-2-(trifluoromethyl)piperidine-1-carboxamide;

4-{3-[(3S,6R)-1-acetyl-6-(trifluoromethyl)piperidin-3-yl]-8-aminoimidazo[1,5-a]pyrazin-1-yl}-N-[4-(trifluoromethyl)pyridin-2-yl]benzamide;

4-(8-amino-3-{(3S,6S)-6-(methoxymethyl)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(3R,6R)-6-(methoxymethyl)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

methyl (2R,5S)-5-[8-amino-1-(4-{[4-(trifluoromethyl)pyridin-2-yl]carbamoyl}-phenyl)imidazo[1,5-a]pyrazin-3-yl]-2-(trifluoromethyl)piperidine-1-carboxylate;

4-(8-amino-3-{(3R,6S)-6-methyl-1-[(3-methyloxetan-3-yl)carbonyl]piperidin-3-yl}imidazo[1,5-a]pyrazin-1-yl)-N-[4-(difluoromethyl)pyridin-2-yl]-3-fluorobenzamide;

4-{3-[(3R,6S)-1-acetyl-6-methylpiperidin-3-yl]-8-aminoimidazo[1,5-a]pyrazin-1-yl}-N-[4-(difluoromethyl)pyridin-2-yl]-3-fluorobenzamide;

4-{8-amino-3-[(3R,6S)-1-(cyclopropylcarbonyl)-6-methylpiperidin-3-yl]imidazo[1,5-a]pyrazin-1-yl}-N-[4-(difluoromethyl)pyridin-2-yl]-3-fluorobenzamide;

4-{8-amino-3-[(3S,6R)-1-(2-hydroxyethyl)-6-(trifluoromethyl)piperidin-3-yl]imidazo[1,5-a]pyrazin-1-yl}-N-[4-(trifluoromethyl)pyridin-2-yl]benzamide;

4-(8-amino-3-{(3R)-3-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(3S)-3-hydroxy-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-{3-[(3R)-1-acetylpiperidin-3-yl]-8-amino-5-chloroimidazo[1,5-a]pyrazin-1-yl}-N-[4-(trifluoromethyl)pyridin-2-yl]benzamide;

4-{8-amino-5-chloro-3-[(3R)-1-(hydroxyacetyl)piperidin-3-yl]imidazo[1,5-a]pyrazin-1-yl}-N-[4-(trifluoromethyl)pyridin-2-yl]benzamide;

4-{8-amino-5-chloro-3-[(3R)-1-(methoxyacetyl)piperidin-3-yl]imidazo[1,5-a]pyrazin-1-yl}-N-[4-(trifluoromethyl)pyridin-2-yl]benzamide;

4-{8-amino-5-chloro-3-[(3R)-1-formylpiperidin-3-yl]imidazo[1,5-a]pyrazin-1-yl}-N-[4-(trifluoromethyl)pyridin-2-yl]benzamide;

4-(8-amino-5-chloro-3-{(3R)-1-[(3-methyloxetan-3-yl)carbonyl]piperidin-3-yl}imidazo[1,5-a]pyrazin-1-yl)-N-(4-methoxypyridin-2-yl)benzamide;

4-(8-amino-5-chloro-3-{(3R)-1-[(3-methyloxetan-3-yl)carbonyl]piperidin-3-yl}imidazo[1,5-a]pyrazin-1-yl)-N-(4-cyanopyridin-2-yl)benzamide;

4-(8-amino-5-chloro-3-{(3R)-1-[(3-methyloxetan-3-yl)carbonyl]piperidin-3-yl}imidazo[1,5-a]pyrazin-1-yl)-N-(4-methylpyridin-2-yl)benzamide;

4-(8-amino-5-chloro-3-{(3R)-1-[(3-methyloxetan-3-yl)carbonyl]piperidin-3-yl}imidazo[1,5-a]pyrazin-1-yl)-3-fluoro-N-[4-(trifluoromethyl)pyridin-2-yl]benzamide;

4-(8-amino-5-chloro-3-{(3R)-1-[(3-methyloxetan-3-yl)carbonyl]piperidin-3-yl}imidazo[1,5-a]pyrazin-1-yl)-3-fluoro-N-(4-methylpyridin-2-yl)benzamide;

4-[8-amino-5-(methoxymethyl)-3-{(3R)-1-[(3-methyloxetan-3-yl)carbonyl]piperidin-3-yl}imidazo[1,5-a]pyrazin-1-yl]-N-[4-(trifluoromethyl)pyridin-2-yl]benzamide;

4-[8-amino-5-(methoxymethyl)-3-{(3R,6S)-6-methyl-1-[(3-methyloxetan-3-yl)carbonyl]piperidin-3-yl}imidazo[1,5-a]pyrazin-1-yl]-N-[4-(trifluoromethyl)pyridin-2-yl]benzamide;

4-[8-amino-5-(methoxymethyl)-3-{(3R)-1-[(3-methyloxetan-3-yl)carbonyl]piperidin-3-yl}imidazo[1,5-a]pyrazin-1-yl]-3-fluoro-N-[4-(trifluoromethyl)pyridin-2-yl]benzamide;

4-{8-amino-3-[(3R)-1-(methoxyacetyl)piperidin-3-yl]-5-(methoxymethyl)imidazo[1,5-a]pyrazin-1-yl}-3-fluoro-N-[4-(trifluoromethyl)pyridin-2-yl]benzamide;

4-(8-amino-5-methyl-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-5-methyl-3-{(3R)-1-[(3-methyloxetan-3-yl)carbonyl]piperidin-3-yl}imidazo[1,5-a]pyrazin-1-yl)-N-[4-(1,1-difluoroethyl)pyridin-2-yl]benzamide;

4-(8-amino-5-methyl-3-{(3R)-1-[(3-methyloxetan-3-yl)carbonyl]piperidin-3-yl}imidazo[1,5-a]pyrazin-1-yl)-N-(4-ethylpyridin-2-yl)benzamide;

4-(8-amino-5-methyl-3-{(3R)-1-[(3-methyloxetan-3-yl)carbonyl]piperidin-3-yl}imidazo[1,5-a]pyrazin-1-yl)-N-[4-(cyclopropyloxy)pyridin-2-yl]benzamide;

4-{8-amino-3-[(3R)-1-(cyclopropylcarbonyl)piperidin-3-yl]-5-methylimidazo[1,5-a]pyrazin-1-yl}-N-[4-(cyclopropyloxy)pyridin-2-yl]benzamide;

4-(8-amino-5-methyl-3-{(3R)-1-[(3-methyloxetan-3-yl)carbonyl]piperidin-3-yl}imidazo[1,5-a]pyrazin-1-yl)-N-[4-(difluoromethyl)pyridin-2-yl]benzamide;

4-(8-amino-5-methyl-3-{(3R)-1-[(3-methyloxetan-3-yl)carbonyl]piperidin-3-yl}imidazo[1,5-a]pyrazin-1-yl)-N-(4-methoxypyridin-2-yl)benzamide;

4-{3-[(3R)-1-acetylpiperidin-3-yl]-8-amino-5-methylimidazo[1,5-a]pyrazin-1-yl}-N-(4-methoxypyridin-2-yl)benzamide;

4-(8-amino-5-methyl-3-{(3R,6S)-6-methyl-1-[(3-methyloxetan-3-yl)carbonyl]-piperidin-3-yl}imidazo[1,5-a]pyrazin-1-yl)-N-[4-(difluoromethyl)pyridin-2-yl]-3-fluorobenzamide;

4-{3-[(3R,6S)-1-acetyl-6-methylpiperidin-3-yl]-8-amino-5-methylimidazo[1,5-a]pyrazin-1-yl}-N-[4-(difluoromethyl)pyridin-2-yl]-3-fluorobenzamide;

4-{8-amino-3-[(3R)-1-(cyclopropylcarbonyl)piperidin-3-yl]-5-fluoroimidazo[1,5-a]pyrazin-1-yl}-N-[4-(trifluoromethyl)pyridin-2-yl]benzamide;

4-(8-amino-5-formyl-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-5-[(1R)-1-hydroxyethyl]-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-5-[(1S)-1-hydroxyethyl]-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-5-[(1R)-1-methoxyethyl]-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-5-[(1S)-1-methoxyethyl]-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-[8-amino-5-(3-hydroxyoxetan-3-yl)-3-{(3R)-1-[(3-methyloxetan-3-yl)carbonyl]piperidin-3-yl}imidazo[1,5-a]pyrazin-1-yl]-N-[4-(trifluoromethyl)pyridin-2-yl]benzamide;

4-[8-amino-3-{(3R)-1-[(3-methyloxetan-3-yl)carbonyl]piperidin-3-yl}-5-(trifluoromethyl)imidazo[1,5-a]pyrazin-1-yl]-N-[4-(trifluoromethyl)pyridin-2-yl]benzamide;

4-[8-amino-5-(hydroxymethyl)-3-{(3R)-1-[(3-methyloxetan-3-yl)carbonyl]piperidin-3-yl}imidazo[1,5-a]pyrazin-1-yl]-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-2-fluoro-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-2-chloro-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-2-methyl-N-[4-(trifluoromethyl)pyridin-2-yl]benzamide;

4-{8-amino-3-[(3R)-1-(3-methoxypropanoyl)piperidin-3-yl]imidazo[1,5-a]pyrazin-1-yl}-3-hydroxy-N-pyridin-2-ylbenzamide;

4-(8-amino-3-{(3R,6S)-6-methyl-1-[(3-methyloxetan-3-yl)carbonyl]piperidin-3-yl}imidazo[1,5-a]pyrazin-1-yl)-2-fluoro-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-3-methoxy-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-N-[4-(difluoromethoxy)pyridin-2-yl]-3-fluorobenzamide;

4-(8-amino-3-{(3R)-1-[(3-methyloxetan-3-yl)carbonyl]piperidin-3-yl}imidazo[1,5-a]pyrazin-1-yl)-3-methyl-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-N-[4-(difluoromethyl)pyridin-2-yl]-3-fluorobenzamide;

4-(8-amino-3-{(3R)-1-[(3-methyloxetan-3-yl)carbonyl]piperidin-3-yl}imidazo[1,5-a]pyrazin-1-yl)-3-fluoro-N-(4-propoxypyridin-2-yl)benzamide;

4-(8-amino-3-{(3R)-1-[(3-methyloxetan-3-yl)carbonyl]piperidin-3-yl}imidazo[1,5-a]pyrazin-1-yl)-N-(4-cyanopyridin-2-yl)-3-fluorobenzamide;

4-(8-amino-3-{(3R)-1-[(3-methyloxetan-3-yl)carbonyl]piperidin-3-yl}imidazo[1,5-a]pyrazin-1-yl)-N-[4-(cyclopropyloxy)pyridin-2-yl]-3-fluorobenzamide;

4-(8-amino-3-{(3R)-1-[(3-methyloxetan-3-yl)carbonyl]piperidin-3-yl}imidazo[1,5-a]pyrazin-1-yl)-N-[4-(1,1-difluoroethyl)pyridin-2-yl]-3-fluorobenzamide;

4-(8-amino-3-{(3R)-1-[(3-methyloxetan-3-yl)carbonyl]piperidin-3-yl}imidazo[1,5-a]pyrazin-1-yl)-N-(4-chloropyridin-2-yl)-3-fluorobenzamide;

4-{3-[(3R)-1-acetylpiperidin-3-yl]-8-aminoimidazo[1,5-a]pyrazin-1-yl}-3-fluoro-N-[4-(trifluoromethyl)pyridin-2-yl]benzamide;

4-{8-amino-3-[(3R)-1-propanoylpiperidin-3-yl]imidazo[1,5-a]pyrazin-1-yl}-3-fluoro-N-[4-(trifluoromethyl)pyridin-2-yl]benzamide;

4-{8-amino-3-[(3R)-1-propanoylpiperidin-3-yl]imidazo[1,5-a]pyrazin-1-yl}-N-[4-(difluoromethyl)pyridin-2-yl]-3-fluorobenzamide;

(3R)-3-[8-amino-1-(2-fluoro-4-{[4-(trifluoromethyl)pyridin-2-yl]carbamoyl}phenyl)imidazo[1,5-a]pyrazin-3-yl]-N-cyclopropylpiperidine-1-carboxamide;

4-{8-amino-3-[(3R)-1-propanoylpiperidin-3-yl]imidazo[1,5-a]pyrazin-1-yl}-3-methoxy-N-[4-(trifluoromethyl)pyridin-2-yl]benzamide;

4-{8-amino-3-[(2R)-4-(2-methoxyethyl)morpholin-2-yl]imidazo[1,5-a]pyrazin-1-yl}-N-[4-(trifluoromethyl)pyridin-2-yl]benzamide;

4-{8-amino-3-[(2R)-4-(2-hydroxyethyl)morpholin-2-yl]imidazo[1,5-a]pyrazin-1-yl}-N-[4-(trifluoromethyl)pyridin-2-yl]benzamide;

4-{8-amino-3-[(2R)-4-(3-methoxypropanoyl)morpholin-2-yl]imidazo[1,5-a]pyrazin-1-yl}-N-[4-(trifluoromethyl)pyridin-2-yl]benzamide;

4-(8-amino-3-{(2R)-4-[(3-methyloxetan-3-yl)carbonyl]morpholin-2-yl}imidazo[1,5-a]pyrazin-1-yl)-N-[4-(trifluoromethyl)pyridin-2-yl]benzamide;

4-(8-amino-3-{(2R)-4-[(1-methyl-1H-pyrazol-4-yl)methyl]morpholin-2-yl}imidazo[1,5-a]pyrazin-1-yl)-N-[4-(trifluoromethyl)pyridin-2-yl]benzamide;

4-{8-amino-3-[(2R)-4-ethylmorpholin-2-yl]imidazo[1,5-a]pyrazin-1-yl}-N-[4-(trifluoromethyl)pyridin-2-yl]benzamide;

4-{8-amino-3-[(2R)-4-methylmorpholin-2-yl]imidazo[1,5-a]pyrazin-1-yl}-N-[4-(trifluoromethyl)pyridin-2-yl]benzamide;

4-(8-amino-3-{(2R)-4-[(1-methyl-1H-pyrazol-4-yl)methyl]morpholin-2-yl}imidazo[1,5-a]pyrazin-1-yl)-N-(4-cyclopropylpyridin-2-yl)benzamide;

4-(8-amino-3-{(2R)-4-[(1-aminocyclobutyl)carbonyl]morpholin-2-yl}imidazo[1,5-a]pyrazin-1-yl)-N-[4-(trifluoromethyl)pyridin-2-yl]benzamide;

4-{8-amino-3-[(2R)-4-{[1-(methoxymethyl)cyclobutyl]carbonyl}morpholin-2-yl]imidazo[1,5-a]pyrazin-1-yl}-N-[4-(trifluoromethyl)pyridin-2-yl]benzamide;

4-(8-amino-3-{(2R)-4-[(1-methylazetidin-3-yl)carbonyl]morpholin-2-yl}imidazo[1,5-a]pyrazin-1-yl)-N-[4-(trifluoromethyl)pyridin-2-yl]benzamide;

4-(8-amino-3-{(2R)-4-[3-(methylsulfanyl)propanoyl]morpholin-2-yl}imidazo[1,5-a]pyrazin-1-yl)-N-[4-(trifluoromethyl)pyridin-2-yl]benzamide;

4-{8-amino-3-[(2R)-4-(3-ethoxypropanoyl)morpholin-2-yl]imidazo[1,5-a]pyrazin-1-yl}-N-[4-(trifluoromethyl)pyridin-2-yl]benzamide;

4-{8-amino-5-chloro-3-[(2R)-morpholin-2-yl]imidazo[1,5-a]pyrazin-1-yl}-N-[4-(trifluoromethyl)pyridin-2-yl]benzamide;

4-(8-amino-5-chloro-3-{(2R)-4-[(3-methyloxetan-3-yl)carbonyl]morpholin-2-yl}imidazo[1,5-a]pyrazin-1-yl)-N-[4-(trifluoromethyl)pyridin-2-yl]benzamide;

4-(8-amino-5-methyl-3-{(2R)-4-[(3-methyloxetan-3-yl)carbonyl]morpholin-2-yl}imidazo[1,5-a]pyrazin-1-yl)-N-[4-(trifluoromethyl)pyridin-2-yl]benzamide;

4-{8-amino-3-{(2R)-4-[(3-methyloxetan-3-yl)methyl]morpholin-2-yl}imidazo[1,5-a]pyrazin-1-yl}-N-[4-(trifluoromethyl)pyridin-2-yl]benzamide;

4-{8-amino-3-[(2R)-4-(cyclopropylmethyl)morpholin-2-yl]imidazo[1,5-a]pyrazin-1-yl}-N-[4-(trifluoromethyl)pyridin-2-yl]benzamide;

4-{8-amino-5-methyl-3-{(2R)-4-[(1-methyl-1H-pyrazol-4-yl)methyl]morpholin-2-yl}imidazo[1,5-a]pyrazin-1-yl}-N-[4-(trifluoromethyl)pyridin-2-yl]benzamide;

4-{8-amino-3-[(2R)-4-(3-methoxypropanoyl)morpholin-2-yl]-5-methylimidazo[1,5-a]pyrazin-1-yl}-N-[4-(trifluoromethyl)pyridin-2-yl]benzamide;

4-{8-amino-3-[(2R)-4-ethylmorpholin-2-yl]-5-methylimidazo[1,5-a]pyrazin-1-yl}-N-[4-(trifluoromethyl)pyridin-2-yl]benzamide;

4-{8-amino-3-[(2R)-4-(cyclopropylcarbonyl)morpholin-2-yl]imidazo[1,5-a]pyrazin-1-yl}-3-fluoro-N-[4-(trifluoromethyl)pyridin-2-yl]benzamide;

4-(8-amino-3-{(2R)-4-[(3-methyloxetan-3-yl)carbonyl]morpholin-2-yl}imidazo[1,5-a]pyrazin-1-yl)-3-fluoro-N-[4-(trifluoromethyl)pyridin-2-yl]benzamide;

4-(8-amino-5-methyl-3-{(2R)-4-[(3-methyloxetan-3-yl)carbonyl]morpholin-2-yl}imidazo[1,5-a]pyrazin-1-yl)-3-fluoro-N-[4-(trifluoromethyl)pyridin-2-yl]benzamide;

4-(8-amino-3-{(2R,5S)-5-methyl-4-[(3-methyloxetan-3-yl)carbonyl]morpholin-2-yl}imidazo[1,5-a]pyrazin-1-yl)-N-[4-(trifluoromethyl)pyridin-2-yl]benzamide;

4-{8-amino-3-[(2R,5S)-4-(cyclopropylcarbonyl)-5-methylmorpholin-2-yl]imidazo[1,5-a]pyrazin-1-yl}-N-[4-(trifluoromethyl)pyridin-2-yl]benzamide;

4-{8-amino-3-[(2R)-4-(hydroxyacetyl)morpholin-2-yl]imidazo[1,5-a]pyrazin-1-yl}-N-[4-(trifluoromethyl)pyridin-2-yl]benzamide;

4-{8-amino-3-[(2R)-4-(ethoxyacetyl)morpholin-2-yl]imidazo[1,5-a]pyrazin-1-yl}-N-[4-(trifluoromethyl)pyridin-2-yl]benzamide;

4-(8-amino-3-{(2R)-4-[(2S)-2-hydroxypropanoyl]morpholin-2-yl}imidazo[1,5-a]pyrazin-1-yl)-N-[4-(trifluoromethyl)pyridin-2-yl]benzamide;

4-(8-amino-3-{(2R)-4-[(2R)-2-hydroxypropanoyl]morpholin-2-yl}imidazo[1,5-a]pyrazin-1-yl)-N-[4-(trifluoromethyl)pyridin-2-yl]benzamide;

4-{8-amino-3-[(2R)-4-(methoxyacetyl)morpholin-2-yl]imidazo[1,5-a]pyrazin-1-yl}-N-[4-(trifluoromethyl)pyridin-2-yl]benzamide;

4-{8-amino-5-chloro-3-[(2R)-4-ethylmorpholin-2-yl]imidazo[1,5-a]pyrazin-1-yl}-N-[4-(trifluoromethyl)pyridin-2-yl]benzamide;

4-(8-amino-5-chloro-3-{(2R)-4-[(2S)-2-hydroxypropanoyl]morpholin-2-yl}imidazo[1,5-a]pyrazin-1-yl)-N-[4-(trifluoromethyl)pyridin-2-yl]benzamide;

4-(8-amino-5-chloro-3-{(2R)-4-[(2R)-2-hydroxypropanoyl]morpholin-2-yl}imidazo[1,5-a]pyrazin-1-yl)-N-[4-(trifluoromethyl)pyridin-2-yl]benzamide;

4-(8-amino-5-chloro-3-{(2R)-4-[(1-hydroxycyclopropyl)carbonyl]morpholin-2-yl}imidazo[1,5-a]pyrazin-1-yl)-N-[4-(trifluoromethyl)pyridin-2-yl]benzamide;

4-{8-amino-5-chloro-3-[(2R)-4-(2,2,2-trifluoroethyl)morpholin-2-yl]imidazo[1,5-a]pyrazin-1-yl}-N-[4-(trifluoromethyl)pyridin-2-yl]benzamide;

4-(8-amino-5-cyano-{(2R)-4-[(3-methyloxetan-3-yl)carbonyl]morpholin-2-yl}imidazo[1,5-a]pyrazin-1-yl)-N-[4-(trifluoromethyl)pyridin-2-yl]benzamide;

4-{8-amino-5-chloro-3-[(2R)-4-(methoxyacetyl)morpholin-2-yl]imidazo[1,5-a]pyrazin-1-yl}-N-[4-(trifluoromethyl)pyridin-2-yl]benzamide;

4-(8-amino-5-chloro-3-{(2R)-4-[(2-methoxyethoxy)acetyl]morpholin-2-yl}imidazo[1,5-a]pyrazin-1-yl)-N-[4-(trifluoromethyl)pyridin-2-yl]benzamide;

4-(8-amino-3-{(2S)-4-[(3-methyloxetan-3-yl)carbonyl]morpholin-2-yl}imidazo[1,5-a]pyrazin-1-yl)-N-[4-(trifluoromethyl)pyridin-2-yl]benzamide;

4-{8-amino-3-[(2R)-4-(cyanomethyl)morpholin-2-yl]imidazo[1,5-a]pyrazin-1-yl}-N-[4-(trifluoromethyl)pyridin-2-yl]benzamide;

4-{8-amino-3-[(2R)-4-(2-cyanoethyl)morpholin-2-yl]imidazo[1,5-a]pyrazin-1-yl}-N-[4-(trifluoromethyl)pyridin-2-yl]benzamide;

4-{8-amino-5-chloro-3-[(2R)-4-(cyanomethyl)morpholin-2-yl]imidazo[1,5-a]pyrazin-1-yl}-N-[4-(trifluoromethyl)pyridin-2-yl]benzamide;

4-{8-amino-3-[(2S)-4-ethylmorpholin-2-yl]imidazo[1,5-a]pyrazin-1-yl}-N-[4-(trifluoromethyl)pyridin-2-yl]benzamide;

4-{8-amino-5-chloro-3-[(2R)-4-(2-hydroxyethyl)morpholin-2-yl]imidazo[1,5-a]pyrazin-1-yl}-N-[4-(trifluoromethyl)pyridin-2-yl]benzamide;

4-{8-amino-3-[(2R)-4-(methoxyacetyl)morpholin-2-yl]-5-methylimidazo[1,5-a]pyrazin-1-yl}-N-[4-(trifluoromethyl)pyridin-2-yl]benzamide;

4-{8-amino-3-[(2R)-4-(ethoxyacetyl)morpholin-2-yl]-5-methylimidazo[1,5-a]pyrazin-1-yl}-N-[4-(trifluoromethyl)pyridin-2-yl]benzamide;

4-{8-amino-3-[(2R)-4-(difluoroacetyl)morpholin-2-yl]-5-methylimidazo[1,5-a]pyrazin-1-yl}-N-[4-(trifluoromethyl)pyridin-2-yl]benzamide;

4-{8-amino-3-[(2R)-4-(2-methoxyethyl)morpholin-2-yl]-5-methylimidazo[1,5-a]pyrazin-1-yl}-N-[4-(trifluoromethyl)pyridin-2-yl]benzamide;

4-{8-amino-3-[(2R)-4-(2-hydroxyethyl)morpholin-2-yl]-5-methylimidazo[1,5-a]pyrazin-1-yl}-N-[4-(trifluoromethyl)pyridin-2-yl]benzamide;

4-{8-amino-3-[(2R)-4-(2-ethoxyethyl)morpholin-2-yl]-5-methylimidazo[1,5-a]pyrazin-1-yl}-N-[4-(trifluoromethyl)pyridin-2-yl]benzamide;

4-{8-amino-5-chloro-3-[(2R)-4-(2-methoxyethyl)morpholin-2-yl]imidazo[1,5-a]pyrazin-1-yl}-N-[4-(trifluoromethyl)pyridin-2-yl]benzamide;

4-(8-amino-3-{(2R)-4-[(2S)-2-hydroxypropanoyl]morpholin-2-yl}-5-methylimidazo[1,5-a]pyrazin-1-yl)-N-[4-(trifluoromethyl)pyridin-2-yl]benzamide;

4-(8-amino-3-{(2R)-4-[(2R)-2-hydroxypropanoyl]morpholin-2-yl}-5-methylimidazo[1,5-a]pyrazin-1-yl)-N-[4-(trifluoromethyl)pyridin-2-yl]benzamide;

4-(8-amino-3-{(2R)-4-[(methylsulfonyl)acetyl]morpholin-2-yl}imidazo[1,5-a]pyrazin-1-yl)-N-[4-(trifluoromethyl)pyridin-2-yl]benzamide;

4-{8-amino-3-[(2R,5S)-5-(hydroxymethyl)morpholin-2-yl]imidazo[1,5-a]pyrazin-1-yl}-N-[4-(trifluoromethyl)pyridin-2-yl]benzamide;

4-{8-amino-3-[(2S,5R)-5-(hydroxymethyl)morpholin-2-yl]imidazo[1,5-a]pyrazin-1-yl}-N-[4-(trifluoromethyl)pyridin-2-yl]benzamide;

4-{8-amino-3-{(2R,5S)-5-(hydroxymethyl)-4-[(1-methyl-1H-pyrazol-4-yl)methyl]morpholin-2-yl}imidazo[1,5-a]pyrazin-1-yl)-N-[4-(trifluoromethyl)pyridin-2-yl]benzamide;

4-{8-amino-3-[(2R,5S)-4-ethyl-5-(hydroxymethyl)morpholin-2-yl]imidazo[1,5-a]pyrazin-1-yl}-N-[4-(trifluoromethyl)pyridin-2-yl]benzamide;

4-{8-amino-3-[(2R)-4-oxetan-3-ylmorpholin-2-yl]imidazo[1,5-a]pyrazin-1-yl}-N-[4-(trifluoromethyl)pyridin-2-yl]benzamide;

4-{8-amino-3-[(2R)-4-(methoxyacetyl)morpholin-2-yl]imidazo[1,5-a]pyrazin-1-yl}-3-fluoro-N-[4-(trifluoromethyl)pyridin-2-yl]benzamide;

4-{4-amino-1-[(4R)-1-methyl-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4S)-1-methyl-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4R)-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4S)-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(3S,6R)-6-(trifluoromethyl)piperidin-3-yl]-1H-pyrazolo[3,4-d]pyrimidin-3-yl}-N-[4-(trifluoromethyl)pyridin-2-yl]benzamide;

4-{4-amino-1-[(4R)-2-methyl-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{4-amino-1-[(4S)-2-methyl-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{4-amino-1-[(4R)-1-ethyl-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4S)-2-ethyl-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{4-amino-1-[(4R)-1-(2-hydroxyethyl)-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4R)-2-(2-hydroxyethyl)-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{4-amino-1-[(4S)-1-(2-hydroxyethyl)-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4S)-2-(2-hydroxyethyl)-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{8-amino-3-[(2R)-1,4-dimethylpiperazin-2-yl]imidazo[1,5-a]pyrazin-1-yl}-N-[4-(trifluoromethyl)pyridin-2-yl]benzamide;

4-(8-amino-3-{(2R)-4-[(1-methyl-1H-pyrazol-4-yl)methyl]piperazin-2-yl}imidazo[1,5-a]pyrazin-1-yl)-N-[4-(trifluoromethyl)pyridin-2-yl]benzamide;

4-(8-amino-3-{(2R)-4-[(1-methylcyclopropyl)carbonyl]piperazin-2-yl}imidazo[1,5-a]pyrazin-1-yl)-N-[4-(trifluoromethyl)pyridin-2-yl]benzamide;

4-{8-amino-3-[(2R)-4-(3-methoxypropanoyl)piperazin-2-yl]imidazo[1,5-a]pyrazin-1-yl}-N-[4-(trifluoromethyl)pyridin-2-yl]benzamide;

4-(8-amino-3-{4-[(1-methyl-1H-pyrazol-4-yl)methyl]-1,1-dioxidothiomorpholin-2-yl}imidazo[1,5-a]pyrazin-1-yl)-N-[4-(trifluoromethyl)pyridin-2-yl]benzamide;

4-[8-amino-3-(4-methyl-1,1-dioxidothiomorpholin-2-yl)imidazo[1,5-a]pyrazin-1-yl]-N-[4-(trifluoromethyl)pyridin-2-yl]benzamide;

4-(8-amino-3-{4-[(1-cyanocyclopropyl)carbonyl]-1,1-dioxidothiomorpholin-2-yl}imidazo[1,5-a]pyrazin-1-yl)-N-[4-(trifluoromethyl)pyridin-2-yl]benzamide;

4-{8-amino-3-[4-(3-methoxypropanoyl)-1,1-dioxidothiomorpholin-2-yl]imidazo[1,5-a]pyrazin-1-yl}-N-[4-(trifluoromethyl)pyridin-2-yl]benzamide;

4-[8-amino-3-(1-ethyl-2-oxopiperidin-4-yl)imidazo[1,5-a]pyrazin-1-yl]-N-[4-(trifluoromethyl)pyridin-2-yl]benzamide;

4-(8-amino-3-{(3R)-1-[(3-methyloxetan-3-yl)carbonyl]azepan-3-yl}imidazo[1,5-a]pyrazin-1-yl)-N-[4-(trifluoromethyl)pyridin-2-yl]benzamide;

4-{8-amino-3-[(3R)-1-(methoxyacetyl)piperidin-3-yl]imidazo[1,5-a]pyrazin-1-yl}-3-fluoro-N-[4-(trifluoromethyl)pyridin-2-yl]benzamide;

4-{8-amino-3-[(3R)-1-(3-methoxypropanoyl)piperidin-3-yl]imidazo[1,5-a]pyrazin-1-yl}-3-fluoro-N-[4-(trifluoromethyl)pyridin-2-yl]benzamide and 4-{8-amino-5-bromo-3-[(3R)-1-(cyclopropylcarbonyl)piperidin-3-yl]imidazo[1,5-a]pyrazin-1-yl}-N-[4-(trifluoromethyl)pyridin-2-yl]benzamide.

Another aspect of the invention is a compound having Formula I or a pharmaceutically acceptable salt or solvate thereof selected from the group consisting of:

4-(8-amino-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-3-fluoro-N-[4-(trifluoromethyl)pyridin-2-yl]benzamide;

4-(8-amino-3-{(3R)-1-[(2S)-2-hydroxypropanoyl]piperidin-3-yl}imidazo[1,5-a]pyrazin-1-yl)-N-[4-(trifluoromethyl)pyridin-2-yl]benzamide;

4-(8-amino-3-{(3R)-1-[(2R)-2-hydroxypropanoyl]piperidin-3-yl}imidazo[1,5-a]pyrazin-1-yl)-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-N-[5-(difluoromethyl)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-3-fluoro-N-[4-(trifluoromethyl)pyridin-2-yl]benzamide;

4-{8-amino-3-[(3R,6S)-1-(cyclopropylcarbonyl)-6-methylpiperidin-3-yl]imidazo[1,5-a]pyrazin-1-yl}-3-fluoro-N-[4-(trifluoromethyl)pyridin-2-yl]benzamide;

4-{8-amino-3-[(3R,6S)-1-(3-methoxypropanoyl)-6-methylpiperidin-3-yl]imidazo[1,5-a]pyrazin-1-yl}-3-fluoro-N-[4-(trifluoromethyl)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-2-chloro-N-[4-(trifluoromethyl)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-N-[4-(1,1-difluoroethyl)pyridin-2-yl]benzamide;

4-{8-amino-3-[(3R,6S)-1-(cyclopropylcarbonyl)-6-methylpiperidin-3-yl]imidazo[1,5-a]pyrazin-1-yl}-N-[4-(difluoromethyl)pyridin-2-yl]-3-fluorobenzamide;

4-[8-amino-5-(methoxymethyl)-3-{(3R)-1-[(3-methyloxetan-3-yl)carbonyl]piperidin-3-yl}imidazo[1,5-a]pyrazin-1-yl]-N-[4-(trifluoromethyl)pyridin-2-yl]benzamide;

4-(8-amino-5-methyl-3-{(3R)-1-[(3-methyloxetan-3-yl)carbonyl]piperidin-3-yl}imidazo[1,5-a]pyrazin-1-yl)-N-[4-(cyclopropyloxy)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-2-fluoro-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-3-methoxy-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-N-[4-(cyclopropyloxy)pyridin-2-yl]-3-fluorobenzamide;

4-(8-amino-3-{(3R)-1-[(3-methyloxetan-3-yl)carbonyl]piperidin-3-yl}imidazo[1,5-a]pyrazin-1-yl)-N-(4-chloropyridin-2-yl)-3-fluorobenzamide;

4-{8-amino-5-chloro-3-[(2R)-4-(methoxyacetyl)morpholin-2-yl]imidazo[1,5-a]pyrazin-1-yl}-N-[4-(trifluoromethyl)pyridin-2-yl]benzamide;

4-{8-amino-3-[(2R)-4-oxetan-3-ylmorpholin-2-yl]imidazo[1,5-a]pyrazin-1-yl}-N-[4-(trifluoromethyl)pyridin-2-yl]benzamide;

4-{8-amino-3-[(3R)-1-(methoxyacetyl)piperidin-3-yl]imidazo[1,5-a]pyrazin-1-yl}-3-fluoro-N-[4-(trifluoromethyl)pyridin-2-yl]benzamide; and 4-{8-amino-3-[(3R)-1-(3-methoxypropanoyl)piperidin-3-yl]imidazo[1,5-a]pyrazin-1-yl}-3-fluoro-N-[4-(trifluoromethyl)pyridin-2-yl]benzamide.

In still another aspect the invention relates to the compounds of Formula I or pharmaceutically acceptable salts or solvates thereof selected from the group consisting of:

4-(8-amino-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide 4-(8-amino-3-{(3R)-1-[(3-methyloxetan-3-yl)carbonyl]piperidin-3-yl}imidazo[1,5-a]pyrazin-1-yl)-3-fluoro-N-[4-(trifluoromethyl)pyridin-2-yl]benzamide 4-(8-amino-3-{(3R,6S)-6-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide 4-(8-amino-3-{(3R,6S)-6-methyl-1-[(3-methyloxetan-3-yl)carbonyl]piperidin-3-yl}imidazo[1,5-a]pyrazin-1-yl)-3-fluoro-N-[4-(trifluoromethyl)pyridin-2-yl]benzamide 4-{8-amino-3-[(3R,6S)-1-(cyclopropylcarbonyl)-6-methylpiperidin-3-yl]imidazo[1,5-a]pyrazin-1-yl}-3-fluoro-N-[4-(trifluoromethyl)pyridin-2-yl]benzamide 4-(8-amino-3-{(3R,6S)-6-methyl-1-[(3-methyloxetan-3-yl)carbonyl]piperidin-3-yl}imidazo[1,5-a]pyrazin-1-yl)-2-chloro-N-[4-(trifluoromethyl)pyridin-2-yl]benzamide 4-[8-amino-5-(methoxymethyl)-3-{(3R)-1-[(3-methyloxetan-3-yl)carbonyl]piperidin-3-yl}imidazo[1,5-a]pyrazin-1-yl]-N-[4-(trifluoromethyl)pyridin-2-yl]benzamide 4-(8-amino-3-{(3R,6S)-6-methyl-1-[(3-methyloxetan-3-yl)carbonyl]piperidin-3-yl}imidazo[1,5-a]pyrazin-1-yl)-2-fluoro-N-[4-(trifluoromethyl)pyridin-2-yl]benzamide 4-(8-amino-3-{(3R)-1-[(3-methyloxetan-3-yl)carbonyl]piperidin-3-yl}imidazo[1,5-a]pyrazin-1-yl)-N-(4-chloropyridin-2-yl)-3-fluorobenzamide 4-{8-amino-3-[(3R)-1-(methoxyacetyl)piperidin-3-yl]imidazo[1,5-a]pyrazin-1-yl}-3-fluoro-N-[4-(trifluoromethyl)pyridin-2-yl]benzamide 4-{8-amino-3-[(3R)-1-(3-methoxypropanoyl)piperidin-3-yl]imidazo[1,5-a]pyrazin-1-yl}-3-fluoro-N-[4-(trifluoromethyl)pyridin-2-yl]benzamide.

In still another aspect the invention relates to 4-(8-amino-3-((cis)-1-(3-methoxypropanoyl)-6-methylpiperidin-3-yl)imidazo[1,5-a]pyrazin-1-yl)-N-(4-cyclopropylpyridin-2-yl)benzamide.

In another aspect the invention relates to 4-(8-amino-3-((cis)-1-(cyclobutanecarbonyl)-6-methylpiperidin-3-yl)imidazo[1,5-a]pyrazin-1-yl)-N-(4-cyclopropylpyridin-2-yl)benzamide.

In yet another aspect the invention relates to (cis)-5-(8-amino-1-(4-(4-(trifluoromethyl)pyridin-2-ylcarbamoyl)phenyl)imidazo[1,5-a]pyrazin-3-yl)-N-ethyl-2-methylpiperidine-1-carboxamide.

In another aspect the invention relates to (R)-4-(8-amino-3-(1-(3-methoxypropanoyl)piperidin-3-yl)imidazo[1,5-a]pyrazin-1-yl)-N-(pyridin-2-yl)benzamide.

In still another aspect the invention relates to 4-(8-amino-3-((cis)-6-methyl-1-(tetrahydrofuran-2-carbonyl)piperidin-3-yl)imidazo[1,5-a]pyrazin-1-yl)-N-(4-(trifluoromethyl)pyridin-2-yl)benzamide.

The 6-5 membered fused pyridine ring compounds of the invention having Formula I inhibit the Btk kinase activity. All compounds of the invention have an EC50 of 10 μM or lower. In another aspect the invention relates to compounds of Formula I which have an EC50 of less than 100 nM. In yet another aspect the invention relates to compounds of Formula I which have an EC50 of less than 10 nM.

The term EC50 means the concentration of the test compound that is required for 50% inhibition of its maximum effect in vitro.

In another aspect the invention relates to compounds of Formula I or pharmaceutically acceptable salts thereof, which have an IC50 of less than 100 nM. In yet another aspect the invention relates to the compounds of Formula I or pharmaceutically acceptable salts thereof, which have an IC50 of less than 10 nM.

The term IC50 means the concentration of the test compound that is required for 50% inhibition of its maximum effect in vitro.

Inhibition of kinase activity can be measured using the Immobilized Metal Assay for Phosphochemicals (IMAP) assay. IMAP is a homogeneous fluorescence polarization (FP) assay based on affinity capture of phosphorylated peptide substrates. IMAP uses fluorescein-labeled peptide substrates that, upon phosphorylation by a protein kinase, bind to so-called IMAP nanoparticles, which are derivatized with trivalent metal complexes. Binding causes a change in the rate of the molecular motion of the peptide, and results in an increase in the FP value observed for the fluorescein label attached to the substrate peptide (Gaudet et al. A homogeneous fluorescence polarization assay adaptable for a range of protein serine/threonine and tyrosine kinases. J. Biomol. Screen (2003) 8, 164-175).

The Btk activity can also be determined in B cell lines such as Ramos cells or in primary cell assays, e.g PBMC or whole blood from human, monkey, rat or mouse or isolated splenocytes from monkey, rat or mouse Inhibition of Btk activity can be investigated measuring anti-IgM-induced MIP1β production (Ramos, PBMC, splenocytes), $H_2O_2$-induced Btk and PLCγ2 phosphorylation (Ramos cells), or anti-IgM-induced B cell proliferation or CD86 expression on primary B cells (PBMC and splenocytes).

Regulation of Btk activity can also be determined on human, monkey, rat or mouse mast cells following activation FcεR induced degranulation, cytokine production and CD63 induced cell surface expression.

Furthermore, regulation of Btk activity can be determined on CD14+ monocytes differentiated following treatment with M-CSF to osteoclasts and activated with RANKL.

Activity of Btk inhibitors can be investigated in mouse splenocytes following administration in vivo. In a typical experiment mice can be euthanized 3h following compound administration. Spleens can be extracted from the treated mice for splenocyte isolation. Splenocytes can be plated in 96 well culture plates and stimulated with anti-IgM, without further addition of compounds. Anti-IgM-induced B cell stimulation and inhibition thereof by Btk inhibitors can be measured by B cell proliferation, MIP1β production or CD86 expression on CD19+ splenocyte B cells.

Efficacy of Btk inhibitors can also be investigated in the mouse collagen induced arthritis model using a therapeutic protocol with start of treatment following onset of disease, measuring disease score, X-ray analysis of bone destruction, cartilage breakdown and histology of joints Efficacy of Btk inhibitors on the regulation of activated mast cells can be investigated in vivo using the passive cutaneous anaphylaxis model.

The effect of Btk inhibitors on bone resorption in vivo can be investigated using the rat OVX model. In this model ovariectomized animals develop symptoms of osteoporosis that may be regulated using a Btk inhibitor.

The compounds of Formula I can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The compounds of Formula I may have the ability to crystallize in more than one form, a characteristic known as polymorphism, and it is understood that such polymorphic forms ("polymorphs") are within the scope of Formula I. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of Formula I may contain asymmetric or chiral centers, and, therefore, exist in different stereoisomeric forms. It is intended that all stereoisomeric forms of the compounds of Formula I as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula I may be atropisomers (e.g. substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The compounds having Formula I or the pharmaceutically acceptable salts or solvates thereof may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

One or more compounds of the invention having Formula I or the pharmaceutically acceptable salts or solvates thereof may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Certain isotopically-labelled compounds of Formula I (e.g. those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labeled reagent for a non-isotopically labeled reagent.

The compounds having Formula I and pharmaceutical compositions thereof can be used to treat or prevent a variety of conditions or diseases mediated by Bruton's Tyrosine kinase (Btk). Such conditions and diseases include, but are not limited to: (1) arthritis, including rheumatoid arthritis, juvenile arthritis, psoriatic arthritis and osteoarthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3)

autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g. precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors, myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; (14) low grade scarring including scleroderma, increased fibrosis, keloids, post-surgical scars, pulmonary fibrosis, vascular spasms, migraine, reperfusion injury, and post-myocardial infarction.

The invention thus provides compounds of Formula (I) and salts, solvates and physiologically functional derivatives thereof for use in therapy, and particularly in the treatment of diseases and conditions mediated by inappropriate Btk activity.

The inappropriate Btk activity referred to herein is any Btk activity that deviates from the normal Btk activity expected in a particular mammalian subject. Inappropriate Btk activity may take the form of, for instance, an abnormal increase in activity, or an aberration in the timing and or control of Btk activity. Such inappropriate activity may result then, for example, from overexpression or mutation of the protein kinase leading to inappropriate or uncontrolled activation.

In a further embodiment, the present invention is directed to methods of regulating, modulating, or inhibiting Btk for the prevention and/or treatment of disorders related to unregulated or inappropriate Btk activity.

In a further embodiment, the present invention provides a method of treatment of a mammal suffering from a disorder mediated by Btk activity, which comprises administering to said mammal an effective amount of a compound of Formula (I) or a pharmaceutically acceptable salt, solvate, or a physiologically functional derivative thereof.

In a further embodiment, the present invention provides for the use of a compound of Formula (I), or a pharmaceutically acceptable salt or solvate thereof, or a physiologically functional derivative thereof, in the preparation of a medicament for the treatment of a disorder mediated by Btk activity.

In a further embodiment said disorder mediated by Btk activity is asthma. In a further embodiment said disorder is rheumatoid arthritis. In yet another embodiment, said disorder is cancer. In a further embodiment said disorder is ocular conjunctivitis.

Yet another aspect of the present invention provides a method for treating diseases caused by or associated with Fc receptor signaling cascades, including FceRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Btk is known to play a critical role in immunotyrosine-based activation motif (ITAM) signaling, B cell receptor signaling, T cell receptor signaling and is an essential component of integrin beta (1), beta (2), and beta (3) signaling in neutrophils. Thus, compounds of the present invention can be used to regulate Fc receptor, ITAM, B cell receptor and integrin signaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

A further aspect of the invention resides in the use of a compound of Formula I or a pharmaceutically acceptable salt thereof for the manufacture of a medicament to be used for the treatment of Btk-mediated diseases or Btk-mediated conditions.

A further aspect of the invention resides in the use of a compound of Formula I or a pharmaceutically acceptable salt thereof for the manufacture of a medicament to be used for the treatment of chronic B cell disorders in which T cells play a prominent role.

In yet another aspect the invention resides in the use of a compound of Formula I or a pharmaceutically acceptable salt thereof for the manufacture of a medicament to be used for the treatment of Btk-mediated diseases or conditions. These include, but are not limited to, the treatment of B cell lymphomas resulting from chronic active B cell receptor signaling.

Thus, the compounds according to the invention may be used in therapies to treat or prevent diseases Bruton's Tyrosine Kinase (Btk) mediated disorders. Btk mediated disorders or Btk mediated condition as used herein, mean any disease state or other deleterious condition in which B cells, mast cells, myeloid cells or osteoclasts play a central role. These diseases include but are not limited to, immune, autoimmune and inflammatory diseases, allergies, infectious diseases, bone resorption disorders and proliferative diseases.

Immune, autoimmune and inflammatory diseases that may be treated or prevented with the compounds of the present invention include rheumatic diseases (e.g. rheumatoid arthritis, psoriatic arthritis, infectious arthritis, progressive chronic arthritis, deforming arthritis, osteoarthritis, traumatic arthritis, gouty arthritis, Reiter's syndrome, polychondritis, acute synovitis and spondylitis), glomerulonephritis (with or without nephrotic syndrome), Goodpasture's syndrome, (and associated glomerulonephritis and pulmonary hemorrhage), atherosclerosis, autoimmune hematologic disorders (e.g. hemolytic anemia, aplasic anemia, idiopathic thrombocytopenia, chronic idiopathic thrombocytopenic purpura (ITP), and neutropenia), autoimmune gastritis, and autoimmune inflammatory bowel diseases (e.g. ulcerative colitis and Crohn's disease), irritable bowel syndrome, host versus graft disease, allograft rejection, chronic thyroiditis, Graves' disease, Sjorgren's disease, scleroderma, diabetes (type I and type II), active hepatitis (acute and chronic), pancreatitis, primary billiary cirrhosis, myasthenia gravis, multiple sclerosis, systemic lupus erythematosis, psoriasis, atopic dermatitis, dermatomyositis, contact dermatitis, eczema, skin sunburns, vasculitis (e.g. Behcet's disease), ANCA-associated and other vasculitudes, chronic renal insufficiency, Stevens-Johnson syndrome, inflammatory pain, idiopathic sprue, cachexia, sarcoidosis, Guillain-Barré syndrome, uveitis, conjunctivitis, kerato conjunctivitis, otitis media, periodontal disease, Addison's disease, Parkinson's disease, Alzheimer's disease, diabetes, septic shock, myasthenia gravis, pulmonary interstitial fibrosis, asthma, bronchitis, rhinitis, sinusitis, pneumoconiosis, pulmonary insufficiency syndrome, pulmonary emphysema, pulmonary fibrosis, silicosis, chronic inflammatory pulmonary disease (e.g. chronic obstructive pulmonary disease) and other inflammatory or obstructive disease on airways.

Allergies that may be treated or prevented include, among others, allergies to foods, food additives, insect poisons, dust mites, pollen, animal materials and contact allergans, type I hypersensitivity allergic asthma, allergic rhinitis, allergic conjunctivitis.

Infectious diseases that may be treated or prevented include, among others, sepsis, septic shock, endotoxic shock, sepsis by Gram-negative bacteria, shigellosis, meningitis, cerebral malaria, pneumonia, tuberculosis, viral myocarditis, viral hepatitis (hepatitis A, hepatitis B and hepatitis C), HIV infection, retinitis caused by cytomegalovirus, influenza, herpes, treatment of infections associated with severe burns, myalgias caused by infections, cachexia secondary to infections, and veterinary viral infections such as lentivirus, caprine arthritic virus, visna-maedi virus, feline immunodeficiency virus, bovine immunodeficiency virus or canine immunodeficiency virus.

Bone resorption disorders that may be treated or prevented include, among others, osteoporosis, osteoarthritis, traumatic arthritis, gouty arthritis and bone disorders related with multiple myeloma.

Proliferative diseases that may be treated or prevented include, among others, non-Hodgkin lymphoma (in particular the subtypes diffuse large B-cell lymphoma (DLBCL) and mantle cell lymphoma (MCL)), B cell chronic lymphocytic leukemia and acute lymphoblastic leukemia (ALL) with mature B cell, ALL in particular.

In particular the compounds of Formula I or pharmaceutically acceptable salts may be used for the treatment of B cell lymphomas resulting from chronic active B cell receptor signaling.

Included herein are methods of treatment and/or pharmaceutical compositions in which at least one compound of Formula I or a pharmaceutically acceptable salt thereof is administered in combination with at least one other active agent. The other active agent is an anti-inflammatory agent, an immunosuppressant agent, or a chemotherapeutic agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory agent is an anti-C5 monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant agent, such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., J. Biol. Chem. 1998, 274, 1646-1656).

It has also been discovered that BTK inhibitors are useful as chemosensitizing agents, and, thus, are useful in combination with other chemotherapeutic agents, in particular, drugs that induce apoptosis. Examples of other chemotherapeutic agents that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Btk activity has also been associated with some leukemias expressing the bcr-abl fusion gene resulting from translocation of parts of chromosome 9 and 22. This abnormality is commonly observed in chronic myelogenous leukemia. Btk is constitutively phosphorylated by the bcr-abl kinase which initiates downstream survival signals which circumvents apoptosis in bcr-abl cells. (N. Feldhahn et al. J. Exp. Med. 2005 201(11):1837-1852).

While it is possible that, for use in therapy, a compound of Formula (I), as well as salts, solvates and physiological functional derivatives thereof, may be administered as the raw chemical, it is possible to present the active ingredient as a pharmaceutical composition. Accordingly, the invention further provides a pharmaceutical composition, which comprises a compound of Formula (I) and salts, solvates and physiological functional derivatives thereof, and one or more pharmaceutically acceptable carriers, diluents or excipients. The compounds of the Formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of the Formula (I), or salts, solvates and physiological functional derivatives thereof, with one or more pharmaceutically acceptable carriers, diluents or excipients.

Pharmaceutical compositions of the present invention may be presented in unit dose forms containing a predetermined amount of active ingredient per unit dose. Such a unit may contain, for example, 5 µg to 1 g, preferably 1 mg to 700 mg, more preferably 5 mg to 100 mg of a compound of the Formula (I), depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, sublingual, subcutaneous, local or parenteral (including intravenous and intramuscular) route, and the like, all in unit dosage forms for administration. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, Chronic Obstructive Pulmonary disease (COPD) or Acute Respiratory Distress Syndrome (ARDS).

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of Formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of Formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of Formula (I) is in a particle-size-reduced form, and more preferably the size-reduced form is obtained or obtainable by micronisation. The preferable particle size of the size-reduced (e.g. micronised) compound or salt or solvate is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of Formula (I) or salt or solvate thereof (preferably in particle-size-reduced form, e.g. in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of Formula (I) or salt thereof. The lactose is preferably lactose hydrate e.g. lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g. 10-1000 microns e.g. 30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Schering-Plough), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurized aerosols, nebulizers or insufflators.

For pharmaceutical compositions suitable and/or adapted for intranasal administration, the compound of Formula (I) or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The invention further includes a pharmaceutical composition of a compound of Formula I or pharmaceutically acceptable salts thereof, as hereinbefore described, in combination with packaging material suitable for said composition, said packaging material including instructions for the use of the composition for the use as hereinbefore described.

The following are examples of representative pharmaceutical dosage forms for the compounds of this invention:

| Injectable Suspension (I.M.) | mg/ml |
|---|---|
| Compound of Formula Ia | 10 |
| Methylcellulose | 5.0 |
| Tween 80 | 0.5 |
| Benzyl alcohol | 9.0 |
| Benzalkonium chloride | 1.0 |

Water for injection to a total volume of 1 ml

| Tablet | mg/tablet |
|---|---|
| Compound of Formula Ia | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula Ia | 25 |
| Lactose Powder | 573.5 |
| Magnesium Stearate | 1.5 |
| | 600 |

| Aerosol | Per canister |
|---|---|
| Compound of Formula Ia | 24 mg |
| Lecithin, NF Liquid Concentrate | 1.2 mg |
| Trichlorofluoromethane, NF | 4.025 gm |
| Dichlorodifluoromethane, NF | 12.15 gm |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavoring agents.

A therapeutically effective amount of a compound of the present invention will depend upon a number of factors including, for example, the age and weight of the animal, the precise condition requiring treatment and its severity, the particular compound having Formula I, the nature of the formulation, and the route of administration, and will ultimately be at the discretion of the attendant physician or veterinarian. However, an effective amount of a compound of Formula (I) for the treatment of diseases or conditions associated with inappropriate Btk activity, will generally be in the range of 5 µg to 100 mg/kg body weight of recipient (mammal) per day and more usually in the range of 5 µg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula (I) per se.

In general parenteral administration requires lower dosages than other methods of administration which are more dependent upon absorption. However, a dosage for humans preferably contains 0.0001-25 mg of a compound of Formula I or pharmaceutically acceptable salts thereof per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

The present invention also relates to a pharmaceutical composition comprising a compound of Formula I or pharmaceutically acceptable salt thereof in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition comprising at least one compound of Formula I or pharmaceutically acceptable salts thereof in combination with at least one other therapeutically active agent.

Compounds of the present invention, and their salts and solvates, and physiologically functional derivatives thereof, may be employed alone or in combination with other therapeutic agents for the treatment of Btk mediated diseases and conditions associated with inappropriate Btk activity. Combination therapies according to the present invention thus comprise the administration of at least one compound of Formula (I) or a pharmaceutically acceptable salt or solvate thereof, or a physiologically functional derivative thereof, and the use of at least one other pharmaceutically active agent. The compound(s) of Formula (I) and the other pharmaceutically active agent(s) may be administered together or separately and, when administered separately this may occur simultaneously or sequentially in any order. The amounts of the compound(s) of Formula (I) and the other pharmaceutically active agent(s) and the relative timings of administration will be selected in order to achieve the desired combined therapeutic effect.

For the treatment of the inflammatory diseases, rheumatoid arthritis, psoriasis, inflammatory bowel disease, COPD, asthma and allergic rhinitis a compound of Formula I may be combined with one or more other active agents such as: (1) TNF-α inhibitors such as infliximab (Remicade®), etanercept (Enbrel®), adalimumab (Humira®), certolizumab pegol (Cimzia®), and golimumab (Simponi®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, etodolac, azapropazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, cilomilast, AWD-12-281 (Elbion), and PD-168787 (Pfizer); (8) antihistaminic H1 receptor antagonists such as cetirizine, levocetirizine, loratadine, desloratadine, fexofenadine, astemizole, azelastine, levocabastine, olopatidine, methapyrilene and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, (R,R)-glycopyrrolate, pirenzepine, and telenzepine; (11) β-adrenoceptor agonists such as metaproterenol, isoproterenol, isoprenaline, albuterol, formoterol (particularly the fumarate salt), salmeterol (particularly the xinafoate salt), terbutaline, orciprenaline, bitolterol mesylate, fenoterol, and pirbuterol, or methylxanthanines including theophylline and aminophylline, sodium cromoglycate; (12) insulin-like growth factor type I (IGF-1) mimetic; (13) glucocorticosteroids, especially inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate; (14) kinase inhibitors such as inhibitors of the Janus Kinases (JAK 1 and/or JAK2 and/or JAK 3 and/or TYK2), p38 MAPK and IKK2; (15) B-cell targeting biologics such as rituximab (Rituxan®); (16) selective costimulation modulators such as abatacept (Orencia); (17) interleukin inhibitors, such as IL-1 inhibitor anakinra (Kineret) and IL-6 inhibitor tocilizumab (Actemra).

The present invention also provides for "triple combination" therapy, comprising a compound of Formula (I) or a pharmaceutically acceptable salt thereof together with beta$_2$-adrenoreceptor agonist and an anti-inflammatory corticosteroid. Preferably this combination is for treatment and/or prophylaxis of asthma, COPD or allergic rhinitis. The beta$_2$-adrenoreceptor agonist and/or the anti-inflammatory corticosteroid can be as described above and/or as described in WO 03/030939 A1. Representative examples of such a "triple" combination are a compound of Formula (I) or a pharmaceutically acceptable salt thereof in combination with the components of Advair® (salmeterol xinafoate and fluticasone propionate), Symbicort® (budesonide and formoterol fumarate), or Dulera® (mometasone furoate and formoterol).

For the treatment of cancer a compound of Formula I may be combined with one or more of an anticancer agents. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: (1) estrogen receptor modulator such as diethylstibestral, tamoxifen, raloxifene, idoxifene, LY353381, LY117081, toremifene, fluoxymestero, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) androgen receptor modulator such as finasteride and other 5α-reductase inhibitors, nilutamide, flutamide, bicalutamide, liarozole, and abiraterone acetate; (4) retinoid receptor modulator such as bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide; (5) antiproliferative agent such asantisense RNA and DNA oligonucleotides such as G3139, ODN698, RVASKRAS, GEM231, and INX3001, and anti-metabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone; (6) prenyl-protein transferase inhibitor including farnesyl-protein transferase (FPTase), geranylgeranyl-protein transferase type I (GGPTase-I), and geranylgeranyl-protein transferase type-II (GGPTase-II, also called Rab GGPTase); (7) HMG-CoA reductase inhibitor such as lovastatin, simvastatin, pravastatin, atorvastatin, fluvastatin and rosuvastatin; (8) angiogenesis inhibitor such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonyl)-fumagillol, thalidomide, angiostatin, troponin-1, angiotensin II antagonists, heparin, carboxypeptidase U inhibitors, and antibodies to VEGF, endostatin, ukrain, ranpirnase, IM862, acetyldinanaline, 5-amino-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, and 3-[(2,4-dimethylpyrrol-5-yl)methylene]-2-indolinone (SU5416); (9) PPAR-γ agonists, PPAR-δ agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and (2R)-7-(3-(2-chloro-4-(4-fluorophenoxy)phenoxy)propoxy)-2-ethylchromane-2-carboxylic acid (disclosed in U.S. Ser. No. 60/235,708 and 60/244,697); (9) inhibitor of inherent multidrug resistance including inhibitors of p-glycoprotein (P-gp), such as LY335979, XR9576, OC144-093, R101922, VX853 and PSC833 (valspodar); (10) inhibitor of cell proliferation and survival signaling such as inhibitors of EGFR (for example gefitinib and erlotinib), inhibitors of ERB-2 (for example trastuzumab), inhibitors of IGF1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) agent that interferes with a cell cycle checkpoint including inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032; (15) BTK inhibitors such as PCI32765, AVL-292 and AVL-101; (16) PARP inhibitors including iniparib, olaparib, AGO14699, ABT888 and MK4827; (16) ERK inhibitors; (17) mTOR inhibitors such as sirolimus, ridaforolimus, temsirolimus, everolimus; (18) cytotoxic/cytostatic agents.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin.

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]-phenanthridinium, 5-(3-aminopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]-formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins include, but are not limited to inhibitors of KSP, inhibitors of MKLP1, inhibitors of CENP-E, inhibitors of MCAK, inhibitors of Kifl4, inhibitors of Mphosph1 and inhibitors of Rab6-KIFL.

Examples of "histone deacetylase inhibitors" include, but are not limited to, vorinostat, trichostatin A, oxamflatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2,4-tetradecadienoyl]glycylamino]-L-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable agents used in cancer therapy that may be combined with compounds of Formula I include, but are not limited to, abarelix; aldesleukin; alemtuzumab; alitretinoin; allopurinol; altretamine; amifostine; anastrozole; arsenic trioxide; asparaginase; azacitidine; bendamustine; bevacuzimab; bexarotene; bleomycin; bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin; darbepoetin alfa; dasatinib; daunorubicin; degarelix; denileukin diftitox; dexrazoxane; docetaxel; doxorubicin; dromostanolone propionate; eculizumab; Elliott's B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; gefitinib; gemcitabine; gemtuzumab ozogamicin; goserelin acetate; histrelin acetate; hydroxyurea; ibritumomab tiuxetan; idarubicin; ifosfamide; imatinib mesylate; interferon alfa 2a; interferon alfa-2b; irinotecan; ixabepilone; lapatinib; lenalidomide; letrozole; leucovorin; leuprolide acetate; levamisole; lomustine; meclorethamine, nitrogen mustard; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofetumomab; ofatumumab; oprelvekin; oxaliplatin; paclitaxel; palifermin; pamidronat; panitumumab; pazopanib; pegademase; pegaspargase; Pegfilgrastim; pemetrexed disodium; pentostatin; pipobroman; plerixafor; plicamycin, mithramycin); porfimer sodium; pralatrexate; procarbazine; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronate.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

General Synthesis

The 8-amino-imidazo[1,5-a]pyrazine, 4-amino-imidazo[1,5-f][1,2,4]triazine, 4-amino-pyrazolo[3,4-d]pyrimidine and 4-amino-pyrrolo[1,2-f][1,2,4]triazine derivatives of the present invention can be prepared by methods well known in the art of organic chemistry. See, for example, J. March, 'Advanced Organic Chemistry' 4th Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts 'Protective Groups in Organic Synthesis' 3rd Edition, John Wiley and Sons, 1999. The protective groups are optionally removed at a convenient subsequent stage using methods well known in the art.

The products of the reactions are optionally isolated and purified, if desired, using conventional techniques, but not limited to, filtration, distillation, crystallization, chromatography and the like. Such materials are optionally characterized using conventional means, including physical constants and spectral data.

8-amino-imidazo[1,5-a]pyrazine compounds of Formula I, wherein $R_1$-$R_x$ have the previously defined meanings, can be prepared by the general synthetic route shown in scheme I.

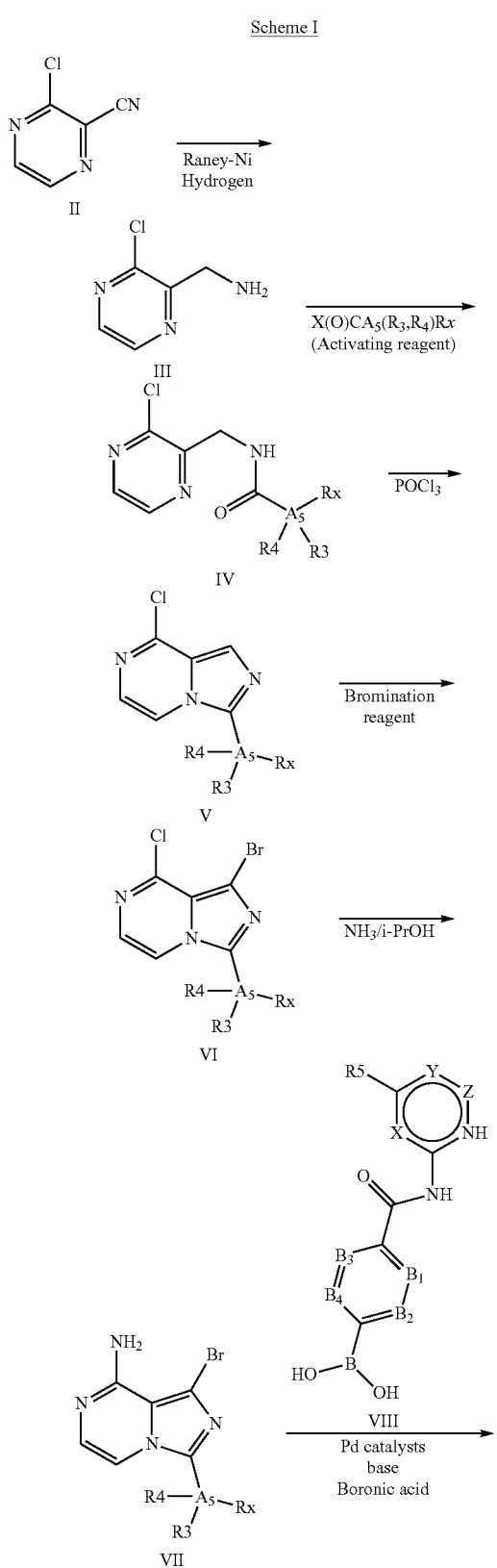

-continued

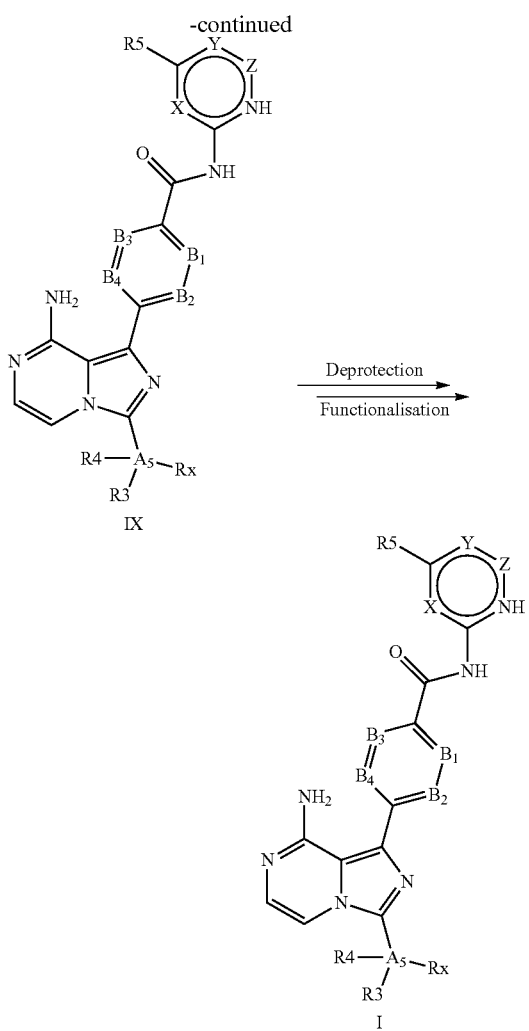

Reduction of 3-chloropyrazine-2-carbonitrile (II) can be accomplished by hydrogenation in the presence of a suitable catalyst system and solvent, for example Raney-Nickel to provide (3-chloropyrazin-2-yl)methanamine (III). This can then be reacted either with an appropriately amine protected amino acid where A5 is equivalent to CH and X is equivalent to OH. The reaction of HO(O)CC($R_3$,$R_4$)$R_x$ can be carried out in a solvent such as DMF, THF or DCM in the presence of a base such as DIPEA, N-methylmorpholine, 4-DMAP or triethylamine and in the presence of a coupling reagent such as PyBOP, TBTU, EDCI or HATU to form N-((3-chloropyrazin-2-yl)methyl)amide (IV). Alternatively, if A5 is equivalent to nitrogen, NH($R_3$,$R_4$)$R_x$ can be activated with trichloromethyl chloroformate or phosgene to introduce COX, where X is equivalent to a leaving group. Subsequent reaction with (3-chloropyrazin-2-yl)methanamine (III) in a suitable solvent like DCM, EtOAc or DMF in the presence of a base such as DiPEA or triethylamine can give compounds of Formula IV. Cyclisation chloropyrazine (IV) can be performed using condensation reagents like phosphorousoxychloride under heating conditions to provide the 8-chloroimidazo[1,5-a]pyrazine derivatives V. Subsequent bromination can be accomplished using bromine or N-bromosuccinimide in a suitable solvent like DCM or DMF at appropriate temperature to obtain compounds of Formula VI. 8-Aminoimidazo[1,5-a]pyrazine derivatives (VII) can be prepared from compounds VI using ammonia(gas) in isopropanol at elevated temperature in a pressure vessel (>4 atm). Compounds of Formula IX can be prepared from compounds of Formula VII using an appropriate boronic acid or pinacol ester (VIII), in the presence of a suitable palladium catalyst system, for example bis(diphenylphosphino)ferrocene palladium(II)chloride complex or tetrakis (triphenylphosphine)palladium(0) in the presence of an organic base like potassium carbonate, cesium carbonate or potassium phosphate in a suitable solvent system like combinations of dioxane and water. Finally, cleaving the protective group of compounds with the Formula IX give the unprotected amine or carboxylic acid which after functionalisation, using methods well known in the art, provided compounds of Formula I.

The compounds like COX$A_5$($R_3$,$R_4$)$R_x$ are either commercially available or they can be readily prepared using methods well known to the skilled organic chemist, to introduce protecting groups like benzyloxycarbonyl or tert-butyloxycarbonyl.

Palladium catalysts and conditions to form either the pinacol esters or to couple the boronic acids or pinacol esters with the 1-bromoimidazo[1,5-a]pyrazin-8-amine are well known to the skilled organic chemist—see, for example, Ei-ichi Negishi (Editor), Armin de Meijere (Associate Editor), Handbook of Organopalladium Chemistry for Organic Synthesis, John Wiley and Sons, 2002.

4-Amino-imidazo[1,5-f][1,2,4]triazine compounds of Formula XVII, wherein $R_1$-$R_x$ have the previously defined meanings, can be prepared by the general synthetic route shown in Scheme II.

Scheme II

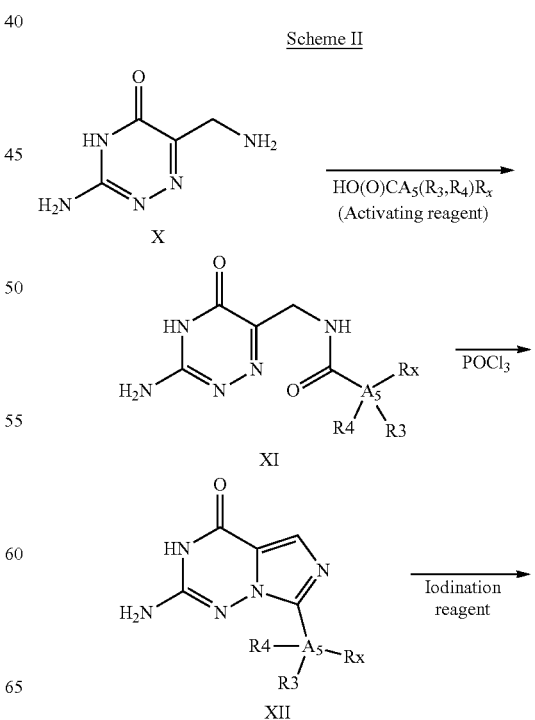

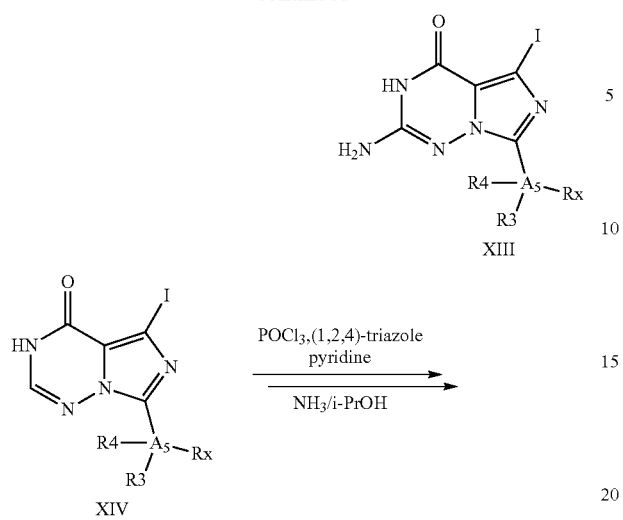
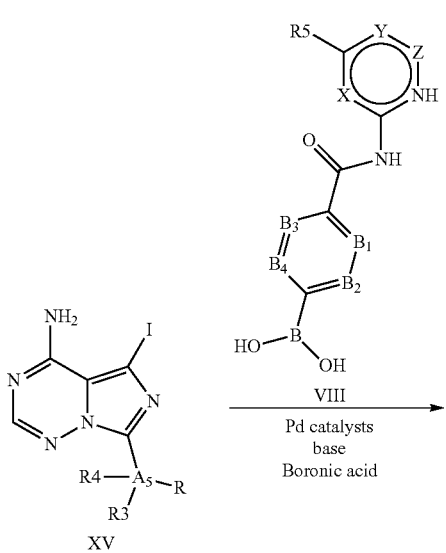
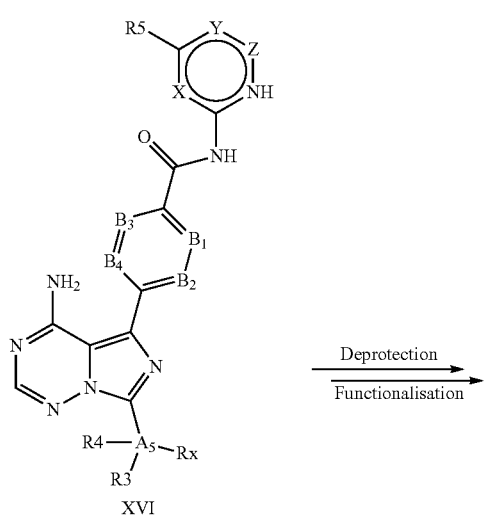
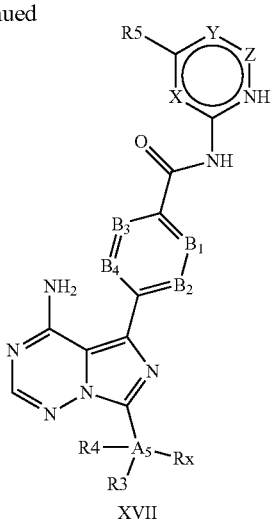

Starting material 3-amino-6-(aminomethyl)-1,2,4-triazin-5(4H)-one (X) can be prepared via a condensation reaction of ethyl bromopyruvate, dibenzylamine, and aminoguanidine carbonate, followed by debenzylation via hydrogenation over Pd—C catalyst [Mitchel, W. L. et al, *J. Heterocycl. Chem.* 21, (1984), pp 697]. The amine can be reacted with an appropriately amine protected amino acid using an activating agent. The reaction of $R_x(R_3,R_4)A_5C(O)OH$ can be carried out in a solvent such as water, THF, DMF or MeCN or combinations of these solvents in the presence of a base such as DIPEA, sodium hydrogen carbonate, N-methylmorpholine, 4-DMAP or triethylamine to form N-((3-amino-5-oxo-4,5-dihydro-1,2,4-triazin-6-yl)methyl)amide (XI). Cyclisation of the amino-triazinone (XI) can be performed using condensation reagents like phosphorousoxychloride under heating conditions to provide the 2-amino-imidazo[1,5-f][1,2,4]triazin-4(3H)-one derivatives XII. Subsequent iodination can be accomplished using iodine or N-iodosuccinimide in a suitable solvent like DCM or DMF at appropriate temperature to obtain compounds of Formula XIII. Removal of the 2-amino group in the 2-aminoimidazo[1,5-f][1,2,4]triazin-4(3H)-one derivatives XIII can be performed using t-butyl nitrite in solvents like DMF/THF at room temperature to form imidazo[1,5-f][1,2,4]triazin-4(3H)-one derivatives XIV. 4-Amino-imidazo[1,5-f][1,2,4]triazine derivatives XV can be prepared from compounds XIV using phosphorousoxychloride, 1,2,4-triazole in pyridine and subsequent ammonolysis with ammonia(gas) in isopropanol at room temperature. Compounds of Formula XVI can be prepared from compounds of Formula XV using an appropriate boronic acid or pinacol ester (VIII), in the presence of a suitable palladium catalyst system, for example bis(diphenylphosphino)ferrocene palladium(II)chloride complex or tetrakis(triphenylphosphine)palladium(0) in the presence of an inorganic base like potassium carbonate, cesium carbonate or potassium phosphate in a suitable solvent system like combinations of dioxane and water. Finally, cleaving the protective group of compounds with the Formula XVI give the unprotected amine which, after functionalisation, using methods well known in the art, provided compounds of Formula XVII. An example of such protective strategy is the use of the benzyloxycarbonyl protecting group to protect the amine from the amino acids used, and after deprotection with 33% HBr/HOAc or conc. HCl gave the resulting amines.

The compounds R$_x$(R$_3$,R$_4$)A$_5$C(O)OH are either commercially available or they can be readily prepared using methods well known to the skilled organic chemist, to introduce protecting groups like benzyloxycarbonyl or tert-butyloxycarbonyl or to introduce activating groups like succinic esters in the presence of carbodiimides in solvents like dioxane.

Palladium catalysts and conditions to form either the pinacol esters or to couple the boronic acids or pinacol esters with the 5-iodoimidazo[1,5-f][1,2,4]triazin-4-amine are well known to the skilled organic chemist—see, for example, Ei-ichi Negishi (Editor), Armin de Meijere (Associate Editor), Handbook of Organopalladium Chemistry for Organic Synthesis, John Wiley and Sons, 2002.

4-Amino-pyrazolo[3,4-d]pyrimidine compounds of Formula XVIII, wherein R$_1$-R$_x$ have the previously defined meanings, can be prepared by the general synthetic route shown in Scheme III.

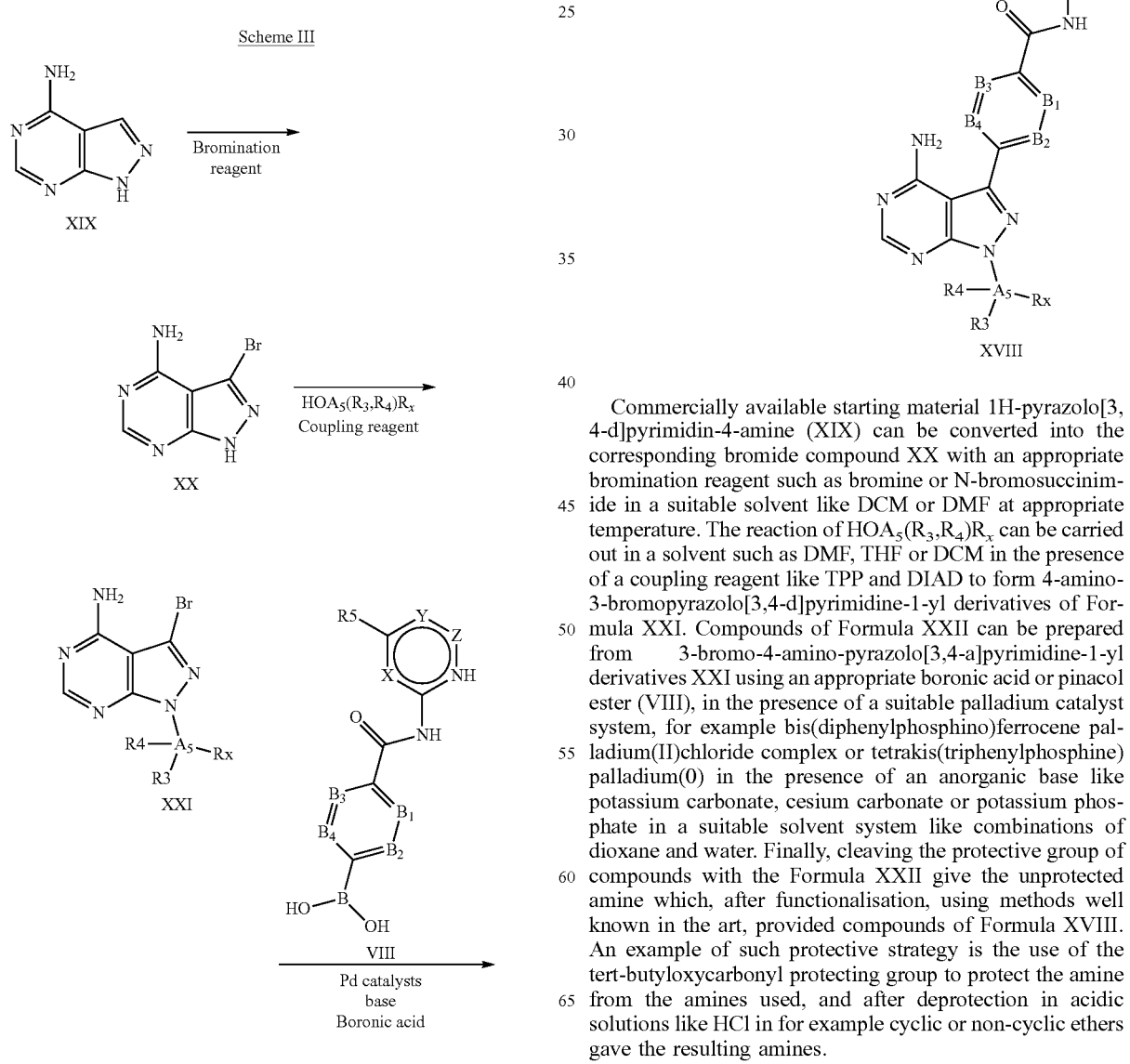

Commercially available starting material 1H-pyrazolo[3,4-d]pyrimidin-4-amine (XIX) can be converted into the corresponding bromide compound XX with an appropriate bromination reagent such as bromine or N-bromosuccinimide in a suitable solvent like DCM or DMF at appropriate temperature. The reaction of HOA$_5$(R$_3$,R$_4$)R$_x$ can be carried out in a solvent such as DMF, THF or DCM in the presence of a coupling reagent like TPP and DIAD to form 4-amino-3-bromopyrazolo[3,4-d]pyrimidine-1-yl derivatives of Formula XXI. Compounds of Formula XXII can be prepared from 3-bromo-4-amino-pyrazolo[3,4-a]pyrimidine-1-yl derivatives XXI using an appropriate boronic acid or pinacol ester (VIII), in the presence of a suitable palladium catalyst system, for example bis(diphenylphosphino)ferrocene palladium(II)chloride complex or tetrakis(triphenylphosphine)palladium(0) in the presence of an anorganic base like potassium carbonate, cesium carbonate or potassium phosphate in a suitable solvent system like combinations of dioxane and water. Finally, cleaving the protective group of compounds with the Formula XXII give the unprotected amine which, after functionalisation, using methods well known in the art, provided compounds of Formula XVIII. An example of such protective strategy is the use of the tert-butyloxycarbonyl protecting group to protect the amine from the amines used, and after deprotection in acidic solutions like HCl in for example cyclic or non-cyclic ethers gave the resulting amines.

The compounds HOA₅(R₃,R₄)Rₓ are either commercially available or they can be readily prepared using methods well known to the skilled organic chemist, to introduce protecting groups like benzyloxycarbonyl or tert-butyloxycarbonyl. Palladium catalysts and conditions to form either the pinacol esters or to couple the boronic acids or pinacol esters with the 4-amino-3-bromopyrazolo[3,4-d]pyrimidine are well known to the skilled organic chemist—see, for example, Ei-ichi Negishi (Editor), Armin de Meijere (Associate Editor), Handbook of Organopalladium Chemistry for Organic Synthesis, John Wiley and Sons, 2002.

4-Amino-pyrrolo[1,2-f][1,2,4]triazine compounds of Formula XXIII, wherein $R_1$-$R_x$ have the previously defined meanings, can be prepared by the general synthetic route shown in Scheme IV.

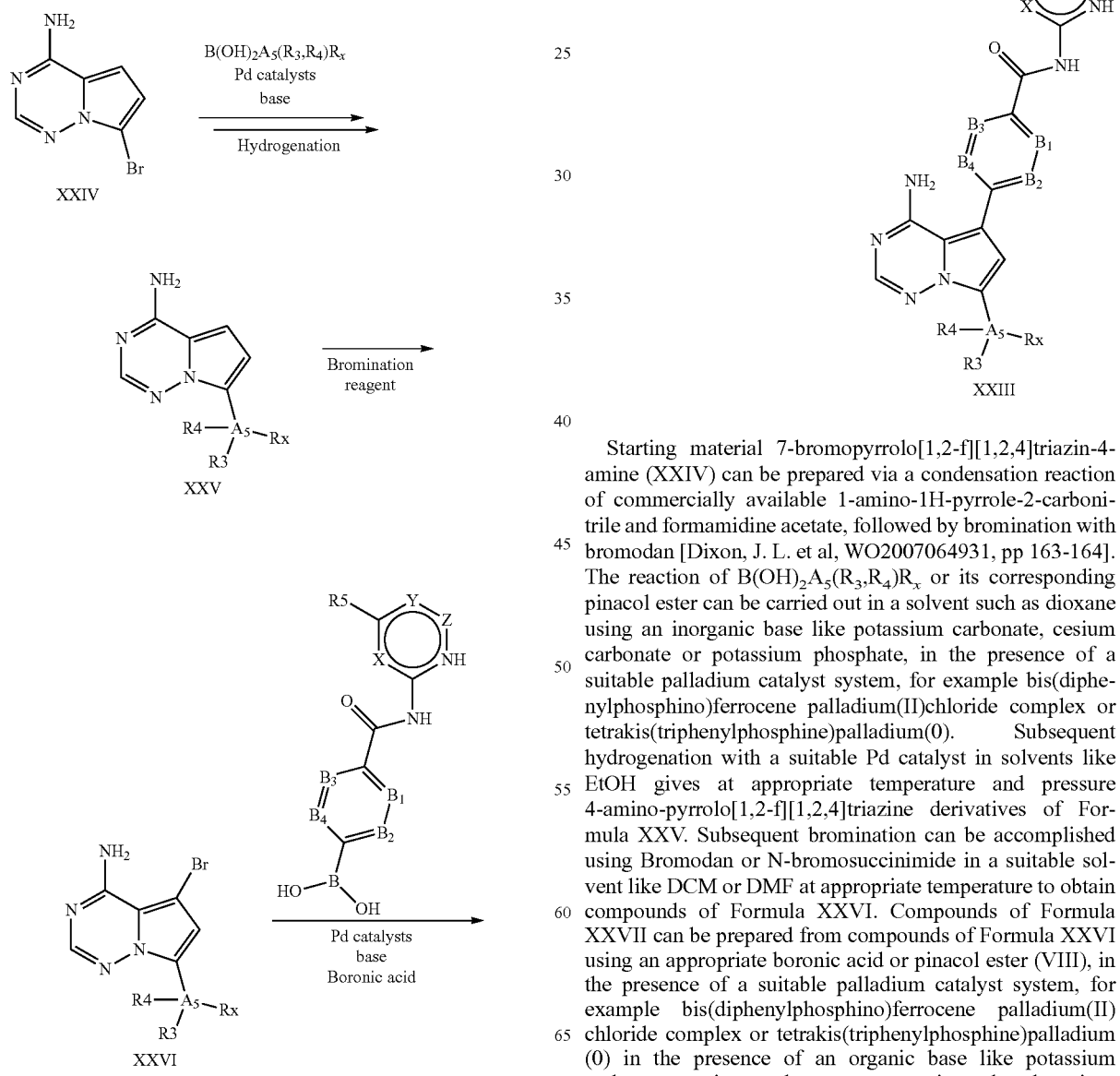

Starting material 7-bromopyrrolo[1,2-f][1,2,4]triazin-4-amine (XXIV) can be prepared via a condensation reaction of commercially available 1-amino-1H-pyrrole-2-carbonitrile and formamidine acetate, followed by bromination with bromodan [Dixon, J. L. et al, WO2007064931, pp 163-164]. The reaction of B(OH)₂A₅(R₃,R₄)Rₓ or its corresponding pinacol ester can be carried out in a solvent such as dioxane using an inorganic base like potassium carbonate, cesium carbonate or potassium phosphate, in the presence of a suitable palladium catalyst system, for example bis(diphenylphosphino)ferrocene palladium(II)chloride complex or tetrakis(triphenylphosphine)palladium(0). Subsequent hydrogenation with a suitable Pd catalyst in solvents like EtOH gives at appropriate temperature and pressure 4-amino-pyrrolo[1,2-f][1,2,4]triazine derivatives of Formula XXV. Subsequent bromination can be accomplished using Bromodan or N-bromosuccinimide in a suitable solvent like DCM or DMF at appropriate temperature to obtain compounds of Formula XXVI. Compounds of Formula XXVII can be prepared from compounds of Formula XXVI using an appropriate boronic acid or pinacol ester (VIII), in the presence of a suitable palladium catalyst system, for example bis(diphenylphosphino)ferrocene palladium(II) chloride complex or tetrakis(triphenylphosphine)palladium (0) in the presence of an organic base like potassium carbonate, cesium carbonate or potassium phosphate in a suitable solvent system like combinations of dioxane and water. Finally, cleaving the protective group of compounds with the Formula XXVII gives the unprotected amine which, after functionalisation, using methods well known in the art, provided compounds of Formula XXIII. An example of such protective strategy is the use of the tert-butyloxycarbonyl protecting group to protect the functionality amine from the boronic acids or esters used. Deprotection in acidic solutions like HCl in, for example, cyclic or non-cyclic ethers gave the resulting amines.

An alternative approach to synthesis of 8-amino-imidazo[1,5-a]pyrazine compounds of Formula I is depicted in Scheme V, whereby chloro intermediate VI is reacted with 2,4-dimethoxybenzylamine in an appropriate solvent such as DMF in presence of a base such as $K_2CO_3$ to provide a DMB-protected amine XXIV. The intermediate can then be coupled to an appropriate boronic acid or pinacol ester using palladium cross-coupling conditions, as described in Scheme I. When so desired, the DMB group can be removed by methods known to those skilled in the art, such as treatment with TFA containing triethylsilane, to provide compounds I.

Scheme V

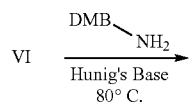

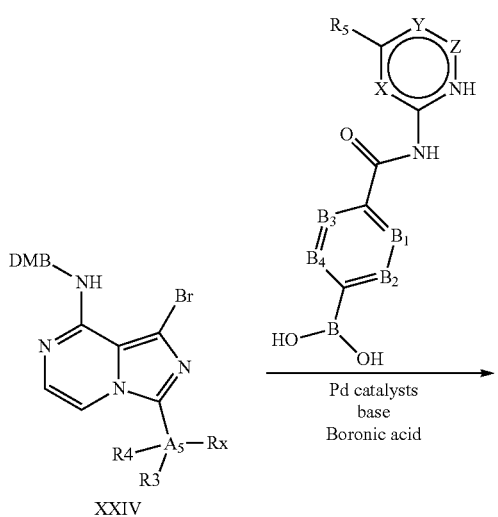

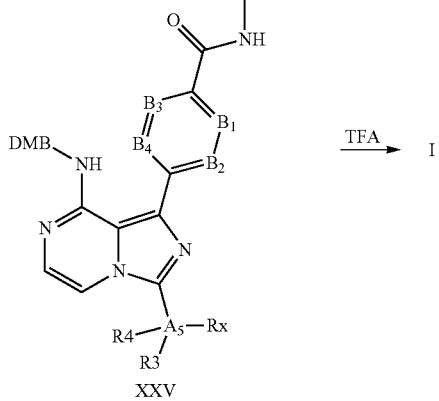

Compounds (I) can also be constructed by coupling of DMB-protected intermediate XXIV to an appropriately substituted boronic acid or ester using suitable palladium coupling conditions as described in previous schemes, to provide a appropriately functionalized intermediates, which may then undergo amide bond forming reactions to afford intermediates XXV. One such approach is shown in Scheme VIa, whereby Pd-mediated cross coupling of XXIV to a boronate ester bearing a primary amide group, such as 4-(4,4,5,5-tetramethyl-1,3,2-dioxaboronolan-2-yl)benzamide, to obtain intermediate XXVI, followed by reaction with a halogenated heterocycle XXVII using a catalyst such as chloro(2-dicyclohexylphosphino-2',6'-di-i-propoxy-1,1'-biphenyl)[2-(2-aminoethylphenyl)]palladium(II), or chloro [2-(dicyclohexyl phosphino)-3,6-dimethoxy-2',4',6'-triisopropyl-1,1'-biphenyl][2-(2-aminoethyl)phenyl]palladium (II) in a solvent such as tert-butanol, followed by removal of the DMB group as described in Scheme V, provides compounds I.

Scheme VIa

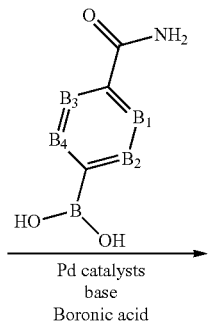

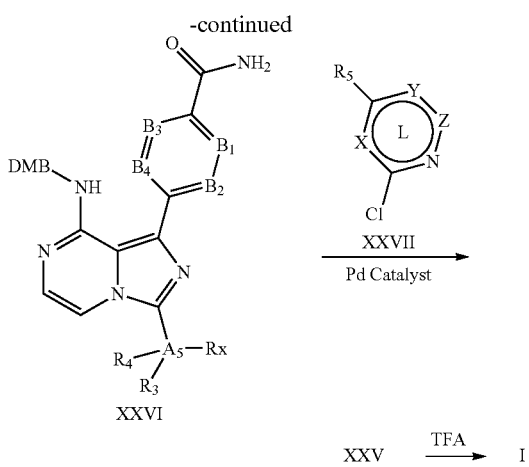

XXV —TFA→ I

Another approach to preparing compounds I is shown in Scheme VIb, involving reaction of XXIV with an appropriate boronic acid or ester bearing a carboxylic acid moiety, such as 4-(4,4,5,5-tetramethyl-1,3,2-dioxaborolan-2-yl)benzoic acid, using an appropriate Pd catalyst system, as described in the Schemes above, to obtain XXVIII. Conversion of the carboxylic acid to the acid chloride using a reagent such as 1-chloro-N,N,2-trimethylprop-1-en-1-amine in an appropriate non-protic solvent such as DCE, followed by reaction with an appropriate aminoheterocycle XXIX in presence of a catalyst such as DMAP provides the amide XXV, which may be deprotected as described above to provide product I.

Pyrrolopyrimidine compounds of Formula XXXIII, wherein $R_1$-$R_x$ have the previously defined meanings, can be prepared using the general synthetic route shown in Scheme VII. Pyrrolopyrimidines can be obtained commercially, or prepared using methods known to those skilled in the art. One such approach involves reaction of commercially available 5-bromo-4-chloro-7H-pyrrolopyrimidine with an appropriate alcohol XXX using Mitsunobu coupling reagents such as triphenylphosphine and DEAD, in an appropriate solvent such as THF, to afford intermediate XXXI, which can be converted to the amine XXXII using ammonia in an appropriate solvent such as isopropanol at elevated temperatures in a sealed tube. The intermediate XXXII can then be modified using analogous procedures to those described for imidazopyrazine compounds in Schemes I-VI to obtain compounds XXXIII.

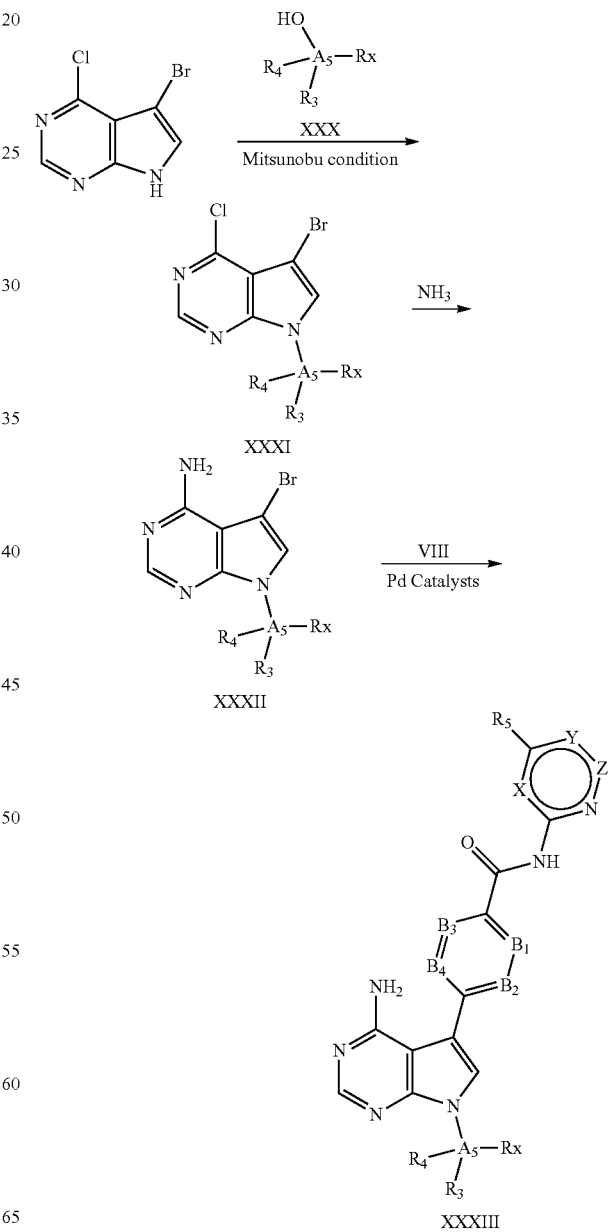

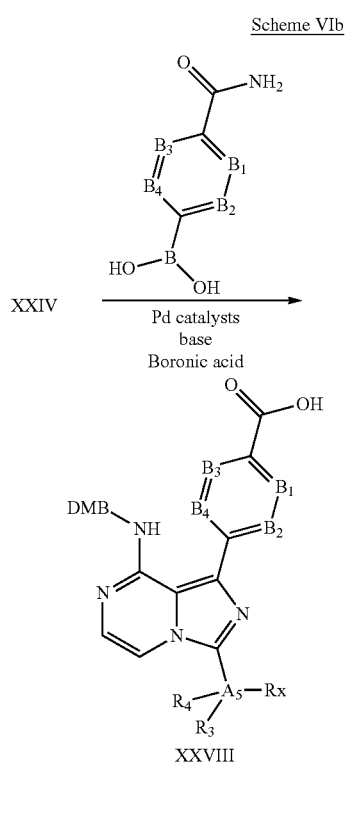

Pyrazolopyridine compounds of Formula XXXVII, wherein $R_1$-$R_x$ have the previously defined meanings, can be prepared by the general synthetic route shown in scheme VIII. Commercially available 4-chloro-1H-pyrazolo[4,3-c] pyridine can be converted to bromide XXXIV using a brominating agent such as NBS in a solvent such as MeCN. Intermediate XXXIV can then be converted to XXXV using Mitsunobu coupling reagents such as triphenylphosphine and DEAD in a solvent such as THF or DCM, which can in turn be converted to aminoheterocycle XXXVI by reaction with 2,4-dimethoxybenzylamine in an appropriate solvent such as MeCN in presence of a base such as DIPEA, followed by removal of the DMB group using methods known by those skilled in the art, such as TFA containing triethylsilane. Intermediate XXXVI can then be coupled to an appropriate boronic acid or pinacol ester VIII using analogous procedures outlined for imidazopyrazine compounds in Schemes I-VI to obtain compounds XXXVII.

Scheme VIII

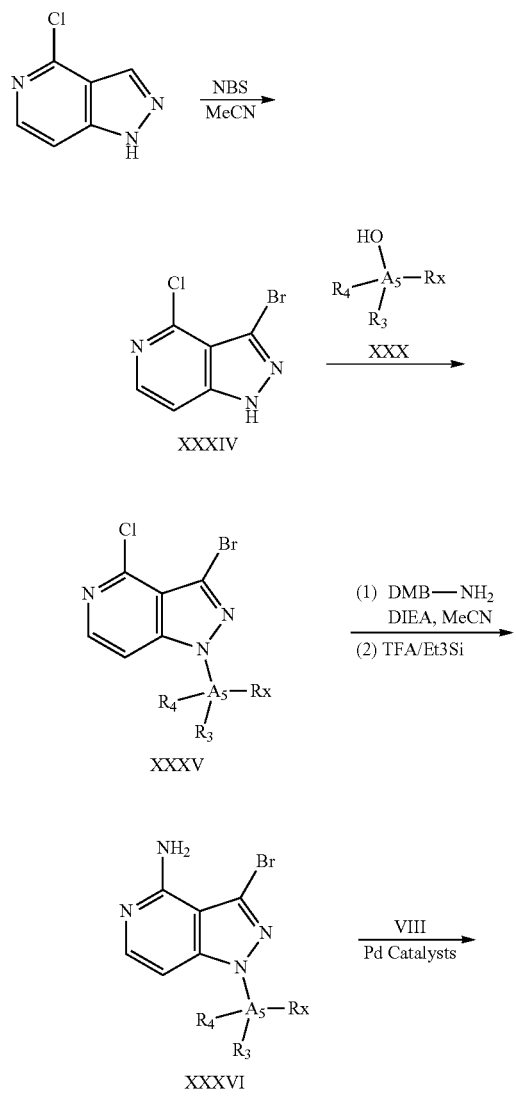

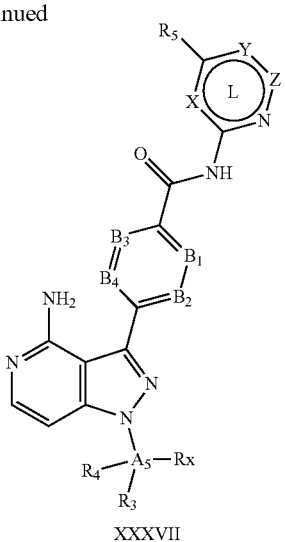

XXXVII

The compounds like B(OH)$_2$A$_5$(R$_3$,R$_4$)R$_x$ are either commercially available or they can be readily prepared using methods well known to the skilled organic chemist, to introduce protecting groups like benzyloxycarbonyl or tert-butyloxycarbonyl. Palladium catalysts and conditions to form either the pinacol esters or to couple the boronic acids or pinacol esters with the 4-amino-pyrrolo[1,2-f][1,2,4]triazine are well known to the skilled organic chemist—see, for example, Ei-ichi Negishi (Editor), Armin de Meijere (Associate Editor), Handbook of Organopalladium Chemistry for Organic Synthesis, John Wiley and Sons, 2002.

The present invention also includes within its scope all stereoisomeric forms of the 6-5 membered fused pyridine ring compounds according to the present invention resulting, for example, because of configurational or geometrical isomerism. Such stereoisomeric forms are enantiomers, diastereoisomers, cis and trans isomers etc. For example where azepane-2-carboxylic acid is used as amino acid, there exists a mixture of two enantiomers. In the case of the individual stereoisomers of compounds of Formula I or salts or solvates thereof, the present invention includes the aforementioned stereoisomers substantially free, i.e., associated with less than 5%, preferably less than 2% and in particular less than 1% of the other stereoisomer. Mixtures of stereoisomers in any proportion, for example a racemic mixture comprising substantially equal amounts of two enantiomers are also included within the scope of the present invention.

For chiral compounds, methods for asymmetric synthesis whereby the pure stereoisomers are obtained are well known in the art, e.g. synthesis with chiral induction, synthesis starting from chiral intermediates, enantioselective enzymatic conversions, separation of stereoisomers using chromatography on chiral media. Such methods are described in *Chirality in Industry* (edited by A. N. Collins, G. N. Sheldrake and J. Crosby, 1992; John Wiley). Likewise methods for synthesis of geometrical isomers are also well known in the art.

The 6-5 membered fused pyridine ring compounds of the present invention, which can be in the form of a free base, may be isolated from the reaction mixture in the form of a pharmaceutically acceptable salt. The pharmaceutically acceptable salts may also be obtained by treating the free base of Formula I with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, and ascorbic acid.

The 6-5 membered fused pyridine ring compounds of the present invention also exist as amorphous forms. Multiple crystalline forms are also possible. All the physical forms are included within the scope of the present invention.

Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.* 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, show the presence of the solvent (or water) in the crystals as a solvate (or hydrate).

The invention is illustrated by the following examples.

EXAMPLES

The following examples are illustrative embodiments of the invention, not limiting the scope of the invention in any way. Reagents are commercially available or are prepared according to procedures in the literature.

Mass Spectrometry: Electron Spray spectra were recorded on the Applied Biosystems API-165 single quad mass spectrometer in alternating positive and negative ion mode using Flow Injection. The mass range was 120-2000 Da and scanned with a step rate of 0.2 Da. and the capillary voltage was set to 5000 V. N2-gas was used for nebulisation.

LC-MS spectrometer (Waters) Detector: PDA (200-320 nm), Mass detector: ZQ and Eluent: A: acetonitrile with 0.05% trifluoroacetic acid, B: acetonitrile/water=1/9 (v/v) with 0.05% trifluoroacetic acid.
Method LCMS (A)
Column 1: Chromolith Performance, RP-18e, 4.6×100 mm, Gradient method: Flow: 4 mL/min

| Time (min) | A (%) | B (%) |
|---|---|---|
| 0.00 | 100 | 0 |
| 3.60 | 0 | 100 |
| 4.00 | 0 | 100 |
| 4.05 | 100 | 0 |
| 6.00 | 100 | 0 |

Method LCMS (B)
Column 2: XBridge C18, 3.5 μm, 4.6×20 mm
Gradient method: Flow: 4 ml/min

| Time (min.) | A (%) | B (%) |
|---|---|---|
| 0.0 | 100 | 0 |
| 1.60 | 0 | 100 |
| 3.10 | 0 | 100 |
| 3.20 | 100 | 0 |
| 5.00 | 100 | 0 |

UPLC: Water acquity UPLC system; Column: BEH C18 1.7 μm, 2.1×100 mm,
Detector: PDA (200-320 nm), Mass detector: SQD
Eluent: A: acetonitrile with 0.035% trifluoroacetic acid, B: acetonitrile/water=1/9 (v/v) with 0.035% trifluoroacetic acid

| | Method | | | | | |
|---|---|---|---|---|---|---|
| | UPLC (A) Method 60_100 Flow: 0.75 mL/min | | UPLC (B) Method 40_80 Flow: 0.65 mL/min | | UPLC (C) Method 0_60 Flow: 0.60 mL/min | |
| Time (min) | A (%) | B (%) | A (%) | B (%) | A (%) | B (%) |
| 0.0 | 40 | 60 | 60 | 40 | 100 | 0 |
| 3.00 | 0 | 100 | 20 | 80 | 40 | 60 |
| 3.20 | 0 | 100 | 0 | 100 | 0 | 100 |
| 3.69 | 0 | 100 | 0 | 100 | 0 | 100 |
| 3.70 | 40 | 60 | 60 | 40 | 100 | 0 |

Method D
Column: Acquity UPLC BEH C18, 2.1×100 mm, 1.7 μm
Detection: UV 210 nm
Conditions: Acidic
Eluent A: MQ-water 900 ml+Acetonitrile 100 ml+0.05% HCOOH
Eluent B: Acetonitrile 900 ml+MQ-water 100 ml+0.05% HCOOH
Gradient method:
Flow: 0.60 ml/min

| Time | A (%) | B (%) |
|---|---|---|
| 0.0 | 98 | 02 |
| 5.00 | 0 | 100 |
| 5.70 | 0 | 100 |
| 5.71 | 98 | 02 |
| 7.00 | 98 | 02 |

Method E
Column: Acquity UPLC BEH C18, 2.1×100 mm, 1.7 μm
Detection: UV 210 nm
Conditions: Basic
Eluent A: MQ-water 900 ml+Acetonitrile 100 ml+10 mM ammonia
Eluent B: Acetonitrile 900 ml+MQ-water 100 ml+10 mM ammonia
Gradient method:
Flow: 0.60 ml/min

| Time | A (%) | B (%) |
|---|---|---|
| 0.0 | 98 | 02 |
| 5.00 | 0 | 100 |
| 5.70 | 0 | 100 |
| 5.71 | 98 | 02 |
| 7.00 | 98 | 02 |

Method F: LC-MS
Final compounds were analyzed by Agilent 1100 series LC-MSD VL on a YMC-Pack ODS-AQ column ((120 Å, 5 um particle size, 2.0 mm×50 mm). The mobile phase was MeCN and $H_2O$, both containing 0.05% (v/v) TFA. The flow rate was 2 ml/min. The effluent was monitored with a wavelength detector at 220.

Method G: LC-MS
Conditions: (1) column: C-18 reverse phase, 5 um, 4.6×50 mm, (2) MS:PE Sciex API-150EX, and (3) HPLC: Shimadzu LC-10 ADvp, 1 ml/min, linear gradient 10% acetonitrile in water to 95% acetonitrile in water, both contain 0.05% TFA.
Preparative HPLC was conducted on a column (50×10 mm ID, 5 µm, Xterra Prep MS C18) at a flow rate of 5 ml/min, injection volume 500 µl, at room temperature and UV Detection at 210 nm.
Method H: LC-MS
Column Agilent TC-C18, 50×2.1 mm, 5 µm
  A: $H_2O$ (0.1% TFA)
Mobile Phase B: CH3CN (0.05% TFA)
  Stop Time: 4.5 min

| Time(min) | B % |
|---|---|
| 0 | 1 |
| 0.4 | 1 |
| 3.4 | 90 |
| 3.9 | 100 |
| 3.91 | 1 |

Gradient
Sample injection
volume 2 µl
Flow Rate 0.8 ml/min
Wavelength 220 nm
Oven Tem. 50° C.
MS polarity ESI POS
Method L: LC-MS
Column Agilent TC-C18, 50×2.1 mm, 5 µm
  A: $H_2O$ (0.1% TFA)
Mobile Phase B: MeCN (0.05% TFA)
  Stop Time: 4.5 min

| Time(min) | B % |
|---|---|
| 0 | 1 |
| 0.4 | 1 |
| 3.4 | 90 |
| 3.9 | 100 |
| 3.91 | 1 |

Gradient
Sample injection
volume 2 µl
Flow Rate 0.8 ml/min
Wavelength 220 nm
Oven Temp. 50° C.
MS polarity ESI POS
Method M:
Sample Info: Easy-Access Method: '1-Short_TFA_Pos'
Method Info: B222 Column Agilent SBC (3.0×50 mm, 1.80; Flow 1.0 mL/min;
solvent A: $H_2O$-0.1% TFA;
solvent B: MeCN-0.1% TFA;
GRADIENT TABLE: 0 min: 10% B, 0.3 min: 10% B, 1.5 min: 95% B, 2.70 min: 95% B, 2.76 min: 10% B
stop time 3.60 min, PostTime 0.70 min.
Method N:
Sample Info: Easy-Access Method: '1_Fast'
  Method Info: A330 Column Agilent Zorbax SB-C18 (2.1×30 mm, 3.5µ); Flow 2.0 mL/min;
solvent A: $H_2O$-0.1% TFA;
solvent B: MeCN-0.1% TFA;
GRADIENT TABLE: 0.01 min: 10% B, 1.01 min: 95% B, 1.37 min: 95% B, 1.38 min: 10% B,
stop time 1.7 min, PostTime=OFF
Method O:
Mobile Phase: 0.1% TFA in MeCN and 0.1% TFA in Water
Column: Xterra 2.1×20 mm 3.5 µm IS or SunFire
Flow rate=1.5 mL/min
Injection Volume=5
Column Heater=50° C.
Run time=4 min
Flow rate=1.5 mL/min
Injection Volume=5 µL
Gradient:

| Time | % A | % B |
|---|---|---|
| 0.00 | 95 | 5 |
| 3.00 | 5 | 95 |
| 3.25 | 2 | 98 |
| 3.26 | 95 | 5 |

Method P:
Mobile Phase: A: 0.1% TFA in MeCN and B: 0.1% TFA in Water
Column: Xterra 2.1×20 mm 3.5 µm IS or SunFire
Flow rate=1.5 mL/min
Injection Volume=5 µL
Column Heater=50° C.
Run time 2 min
Flow rate=1.5 mL/min
Injection Volume=5 µl,
Gradient:

| Time | % A | % B |
|---|---|---|
| 0.00 | 95 | 5 |
| .75 | 5 | 95 |
| 1.25 | 2 | 98 |
| 1.26 | 95 | 5 |

Method Q:
Acquity UPLC BEH-C18, 1.7 µm, 2.1×50 mm
1 mL/min flow
5%-100% MeCN in 1.4 min
0.1% $NH_3$
Preparative HPLC was conducted on a column (50×10 mm ID, 5 µm, Xterra Prep MS C18) at a flow rate of 5 ml/min, injection volume 500 µl, at room temperature and UV Detection at 210 nm.
The following abbreviations are used throughout the application with respect to chemical terminology:
HATU O-(7-Azabenzotriazol-1-yl)-1,1,3,3-tetramethyluroniumhexafluoro phosphate
Cbz Benzyloxycarbonyl
DMF N,N-Dimethylformamide
DCM Dichloromethane
EtOAc Ethyl acetate
DIPEA N,N-Diisopropylethylamine
THF Tetrahydrofuran
EtOH Ethanol
EDCI.HCl 1-(3-Dimethylaminopropyl)-3-ethylcarbodiimide. hydrochloride
4-DMAP 4-Dimethylamino pyridine
PyBOP O-Benzotriazole-1-yl-oxy-trispyrrolidinophosphonium hexafluorophosphate TBTU O-Benzotriazol-1-yl-N,N,N',N'-tetramethyluronium tetrafluoroborate
HBr Hydrogen bromide
HCl Hydrogen chloride
HOAc Acetic acid
POCl₃ Phosphorous oxychloride
HPLC High Pressure Liquid Chromatography
UPLC Ultra Performance Liquid Chromatography
LiHMDS Lithium hexamethyldisilazide
MeOH Methanol
DCM Dichloromethane
n-BuLi n-Butyllithium
CO₂ Carbondioxide
NaHCO₃ Sodiumbicarbonate
K₃PO₄ Potassium phosphate
P(Cy)₃ Tricyclohexylphosphine
Pd(OAc)₂ Palladium(II) acetate
Na₂SO₄ Sodium sulfate
Na₂CO₃ Sodium carbonate
DAST Diethylaminosulfur trifluoride
Cs₂CO₃ Cesium carbonate
Et₂O Diethylether
Na₂S₂O₃ Sodium thiosulfate
Na₂S₂O₄ Sodium hydrosulfite
NaCNBH₃ Sodium cyanoborohydride
NH₄Cl Ammonium chloride
MgSO₄ Magnesium sulfate
LiOH Lithium hydroxide
IPA Isopropylamine
TFA Trifluoro acetic acid
Cbz-Cl Benzylchloroformate
PE Petroleum ether
EA Ethyl acetate
NaHMDS Sodium hexamethyldisilazide
10% Pd/C 10% Palladium on carbon
TEA Triethyl amine
CDI 1,1'-Carbonyl diimidazole
DMI 1,3-Dimethyl-2-imidazolidinone
NBS N-Bromosuccinimide
i-PrOH 2-Propanol
K₂CO₃ Potassium carbonate
Pd(dppf)Cl₂ 1,1'-Bis(diphenylphosphino)ferrocene palladium (II) chloride, complex with dichloromethane
Et₃N Triethylamine
2-BuOH 2-Butanol
LCMS Liquid Chromatography/Mass Spectrometry
MeCN Acetonitril
NH₃ Ammonia
CD₃I Trideuteromethyl iodide
CD₃OD Tetradeuteromethanol
CH₃I Iodomethane
CBr₄ Carbon tetrabromide
Tris-HCl Tris(hydroxymethyl)aminomethane.hydrochloride
MgCl₂ Magnesium chloride
NaN₃ Sodium azide
DTT Dithiothreitol
DMSO Dimethyl sulfoxide
IMAP Immobilized Metal Ion Affinity-Based Fluorescence Polarization
ATP Adenosine triphosphate
MnCl₂ Manganese(II)chloride
DMA Dimethylacetamide
IPA Isopropyl alcohol
TPP triphenylphosphine DIAD Diisopropyl azodicarboxylate
DMB 2,4-dimethoxybenzyl
DCE Dichloroethane
DEAD Diethyl azodicarboxylate
ACN Acetonitrile
RT (rt) Room Temperature
Aq Aqueous
EtOH Ethanol
MPLC Medium Pressure Liquid Chromatography
Xantphos 4,5-Bis(diphenylphosphino)-9,9-dimethylxanthene
X-phos 2-Dicyclohexylphosphino-2',4',6'-triisopropylbiphenyl
TFA trifluoroacetic acid Intermediate 1

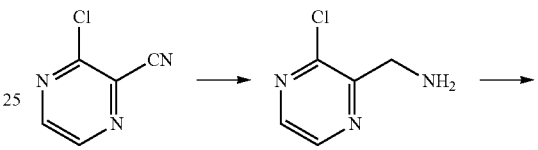

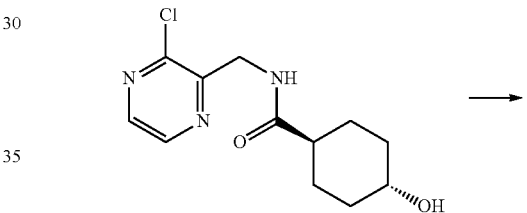

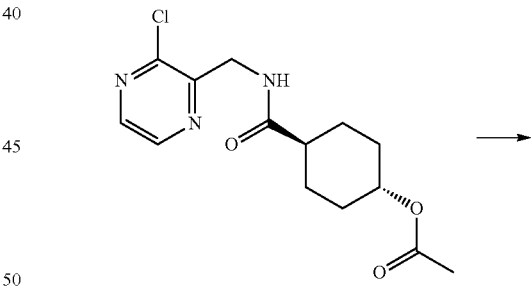

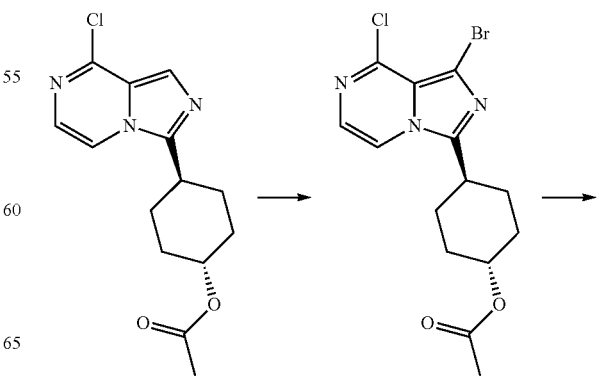

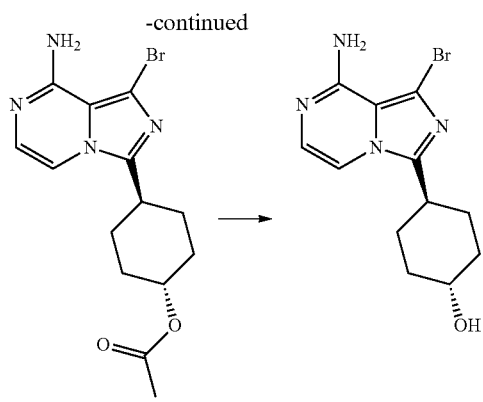

(trans)-4-(8-Amino-1-bromoimidazo[1,5-a]pyrazin-3-yl)cyclohexanol (a) (3-Chloropyrazin-2-yl)methanamine.hydrochloride To a solution of 3-chloropyrazine-2-carbonitrile (160 g, 1.147 mol) in acetic acid (1.5 L) was added Raney Nickel (50% slurry in water, 70 g, 409 mmol). The resulting mixture was stirred under 4 bar hydrogen at room temperature overnight. Raney Nickel was removed by filtration over decalite and the filtrate was concentrated under reduced pressure and co-evaporated with toluene. The remaining brown solid was dissolved in ethyl acetate at 50° C. and cooled on an ice-bath. 2M HCl solution in diethyl ether (1.14 L) was added in 30 min. The mixture was allowed to stir at room temperature over weekend. The crystals were collected by filtration, washed with diethyl ether and dried under reduced pressure at 40° C. The product brown solid obtained was dissolved in methanol at 60° C. The mixture was filtered and partially concentrated, cooled to room temperature and diethyl ether (1000 ml) was added. The mixture was allowed to stir at room temperature overnight. The solids formed were collected by filtration, washed with diethyl ether and dried under reduced pressure at 40° C. to give 153.5 g of (3-chloropyrazin-2-yl)methanamine.hydrochloride as a brown solid (74.4%, content 77%).

(b) (trans)-N-((3-Chloropyrazin-2-yl)methyl)-4-hydroxycyclohexane-carboxamide

To a solution of (3-chloropyrazin-2-yl)methanamine.hydrochloride (20 g, 108 mmol) and trans-4-hydroxycyclohexanecarboxylic acid (15.54 g, 108 mmol) EDCI.HCl (22.72 g, 119 mmol), 1-hydroxy-7-azabenzotriazole (7.33 g, 53.9 mmol) in dichloromethane (250 mL) was added triethylamine (23.96 mL, 172 mmol) and the reaction mixture was stirred at room temperature over night. The mixture was washed with 0.1 M HCl (aq), 5% NaHCO$_3$, water and brine, dried over sodium sulfate and concentrated in vacuo. The product was purified using silica gel chromatography (dichloromethane/methanol=9/1 v/v %) to give 31.1 g of (trans)-N-((3-chloropyrazin-2-yl)methyl)-4-hydroxycyclohexanecarboxamide (98%).

(c) (trans)-4((3-chloropyrazin-2-yl)methylcarbamoyl)cyclohexyl acetate (trans)-N-((3-chloropyrazin-2-yl)methyl)-4-hydroxycyclohexanecarboxamide (31.1 g, 106 mmol) and 4-dimethylaminopyridine (1.296 g, 10.61 mmol) were dissolved in pyridine (300 ml). Acetic anhydride (10.46 ml, 111 mmol) was added and the resulting mixture was stirred at room temperature for 1 h. The reaction was quenched with ~700 ml of 3M HCl (aq) (to pH=4) and extracted with EtOAc (3×). The organic layers were combined and washed with brine, dried over sodium sulfate, filtered and evaporated to give 35 g crude (trans)-4-((3-chloropyrazin-2-yl)methylcarbamoyl)cyclohexyl acetate (95%). The crude product was used directly in the next step.

(d) (trans)-4-(8-chloroimidazo[1,5-a]pyrazin-3-yl)cyclohexyl acetate (trans)-4-((3-chloropyrazin-2-yl)methylcarbamoyl)cyclohexyl acetate (35 g, 101 mmol) was dissolved in acetonitrile (350 ml), phosphorus oxychloride (28.3 ml, 303 mmol) and DMF (a drop) were added and the mixture was stirred at 60° C. overnight. The mixture was concentrated, dissolved in dichloromethane and quenched with an excess of 7M ammonia in MeOH (50 ml). The mixture was concentrated, dichloromethane was added and the white solid formed was filtered off to yield 31.4 g of crude (trans)-4-(8-chloroimidazo[1,5-a]pyrazin-3-yl)cyclohexyl acetate (88%). Product contains 13 wt % (50 mol %) ammonium chloride and was used directly in the next step.

(e) (trans)-4-(1-bromo-8-chloroimidazo[1,5-a]pyrazin-3-yl)cyclohexyl acetate

N-Bromosuccinimide (15.09 g, 85 mmol) was added to a stirred solution of (trans)-4-(8-chloroimidazo[1,5-a]pyrazin-3-yl)cyclohexyl acetate (85 mmol, 30 g) in DMF (90 mL). The reaction was stirred 1.5 h at rt. The reaction was quenched with sat. NaHCO$_3$ (aq) and subsequently extracted with DCM (3×). The combined organic layers were washed with brine, dried over sodium sulfate, filtered and evaporated to give 26.9 g of (trans)-4-(1-bromo-8-chloroimidazo[1,5-a]pyrazin-3-yl)cyclohexyl acetate (81%).

(f) (trans)-4-(8-amino-1-bromoimidazo[1,5-a]pyrazin-3-yl)cyclohexyl acetate

2-Propanol (300 ml) was cooled to −70° C. in a pre-weighed flask (with stopper and stirring bar) and ammonia gas was bubbled through for 30 min. The resulting solution was transferred to a pressure vessel after warming to room temperature and (trans)-4-(1-bromo-8-chloroimidazo[1,5-a]pyrazin-3-yl)cyclohexyl acetate (68.3 mmol, 26.8 g) was added. The reaction mixture was heated to 110° C. which resulted in an increased pressure to 8 bar. The reaction mixture was stirred at 110° C., overnight. The reaction mixture was concentrated in vacuo, the residue was suspended in ethyl acetate and subsequent washed with water. The layers were separated and the aqueous layer was extracted with ethyl acetate. The combined organic layers were washed with water, saturated sodium chloride solution, dried over sodium sulfate and concentrated to give 23.4 g of (trans)-4-(8-amino-1-bromoimidazo[1,5-a]pyrazin-3-yl)cyclohexyl acetate (97%).

(g) (trans)-4-(8-amino-1-bromoimidazo[1,5-a]pyrazin-3-yl)cyclohexyl acetate (trans)-4-(8-amino-1-bromoimidazo[1,5-a]pyrazin-3-yl)cyclohexyl acetate (22.9 g, 64.8 mmol) was suspended in ethanol (96%) (200 ml) and 2M NaOH (aq) (35.7 ml, 71.3 mmol) was added. The resulting mixture was stirred at 50° C. After 2 h additional 2M NaOH (aq) (16.21 ml, 32.4 mmol) was added and the mixture was stirred at 50° C. for another 2 h. The mixture was allowed to cool to room temperature and filtered to give 11.08 g of (trans)-4-(8-amino-1-bromoimidazo[1,5-a]pyrazin-3-yl)cyclohexanol (53.8%) as an off white solid. The filtrate was concentrated. The concentrate was re-crystallized from MeOH (3×) to afford another batch of the title compound as a yellow solid (9.05 g, 44.0%).

Intermediate 2

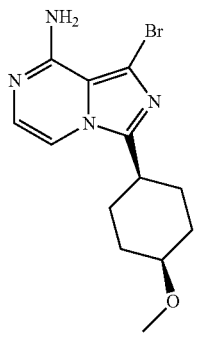

1-bromo-3-((cis)-4-methoxycyclohexyl)imidazo[1,5-a]pyrazin-8-amine

This intermediate was prepared, in an analogous manner as described for intermediate 1, from cis-4-hydroxycyclohexanecarboxylic acid to obtain the title compound (796 mg, 102%).

Intermediate 3

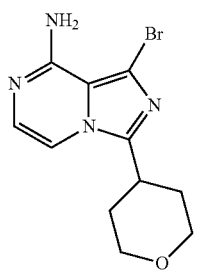

1-bromo-3-(tetrahydro-2H-pyran-4-yl)imidazo[1,5-a]pyrazin-8-amine

This intermediate was prepared, in an analogous manner as described for intermediate 1, from tetrahydro-2h-pyran-4-carboxylic acid to obtain the title compound (3.9 g, 54.2%).

Intermediate 4a

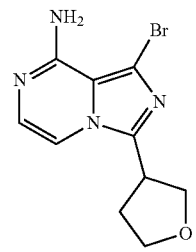

1-bromo-3-(tetrahydrofuran-3-yl)imidazo[1,5-a]pyrazin-8-amine

This intermediate was prepared in an analogous manner as described for Intermediate 1, from tetrahydro-3-furoic acid to obtain the title compound (1.4 g, 66.8%).

Intermediate 4b and 4c

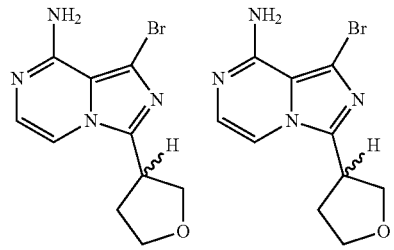

Stereoisomer 1    Stereoisomer 2

1-bromo-3-(tetrahydrofuran-3-yl)imidazo[1,5-a]pyrazin-8-amine

These intermediates were prepared in an analogous manner as described for Intermediate 1, from tetrahydro-3-furoic acid, followed by chiral separation (IA column; eluent EtOH, DCM, Heptane (3/2/5 v/v %), isocratic, 50 minutes) to obtain the title compounds (4a, 48 mg, (49%) and 4b, 41 mg, 42%).

Intermediate 5

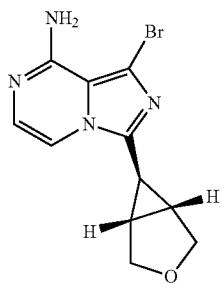

3-((1R,5S,6S)-3-oxabicyclo[3.1.0]hexan-6-yl)-1-bromoimidazo[1,5-a]pyrazin-8-amine This intermediate was prepared in an analogous manner as described for Intermediate 1, from (1R,5S,6R)-3-oxabicyclo[3.1.0]hexane-6-carboxylic acid to obtain the title compound (3.1 g, 97%).

Intermediate 6a

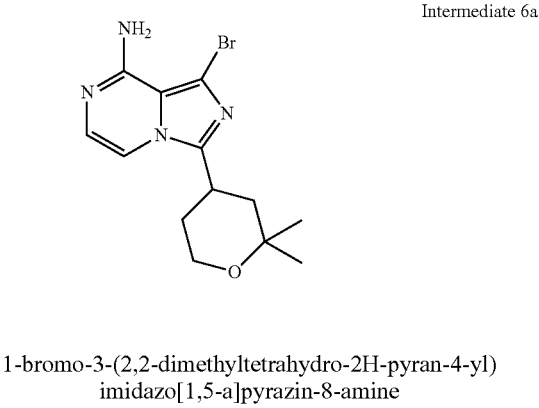

1-bromo-3-(2,2-dimethyltetrahydro-2H-pyran-4-yl)
imidazo[1,5-a]pyrazin-8-amine

This intermediate was prepared in an analogous manner as described for Intermediate 1, from 2,2-dimethyltetrahydro-2h-pyran-4-carboxylic acid to obtain the title compound (10.25 g, 53.3%).

Intermediate 6b and 6c

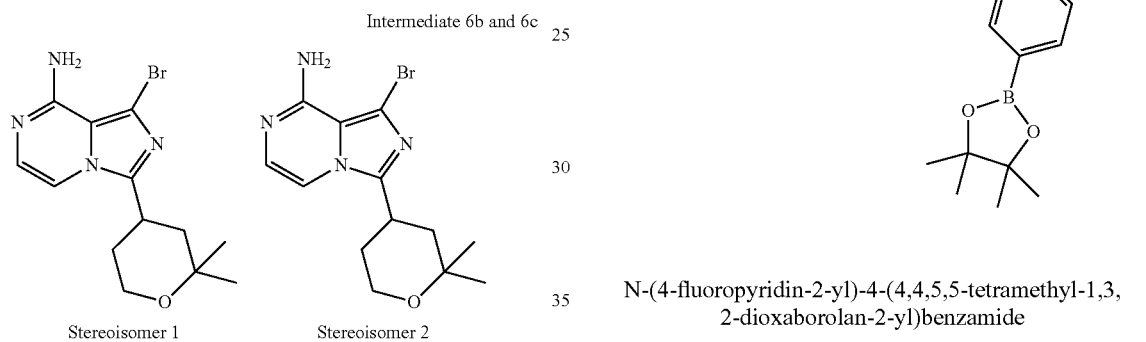

Stereoisomer 1      Stereoisomer 2

1-bromo-3-(2,2-dimethyltetrahydro-2H-pyran-4-yl)
imidazo[1,5-a]pyrazin-8-amine

These intermediates were prepared in an analogous manner as described for Intermediate 1, from 2,2-dimethyltetrahydro-2H-pyran-4-carboxylic acid, followed by chiral separation (Chiralpack AD, MeOH, isocatic) to obtain the title compounds (6b, 34.1 g, 33.5%; 6c, 35.5 g, 34.9%).

Intermediate 7

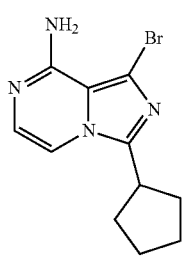

1-bromo-3-cyclopentylimidazo[1,5-a]pyrazin-8-amine

This intermediate was prepared in an analogous manner as described for Intermediate 1, from cyclopentanecarboxylic acid to obtain the title compound (275 mg, 58.8%).

Intermediate A

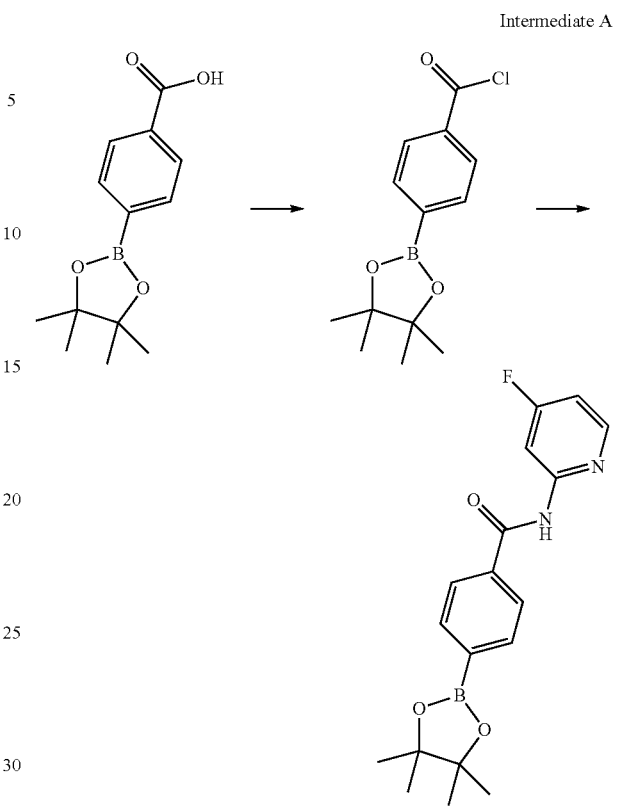

N-(4-fluoropyridin-2-yl)-4-(4,4,5,5-tetramethyl-1,3,2-dioxaborolan-2-yl)benzamide (a) 4-(4,4,5,5-Tetramethyl-1,3,2-dioxaborolan-2-yl)
benzoyl chloride To a cold (0° C.) solution of 4-(4,4,5,5-tetramethyl-1,3,2-dioxaborolan-2-yl)benzoic acid (40.3 mmol, 10.01 g) in dichloromethane (206 mL) was added a catalytic amount of DMF. A solution of oxalyl chloride (101 mmol, 8.66 mL, 12.8 g) was added dropwise. After stirring for 30 min at 0° C., the reaction mixture was allowed to warm up to room temperature and the mixture was stirred for an additional 3 h. The reaction mixture was concentrated to give 10.9 g. of crude 4-(4,4,5,5-tetramethyl-1,3,2-dioxaborolan-2-yl)benzoyl chloride (101%).

(b) N-(4-fluoropyridin-2-yl)-4-(4,4,5,5-tetramethyl-1,3,2-dioxaborolan-2-yl)benzamide To a solution of 4-(4,4,5,5-tetramethyl-1,3,2-dioxaborolan-2-yl)benzoyl chloride (1.688 mmol, 450 mg) in acetonitrile (24.8 mL) was added 2-amino-4-fluoropyridine (4.22 mmol, 473 mg). The reaction mixture was stirred at room temperature for 1.5 h. The reaction mixture was concentrated to a small volume, 3% aq. citric acid solution (18 mL) was added and the mixture was extracted with dichloromethane (2×15 mL). The combined organic layer was washed with 3% aq. citric acid solution, dried over magnesium sulfate, filtered and volatiles evaporated to afford 542 mg of N-(4-fluoropyridin-2-yl)-4-(4,4,5,5-tetramethyl-1,3,2-dioxaborolan-2-yl)benzamide (94%) as an off-white solid.

Intermediate B

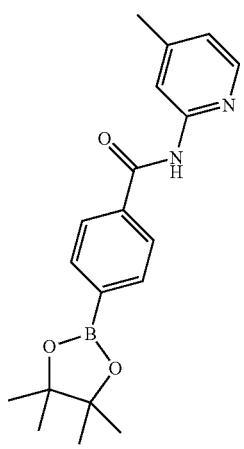

N-(4-Methylpyridin-2-yl)-4-(4,4,5,5-tetramethyl-1,3,2-dioxaborolan-2-yl)benzamide To a stirred solution of 4-methylpyridin-2-amine (7.86 mmol, 850 mg) in THF (50 mL) was added dropwise a solution of 1M LiHMDS in THF (8.0 mmol, 8 mL) at room temperature. After the reaction mixture turned dark green, a solution of 4-(4,4,5,5-tetramethyl-1,3,2-dioxaborolan-2-yl)benzoyl chloride (9.6 mmol, 2.56 g) in dichloromethane (55 mL) was added dropwise. The mixture was stirred at room temperature for 2.5 h and was then concentrated. 3% aq. Citric acid solution (18 mL) was added and the mixture was extracted with dichloromethane (2×15 mL). The combined organic layer was washed with 3% aq. citric acid solution, dried over magnesium sulfate, filtered and evaporated. The residue was dissolved in THF (15 mL) and 6M aq. NaOH (15 mL) was added. The mixture was stirred for 4 h. at room temperature. Ethyl acetate was added and the layers were separated. The organic layer was washed with water and brine, dried over sodium sulfate, filtered and evaporated. The residue was purified by chromatography on silica gel (eluent: DCM/MeOH=98/2 to DCM/MeOH=95/5) to yield 1.1 g of N-(4-methylpyridin-2-yl)-4-(4,4,5,5-tetramethyl-1,3,2-dioxaborolan-2-yl)benzamide (40.7%).

Intermediate C

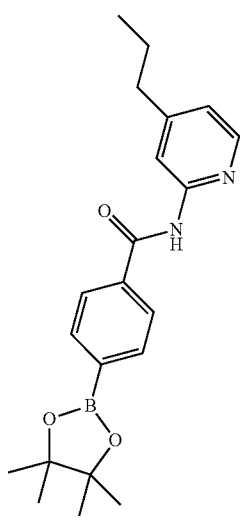

N-(4-Propylpyridin-2-yl)-4-(4,4,5,5-tetramethyl-1,3,2-dioxaborolan-2-yl)benzamide This compound was prepared in an analogous manner as described in Intermediate B, starting from 4-propylpyridin-2-amine, to afford the title compound (371.5 mg, 54.1%).

Intermediate D

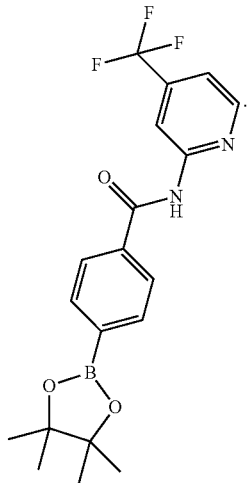

4-(4,4,5,5-Tetramethyl-1,3,2-dioxaborolan-2-yl)-N-(4-(trifluoromethyl)pyridin-2-yl)benzamide This compound was prepared in an analogous manner as described in Intermediate B, starting from 4-(trifluoromethyl)pyridin-2-amine, to afford the title compound (657.2 mg, 89%).

Intermediate E

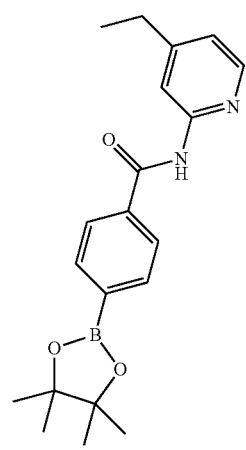

N-(4-Ethylpyridin-2-yl)-4-(4,4,5,5-tetramethyl-1,3,2-dioxaborolan-2-yl)benzamide This compound was prepared in an analogous manner as described in Intermediate A, starting from 4-ethylpyridin-2-amine, to afford the title compound (334.5 mg, 50.6%).

Intermediate F

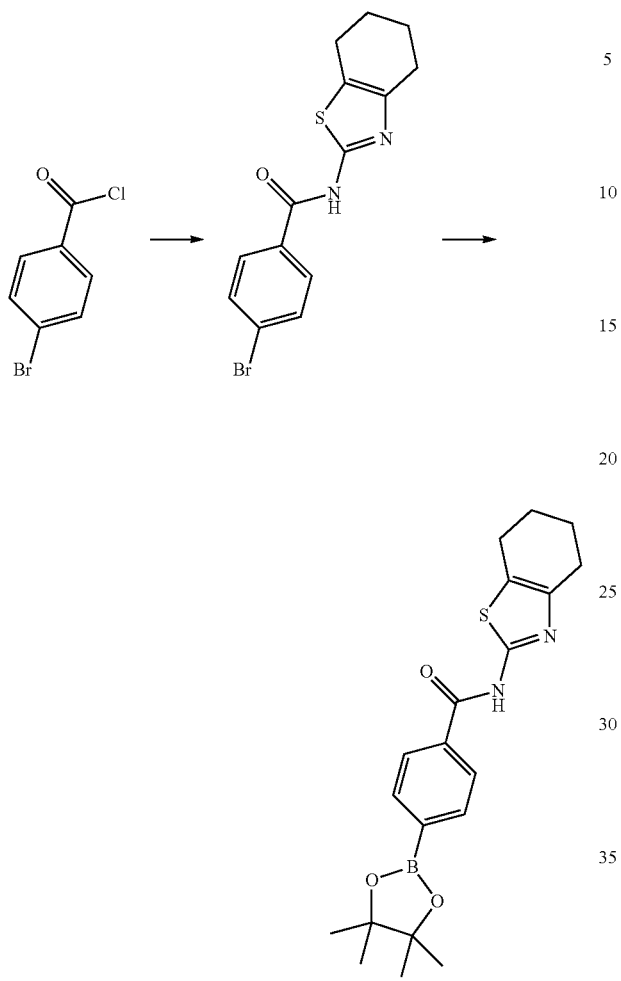

N-(4,5,6,7-Tetrahydrobenzo[d]thiazol-2-yl)-4-(4,4,5,5-tetramethyl-1,3,2-dioxaborolan-2-yl)benzamide (a) 4-Bromo-N-(4,5,6,7-tetrahydrobenzo[d]thiazol-2-yl)benzamide 4-Bromobenzoyl chloride (1.5 g, 6.83 mmol) and 4,5,6,7-tetrahydro-1,3-benzothiazol-2-amine (1.054 g, 6.83 mmol) were dissolved in pyridine (15 ml) and stirred at 50° C. for 1.5 h. The reaction mixture was cooled to room temperature and poured in water. The solid formed was filtered, washed with water. The solids were co-evaporated with toluene twice to afford 1.8 g of 4-bromo-N-(4,5,6,7-tetrahydrobenzo[d]thiazol-2-yl)benzamide (78%) as a yellow solid.

(b) N-(4,5,6,7-Tetrahydrobenzo[d]thiazol-2-yl)-4-(4,4,5,5-tetramethyl-1,3,2-dioxaboro-lan-2-yl)benzamide To a solution of 4-bromo-N-(4,5,6,7-tetrahydrobenzo[d]thiazol-2-yl)benzamide (1.8 g, 5.34 mmol) dioxane (40 ml) was added bis(pinacolato)diboron (1.762 g, 6.94 mmol) and potassium acetate (1.048 g, 10.68 mmol). The reaction mixture was degassed with nitrogen. Subsequently 1,1'-bis(diphenylphosphino)ferrocene-palladium(II) dichloride (0.218 g, 0.267 mmol) was added and the reaction mixture was stirred at 80° C. for 5 days. The mixture was cooled to room temperature and after addition of water extracted three times with EtOAc. The organic layers were combined, washed with brine, dried over sodium sulfate, filtered and evaporated. The crude product was purified using silica gel chromatography (heptane/ethyl acetate 3/7 to 7/3 v/v %) to give 600 mg of N-(4,5,6,7-tetrahydrobenzo[d]thiazol-2-yl)-4-(4,4,5,5-tetramethyl-1,3,2-dioxaboro-lan-2-yl)benzamide (29.3%).

Intermediate F

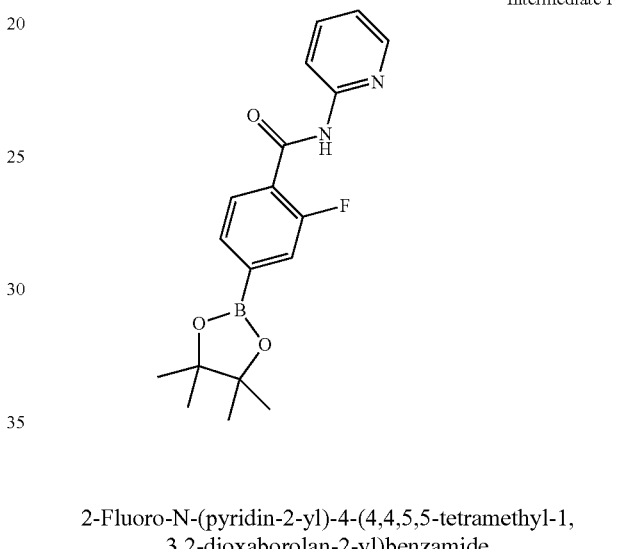

2-Fluoro-N-(pyridin-2-yl)-4-(4,4,5,5-tetramethyl-1,3,2-dioxaborolan-2-yl)benzamide This compound was prepared in an analogous manner as described in Intermediate F, starting from 4-bromo-2-fluorobenzoic acid, to afford the title compound (2.54 g, 76%).

Intermediate H

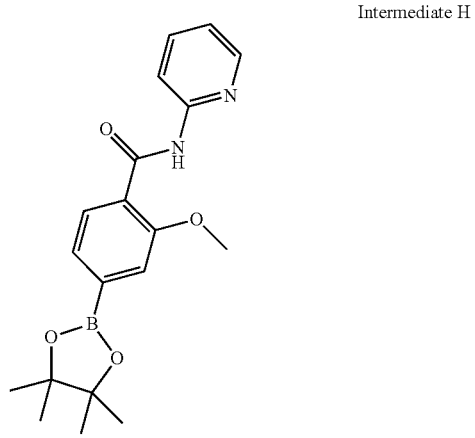 [SMILES: COc1cc(B2OC(C)(C)C(C)(C)O2)ccc1C(=O)Nc1ccccn1]

103

2-Methoxy-N-(pyridin-2-yl)-4-(4,4,5,5-tetramethyl-1,3,2-dioxaborolan-2-yl)benzamide This compound was prepared in an analogous manner as described in Intermediate F, starting from 4-bromo-2-methoxybenzoic acid, to afford the title compound (2.6 g, 90%).

104

N-(Pyrimidin-2-yl)-4-(4,4,5,5-tetramethyl-1,3,2-dioxaborolan-2-yl)benzamide

This compound was prepared in an analogous manner as described in Intermediate F, starting from 2-aminopyrimidine, to afford the title compound (855 mg, 42.6%).

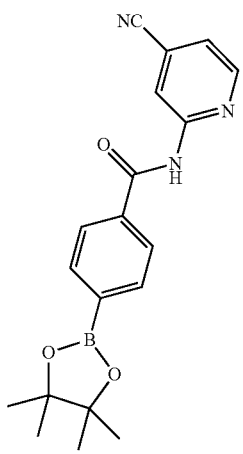

Intermediate I

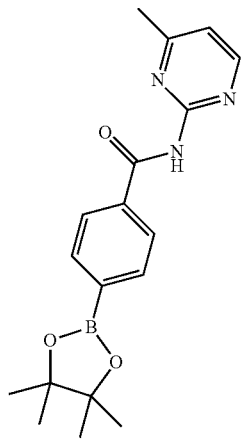

Intermediate K

N-(4-Cyanopyridin-2-yl)-4-(4,4,5,5-tetramethyl-1,3,2-dioxaborolan-2-yl)benzamide This compound was prepared in an analogous manner as described in Intermediate A, starting from 2-aminoisonicotinonitrile, to afford the title compound (1.3 g, 99%).

N-(4-Methylpyrimidin-2-yl)-4-(4,4,5,5-tetramethyl-1,3,2-dioxaborolan-2-yl)benzamide This compound was prepared in an analogous manner as described in Intermediate F, starting from 2-amino-4-methylpyrimidine, to afford the title compound (420 mg, 60.6%).

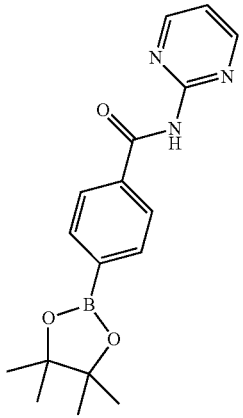

Intermediate J

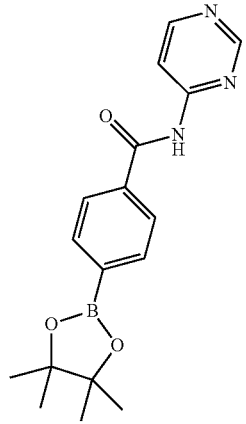

Intermediate L

N-(Pyrimidin-4-yl)-4-(4,4,5,5-tetramethyl-1,3,2-dioxaborolan-2-yl)benzamide

This compound was prepared in an analogous manner as described in Intermediate F, starting from 4-aminopyrimidine, to afford the title compound (1 g, 59.4%).

N-(Isoxazol-3-yl)-4-(4,4,5,5-tetramethyl-1,3,2-dioxaborolan-2-yl)benzamide

This compound was prepared in an analogous manner as described in Intermediate F, starting from 3-aminoisoxazole, to afford the title compound (1.64 g, 95%).

Intermediate M

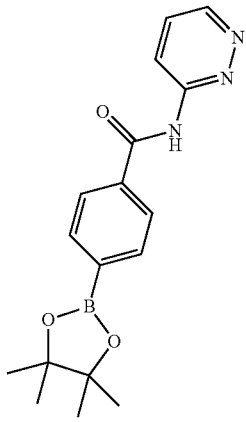

Intermediate O

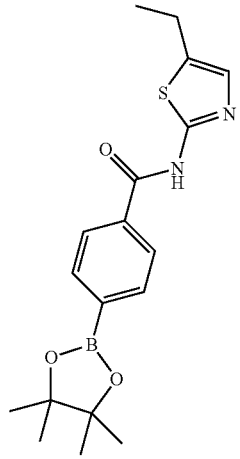

N-(Pyridazin-3-yl)-4-(4,4,5,5-tetramethyl-1,3,2-dioxaborolan-2-yl)benzamide

This compound was prepared, in an analogous manner as described in Intermediate F, starting from 3-aminopyridazine, to afford the title compound (1.25 g, 71.3%).

N-(5-Ethylthiazol-2-yl)-4-(4,4,5,5-tetramethyl-1,3,2-dioxaborolan-2-yl)benzamide This compound was prepared in an analogous manner as described in Intermediate A, starting from 5-ethylthiazol-2-amine, to afford the title compound (191 mg, 34.2%).

Intermediate N

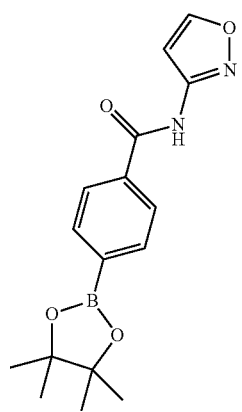

Intermediate P

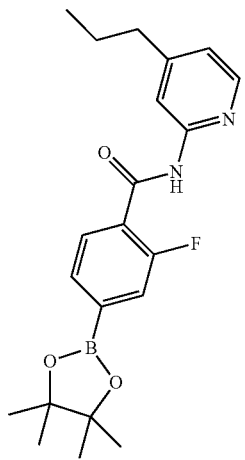

2-Fluoro-N-(4-propylpyridin-2-yl)-4-(4,4,5,5-tetramethyl-1,3,2-dioxaborolan-2-yl)benzamide This compound was prepared in an analogous manner as described in Intermediate A, starting from commercially available 2-fluoro-4-(4,4,5,5-tetramethyl-1,3,2-dioxaborolan-2-yl)benzoic acid and 4-propyl-pyridin-2-ylamine, to afford the title compound (830 mg, 63.3%).

Intermediate Q

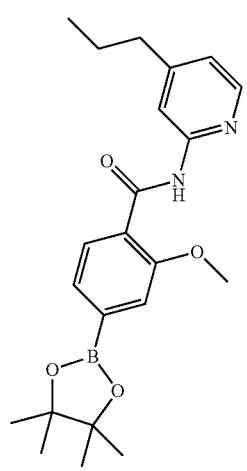

2-Methoxy-N-(4-propylpyridin-2-yl)-4-(4,4,5,5-tetramethyl-1,3,2-dioxaborolan-2-yl)benzamide This compound was prepared in an analogous manner as described in Intermediate F, starting from commercially available 4-bromo-2-methoxybenzoic acid and 4-propyl-pyridin-2-ylamine, to afford the title compound (240 mg, 15.1%).

Intermediate R

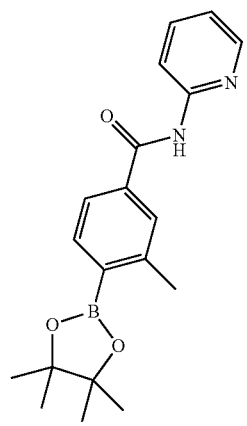

3-Methyl-N-(pyridin-2-yl)-4-(4,4,5,5-tetramethyl-1,3,2-dioxaborolan-2-yl)benzamide This compound was prepared in an analogous manner as described in Intermediate F, starting from commercially available 4-bromo-3-methylbenzoic acid and 2-aminopyridine, to afford the title compound (2.5 g, 71.3%).

Intermediate S

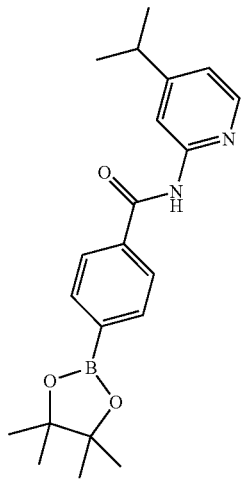

N-(4-isopropylpyridin-2-yl)-4-(4,4,5,5-tetramethyl-1,3,2-dioxaborolan-2-yl)benzamide This compound was prepared in an analogous manner as described in Intermediate F, starting from commercially available 4-bromobenzoyl chloride acid and 4-isopropylpyridin-2-amine, to afford the title compound (2.4 g, 68.6%).

Intermediate T

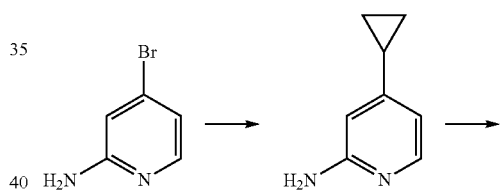

N-(4-cyclopropylpyridin-2-yl)-4-(4,4,5,5-tetramethyl-1,3,2-dioxaborolan-2-yl)benzamide (a) 4-cyclopropylpyridin-2-amine To a solution of 4-bromopyridin-2-amine (80.0 g, 465 mmol) cyclopropylboronic acid (52.0 g, 600 mmol), $K_3PO_4$ (296 g, 1.40 mol), P(Cy)₃ (13.0 g, 46.5 mmol) dissolved in 1.60 L of toluene was added Pd(OAc)₂. The reaction was stirred for 18 h at 100° C. The reaction mixture was cooled and 400 mL of H₂O was added. The mixture was extracted with EtOAc (2×400 mL). The combined organic layers were dried (Na₂SO₄), filtered and concentrated and the residue was purified using silica gel chromatography (Petroleum ether:EtOAc 10:1 to 3:1) to give 4-cyclopropylpyridin-2-amine (28.0 g, 56.2%).

(b) N-(4-cyclopropylpyridin-2-yl)-4-(4,4,5,5-tetramethyl-1,3,2-dioxaborolan-2-yl)benzamide To a solution of 4-cyclopropylpyridin-2-amine (28.0 g, 0.209 mol), DIPEA (92.6 mL, 0.52 mol), O-Benzotriazol-1-yl-N,N,N',N'-tetra-methyluronium tetrafluoroborate (TBTU) (67.1 g, 0.209 mol) dissolved in 500 mL DCM was added 4-(4,4,5,5-tetramethyl-1,3,2-dioxaborolan-2-yl)benzoic acid (51.8 g, 0.209 mmol). The reaction mixture was stirred 18 h at rt. The reaction mixture was washed with 2×250 mL Na₂CO₃ solution and 2×250 mL citric acid solution. The organic layer was dried (Na₂SO₄), filtered and concentrated. The crude product was purified using silica gel chromatography (petroleum ether:EtOAc 5:1) to give N-(4-cyclopropylpyridin-2-yl)-4-(4,4,5,5-tetramethyl-1,3,2-dioxaborolan-2-yl)benzamide (46.5 g, 61.2%).

Intermediate U

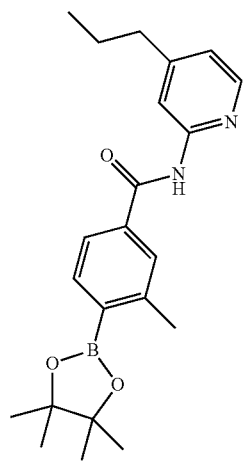

3-methyl-N-(4-propylpyridin-2-yl)-4-(4,4,5,5-tetramethyl-1,3,2-dioxaborolan-2-yl)benzamide This compound was prepared in an analogous manner as described in Intermediate F, starting from commercially available 4-bromo-3-methylbenzoyl chloride and 4-propylpyridin-2-amine hydrochloride, to afford the title compound (800 mg, 43.8%).

Intermediate V

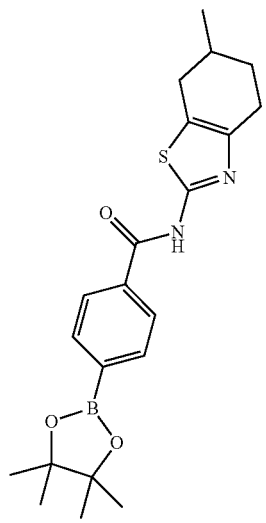

N-(6-methyl-4,5,6,7-tetrahydrobenzo[d]thiazol-2-yl)-4-(4,4,5,5-tetramethyl-1,3,2-dioxaborolan-2-yl)benzamide To a stirred solution of 4-(4,4,5,5-tetramethyl-1,3,2-dioxaborolan-2-yl)benzoic acid (1460 mg, 5.88 mmol), 6-methyl-4,5,6,7-tetrahydrobenzo[d]thiazol-2-amine (990 mg, 5.88 mmol) and O-benzotriazol-1-yl-N,N,N',N'-tetramethyluronium tetrafluoroborate (TBTU) (2267 mg, 7.06 mmol) in dichloromethane (100 mL) was added N,N-diisopropylethylamine (1.233 ml, 7.06 mmol) at rt. The reaction mixture was stirred overnight at rt. The reaction was washed with 20 mL sat. Na₂CO₃ solution, 20 mL water, 20 mL brine, dried (Na₂SO₄), filtered and concentrated. The residue was purified using silica gel chromatography (EtOAc:heptane 10:90 to 30:70) to give the title compound (1.50 g, 55.5%).

Intermediate W

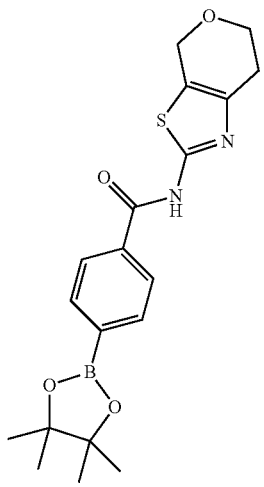

N-(6,7-dihydro-4H-pyrano[4,3-d]thiazol-2-yl)-4-(4,4,5,5-tetramethyl-1,3,2-dioxaborolan-2-yl)benzamide This compound was prepared in an analogous manner as described in Intermediate V, starting from commercially available 4-(4,4,5,5-tetramethyl-1,3,2-dioxaborolan-2-yl)benzoic acid and 6,7-dihydro-4H-pyrano[4,3-d]thiazol-2-amine, to afford the title compound (750 mg, 32.3%).

Intermediate X

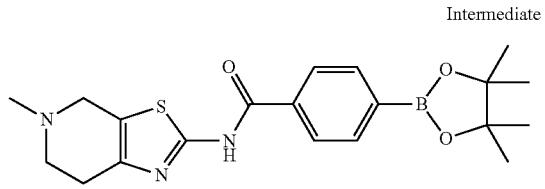

N-(5-methyl-4,5,6,7-tetrahydrothiazolo[5,4-c]pyridin-2-yl)-4-(4,4,5,5-tetramethyl-1,3,2-dioxaborolan-2-yl)benzamide This compound was prepared, in an analogous manner as described in Intermediate V, starting from commercially available 4-(4,4,5,5-tetramethyl-1,3,2-dioxaborolan-2-yl)benzoic acid and 5-methyl-4,5,6,7-tetrahydrothiazolo[5,4-c]pyridin-2-amine, to afford the title compound (810 mg, 27.2%).

Intermediate Y

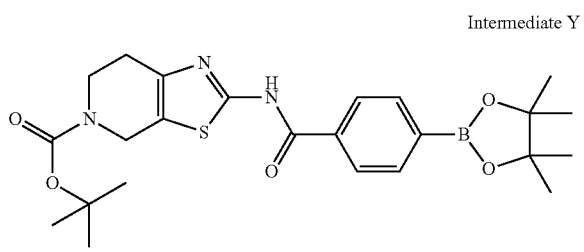 [SMILES: CC(C)(C)OC(=O)N1CCc2nc(NC(=O)c3ccc(B4OC(C)(C)C(C)(C)O4)cc3)sc2C1]

tert-butyl 2-(4-(4,4,5,5-tetramethyl-1,3,2-dioxaborolan-2-yl)benzamido)-6,7-dihydrothiazolo[5,4-c]pyridine-5(4H)-carboxylate This compound was prepared in an analogous manner as described in Intermediate V, starting from commercially available 4-(4,4,5,5-tetramethyl-1,3,2-dioxaborolan-2-yl)benzoic acid and 2 tert-butyl 2-amino-6,7-dihydrothiazolo[5,4-c]pyridine-5(4H)-carboxylate, to afford the title compound (1.30 g, 71.2%).

Intermediate Z

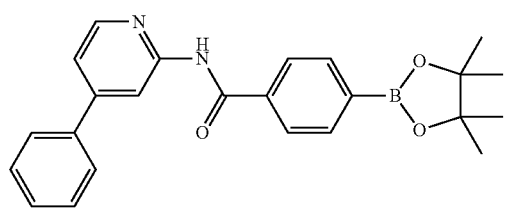

N-(4-phenylpyridin-2-yl)-4-(4,4,5,5-tetramethyl-1,3,2-dioxaborolan-2-yl)benzamide This compound was prepared, in an analogous manner as described in Intermediate B, starting from commercially available 4-phenylpyridin-2-amine, to afford the title compound (0.969 g, 82.0%).

Intermediate AA

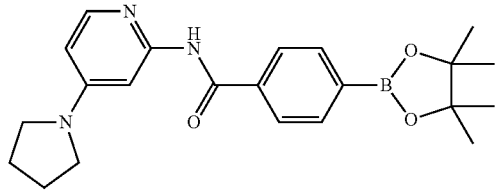

N-(4-(pyrrolidin-1-yl)pyridin-2-yl)-4-(4,4,5,5-tetramethyl-1,3,2-dioxaborolan-2-yl)benzamide This compound was prepared in an analogous manner as described in Intermediate B, starting from commercially available 4-(pyrrolidin-1-yl)pyridin-2-amine, to afford the title compound (725 mg, 40.1%).

Intermediate AB

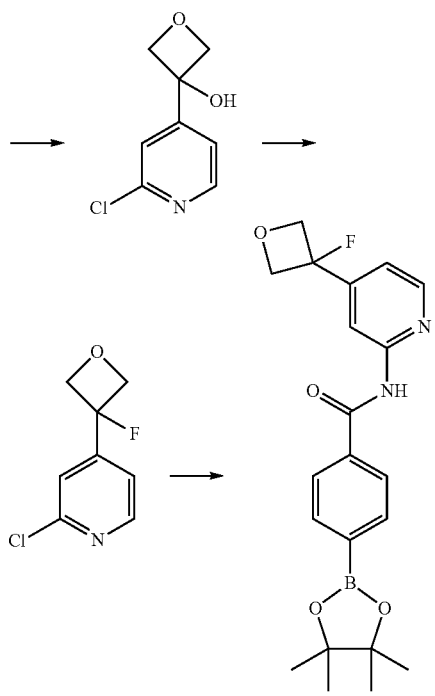

N-(4-(3-fluorooxetan-3-yl)pyridin-2-yl)-4-(4,4,5,5-tetramethyl-1,3,2-dioxaborolan-2-yl)benzamide (a) 3-(2-chloropyridin-4-yl)oxetan-3-ol 2-Chloro-4-iodopyridine (19.04 mmol, 4.56 g) in THF (10 ml) was added dropwise to isopropylmagnesium chloride (21.90 mmol, 10.95 ml) (2M solution in THF) at −40° C. under $N_2$-atmosphere. The reaction mixture was stirred at −40° C. for 0.5 h, followed by addition of oxetan-3-one (19.04 mmol, 1.372 g) in 5 ml THF. The reaction mixture was stirred 1.5 h at −40° C. after which the temperature was allowed to come to 0° C. and stirred 2 h. The reaction mixture was added dropwise to brine (cooled with an icebath), and extracted twice with EtOAc. The combined organic layers were dried ($Na_2SO_4$) filtered and concentrated. The residue was crystallized from EtOH (p.a.) to give 3-(2-chloropyridin-4-yl)oxetan-3-ol (2.31 g, 65.3%).

(b) 2-chloro-4-(3-fluorooxetan-3-yl)pyridine

H3-(2-chloropyridin-4-yl)oxetan-3-ol (5.39 mmol, 1 g) was dissolved in DCM (20 ml) and cooled to −78° C. Diethylaminosulfur trifluoride (DAST) (7.54 mmol, 1.216 g) was added and the reaction mixture was stirred at −78° C. for 90 min after which the temperature was allowed to come to rt. The reaction mixture was quenched carefully in NaHCO₃ (aq). The mixture was extracted with DCM twice, filtered and dried over PS-filter and concentrated. The crude sample was purification using silica gel chromatography (heptane:EtOAc 9:1 to 1:1) to give 2-chloro-4-(3-fluorooxetan-3-yl)pyridine (970 mg, 96%).

(c) N-(4-(3-fluorooxetan-3-yl)pyridin-2-yl)-4-(4,4,5,5-tetramethyl-1,3,2-dioxaborolan-2-yl)-benzamide 2-chloro-4-(3-fluorooxetan-3-yl)pyridine (5.17 mmol, 970 mg), Cs₂CO₃ (5.95 mmol, 1937 mg), 4-(4,4,5,5-tetramethyl-1,3,2-dioxaborolan-2-yl)benzamide (5.69 mmol, 1405 mg) and palladium(II) acetate (0.414 mmol, 93 mg) were suspended in dioxane (20 mL). The reaction mixture was stirred at 40° C. under N₂-atmosphere. Then, 4,5-bis(diphenylphosphino)-9,9-dimethylxanthene (Xantphos) (0.776 mmol, 449 mg) was added and the reaction was stirred 1.5 h at reflux. The reaction mixture was cooled and filtered over decalite. The residue was rinsed with EtOAc and EtOH. The filtrate was concentrated. The residue was purified using silica gel chromatography (DCM/MeOH 9:1). The fractions containing desired product were combined and concentrated and triturated with Et₂O (3×) to give N-(4-(3-fluorooxetan-3-yl)pyridin-2-yl)-4-(4,4,5,5-tetramethyl-1,3,2-dioxaborolan-2-yl)benzamide (1.01 g, 49.0%).

Intermediate AC

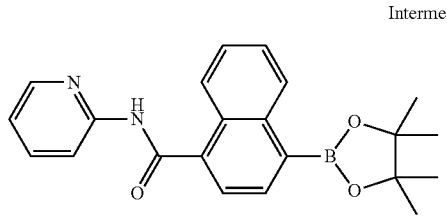

N-(pyridin-2-yl)-4-(4,4,5,5-tetramethyl-1,3,2-dioxaborolan-2-yl)-1-naphthamide

This compound was prepared, in an analogous manner as described in Intermediate V, starting from commercially available 4-(4,4,5,5-tetramethyl-1,3,2-dioxaborolan-2-yl)-1-naphthoic acid and 2-aminopyridine, to afford the title compound (400 mg, 31.9%).

Intermediate AD

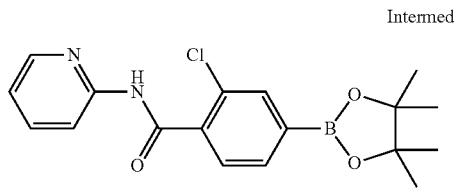

2-chloro-N-(pyridin-2-yl)-4-(4,4,5,5-tetramethyl-1,3,2-dioxaborolan-2-yl)benzamide This compound was prepared in an analogous manner as described in Intermediate V, starting from commercially available 2-chloro-4-(4,4,5,5-tetramethyl-1,3,2-dioxaborolan-2-yl)benzoic acid and 2-aminopyridine, to afford the title compound (1.7 g, 67.0%).

Intermediate AE

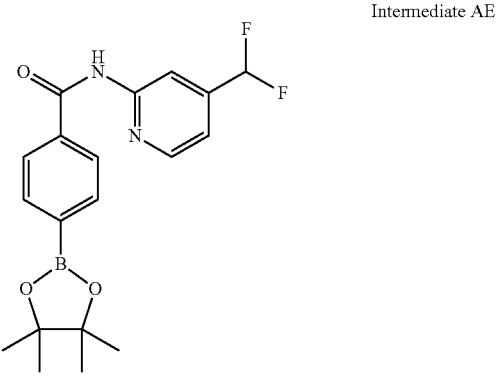 [SMILES: CC1(C)OB(c2ccc(C(=O)Nc3cc(C(F)F)ccn3)cc2)OC1(C)C]

N-(4-(difluoromethyl)pyridin-2-yl)-4-(4,4,5,5-tetramethyl-1,3,2-dioxaborolan-2-yl)benzamide (a) 2-bromo-4-(difluoromethyl)pyridine To a mixture of 2-bromoisonicotinaldehyde (2 g, 10.752 mmol) in dichloromethane was added DAST (6.613 g, 32.257 mmol) at −78° C. The mixture was warmed to room temperature over 2 h. The reaction mixture was quenched with saturated sodium bicarbonate and extracted with dichloromethane. The combined organic layer was washed with brine, dried over anhydrous sodium sulfate and evaporated to give 2-bromo-4-(difluoromethyl)pyridine (2 g). ¹HNMR (400 MHz, CDCl3): δ=8.52~8.51 (d, J=8.0 Hz, 1 H), 7.63 (s, 1 H), 7.40~7.38 (d, J=8.0 Hz, 1 H), MS (ESI): M/Z (M+1)=207.95.

(b) N-(4-(difluoromethyl)pyridin-2-yl)-4-(4,4,5,5-tetramethyl-1,3,2-dioxaborolan-2-yl)benzamide To a degassed mixture of 4-(4,4,5,5-tetramethyl-1,3,2-dioxaborolan-2-yl)benzamide (1.5 g, 6.07 mmol) and 2-bromo-4-(difluoromethyl)pyridine (1.5 g, 7.3 mmol) in dioxane was added Pd₂(dba)₃ (catalytic amount), X-phos (catalytic amount) and Cs₂CO₃ (3.96 g, 12.14 mmol) under N₂ atmosphere. The mixture was heated to 100° C. overnight. The reaction mixture was cooled to room temperature and filtered. The filtrate was concentrated, and the residue was purified by column chromatography with silica gel eluted by 0 to 70% ethyl acetate in petroleum ether to give the title compound (1.8 g). ¹HNMR (400 MHz, DMSO-d6): δ=8.55~8.54 (d, J=4 Hz, 1 H), 8.39 (s, 1 H), 8.02~8.00 (d, J=8.0 Hz, 2 H), 7.79~7.77 (d, J=8.0 Hz, 2 H), 7.34~7.33 (d, J=4 Hz, 1 H), 7.29~7.01 (t, J=52 Hz, 1 H), 1.30 (s, 12 H), MS (ESI): M/Z (M+1)=375.16.

Intermediate AF

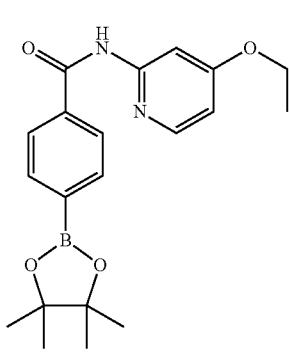

N-(4-ethoxypyridin-2-yl)-4-(4,4,5,5-tetramethyl-1,3,2-dioxaborolan-2-yl)benzamide To a degassed mixture of 4-(4,4,5,5-tetramethyl-1,3,2-dioxaborolan-2-yl)benzamide (9.4 g, 38 mmol) and 2-chloro-4-ethoxypyridine (5 g, 31.7 mmol) in dioxane was added Brettphos-prePd (catalytic amount) and $Cs_2CO_3$ (12.3 g, 37.8 mmol) under $N_2$ atmosphere. The mixture was heated to 100° C. for 3.5 h. The reaction mixture was cooled to room temperature and filtered. The filtrate was concentrated, and the residue was purified on silica gel (PE: EA=100%~30%) to give N-(4-ethoxypyridin-2-yl)-4-(4,4,5,5-tetramethyl-1,3,2-dioxaborolan-2-yl)benzamide (8.8 g, yield 75%). $^1$HNMR (400 MHz, CDCl3): β=8.74 (s, 1 H), 8.05~8.02 (m, 1 H), 8.01 (s, 1 H), 7.94~7.89 (m, 4 H), 6.60~6.59 (m, 1 H), 4.20~4.14 (m, 2 H), 1.47~1.43 (m, 3 H), 1.36 (s, 12 H), MS (ESI): M/Z (M+1)=369.19.

Intermediate AG

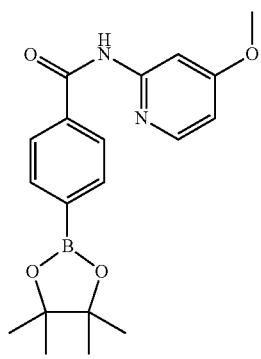

N-(4-methoxypyridin-2-yl)-4-(4,4,5,5-tetramethyl-1,3,2-dioxaborolan-2-yl)benzamide The title compound was prepared using analogous procedures as used for the preparation of Intermediate A, starting with 4-methoxy-2-aminopyridine. LC-MS (ESI) [M+H]$^+$: calculated: 355.2, found: 355.2. Rt=1.69 min (Method O).

Intermediate AH

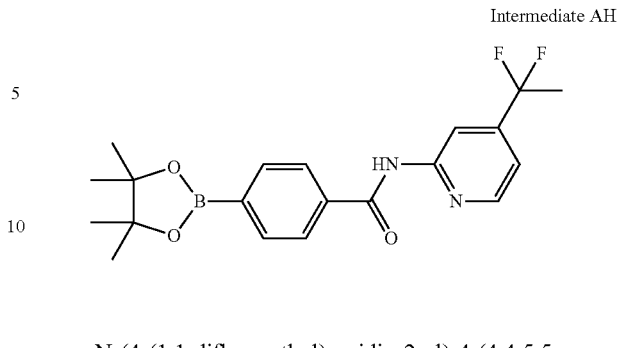

N-(4-(1,1-difluoroethyl)pyridin-2-yl)-4-(4,4,5,5-tetramethyl-1,3,2-dioxaborolan-2-yl)benzamide (a) 2-bromo-N-methoxy-N-methylisonicotinamide To a solution of 2-bromoisonicotinic acid (40.4 g, 0.2 mol) in 200 mL of dry DMF was added CDI (32.4 g, 0.2 mol) portionwise. After stirring for 30 min under $N_2$ atmosphere N,O-methylhydroxylamine hydrochloride (19.5 g, 0.2 mol) was added, the mixture was stirred at room temperature overnight under $N_2$ atmosphere. The mixture was diluted with water and extracted with EtOAc. The combined organic phase was washed with water and brine, dried over $Na_2SO_4$, filtered and concentrated in vacuo, purified by column chromatography with silica gel eluted by 0~40% ethyl acetate in petroleum ether to give 2-bromo-N-methoxy-N-methylisonicotinamide (28 g). $^1$HNMR (400 MHz, DMSO-d6): δ=8.50 (d, J=4.8 Hz, 1 H), 7.79 (s, 1 H), 7.59 (d, J=4.8 Hz, 1 H), 3.56 (s, 3 H), 3.27 (s, 3 H). MS (ESI): M/Z (M/M+2=1/1) 244.7/246.7.

(b) 1-(2-bromopyridin-4-yl)ethanone

To a solution of 2-bromo-N-methoxy-N-methylisonicotinamide (27 g, 0.11 mol) in 200 mL of dry THF was added 3 M MeMgBr (44 mL, 0.132 mol) at −78° C. under $N_2$ atmosphere. The mixture was stirred at −78° C. for 2 h under $N_2$, quenched with aq. $NH_4Cl$, and extracted with EtOAc. The organic phase was washed with water and brine, dried over $Na_2SO_4$, filtered and concentrated in vacuo. Purification by column chromatography with silica gel eluted by 0~30% ethyl acetate in petroleum ether (60-90 fraction) provided 1-(2-bromopyridin-4-yl)ethanone (20 g, yield: 90.9%). $^1$HNMR (400 MHz, DMSO-d6): δ=8.59 (d, J=4.8 Hz, 1 H), 8.01 (s, 1 H), 7.82 (d, J=4.8 Hz, 1 H), 2.61 (s, 3 H).

(c) 2-bromo-4-(1,1-difluoroethyl)pyridine

To a mixture of 1-(2-bromopyridin-4-yl)ethanone (20 g, 0.1 mol) in 200 mL of DCM was added DAST (40.3 g, 0.25 mol) at 0° C. The reaction mixture was stirred overnight, then poured carefully into aq. $NaHCO_3$, and extracted with DCM. The organic phases were washed with water and brine, dried over $Na_2SO_4$, filtered and concentrated in vacuo, purified by column chromatography with silica gel eluted by 0~20% ethyl acetate in petroleum ether to give 2-bromo-4-(1,1-difluoroethyl)pyridine (18.5 g, yield: 84.1%). $^1$HNMR (400 MHz, DMSO-d6): δ=8.56 (d, J=5.2 Hz, 1 H), 7.86 (s, 1 H), 7.65 (d, J=4.8 Hz, 1 H), 2.00 (t, J=19.2 Hz, 3 H). MS (ESI): M/Z (M/M+2=1/1) 222.0/224.0

(d) N-(4-(1,1-difluoroethyl)pyridin-2-yl)-4-(4,4,5,5-tetramethyl-1,3,2-dioxaborolan-2-yl)benzamide The title compound was prepared using procedures analogous to those described for synthesis of Intermediate AF, starting with 2-bromo-4-(1,1-difluoroethyl)pyridine. 1H NMR (400 MHz, CHLOROFORM-d) δ=8.73 (s, 1H), 8.56 (s, 1H), 8.38 (d, J=5.3 Hz, 1H), 7.97~7.89 (m, 4H), 7.22 (d, J=5.3 Hz, 1H), 1.96 (t, J=18.3 Hz, 3H), 1.37 (s, 12H)

Intermediate AG

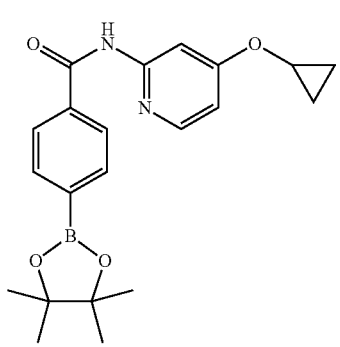

N-(4-cyclopropoxypyridin-2-yl)-4-(4,4,5,5-tetramethyl-1,3,2-dioxaborolan-2-yl)benzamide (a) 2-chloro-4-cyclopropoxypyridine To a solution of 2-chloropyridin-4-ol (1 g, 7.75 mmol) in DMA (10 ml) was added bromocyclopropane (2.8 g, 23.2 mmol), NaI (1.16 g, 7.75 mmol) and $Cs_2CO_3$ (5 g, 15.5 mmol). The mixture was stirred at 170° C. for 20 min, and then 180° C. for 30 min. The reaction mixture was extracted with EtOAc. The organic layer was dried and concentrated, and the residue was purified by column chromatography with silica gel eluted by 0~30% ethyl acetate in petroleum ether to give 300 mg of 2-chloro-4-cyclopropoxypyridine. $^1$HNMR (400 MHz, $CDCl_3$) δ=8.19 (d, J=5.8 Hz, 1H), 7.02 (d, J=2.0 Hz, 1H), 6.87 (dd, J=2.0, 5.8 Hz, 1H), 3.80 (tt, J=3.0, 6.0 Hz, 1H), 0.91-0.75 (m, 4H)

(b) N-(4-cyclopropoxypyridin-2-yl)-4-(4,4,5,5-tetramethyl-1,3,2-dioxaborolan-2-yl)benzamide N-(4-cyclopropoxypyridin-2-yl)-4-(4,4,5,5-tetramethyl-1,3,2-dioxaborolan-2-yl)benzamide was prepared following the procedure of intermediate AF. $^1$H NMR (400 MHz, CHLOROFORM-d) δ=9.12 (br. s., 1H), 8.27 (d, J=2.01 Hz, 1H), 8.20 (d, J=5.52 Hz, 1H), 8.07 (d, J=6.02 Hz, 1H), 7.66 (d, J=7.78 Hz, 1H), 7.37 (d, J=7.78 Hz, 1H), 6.62-6.73 (m, 1H), 6.42-6.49 (m, 1H), 3.84-3.94 (m, 1H), 1.37 (s, 12H), 0.78-0.94 (m, 4H)

Intermediate AJ:

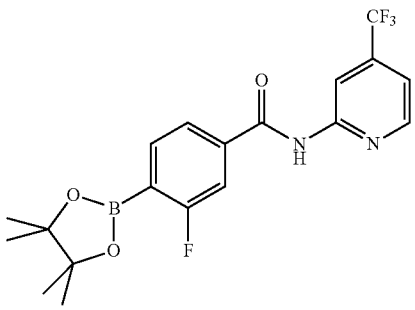

3-fluoro-4-(4,4,5,5-tetramethyl-1,3,2-dioxaborolan-2-yl)-N-(4-(trifluoromethyl)-pyridin-2-yl)benzamide (a) 4-bromo-3-fluorobenzoyl chloride To a stirred mixture 4-bromo-3-fluorobenzoic acid (10.0 g, 45.7 mmol) in DCM (100 ml) at 0° C. was added oxalyl chloride (4.80 ml, 54.8 mmol) and several drops of DMF. The mixture was then stirred at room temperature overnight. The mixture was then concentrated by rotary evaporation and coevaporated with toluene to provide 4-bromo-3-fluorobenzoyl chloride (10.5 g) as a yellow solid, which was taken to the next step.

(b) 4-bromo-3-fluoro-N-(4-(trifluoromethyl)pyridin-2-yl)benzamide 4-bromo-3-fluorobenzoyl chloride (3.60 g, 14.40 mmol) was added to a stirred solution of DIPEA (3.02 ml, 17.28 mmol), DMAP (0.176 g, 1.440 mmol) and 4-(trifluoromethyl)pyridin-2-amine (2.45 g, 15.11 mmol) in THF (36 ml) and then the mixture was stirred at 50° C. for 12 h. The mixture was diluted with EtOAc, extracted twice with 0.1 N HCl, twice with 0.1 M KOH, washed with brine, dried over $MgSO_4$, and filtered. The filtrate was concentrated to afford the title compound as a tan solid (4.59 g).

(c) 3-fluoro-4-(4,4,5,5-tetramethyl-1,3,2-dioxaborolan-2-yl)-N-(4-(trifluoromethyl)pyridin-2-yl)benzamide To a premixed and degassed solution of $Pd(OAc)_2$ (15.46 mg, 0.069 mmol) and X-Phos (65.6 mg, 0.138 mmol) in 1 mL of dioxane that had been stirred for 20 min was added to a stirred, degassed mixture of bis(pinicolato)diboron (699 mg, 2.75 mmol), potassium acetate (405 mg, 4.13 mmol) and 4-bromo-3-fluoro-N-(4-(trifluoromethyl)-pyridin-2-yl)benzamide (500 mg, 1.377 mmol) in dioxane (10 ml). The mixture was stirred at 90° C. for 6 h. The reaction mixture was filtered and concentrated in vacuo. The residue was purified by MPLC (10 to 30% ethyl acetate in hexanes) to afford the title compound as a white solid (424 mg). $^1$HNMR (400 MHz, $CD_3Cl$, δ, ppm): 8.79 (s, 1H), 8.71 (s, 1H), 8.51 (d, 1H), 7.92 (dd, 1H), 7.68 (dd, 1H), 7.64 (dd, 1H), 7.35 (dd, 1H), 1.41 (s, 12H).

Intermediate AK

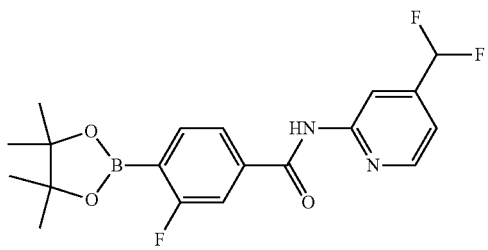

N-(4-(difluoromethyl)pyridin-2-yl)-3-fluoro-4-(4,4,5,5-tetramethyl-1,3,2-dioxaborolan-2-yl)benzamide (a) tert-butyl (4-(difluoromethyl)pyridin-2-yl)carbamate A degassed mixture of 2-chloro-4-(difluoromethyl)pyridine (6.3 g, 38.5 mmol), carbamic acid tert-butyl ester (5.4 g, 46.2 mmol), $Cs_2CO_3$ (25 g, 77 mmol), X-phos (1.83 g, 3.85 mmol) and $Pd(OAc)_2$ (430 mg, 1.925 mmol) in 40 mL of 1,4-dioxane was stirred at 90° C. for 2 h under $N_2$. The mixture was concentrated in vacuo and the residue was purified by column chromatography with silica gel eluted by 0~30% ethyl acetate in petroleum ether (60-90 fraction) to give tert-butyl (4-(difluoromethyl)-pyridin-2-yl)carbamate (7.57 g). $^1$HNMR (400 MHz, DMSO-d6): δ=10.11 (s, 1 H), 8.38 (d, J=5.2 Hz, 1 H), 7.99 (s, 1 H), 7.16 (d, J=4.8 Hz, 1 H), 7.07 (t, J=55.2 Hz, 1 H), 1.46 (s, 9 H).

(b) 4-(difluoromethyl)pyridin-2-amine

To a mixture of tert-butyl (4-(difluoromethyl)pyridin-2-yl)carbamate (6.8 g, 27.8 mmol) in 40 mL of DCM was added 20 mL of trifluoroacetic acid. The reaction was stirred at r.t. for 1 h and concentrated in vacuo. Aq. $NaHCO_3$ was added and the reaction mixture was extracted with EtOAc. The organic layer was washed with brine, dried over $Na_2SO_4$, concentrated in vacuo to give the title compound (4 g). $^1$HNMR (400 MHz, DMSO-D6): δ=8.00 (d, J=5.2 Hz, 1 H), 6.88 (t, J=55.6 Hz, 1 H), 6.56 (d, J=5.6 Hz, 1 H), 6.54 (s, 1 H), 6.27 (s, 2 H).

(c) N-(4-(difluoromethyl)pyridin-2-yl)-3-fluoro-4-(4,4,5,5-tetramethyl-1,3,2-dioxaborolan-2-yl)benzamide 4-(difluoromethyl)pyridin-2-amine was converted to the title compound using procedures analogous to those described for Intermediate AJ. $^1$H NMR (400 MHz, DMSO-d6): δ=11.25 (s, 1 H), 8.56 (d, J=4.8 Hz, 1 H), 8.37 (s, 1 H), 7.85 (d, J=7.6 Hz, 1 H), 7.74~7.79 (m, 2 H), 7.35 (d, J=5.2 Hz, 1 H), 7.15 (t, J=55.2 Hz, 1 H), 1.31 (s, 12 H). MS (ESI): M/Z (M+1): 392.9.

Intermediate AL

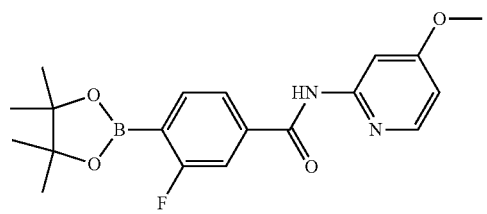

3-fluoro-N-(4-methoxypyridin-2-yl)-4-(4,4,5,5-tetramethyl-1,3,2-dioxaborolan-2-yl)benzamide 4-methoxy-2-aminopyridine was converted to the title compound using procedures analogous to those described for Intermediate AJ. $^1$HNMR (400 MHz, CDCl3): δ=8.72 (brs, 1 H), 8.07 (d, J=5.6 Hz, 1 H), 8.00 (d, J=2.0 Hz, 1 H), 7.86 (dd, $J_1$=5.6 Hz, $J_2$=7.6 Hz, 1 H), 7.59~7.66 (m, 2 H), 6.64 (dd, $J_1$=2.0 Hz, $J_2$=6.0 Hz, 1 H), 3.91 (s, 3 H), 1.37 (s, 12 H).

Intermediate AM

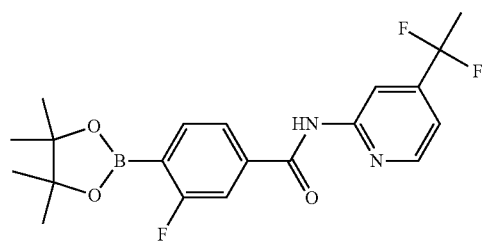

N-(4-(1,1-difluoroethyl)pyridin-2-yl)-3-fluoro-4-(4,4,5,5-tetramethyl-1,3,2-dioxaborolan-2-yl)benzamide (a) 2-bromo-N-methoxy-N-methylisonicotinamide To a solution of 2-bromoisonicotinic acid (40.4 g, 0.2 mol) in 200 mL of dry DMF was added CDI (32.4 g, 0.2 mol) portionwise. After stirring for 30 min under $N_2$ atmosphere N,O-methylhydroxylamine hydrochloride (19.5 g, 0.2 mol) was added, the mixture was stirred at room temperature overnight under $N_2$ atmosphere. The mixture was diluted with water and extracted with EtOAc. The combined organic phase was washed with water and brine, dried over $Na_2SO_4$, filtered and concentrated in vacuo, purified by flash chromatography on silica gel to give compound 2-bromo-N-methoxy-N-methylisonicotinamide (28 g, yield 57%). $^1$HNMR (400 MHz, DMSO-d6): δ=8.50 (d, J=4.8 Hz, 1 H), 7.79 (s, 1 H), 7.59 (d, J=4.8 Hz, 1 H), 3.56 (s, 3 H), 3.27 (s, 3 H). MS (ESI): M/Z (M/M+2=1/1) 244.7/246.7

(b) 1-(2-bromopyridin-4-yl)ethanone

To a solution of 2-bromo-N-methoxy-N-methylisonicotinamide (27 g, 0.11 mol) in 200 mL of dry THF was added 3 M MeMgBr (44 mL, 0.132 mol) at −78° C. under $N_2$ atmosphere. The mixture was stirred at −78° C. for 2 h under $N_2$, and then quenched with aq.$NH_4Cl$, extracted with EtOAc. The organic phase was washed with water and brine, dried over $Na_2SO_4$, filtered and concentrated in vacuo, purified by flash chromatography on silica gel to give 1-(2-bromopyridin-4-yl)ethanone (20 g, yield: 90.9%). $^1$HNMR (400 MHz, DMSO-d6): δ=8.59 (d, J=4.8 Hz, 1 H), 8.01 (s, 1 H), 7.82 (d, J=4.8 Hz, 1 H), 2.61 (s, 3 H).

(c) 2-bromo-4-(1,1-difluoroethyl)pyridine

To a mixture of 1-(2-bromopyridin-4-yl)ethanone (20 g, 0.1 mol) in 200 mL of DCM was added DAST (40.3 g, 0.25 mol) at 0° C. The reaction mixture was stirred overnight, poured carefully into aq. $NaHCO_3$, and extracted with DCM. The organic phases were washed with water and brine, dried over Na₂SO₄, filtered and concentrated in vacuo. Purification by flash chromatography on silica gel to gave 2-bromo-4-(1,1-difluoroethyl)pyridine (18.5 g, yield: 84.1%). ¹HNMR (400 MHz, DMSO-d6): δ=8.56 (d, J=5.2 Hz, 1 H), 7.86 (s, 1 H), 7.65 (d, J=4.8 Hz, 1 H), 2.00 (t, J=19.2 Hz, 3 H). MS (ESI): M/Z (M/M+2=1/1) 222.0/224.0

(d) tert-butyl (4-(1,1-difluoroethyl)pyridin-2-yl) carbamate 4-(1,1-difluoroethyl)-2-aminopyridine was converted to the title compound using procedures analogous to those described for Intermediate AJ. ¹HNMR (400 MHz, CDCl₃): δ=9.56 (brs, 1 H), 8.60 (s, 1 H), 8.36 (d, J=5.2 Hz, 1 H), 7.88 (dd, J₁=6.0 Hz, J₂=7.6 Hz, 1 H), 7.67~7.76 (m, 2 H), 7.24~7.25 (m, 1 H), 1.96 (t, J=18.4 Hz, 3 H), 1.38 (s, 12 H).

Intermediate AN

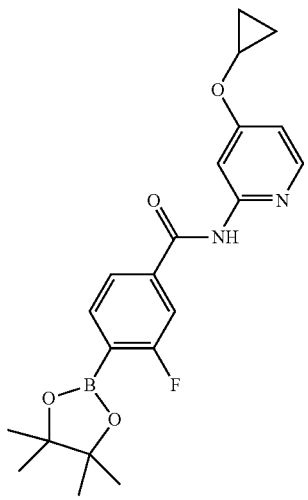

N-(4-cyclopropoxypyridin-2-yl)-3-fluoro-4-(4,4,5,5-tetramethyl-1,3,2-dioxaborolan-2-yl)benzamide The title compound was prepared using analogous procedures to preparation of Intermediate AJ, starting with 4-cyclopropoxy-2-aminopyridine. LC-MS (ESI), [M+H]⁺: calc, 399.2, found: 399.2.

Intermediate AO

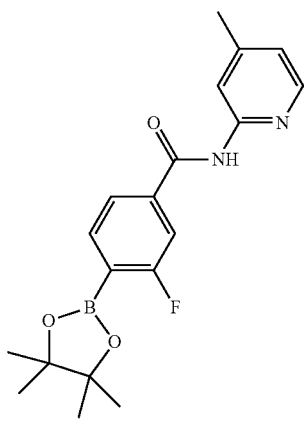

3-fluoro-N-(4-methylpyridin-2-yl)-4-(4,4,5,5-tetramethyl-1,3,2-dioxaborolan-2-yl)benzamide The title compound was prepared following same procedure of Intermediate AJ starting with 2-amino-4-methylaminopyridine. ¹HNMR (400 MHz, CDCl3)=8.61 (br. s, 1H), 8.21 (s, 1H), 8.14 (d, J=5.0 Hz, 1H), 7.91-7.82 (m, 1H), 7.62 (dd, J=8.8, 15.8 Hz, 2H), 6.92 (d, J=4.5 Hz, 1H), 2.41 (s, 3H), 1.38 (s, 12H); MS (APCI): M/Z (M+1): 357.2.

Intermediate AP

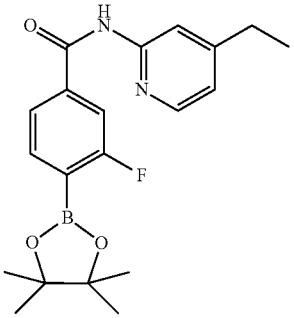

N-(4-ethylpyridin-2-yl)-3-fluoro-4-(4,4,5,5-tetramethyl-1,3,2-dioxaborolan-2-yl)benzamide The title compound was prepared using procedures analogous to Intermediate AJ, starting with 2-amino-4-ethylpyridine. ¹HNMR (400 MHz, CDCl3): δ=8.81 (s, 1 H), 8.24 (s, 1 H), 8.12~8.11 (d, J=4 Hz, 1 H), 7.86~7.83 (m, 1 H), 7.66~7.59 (m, 2 H), 6.93~6.92 (d, J=4 Hz, 1 H), 2.73~2.67 (m, 2H), 1.38 (s, 12 H), 1.30~1.26 (t, J=8 Hz, 3 H), MS MS (EI): M/Z (M+1): 371.19.

Intermediate AQ

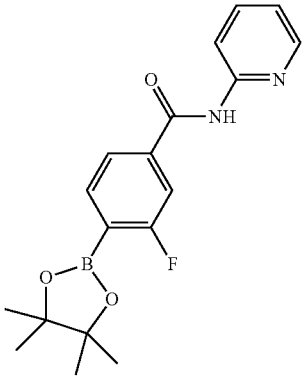

3-fluoro-N-(pyridin-2-yl)-4-(4,4,5,5-tetramethyl-1,3, 2-dioxaborolan-2-yl)benzamide The title compound was prepared using procedures analogous to Intermediate AJ, starting with 2-aminopyridine. ¹HNMR (400 MHz, CDCl3): δ=8.64 (brs, 1 H), 8.36 (d, J=8.0 Hz, 1 H), 8.28~8.30 (m, 1 H), 7.86 (dd, J₁=6.0 Hz, J₂=7.6 Hz, 1 H), 7.75~7.79 (m, 1 H), 7.10 (dd, J₁=0.8 Hz, J₂=5.2 Hz, 1 H), 7.08 (dd, J₁=0.8 Hz, J₂=5.2 Hz, 1 H), 7.07~7.11 (m, 1 H), 1.38 (s, 12 H).

Intermediate AR

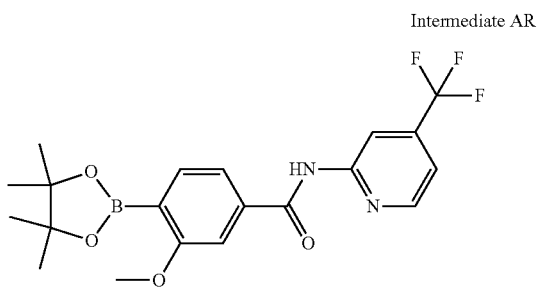 [SMILES: COc1cc(C(=O)Nc2cc(C(F)(F)F)ccn2)ccc1B1OC(C)(C)C(C)(C)O1]

3-methoxy-4-(4,4,5,5-tetramethyl-1,3,2-dioxaborolan-2-yl)-N-(4-(trifluoromethyl)-pyridin-2-yl)benzamide (a) 3-methoxy-4-(4,4,5,5-tetramethyl-1,3,2-dioxaborolan-2-yl)benzoic acid A solution of 4-borono-3-methoxybenzoic acid (500 mg, 2.55 mmol) and pinacol (330 mg, 2.79 mmol) in THF (5 ml) and toluene (5 ml) was stirred at 40° C. overnight. After cooling the mixture was partitioned with water and extracted with ethyl acetate three times. The combined organic layers were washed with brine, dried over anhydrous $Na_2SO_4$ and concentrated in vacuo. The crude title compound was used in the next step without further purification.

(b) 3-methoxy-4-(4,4,5,5-tetramethyl-1,3,2-dioxaborolan-2-yl)benzoyl chloride

To a solution of 3-methoxy-4-(4,4,5,5-tetramethyl-1,3,2-dioxaborolan-2-yl)benzoic acid (700 mg, 2.52 mmol) in DCM (20 ml) was added 2 drops of DMF. The mixture was cooled to 0° C. and oxalyl chloride (629 mg, 5.03 mmol) was added. The reaction mixture was stirred at 0° C. for 2 h. The solvent was concentrated in vacuo, and the crude 3-methoxy-4-(4,4,5,5-tetramethyl-1,3,2-dioxaborolan-2-yl) benzoyl chloride was used in the next step directly.

(c) 3-methoxy-4-(4,4,5,5-tetramethyl-1,3,2-dioxaborolan-2-yl)-N-(4-(trifluoromethyl)pyridin-2-yl) benzamide To a solution of 3-methoxy-4-(4,4,5,5-tetramethyl-1,3,2-dioxaborolan-2-yl)benzoyl chloride (700 mg, 2.36 mmol) in THF (50 ml) was added 4-(trifluoromethyl)pyridin-2-amine (574 mg, 3.55 mmol). The resulting mixture was stirred at 80° C. overnight. The mixture was cooled to room temperature, concentrated in vacuo and the residue was purified by silica gel chromatography (petroleum ether/ethyl acetate=3/1 v/v %) to afford the title product (546 mg, three steps). MS-ESI (m/z): 423 (M+1)$^+$ (Acq Method: 10-80AB_2 min; Rt: 1.26 min).

Intermediate AS

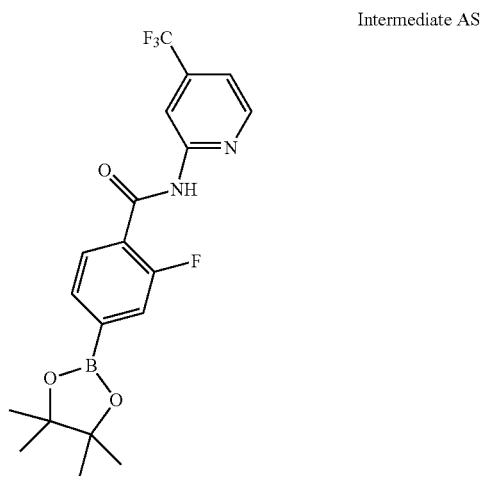 [SMILES: CC1(C)OB(c2ccc(C(=O)Nc3cc(C(F)(F)F)ccn3)c(F)c2)OC1(C)C]

2-fluoro-4-(4,4,5,5-tetramethyl-1,3,2-dioxaborolan-2-yl)-N-(4-(trifluoromethyl)-pyridin-2-yl)benzamide The title compound was prepared using procedures analogous to Intermediate F, starting from 4-bromo-2-fluorobenzoic acid, to afford the title compound. MS-ESI (m/z): 411 (M+1)$^+$ (Acq Method: 10-80AB_2 min; Rt: 1.55 min). $^1$H NMR (400 MHz, DMSO-d$_6$) δ 11.41 (s, 1H), 8.66 (d, J=5.1 Hz, 1H), 8.51 (s, 1H), 7.84-7.66 (m, 1H), 7.64-7.51 (m, 2H), 7.45 (d, J=10.2 Hz, 2H), 1.29 (s, 12H).

Intermediate AT

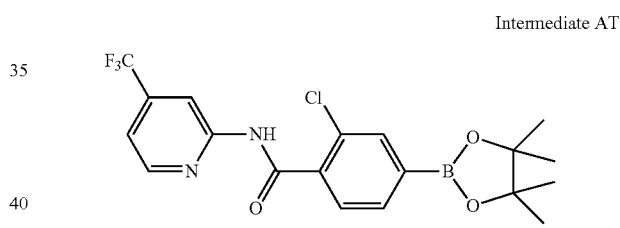

2-chloro-4-(4,4,5,5-tetramethyl-1,3,2-dioxaborolan-2-yl)-N-(4-(trifluoromethyl)-pyridin-2-yl)benzamide (a) 4-bromo-2-chloro-N-(4-(trifluoromethyl)pyridin-2-yl)benzamide To a solution of methyl 4-bromo-2-chlorobenzoate (1.15 g, 7.1 mmol) in toluene (20 ml) was added dropwise Me$_3$Al (5 ml, 2 M in toluene, 10 mmol) under nitrogen protection at room temperature. After the addition was complete the mixture was stirred for 10 min, and 4-(trifluoromethyl) pyridin-2-amine (1.76 g, 7.1 mmol) was added. The resulting mixture was heated to reflux for 8 h. After cooling the mixture was quenched with water, extracted with EtOAc three times. The combined organic layers were washed with brine, dried over anhydrous Na$_2$SO$_4$, and concentrated in vacuo. The residue was purified by silica gel chromatography (petroleum ether/ethyl acetate=6/1 v/v %) to give the title compound (1.88 g).

(b) 2-chloro-4-(4,4,5,5-tetramethyl-1,3,2-dioxaborolan-2-yl)-N-(4-(trifluoromethyl)pyridin-2-yl)benzamide This compound was prepared in an analogous manner as described in Intermediate AJ step b, starting with 4-bromo- 2-chloro-N-(4-(trifluoromethyl)pyridin-2-yl)benzamide (6.8 g), to afford the title compound (3.2 g). MS-ESI (m/z): 427 (M+1)+ (Acq Method: 10-80AB_2 min; Rt: 1.44 min). ¹H NMR (400 MHz, METHANOL-d4) δ 8.63-8.46 (m, 2H), 7.84-7.69 (m, 2H), 7.58 (s, 1H), 7.40 (br. s., 1H), 1.35 (s, 12H).

Intermediate AU

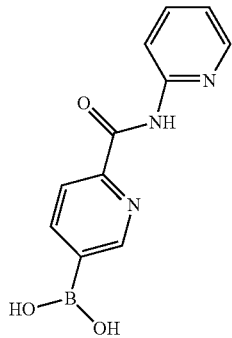

6-(pyridin-2-ylcarbamoyl)pyridin-3-ylboronic acid

This compound was prepared using procedures analogous to those described for synthesis of Intermediate AJ, starting from 5-bromopicolinic acid, to afford the title compound. MS-ESI (m/z): 244 (M+1)+ (Acq Method: 10-80AB_2 min; Rt: 0.75 min).

Intermediate AV

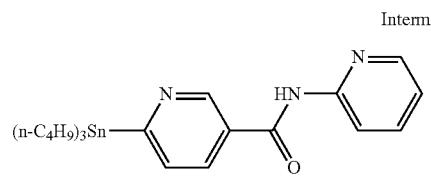

N-(pyridin-2-yl)-6-(tributylstannyl)nicotinamide (a) 6-bromo-N-(pyridin-2-yl)nicotinamide This compound was prepared using procedures analogous to those described for synthesis of Intermediate AJ step (a), starting from 2 g of 6-bromonicotinic acid, to afford 6-bromo-N-(pyridin-2-yl)nicotinamide (1.9 g, 70%).

(b) N-(pyridin-2-yl)-6-(tributylstannyl)nicotinamide

To a solution of 6-bromo-N-(pyridin-2-yl)nicotinamide (200 mg, 0.72 mmol) in dioxane (5 ml) was added Sn₂(n-Bu)₆ (1.3 g, 2.2 mmol), followed by Pd(PPh₃)₂Cl₂ (20 mg, 0.03 mmol) under a nitrogen atmosphere. The resulting mixture was stirred at 120° C. for 30 h. After cooling, the mixture was filtered and the filtrate was used without further purification. MS-ESI (m/z): 490 (M+1)+

Example 1

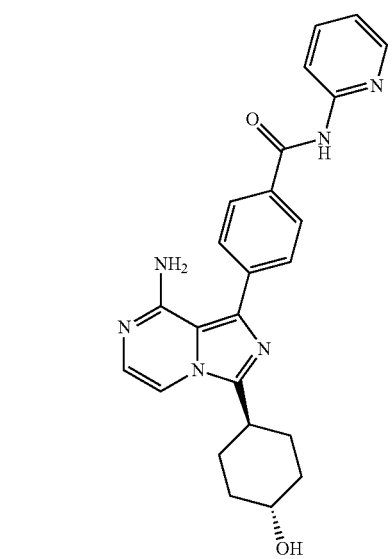 [SMILES: Nc1nccn2c1c(-c1ccc(C(=O)Nc3ccccn3)cc1)nc2[C@H]1CC[C@H](O)CC1]

4-(8-amino-3-((trans)-4-hydroxycyclohexyl)imidazo[1,5-a]pyrazin-1-yl)-N-(pyridin-2-yl)benzamide (trans)-4-(8-Amino-1-bromoimidazo[1,5-a]pyrazin-3-yl)cyclohexyl acetate (0.129 mmol, 40 mg) and 4-(pyridin-2-yl-aminocarbonyl)benzeneboronic acid (0.14 mmol, 45.8 mg) were suspended in a mixture of 2N aqueous potassium carbonate solution (0.386 mmol, 193 μL) dioxane (6 mL) and water (3 mL). Nitrogen was bubbled through the mixture, followed by the addition of 1,1'-bis(diphenylphosphino)-ferrocene palladium (II) chloride (0.013 mmol, 10.39 mg). The reaction mixture was stirred at 100° C. overnight. Water was added to the reaction mixture, followed by an extraction with ethyl acetate (2×). The combined organic layer was washed with brine, dried over magnesium sulfate and evaporated. After evaporation, the residue was purified by preparative HPLC. Fractions containing product were collected and lyophilized to afford 27 mg of 4-(8-amino-3-((trans)-4-hydroxycyclohexyl)-imidazo[1,5-a]pyrazin-1-yl)-N-(pyridin-2-yl)benzamide (48.8% yield). Data: UPLC (C) R$_t$: 1.05 min; m/z 429.3 (M+H)+.

Example 2

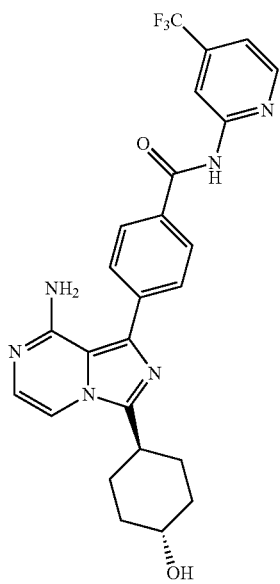 [SMILES: Nc1nccn2c1c(-c1ccc(C(=O)Nc3cc(C(F)(F)F)ccn3)cc1)nc2[C@H]1CC[C@H](O)CC1]

4-(8-amino-3-((trans)-4-hydroxycyclohexyl)imidazo[1,5-a]pyrazin-1-yl)-N-(4-(trifluoromethyl)pyridin-2-yl)benzamide This compound was prepared in an analogous manner as described in Example 1, from Intermediate 1 and Intermediate D, to afford the title compound (4.2 mg, 6.6%). Data: UPLC(C) $R_t$: 2.05 min; m/z 497.2 (M+H)$^+$.

Example 3

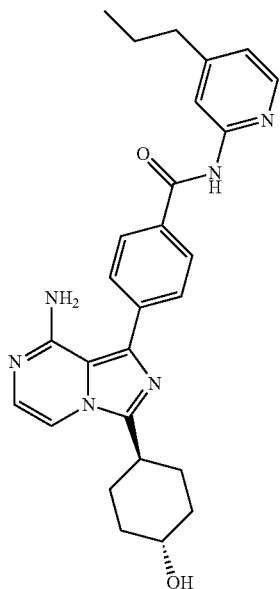 [SMILES: CCCc1ccnc(NC(=O)c2ccc(-c3nc([C@H]4CC[C@H](O)CC4)n4ccnc(N)c34)cc2)c1]

4-(8-amino-3-((trans)-4-hydroxycyclohexyl)imidazo[1,5-a]pyrazin-1-yl)-N-(4-propylpyridin-2-yl)benzamide This compound was prepared, in an analogous manner as described in Example 1, from Intermediate 1 and Intermediate C, to afford the title compound (10.6 mg, 17.5%). Data: UPLC(C) $R_t$: 1.44 min; m/z 471.3 (M+H)$^+$.

Example 4

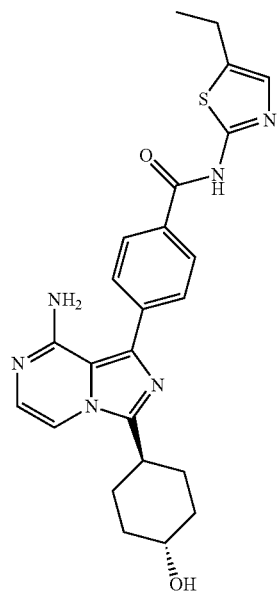 [SMILES: CCc1cnc(NC(=O)c2ccc(-c3nc([C@H]4CC[C@H](O)CC4)n4ccnc(N)c34)cc2)s1]

4-(8-amino-3-((trans)-4-hydroxycyclohexyl)imidazo[1,5-a]pyrazin-1-yl)-N-(5-ethylthiazol-2-yl)benzamide This compound was prepared in an analogous manner as described in Example 1, from Intermediate 1 and Intermediate O, to afford the title compound (4.6 mg, 7.7%). Data: UPLC(C) $R_t$: 1.83 min; m/z 463.2 (M+H)$^+$.

Example 5

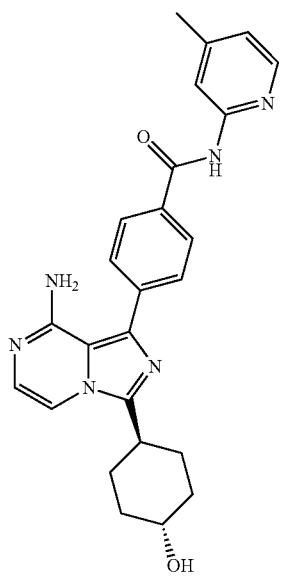 [SMILES: Cc1ccnc(NC(=O)c2ccc(-c3nc([C@H]4CC[C@H](O)CC4)n4ccnc(N)c34)cc2)c1]

4-(8-amino-3-((trans)-4-hydroxycyclohexyl)imidazo[1,5-a]pyrazin-1-yl)-N-(4-methylpyridin-2-yl)benzamide This compound was prepared, in an analogous manner as described in Example 1, from Intermediate 1 and Intermediate B, to afford the title compound (7 mg, 14%). Data: UPLC(C) R$_t$: 1.05 min; m/z 443.2 (M+H)$^+$.

Example 6

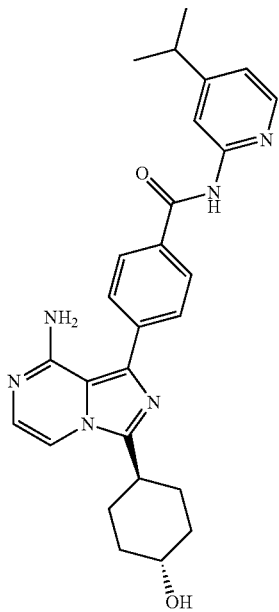 [SMILES: CC(C)c1ccnc(NC(=O)c2ccc(-c3nc([C@H]4CC[C@H](O)CC4)n4ccnc(N)c34)cc2)c1]

4-(8-amino-3-((trans)-4-hydroxycyclohexyl)imidazo[1,5-a]pyrazin-1-yl)-N-(4-isopropylpyridin-2-yl)benzamide This compound was prepared in an analogous manner as described in Example 1, from Intermediate 1 and Intermediate S, to afford the title compound (7 mg, 13%). Data: UPLC(C) R$_t$: 1.43 min; m/z 471.3 (M+H)$^+$.

Example 7

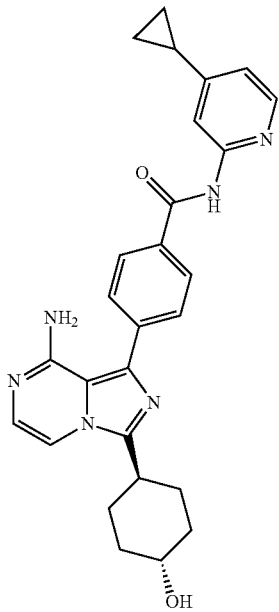 [SMILES: Nc1nccn2c1c(-c1ccc(C(=O)Nc3cc(C4CC4)ccn3)cc1)nc2[C@H]1CC[C@H](O)CC1]

4-(8-amino-3-((trans)-4-hydroxycyclohexyl)imidazo[1,5-a]pyrazin-1-yl)-N-(4-cyclopropylpyridin-2-yl)benzamide This compound was prepared in an analogous manner as described in Example 1, from Intermediate 1 and Intermediate T, to afford the title compound (12 mg, 22.8%). Data: UPLC(C) R$_t$: 1.21 min; m/z 469.3 (M+H)$^+$.

Example 8

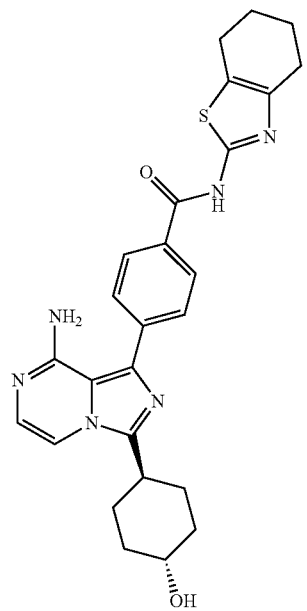 [SMILES: Nc1nccn2c1c(-c1ccc(C(=O)Nc3nc4c(s3)CCCC4)cc1)nc2[C@H]1CC[C@H](O)CC1]

4-(8-amino-3-((trans)-4-hydroxycyclohexyl)imidazo[1,5-a]pyrazin-1-yl)-N-(4,5,6,7-tetrahydrobenzo[d]thiazol-2-yl)benzamide This compound was prepared in an analogous manner as described in Example 1, from Intermediate 1 and Intermediate F, to afford the title compound (8 mg, 12.7%). Data: UPLC(C) R$_t$: 1.98 min; m/z 489.2 (M+H)$^+$.

Example 9

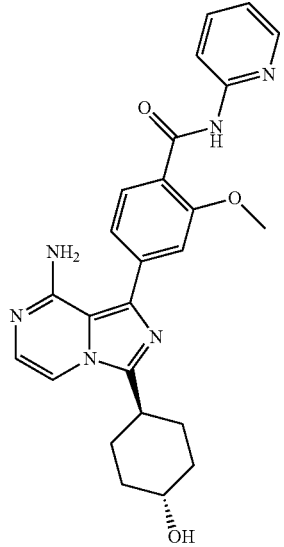 [SMILES: COc1cc(-c2nc([C@H]3CC[C@H](O)CC3)n3ccnc(N)c23)ccc1C(=O)Nc1ccccn1]

4-(8-amino-3-((trans)-4-hydroxycyclohexyl)imidazo[1,5-a]pyrazin-1-yl)-2-methoxy-N-(pyridin-2-yl)benzamide This compound was prepared in an analogous manner as described in Example 1, from Intermediate 1 and Intermediate H, to afford the title compound (24 mg, 40.7%). Data: UPLC(C) $R_t$: 119 min; m/z 4591 (M+H)$^+$.

Example 10

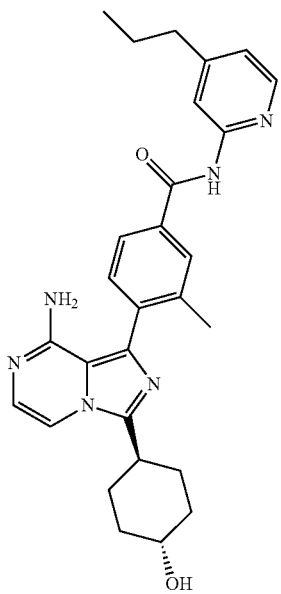 [SMILES: CCCc1ccnc(NC(=O)c2ccc(-c3nc([C@H]4CC[C@H](O)CC4)n4ccnc(N)c34)c(C)c2)c1]

4-(8-amino-3-((trans)-4-hydroxycyclohexyl)imidazo[1,5-a]pyrazin)-3-methyl-N-(4-propylpyridin-2-yl)benzamide This compound was prepared in an analogous manner as described in Example 1, from Intermediate 1 and Intermediate U, to afford the title compound (30 mg, 48.1%). Data: UPLC(C) $R_t$: 1.48 min; m/z 485.3 (M+H)$^+$.

Example 11

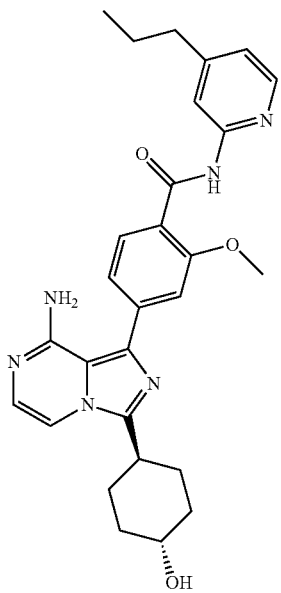 [SMILES: CCCc1ccnc(NC(=O)c2ccc(-c3nc([C@H]4CC[C@H](O)CC4)n4ccnc(N)c34)cc2OC)c1]

4-(8-amino-3-((trans)-4-hydroxycyclohexyl)imidazo[1,5-a]pyrazin-1-yl)-2-methoxy-N-(4-propylpyridin-2-yl)benzamide This compound was prepared in an analogous manner as described in Example 1, from Intermediate 1 and Intermediate Q, to afford the title compound (20 mg, 31.1%). Data: UPLC(C) $R_t$: 1.68 min; m/z 501.2 (M+H)$^+$.

Example 12

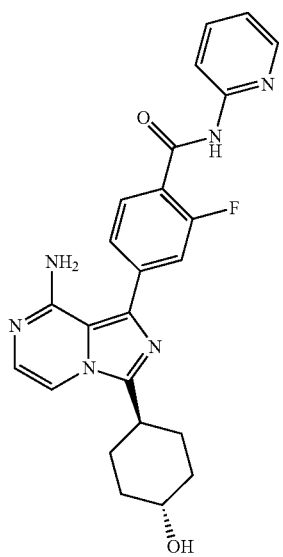 [SMILES: Nc1nccn2c1c(-c1ccc(C(=O)Nc3ccccn3)c(F)c1)nc2[C@H]1CC[C@H](O)CC1]

4-(8-amino-3-((trans)-4-hydroxycyclohexyl)imidazo[1,5-a]pyrazin-1-yl)-2-fluoro-N-(pyridin-2-yl)benzamide This compound was prepared in an analogous manner as described in Example 1, from Intermediate 1 and Intermediate G, to afford the title compound (7 mg, 12.2%). Data: UPLC(C) $R_t$: 1.21 min; m/z 447.2 (M+H)$^+$.

Example 13

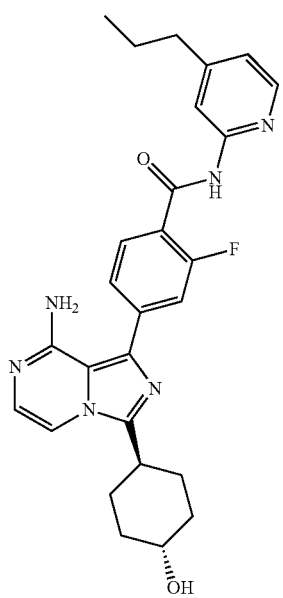 [SMILES: CCCc1ccnc(NC(=O)c2ccc(-c3nc([C@H]4CC[C@H](O)CC4)n4ccnc(N)c34)cc2F)c1]

4-(8-amino-3-((trans)-4-hydroxycyclohexyl)imidazo[1,5-a]pyrazin-1-yl)-2-fluoro-N-(4-propylpyridin-2-yl)benzamide This compound was prepared in an analogous manner as described in Example 1, from Intermediate 1 and Intermediate P, to afford the title compound (7 mg, 11.1%). Data: UPLC(C) R$_t$: 1.66 min; m/z 489.2 (M+H)$^+$.

Example 14

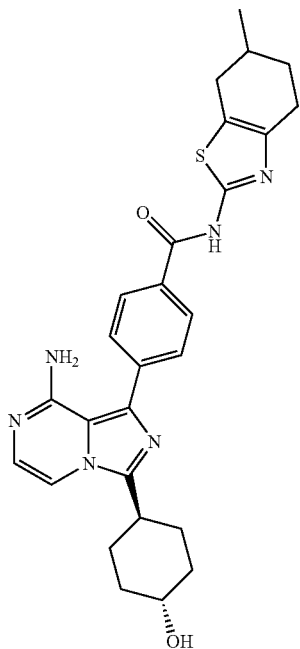

4-(8-amino-3-((trans)-4-hydroxycyclohexyl)imidazo[1,5-a]pyrazin-1-yl)-N-(6-methyl-4,5,6,7-tetrahydrobenzo[d]thiazol-2-yl)benzamide This compound was prepared in an analogous manner as described in Example 1, from Intermediate 1 and Intermediate V, to afford the title compound (20 mg, 31%). Data: UPLC(C) R$_t$: 2.25 min; m/z 503.2 (M+H)$^+$.

Example 15

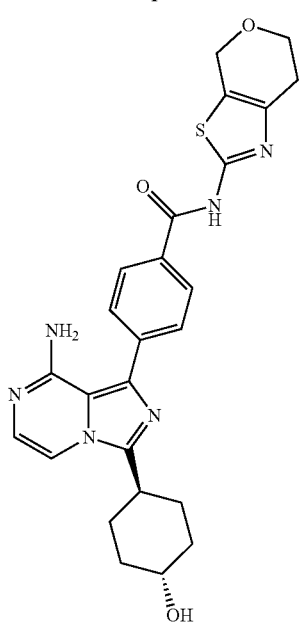

4-(8-amino-3-((trans)-4-hydroxycyclohexyl)imidazo[1,5-a]pyrazin-1-yl)-N-(6,7-dihydro-4H-pyrano[4,3-d]thiazol-2-yl)benzamide This compound was prepared in an analogous manner as described in Example 1, from Intermediate 1 and Intermediate W, to afford the title compound (20 mg, 31.7%). Data: UPLC(C) R$_t$: 1.43 min; m/z 491.2 (M+H)$^+$.

Example 16

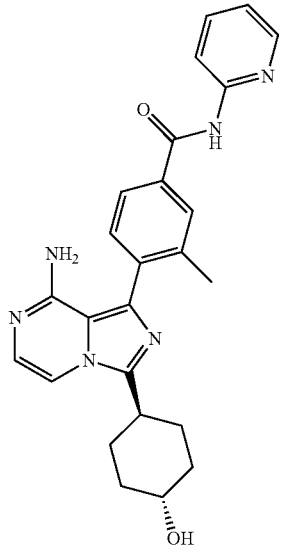 [SMILES: Cc1cc(C(=O)Nc2ccccn2)ccc1-c1nc([C@H]2CC[C@H](O)CC2)n2ccnc(N)c12]

4-(8-amino-3-((trans)-4-hydroxycyclohexyl)imidazo[1,5-a]pyrazin-1-yl)-3-methyl-N-pyridin-2-yl)benzamide This compound was prepared in an analogous manner as described in Example 1, from Intermediate 1 and Intermediate R, to afford the title compound (30 mg, 52.7%). Data: UPLC(C) R$_t$: 1.09 min; m/z 443.2 (M+H)$^+$.

Example 17

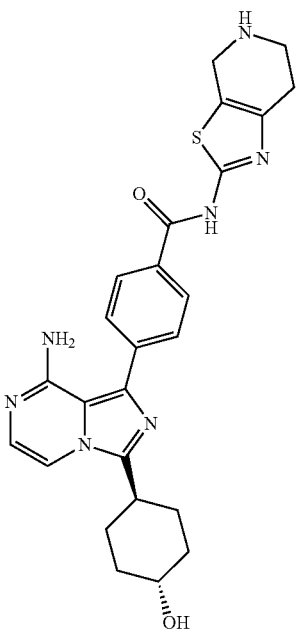 [SMILES: Nc1nccn2c1c(-c1ccc(C(=O)Nc3nc4c(s3)CNCC4)cc1)nc2[C@H]1CC[C@H](O)CC1]

4-(8-amino-3-((trans)-4-hydroxycyclohexyl)imidazo[1,5-a]pyrazin-1-yl)-N-(4,5,6,7-tetrahydrothiazolo[5,4-c]pyridin-2-yl)benzamide This compound was prepared in an analogous manner as described in Example 1, from Intermediate 1 and Intermediate Y, to afford the title compound (59 mg, 62.4%). Data: UPLC(C) $R_t$: 0.86 min; m/z 490.2 (M+H)$^+$.

Example 18

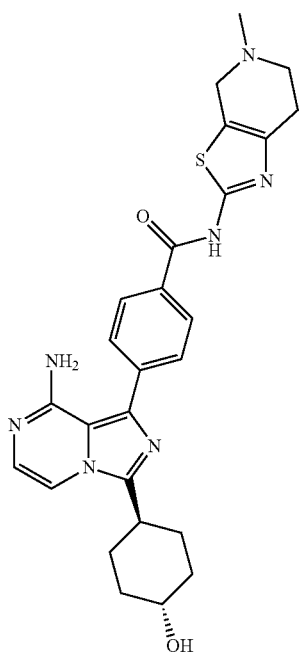 [SMILES: CN1CCc2nc(NC(=O)c3ccc(-c4nc([C@H]5CC[C@H](O)CC5)n5ccnc(N)c45)cc3)sc2C1]

4-(8-amino-3-((trans)-4-hydroxycyclohexyl)imidazo[1,5-a]pyrazin-1-yl)-N-(5-methyl-4,5,6,7-tetrahydrothiazolo[5,4-c]pyridin-2-yl)benzamide This compound was prepared in an analogous manner as described in Example 1, from Intermediate 1 and Intermediate X, to afford the title compound (20 mg, 30.9%). Data: UPLC(C) $R_t$: 0.89 min; m/z 504.2 (M+H)$^+$.

Example 19

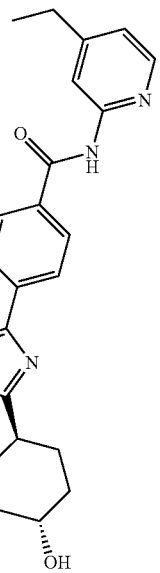

4-(8-amino-3-((trans)-4-hydroxycyclohexyl)imidazo[1,5-a]pyrazin-1-yl)-N-(4-ethylpyridin-2-yl)benzamide This compound was prepared in an analogous manner as described in Example 1, from Intermediate 1 and Intermediate E, to afford the title compound (17.8 mg, 30.3%). Data: UPLC(C) $R_t$: 1.25 min; m/z 457.2 (M+H)$^+$.

Example 20

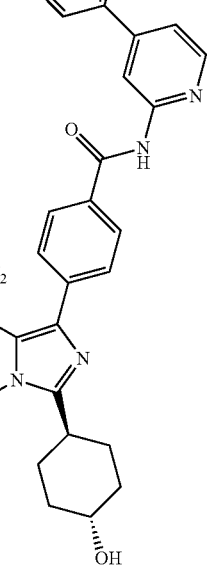

4-(8-amino-3-((trans)-4-hydroxycyclohexyl)imidazo[1,5-a]pyrazin-1-yl)-N-(4-phenylpyridin-2-yl)benzamide This compound was prepared in an analogous manner as described in Example 1, from Intermediate 1 and Intermediate Z, to afford the title compound (1.9 mg, 3%). Data: UPLC(C) $R_t$: 1.88 min; m/z 505.2 (M+H)$^+$.

Example 21

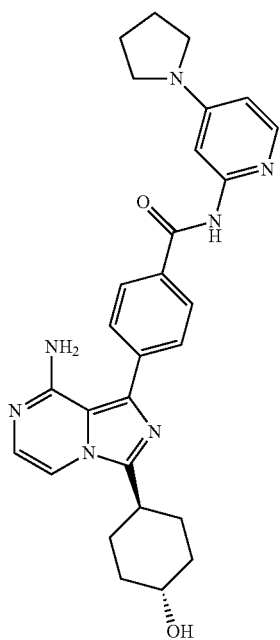 [SMILES: Nc1nccn2c1c(-c1ccc(C(=O)Nc3cc(N4CCCC4)ccn3)cc1)nc2[C@H]1CC[C@H](O)CC1]

4-(8-amino-3-((trans)-4-hydroxycyclohexyl)imidazo[1,5-a]pyrazin-1-yl)-N-(4-(pyrrolidin-1-yl)pyridin-2-yl)benzamide This compound was prepared in an analogous manner as described in Example 1, from Intermediate 1 and Intermediate AA, to afford the title compound (1.9 mg, 3%). Data: UPLC(C) $R_t$: 1.26 min; m/z 498.3 (M+H)$^+$.

Example 22

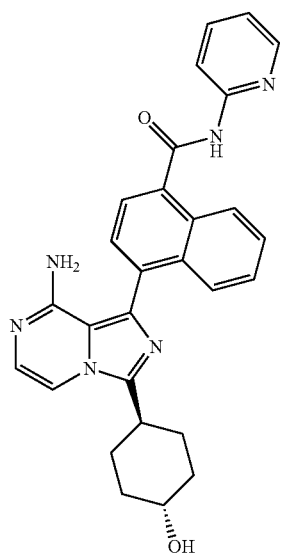 [SMILES: Nc1nccn2c1c(-c1ccc(C(=O)Nc3ccccn3)c3ccccc13)nc2[C@H]1CC[C@H](O)CC1]

4-(8-amino-3-((trans)-4-hydroxycyclohexyl)imidazo[1,5-a]pyrazin-1-yl)-N-(pyridin-2-yl)-1-naphthamide This compound was prepared, in an analogous manner as described in Example 1, from Intermediate 1 and Intermediate AC, to afford the title compound (10 mg, 16.3%). Data: UPLC(C) $R_t$: 1.35 min; m/z 479.2 (M+H)$^+$.

Example 23

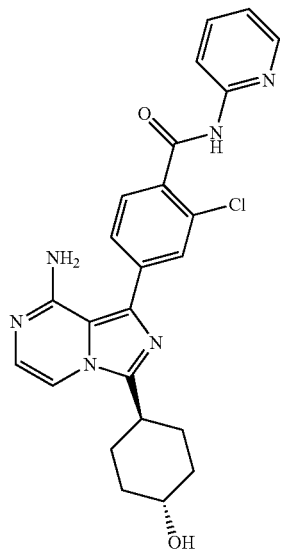 [SMILES: Nc1nccn2c1c(-c1ccc(C(=O)Nc3ccccn3)c(Cl)c1)nc2[C@H]1CC[C@H](O)CC1]

4-(8-amino-3-((trans)-4-hydroxycyclohexyl)imidazo[1,5-a]pyrazin-1-yl)-2-chloro-N-(pyridin-2-yl)benzamide This compound was prepared in an analogous manner as described in Example 1, from Intermediate 1 and Intermediate AD, to afford the title compound (5 mg, 8.4%). Data: UPLC(C) $R_t$: 1.33 min; m/z 463.1 (M+H)$^+$.

The following Examples were synthesized following the methods described for example 1-23.

| Example | Structure | Name | LC-MS [M + 1]+ | Retention time |
|---|---|---|---|---|
| 24 | 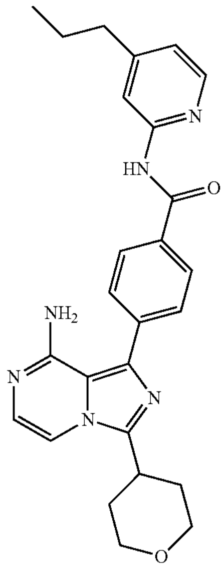 [SMILES: CCCc1ccnc(NC(=O)c2ccc(-c3nc(C4CCOCC4)n4ccnc(N)c34)cc2)c1] | 4-(8-amino-3-(tetrahydro-2H-pyran-4-yl)imidazo[1,5-a]pyrazin-1-yl)-N-(4-propylpyridin-2-yl)benzamide | 457.4 | 1.61 min |
| 25 | 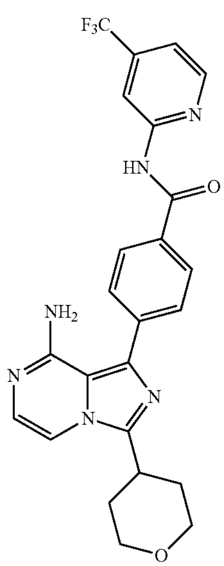 [SMILES: Nc1nccn2c(C3CCOCC3)nc(-c3ccc(C(=O)Nc4cc(C(F)(F)F)ccn4)cc3)c12] | 4-(8-amino-3-(tetrahydro-2H-pyran-4-yl)imidazo[1,5-a]pyrazin-1-yl)-N-(4-(trifluoromethyl)pyridin-2-yl)benzamide | 483.3 | 2.23 min |

-continued
| Example | Structure | Name | LC-MS [M + 1]+ | Retention time |
|---------|-----------|------|----------------|----------------|
| 26 | 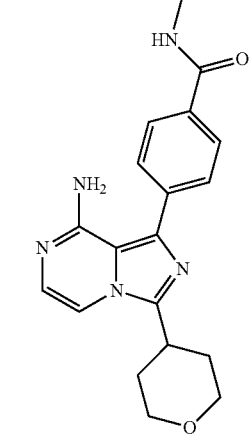 | 4-(8-amino-3-(tetrahydro-2H-pyran-4-yl)imidazo[1,5-a]pyrazin-1-yl)-N-(4-cyanopyridin-2-yl)benzamide | 440.2 | 1.63 min |
| 27 | 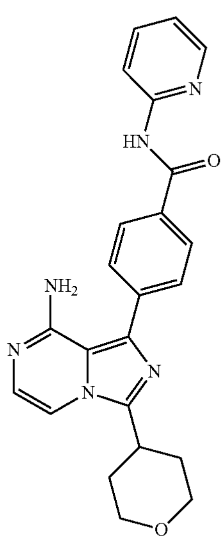 [SMILES: Nc1nccn2c(C3CCOCC3)nc(-c3ccc(C(=O)Nc4ccccn4)cc3)c12] | 4-(8-amino-3-(tetrahydro-2H-pyran-4-yl)imidazo[1,5-a]pyrazin-1-yl)-N-(pyridin-2-yl)benzamide | 415.3 | 1.38 min |

-continued
| Example | Structure | Name | LC-MS [M + 1]+ | Retention time |
|---|---|---|---|---|
| 28 | 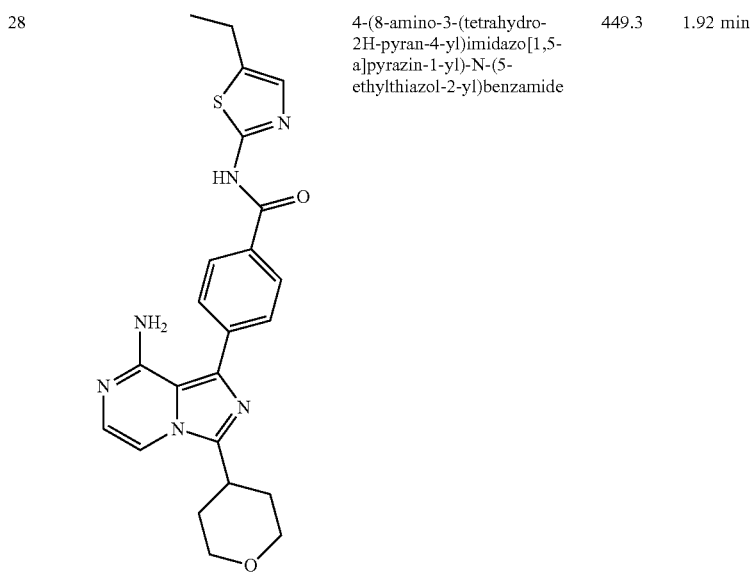 | 4-(8-amino-3-(tetrahydro-2H-pyran-4-yl)imidazo[1,5-a]pyrazin-1-yl)-N-(5-ethylthiazol-2-yl)benzamide | 449.3 | 1.92 min |
| 29 | 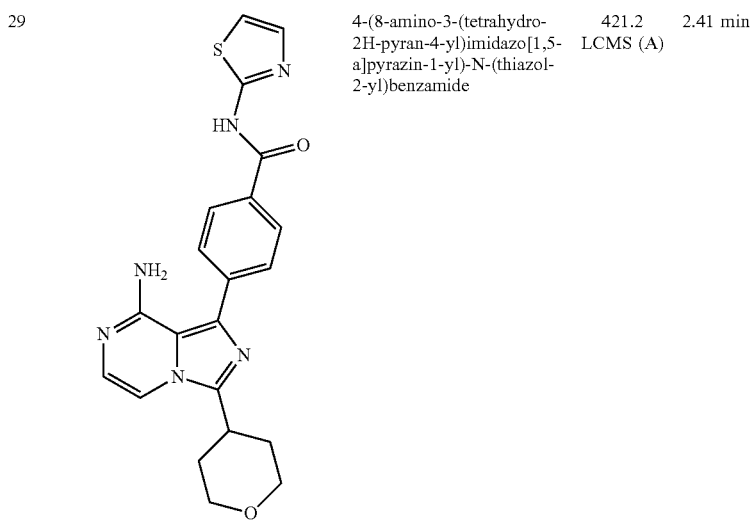 | 4-(8-amino-3-(tetrahydro-2H-pyran-4-yl)imidazo[1,5-a]pyrazin-1-yl)-N-(thiazol-2-yl)benzamide | 421.2 LCMS (A) | 2.41 min |

-continued
| Example | Structure | Name | LC-MS [M + 1]+ | Retention time |
|---|---|---|---|---|
| 30 | 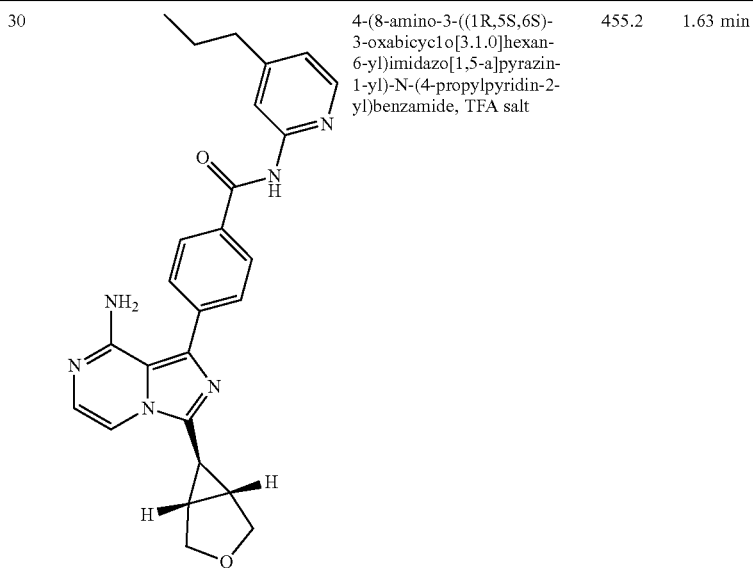 | 4-(8-amino-3-((1R,5S,6S)-3-oxabicyclo[3.1.0]hexan-6-yl)imidazo[1,5-a]pyrazin-1-yl)-N-(4-propylpyridin-2-yl)benzamide, TFA salt | 455.2 | 1.63 min |
| 31 | 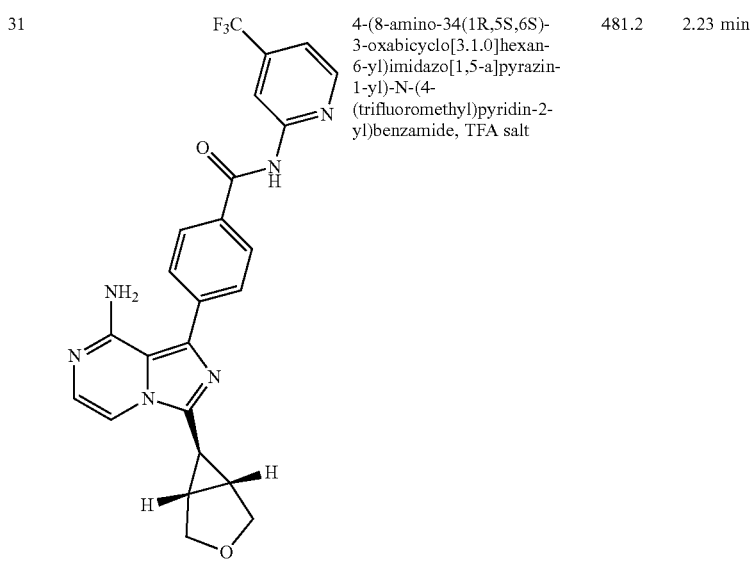 | 4-(8-amino-34(1R,5S,6S)-3-oxabicyclo[3.1.0]hexan-6-yl)imidazo[1,5-a]pyrazin-1-yl)-N-(4-(trifluoromethyl)pyridin-2-yl)benzamide, TFA salt | 481.2 | 2.23 min |

-continued
| Example | Structure | Name | LC-MS [M + 1]+ | Retention time |
|---------|-----------|------|----------------|----------------|
| 32 | 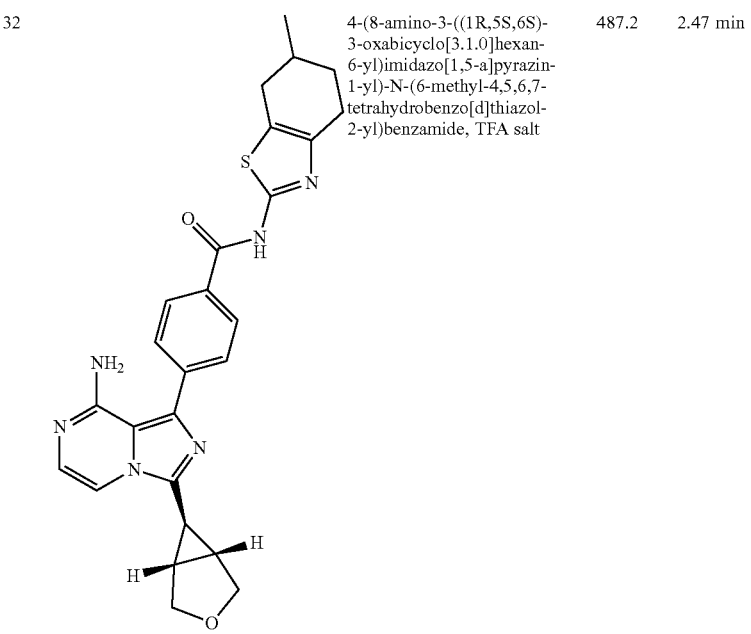 | 4-(8-amino-3-((1R,5S,6S)-3-oxabicyclo[3.1.0]hexan-6-yl)imidazo[1,5-a]pyrazin-1-yl)-N-(6-methyl-4,5,6,7-tetrahydrobenzo[d]thiazol-2-yl)benzamide, TFA salt | 487.2 | 2.47 min |
| 33 | 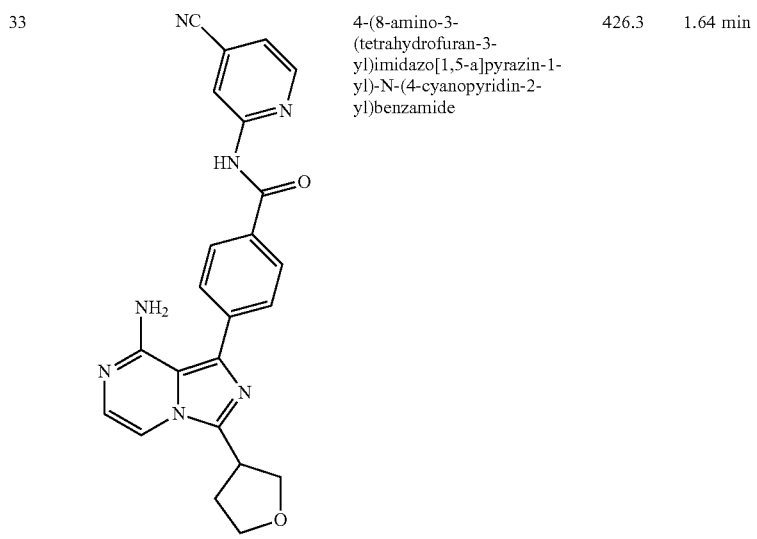 | 4-(8-amino-3-(tetrahydrofuran-3-yl)imidazo[1,5-a]pyrazin-1-yl)-N-(4-cyanopyridin-2-yl)benzamide | 426.3 | 1.64 min |

-continued
| Example | Structure | Name | LC-MS [M + 1]+ | Retention time |
|---|---|---|---|---|
| 34 | 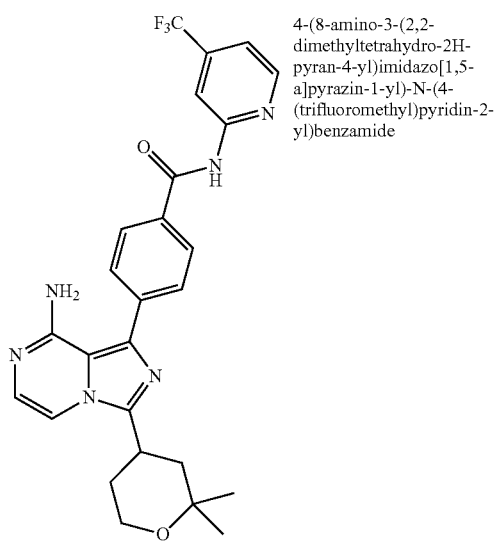<br>Stereoisomer 1 | 4-(8-amino-3-(2,2-dimethyltetrahydro-2H-pyran-4-yl)imidazo[1,5-a]pyrazin-1-yl)-N-(4-(trifluoromethyl)pyridin-2-yl)benzamide | 511.2 | 2.45 min |
| 35 | 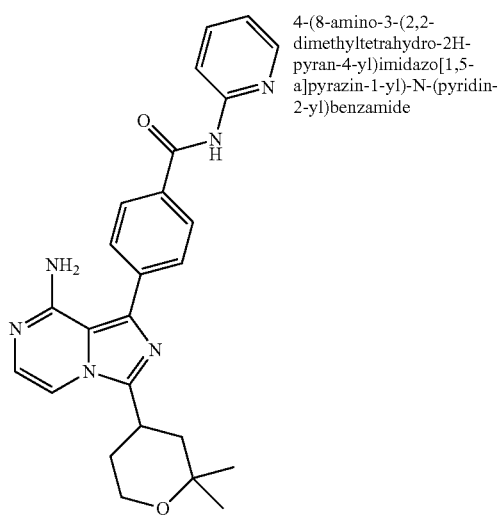<br>Stereoisomer 1 | 4-(8-amino-3-(2,2-dimethyltetrahydro-2H-pyran-4-yl)imidazo[1,5-a]pyrazin-1-yl)-N-(pyridin-2-yl)benzamide | 443.2 | 1.41 min |

-continued
| Example | Structure | Name | LC-MS [M + 1]+ | Retention time |
|---|---|---|---|---|
| 36 | 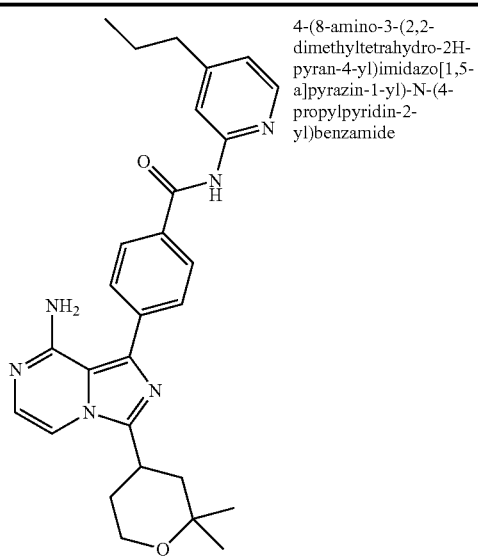<br>Stereoisomer 1 | 4-(8-amino-3-(2,2-dimethyltetrahydro-2H-pyran-4-yl)imidazo[1,5-a]pyrazin-1-yl)-N-(4-propylpyridin-2-yl)benzamide | 485.3 | 1.78 min |
| 37 | 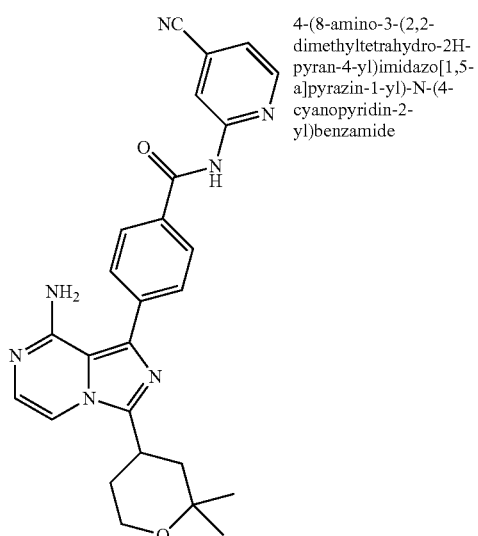<br>Stereoisomer 1 | 4-(8-amino-3-(2,2-dimethyltetrahydro-2H-pyran-4-yl)imidazo[1,5-a]pyrazin-1-yl)-N-(4-cyanopyridin-2-yl)benzamide | 468.2 | 1.96 min |

-continued
| Example | Structure | Name | LC-MS [M + 1]+ | Retention time |
|---|---|---|---|---|
| 38 | 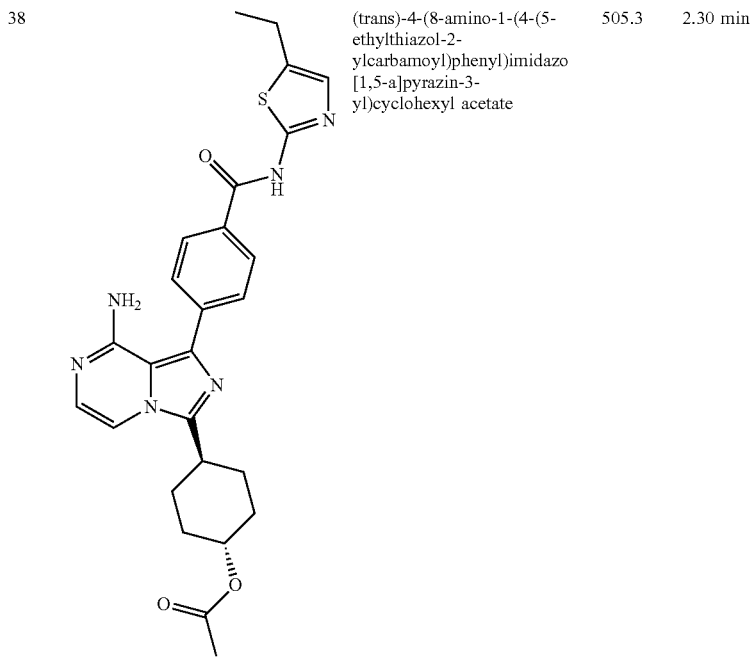 | (trans)-4-(8-amino-1-(4-(5-ethylthiazol-2-ylcarbamoyl)phenyl)imidazo[1,5-a]pyrazin-3-yl)cyclohexyl acetate | 505.3 | 2.30 min |
| 39 | 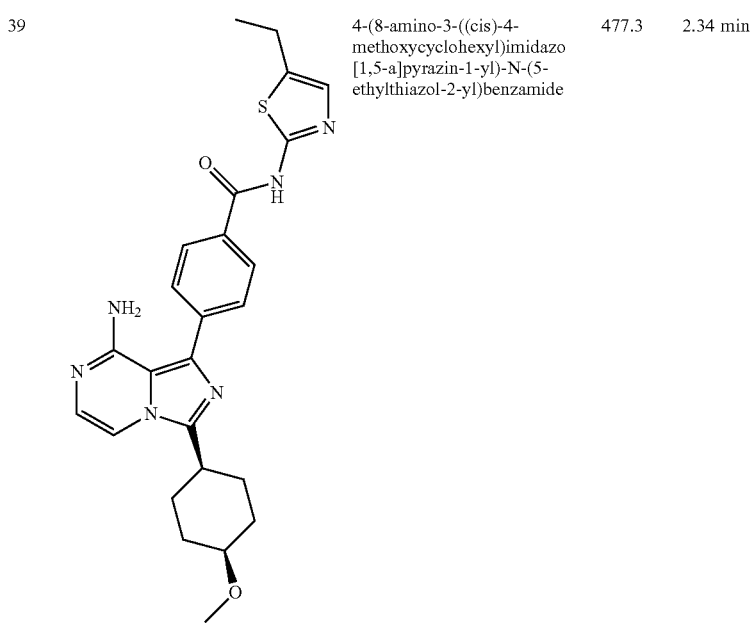 | 4-(8-amino-3-((cis)-4-methoxycyclohexyl)imidazo[1,5-a]pyrazin-1-yl)-N-(5-ethylthiazol-2-yl)benzamide | 477.3 | 2.34 min |

-continued
| Example | Structure | Name | LC-MS [M + 1]+ | Retention time |
|---|---|---|---|---|
| 40 | 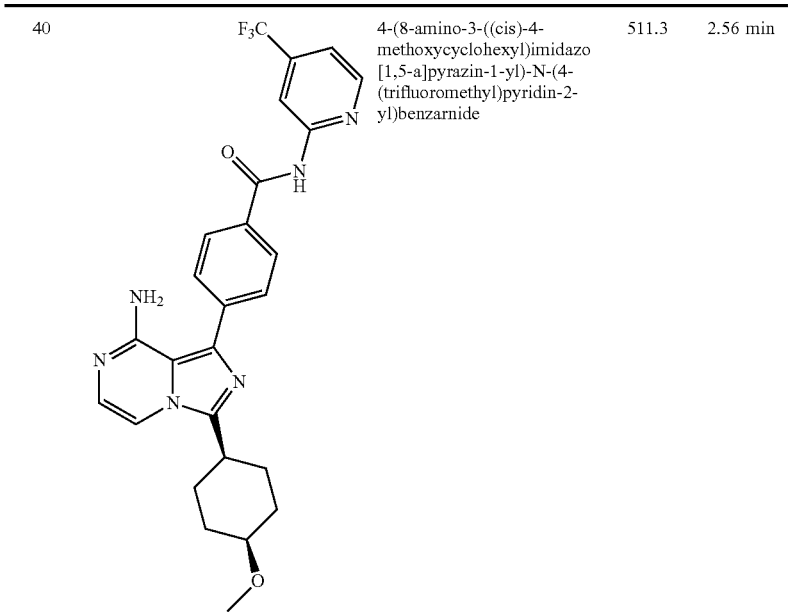 | 4-(8-amino-3-((cis)-4-methoxycyclohexyl)imidazo[1,5-a]pyrazin-1-yl)-N-(4-(trifluoromethyl)pyridin-2-yl)benzamide | 511.3 | 2.56 min |
| 41 | 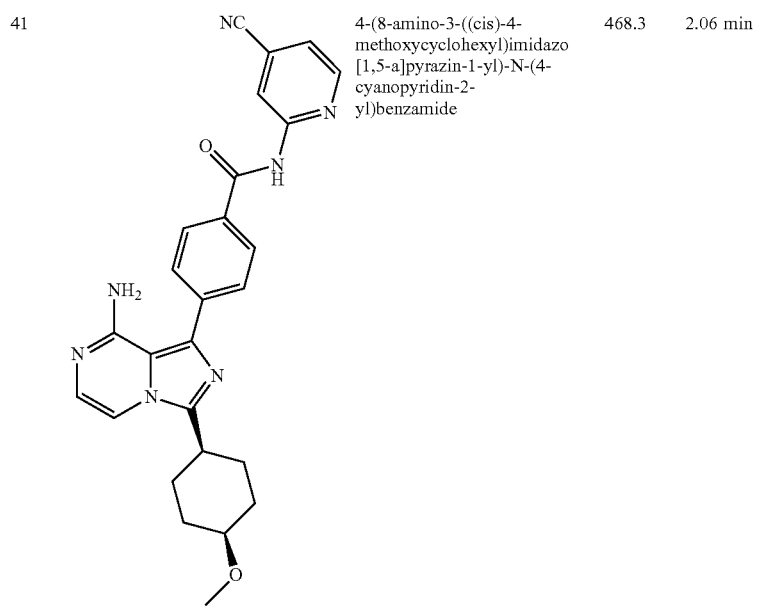 | 4-(8-amino-3-((cis)-4-methoxycyclohexyl)imidazo[1,5-a]pyrazin-1-yl)-N-(4-cyanopyridin-2-yl)benzamide | 468.3 | 2.06 min |

-continued

| Example | Structure | Name | LC-MS [M + 1]+ | Retention time |
|---------|-----------|------|----------------|----------------|
| 42 | 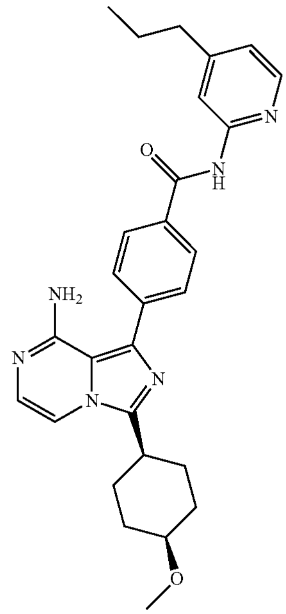 [SMILES: CCCc1ccnc(NC(=O)c2ccc(-c3nc([C@H]4CC[C@@H](OC)CC4)n4ccnc(N)c34)cc2)c1] | 4-(8-amino-3-((cis)-4-methoxycyclohexyl)imidazo[1,5-a]pyrazin-1-yl)-N-(4-propylpyridin-2-yl)benzamide | 485.3 | 1.91 min |
| 43 | 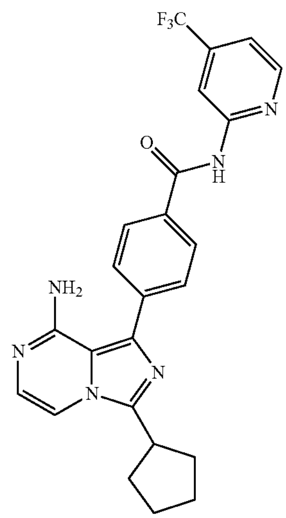 [SMILES: Nc1nccn2c(C3CCCC3)nc(-c3ccc(C(=O)Nc4cc(C(F)(F)F)ccn4)cc3)c12] | 4-(8-amino-3-cyclopentylimidazo[1,5-a]pyrazin-1-yl)-N-(4-(trifluoromethyl)pyridin-2-yl)benzamide, TFA salt | 466.9 LCMS (A) | 2.86 min UPLC (E) |

-continued
| Example | Structure | Name | LC-MS [M + 1]+ | Retention time |
|---|---|---|---|---|
| 44 | 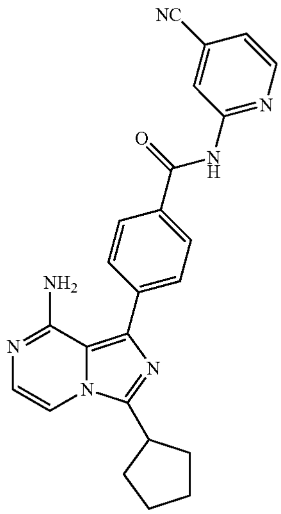 [SMILES: N#Cc1ccnc(NC(=O)c2ccc(-c3nc(C4CCCC4)n4ccnc(N)c34)cc2)c1] | 4-(8-amino-3-cyclopentylimidazo[1,5-a]pyrazin-1-yl)-N-(4-cyanopyridin-2-yl)benzamide, TFA salt | 425.2 | 2.25 min UPLC (E) |
| 45 | 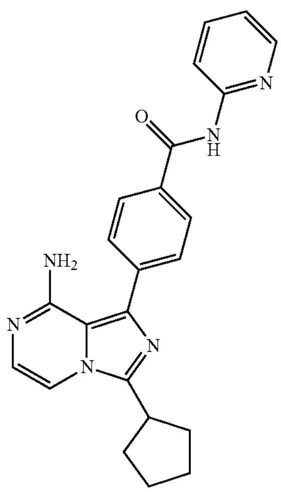 [SMILES: Nc1nccn2c(C3CCCC3)nc(-c3ccc(C(=O)Nc4ccccn4)cc3)c12] | 4-(8-amino-3-cyclopentylimidazo[1,5-a]pyrazin-1-yl)-N-(pyridin-2-yl)benzamide, TFA salt | 399.0 LCMS (A) | 2.01 UPLC (E) |
Intermediate 8
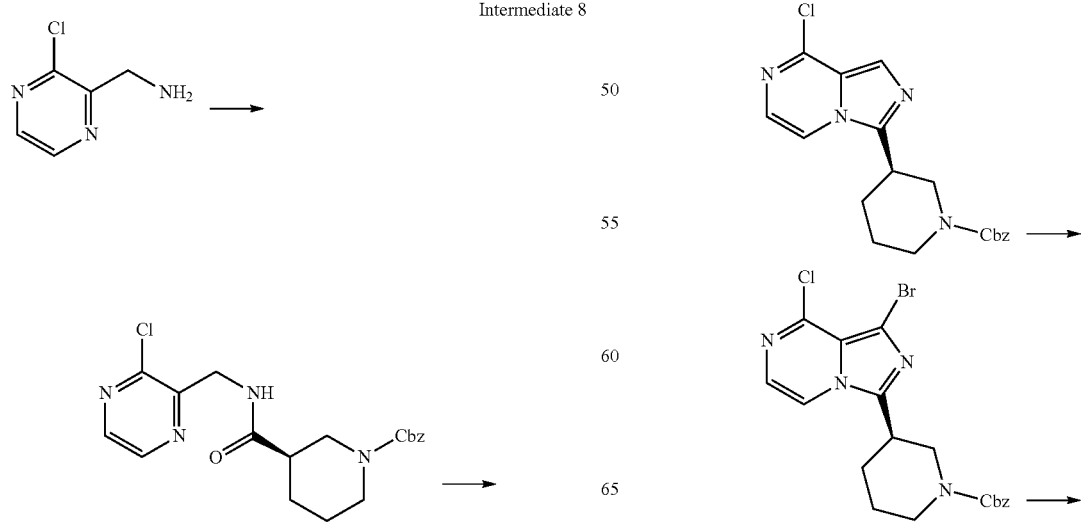

161

-continued

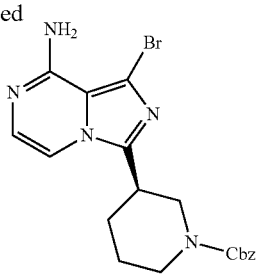

(R)-benzyl 3-(8-amino-1-bromoimidazo[1,5-a]
pyrazin-3-yl)piperidine-1-carboxylate

(a) (R)-benzyl 3-((3-chloropyrazin-2-yl)methylcarbamoyl)piperidine-1-carboxylate To a solution of (3-chloropyrazin-2-yl)methanamine.hydrochloride (1.85 g, 10.28 mmol), (R)-piperidine-1,3-dicarboxylic acid 1-benzylester (2.71 g, 10.28 mmol) and HATU (4.1 g, 10.79 mmol) in dichloromethane (75 mL) was added triethylamine (5.73 mL, 41.1 mmol) and the reaction mixture was stirred at 0° C. for 4 hr. and after warming up to room temperature over night. The mixture was washed with 0.1 M HCl-solution, 5% NaHCO$_3$, water and brine, dried over sodium sulfate and concentrated in vacuo to give 5.03 g of crude (R)-benzyl 3-((3-chloropyrazin-2-yl)methylcarbamoyl)piperidine-1-carboxylate (126%) which was used directly in the next step.

(b) (R)-benzyl 3-(8-chloroimidazo[1,5-a]pyrazin-3-yl)piperidine-1-carboxylate (R)-benzyl 3-((3-chloropyrazin-2-yl)methylcarbamoyl) piperidine-1-carboxylate (5.03 g, 10.28 mmol theor.) was dissolved in acetonitrile (40 ml), phosphorus oxychloride (4.82 ml, 51.7 mmol) was added and the mixture was stirred for 5 h at 80° C. The mixture was added dropwise to 25% aq. ammonia (81 mL) in 250 mL crushed ice keeping the temperature below 0° C. The resulting suspension was stirred another 15 min after which it was extracted with ethyl acetate (3×). The combined organic layers were washed with water, brine, dried over sodium sulfate and concentrated in vacuo. The product was purified using silica gel chromatography (heptane/ethyl acetate=100/0 to 50/50 v/v %)) to give 2.77 g of (R)-benzyl 3-(8-chloroimidazo[1,5-a]pyrazin-3-yl)piperidine-1-carboxylate (57.7%).

(c) (R)-benzyl 3-(1-bromo-8-chloroimidazo[1,5-a]pyrazin-3-yl)piperidine-1-carboxylate N-Bromosuccinimide (1.329 g, 7.47 mmol) was added to a stirred solution of (R)-benzyl 3-(8-chloroimidazo[1,5-a]pyrazin-3-yl)piperidine-1-carboxylate (7.47 mmol, 2.77 g) in DMF (40 mL). The reaction was stirred 1 h at room temperature. The reaction was quenched with 50 mL sat. Na$_2$S$_2$O$_3$ (aq) and ethyl acetate (50 mL). Brine (50 mL) was added and the mixture was then separated. The aqueous layer was extracted with ethyl acetate. The combined organic layers were washed with water, brine, dried over sodium sulfate, filtered and evaporated to give 3.18 g of (R)-benzyl 3-(1-bromo-8-chloroimidazo[1,5-a]pyrazin-3-yl)piperidine-1-carboxylate (95%).

162

(d) (R)-benzyl 3-(8-amino-1-bromoimidazo[1,5-a]pyrazin-3-yl)piperidine-1-carboxylate (R)-benzyl 3-(1-bromo-8-chloroimidazo[1,5-a]pyrazin-3-yl)piperidine-1-carboxylate (2.76 g, 6.14 mmol) was divided in 5 batches (approx. 520-560 mg/batch) over 5 microwave vials (25 mL) and 16 mL 2M ammonia/i-PrOH was added. The mixtures were heated for 4 h at 120° C. in a microwave. All batches were combined and concentrated in vacuo, dissolved in ethyl acetate (200 mL) and washed with water (150 mL). The aqueous layer was extracted with ethyl acetate (80 mL). The combined organic layers were washed with brine (100 mL), dried over sodium sulfate and concentrated to give 2.56 g of (R)-benzyl 3-(8-amino-1-bromoimidazo[1,5-a]pyrazin-3-yl)piperidine-1-carboxylate (97%).

Intermediate 9

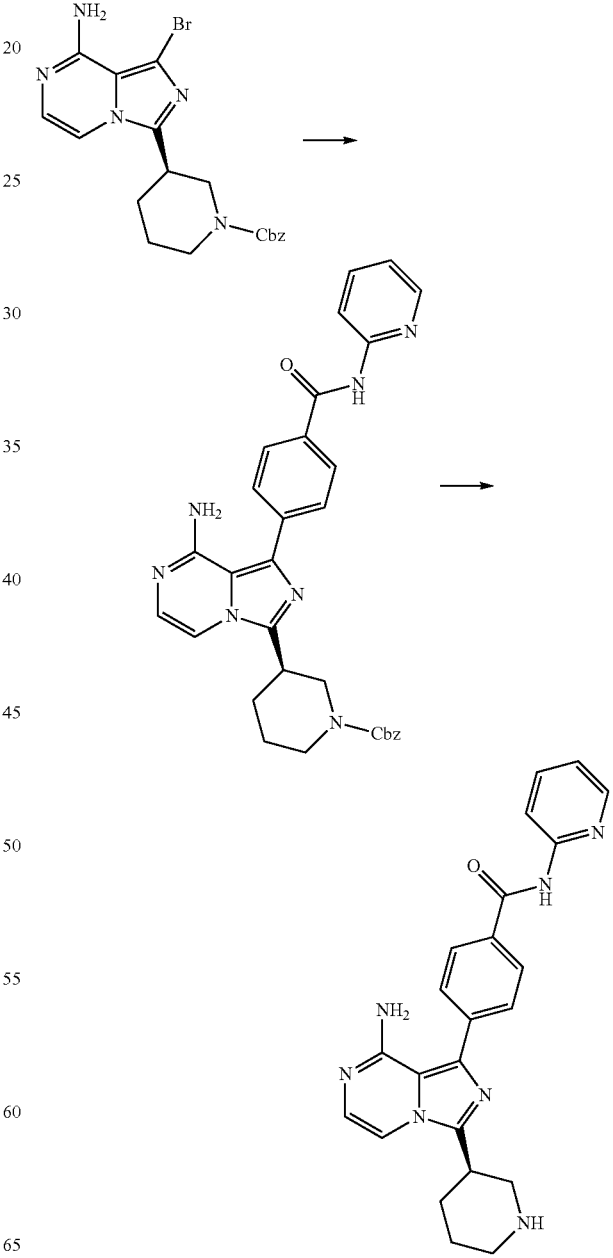

(R)-4-(8-amino-3-(piperidin-3-yl)imidazo[1,5-a]
pyrazin-1-yl)-N-(pyridin-2-yl)benzamide (a) (R)-benzyl 3-(8-amino-1-(4-(pyridin-2-ylcarbamoyl)phenyl)imidazo[1,5-a]pyrazin-3-yl)piperidine-1-carboxylate This compound was prepared in an analogous manner as described in Example 1, from Intermediate 8d and N-(pyridin-2-yl)-4-(4,4,5,5-tetramethyl-1,3,2-dioxaborolan-2-yl)benzamide, to afford (R)-benzyl 3-(8-amino-1-(4-(pyridin-2-ylcarbamoyl)phenyl)imidazo[1,5-a]pyrazin-3-yl)piperidine-1-carboxylate (470 mg, 73.9%).

(b) (R)-4-(8-amino-3-(piperidin-3-yl)imidazo[1,5-a]
pyrazin-1-yl)-N-(pyridin-2-yl)benzamide To (R)-benzyl 3-(8-amino-1-(4-(pyridin-2-ylcarbamoyl)phenyl)imidazo[1,5-a]pyrazin-3-yl)piperidine-1-carboxylate (470 mg, 0.858 mmol) was added a 33% hydrobromic acid/acetic acid solution (5.93 mL, 34.3 mmol) and the mixture was left at room temperature for 2 hours. The mixture was diluted with brine/water (80 mL) and extracted with dichloromethane. The aqueous phase was neutralized using 2N sodium hydroxide solution, and then extracted with dichloromethane/methanol (9/1 v/v %). The organic layer was washed with brine, dried over sodium sulfate, filtered and concentrated in vacuo to afford 360 mg of (R)-4-(8-amino-3-(piperidin-3-yl)imidazo[1,5-a]pyrazin-1-yl)-N-(pyridin-2-yl)benzamide (101%, crude).

Intermediate 9B

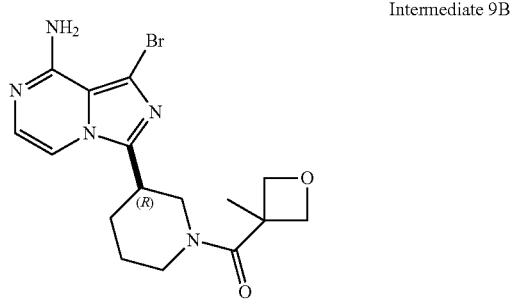

(R)-(3-(8-amino-1-bromoimidazo[1,5-a]pyrazin-3-yl)piperidin-1-yl)(3-methyloxetan-3-yl)methanone (a) (R)-1-bromo-3-(piperidin-3-yl)imidazo[1,5-a]
pyrazin-8-amine To a solution of (R)-benzyl 3-(8-amino-1-bromoimidazo[1,5-a]pyrazin-3-yl)piperidine-1-carboxylate (Intermediate 8, 26 g, 60.4 mmol) in DCM (300 mL) was added TMSI (25.4 g, 127 mmol). The resulting reaction mixture was then stirred at room temperature for 4 h. The reaction mixture was quenched by pouring into aqueous HCl (12 N). The organic layer was separated and the aqueous layer was adjusted to pH 12 with KOH and extracted with DCM (3×) and DCM with 5% MeOH (3×). The combined organic layers were concentrated to afford the title compound (13.91 g). The aqueous layer was further extracted with i-BuOH concentrated to afford another crop of product (R)-1-bromo-3-(piperidin-3-yl)imidazo[1,5-a]pyrazin-8-amine (2.36 g).

(b) (R)-(3-(8-amino-1-bromoimidazo[1,5-a]pyrazin-3-yl)piperidin-1-yl)(3-methyloxetan-3-yl)methanone To a solution of (R)-1-bromo-3-(piperidin-3-yl)imidazo[1,5-a]pyrazin-8-amine (13.9 g, 47.0 mmol) in 150 ml 10% IPA in DCM, was added 3-methyloxetane-3-carboxylic acid (5.45 g, 47.0 mmol) and triethylamine (9.51 g, 94.0 mmol). The mixture was then cooled to 5° C., followed by the addition of 2,4,6-tripropyl-1,3,5,2,4,6-trioxatriphosphinane 2,4,6-trioxide (32.9 g, 50%, 51.7 mmol). The mixture was stirred at room temperature for 20 min, then quenched with water diluted with DCM, and the resultant mixture was washed with brine. The organic layer was dried over Mg$_2$SO$_4$, filtered and concentrated. The residue was purified by MPLC on silica gel (7% MeOH-DCM) to afford the title compound (14.41 g). LC-MS, [M+H]$^+$ 429.9.

To a solution of (R)-benzyl-3-(8-(2,4-dimethoxybenzylamino)-1-bromoimidazo[1,5-a]pyrazin-3-yl)piperidine-1-carboxylate (17.3 g, 29.8 mmol) and 3-fluoro-4-(4,4,5,5-tetramethyl-1,3,2-dioxaborolan-2-yl)benzonitrile (14.7 g, 59.6 mmol) in dioxane (200 ml) and water (20 ml) was added Na$_2$CO$_3$ (9.4 g, 89.5 mmol). The mixture was degassed with nitrogen, and Pd(PPh$_3$)$_2$Cl$_2$ (1.3 g, 1.78 mmol) was added. The resulting mixture was stirred at 95° C. for 24 h. The mixture was cooled to room temperature, filtered and partitioned between water and ethyl acetate. The aqueous layer was extracted with ethyl acetate and the combined organic layers were washed with water and brine, dried over Na$_2$SO$_4$ and concentrated in vacuo. The residue was purified by column chromatography with silica gel eluted by 0~50% ethyl acetate in petroleum ether (60-90 fraction) to give (3R)-benzyl-3-(8-(2,4-dimethoxybenzylamino)-1-(4-cyano-2-fluorophenyl)imidazo[1,5-a]pyrazin-3-yl)piperidine-1-carboxylate (12 g, 64%). MS-ESI (m/z): 621 (M+1)$^+$ (Acq Method: 10-80AB_2 min; Rt: 1.14 min).

(b) (3R)-benzyl-3-(8-(2,4-dimethoxybenzylamino)-1-(4-carbamoyl-2-fluorophenyl)imidazo[1,5-a]
pyrazin-3-yl)piperidine-1-carboxylate A solution of (3R)-benzyl-3-(8-(2,4-dimethoxybenzylamino)-1-(4-cyano-2-fluorophenyl)imidazo[1,5-a]pyrazin-3-yl)piperidine-1-carboxylate (8.8 g, 14.2 mmol) in DMSO (20 ml) was added K$_2$CO$_3$ (4 g, 28.3 mmol), the mixture was cooled to 0° C., followed by the addition of H$_2$O$_2$ (4 mL, 40% in water). The resulting mixture was stirred at 0° C. for 20 min, then allowed to warm to room temperature. H$_2$O (3 ml) was added, and the mixture was stirred for 12 h. The aqueous layer was extracted with DCM three times. The combined organic layers were washed with water and brine, dried over Na$_2$SO$_4$ and concentrated in vacuo. The residue was purified by column chromatography on silica gel (DCM/methanol=40/1 v/v %) to give the title compound (6.2 g, 68%). MS-ESI (m/z): 639 (M+1)$^+$ (Acq Method: 10-80AB_2 min; R$_t$: 1.05 min).

(c) 4-(8-(2,4-dimethoxybenzylamino)-3-((R)-piperidin-3-yl)imidazo[1,5-a]pyrazin-1-yl)-3-fluoro benzamide (3R)-benzyl-3-(8-(2,4-dimethoxybenzylamino)-1-(4-carbamoyl-2-fluorophenyl)imidazo[1,5-a]pyrazin-3-yl)piperidine-1-carboxylate (6.1 g, 9.6 mmol)

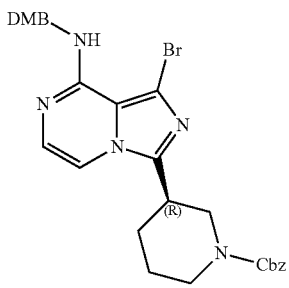

Intermediate 9C (R)-benzyl 3-(1-bromo-8-((2,4-dimethoxybenzyl)amino)imidazo[1,5-a]pyrazin-3-yl) piperidine-1-carboxylate (R)-benzyl 3-(1-bromo-8-chloroimidazo[1,5-a]pyrazin-3-yl)piperidine-1-carboxylate (2.96 g, from Intermediate 8c, 4.61 mmol) was dissolved in DMA (20 mL) along with cesium carbonate (4.50 g, 13.82 mmol) and 2,4-dimethoxybenzylamine (0.770 g, 4.61 mmol). The resulting reaction mixture was then stirred at 75° C. for 72 h. The reaction was partitioned between EtOAc and water. The organic layer was separated, dried and concentrated. The crude was purified by silica gel chromatography (60% EtOAc-hexanes, UV=254 nm) to afford 2.3 g of the title compound as an orange oil. LC-MS (ESI) [M+H]+: calc 579.2, found 579.15.

4-(8-(2,4-dimethoxybenzylamino)-3-((R)-1-(3-methyloxetane-3-carbonyl)piperidin-3-yl)imidazo[1,5-a]pyrazin-1-yl)-3-fluorobenzamide (a) (3R)-benzyl-3-(8-(2,4-dimethoxybenzylamino)-1-(4-cyano-2-fluorophenyl)-imidazo[1,5-a]pyrazin-3-yl)piperidine-1-carboxylate was dissolved in 33% HBr/acetic acid (25 ml). The mixture was stirred at room temperature for 2 h. To the mixture was added t-butylmethyl ether (50 ml). The resulting mixture was stirred for 30 min, filtered and the filter cake was washed with t-butylmethyl ether. The cake was treated with water and adjusted pH to 8 by 1 M $Na_2CO_3$ solution. The mixture was extracted with DCM twice, the combined organic layer was washed with brine, dried over anhydrous $Na_2SO_4$ and concentrated in vacuo to afford the title compound (4.8 g) as a yellow solid. MS-ESI (m/z): 505 (M+1)+ (Acq Method: 0-60AB_2 min; $R_t$: 1.00 min).

(d) 4-(8-(2,4-dimethoxybenzylamino)-3-((R)-1-(3-methyloxetane-3-carbonyl)piperidin-3-yl) imidazo[1,5-a]pyrazin-1-yl)-3-fluorobenzamide To a solution of 4-(8-(2,4-dimethoxybenzylamino)-3-((R)-piperidin-3-yl)imidazo[1,5-a]pyrazin-1-yl)-3-fluorobenzamide (4.5 g, 9.5 mmol) in DMF (20 ml) was added DIPEA (2.6 g, 20 mmol) and 3-methyloxetane-3-carboxylic acid (1.2 g, 9.5 mmol), followed by the addition of HATU (3.8 g, 10 mmol) at 0° C. The mixture was allowed to warm to room temperature and stirred for another 20 min. The mixture was diluted with water and extracted with DCM twice. The combined organic layers were washed with water and brine, dried over $Na_2SO_4$ and concentrated in vacuo. The residue was purified by silica gel chromatography (DCM/methanol=40/1 v/v %) to give the title product (4.3 g). MS-ESI (m/z): 603 (M+1)+ (Acq Method: 0-60AB_2 min; $R_t$: 1.11 min). $^1$H NMR (400 MHz, CHLOROFORM-d) δ 7.69-7.36 (m, 3H), 7.32-7.05 (m, 3H), 6.45-6.23 (m, 2H), 4.99-4.98 (d, J=5.5 Hz, 2H), 4.52-4.51 (d, J=5.1 Hz, 2H), 4.35 (br. s., 2H), 3.75 (s, 3H), 3.58-3.41 (m, 3H), 3.05 (br s., 2H), 2.25-2.03 (m, 2H), 1.98-1.73 (m, 4H), 1.69 (s, 4H).

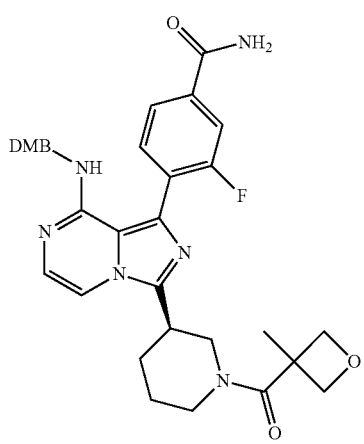

Intermediate 9D

Intermediate 9E (R)-4-(3-(1-((benzyloxy)carbonyl)piperidin-3-yl)-8-((2,4-dimethoxybenzyl)amino)-imidazo[1,5-a]pyrazin-1-yl)benzoic acid To the mixtures of Intermediate 9C (200 mg, 0.367 mmol), 4-boronobenzoic acid (91 mg, 0.551 mmol, 1.5 equiv.), and [1,1'-bis(diphenylphosphino) ferrocene] dichloropalladium(II) (53.8 mg, 0.073 mmol, 0.2 equiv.) in 1,4-dioxane (12 ml) was added potassium carbonate aqueous solution (1.0 N, 1.102 ml, 1.102 mmol, 3 equiv.). The reactions was carried out at 120° C. for 20 minutes under microwave reaction condition.

The reaction mixture was combined, to which water (50 mL) and EtOAc (100 mL) were added). The organic layer was separated, concentrated down, and stirred vigorously with LiOH aqueous solution (1.0 N, 20 mL) for 10 minutes, then washed with EtOAc (20 mL×3). The resulting aqueous layer was adjusted to pH about 4~5 using 10% citric acid, extracted with CH$_2$Cl$_2$ (20 mL×3). The combined organic layers were washed with brine, dried, then concentrated down to give Intermediate 9C LC-MS (ESI), [M+H]$^+$: calc 386.3, found 386.2.

Example 46

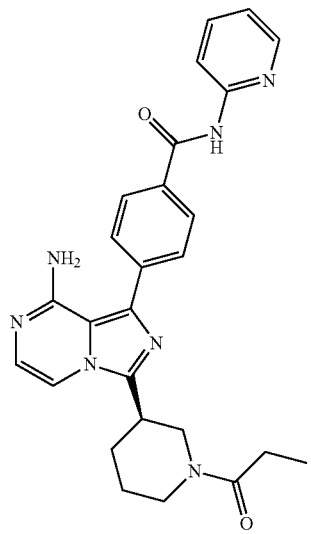 [SMILES: CCC(=O)N1CCC[C@@H](c2nc(-c3ccc(C(=O)Nc4ccccn4)cc3)c3c(N)nccn23)C1]

(R)-4-(8-amino-3-(1-propionylpiperidin-3-yl) imidazo[1,5-a]pyrazin-1-yl)-N-(pyridin-2-yl)benzamide To a solution of (R)-4-(8-amino-3-(piperidin-3-yl)imidazo[1,5-a]pyrazin-1-yl)-N-(pyridin-2-yl)benzamide (Intermediate 9b, 50 mg, 0.121 mmol), DIPEA (60 μL, 0.121 mmol) and propionic acid (8.96 mg, 0.121 mmol) in dichloromethane (6.3 mL) was added HATU (41.4 mg, 0.109 mmol). The mixture was stirred for 1 h at 0° C. The mixture was washed with 5% aq. Sodium bicarbonate solution, brine, dried over sodium sulfate and concentrated in vacuo. The residue was purified by preparative HPLC. Fractions containing the product were collected and reduced to dryness to afford 34 mg of (R)-4-(8-amino-3-(1-propionylpiperidin-3-yl)imidazo[1,5-a]pyrazin-1-yl)-N-(pyridin-2-yl)benzamide (59.9% yield). Data: UPLC(C) R$_t$: 1.46 min; m/z 470.1 (M+H)$^+$.

Example 47

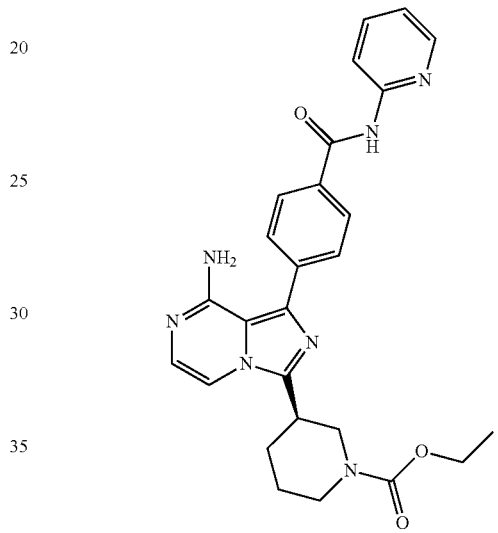

(R)-ethyl 3-(8-amino-1-(4-(pyridin-2-ylcarbamoyl)phenyl)imidazo[1,5-a]pyrazin-3-yl)piperidine-1-carboxylate To a solution of (R)-4-(8-amino-3-(piperidin-3-yl)imidazo[1,5-a]pyrazin-1-yl)-N-(pyridin-2-yl)benzamide (Intermediate 9b, 35 mg, 85 μmol), triethylamine (35 μL, 0.254 mmol) in dichloromethane (1 mL) was added ethyl chloroformate (9.19 mg, 8.13 μL, 85 μmol). The mixture was stirred for 1 h. at 0° C. The mixture was washed water, brine, dried over sodium sulfate and concentrated in vacuo. The residue was purified by preparative HPLC. Fractions containing the product were collected and reduced to dryness to afford 14.1 mg of (R)-ethyl 3-(8-amino-1-(4-(pyridin-2-ylcarbamoyl)-phenyl)imidazo[1,5-a]pyrazin-3-yl)piperidine-1-carboxylate (34.3% yield). Data: UPLC(C) R$_t$: 1.84 min; m/z 486.2 (M+H)$^+$.

169
Example 48

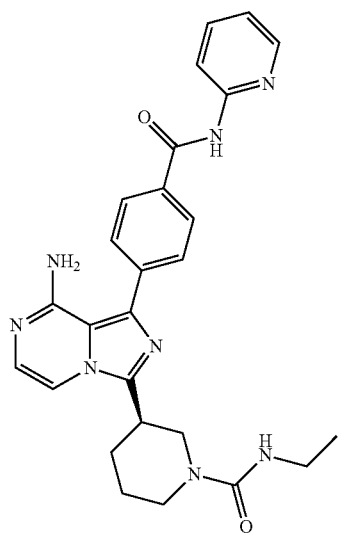 [SMILES: CCNC(=O)N1CCC[C@@H](c2nc(-c3ccc(C(=O)Nc4ccccn4)cc3)c3c(N)nccn23)C1]

(R)-3-(8-amino-1-(4-(pyridin-2-ylcarbamoyl)phenyl)
imidazo[1,5-a]pyrazin-3-yl)-N-ethylpiperidine-1-
carboxamide To a solution of (R)-4-(8-amino-3-(piperidin-3-yl)imidazo[1,5-a]pyrazin-1-yl)-N-(pyridin-2-yl)benzamide (Intermediate 9b, 35 mg, 85 μmol) in THF (1 mL) was added ethyl isocyanate (6.02 mg, 4.86 μL, 85 μmol). The mixture was stirred for 2 h. at room temperature. The mixture was concentrated in vacuo. The residue was purified by preparative HPLC. Fractions containing the product were collected and reduced to dryness to afford 21.5 mg of (R)-3-(8-amino-1-(4-(pyridin-2-ylcarbamoyl)phenyl)-imidazo[1,5-a]pyrazin-3-yl)-N-ethylpiperidine-1-carboxamide. Data: UPLC(C) $R_t$: 1.49 min; m/z 485.3 (M+H)⁺.

170
Example 49

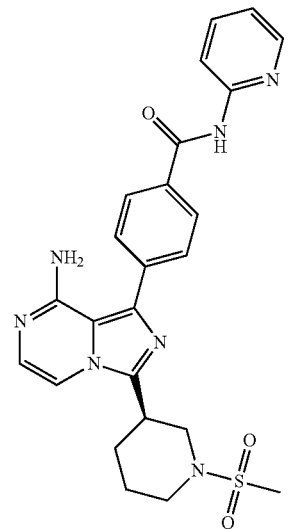 [SMILES: CS(=O)(=O)N1CCC[C@@H](c2nc(-c3ccc(C(=O)Nc4ccccn4)cc3)c3c(N)nccn23)C1]

(R)-4-(8-amino-3-(1-(methylsulfonyl)piperidin-3-yl)
imidazo[1,5-a]pyrazin-1-yl)-N-(pyridin-2-yl)benz-
amide To a solution of (R)-4-(8-amino-3-(piperidin-3-yl)imidazo[1,5-a]pyrazin-1-yl)-N-(pyridin-2-yl)benzamide (Intermediate 9b, 30 mg, 73 μmol), triethylamine (20 μL, 0.145 mmol) in dichloromethane (1 mL) was added methanesulphonylchloride (7.48 mg, 5.05 μL, 65 μmol). The mixture was stirred at 0° C. to room temperature for 2 h. The mixture was washed water, brine, dried over sodium sulfate and concentrated in vacuo. The residue was purified by preparative HPLC. Fractions containing the product were collected and reduced to dryness to afford 10.5 mg of (R)-4-(8-amino-3-(1-(methylsulfonyl)piperidin-3-yl)imidazo[1,5-a]pyrazin-1-yl)-N-(pyridin-2-yl)benzamide (29.4% yield). Data: UPLC(C) $R_t$: 1.50 min; m/z 491.9 (M+H)⁺.

The following Examples were synthesized following the methods described for example 46-49.

| Example | Structure | Name | LC-MS [M + H]⁺ | Retention time |
|---|---|---|---|---|
| 50 | ![structure] | (R)-4-(8-amino-3-(1-(3-methoxypropanoyl)piperidin-3-yl)imidazo[1,5-a]pyrazin-1-yl)-N-(pyridin-2-yl)benzamide | 500.3 | 1.35 min |

| Example | Structure | Name | LC-MS [M + H]+ | Retention time |
|---------|-----------|------|----------------|----------------|
| 51 | 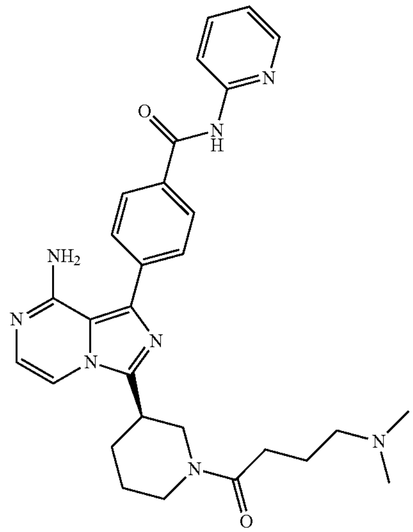 [SMILES: CN(C)CCCC(=O)N1CCC[C@@H](c2nc(-c3ccc(C(=O)Nc4ccccn4)cc3)c3c(N)nccn23)C1] | (R)-4-(8-amino-3-(1-(4-(dimethylamino)butanoyl)piperidin-3-yl)imidazo[1,5-a]pyrazin-1-yl)-N-(pyridin-2-yl)benzamide | 527.1 | 1.16 min |
| 52 | 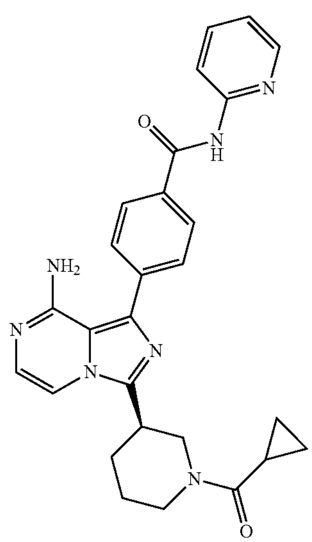 [SMILES: Nc1nccn2c([C@@H]3CCCN(C(=O)C4CC4)C3)nc(-c3ccc(C(=O)Nc4ccccn4)cc3)c12] | (R)-4-(8-amino-3-(1-(cyclopropanecarbonyl)piperidin-3-yl)imidazo[1,5-a]pyrazin-1-yl)-N-(pyridin-2-yl)benzamide | 482.3 | 1.45 min |

| Example | Structure | Name | LC-MS [M + H]+ | Retention time |
|---|---|---|---|---|
| 53 | 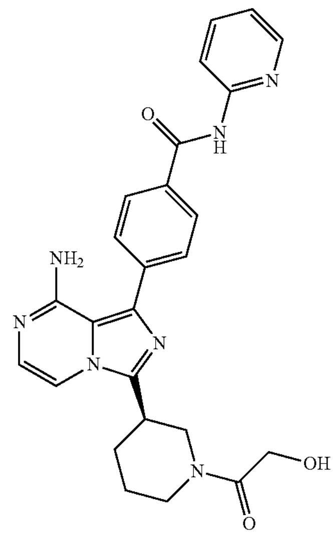 [SMILES: Nc1nccn2c([C@@H]3CCCN(C(=O)CO)C3)nc(-c3ccc(C(=O)Nc4ccccn4)cc3)c12] | (R)-4-(8-amino-3-(1-(2-hydroxyacetyl)piperidin-3-yl)imidazo[1,5-a]pyrazin-1-yl)-N-(pyridin-2-yl)benzamide | 472.2 | 1.04 min |
| 54 | 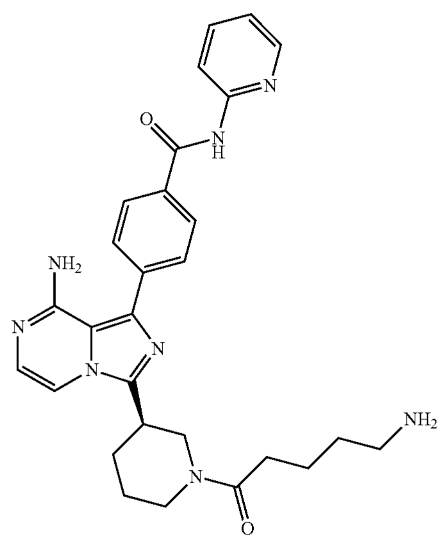 [SMILES: NCCCCC(=O)N1CCC[C@@H](c2nc(-c3ccc(C(=O)Nc4ccccn4)cc3)c3c(N)nccn23)C1] | (R)-4-(8-amino-3-(1-(5-aminopentanoyl)piperidin-3-yl)imidazo[1,5-a]pyrazin-1-yl)-N-(pyridin-2-yl)benzamide | 513.3 | 0.98 min |
| 55 | 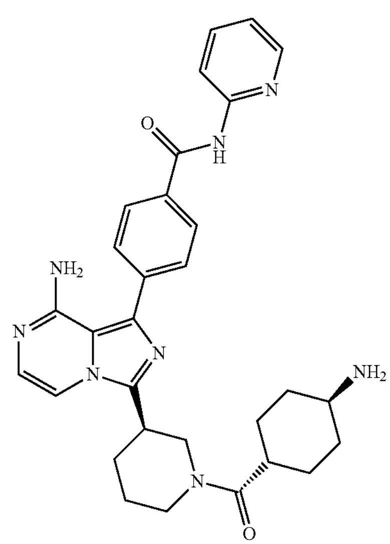 | 4-(8-amino-3-((R)-1-((trans)-4-aminocyclohexanecarbonyl)piperidin-3-yl)imidazo[1,5-a]pyrazin-1-yl)-N-(pyridin-2-yl)benzamide, TFA salt | 539.3 | 0.98 min |

| Example | Structure | Name | LC-MS [M + H]+ | Retention time |
|---------|-----------|------|----------------|----------------|
| 56 | 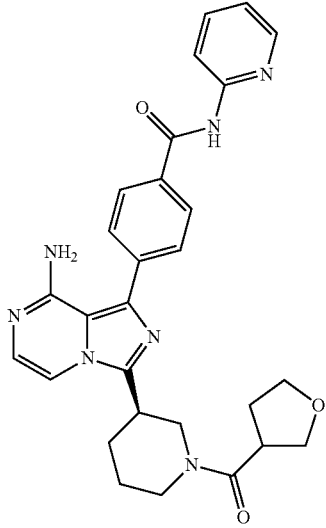 [SMILES: Nc1nccn2c([C@@H]3CCCN(C(=O)C4CCOC4)C3)nc(-c3ccc(C(=O)Nc4ccccn4)cc3)c12] | 4-(8-amino-3-((3R)-1-(tetrahydrofuran-3-carbonyl)piperidin-3-yl)imidazo[1,5-a]pyrazin-1-yl)-N-(pyridin-2-yl)benzamide, TFA salt | 512.2 | 1.31 min |
| 57 | 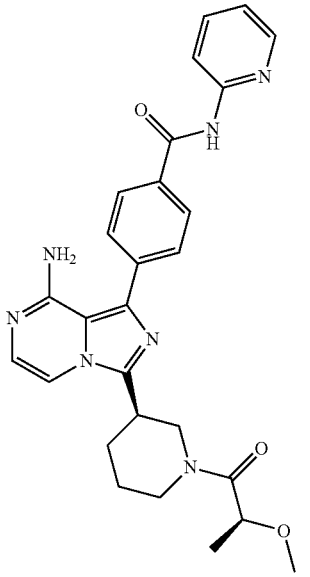 [SMILES: CO[C@@H](C)C(=O)N1CCC[C@@H](c2nc(-c3ccc(C(=O)Nc4ccccn4)cc3)c3c(N)nccn23)C1] | 4-(8-amino-3-((R)-1-((S)-2-methoxypropanoyl)piperidin-3-yl)imidazo[1,5-a]pyrazin-1-yl)-N-(pyridin-2-yl)benzamide | 500.2 | 1.33 min |

| Example | Structure | Name | LC-MS [M + H]+ | Retention time |
|---|---|---|---|---|
| 58 | 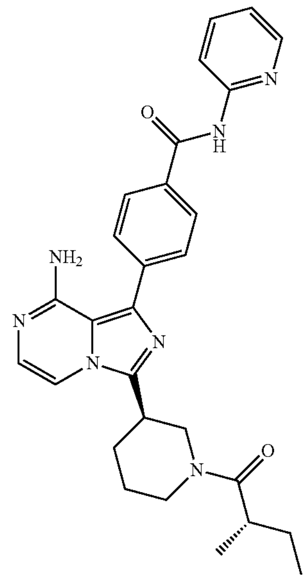 [SMILES: CC[C@H](C)C(=O)N1CCC[C@@H](c2nc(-c3ccc(C(=O)Nc4ccccn4)cc3)c3c(N)nccn23)C1] | 4-(8-amino-3-((R)-1-((S)-2-methylbutanoyl)piperidin-3-yl)imidazo[1,5-a]pyrazin-1-yl)-N-(pyridin-2-yl)benzamide | 498.3 | 1.74 min |
| 59 | 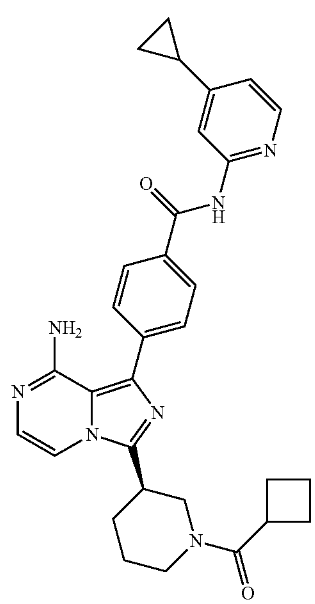 [SMILES: Nc1nccn2c([C@@H]3CCCN(C(=O)C4CCC4)C3)nc(-c3ccc(C(=O)Nc4cc(C5CC5)ccn4)cc3)c12] | (R)-4-(8-amino-3-(1-(cyclobutanecarbonyl)piperidin-3-yl)imidazo[1,5-a]pyrazin-1-yl)-N-(4-cyclopropylpyridin-2-yl)benzamide | 536.3 | 1.72 min |

| Example | Structure | Name | LC-MS [M + H]+ | Retention time |
|---|---|---|---|---|
| 60 | 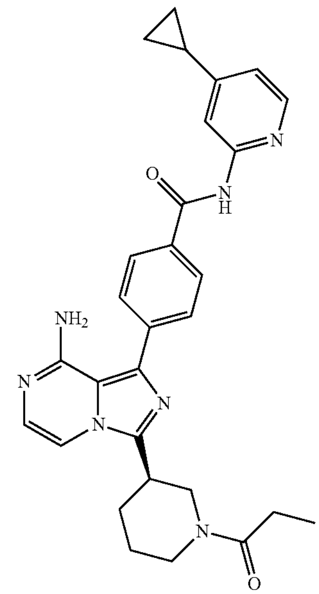 [SMILES: CCC(=O)N1CCC[C@@H](c2nc(-c3ccc(C(=O)Nc4cc(C5CC5)ccn4)cc3)c3c(N)nccn23)C1] | (R)-4-(8-amino-3-(1-propionylpiperidin-3-yl)imidazo[1,5-a]pyrazin-1-yl)-N-(4-cyclopropylpyridin-2-yl)benzamide | 510.3 | 1.46 min |
| 61 | 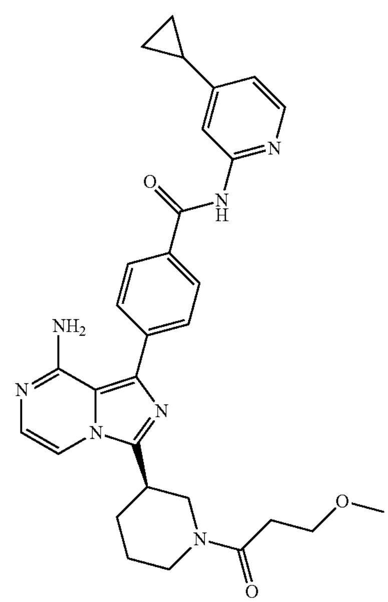 [SMILES: COCCC(=O)N1CCC[C@@H](c2nc(-c3ccc(C(=O)Nc4cc(C5CC5)ccn4)cc3)c3c(N)nccn23)C1] | (R)-4-(8-amino-3-(1-(3-methoxypropanoyl)piperidin-3-yl)imidazo[1,5-a]pyrazin-1-yl)-N-(4-cyclopropylpyridin-2-yl)benzamide | 540.3 | 1.41 min |

-continued
| Example | Structure | Name | LC-MS [M + H]+ | Retention time |
|---|---|---|---|---|
| 62 | 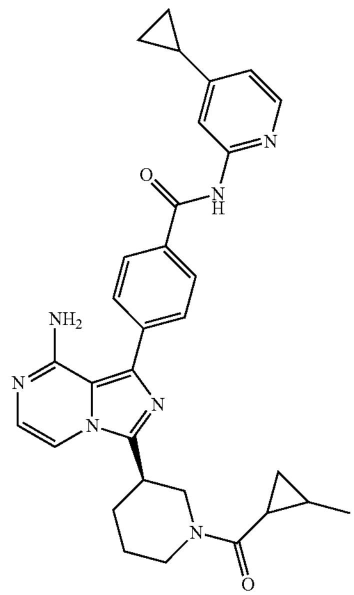 [SMILES: CC1CC1C(=O)N1CCC[C@@H](c2nc(-c3ccc(C(=O)Nc4cc(C5CC5)ccn4)cc3)c3c(N)nccn23)C1] | 4-(8-amino-3-((3R)-1-(2-methylcyclopropanecarbonyl)piperidin-3-yl)imidazo[1,5-a]pyrazin-1-yl)-N-(4-cyclopropylpyridin-2-yl)benzamide | 536.3 | 1.77 min |
| 63 | 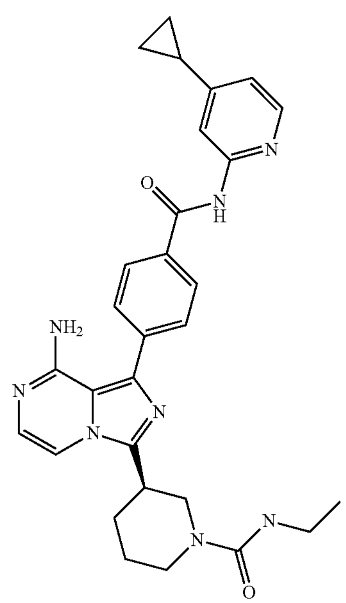 [SMILES: CCNC(=O)N1CCC[C@@H](c2nc(-c3ccc(C(=O)Nc4cc(C5CC5)ccn4)cc3)c3c(N)nccn23)C1] | (R)-3-(8-amino-1-(4-(4-cyclopropylpyridin-2-ylcarbamoyl)phenyl)imidazo[1,5-a]pyrazin-3-yl)-N-ethylpiperidine-1-carboxamide | 525.3 | 1.42 min |

-continued

| Example | Structure | Name | LC-MS [M + H]+ | Retention time |
|---------|-----------|------|----------------|----------------|
| 64 | 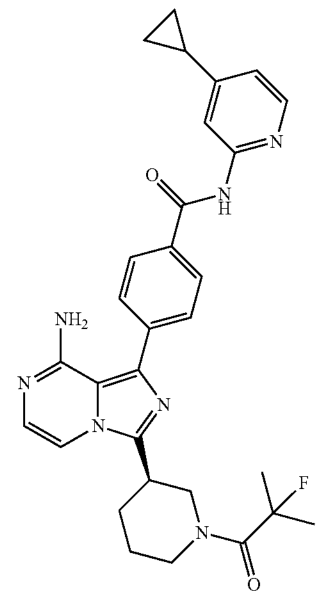 [SMILES: CC(C)(F)C(=O)N1CCC[C@@H](c2nc(-c3ccc(C(=O)Nc4cc(C5CC5)ccn4)cc3)c3c(N)nccn23)C1] | (R)-4-(8-amino-3-(1-(2-fluoro-2-methylpropanoyl)piperidin-3-yl)imidazo[1,5-a]pyrazin-1-yl)-N-(4-cyclopropylpyridin-2-yl)benzamide | 542.3 | 1.76 min |
| 65 | 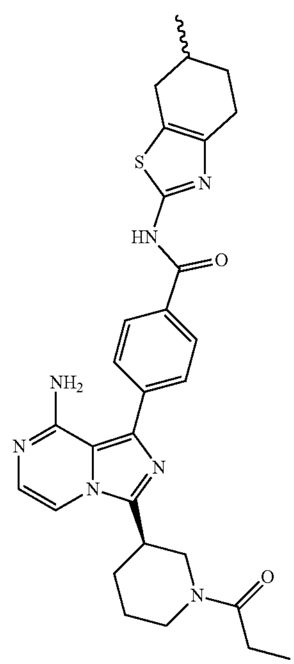 [SMILES: CCC(=O)N1CCC[C@@H](c2nc(-c3ccc(C(=O)Nc4nc5c(s4)CC(C)CC5)cc3)c3c(N)nccn23)C1] | (R)-4-(8-amino-3-(1-propionylpiperidin-3-yl)imidazo[1,5-a]pyrazin-1-yl)-N-(6-methyl-4,5,6,7-tetrahydrobenzo[d]thiazol-2-yl)benzamide | 544.3 | 2.58 min (UPLC E) |

| Example | Structure | Name | LC-MS [M + H]+ | Retention time |
|---|---|---|---|---|
| 66 | 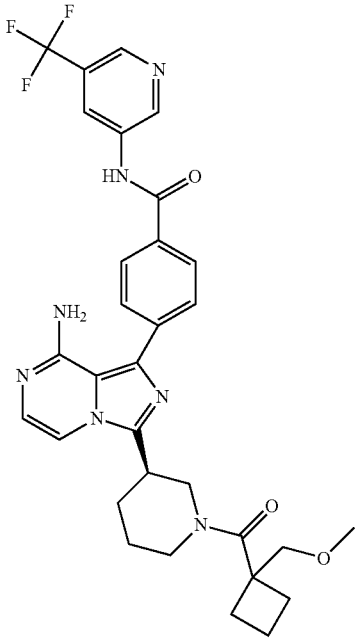 [SMILES: COCC1(C(=O)N2CCC[C@@H](c3nc(-c4ccc(C(=O)Nc5cncc(C(F)(F)F)c5)cc4)c4c(N)nccn34)C2)CCC1] | (R)-4-(8-amino-3-(1-(1-(methoxymethyl)cyclobutane-carbonyl)piperidin-3-yl)imidazo[1,5-a]pyrazin-1-yl)-N-(4-(trifluoromethyl)pyridin-2-yl)benzamide | 608.3 | 2.69 min (UPLC E) |
| 67 | 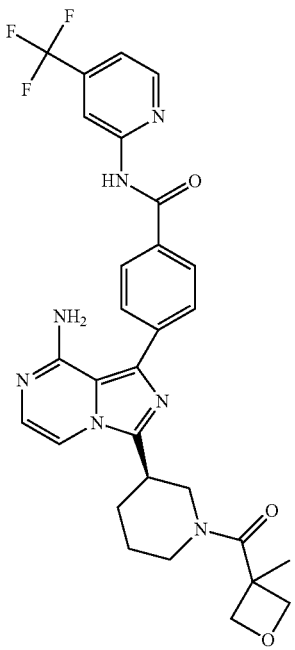 | (R)-4-(8-amino-3-(1-(3-methyloxetane-3-carbonyl)piperidin-3-yl)imidazo[1,5-a]pyrazin-1-yl)-N-(4-(trifluoromethyl)pyridin-2-yl)benzamide | 580.2 | 2.21 min |

| Example | Structure | Name | LC-MS [M + H]+ | Retention time |
|---------|-----------|------|----------------|----------------|
| 68 | 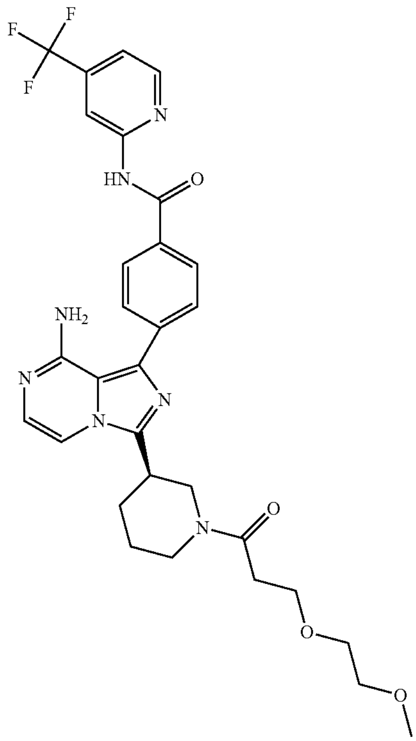 [SMILES: COCCOCCC(=O)N1CCC[C@@H](c2nc(-c3ccc(C(=O)Nc4cc(C(F)(F)F)ccn4)cc3)c3c(N)nccn23)C1] | (R)-4-(8-amino-3-(1-(3-(2-methoxyethoxy)propanoyl)piperidin-3-yl)imidazo[1,5-a]pyrazin-1-yl)-N-(4-(trifluoromethyl)pyridin-2-yl)benzamide | 612.2 | 2.32 min (UPLC E) |
| 69 | 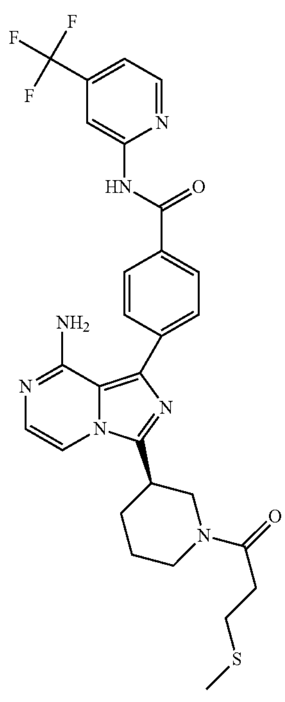 [SMILES: CSCCC(=O)N1CCC[C@@H](c2nc(-c3ccc(C(=O)Nc4cc(C(F)(F)F)ccn4)cc3)c3c(N)nccn23)C1] | (R)-4-(8-amino-3-(1-(3-(methylthio)propanoyl)piperidin-3-yl)imidazo[1,5-a]pyrazin-1-yl)-N-(4-(trifluoromethyl)pyridin-2-yl)benzamide | 585.2 | 2.34 min (UPLC E) |

-continued

| Example | Structure | Name | LC-MS [M + H]+ | Retention time |
|---------|-----------|------|----------------|----------------|
| 70 | 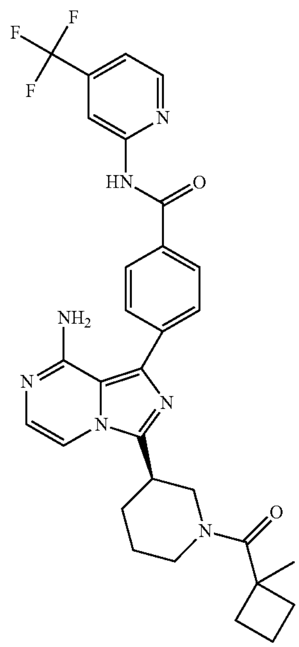 [SMILES: CC1(C(=O)N2CCC[C@@H](c3nc(-c4ccc(C(=O)Nc5cc(C(F)(F)F)ccn5)cc4)c4c(N)nccn34)C2)CCC1] | (R)-4-(8-amino-3-(1-(1-methylcyclobutanecarbonyl)piperidin-3-yl)imidazo[1,5-a]pyrazin-1-yl)-N-(4-(trifluoromethyl)pyridin-2-yl)benzamide | 579.2 | 2.67 min (UPLC E) |
| 71 | 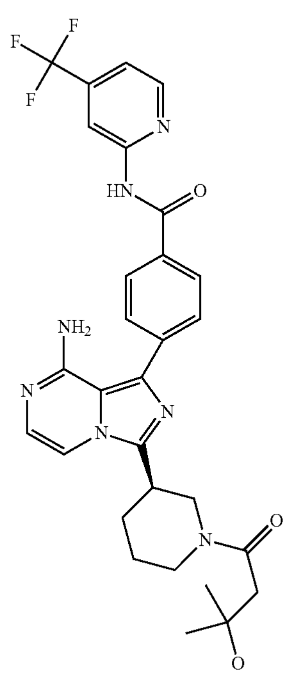 [SMILES: CC(C)(O)CC(=O)N1CCC[C@@H](c2nc(-c3ccc(C(=O)Nc4cc(C(F)(F)F)ccn4)cc3)c3c(N)nccn23)C1] | (R)-4-(8-amino-3-(1-(3-hydroxy-3-methylbutanoyl)piperidin-3-yl)imidazo[1,5-a]pyrazin-1-yl)-N-(4-(trifluoromethyl)pyridin-2-yl)benzamide | 583.2 | 2.12 min (UPLC E) |

| Example | Structure | Name | LC-MS [M + H]+ | Retention time |
|---|---|---|---|---|
| 72 | 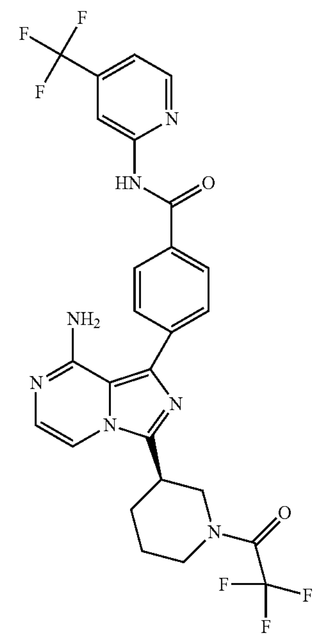 [SMILES: Nc1nccn2c([C@@H]3CCCN(C(=O)C(F)(F)F)C3)nc(-c3ccc(C(=O)Nc4cc(C(F)(F)F)ccn4)cc3)c12] | (R)-4-(8-amino-3-(1-(2,2,2-trifluoroacetyl)piperidin-3-yl)imidazo[1,5-a]pyrazin-1-yl)-N-(4-(trifluoromethyl)pyridin-2-yl)benzamide | 579.1 | 2.66 min (UPLC E) |
| 73 | 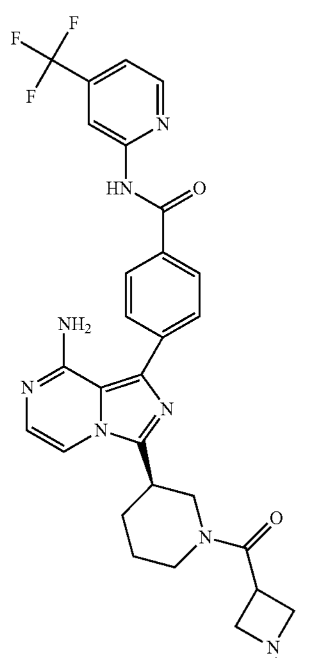 | (R)-4-(8-amino-3-(1-(1-(methylsulfonyl)azetidine-3-carbonyl)piperidin-3-yl)imidazo[1,5-a]pyrazin-1-yl)-N-(4-(trifluoromethyl)pyridin-2-yl)benzamide | 643.2 | 2.27 min (UPLC E) |

| Example | Structure | Name | LC-MS [M + H]+ | Retention time |
|---|---|---|---|---|
| 74 | 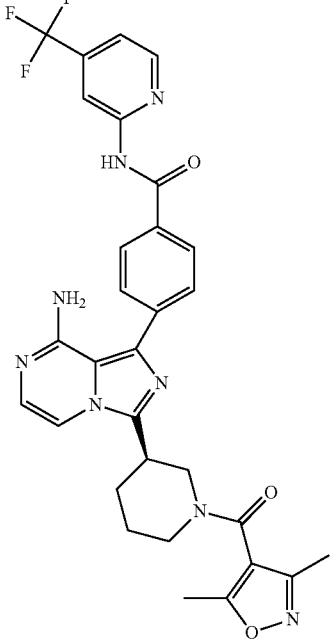 | (R)-4-(8-amino-3-(1-(3,5-dimethylisoxazole-4-carbonyl)piperidin-3-yl)imidazo[1,5-a]pyrazin-1-yl)-N-(4-(trifluoromethyl)pyridin-2-yl)benzamide | 606.2 | 2.27 min (UPLC E) |
| 75 | 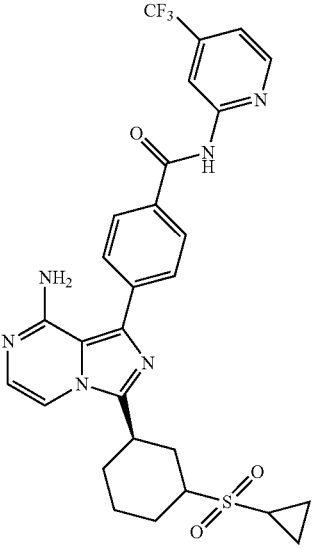 [SMILES: Nc1nccn2c([C@@H]3CCCC(S(=O)(=O)C4CC4)C3)nc(-c3ccc(C(=O)Nc4cc(C(F)(F)F)ccn4)cc3)c12] | (R)-4-(8-amino-3-(1-(cyclopropylsulfonyl)piperidin-3-yl)imidazo[1,5-a]pyrazin-1-yl)-N-(4-(trifluoromethyl)pyridin-2-yl)benzamide | 587.2 | 2.38 min (UPLC E) |

-continued
| Example | Structure | Name | LC-MS [M + H]+ | Retention time |
|---|---|---|---|---|
| 76 | 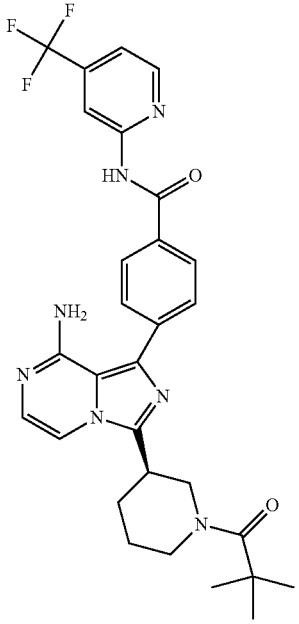 [SMILES: CC(C)(C)C(=O)N1CCC[C@@H](c2nc(-c3ccc(C(=O)Nc4cc(C(F)(F)F)ccn4)cc3)c3c(N)nccn23)C1] | (R)-4-(8-amino-3-(1-pivaloylpiperidin-3-yl)imidazo[1,5-a]pyrazin-1-yl)-N-(4-(trifluoromethyl)pyridin-2-yl)benzamide | 566.3 | 2.65 min (UPLC E) |
| 77 | 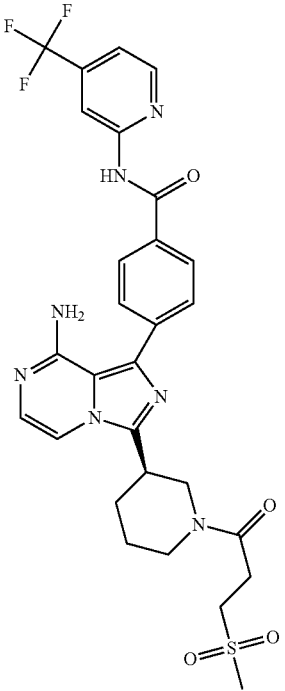 [SMILES: CS(=O)(=O)CCC(=O)N1CCC[C@@H](c2nc(-c3ccc(C(=O)Nc4cc(C(F)(F)F)ccn4)cc3)c3c(N)nccn23)C1] | (R)-4-(8-amino-3-(1-(3-(methylsulfonyl)propanoyl)piperidin-3-yl)imidazo[1,5-a]pyrazin-1-yl)-N-(4-(trifluoromethyl)pyridin-2-yl)benzamide | 617.2 | 1.95 min (UPLC E) |

| Example | Structure | Name | LC-MS [M + H]+ | Retention time |
|---|---|---|---|---|
| 78 | 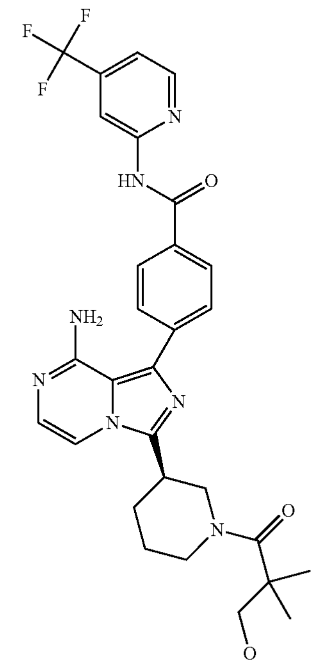 [SMILES: CC(C)(CO)C(=O)N1CCC[C@@H](c2nc(-c3ccc(C(=O)Nc4cc(C(F)(F)F)ccn4)cc3)c3c(N)nccn23)C1] | (R)-4-(8-amino-3-(1-(3-hydroxy-2,2-dimethylpropanoyl)piperidin-3-yl)imidazo[1,5-a]pyrazin-1-yl)-N-(4-(trifluoromethyl)pyridin-2-yl)benzamide | 583.2 | 2.12 min (UPLC E) |
| 79 | 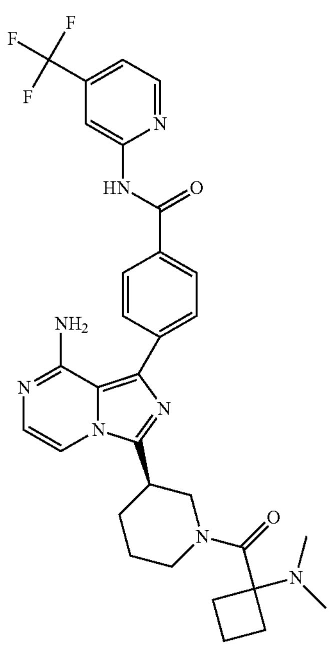 [SMILES: CN(C)C1(C(=O)N2CCC[C@@H](c3nc(-c4ccc(C(=O)Nc5cc(C(F)(F)F)ccn5)cc4)c4c(N)nccn34)C2)CCC1] | (R)-4-(8-amino-3-(1-(1-(dimethylamino)cyclobutane-carbonyl)piperidin-3-yl)imidazo[1,5-a]pyrazin-1-yl)-N-(4-(trifluoromethyl)pyridin-2-yl)benzamide | 607.2 | 1.72 min (UPLC E) |

| Example | Structure | Name | LC-MS [M + H]+ | Retention time |
|---|---|---|---|---|
| 80 | 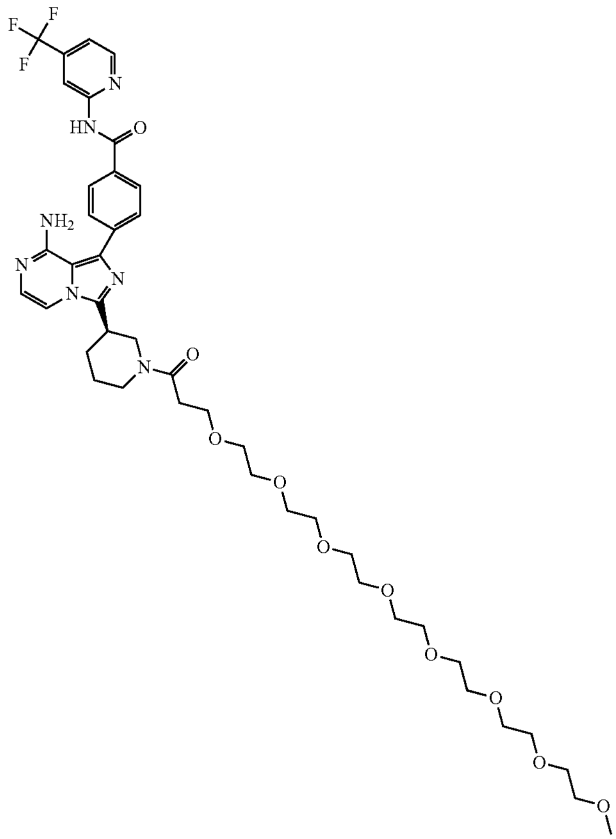 [SMILES: COCCOCCOCCOCCOCCOCCOCCOCCC(=O)N1CCC[C@@H](c2nc(-c3ccc(C(=O)Nc4cc(C(F)(F)F)ccn4)cc3)c3c(N)nccn23)C1] | (R)-4-(3-(1-2,5,8,11,14,17,20,23-octaoxahexacosanepiperidin-3-yl)-8-aminoimidazo[1,5-a]pyrazin-1-yl)-N-(4-(trifluoromethyl)pyridin-2-yl)benzamide | 876.4 | 2.42 min (UPLC E) |
| 81 | 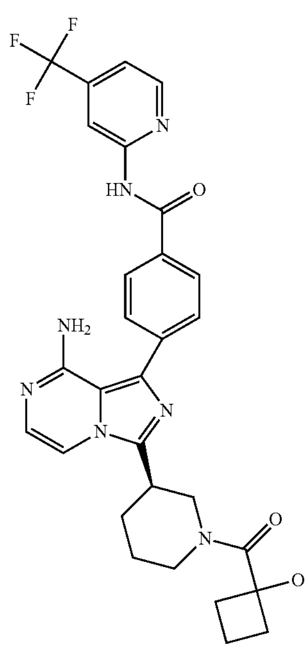 [SMILES: Nc1nccn2c([C@@H]3CCCN(C(=O)C4(O)CCC4)C3)nc(-c3ccc(C(=O)Nc4cc(C(F)(F)F)ccn4)cc3)c12] | (R)-4-(8-amino-3-(1-(1-hydroxycyclobutanecarbonyl)piperidin-3-yl)imidazo[1,5-a]pyrazin-1-yl)-N-(4-(trifluoromethyl)pyridin-2-yl)benzamide | 580.2 | 2.25 min (UPLC E) |

-continued
| Example | Structure | Name | LC-MS [M + H]+ | Retention time |
|---------|-----------|------|----------------|----------------|
| 82 | 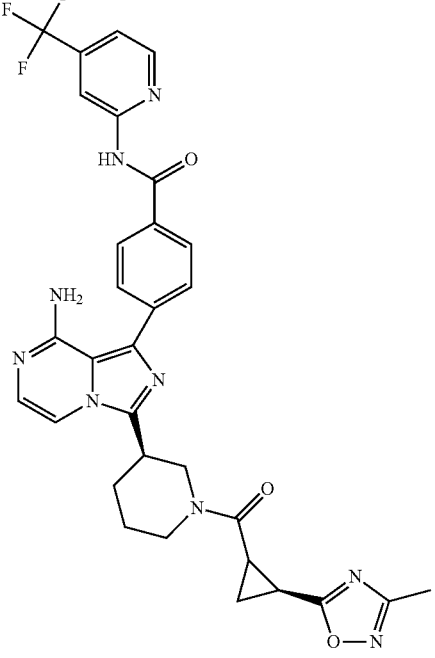 | 4-(8-amino-3-((R)-1-((1S,2S)-2-(3-methyl-1,2,4-oxadiazol-5-yl)cyclopropanecarbonyl)piperidin-3-yl)imidazo[1,5-a]pyrazin-1-yl)-N-(4-(trifluoromethyl)pyridin-2-yl)benzamide | 632.2 | 2.39 min (UPLC E) |
| 83 | 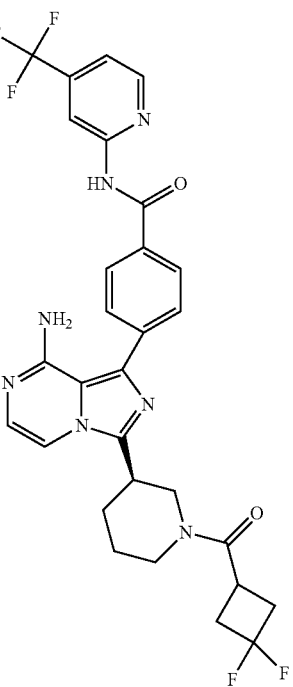 | (R)-4-(8-amino-3-(1-(3,3-difluorocyclobutanecarbonyl)piperidin-3-yl)imidazo[1,5-a]pyrazin-1-yl)-N-(4-(trifluoromethyl)pyridin-2-yl)benzamide | 601.2 | 2.58 min (UPLC E) |

| Example | Structure | Name | LC-MS [M + H]+ | Retention time |
|---|---|---|---|---|
| 84 | 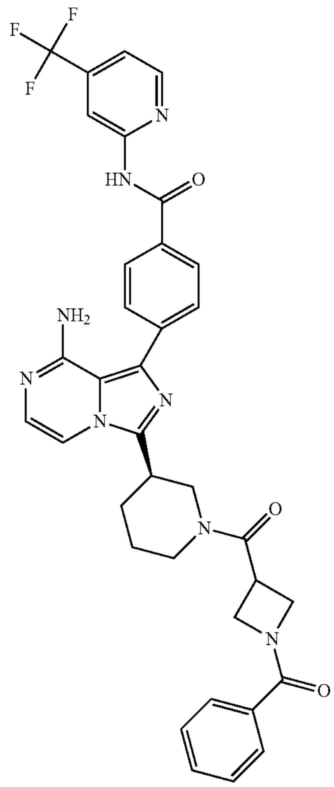 [SMILES: Nc1nccn2c([C@@H]3CCCN(C(=O)C4CN(C(=O)c5ccccc5)C4)C3)nc(-c3ccc(C(=O)Nc4cc(C(F)(F)F)ccn4)cc3)c12] | (R)-4-(8-amino-3-(1-(1-benzoylazetidine-3-carbonyl)piperidin-3-yl)imidazo[1,5-a]pyrazin-1-yl)-N-(4-(trifluoromethyl)pyridin-2-yl)benzamide | 669.2 | 2.57 min (UPLC E) |
| 85 | 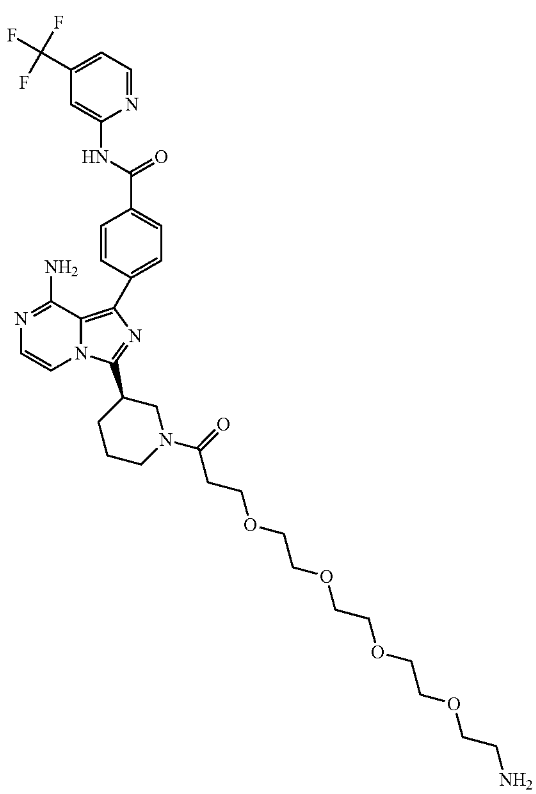 [SMILES: NCCOCCOCCOCCOCCC(=O)N1CCC[C@@H](c2nc(-c3ccc(C(=O)Nc4cc(C(F)(F)F)ccn4)cc3)c3c(N)nccn23)C1] | (R)-4-(8-amino-3-(1-(1-amino-3,6,9,12-tetraoxapentadecane)piperidin-3-yl)imidazo[1,5-a]pyrazin-1-yl)-N-(4-(trifluoromethyl)pyridin-2-yl)benzamide | 729.3 | 1.64 min (UPLC E) |

| Example | Structure | Name | LC-MS [M + H]+ | Retention time |
|---|---|---|---|---|
| 86 | 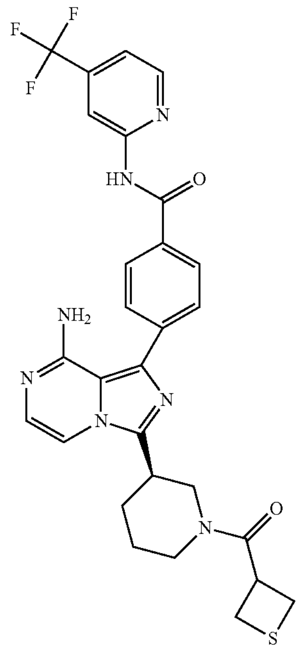 [SMILES: Nc1nccn2c([C@@H]3CCCN(C(=O)C4CSC4)C3)nc(-c3ccc(C(=O)Nc4cc(C(F)(F)F)ccn4)cc3)c12] | (R)-4-(8-amino-3-(1-(thietane-3-carbonyl)piperidin-3-yl)imidazo[1,5-a]pyrazin-1-yl)-N-(4-(trifluoromethyl)pyridin-2-yl)benzamide | 582.2 | 2.42 min (UPLC E) |
| 87 | 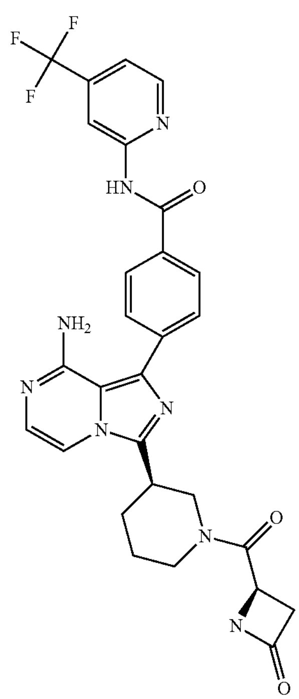 [SMILES: Nc1nccn2c([C@@H]3CCCN(C(=O)[C@H]4CC(=O)N4)C3)nc(-c3ccc(C(=O)Nc4cc(C(F)(F)F)ccn4)cc3)c12] | 4-(8-amino-3-((R)-1-((R)-4-oxoazetidine-2-carbonyl)piperidin-3-yl)imidazo[1,5-a]pyrazin-1-yl)-N-(4-(trifluoromethyl)pyridin-2-yl)benzamide | 579.2 | 1.88 min (UPLC E) |

| Example | Structure | Name | LC-MS [M + H]+ | Retention time |
|---|---|---|---|---|
| 88 | 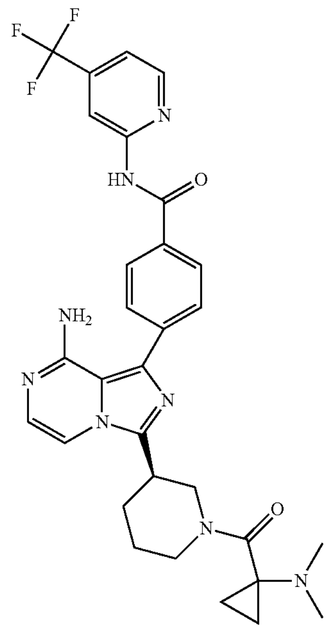 [SMILES: CN(C)C1(C(=O)N2CCC[C@@H](c3nc(-c4ccc(C(=O)Nc5cc(C(F)(F)F)ccn5)cc4)c4c(N)nccn34)C2)CC1] | (R)-4-(8-amino-3-(1-(1-(dimethylamino)cyclopropane-carbonyl)piperidin-3-yl)imidazo[1,5-a]pyrazin-1-yl)-N-(4-(trifluoromethyl)pyridin-2-yl)benzamide | 593.2 | 1.66 min (UPLC E) |
| 89 | 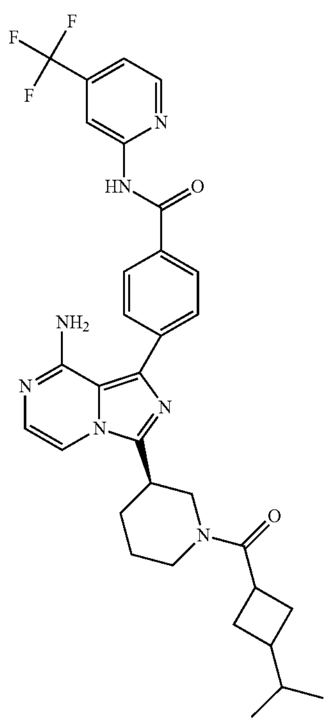 [SMILES: CC(C)C1CC(C(=O)N2CCC[C@@H](c3nc(-c4ccc(C(=O)Nc5cc(C(F)(F)F)ccn5)cc4)c4c(N)nccn34)C2)C1] | (R)-4-(8-amino-3-(1-(3-isopropylcyclobutanecarbonyl)piperidin-3-yl)imidazo[1,5-a]pyrazin-1-yl)-N-(4-(trifluoromethyl)pyridin-2-yl)benzamide | 606.6 | 3.11 min |

| Example | Structure | Name | LC-MS [M + H]+ | Retention time |
|---|---|---|---|---|
| 90 | 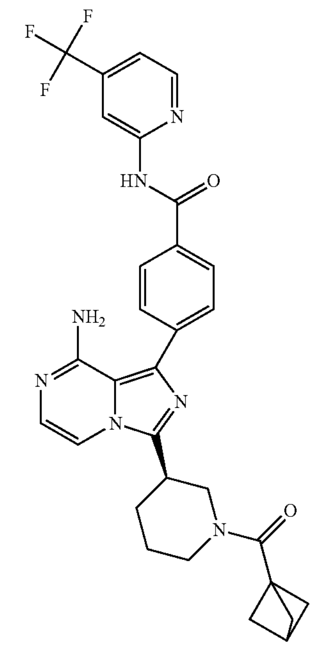 [SMILES: Nc1nccn2c([C@@H]3CCCN(C(=O)C45CC(C4)C5)C3)nc(-c3ccc(C(=O)Nc4cc(C(F)(F)F)ccn4)cc3)c12] | (R)-4-(8-amino-3-(1-(bicyclo[1.1.1]pentane-1-carbonyl)piperidin-3-yl)imidazo[1,5-a]pyrazin-1-yl)-N-(4-(trifluoromethyl)pyridin-2-yl)benzamide | 576.2 | 2.56 min (UPLC E) |
| 91 | 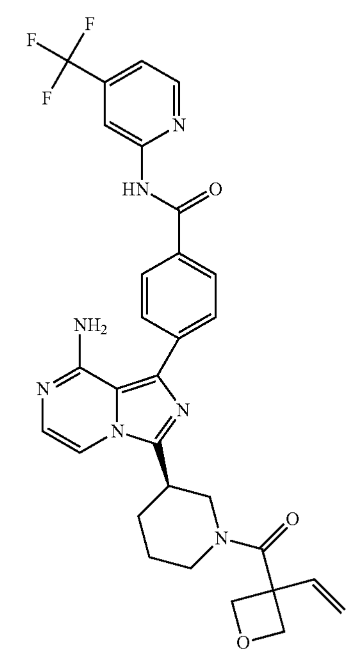 [SMILES: C=CC1(C(=O)N2CCC[C@@H](c3nc(-c4ccc(C(=O)Nc5cc(C(F)(F)F)ccn5)cc4)c4c(N)nccn34)C2)COC1] | (R)-4-(8-amino-3-(1-(3-vinyloxetane-3-carbonyl)piperidin-3-yl)imidazo[1,5-a]pyrazin-1-yl)-N-(4-(trifluoromethyl)pyridin-2-yl)benzamide | 592.2 | 2.33 min (UPLC E) |

| Example | Structure | Name | LC-MS [M + H]+ | Retention time |
|---|---|---|---|---|
| 92 | 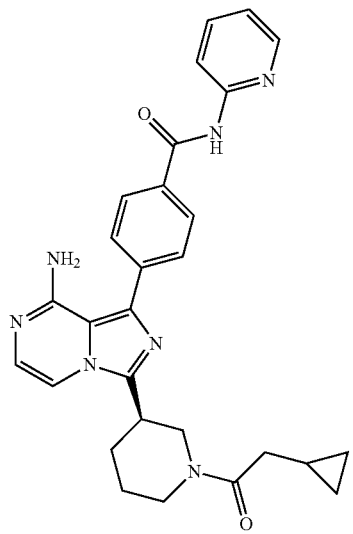 [SMILES: Nc1nccn2c([C@@H]3CCCN(C(=O)CC4CC4)C3)nc(-c3ccc(C(=O)Nc4ccccn4)cc3)c12] | (R)-4-(8-amino-3-(1-(2-cyclopropylacetyl)piperidin-3-yl)imidazo[1,5-a]pyrazin-1-yl)-N-(pyridin-2-yl)benzamide | 496.2 | 1.58 min |
| 93 | 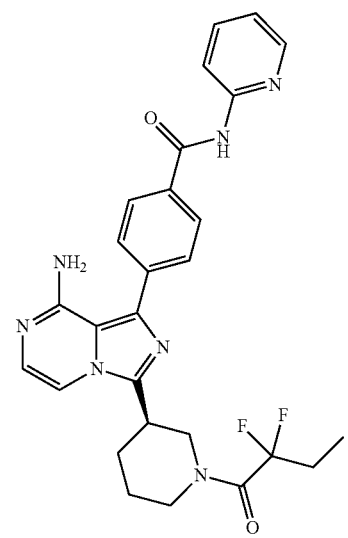 [SMILES: CCC(F)(F)C(=O)N1CCC[C@@H](c2nc(-c3ccc(C(=O)Nc4ccccn4)cc3)c3c(N)nccn23)C1] | (R)-4-(8-amino-3-(1-(2,2-difluorobutanoyl)piperidin-3-yl)imidazo[1,5-a]pyrazin-1-yl)-N-(pyridin-2-yl)benzamide | 520.3 | 1.88 min |
| 94 | 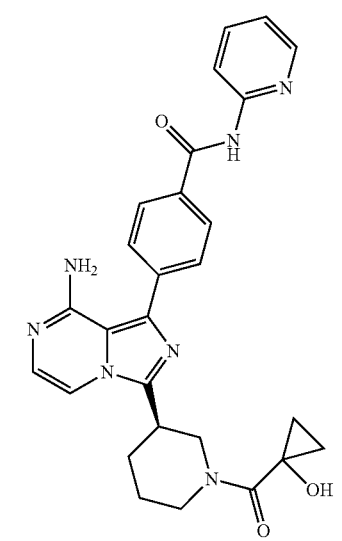 [SMILES: Nc1nccn2c([C@@H]3CCCN(C(=O)C4(O)CC4)C3)nc(-c3ccc(C(=O)Nc4ccccn4)cc3)c12] | (R)-4-(8-amino-3-(1-(1-hydroxycyclopropanecarbonyl)piperidin-3-yl)imidazo[1,5-a]pyrazin-1-yl)-N-(pyridin-2-yl)benzamide | 498.3 | 1.27 min |

-continued
| Example | Structure | Name | LC-MS [M + H]+ | Retention time |
|---|---|---|---|---|
| 95 | 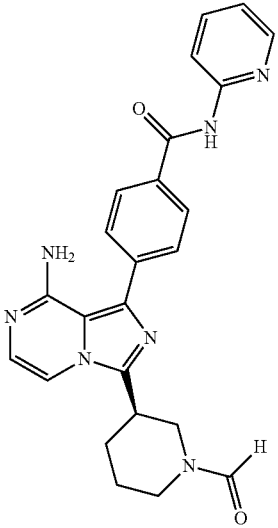 [SMILES: Nc1nccn2c([C@@H]3CCCN(C=O)C3)nc(-c3ccc(C(=O)Nc4ccccn4)cc3)c12] | (R)-4-(8-amino-3-(1-formylpiperidin-3-yl)imidazo[1,5-a]pyrazin-1-yl)-N-(pyridin-2-yl)benzamide | 442.3 | 1.17 min |
| 96 | 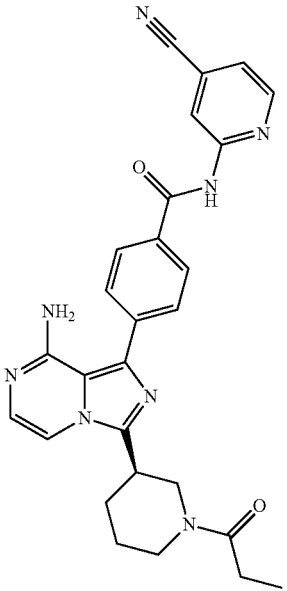 [SMILES: CCC(=O)N1CCC[C@@H](c2nc(-c3ccc(C(=O)Nc4cc(C#N)ccn4)cc3)c3c(N)nccn23)C1] | (R)-4-(8-amino-3-(1-propionylpiperidin-3-yl)imidazo[1,5-a]pyrazin-1-yl)-N-(4-cyanopyridin-2-yl)benzamide | 495.3 | 1.86 min |

-continued

| Example | Structure | Name | LC-MS [M + H]+ | Retention time |
|---|---|---|---|---|
| 97 | 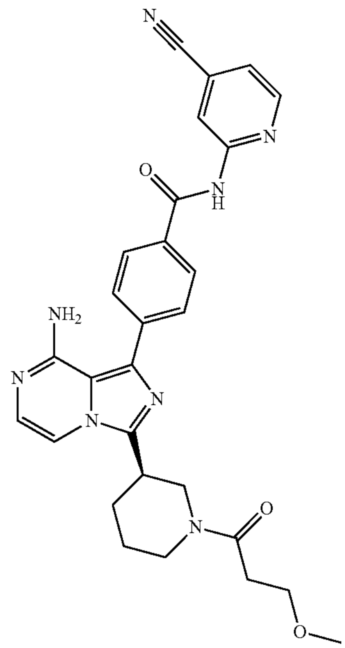 [SMILES: COCCC(=O)N1CCC[C@@H](c2nc(-c3ccc(C(=O)Nc4cc(C#N)ccn4)cc3)c3c(N)nccn23)C1] | (R)-4-(8-amino-3-(1-(3-methoxypropanoyl)piperidin-3-yl)imidazo[1,5-a]pyrazin-1-yl)-N-(4-cyanopyridin-2-yl)benzamide | 525.3 | 1.78 min |
| 98 | 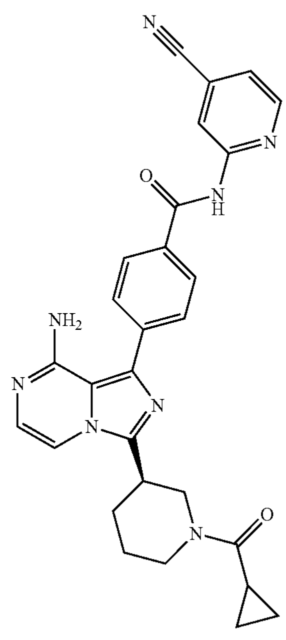 [SMILES: N#Cc1ccnc(NC(=O)c2ccc(-c3nc([C@@H]4CCCN(C(=O)C5CC5)C4)n4ccnc(N)c34)cc2)c1] | (R)-4-(8-amino-3-(1-(cyclopropanecarbonyl)piperidin-3-yl)imidazo[1,5-a]pyrazin-1 yl)-N-(4-cyanopyridin-2-yl)benzamide | 507.3 | 1.95 min |

-continued

| Example | Structure | Name | LC-MS [M + H]+ | Retention time |
|---|---|---|---|---|
| 99 | 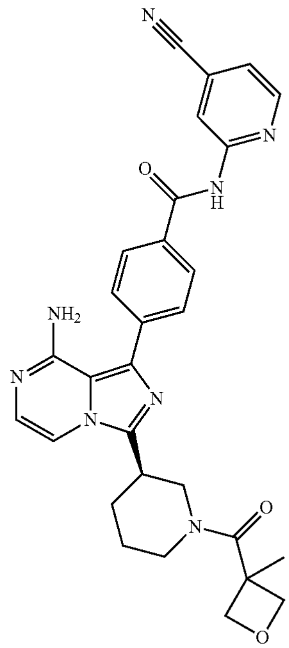 [SMILES: CC1(C(=O)N2CCC[C@@H](c3nc(-c4ccc(C(=O)Nc5cc(C#N)ccn5)cc4)c4c(N)nccn34)C2)COC1] | (R)-4-(8-amino-3-(1-(3-methyloxetane-3 carbonyl)piperidin-3-yl)imidazo[1,5-a]pyrazin-1-yl)-N-(4-cyanopyridin-2-yl)benzamide | 537.3 | 1.77 min |
| 100 | 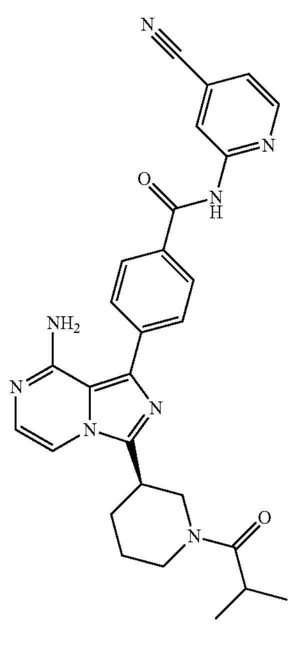 [SMILES: CC(C)C(=O)N1CCC[C@@H](c2nc(-c3ccc(C(=O)Nc4cc(C#N)ccn4)cc3)c3c(N)nccn23)C1] | (R)-4-(8-amino-3-(1-isobutyrylpiperidin-3 yl)imidazo[1,5-a]pyrazin-1-yl)-N-(4-cyanopyridin-2-yl)benzamide | 509.3 | 2.05 min |

-continued

| Example | Structure | Name | LC-MS [M + H]+ | Retention time |
|---|---|---|---|---|
| 101 | 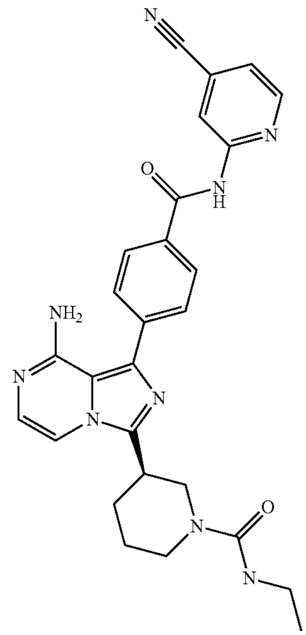 [SMILES: CCNC(=O)N1CCC[C@@H](c2nc(-c3ccc(C(=O)Nc4cc(C#N)ccn4)cc3)c3c(N)nccn23)C1] | (R)-3-(8-amino-1-(4-(4-cyanopyridin-2-ylcarbamoyl)phenyl)imidazo[1,5-a]pyrazin-3-yl)-N-ethylpiperidine-1-carboxamide | 510.3 | 1.79 min |
| 102 | 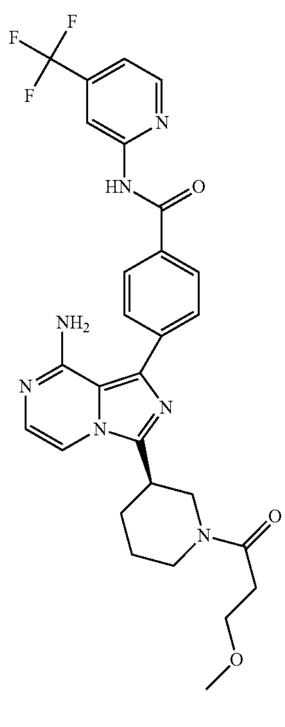 [SMILES: COCCC(=O)N1CCC[C@@H](c2nc(-c3ccc(C(=O)Nc4cc(C(F)(F)F)ccn4)cc3)c3c(N)nccn23)C1] | (R)-4-(8-amino-3-(1-(3-methoxypropanoyl)piperidin-3-yl)imidazo[1,5-a]pyrazin-1-yl)-N-(4-(trifluoromethyl)pyridin-2-yl)benzamide | 568.3 | 2.27 min (UPLC D) |

| Example | Structure | Name | LC-MS [M + H]+ | Retention time |
|---|---|---|---|---|
| 103 | 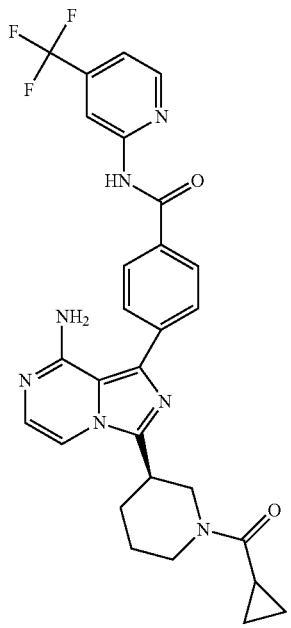 [SMILES: Nc1nccn2c([C@@H]3CCCN(C(=O)C4CC4)C3)nc(-c3ccc(C(=O)Nc4cc(C(F)(F)F)ccn4)cc3)c12] | (R)-4-(8-amino-3-(1-(cyclopropanecarbonyl)piperidin-3-yl)imidazo[1,5-a]pyrazin-1-(trifluoromethyl)pyridin-2-yl)benzamide | 550.3 | 2.40 min (UPLC E) |
| 104 | 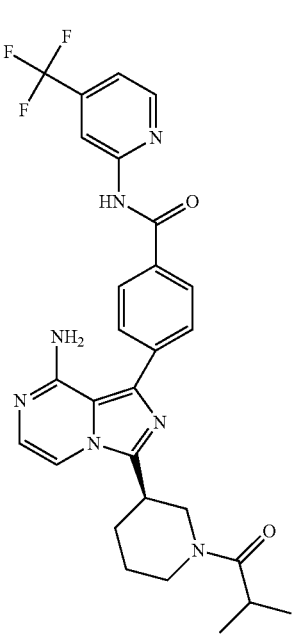 [SMILES: CC(C)C(=O)N1CCC[C@@H](c2nc(-c3ccc(C(=O)Nc4cc(C(F)(F)F)ccn4)cc3)c3c(N)nccn23)C1] | (R)-4-(8-amino-3-(1-isobutyrylpiperidin-3-yl)imidazo[1,5-a]pyrazin-1-yl)-N-(4-(trifluoromethyl)pyridin-2-yl)benzamide | 552.3 | 2.47 min (UPLC-E) |

-continued
| Example | Structure | Name | LC-MS [M + H]+ | Retention time |
|---|---|---|---|---|
| 105 | 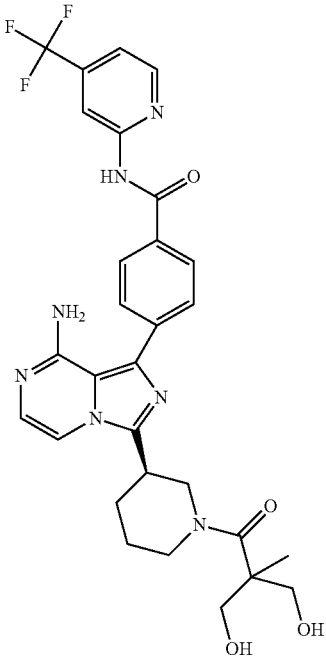 [SMILES: CC(CO)(CO)C(=O)N1CCC[C@@H](c2nc(-c3ccc(C(=O)Nc4cc(C(F)(F)F)ccn4)cc3)c3c(N)nccn23)C1] | (R)-4-(8-amino-3-(1-(3-hydroxy-2-(hydroxymethyl)-2-methylpropanoyl)piperidin-3-yl)imidazo[1,5-a]pyrazin-1-yl)-N-(4-(trifluoromethyl)pyridin-2-yl)benzamide | 598.2 | 2.05 min (UPLC-E) |
| 106 | 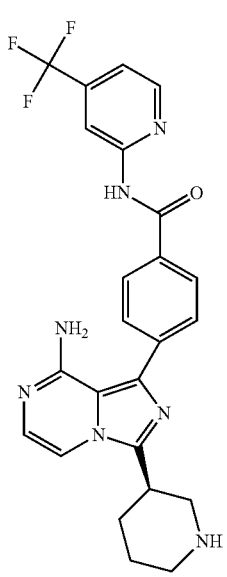 [SMILES: Nc1nccn2c([C@@H]3CCCNC3)nc(-c3ccc(C(=O)Nc4cc(C(F)(F)F)ccn4)cc3)c12] | (R)-4-(8-amino-3-(piperidin-3-yl)imidazo[1,5-a]pyrazin-1-yl)-N-(4-(trifluoromethyl)pyridin-2-yl)benzamide | 482.2 | 1.61 min |

-continued
| Example | Structure | Name | LC-MS [M + H]+ | Retention time |
|---|---|---|---|---|
| 107 | 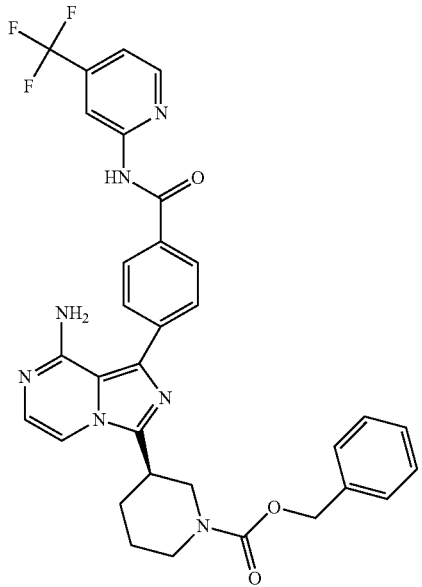 [SMILES: Nc1nccn2c([C@@H]3CCCN(C(=O)OCc4ccccc4)C3)nc(-c3ccc(C(=O)Nc4cc(C(F)(F)F)ccn4)cc3)c12] | (R)-benzyl 3-(8-amino-1-(4-(4-(trifluoromethyl)pyridin-2-ylcarbamoyl)phenyl)imidazo[1,5-a]pyrazin-3-yl)piperidine-1-carboxylate | 616.2 | 1.17 min (UPLC-B) |
| 108 | 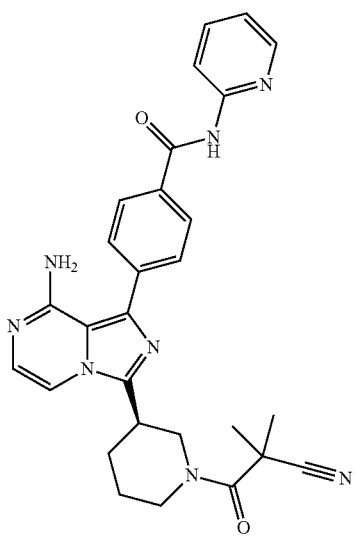 [SMILES: CC(C)(C#N)C(=O)N1CCC[C@@H](c2nc(-c3ccc(C(=O)Nc4ccccn4)cc3)c3c(N)nccn23)C1] | (R)-4-(8-amino-3-(1-(2-cyano-2-methylpropanoyl)piperidin-3-yl)imidazo[1,5-a]pyrazin-1-yl)-N-(pyridin-2-yl)benzamide | 509.2 | 1.58 min |

| Example | Structure | Name | LC-MS [M + H]+ | Retention time |
|---|---|---|---|---|
| 109 | 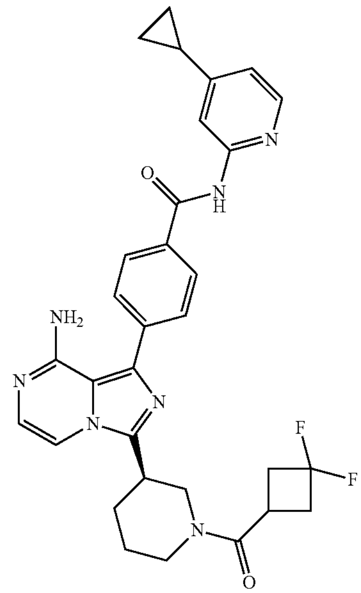 [SMILES: Nc1nccn2c([C@@H]3CCCN(C(=O)C4CC(F)(F)C4)C3)nc(-c3ccc(C(=O)Nc4cc(C5CC5)ccn4)cc3)c12] | (R)-4-(8-amino-3-(1-(3,3-difluorocyclobutanecarbonyl)piperidin-3-yl)imidazo[1,5-a]pyrazin-1-yl)-N-(4-cyclopropylpyridin-2-yl)benzamide | 572.3 | 2.40 min (UPLC-F) |
| 110 | 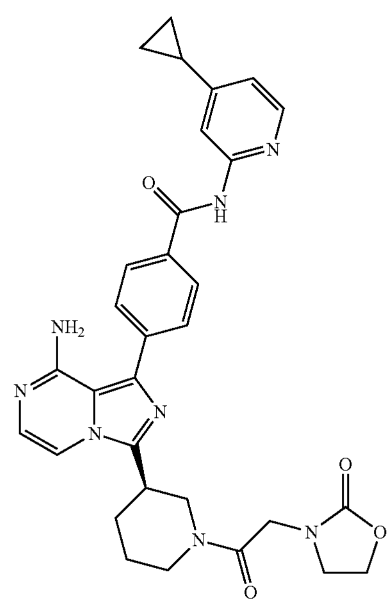 [SMILES: Nc1nccn2c([C@@H]3CCCN(C(=O)CN4CCOC4=O)C3)nc(-c3ccc(C(=O)Nc4cc(C5CC5)ccn4)cc3)c12] | (R)-4-(8-amino-3-(1-(2-(2-oxooxazolidin-3-yl)acetyl)piperidin-3-yl)imidazo[1,5-a]pyrazin-1-yl)-N-(4-cyclopropylpyridin-2-yl)benzamide | 581.3 | 1.78 min (UPLC-F) |

| Example | Structure | Name | LC-MS [M + H]⁺ | Retention time |
|---|---|---|---|---|
| 111 | 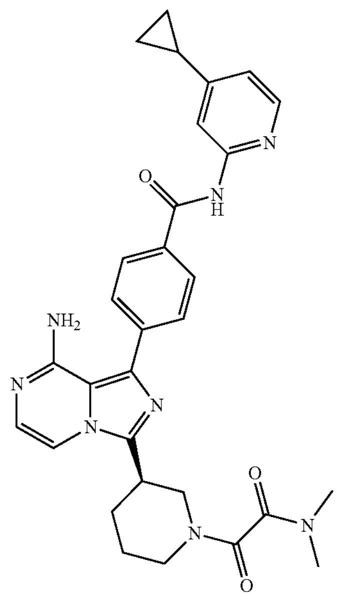 [SMILES: CN(C)C(=O)C(=O)N1CCC[C@@H](c2nc(-c3ccc(C(=O)Nc4cc(C5CC5)ccn4)cc3)c3c(N)nccn23)C1] | (R)-4-(8-amino-3-(1-(2-(dimethylamino)-2-oxoacetyl)piperidin-3-yl)imidazo[1,5-a]pyrazin-1-yl)-N-(4-cyclopropylpyridin-2-yl)benzamide | 553.3 | 2.14 min (UPLC-F) |
| 112 | 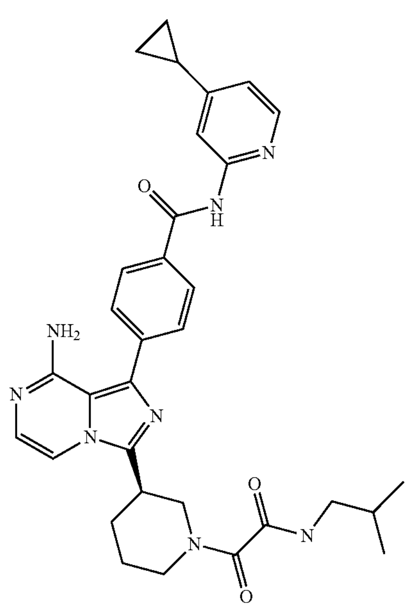 [SMILES: CC(C)CNC(=O)C(=O)N1CCC[C@@H](c2nc(-c3ccc(C(=O)Nc4cc(C5CC5)ccn4)cc3)c3c(N)nccn23)C1] | (R)-4-(8-amino-3-(1-(2-(isobutylamino)-2-oxoacetyl)piperidin-3-yl)imidazo[1,5-a]pyrazin-1-yl)-N-(4-cyclopropylpyridin-2-yl)benzamide | 581.2 | 2.25 min (UPLC-F) |

-continued

| Example | Structure | Name | LC-MS [M + H]+ | Retention time |
|---|---|---|---|---|
| 113 | 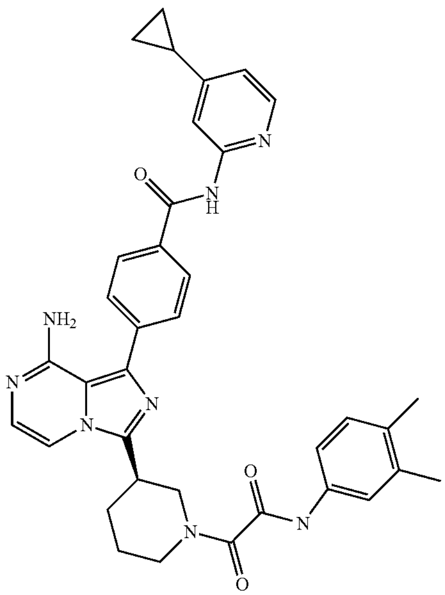 [SMILES: Cc1ccc(NC(=O)C(=O)N2CCC[C@@H](c3nc(-c4ccc(C(=O)Nc5cc(C6CC6)ccn5)cc4)c4c(N)nccn34)C2)cc1C] | (R)-4-(8-amino-3-(1-(2-(3,4-dimethylphenylamino)-2-oxoacetyl)piperidin-3-yl)imidazo[1,5-a]pyrazin-1-yl)-N-(4-cyclopropylpyridin-2-yl)benzamide | 629.3 | 2.19 min (UPLC-F) |
| 114 | 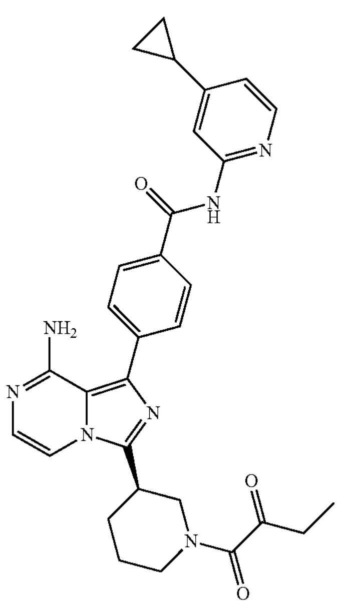 [SMILES: CCC(=O)C(=O)N1CCC[C@@H](c2nc(-c3ccc(C(=O)Nc4cc(C5CC5)ccn4)cc3)c3c(N)nccn23)C1] | (R)-4-(8-amino-3-(1-(2-oxobutanoyl)piperidin-3-yl)imidazo[1,5-a]pyrazin-1-yl)-N-(4-cyclopropylpyridin-2-yl)benzamide | 538.3 | 2.25 min (UPLC-F) |

| Example | Structure | Name | LC-MS [M + H]+ | Retention time |
|---|---|---|---|---|
| 115 | 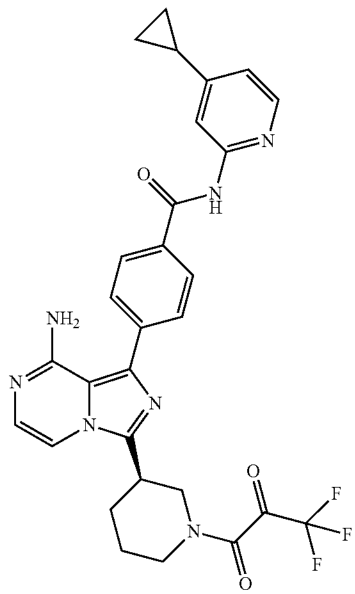 [SMILES: Nc1nccn2c([C@@H]3CCCN(C(=O)C(=O)C(F)(F)F)C3)nc(-c3ccc(C(=O)Nc4cc(C5CC5)ccn4)cc3)c12] | (R)-4-(8-amino-3-(1-(3,3,3-trifluoro-2-oxopropanoyl)piperidin-3-yl)imidazo[1,5-a]pyrazin-1-yl)-N-(4-cyclopropylpyridin-2-yl)benzamide | 578.3 | 1.86 min (UPLC-F) |
| 116 | 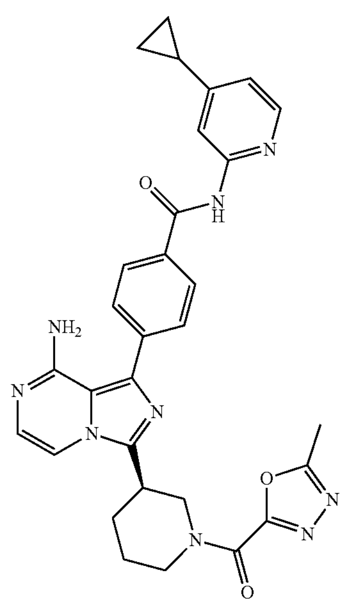 [SMILES: Cc1nnc(C(=O)N2CCC[C@@H](c3nc(-c4ccc(C(=O)Nc5cc(C6CC6)ccn5)cc4)c4c(N)nccn34)C2)o1] | (R)-4-(8-amino-3-(1-(5-methyl-1,3,4-oxadiazole-2-carbonyl)piperidin-3-yl)imidazo[1,5-a]pyrazin-1-yl)-N-(4-cyclopropylpyridin-2-yl)benzamide | 564.3 | 2.31 min (UPLC-F) |

-continued

| Example | Structure | Name | LC-MS [M + H]+ | Retention time |
|---------|-----------|------|----------------|----------------|
| 117 | 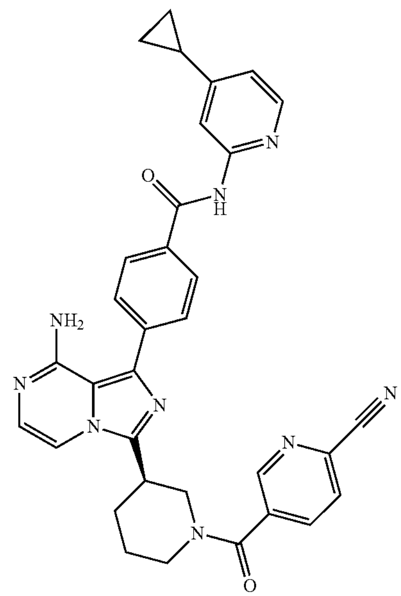 [SMILES: N#Cc1ccc(C(=O)N2CCC[C@@H](c3nc(-c4ccc(C(=O)Nc5cc(C6CC6)ccn5)cc4)c4c(N)nccn34)C2)cn1] | (R)-4-(8-amino-3-(1-(6-cyanonicotinoyl)piperidin-3-yl)imidazo[1,5-a]pyrazin-1-yl)-N-(4-cyclopropylpyridin-2-yl)benzamide | 584.3 | 1.92 min (UPLC-F) |
| 118 | 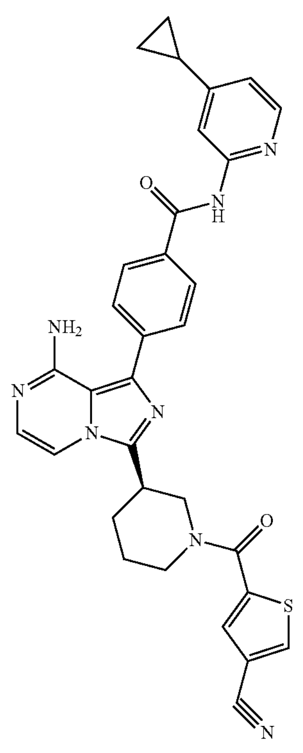 [SMILES: N#Cc1csc(C(=O)N2CCC[C@@H](c3nc(-c4ccc(C(=O)Nc5cc(C6CC6)ccn5)cc4)c4c(N)nccn34)C2)c1] | (R)-4-(8-amino-3-(1-(4-cyanothiophene-2-carbonyl)piperidin-3-yl)imidazo[1,5-a]pyrazin-1-yl)-N-(4-cyclopropylpyridin-2-yl)benzamide | 589.0 | 2.25 min (UPLC-F) |

| Example | Structure | Name | LC-MS [M + H]+ | Retention time |
|---|---|---|---|---|
| 119 | 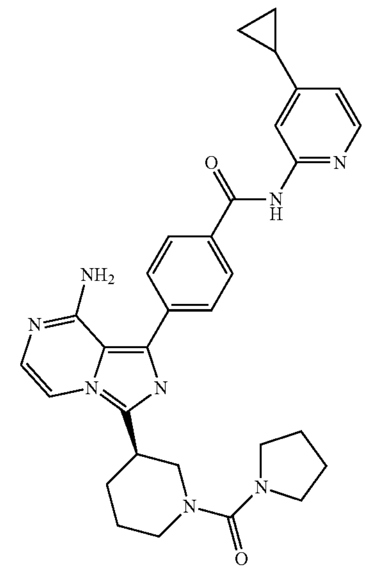 | (R)-4-(8-amino-3-(1-(pyrrolidine-1-carbonyl)piperidin-3-yl)imidazo[1,5-a]pyrazin-1-yl)-N-(4-cyclopropylpyridin-2-yl)benzamide | 551.2 | 2.00 min (UPLC-F) |
| 120 | 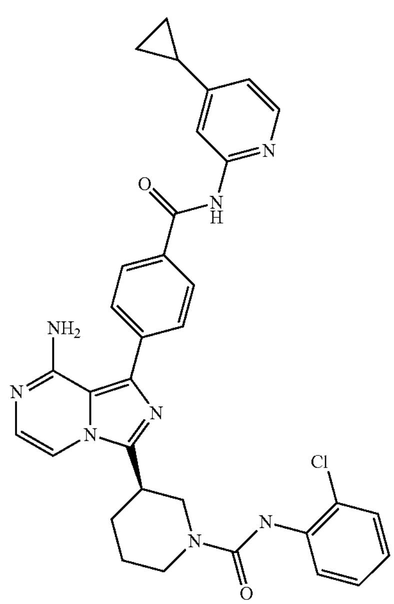 [SMILES: Nc1nccn2c([C@@H]3CCCN(C(=O)Nc4ccccc4Cl)C3)nc(-c3ccc(C(=O)Nc4cc(C5CC5)ccn4)cc3)c12] | (R)-3-(8-amino-1-(4-(4-cyclopropylpyridin-2-ylcarbamoyl)phenyl)imidazo[1,5-a]pyrazin-3-yl)-N-(2-chlorophenyl)piperidine-1-carboxamide | 607.1 | 2.37 min (UPLC-F) |

| Example | Structure | Name | LC-MS [M + H]+ | Retention time |
|---------|-----------|------|----------------|----------------|
| 121 | 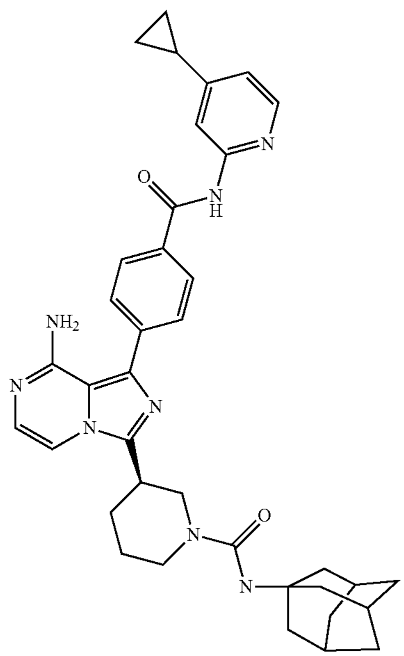 [SMILES: Nc1nccn2c([C@@H]3CCCN(C(=O)NC45CC6CC(CC(C6)C4)C5)C3)nc(-c3ccc(C(=O)Nc4cc(C5CC5)ccn4)cc3)c12] | (R)-4-(8-amino-3-(1-(adamantyl-1 carbonyl)piperidin-3-yl)imidazo[1,5-a]pyrazin-1-yl)-N-(4-cyclopropylpyridin-2-yl)benzamide | 631.2 | 1.87 min (UPLC-F) |
| 122 | 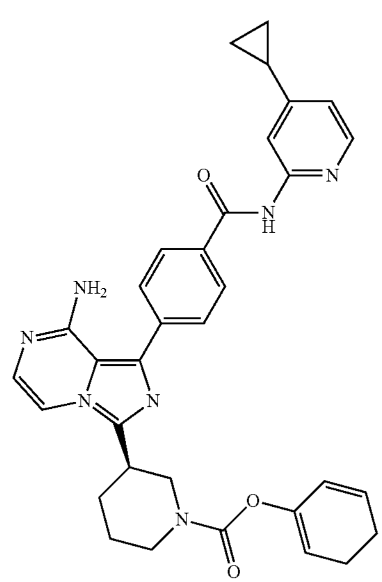 | (R)-phenyl 3-(8-amino-1-(4-(4-cyclopropylpyridin-2-ylcarbamoyl)phenyl)imidazo[1,5-a]pyrazin-3-yl)piperidine-1-carboxylate | 574.2 | 2.16 min (UPLC-F) |

| Example | Structure | Name | LC-MS [M + H]+ | Retention time |
|---|---|---|---|---|
| 123 | 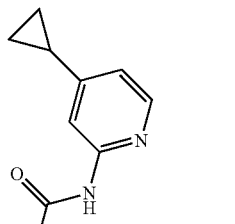 | (R)-4-(8-amino-3-(1-(2-(furan-2-yl)-2-oxoacetyl)piperidin-3-yl)imidazo[1,5-a]pyrazin-1-yl)-N-(4-cyclopropylpyridin-2-yl)benzamide | 576.2 | |

Intermediate 10

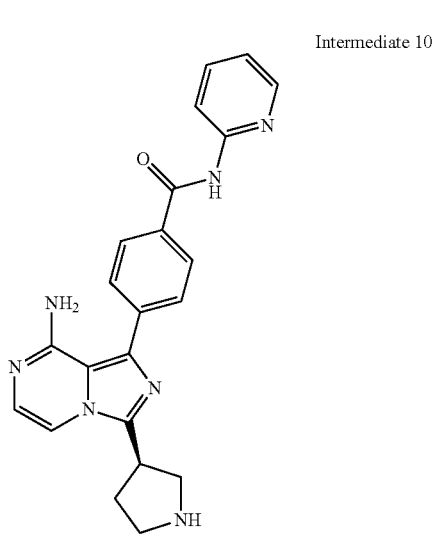 [SMILES: Nc1nccn2c([C@@H]3CCNC3)nc(-c3ccc(C(=O)Nc4ccccn4)cc3)c12]

(R)-4-(8-amino-3-(pyrrolidin-3-yl)imidazo[1,5-a]pyrazin-1-yl)-N-(pyridin-2-yl)benzamide This intermediate was prepared in an analogous manner as described for intermediate 8, from (R)-1-Cbz-pyrrolidine-3-carboxylic acid to obtain (R)-benzyl 3-(8-amino-1-bromoimidazo[1,5-a]pyrazin-3-yl)pyrrolidine-1-carboxylate. Subsequent reaction with N-(pyridin-2-yl)-4-(4,4,5,5-tetramethyl-1,3,2-dioxaborolan-2-yl)benzamide and deprotection with 33% HBr/HOAc was performed as described for intermediate 9 afforded the title compound (1.49 g, 99%)

Example 124

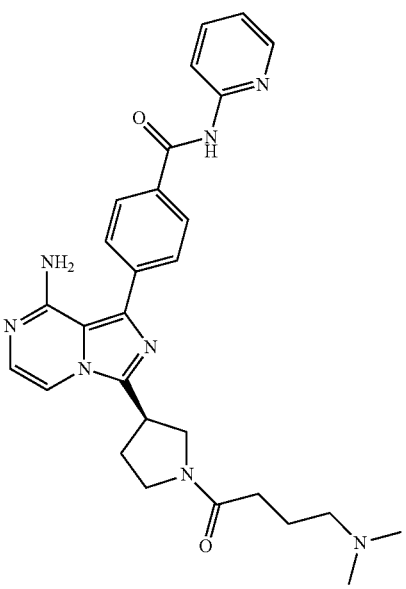 [SMILES: CN(C)CCCC(=O)N1CC[C@@H](c2nc(-c3ccc(C(=O)Nc4ccccn4)cc3)c3c(N)nccn23)C1]

(R)-4-(8-amino-3-(1-(4-(dimethylamino)butanoyl)pyrrolidin-3-yl)imidazo[1,5-a]pyrazin-1-yl)-N-(pyridin-2-yl)benzamide This compound was prepared in an analogous manner as described in Example 46, from Intermediate 10 and 4-dimethylaminobutyric acid.hydrochloride, to afford the title compound (17.6 mg, 37.4%). Data: UPLC(C) $R_t$: 0.88 min; m/z 513.2 (M+H)+.

The following Examples were synthesized following the methods described for example 124.

| Example | Structure | Name | LC-MS [M + H]+ | Retention time |
|---|---|---|---|---|
| 125 | 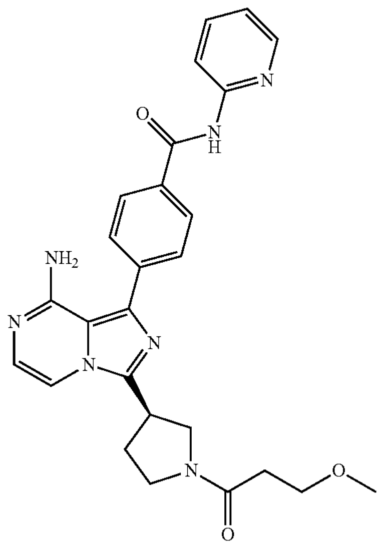 [SMILES: COCCC(=O)N1CC[C@@H](c2nc(-c3ccc(C(=O)Nc4ccccn4)cc3)c3c(N)nccn23)C1] | (R)-4-(8-amino-3-(1-(3-methoxypropanoyl)pyrrolidin-3-yl)imidazo[1,5-a]pyrazin-1-yl)-N-(pyridin-2-yl)benzamide, TFA salt | 486.2 | 1.12 min |
| 126 | 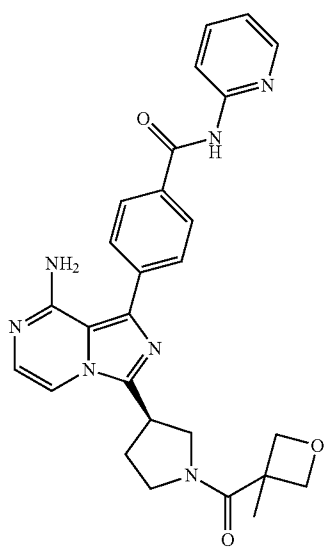 [SMILES: CC1(C(=O)N2CC[C@@H](c3nc(-c4ccc(C(=O)Nc5ccccn5)cc4)c4c(N)nccn34)C2)COC1] | (R)-4-(8-amino-3-(1-(3-methyloxetane-3-carbonyl)pyrrolidin-3-yl)imidazo[1,5-a]pyrazin-1-yl)-N-(pyridin-2-yl)benzamide, TFA salt | 498.2 | 1.11 min |
| 127 | 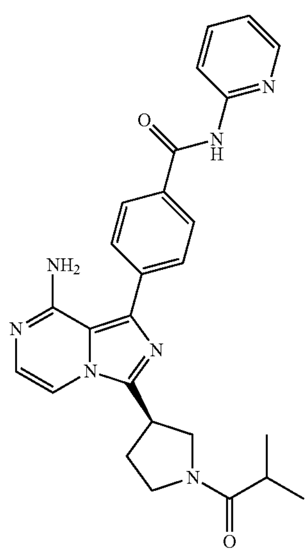 [SMILES: CC(C)C(=O)N1CC[C@@H](c2nc(-c3ccc(C(=O)Nc4ccccn4)cc3)c3c(N)nccn23)C1] | (R)-4-(8-amino-3-(1-isobutyrylpyrrolidin-3-yl)imidazo[1,5-a]pyrazin-1-yl)-N-(pyridin-2-yl)benzamide, TFA salt | 470.3 | 1.37 min |

| Example | Structure | Name | LC-MS [M + H]+ | Retention time |
|---|---|---|---|---|
| 128 | 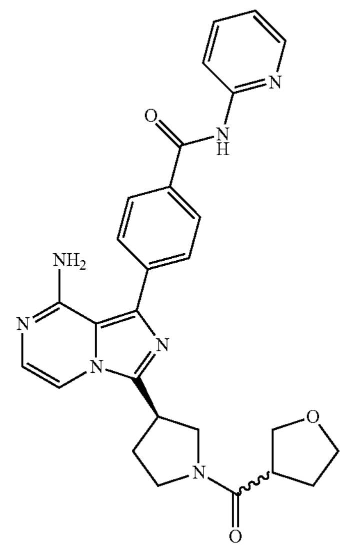 [SMILES: Nc1nccn2c([C@@H]3CCN(C(=O)C4CCOC4)C3)nc(-c3ccc(C(=O)Nc4ccccn4)cc3)c12] | (R)-4-(8-amino-3-(1-(tetrahydrofuran-3-carbonyl)pyrrolidin-3-yl)imidazo[1,5-a]pyrazin-1-yl)-N-(pyridin-2-yl)benzamide, TFA salt | 498.2 | 1.12 min |

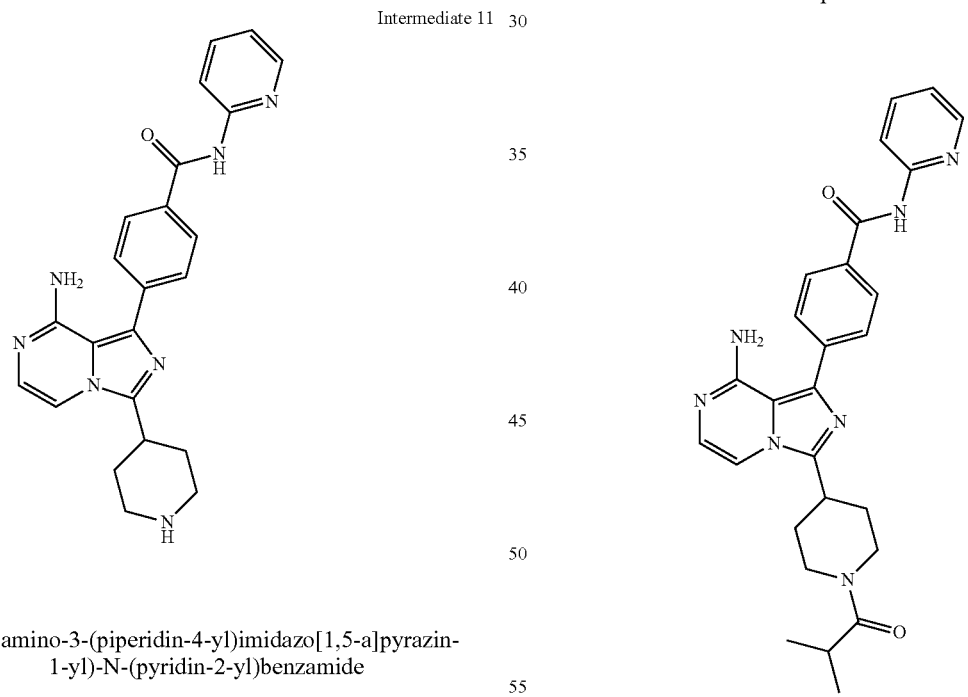

Intermediate 11

4-(8-amino-3-(piperidin-4-yl)imidazo[1,5-a]pyrazin-1-yl)-N-(pyridin-2-yl)benzamide This intermediate was prepared in an analogous manner as described for intermediate 8, from 1-[(benzyloxy)carbonyl]piperidine-4-carboxylic acid to obtain benzyl 4-(8-amino-1-bromoimidazo[1,5-a]pyrazin-3-yl)piperidine-1-carboxylate. Subsequent reaction with N-(pyridin-2-yl)-4-(4,4,5,5-tetramethyl-1,3,2-dioxaborolan-2-yl)benzamide and deprotection with 33% HBr/HOAc as described for intermediate 9 afforded the title compound (314 mg, 95%).

Example 129

4-(8-amino-3-(1-isobutyrylpiperidin-4-yl)imidazo[1,5-a]pyrazin-1-yl)-N-(pyridin-2-yl)benzamide This compound was prepared in an analogous manner as described in Example 46, from Intermediate 11 and isobutyric acid, to afford the title compound (20 mg, 53.4%). Data: UPLC(C) $R_t$: 1.48 min; m/z 484.2 (M+H)+.

Intermediate 12

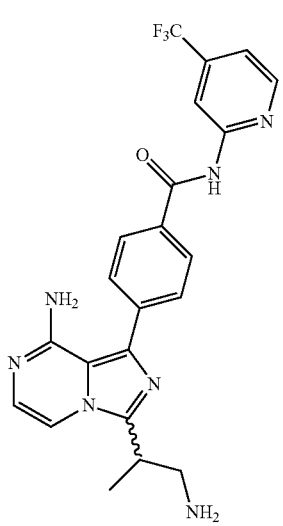

4-(8-amino-3-(1-aminopropan-2-yl)imidazo[1,5-a]pyrazin-1-yl)-N-(4-(trifluoromethyl)pyridin-2-yl)benzamide This intermediate was prepared in an analogous manner as described for intermediate 8, from Cbz-DL-3-aminoisobutyric acid to obtain benzyl bromoimidazo[1,5-a]pyrazin-3-yl)propylcarbamate. Subsequent reaction with 4-(4,4,5,5-Tetramethyl-1,3,2-dioxaborolan-2-yl)-N-(4-(trifluoromethyl)pyridin-2-yl)benzamide (Intermediate D) and deprotection with 33% HBr/HOAc as described for intermediate 9 afforded the title compound (130 mg, 84%).

Example 130

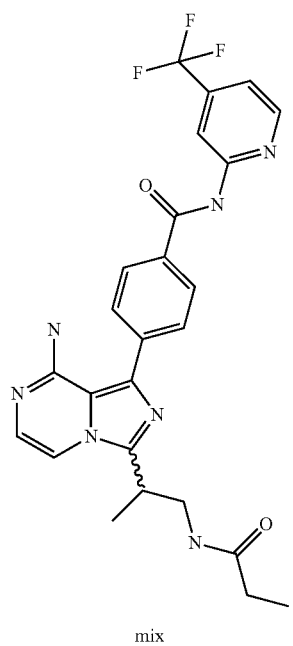 [SMILES: CCC(=O)NCC(C)c1nc(-c2ccc(C(=O)Nc3cc(C(F)(F)F)ccn3)cc2)c2c(N)nccn12]

mix 4-(8-amino-3-(1-propionamidopropan-2-yl)imidazo[1,5-a]pyrazin-1-yl)-N-(4-(trifluoromethyl)pyridin-2-yl)benzamide This compound was prepared in an analogous manner as described in Example 46, from Intermediate 12 and propionic acid, to afford the title compound (21.3 mg, 63.2%). Data: UPLC(E) $R_t$: 2.36 min; m/z 512.3 (M+H)$^+$.

The following Examples were synthesized following the methods described for example 130.

| Example | Structure | Name | LC-MS [M + H]$^+$ | Retention time |
|---|---|---|---|---|
| 131 | (structure shown, mix) | N-(2-(8-amino-1-(4-(4-(trifluoromethyl)pyridin-2-ylcarbamoyl)phenyl)imidazo[1,5-a]pyrazin-3-yl)propyl)-3-methyloxetane-3-carboxamide | 554.3 | 2.07 min (UPLC-E) |

-continued

| Example | Structure | Name | LC-MS [M + H]+ | Retention time |
|---------|-----------|------|----------------|----------------|
| 132 | 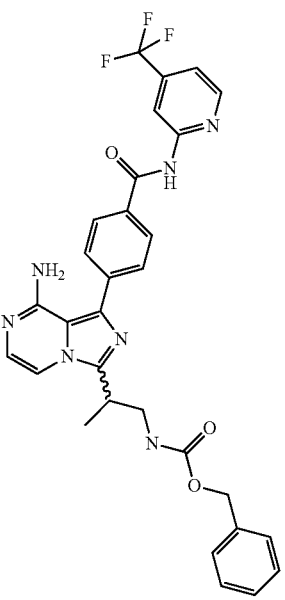 mix | benzyl 2-(8-amino-1-(4-(4-(trifluoromethyl)pyridin-2-ylcarbamoyl)phenyl)imidazo[1,5-a]pyrazin-3-yl)propylcarbamate | 590.3 | 2.92 min (UPLC-E) |

Example 133

(R)-4-(8-amino-3-(1-benzylpiperidin-3-yl)imidazo[1,5-a]pyrazin-1-yl)-N-(pyridin-2-yl)benzamide

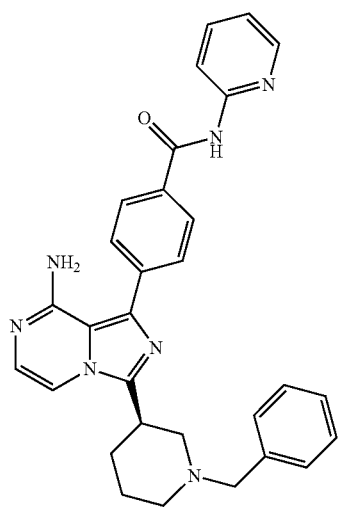 [SMILES: Nc1nccn2c([C@@H]3CCCN(Cc4ccccc4)C3)nc(-c3ccc(C(=O)Nc4ccccn4)cc3)c12]

Intermediate 9 (30 mg, 0.073 mmol) was dissolved in ethane-1,2-diol (3 mL), to which benzaldehyde (24 mg, 0.219 mmol), and NaCNBH$_3$ (15 mg, 0.219 mmol) were added. The resulting mixture was stirred at room temperature for 12 h. The mixture was diluted with water and extracted with ethyl acetate (3×). The organic phase was dried, filtered and concentrated in vacuo. The residue was purified by preparative HPLC. Fractions containing product were collected and lyophilized to afford (R)-4-(8-amino-3-(1-benzylpiperidin-3-yl)imidazo[1,5-a]pyrazin-1-yl)-N-(pyridin-2-yl)benzamide (10 mg, 28% yield). Data: UPLC (F) R$_t$: 1.81 min; m/z 504.3 (M+H)+.

The following Examples were synthesized following the methods described for example 133.

| Example | Structure | Name | LC-MS [M + H]+ | Retention time |
|---|---|---|---|---|
| 134 | 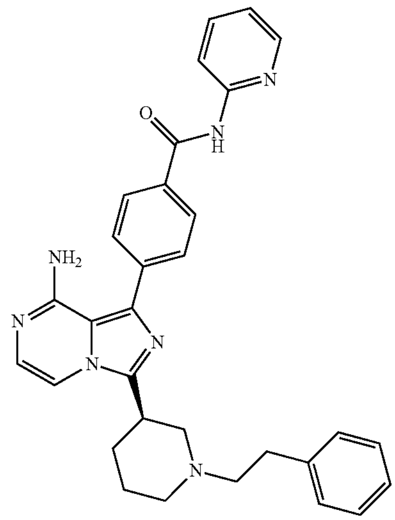 [SMILES: Nc1nccn2c([C@@H]3CCCN(CCc4ccccc4)C3)nc(-c3ccc(C(=O)Nc4ccccn4)cc3)c12] | (R)-4-(8-amino-3-(1-phenethylpiperidin-3-yl)imidazo[1,5-a]pyrazin-1-yl)-N-(pyridin-2-yl)benzamide, TFA salt | 518.2 | 1.87 min |
| 135 | 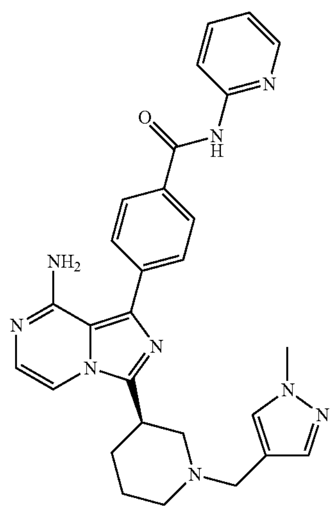 [SMILES: Cn1cc(CN2CCC[C@@H](c3nc(-c4ccc(C(=O)Nc5ccccn5)cc4)c4c(N)nccn34)C2)cn1] | (R)-4-(8-amino-3-(1-((1-methyl-1H-pyrazol-4-yl)methyl)piperidin-3-yl)imidazo[1,5-a]pyrazin-1-yl)-N-(pyridin-2-yl)benzamide, TFA salt | 508.2 | 2.33 min |
| 136 | 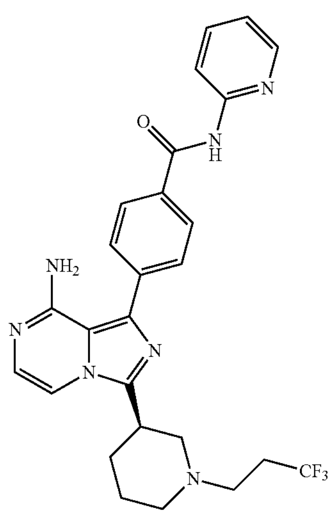 [SMILES: Nc1nccn2c([C@@H]3CCCN(CCC(F)(F)F)C3)nc(-c3ccc(C(=O)Nc4ccccn4)cc3)c12] | (R)-4-(8-amino-3-(1-(3,3,3-trifluoropropyl)piperidin-3-yl)imidazo[1,5-a]pyrazin-1-yl)-N-(pyridin-2-yl)benzamide TFA salt | 510.2 | |

| Example | Structure | Name | LC-MS [M + H]+ | Retention time |
|---|---|---|---|---|
| 137 | 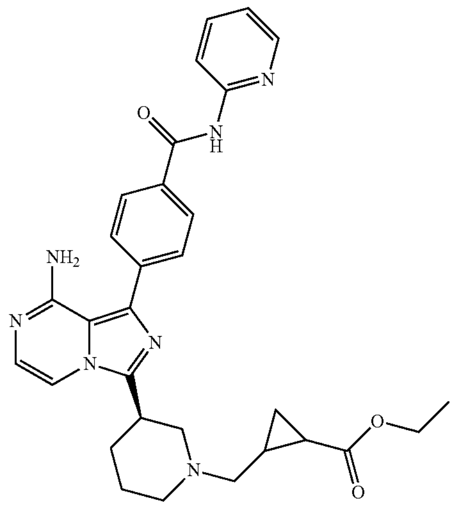 [SMILES: CCOC(=O)C1CC1CN1CCC[C@@H](c2nc(-c3ccc(C(=O)Nc4ccccn4)cc3)c3c(N)nccn23)C1] | ethyl 2-(((R)-3-(8-amino-1-(4-(pyridin-2-ylcarbamoyl)phenyl)imidazo[1,5-a]pyrazin-3-yl)piperidin-1-yl)methyl)cyclopropanecarboxylate, TFA salt | 530.3 | |
| 138 | 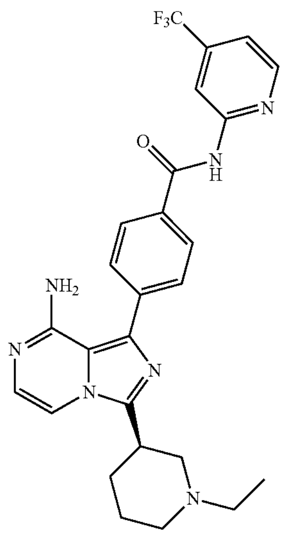 [SMILES: CCN1CCC[C@@H](c2nc(-c3ccc(C(=O)Nc4cc(C(F)(F)F)ccn4)cc3)c3c(N)nccn23)C1] | (R)-4-(8-amino-3-(1-ethylpiperidin-3-yl)imidazo[1,5-a]pyrazin-1-yl)-N-(4-(trifluoromethyl)pyridin-2-yl)benzamide, TFA salt | 510.1 | 2.04 min |
| 139 | 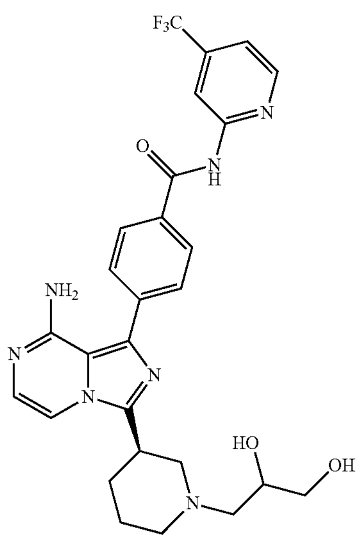 [SMILES: Nc1nccn2c([C@@H]3CCCN(CC(O)CO)C3)nc(-c3ccc(C(=O)Nc4cc(C(F)(F)F)ccn4)cc3)c12] | 4-(8-amino-3-((3R)-1-(2,3-dihydroxypropyl)piperidin-3-yl)imidazo[1,5-a]pyrazin-1-yl)-N-(4-(trifluoromethyl)pyridin-2-yl)benzamide, TFA salt | 556.2 | 2.29 min |

-continued
| Example | Structure | Name | LC-MS [M + H]+ | Retention time |
|---|---|---|---|---|
| 140 | 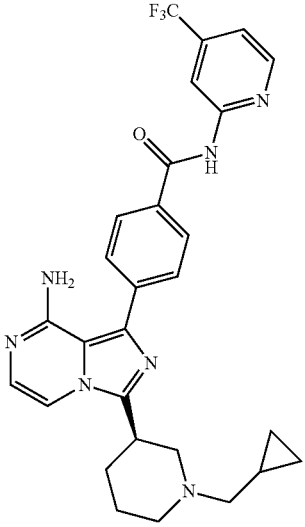 [SMILES: Nc1nccn2c([C@@H]3CCCN(CC4CC4)C3)nc(-c3ccc(C(=O)Nc4cc(C(F)(F)F)ccn4)cc3)c12] | (R)-4-(8-amino-3-(1-(cyclopropylmethyl)piperidin-3-yl)imidazo[1,5-a]pyrazin-1-yl)-N-(4-(trifluoromethyl)pyridin-2-yl)benzamide, TFA salt | 536.2 | 2.21 min |
| 141 | 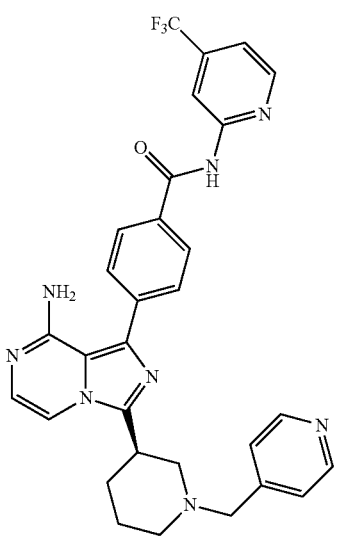 [SMILES: Nc1nccn2c([C@@H]3CCCN(Cc4ccncc4)C3)nc(-c3ccc(C(=O)Nc4cc(C(F)(F)F)ccn4)cc3)c12] | (R)-4-(8-amino-3-(1-(pyridin-4-ylmethyl)piperidin-3-yl)imidazo[1,5-a]pyrazin-1-yl)-N-(4-(trifluoromethyl)pyridin-2-yl)benzamide, TFA salt | 573.2 | 3.01 min |

| Example | Structure | Name | LC-MS [M + H]+ | Retention time |
|---|---|---|---|---|
| 142 | 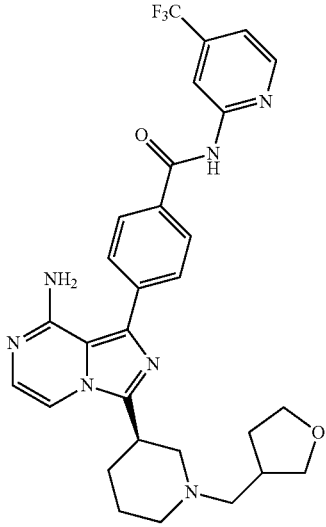 [SMILES: Nc1nccn2c([C@@H]3CCCN(CC4CCOC4)C3)nc(-c3ccc(C(=O)Nc4cc(C(F)(F)F)ccn4)cc3)c12] | 4-(8-amino-3-((3R)-1-((tetrahydrofuran-3-yl)methyl)piperidin-3-yl)imidazo[1,5-a]pyrazin-1-yl)-N-(4-(trifluoromethyl)pyridin-2-yl)benzamide, TFA salt | 566.2 | 2.37 min |
| 143 | 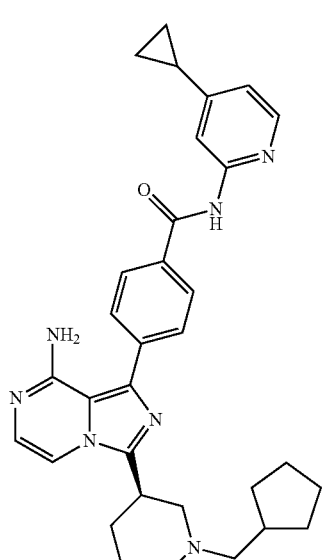 | (R)-4-(8-amino-3-(1-(cyclopentylmethyl)piperidin-3-yl)imidazo[1,5-a]pyrazin-1-yl)-N-(4-cyclopropylpyridin-2-yl)benzamide, TFA salt | 536.3 | 2.70 min |

-continued

| Example | Structure | Name | LC-MS [M + H]+ | Retention time |
|---------|-----------|------|----------------|----------------|
| 144 | 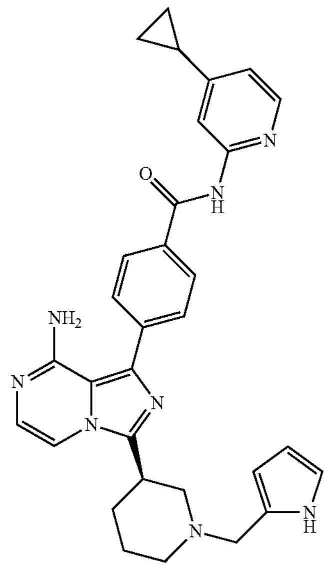 [SMILES: Nc1nccn2c([C@@H]3CCCN(Cc4ccc[nH]4)C3)nc(-c3ccc(C(=O)Nc4cc(C5CC5)ccn4)cc3)c12] | (R)-4-(3-(1-((1H-pyrrol-2-yl)methyl)piperidin-3-yl)-8-aminoimidazo[1,5-a]pyrazin-1-yl)-N-(4-cyclopropylpyridin-2-yl)benzamide, TFA salt | 533.2 | 1.78 min |
| 145 | 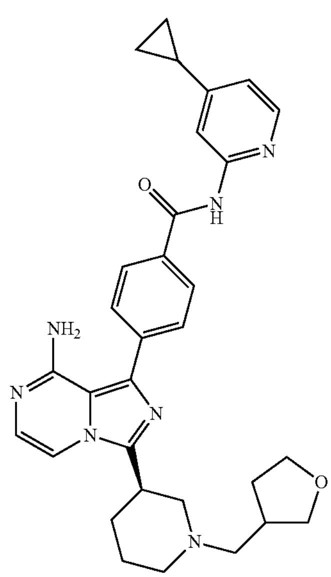 [SMILES: Nc1nccn2c([C@@H]3CCCN(CC4CCOC4)C3)nc(-c3ccc(C(=O)Nc4cc(C5CC5)ccn4)cc3)c12] | 4-(8-amino-3-((3R)-1-((tetrahydrofuran-3-yl)methyl)piperidin-3-yl)imidazo[1,5-a]pyrazin-1-yl)-N-(4-cyclopropylpyridin-2-yl)benzamide, TFA salt | 538.3 | 2.02 min |

261

Intermediate 13

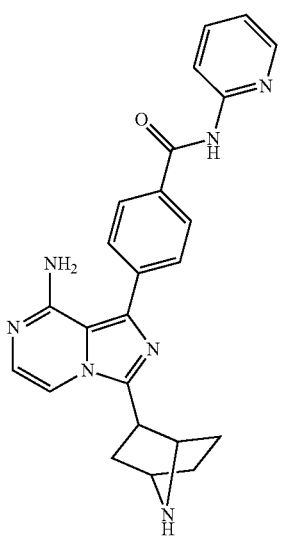

262

4-(8-amino-3-(7-azabicyclo[2.2.1]heptan-2-yl)imidazo[1,5-a]pyrazin-1-yl)-N-(pyridin-2-yl)benzamide This intermediate was prepared in an analogous manner as described for intermediate 8, from 7-(benzyloxycarbonyl)-7-azabicyclo[2.2.1]heptane-2-carboxylic acid (prepared as described by Otani, Y. et. Al. in Tetrahedron 62 (2006) 11635) to obtain benzyl 2-(8-amino-1-bromoimidazo[1,5-a]pyrazin-3-yl)-7-azabicyclo[2.2.1]heptane-7-carboxylate. Subsequent reaction with N-(pyridin-2-yl)-4-(4,4,5,5-tetramethyl-1,3,2-dioxaborolan-2-yl)benzamide and deprotection with 33% HBr/HOAc as described for intermediate 9 afforded the title compound (220 mg, 51.7%).

The following Examples were synthesized following the methods described for example 46 using Intermediate 13.

| Example | Structure | Name | LC-MS [M + H]$^+$ | Retention time |
|---------|-----------|------|-------------------|----------------|
| 146 | 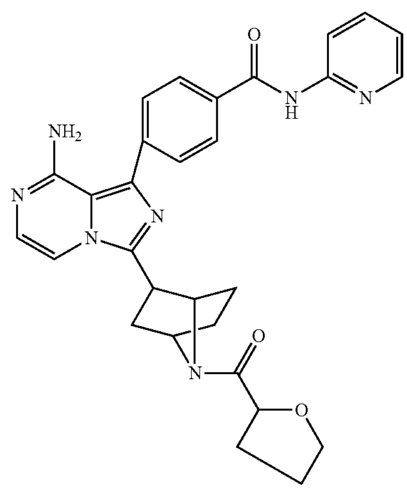 [SMILES: Nc1nccn2c(C3CC4CCC3N4C(=O)C3CCCO3)nc(-c3ccc(C(=O)Nc4ccccn4)cc3)c12] | 4-(8-amino-3-(7-(tetrahydrofuran-2-carbonyl)-7-azabicyclo[2.2.1]heptan-2-yl)imidazo[1,5-a]pyrazin-1-yl)-N-(pyridin-2-yl)benzamide | 524.2 | 1.47 min |
| 147 | 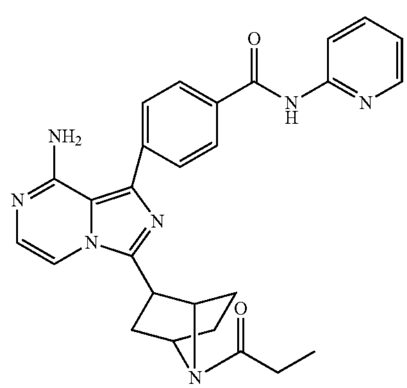 [SMILES: CCC(=O)N1C2CCC1C(c1nc(-c3ccc(C(=O)Nc4ccccn4)cc3)c3c(N)nccn13)C2] | 4-(8-amino-3-(7-propionyl-7-azabicyclo[2.2.1]heptan-2-yl)imidazo[1,5-a]pyrazin-1-yl)-N-(pyridin-2-yl)benzamide | 482.2 | 1.52 min |

| Example | Structure | Name | LC-MS [M + H]+ | Retention time |
|---|---|---|---|---|
| 148 | 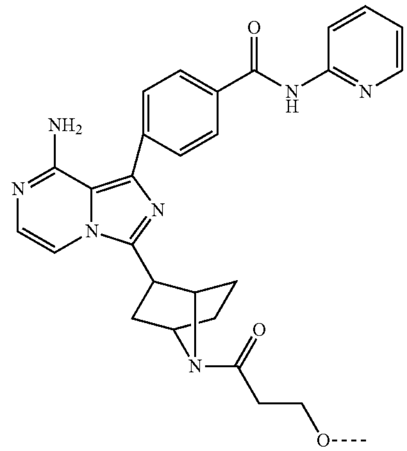 | 4-(8-amino-3-(7-(3-methoxypropanoyl)-7-azabicyclo[2.2.1]heptan-2-yl)imidazo[1,5-a]pyrazin-1-yl)-N-(pyridin-2-yl)benzamide | 512.2 | 1.42 min |
| 149 | 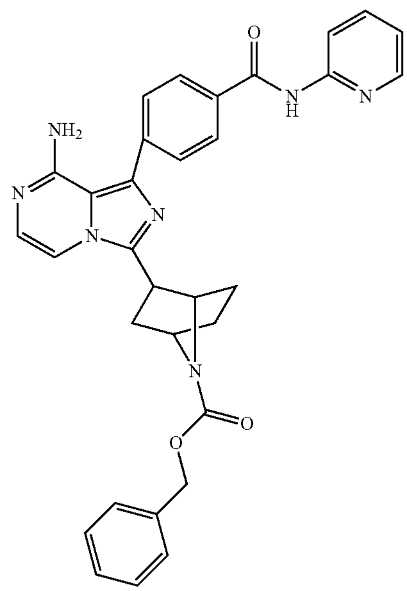 [SMILES: Nc1nccn2c(C3CC4CCC3N4C(=O)OCc3ccccc3)nc(-c3ccc(C(=O)Nc4ccccn4)cc3)c12] | benzyl 2-(8-amino-1-(4-(pyridin-2-ylcarbamoyl)phenyl)imidazo[1,5-a]pyrazin-3-yl)-7-azabicyclo[2.2.1]heptane-7-carboxylate | 560.2 | 2.39 min |
Intermediate 14
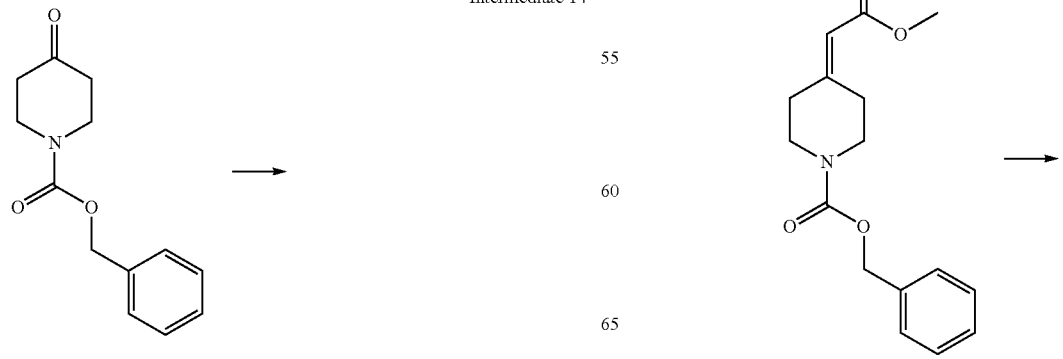

-continued

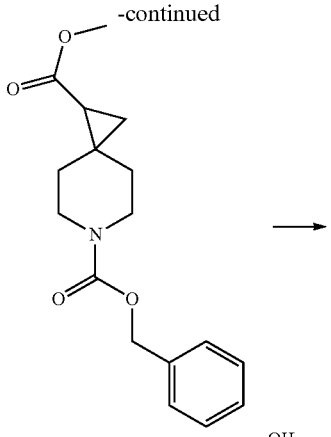

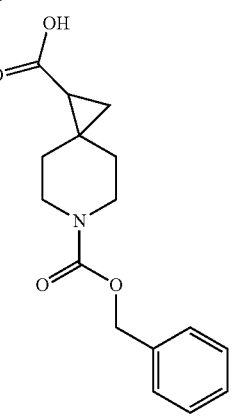

6-(Benzyloxycarbonyl)-6-azaspiro[2.5]octane-1-carboxylic acid (a) Benzyl 4-(2-methoxy-2-oxoethylidene)piperidine-1-carboxylate To a solution of benzyl 4-oxopiperidine-1-carboxylate (4.22 g, 18.09 mmol) in toluene (dry) (16 mL) was added trimethylphosphonoacetate (1.5 eq) and DIPEA (1.5 eq). The reaction mixture was heated to reflux and stirred for 17 h. The reaction was cooled to room temperature and concentrated in vacuo. Et$_2$O was added and a white precipitate was formed and filtrated. The residue was washed with Et$_2$O. The filtrate Et$_2$O was evaporated yielding 5.5 g of crude product as an orange oil which was purified using silica gel chromatography (EtOAc/heptane 1/5 to 1/3) to give 4.5 g of benzyl 4-(2-methoxy-2-oxoethylidene)piperidine-1-carboxylate (86%).

(b) 6-benzyl 1-methyl 6-azaspiro[2.5]octane-1,6-dicarboxylate

To a stirred solution of trimethylsulfoxonium iodide (6161 mg, 28.0 mmol) in Dimethyl sulfoxide (dry) (45 mL) was added potassium t-butoxide (3141 mg, 28.0 mmol) in one portion. The reaction mixture was stirred 1 h at rt. Next, 4-(2-methoxy-2-oxoethylidene)piperidine-1-carboxylate (4500 mg, 15.55 mmol) in DMSO (dry) (12 mL) was added. The reaction mixture was stirred for 20 h at room temperature, cooled to 0° C., slowly added to a cold solution of NH$_4$Cl (50 mL) and extracted with Et$_2$O. The combined ether layers were washed with water and brine, dried (Mg$_2$SO$_4$), filtered, and concentrated in vacuo. The product was purified using silica gel chromatography (EtOAc/heptane=1/4 to 1/2 v/v %) to give 3.7 g of 6-benzyl 1-methyl 6-azaspiro[2.5]octane-1,6-dicarboxylate (55%).

(c) 6-(benzyloxycarbonyl)-6-azaspiro[2.5]octane-1-carboxylic acid

To 6-benzyl 1-methyl 6-azaspiro[2.5]octane-1,6-dicarboxylate (2.6 g, 8.57 mmol) in THF (8.57 mL) was added LiOH solution (2 N, 8.57 mL). The reaction mixture was stirred 17 h at rt. The reaction was diluted with water (10 mL) and washed with ether. The water layer was acidified to pH 3-4 with 6 N HCl and extracted with ether (2×). The combined ether extracts were washed with water and brine, dried (Mg$_2$SO$_4$), filtered, and concentrated in vacuo to give 2.5 g 6-(benzyloxycarbonyl)-6-azaspiro[2.5]octane-1-carboxylic acid (99%).

Intermediate 15

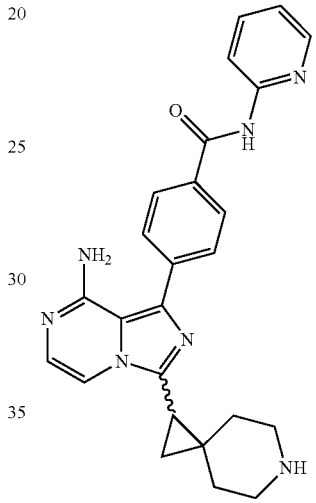

Stereoisomer 1

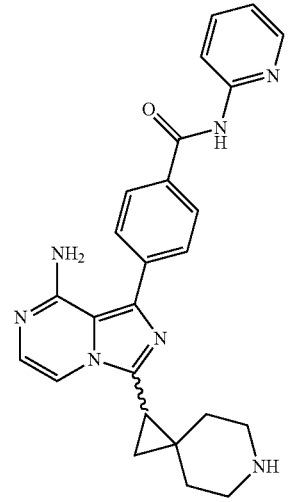

Stereoisomer 2

4-(8-amino-3-(6-azaspiro[2.5]octan-1-yl)imidazo[1,5-a]pyrazin-1-yl)-N-(pyridin-2-yl)benzamide These intermediates were prepared in an analogous manner to Intermediate 8, from 6-(benzyloxycarbonyl)-6- azaspiro[2.5]octane-1-carboxylic acid (Intermediate 14), followed by chiral separation (IA column; eluents: heptane/DCM/IPA (75/15/10 v/v %), isocratic, 25 minutes) to obtain pure stereoisomers 1 and 2 of benzyl 1-(8-amino-1-bromoimidazo[1,5-a]pyrazin-3-yl)-6-azaspiro[2.5]octane-6-carboxylate. Subsequent reaction with N-(pyridin-2-yl)-4-(4,4,5,5-tetramethyl-1,3,2-dioxaborolan-2-yl)benzamide and deprotection with 33% HBr/HOAc as described for intermediate 9 afforded the title compound stereoisomer 1 (682 mg, 83%) and stereoisomer 2 (550 mg, 98%) respectively.

The following Examples were synthesized following the methods described for example 46 using Intermediate 15.

| Example | Structure | Name | LC-MS [M + H]+ | Retention time |
|---|---|---|---|---|
| 150 | Stereoisomer 2 | 4-(8-amino-3-(6-isobutyryl-6-azaspiro[2.5]octan-1-yl)imidazo[1,5-a]pyrazin-1-yl)-N-(pyridin-2-yl)benzamidee | 510.3 | 1.60 min |
| 151 | Stereoisomer 2 | 4-(8-amino-3-(6-(3-methoxypropanoyl)-6-azaspiro[2.5]octan-1-yl)imidazo[1,5-a]pyrazin-1-yl)-N-(pyridin-2-yl)benzamide | 526.2 | 1.38 min |

| Example | Structure | Name | LC-MS [M + H]+ | Retention time |
|---|---|---|---|---|
| 152 | 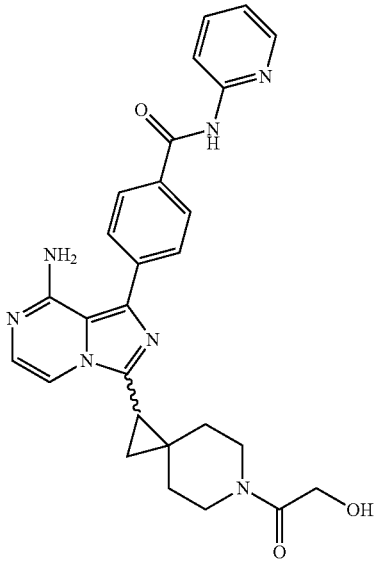 Stereoisomer 2 | 4-(8-amino-3-(6-(2-hydroxyacetyl)-6-azaspiro[2.5]octan-1-yl)imidazo[1,5-a]pyrazin-1-yl)-N-(pyridin-2-yl)benzamide | 498.2 | 1.19 min |
| 153 | 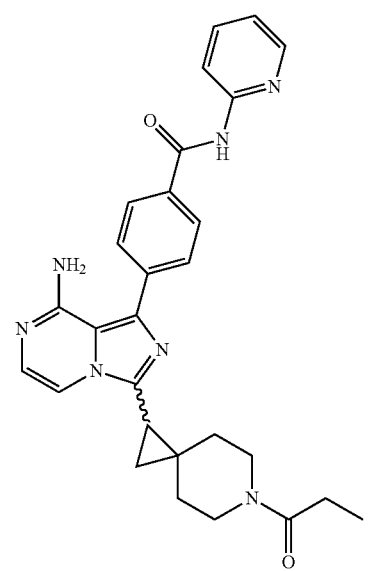 Stereoisomer 2 | 4-(8-amino-3-(6-propionyl-6-azaspiro[2.5]octan-1-yl)imidazo[1,5-a]pyrazin-1-yl)-N-(pyridin-2-yl)benzamide | 496.2 | 1.44 min |

Intermediate 16

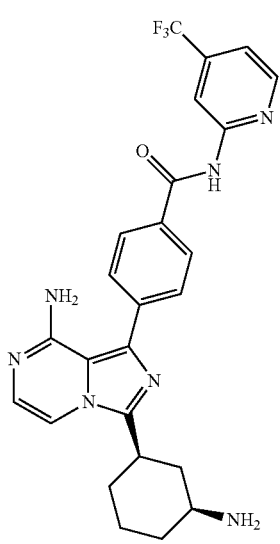

4-(8-amino-3-((cis)-3-aminocyclohexyl)imidazo[1,5-a]pyrazin-1-yl)-N-(4-(trifluoromethyl)pyridin-2-yl)benzamide This intermediate was prepared in an analogous manner as described for Intermediate 8, from commercially available cis-3-(((benzyloxy)carbonyl)amino)cyclohexanecarboxylic acid to obtain benzyl (cis)-3-(8-amino-1-bromoimidazo[1,5-a]pyrazin-3-yl)cyclohexyl-carbamate. Subsequent reaction with 4-(4,4,5,5-tetramethyl-1,3,2-dioxaborolan-2-yl)-N-(4-(trifluoromethyl)pyridin-2-yl)benzamide (Intermediate D) and deprotection with 33% HBr/HOAc as described for intermediate 9 afforded the title compound (577 mg, 85.9%)

The following Examples were synthesized following the methods described for example 46-49.

| Example | Structure | Name | LC-MS [M + H]+ | Retention time |
|---|---|---|---|---|
| 154 | 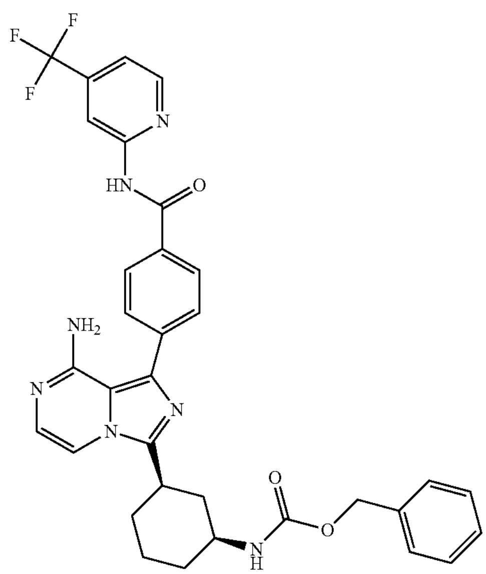 [SMILES: Nc1nccn2c([C@@H]3CCC[C@H](NC(=O)OCc4ccccc4)C3)nc(-c3ccc(C(=O)Nc4cc(C(F)(F)F)ccn4)cc3)c12] | benzyl (cis)-3-(8-amino-1-(4-(4-(trifluoromethyl)pyridin-2-ylcarbamoyl)phenyl)imidazo[1,5-a]pyrazin-3-yl)cyclohexylcarbamate | 630.1 (LCMS-A) | 3.49 min (UPLC-E) |

-continued

| Example | Structure | Name | LC-MS [M + H]+ | Retention time |
|---|---|---|---|---|
| 155 | 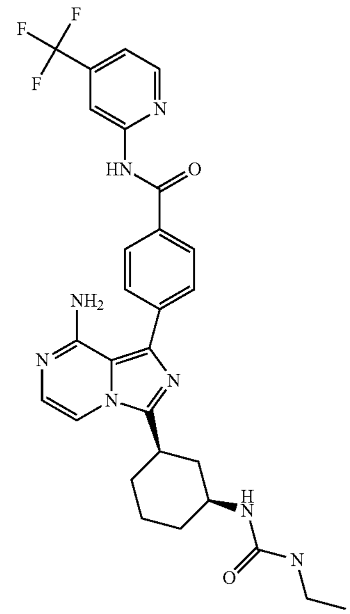 [SMILES: CCNC(=O)N[C@H]1CCC[C@@H](c2nc(-c3ccc(C(=O)Nc4cc(C(F)(F)F)ccn4)cc3)c3c(N)nccn23)C1] | 4-(8-amino-3-((cis)-3-(3-ethylureido)cyclohexyl)imidazo[1,5-a]pyrazin-1-yl)-N-(4-(trifluoromethyl)pyridin-2-yl)benzamide | 567.1 (LCMS-A) | 2.97 min (UPLC-D) |
| 156 | 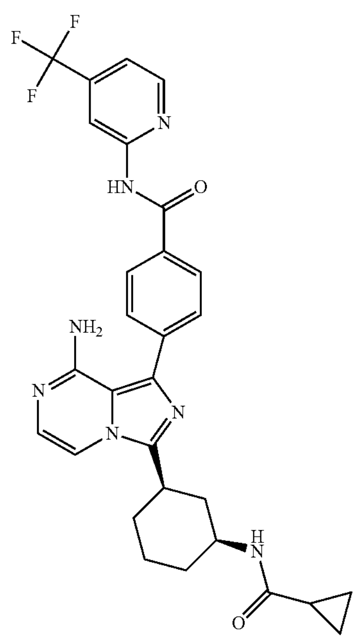 [SMILES: Nc1nccn2c([C@@H]3CCC[C@H](NC(=O)C4CC4)C3)nc(-c3ccc(C(=O)Nc4cc(C(F)(F)F)ccn4)cc3)c12] | 4-(8-amino-3-((cis)-3-(cyclopropanecarboxamido)cyclohexyl)imidazo[1,5-a]pyrazin-1-yl)-N-(4-(trifluoromethyl)pyridin-2-yl)benzamide | 564.1 (LCMS-A) | 3.15 min (UPLC-D) |

-continued

| Example | Structure | Name | LC-MS [M + H]+ | Retention time |
|---|---|---|---|---|
| 157 | 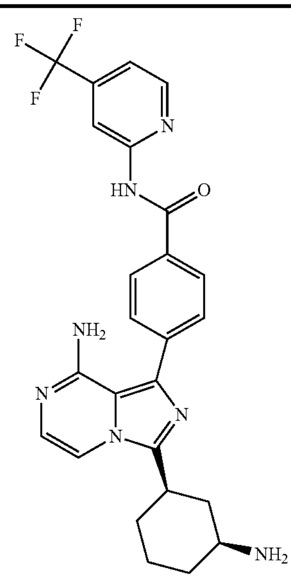 | 4-(8-amino-3-((cis)-3-aminocyclohexyl)imidazo[1,5-a]pyrazin-1-yl)-N-(4-(trifluoromethyl)pyridin-2-yl)benzamide | 496.3 | 1.71 min |
| 158 | 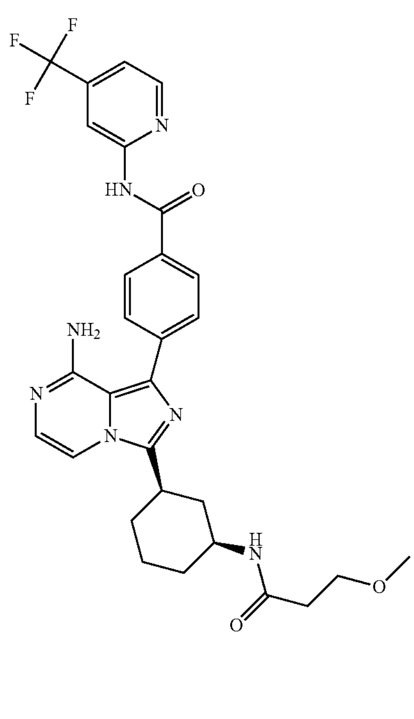 [SMILES: COCCC(=O)N[C@H]1CCC[C@@H](c2nc(-c3ccc(C(=O)Nc4cc(C(F)(F)F)ccn4)cc3)c3c(N)nccn23)C1] | 4-(8-amino-3-((cis)-3-(3-methoxypropanamido)cyclohexyl)imidazo[1,5-a]pyrazin-1-yl)-N-(4-(trifluoromethyl)pyridin-2-yl)benzamide | 582.1 (LCMS-A) | 2.96 min (UPLC-D) |

-continued

| Example | Structure | Name | LC-MS [M + H]+ | Retention time |
|---------|-----------|------|----------------|----------------|
| 159 | 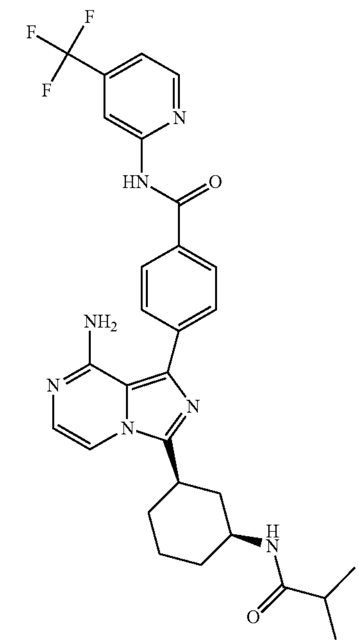 [SMILES: CC(C)C(=O)N[C@H]1CCC[C@@H](c2nc(-c3ccc(C(=O)Nc4cc(C(F)(F)F)ccn4)cc3)c3c(N)nccn23)C1] | 4-(8-amino-3-((cis)-3-isobutyramidocyclohexyl)imidazo[1,5-a]pyrazin-1-yl)-N-(4-(trifluoromethyl)pyridin-2-yl)benzamide | 566.0 (LCMS-A) | 3.25 min (UPLC-D) |
| 160 | 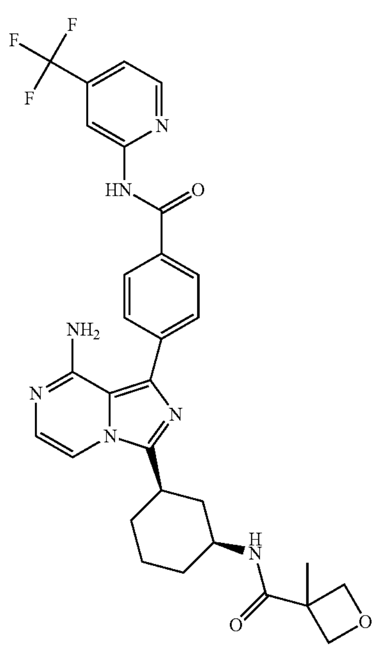 [SMILES: CC1(C(=O)N[C@H]2CCC[C@@H](c3nc(-c4ccc(C(=O)Nc5cc(C(F)(F)F)ccn5)cc4)c4c(N)nccn34)C2)COC1] | N-((cis)-3-(8-amino-1-(4-(4-(trifluoromethyl)pyridin-2-ylcarbamoyl)phenyl)imidazo[1,5-a]pyrazin-3-yl)cyclohexyl)-3-methyloxetane-3-carboxamide | 594.1 (LCMS-A) | 2.96 min (UPLC-D) |

| Example | Structure | Name | LC-MS [M + H]+ | Retention time |
|---|---|---|---|---|
| 161 | 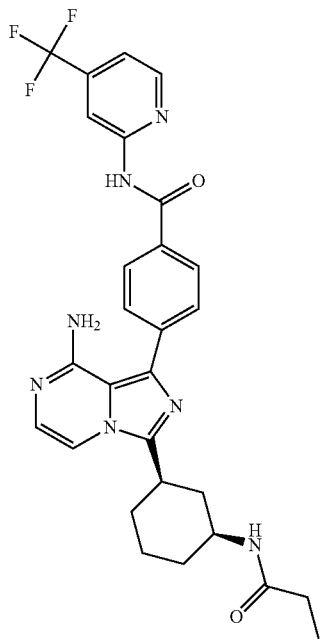 [SMILES: CCC(=O)N[C@H]1CCC[C@@H](c2nc(-c3ccc(C(=O)Nc4cc(C(F)(F)F)ccn4)cc3)c3c(N)nccn23)C1] | 4-(8-amino-3-((cis)-3-propionamidocyclohexyl)imidazo[1,5-a]pyrazin-1-yl)-N-(4-(trifluoromethyl)pyridin-2-yl)benzamide | 552.3 | 2.33 min |

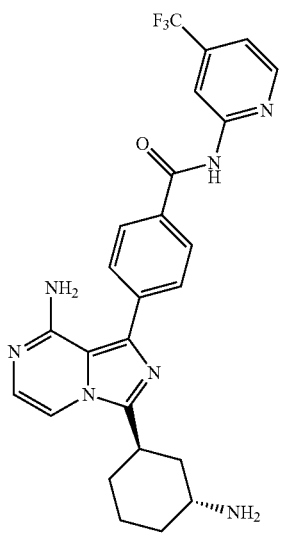

Intermediate 17

4-(8-amino-3-((trans)-3-aminocyclohexyl)imidazo[1,5-a]pyrazin-1-yl)-N-(4-(trifluoromethyl)pyridin-2-yl)benzamide This intermediate was prepared in an analogous manner as described for intermediate 8, from commercially available trans-3-(((benzyloxy)carbonyl)amino)cyclohexanecarboxylic acid to obtain benzyl (trans)-3-(8-amino-1-bromoimidazo[1,5-a]pyrazin-3-yl)cyclohexylcarbamate. Subsequent reaction with 4-(4,4,5,5-Tetramethyl-1,3,2-dioxaborolan-2-yl)-N-(4-(trifluoromethyl)pyridin-2-yl)benzamide (Intermediate D) and deprotection with 33% HBr/HOAc as described for intermediate 9 afforded the title compound (530 mg, 70.9%)

The following Examples were synthesized following the methods described for example 46-49.

| Example | Structure | Name | LC-MS [M + H]+ | Retention time |
|---|---|---|---|---|
| 162 | 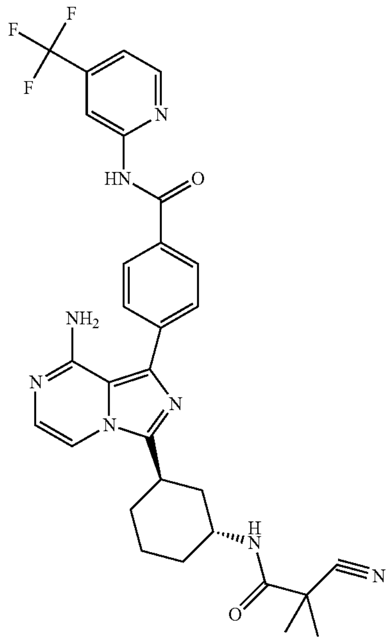 [SMILES: CC(C)(C#N)C(=O)N[C@@H]1CCC[C@@H](c2nc(-c3ccc(C(=O)Nc4cc(C(F)(F)F)ccn4)cc3)c3c(N)nccn23)C1] | 4-(8-amino-3-((trans)-3-(2-cyano-2-methylpropanamido)-cyclohexyl)imidazo[1,5-a]pyrazin-1-yl)-N-(4-(trifluoromethyl)pyridin-2-yl)benzamide | 591.2 | 1.00 min (UPLC-B) |
| 163 | 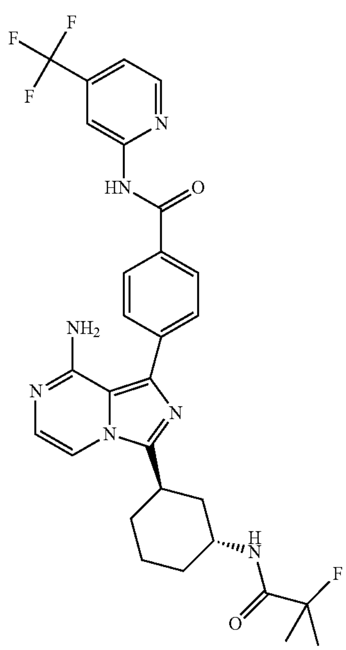 [SMILES: CC(C)(F)C(=O)N[C@@H]1CCC[C@@H](c2nc(-c3ccc(C(=O)Nc4cc(C(F)(F)F)ccn4)cc3)c3c(N)nccn23)C1] | 4-(8-amino-3-((trans)-3-(2-fluoro-2-methylpropanamido)cyclohexyl)imidazo[1,5-a]pyrazin-1-yl)-N-(4-(trifluoromethyl)pyridin-2-yl)benzamide | 584.2 | 2.59 min |

| Example | Structure | Name | LC-MS [M + H]+ | Retention time |
|---|---|---|---|---|
| 164 | 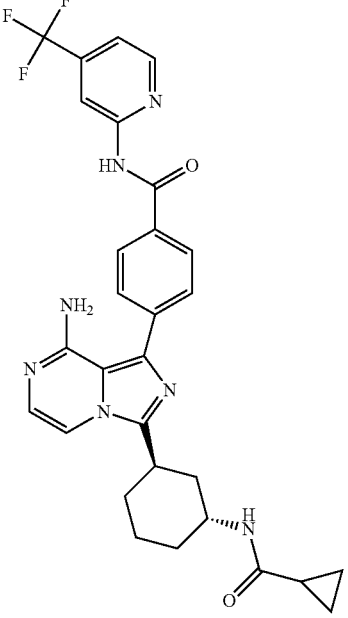 | 4-(8-amino-3-((trans)-3-(cyclopropanecarboxamido)cyclohexyl)imidazo[1,5-a]pyrazin-1-yl)-N-(4-(trifluoromethyl)pyridin-2-yl)benzamide | 564.2 | 2.33 min |
| 165 | 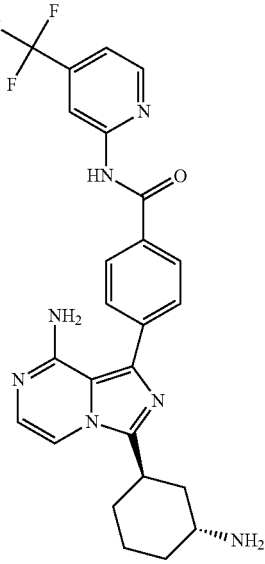 | 4-(8-amino-3-((trans)-3-aminocyclohexyl)imidazo[1,5-a]pyrazin-1-yl)-N-(4-(trifluoromethyl)pyridin-2-yl)benzamide | 495.9 | 1.91 min (LCMS-A) |

-continued
| Example | Structure | Name | LC-MS [M + H]+ | Retention time |
|---|---|---|---|---|
| 166 | 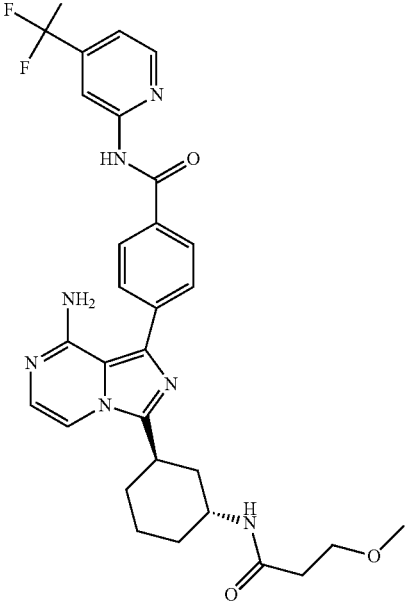 | 4-(8-amino-3-((trans)-3-(3-methoxypropanamido)cyclohexyl)imidazo[1,5-a]pyrazin-1-yl)-N-(4-(trifluoromethyl)pyridin-2-yl)benzamide | 582.2 | 0.67 min (UPLC-B) |
| 167 | 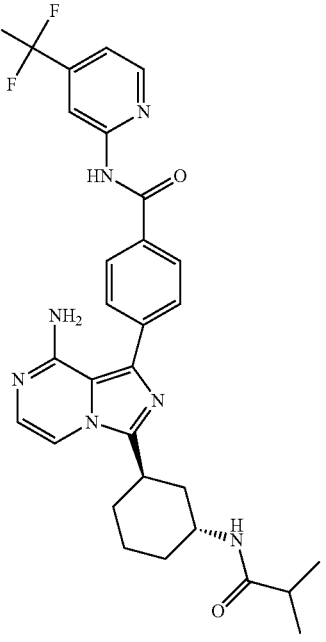 | 4-(8-amino-3-((trans)-3-isobutyramidocyclohexyl)imidazo[1,5-a]pyrazin-1-yl)-N-(4-(trifluoromethyl)pyridin-2-yl)benzamide | 566.3 | 2.46 |

-continued
| Example | Structure | Name | LC-MS [M + H]+ | Retention time |
|---|---|---|---|---|
| 168 | 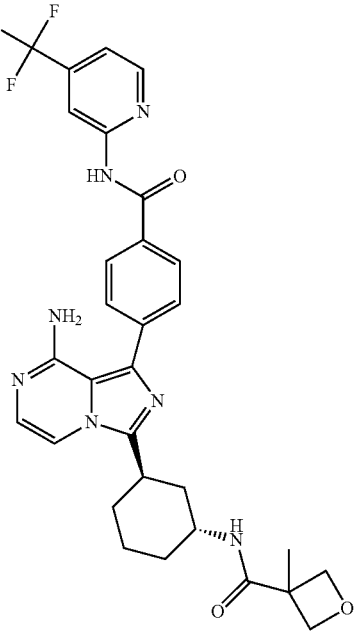 | N-((trans)-3-(8-amino-1-(4-(4-(trifluoromethyl)pyridin-2-ylcarbamoyl)phenyl)imidazo[1,5-a]pyrazin-3-yl)cyclohexyl)-3-methyloxetane-3-carboxamide | 594.2 | 2.25 min |
| 169 | 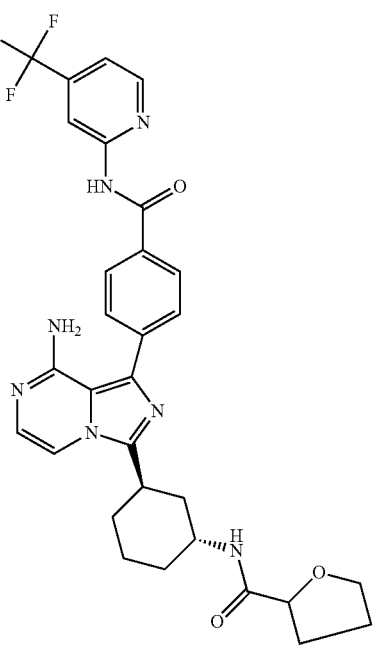 | N-((trans)-3-(8-amino-1-(4-(4-(trifluoromethyl)pyridin-2-ylcarbamoyl)phenyl)imidazo[1,5-a]pyrazin-3-yl)cyclohexyl)tetrahydrofuran-2-carboxamide | 594.2 | 2.34 min |

| Example | Structure | Name | LC-MS [M + H]+ | Retention time |
|---|---|---|---|---|
| 170 | 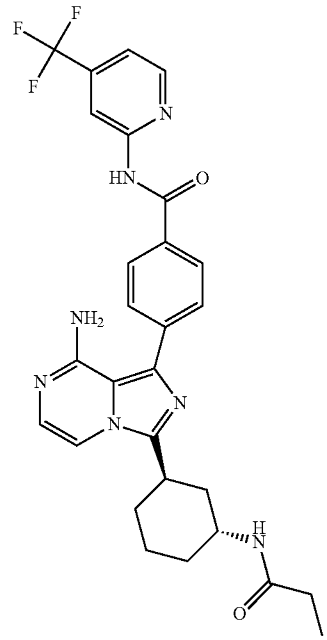 [SMILES: CCC(=O)N[C@@H]1CCC[C@@H](c2nc(-c3ccc(C(=O)Nc4cc(C(F)(F)F)ccn4)cc3)c3c(N)nccn23)C1] | 4-(8-amino-3-((trans)-3-propionamidocyclohexyl) imidazo [1,5-a]pyrazin-1-yl)-N-(4-(trifluoromethyl)pyridin-2-yl)benzamide | 552.0 | 2.48 min (LCMS-B) |
| 171 | 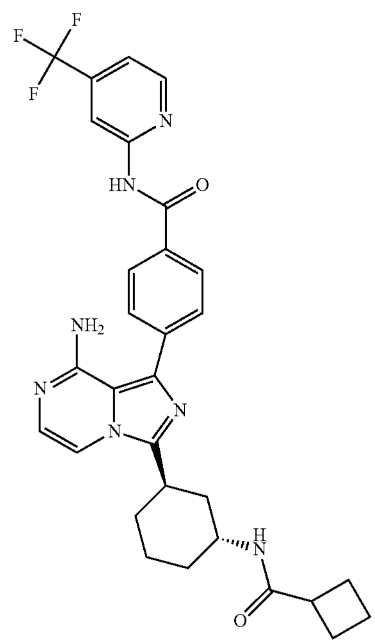 [SMILES: Nc1nccn2c([C@@H]3CCC[C@@H](NC(=O)C4CCC4)C3)nc(-c3ccc(C(=O)Nc4cc(C(F)(F)F)ccn4)cc3)c12] | 4-(8-amino-3-((trans)-3-(cyclobutanecarboxamido) cyclohexyl) imidazo[1,5-a]pyrazin-1-yl)-N-(4-(trifluoromethyl)pyridin-2-yl)benzamide | 578.2 | 2.58 min |

Intermediate 18

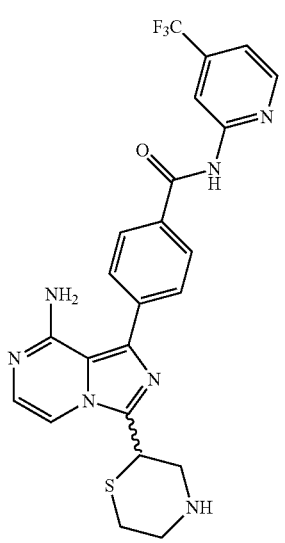

Stereoisomer 1

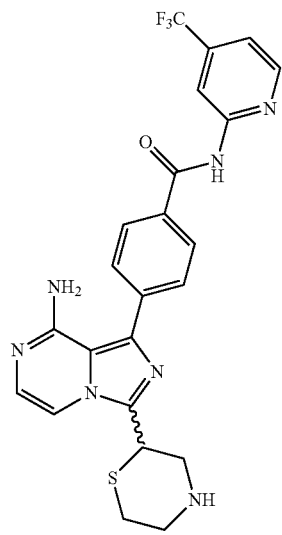

Stereoisomer 2

4-(8-amino-3-(thiomorpholin-2-yl)imidazo[1,5-a]pyrazin-1-yl)-N-(4-(trifluoromethyl)-pyridin-2-yl)benzamide These intermediates were prepared in an analogous manner as described for Intermediate 8, from thiomorpholine-2,4-dicarboxylic acid 4-tert-butylester, followed by chiral separation (IA column; eluent Heptane/DCM/IPA (75/15/10 v/v %), isocratic, 25 minutes) to obtain stereoisomers 1 and 2 of benzyl 2-(8-amino-1-bromoimidazo[1,5-a]pyrazin-3-yl)thiomorpholine-4-carboxylate. Subsequent reaction with 4-(4,4,5,5-tetramethyl-1,3,2-dioxaborolan-2-yl)-N-(4-(trifluoromethyl)pyridin-2-yl)benzamide (Intermediate D) and deprotection with TFA at 60° C. as described for intermediate 9 afforded the title compounds stereoisomer 1 (36.5 mg, 46.3%) and stereoisomer 2 (37.4 mg, 47.4%)

Intermediate 18B

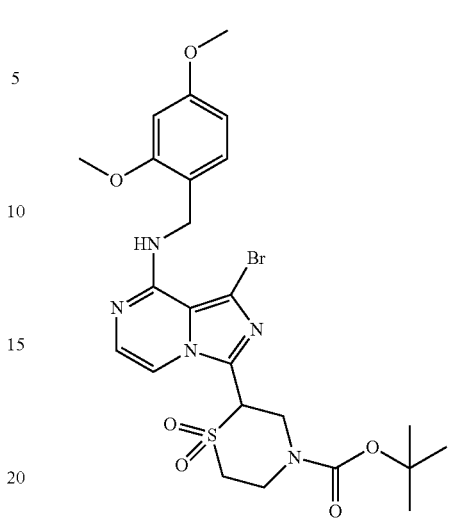

(a) tert-butyl 2-(8-chloroimidazo[1,5-a]pyrazin-3-yl)thiomorpholine-4-carboxylate 1,1-dioxide To tert-butyl 2-(8-chloroimidazo[1,5-a]pyrazin-3-yl)thiomorpholine-4-carboxylate (2.5 g, 7.05 mmol) dissolved in DCM (50 mL) was added 3-chlorobenzoperoxoic acid (2.67 g, 15.50 mmol) and stirred for 1 h. The formation of product was determined by LCMS. Upon completion sat. NaHCO$_3$ (50 mL) was added to the mixture and extracted with DCM (3×80 mL). The combined organic phase was dried over anhydrous Na$_2$SO$_4$ and filtered. The filtrate was concentrated to dryness to afford the crude tert-butyl 2-(8-chloroimidazo[1,5-a]pyrazin-3-yl)thiomorpholine-4-carboxylate 1,1-dioxide (3.05 g). [M+H]$^+$: 387.0; Rt=2.316 min, Method M).

(b) tert-butyl 2-(1-bromo-8-chloroimidazo[1,5-a]pyrazin-3-yl)thiomorpholine-4-carboxylate 1,1-dioxide tert-Butyl 2-(8-chloroimidazo[1,5-a]pyrazin-3-yl)thiomorpholine-4-carboxylate 1,1-dioxide (2.7 g, 6.98 mmol) was dissolved in DMF (30 ml) and cooled to 0° C. 1-Bromopyrrolidine-2,5-dione (1.491 g, 8.38 mmol) dissolved in 2 mL DMF was added slowly and stirred for 1 h at room temperature. Upon completion the reaction mixture was quenched with sat. NaHCO$_3$ solution (80 mL) and extracted with EtOAc (3×100 mL). The combined organic phase was washed with sat. NaCl (3×100 mL) and dried over anhydrous Na$_2$SO$_4$. The mixture was filtered and the filtrate was concentrated to dryness to afford the title compound (3.4 g) which was used without further purification. LCMS: [M+H]$^+$: 464.9; Rt=2.53 min, 3.5 min run, Method M).

(c) tert-butyl 2-(1-bromo-8-(2,4-dimethoxybenzylamino)imidazo[1,5-a]pyrazin-3-yl)thiomorpholine-4-carboxylate 1,1-dioxide tert-Butyl 2-(1-bromo-8-chloroimidazo[1,5-a]pyrazin-3-yl)thiomorpholine-4-carboxylate 1,1-dioxide (3.0 g, 6.44 mmol) was dissolved in 1,4-dioxane (60 mL). (2,4-dimethoxyphenyl)methanamine (3.39 mL, 22.54 mmol) and N-ethyl-N-isopropylpropan-2-amine (2.91 g, 22.54 mmol)

were added to the mixture and allowed to stir overnight. The reaction mixture was concentrated and purified by chromatography on silica gel (50-70% EtOAc in hexanes) to afford the title compound (2.82 g) as a yellow solid. [M+H]⁺: 596.0; Rt=2.15 min, 3.5 min, Method M).

Intermediate 18C

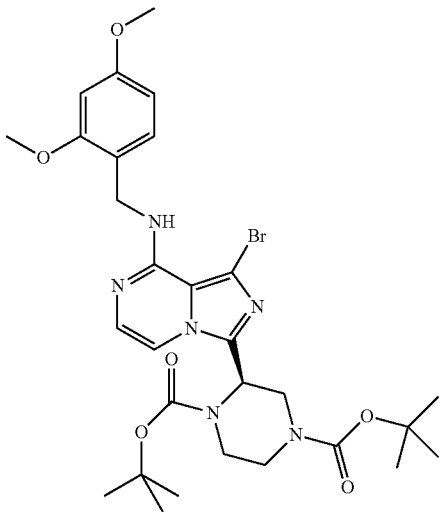

(R)-di-tert-butyl 2-(1-bromo-8-((2,4-dimethoxybenzyl)amino)imidazo[1,5-a]pyrazin-3-yl)piperazine-1,4-dicarboxylate (a) (R)-di-tert-butyl 2-(((3-chloropyrazin-2-yl)methyl)carbamoyl)piperazine-1,4-dicarboxylate (R)-1,4-bis(tert-butoxycarbonyl)piperazine-2-carboxylic acid (2.3 g, 6.97 mmol) and (3-chloropyrazin-2-yl)methanamine. HCl salt (1 g, 6.97 mmol) were dissolved in DMF 100 mL. To the reaction mixture was added Et₃N (4.5 g, 34.8 mmol) and then HATU (3.18 g, 8.36 mmol) slowly at 0° C. The crude was stirred at rt for 1 day under a stream of nitrogen. The crude was quenched with sat. NaHCO₃ (100 mL) at rt, and diluted in EtOAc (2×150 mL). The organic layer was washed with water (200 mL), brine (200 mL), dried over Na₂SO₄, filtered, and evaporated. Purification on silica gel using 20-50% EtOAc/hexanes gave the title compound (2.4 g, 76%). LCMS: [M+Na]⁺: 478.2, Rt=2.10 min, 3.5 min, Method M).

(b) (R)-di-tert-butyl 2-(8-chloroimidazo[1,5-a]pyrazin-3-yl)piperazine-1,4-dicarboxylate ((R)-di-tert-butyl 2-(((3-chloropyrazin-2-yl)methyl)carbamoyl)piperazine-1,4-dicarboxylate (2.5 g, 5.48 mmol) dissolved in EtOAc (60 mL) added POCl₃ (1.75 mL, 19.19 mmol) and 1 mL of DMF slowly at 0° C. and for 1 O.N at r.t. The reaction was cooled in an ice bath and added slowly to a mixture of crushed ice and aq. NH₄OH (60 mL) cooled in an ice bath. The resultant mixture was extracted with EtOAc (3×50 ml), washed with brine, dried over Na₂SO₄, and concentrated in vacuo to give (R)-di-tert-butyl 2-(8-chloroimidazo[1,5-a]pyrazin-3-yl)piperazine-1,4-dicarboxylate (2.1 g), which was taken to the next step without further purification. LCMS: [M+H]⁺: 438.2, Rt=2.25 min, 3.5 min, Method M).

(c) (R)-di-tert-butyl 2-(1-bromo-8-chloroimidazo[1,5-a]pyrazin-3-yl)piperazine-1,4-dicarboxylate To (R)-di-tert-butyl 2-(8-chloroimidazo[1,5-a]pyrazin-3-yl)piperazine-1,4-dicarboxylate (1.5 g, 3.43 mmol) in 50 mL DMF at 0° C., was added NBS (0.62 g, 3.43 mmol) and stirred for 1 h at rt. The reaction was quenched with 1M. Na₂S₂O₃ (aq) solution (20 mL), extracted with EtOAc (3×25 mL), dried with Na₂SO₄, concentrated to dryness to give the product (2R,5R)-tert-butyl 2-(1-bromo-8-chloroimidazo[1,5-a]pyrazin-3-yl)-5-(((tert-butyldiphenylsilyl)oxy)methyl)morpholine-4-carboxylate (1.16 g, 66%). Taken to next step with out purification. LCMS: [M+Na]⁺: 570.0; Rt=2.37 min, 15 min, Method M).

(d) (R)-di-tert-butyl 2-(1-bromo-8-((2,4-dimethoxybenzyl)amino)imidazo[1,5-a]pyrazin-3-yl)piperazine-1,4-dicarboxylate (R)-di-tert-butyl 2-(1-bromo-8-chloroimidazo[1,5-a]pyrazin-3-yl)piperazine-1,4-dicarboxylate (1.2 g, 2.32 mmol), (2,4-dimethoxyphenyl)methanamine (1.36 g, 8.13 mmol) and N-ethyl-N-isopropylpropan-2-amine (1.1 g, 8.13 mmol) were dissolved in 20 mL of 1,4-dioxane and stirred at rt overnight. The reaction was concentrated in vacuo and the residue was subjected to chromatography on silica gel using 3-6% MeOH in DCM to give (R)-di-tert-butyl 2-(1-bromo-8-((2,4-dimethoxybenzyl)amino)imidazo[1,5-a]pyrazin-3-yl)piperazine-1,4-dicarboxylate (1.26 g, 84%). LCMS: [M-Boc]⁺: 646.8, Rt=2.18 min, 3.5 min, Method M).

Example 172

Stereoisomer 2

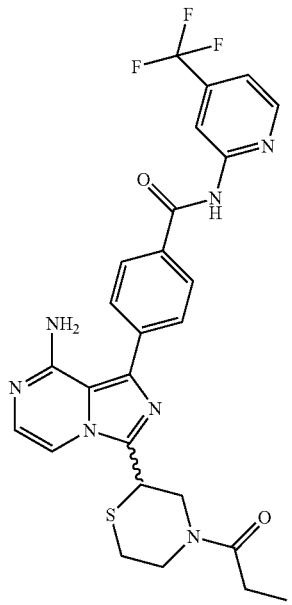

4-(8-amino-3-(4-propionylthiomorpholin-2-yl)imidazo[1,5-a]pyrazin-1-yl)-N-(4-(trifluoromethyl)pyridin-2-yl)benzamide This compound was prepared in an analogous manner as Example 46, from Intermediate 18b and propionic acid, to afford the title compound (2.9 mg, 7%). Data: UPLC(E) R$_t$: 2.43 min; m/z 556.3 (M+H)$^+$.

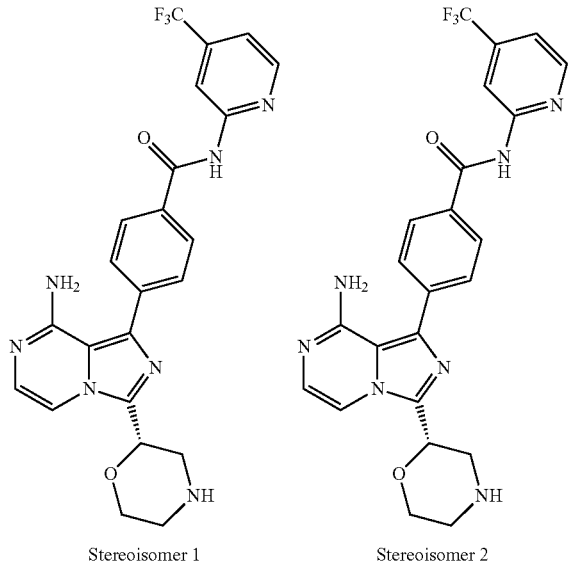

Intermediate 19

Stereoisomer 1        Stereoisomer 2

4-(8-amino-3-(morpholin-2-yl)imidazo[1,5-a]
pyrazin-1-yl)-N-(4-(trifluoromethyl)-pyridin-2-yl)
benzamide These intermediates were prepared, in an analogous manner as Intermediate 8, from morpholine-2-carboxylic acid. Chiral separation (IA column; eluent Heptane/DCM/IPA (85/15/10 v/v %), isocratic, 25 minutes) provided stereoisomers 1 and 2 of benzyl 2-(8-amino-1-bromoimidazo[1,5-a]pyrazin-3-yl)morpholine-4-carboxylate. Subsequent reaction with 4-(4,4,5,5-tetramethyl-1,3,2-dioxaborolan-2-yl)-N-(4-(trifluoromethyl)pyridin-2-yl)benzamide (Intermediate D) and deprotection with TFA at 60° C. as described for intermediate 9 afforded title stereoisomer 1 (107 mg, 67.7%) and stereoisomer 2 (317.5 mg, 95%)

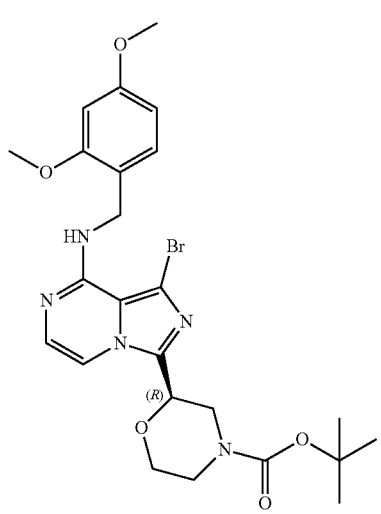

Intermediate 19B (a) (R)-tert-butyl 2-(2-((3-chloropyrazin-2-yl)amino)
acetyl)morpholine-4-carboxylate (3-chloropyrazin-2-yl)methanamine hydrochloride (7.79 g, 43.2 mmol) and (R)-4-(tert-butoxycarbonyl)morpholine-2-carboxylic acid (10 g, 43.2 mmol) were dissolved in DMF (200 mL). To the reaction mixture was added N-ethyl-N-isopropylpropan-2-amine (16.77 g, 130 mmol) and HATU (24.66 g, 64.9 mmol) slowly. The mixture was stirred at room temperature overnight under a nitrogen atmosphere. Upon completion, the reaction mixture was quenched with sat. NaHCO$_3$ (150 mL) and extracted with EtOAc (3×200 mL). The combined organic phase was washed with sat. NaCl (3×200 mL) and then dried over anhydrous Na$_2$SO$_4$. The mixture was filtered and concentrated. The crude product was purified on silica gel (30% EtOAc: hexane) to afford (R)-tert-butyl 2-(2((3-chloropyrazin-2-yl)amino)acetyl) morpholine-4-carboxylate (13.1 g) as a yellow solid. LCMS: [M+Na]$^+$: 379.00; Rt=1.09 min, 2.0 min, Method P).

(b) (R)-tert-butyl 2-(8-chloroimidazo[1,5-a]pyrazin-
3-yl)morpholine-4-carboxylate (R)-tert-butyl 2-(2-((3-chloropyrazin-2-yl)amino)acetyl) morpholine-4-carboxylate (5.0 g, 14.0 mmol) was dissolved in a 1:1 mixture of acetonitrile and DMF (50 mL). Phosphoryl trichloride (4.48 ml, 49.0 mmol) was added slowly at 0° C. The reaction mixture was stirred at 35° C. for 45 min under a stream of nitrogen. Upon completion the reaction mixture was cooled down to 0° C. and added slowly to a 30% ammonium hydroxide solution (100 mL) cooled in an ice bath. The resultant mixture was extracted with EtOAc (3×100 mL) and the combined organic phase was dried over anhydrous Na$_2$SO$_4$ and filtered. The organic filtrate was evaporated to dryness and purified on silica gel (30% EtOAc in Hexanes) to afford the title compound (3.28 g). LCMS: [M+H]$^+$: 339.0; Rt=1.89 min, Method O).

(c) (R)-tert-butyl-2-(1-bromo-8-chloroimidazo[1,5-
a]pyrazin-3-yl)morpholine-4-carboxylate (R)-tert-butyl 2-(8-chloroimidazo[1,5-a]pyrazin-3-yl) morpholine-4-carboxylate (1.3 g, 3.84 mmol) was dissolved in DMF (20 mL) and cooled to 0° C. 1-Bromopyrrolidine-2,5-dione (0.820 g, 4.60 mmol) dissolved in 2 mL of DMF was added slowly and stirred for 1 h at room temperature. The reaction mixture was quenched with sat. NaHCO$_3$ (50 mL) and extracted with EtOAc (3×50 mL). The combined organic phase was washed with sat. NaCl (3×50 mL) and dried with anhydrous Na$_2$SO$_4$. The mixture was filtered and the filtrate was concentrated to dryness to afford the title compound (1.42 g) as a crude product. LCMS: [M+H]$^+$: 418.81; Rt=2.14 min, Method O).

(d) (R)-tert-butyl 2-(1-bromo-8-(2,4-dimethoxyben-
zylamino)imidazo[1,5-a]pyrazin-3-yl)morpholine-4-
carboxylate (R)-tert-butyl 2-(1-bromo-8-chloroimidazo[1,5-a] pyrazin-3-yl)morpholine-4-carboxylate (1.2 g, 2.87 mmol)

was dissolved in 1,4-dioxane (30 mL). (2,4-dimethoxyphenyl)methanamine (1.5 mL, 10.06 mmol) and N-ethyl-N-isopropylpropan-2-amine (1.71 mL, 10.1 mmol) were added to the mixture and allowed to stir at room temperature overnight. The reaction mixture was concentrated and purified on silica gel (50-70% EtOAc in hexanes) to afford the title compound (1.49 g) as a yellow solid. [M+H]$^+$: 549.92; Rt=1.92 min, Method O).

Intermediate 19C

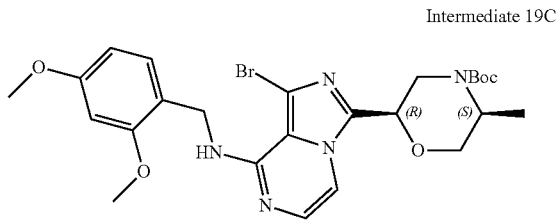

(2R,5S)-tert-butyl 2-(1-bromo-8-((2,4-dimethoxybenzyl)amino)imidazo[1,5-a]pyrazin-3-yl)-5-methylmorpholine-4-carboxylate (a) ((2R,5S)-4-(4-methoxybenzyl)-5-methylmorpholin-2-yl)methanol (S)-2-((4-methoxybenzyl)amino)propan-1-ol (5 g, 25.6 mmol) was dissolved in 100 mL toluene, (S)-(+)-epichlorohydrin (2.72 g, 25.6 mmol) was added, followed by the slow addition of lithium perchlorate (2.84 g, 30.87 mmol) over 30 min. The resultant reaction mixture was stirred at rt for 48 h. A solution of sodium methoxide (25 wt % in CH$_3$OH, 25 mL) was added and the mixture was stirred for 3 days. Saturated aq NH$_4$Cl (100 mL) was added, and the product was extracted with EtOAc (3×100 mL). The combined organic phase was washed with brine, dried (MgSO$_4$), filtered, and evaporated to give the crude product, which was purified by silica gel chromatography eluting with 20-50% EtOAc in hexanes to afford the title compound (5.4 g). LCMS: [M+H]$^+$: 252.2, Rt=0.839 min, 3.5 min, Method M).

(b) (2R,5S)-tert-butyl 2-(hydroxymethyl)-5-methylmorpholine-4-carboxylate

To the solution of ((2R,5S)-4-(4-methoxybenzyl)-5-methylmorpholin-2-yl)methanol (150 mg, 0.6 mmol) in 2.5 mL of EtOH was added Boc$_2$O (193 mg, 0.9 mmol), 1-methyl-1,4-cyclohexadiene/BHT (224 mg, 2.4 mmol) and 20 mg of 10% Pd/C. The reaction was heated to reflux under N$_2$ for 3 h and at room temperature overnight. The reaction mixture was filtered and the filtrate was purified by column chromatography on silica gel eluting with petrolene/ethyl acetate to give the title compound (110 mg). $^1$HNMR (300 MHz, CDCl3): δ=4.21 (s, 1 H), 3.95~4.07 (m, 1H), 3.41~3.66 (m, 5 H), 2.65~2.93 (m, 1 H), 1.40 (s, 9 H), 1.15 (d, J=6.9 Hz, 3 H).

(c) (2R,5S)-tert-butyl 2-(((3-chloropyrazin-2-yl)methyl)carbamoyl)-5-methylmorpholine-4-carboxylate To the solution of (2R,5S)-tert-butyl 2-(hydroxymethyl)-5-methylmorpholine-4-carboxylate (1.9 g, 8.23 mmol) in 30 mL of DCM in an ice bath was added TEMPO (0.257 g, 1.65 mmol) and PhI(OAc)$_2$ (5.3 g, 16.5 mmol). The reaction was stirred at ambient temperature for 24 h, quenched with MeOH, and concentrated in vacuo. The crude product (2R,5S)-4-(tert-butoxycarbonyl)-5-methylmorpholine-2-carboxylic acid was taken up in 20 mL DCM, HATU (3.75 g, 8.23 mmol) was added, and the reaction was stirred at 20~25° C. for 1 h. To the mixture was added TEA (3.32 g, 32.87 mmol) and C-(3-Chloro-pyrazin-2-yl)-methylamine hydrochloride (2 g, 8.23 mmol). The reaction was stirred at 25° C. for 2 h, the reaction was diluted with DCM and H$_2$O, and the organic layer was dried over Na$_2$SO$_4$. The crude product was purified by column chromatography on silica gel eluting with petroleum ether/EtOAc to give the title compound (2.42 g). $^1$HNMR (400 MHz, CDCl3): δ=8.49 (d, J=2.4 Hz, 1 H), 8.32 (d, J=2.4 Hz, 1 H), 7.78 (br, 1 H), 4.66~4.80 (m, 2 H), 3.95~4.21 (m, 3 H), 3.70~3.88 (m, 2 H), 2.90~3.01 (m, 1 H), 1.46 (s, 11), 1.24 (d, J=6.8 Hz, 3 H).

(d) (2R,5S)-tert-butyl 2-(1-bromo-8-((2,4-dimethoxybenzyl)amino)-imidazo[1,5-a]pyrazin-3-yl)-5-methylmorpholine-4-carboxylate 2-(((3-chloropyrazin-2-yl)methyl)carbamoyl)-5-methylmorpholine-4-carboxylate (150 mg, 0.42 mmol) was converted to the title compound using procedures analogous to Intermediate 9B, steps b-d (410 mg). MS (ESI): M/Z (M+1) 562.1 (M+3) 564.1

Intermediate 19D

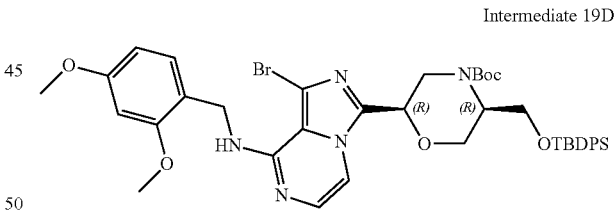

(a) (S)-methyl 2-(benzylamino)-3-((tert-butyldiphenylsilyl)oxy)propanoate

To (S)-methyl 2-(benzylamino)-3-hydroxypropanoate (5 g, 23.9 mmol) in 100 mL of DCM were added NEt$_3$ (2.9 g, 28.7 mmol) and DMAP (0.15 g, 1.2 mmol). The reaction was cooled to 0° C. and TBS-Cl (6.9 g, 25.09 mmol) was added. The reaction was warmed to rt and stirred overnight. Water (100 mL) and DCM (100 mL) were added, the organic layer was collected and washed with sat NH$_4$Cl, dried over Na$_2$SO$_4$ and concentrated to give the title compound (10.2 g), which was used without further purification. LCMS: [M+H]$^+$: 448.13; Rt=2.01 min (Method O).

(b) (R)-2-(benzylamino)-3-((tert-butyldiphenylsilyl)oxy)propan-1-ol

To (S)-methyl 2-(benzylamino)-3-((tert-butyldiphenylsilyl)oxy)propanoate (5 g, 11.17 mmol) in 100 mL of THF was added MeOH (0.5 ml) and then 2.0 M LiBH$_4$ in THF (6.7 mL). The reaction was stirred at rt for 16 h, quenched by slow addition of sat. aq NH$_4$Cl (100 mL) and extracted with EtOAc (3×100 mL). The organic phase was dried over Na$_2$SO$_4$, filtered and concentrated to give (R)-2-(benzylamino)-3-((tert-butyldiphenylsilyl)oxy)propan-1-ol (4.4 g). LCMS: [M+H]$^+$: 422.20; Rt=1.22 min, Method P).

(c) ((2R,5R)-4-benzyl-5-(((tert-butyldiphenylsilyl)oxy)methyl)morpholin-2-yl)methanol (R)-2-(benzylamino)-3-((tert-butyldiphenylsilyl)oxy)propan-1-ol (6 g, 14.3 mmol) was dissolved in 100 mL toluene, (S)-(+)-epichlorohydrin (1.58 g, 17.2 mmol) was added, followed by the slow addition of lithium perchlorate (1.82 g, 17.2 mmol) over 30 min. The resultant mixture was stirred at rt for 48 h. A solution of sodium methoxide (25 wt % in CH$_3$OH) 25 mL was then added and the mixture was stirred for 3 days. Saturated aq NH$_4$Cl (100 mL) was added, and the product was extracted with EtOAc (3×100 mL). The combined organics were washed with brine, dried (MgSO$_4$), filtered, and evaporated to give the crude product, which was purified by silica gel chromatography eluting with 20-50% EtOAc in hexanes to afford the title product (2.6 g). LCMS: [M+H]$^+$:476.17, Rt=1.15 min, Method P).

(d) (2R,5R)-tert-butyl 5-(((tert-butyldiphenylsilyl)oxy)methyl)-2-(hydroxymethyl)morpholine-4-carboxylate ((2R,5R)-4-benzyl-5-(((tert-butyldiphenylsilyl)oxy)methyl)morpholin-2-yl)methanol (4 g, 8.41 mmol) was dissolved in 100 mL of EtOH at 20° C., Boc$_2$O (2.2 g, 10.09 mmol) was added, followed by Et$_3$N (0.86 g, 8.41 mmol). The reaction was degassed with N$_2$ for ~10 min. Pd(OH)$_2$ (1.2 g, 1.68 mmol) was added slowly, and the reaction was shaken with a Parr apparatus at 45-50 psi of H$_2$ for 20 h. The reaction mixture was purged with N$_2$, filtered on a celite pad, which was then rinsed with EtOH (200 mL). The filtrate was concentrated. EtOAc (200 ml) was added, and the solution was washed with water (2×150 mL), dried over MgSO$_4$, filtered and concentrated. Column purification on silica gel eluting with 5-20% MeOH in DCM provided the title compound (2.6 g). LCMS: [M+H]$^+$:486.11, Rt=1.43 min, 2 min, Method P.

(e) (2R,5R)-tert-butyl 2-(1-bromo-8-((2,4-dimethoxybenzyl)amino)imidazo-[1,5-a]pyrazin-3-yl)-5-(((tert-butyldiphenylsilyl)oxy)methyl)morpholine-4-carboxylate (2R,5R)-tert-butyl 5-(((tert-butyldiphenylsilyl)oxy)methyl)-2-(hydroxymethyl)-morpholine-4-carboxylate was converted to the title compound using procedures analogous to Intermediate 19B, steps b-d (0.516 g). LCMS: [M+H]$^+$: 818.31, Rt=1.28 min, Method P).

The following Examples were synthesized following the methods described for example 46-49.

| Example | Structure | Name | LC-MS {M + H}$^+$ | Retention time |
|---|---|---|---|---|
| 173 | 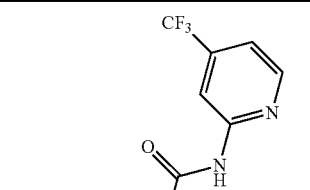 Stereoisomer 2 | 4-(8-amino-3-(4-isobutyrylmorpholin-2-yl)imidazo[1,5-a]pyrazin-1-yl)-N-(4-(trifluoromethyl)pyridin-2-yl)benzamide | 554.2 | 2.44 min |

-continued
| Example | Structure | Name | LC-MS {M + H}+ | Retention time |
|---|---|---|---|---|
| 174 | 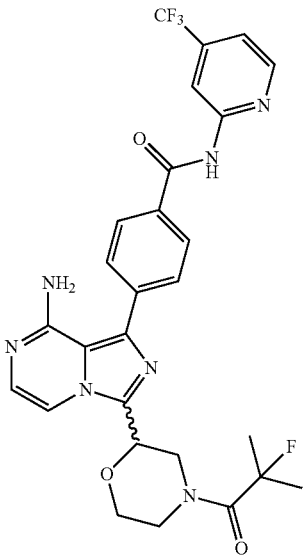<br>Stereoisomer 2 | 4-(8-amino-3-(4-(2-fluoro-2-methylpropanoyl)morpholin-2-yl)imidazo[1,5-a]pyrazin-1-yl)-N-(4-(trifluoromethyl)pyridin-2-yl)benzamide | 572.2 | 2.64 min (UPLC-E) |
| 175 | 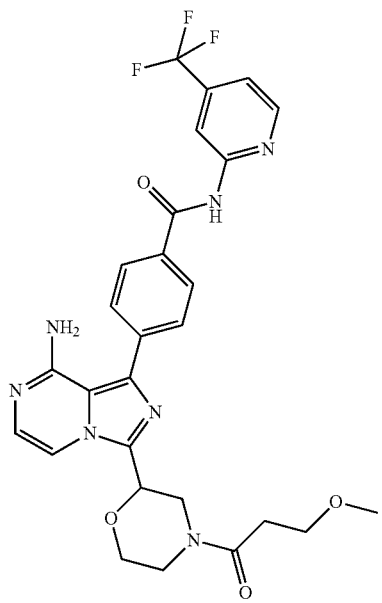<br>Stereoisomer 2 | 4-(8-amino-3-(4-(3-methoxypropanoyl)morpholin-2-yl)imidazo[1,5-a]pyrazin-1-yl)-N-(4-(trifluoromethyl)pyridin-2-yl)benzamide | 570.2 | 2.20 min |

-continued
| Example | Structure | Name | LC-MS {M + H}+ | Retention time |
|---|---|---|---|---|
| 176 | 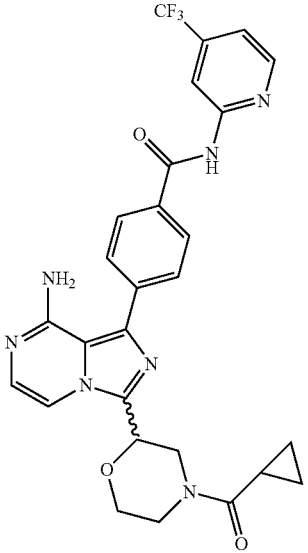 Stereoisomer 2 | 4-(8-amino-3-(4-(cyclopropanecarbonyl)morpholin-2-yl)imidazo[1,5-a]pyrazin-1-yl)-N-(4-(trifluoromethyl)pyridin-2-yl)benzamide | 552.2 | 2.39 min (UPLC-E) |
| 177 | 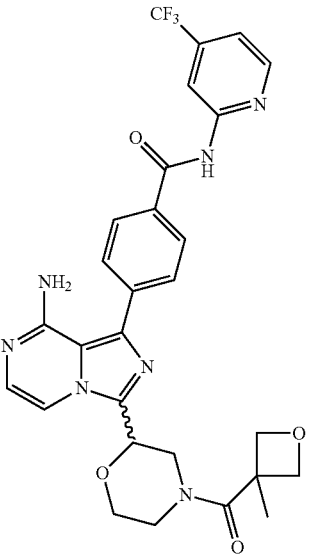 Stereoisomer 2 | 4-(8-amino-3-(4-(3-methyloxetane-3-carbonyl)morpholin-2-yl)imidazo[1,5-a]pyrazin-1-yl)-N-(4-(trifluoromethyl)pyridin-2-yl)benzamide | 582.2 | 2.18 min (UPLC-E) |

| Example | Structure | Name | LC-MS {M + H}+ | Retention time |
|---|---|---|---|---|
| 178 | 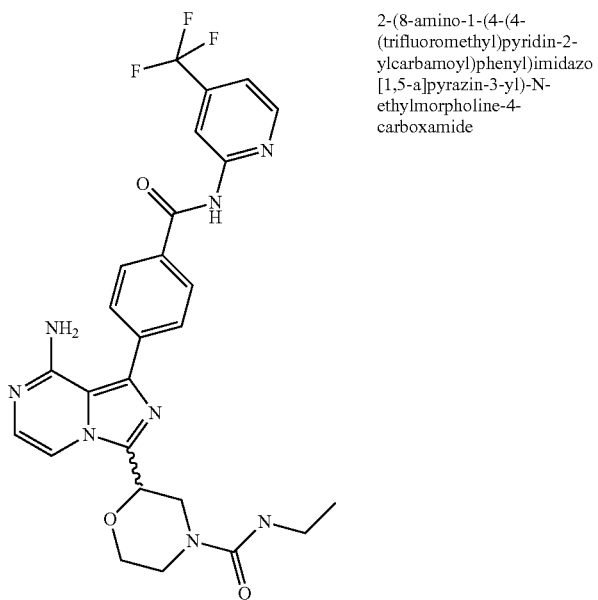 Stereoisomer 2 | 2-(8-amino-1-(4-(4-(trifluoromethyl)pyridin-2-ylcarbamoyl)phenyl)imidazo[1,5-a]pyrazin-3-yl)-N-ethylmorpholine-4-carboxamide | 555.3 | 1.05 min |

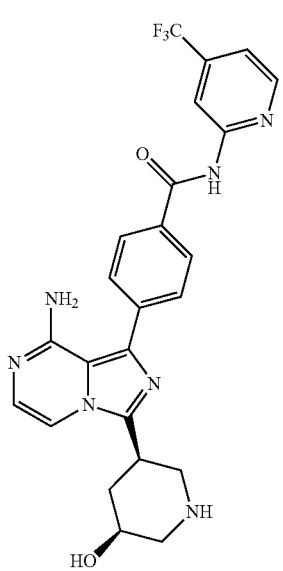

Intermediate 20

4-(8-amino-3-((cis)-5-hydroxypiperidin-3-yl)imidazo[1,5-a]pyrazin-1-yl)-N-(4-(trifluoromethyl)pyridin-2-yl)benzamide This intermediate was prepared in an analogous manner as described for Intermediate 8, from 5-acetoxy-1-(benzyloxycarbonyl)piperidine-3-carboxylic acid to obtain benzyl 3-acetoxy-5-(8-amino-1-bromoimidazo[1,5-a]pyrazin-3-yl)piperidine-1-carboxylate. Subsequent reaction with 4-(4,4,5,5-Tetramethyl-1,3,2-dioxaborolan-2-yl)-N-(4-(trifluoromethyl)pyridin-2-yl)benzamide (Intermediate D) and deprotection with TFA at 60° C. as described for intermediate 9 afforded the title compound (105 mg, 57.2%)

The following Examples were synthesized following the methods described for example 46-49.

| Example | Structure | Name | LC-MS [M + H]+ | Retention time |
|---|---|---|---|---|
| 179 | 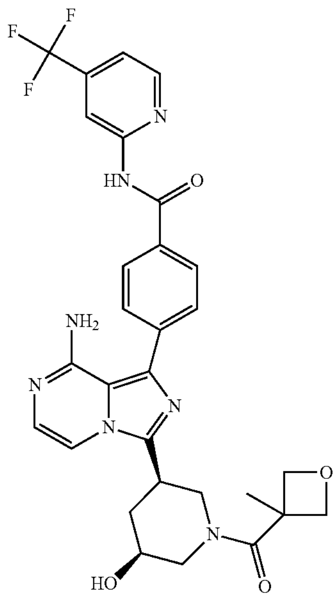 [SMILES: CC1(C(=O)N2C[C@@H](O)C[C@@H](c3nc(-c4ccc(C(=O)Nc5cc(C(F)(F)F)ccn5)cc4)c4c(N)nccn34)C2)COC1] | 4-(8-amino-3-((cis)-5-hydroxy-1-(3-methyloxetane-3-carbonyl)piperidin-3-yl)imidazo[1,5-a]pyrazin-1-yl)-N-(4-(trifluoromethyl)pyridin-2-yl)benzamide | 596.3 | 2.36 min |
| 180 | 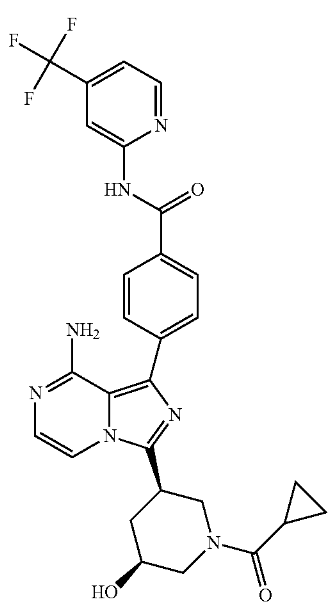 [SMILES: Nc1nccn2c([C@@H]3C[C@H](O)CN(C(=O)C4CC4)C3)nc(-c3ccc(C(=O)Nc4cc(C(F)(F)F)ccn4)cc3)c12] | 4-(8-amino-3-((cis)-1-(cyclopropanecarbonyl)-5-hydroxypiperidin-3-yl)imidazo[1,5-a]pyrazin-1-yl)-N-(4-(trifluoromethyl)pyridin-2-yl)benzamide | 566.3 | 2.51 min |

| Example | Structure | Name | LC-MS [M + H]+ | Retention time |
|---|---|---|---|---|
| 181 | 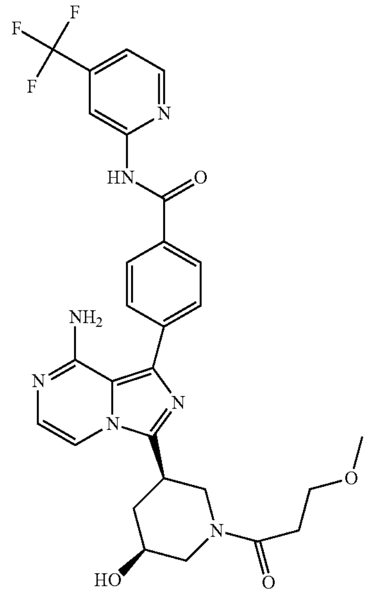 [SMILES: COCCC(=O)N1C[C@@H](O)C[C@@H](c2nc(-c3ccc(C(=O)Nc4cc(C(F)(F)F)ccn4)cc3)c3c(N)nccn23)C1] | 4-(8-amino-3-((cis)-5-hydroxy-1-(3-methoxypropanoyl)piperidin-3-yl)imidazo[1,5-a]pyrazin-1-yl)-N-(4-(trifluoromethyl)pyridin-2-yl)benzamide | 584.3 | 2.37 min |

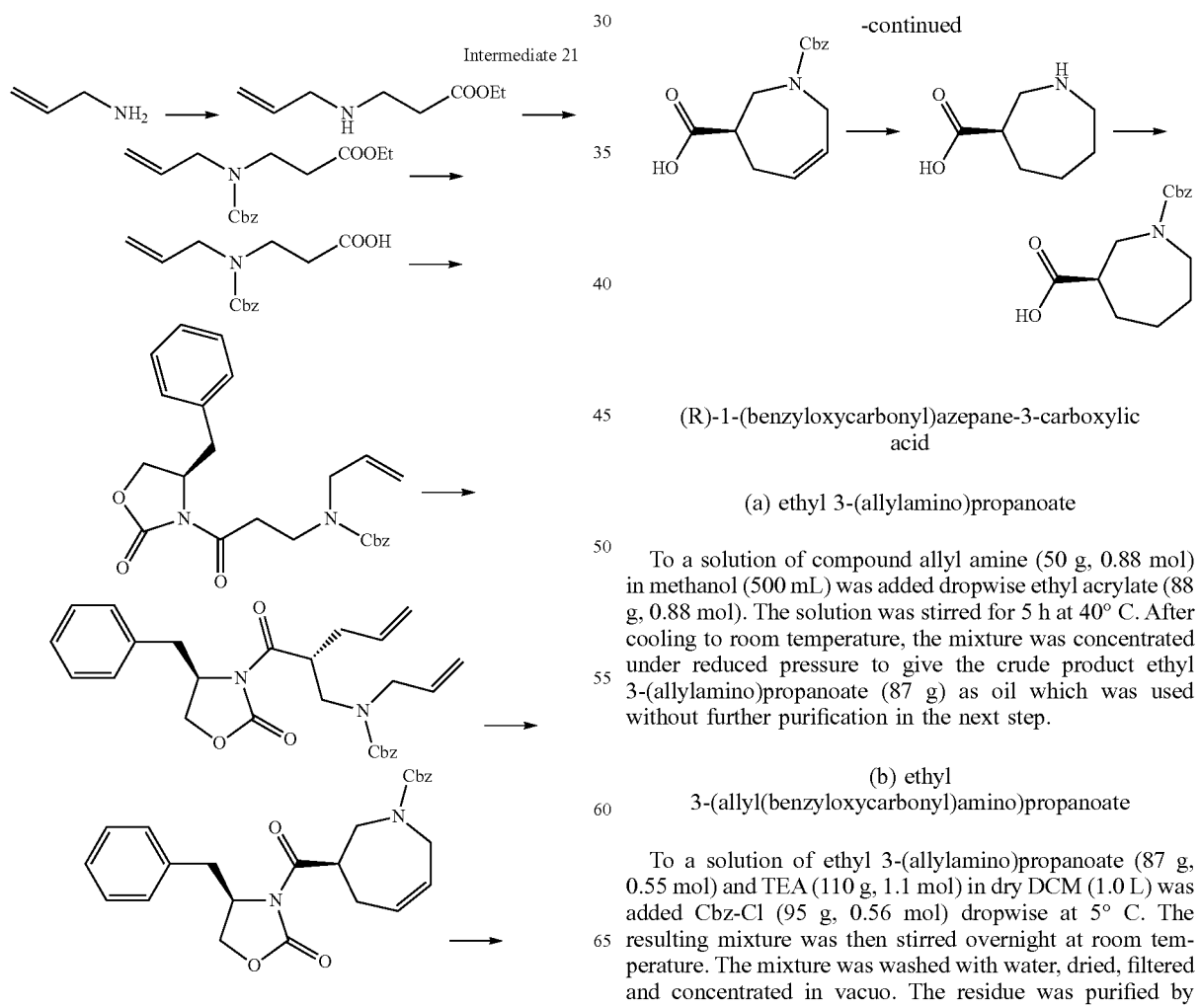

Intermediate 21

(R)-1-(benzyloxycarbonyl)azepane-3-carboxylic acid (a) ethyl 3-(allylamino)propanoate To a solution of compound allyl amine (50 g, 0.88 mol) in methanol (500 mL) was added dropwise ethyl acrylate (88 g, 0.88 mol). The solution was stirred for 5 h at 40° C. After cooling to room temperature, the mixture was concentrated under reduced pressure to give the crude product ethyl 3-(allylamino)propanoate (87 g) as oil which was used without further purification in the next step.

(b) ethyl 3-(allyl(benzyloxycarbonyl)amino)propanoate

To a solution of ethyl 3-(allylamino)propanoate (87 g, 0.55 mol) and TEA (110 g, 1.1 mol) in dry DCM (1.0 L) was added Cbz-Cl (95 g, 0.56 mol) dropwise at 5° C. The resulting mixture was then stirred overnight at room temperature. The mixture was washed with water, dried, filtered and concentrated in vacuo. The residue was purified by column chromatography (silica gel PE:EA=10:1 v/v %) to afford ethyl 3-(allyl(benzyloxycarbonyl)amino)propanoate (105 g, 65% yield).

(c) 3-allyl(benzyloxycarbonyl)amino)propanoic acid

To a solution of ethyl 3-(allyl(benzyloxycarbonyl)amino) propanoate (105 g, 0.36 mol) in MeOH (1.0 L) was added LiOH.H$_2$O (46 g, 1.1 mol) in water (500 mL). The solution was stirred overnight at room temperature. MeOH was removed. The aqueous layer was extracted with t-butyl methyl ether and acidified with diluted aq. HCl, extracted with ethyl acetate. The organic layer was dried, filtered and concentrated to afford 3-(allyl(benzyloxycarbonyl)amino) propanoic acid (92 g, 97% yield) as an oil.

(d) (R)-benzyl allyl(3-(4-benzyl-2-oxooxazolidin-3-yl)-3-oxopropyl)carbamate

To a solution of 3-(allyl(benzyloxycarbonyl)amino)propanoic acid (20 g, 76 mmol) and DIPEA (25 g, 194 mmol) in DCM (800 mL) was added HATU (31 g, 82 mmol). Then (R)-4-benzyloxazolidin-2-one (14.8 g, 84 mmol) was added. The resulting mixture was stirred overnight at room temperature. The mixture was washed with water, dried and concentrated under reduced pressure. The residue was purified by column chromatography (silica gel PE:EA=5:1) to give (R)-benzyl allyl(3-(4-benzyl-2-oxooxazolidin-3-yl)-3-oxopropyl)carbamate (22 g, 69% yield).

(e) benzyl allyl((R)-2-((R)-4-benzyl-2-oxooxazolidine-3-carbonyl)pent-4-enyl)carbamate To a solution of (R)-benzyl allyl(3-(4-benzyl-2-oxooxazolidin-3-yl)-3-oxopropyl)carbamate (50 g, 0.12 mol) in THF (500 mL) was added dropwise a THF solution of NaHMDS (120 mL, 0.12 mol) at −78° C. The reaction mixture was then warmed to −40° C., stirred for 1 h, then re-cooled to −78° C. and allyl bromide (14.5 g, 0.12 mol) in THF (200 mL) was added dropwise. The resulting solution was allowed to warm up to 0° C. and stirred for 3 h. The reaction was quenched with aq. NH$_4$Cl and extracted with ethyl acetate. The ethyl acetate layer was washed with water, dried and concentrated under reduced pressure. The residue was purified by column chromatography (silica gel PE:EA=5:1) to give benzyl allyl((R)-2-((R)-4-benzyl-2-oxooxazolidine-3-carbonyl)pent-4-enyl)carbamate (26 g, 47% yield).

(f) (R,Z)-benzyl 3-((R)-4-benzyl-2-oxooxazolidine-3-carbonyl)-2,3,4,7-tetrahydro-1H-azepine-1-carboxylate To a degassed DCM (200 mL) solution of benzyl allyl (R)-2-((R)-4-benzyl-2-oxooxazolidine-3-carbonyl)pent-4-enyl)carbamate (18.5 g, 40 mmol) was added dropwise a degassed DCM solution of Grubbs 2$^{nd}$ catalyst (1.7 g, 2 mmol). The resulting mixture was refluxed for 4 h, cooled to room temperature and concentrated in vacuum. The residue was purified by column chromatography (silica gel petroleum ether:EtOAc=5:1) to give (R,Z)-benzyl 3-((R)-4-benzyl-2-oxooxazolidine-3-carbonyl)-2,3,4,7-tetrahydro-1H-azepine-1-carboxylate (10.5 g, 60% yield).

(g) (R,Z)-1-(benzyloxycarbonyl)-2,3,4,7-tetrahydro-1H-azepine-3-carboxylic acid

To a solution of (R,Z)-benzyl 3-((R)-4-benzyl-2-oxooxazolidine-3-carbonyl)-2,3,4,7-tetrahydro-1H-azepine-1-carboxylate (21 g, 48 mmol) in MeOH (200 mL) was added an aqueous solution of LiOH.H$_2$O (6 g, 143 mmol) in water (60 mL). The mixture was stirred at room temperature overnight. The mixture was concentrated under reduced pressure. The residue was dissolved in water, extracted with methyl t-butyl ether. The aqueous layer was acidified by aq.HCl. The mixture was extracted with ethyl acetate. The organic layer was dried and concentrated to afford crude (R,Z)-1-(benzyloxycarbonyl)-2,3,4,7-tetrahydro-1H-azepine-3-carboxylic acid (12 g, 90% yield).

(h) (R)-azepane-3-carboxylic acid

To a solution of (R,Z)-1-(benzyloxycarbonyl)-2,3,4,7-tetrahydro-1H-azepine-3-carboxylic acid (12 g, 44 mol) in MeOH (120 mmol) was added 10% Pd/C (1.2 g). The mixture was stirred for 5 h at room temperature under H$_2$ balloon and then filtered. The filtrate was concentrated to afford (R)-azepane-3-carboxylic acid (5.3 g, 85% yield).

(i) (R)-1-(benzyloxycarbonyl)azepane-3-carboxylic acid

To a solution of (R)-azepane-3-carboxylic acid (5.1 g, 36 mmol) in aqueous NaHCO$_3$ (50 mL) was added dropwise a THF solution of Cbz-Cl (6.1 g, 36 mmol) at 0° C. The resulting solution was stirred at room temperature for 3 h. The solution was neutralized with aq. HCl. THF and most of the water were removed under reduced pressure. The residue aqueous layer was extracted with ethyl acetate. The ethyl acetate layer was dried, filtered and concentrated to afford (R)-1-(benzyloxycarbonyl)azepane-3-carboxylic acid (5.8 g, 59% yield)

Intermediate 22

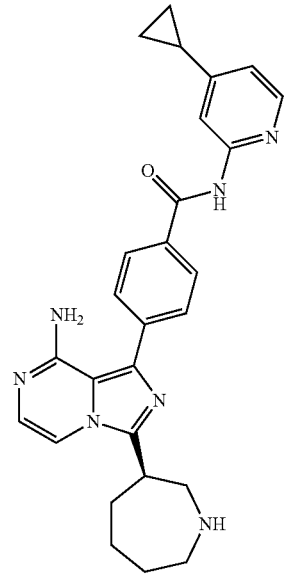

(R)-4-(8-amino-3-(azepan-3-yl)imidazo[1,5-a]pyrazin-1-yl)-N-(4-cyclopropylpyridin-2-yl)benzamide This intermediate was prepared, in an analogous manner as described for intermediate 8, from (R)-1-(benzyloxycarbonyl)azepane-3-carboxylic acid (Intermediate 21) to obtain (R)-benzyl 3-(8-amino-1-bromoimidazo[1,5-a]pyrazin-3-yl)azepane-1-carboxylate. Subsequent reaction with N-(4-cyclopropylpyridin-2-yl)-4-(4,4,5,5-tetramethyl-1,3,2-dioxaborolan-2-yl)benzamide (Intermediate T) and deprotection with 33% HBr/HOAc as described for intermediate 9 afforded the title compound (600 mg, 97%)

Intermediate 23a and 23b

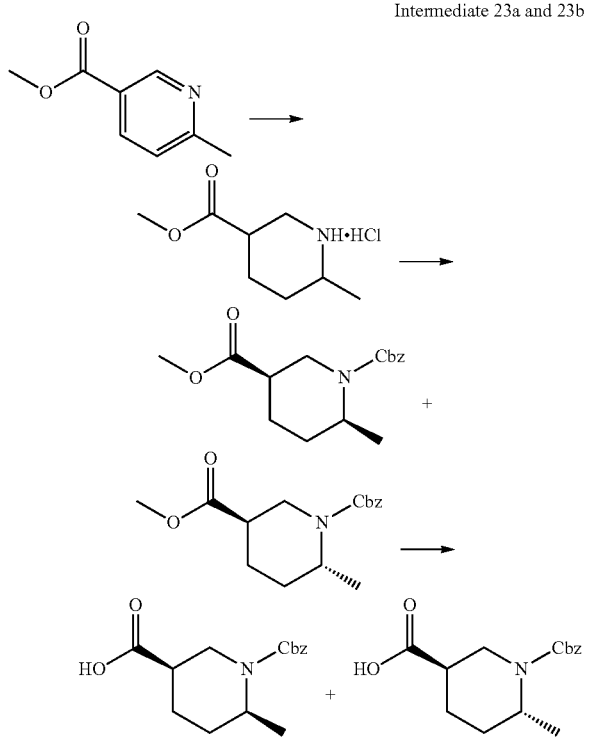

(cis)-1-(benzyloxycarbonyl)-6-methylpiperidine-3-carboxylic acid and (trans)-1-(benzyloxycarbonyl)-6-methylpiperidine-3-carboxylic acid (a) methyl 6-methylpiperidine-3-carboxylate.hydrochloride To a solution of commercially available methyl 6-methylnicotinate (100 g, 0.66 mol) in methanol (1500 mL) and con.HCl (65 g) was added 10% Pd/C (20 g). The resulting solution was heated to 75° C. under 55 psi of hydrogen overnight. The mixture was cooled to room temperature and filtered. The filtrate was concentrated under reduced pressure to afford methyl 6-methylpiperidine-3-carboxylate.hydrochloride (132 g, yield 100%).

(b) (cis)-1-benzyl 3-methyl 6-methylpiperidine-1,3-dicarboxylate and (trans)-1-benzyl 3-methyl 6-methylpiperidine-1,3-dicarboxylate To a solution of methyl 6-methylpiperidine-3-carboxylate.hydrochloride (132 g, 0.682 mol) in THF/H$_2$O (1:1, 1700 mL) was added NaHCO$_3$ (143 g, 1.71 mol). While keeping pH 8-9, Cbz-Cl (174 g, 1.023 mol) was added in portionwise. The resulting mixture was stirred at room temperature for 12 h. The mixture was concentrated under reduced pressure and extracted with ethyl acetate, dried, filtered and concentrated in vacuum. The residue was separated by column chromatography (PE:EA=50:1 v/v %) on silica gel twice to give (cis)-1-benzyl 3-methyl 6-methylpiperidine-1,3-dicarboxylate (49 g, 24.7% yield) and (trans)-1-benzyl 3-methyl 6-methylpiperidine-1,3-dicarboxylate (25 g, 12.6%) respectively.

(c) (cis)-1-(benzyloxycarbonyl)-6-methylpiperidine-3-carboxylic acid

To a solution of (cis)-1-benzyl 3-methyl 6-methylpiperidine-1,3-dicarboxylate (49 g, 0.17 mol) in THF/H$_2$O (1:1, 500 mL) was added LiOH.2H$_2$O (15 g, 0.34 mol) portionwise. The resulting solution was stirred at room temperature overnight. The mixture was concentrated to remove THF, and extracted with ethyl acetate, acidified to pH 5-6 with citric acid monohydrate, then extracted with ethyl acetate. The combined organic layers were dried over MgSO$_4$, filtered, and concentrated in vacuum to afford (cis)-1-(benzyloxycarbonyl)-6-methylpiperidine-3-carboxylic acid (39 g, yield 85%).

(d) (trans)-1-(benzyloxycarbonyl)-6-methylpiperidine-3-carboxylic acid

The title compound was prepared from (trans)-1-benzyl 3-methyl 6-methylpiperidine-1,3-dicarboxylate as described for the corresponding cis-isomer in quantitative yield.

Intermediate 23C

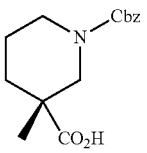

(R)-1-((benzyloxy)carbonyl)-3-methylpiperidine-3-carboxylic acid (a) (R)-ethyl 3-methylpiperidine-3-carboxylate A mixture of (R)-ethyl 3-methylpiperidine-3-carboxylate, hemi((2S,3S)-2,3-bis(2-oxo-2-(p-tolyl)ethyl)succinate) (4.76 g) and sodium carbonate (2.92 g, 27.6 mmol) in water (50 mL) were stirred at rt until all dissolved. The reaction mixture was extracted with MTBE for three times, and then extracted with DCM. The combined organic layers were dried and concentrated in vacuo to give crude (R)-ethyl 3-methylpiperidine-3-carboxylate (3.12 g), which was used in the next step without further purification.

(b) (R)-1-benzyl 3-ethyl 3-methylpiperidine-1,3-dicarboxylate

To a stirred solution of (R)-ethyl 3-methylpiperidine-3-carboxylate (3.12 g, 18.22 mmol) in DCM (60 ml) at 0° C. was added triethylamine (5.08 ml, 36.4 mmol) followed by benzyl chloroformate (3.90 ml, 27.3 mmol). The reaction mixture was warmed to rt and stirred overnight. EtOAc was added and the reaction mixture was washed with 1N HCl, water and brine. Flash chromatography on silica gel with 0 to 10% EtOAc in hexanes gave (R)-1-benzyl 3-ethyl 3-methylpiperidine-1,3-dicarboxylate (3.94 g), (c) (R)-1-((benzyloxy)carbonyl)-3-methylpiperidine-3-carboxylic acid LiOH.H$_2$O (10.31 mg, 0.246 mmol) was added to a stirred solution of (R)-1-benzyl 3-ethyl 3-methylpiperidine-1,3-dicarboxylate (186 mg) in THF (1 ml), water (0.5 ml) and MeOH (0.5 ml). The reaction mixture was stirred at 70° C. for 3 h, then acidified with 0.5 ml of 1N HCl and extracted with EtOAc. The organic layer was washed with water, dried with Mg$_2$SO$_4$ and concentrated in vacuo to give (R)-1-((benzyloxy)carbonyl)-3-methylpiperidine-3-carboxylic acid (163 mg) which was used in next step without further purification.

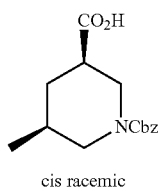

Intermediate 23D cis-1-((benzyloxy)carbonyl)-5-methylpiperidine-3-carboxylic acid To a stirred solution of cis-1-benzyl 3-methyl 5-methylpiperidine-1,3-dicarboxylate (886 mg, 3.04 mmol) in THF (15 ml) was added potassium trimethylsilanolate (585 mg, 4.56 mmol). The reaction mixture was stirred at rt for several hours until no starting material was detected by TLC. The reaction mixture was partitioned between EtOAc and sat NH$_4$Cl and 5 ml 1N HCl. The organic layer was washed with water and brine, dried with Mg$_2$SO$_4$ and concentrated to give cis-1-((benzyloxy)carbonyl)-5-methylpiperidine-3-carboxylic acid (865 mg), which was used in the next step without further purification.

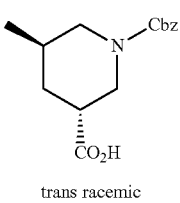

Intermediate 23E trans-1-((benzyloxy)carbonyl)-5-methylpiperidine-3-carboxylic acid To a stirred solution of trans-1-benzyl 3-methyl 5-methylpiperidine-1,3-dicarboxylate (1.343 g, 4.4 mmol)) in THF (10 ml), water (5 ml) and MeOH (5 ml) was added lithium hydroxide monohydrate (0.277 g, 6.60 mmol). The reaction mixture was stirred at 70° C. for 5 h. The reaction mixture was reduced in vacuo, acidified with 8 ml of 1N HCl, and extracted with EtOAc. The EtOAc layer was washed with water, dried with Mg$_2$SO$_4$ and concentrated to give trans-1-((benzyloxy)carbonyl)-5-methylpiperidine-3-carboxylic acid (129 mg), which was used in the next step without further purification.

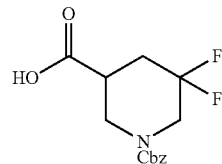

Intermediate 23F 1-((Benzyloxy)carbonyl)-5,5-difluoropiperidine-3-carboxylic acid (a) 1-Benzyl 3-ethyl 5-oxopiperidine-1,3-dicarboxylate To a stirred solution of 1-benzyl 3-ethyl 5-hydroxypiperidine-1,3-dicarboxylate (6.748 g, 21.96 mmol) in DCM (200 ml) was added Dess-Martin periodinate (10.24 g, 24.15 mmol). The reaction mixture was stirred at rt for 2 h. 0.5 N NaOH was added, and the mixture was extracted with DCM. The organic phase was dried with Mg$_2$SO$_4$ and concentrated. Ether was added to the crude, and the resulting slurry was filtered. The filtrate was concentrated and the residue was purified by flash column chromatography on silica gel with 0 to 35% EtOAc in hexanes to give 1-benzyl 3-ethyl 5-oxopiperidine-1,3-dicarboxylate (5.83 g).

(b) 1-Benzyl 3-ethyl 5,5-difluoropiperidine-1,3-dicarboxylate

1-Benzyl 3-ethyl 5-oxopiperidine-1,3-dicarboxylate (5.83 g, 19.1 mmol) was dissolved in DCM (100 ml) and cooled to −78° C., to which DAST (6.31 ml, 47.7 mmol) in DCM (15 ml) was added dropwise. The reaction mixture was stirred at −78° C. for 10 min, 0° C. for 1.5 h and rt for 4.5 h. The reaction mixture was cooled to 0° C., sat NaHCO$_3$ was added, and the mixture was extracted with DCM. The organic phase was reduced. Flash chromatography on silica gel eluting with 0 to 15% EtOAc in hexanes gave 1-benzyl 3-ethyl 5,5-difluoropiperidine-1,3-dicarboxylate (5.48 g).

(c) 1-((Benzyloxy)carbonyl)-5,5-difluoropiperidine-3-carboxylic acid

To a stirred solution of 1-benzyl 3-ethyl 5,5-difluoropiperidine-1,3-dicarboxylate (5.48 g, 16.74 mmol) in THF (80 ml) was added potassium trimethylsilanolate (3.22 g, 25.1 mmol). The reaction mixture was stirred at it for a few hours until no starting material was detected by TLC. The reaction was reduced in vacuo, diluted with Et$_2$O, and washed with water. The water layer was acidified with 26 ml of 1N HCl, and extracted with EtOAc. The EtOAc layer was washed with water and brine, dried with Mg$_2$SO$_4$ and concentrated in vacuo to give the crude product 1-((benzyloxy)carbonyl)-5,5-difluoropiperidine-3-carboxylic acid (4.82 g) which was used in next step without further purification.

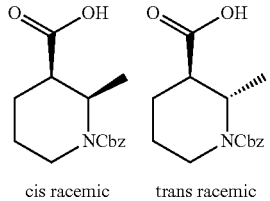

Intermediate 23G, isomers 1 and 2 cis-1-((benzyloxy)carbonyl)-2-methylpiperidine-3-carboxylic acid (a) cis-1-benzyl 3-methyl 2-methylpiperidine-1,3-dicarboxylate and trans-1-benzyl 3-methyl 2-methylpiperidine-1,3-dicarboxylate Methyl 2-methylpiperidine-3-carboxylate (5.41 g, 34.4 mmol) in DCM (50 ml) was cooled to 0° C., to which triethylamine (9.59 ml, 68.8 mmol) and benzyl chloroformate (7.37 ml, 51.6 mmol) were added. The reaction mixture was warmed to rt for a few h, then poured into iced 2N HCl (75 ml), and extracted with DCM. The combined organic phase was washed with ice-cold sat. NaHCO₃. Flash chromatography on silica gel eluting with 0 to 10% EtOAc in hexanes gave cis-1-benzyl 3-methyl 2-methylpiperidine-1,3-dicarboxylate (5.6 g) as the first-eluting product, followed by trans-1-benzyl 3-methyl 2-methylpiperidine-1,3-dicarboxylate as the second-eluting product (445 mg).

1H NMR data for cis-1-benzyl 3-methyl 2-methylpiperidine-1,3-dicarboxylate (CDCl₃, 500 Hz): 7.26-7.36 (m, 5), 5.10-5.22 (m, 2), 4.83 (ddd, 1, J=29, 6.5, 5.6 Hz), 4.03 (dd, 1, J=32.8, 15.2 Hz), 3.68 (s, 3), 2.85 (dd, 1), 2.63-2.67 (m, 1), 1.67-2.08 (m, 3), 1.37-1.45 (m, 1), 1.07 (d, 3, J=6.8 Hz).

1H NMR data for trans-1-benzyl 3-methyl 2-methylpiperidine-1,3-dicarboxylate (CDCl₃, 500 Hz): 7.26-7.36 (m, 5), 5.14 (dd, 2), 4.97 (m, 1), 4.03 (d, 1, J=13.2 Hz), 3.63 (s, 3), 2.90 (ddd, 1), 2.44 (s, 1), 2.07 (d, 1, J=13.6 Hz), 1.50-1.80 (m, 3), 1.24 (d, 3, J=7.2 Hz).

(b) piperidine-3-carboxylic acid

To a stirred solution of cis-1-benzyl 3-methyl 2-methylpiperidine-1,3-dicarboxylate (5.6 g, 19.22 mmol) in THF (30 ml), MeOH (15 ml) and water (15 ml) was added lithium hydroxide monohydrate (1.210 g, 28.8 mmol) and the mixture was stirred at 70° C. for overnight. 10 ml of 1N HCl was added, and the resulting mixture was extracted with EtOAc. The organic layer was washed with water, and brine, dried and concentrated to give cis-1-((benzyloxy)carbonyl)-2-methylpiperidine-3-carboxylic acid (5.12 g), which was use in next step without further purification.

(c) trans-1-((benzyloxy)carbonyl)-2-methylpiperidine-3-carboxylic acid

To a stirred solution of trans-1-benzyl 3-methyl 2-methylpiperidine-1,3-dicarboxylate (445 mg) in THF (4 ml), MeOH (2 ml) and Water (2 ml) was added lithium hydroxide monohydrate and the mixture was stirred at 70° C. overnight. 10 ml of 1N HCl was added, and the resulting mixture was extracted with EtOAc. The organic layer was washed with water, brine, dried and concentrated to give cis-1-((benzyloxy)carbonyl)-4-methylpiperidine-3-carboxylic acid (403 mg, 95%), which was used in the next step without further purification.

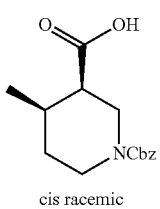

Intermediate 23H cis racemic cis-1-((benzyloxy)carbonyl)-4-methylpiperidine-3-carboxylic acid

To a stirred solution of cis-1-benzyl 3-methyl 4-methylpiperidine-1,3-dicarboxylate (1.76 g, 6.04 mmol) was dissolved in THF (10 ml), MeOH (5 ml) and Water (5 ml) was added lithium hydroxide monohydrate (0.380 g, 9.06 mmol) and the mixture was stirred at 70° C. for a few hours. After removal of solvent, 10 ml of 1N HCl was added, and the resulting mixture was extracted with EtOAc. The organic layer was washed with water, brine, dried and concentrated to give cis-1-((benzyloxy)carbonyl)-4-methylpiperidine-3-carboxylic acid., which was used in the next step without further purification.

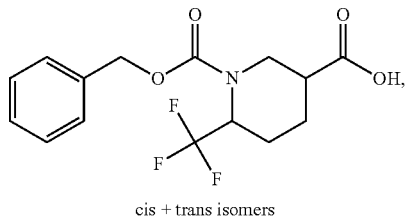

Intermediate 23I cis + trans isomers

1-(benzyloxycarbonyl)-6-(trifluoromethyl)piperidine-3-carboxylic acid (a) Methyl 6-(trifluoromethyl)piperidine-3-carboxylate To a solution of methyl 6-(trifluoromethyl)nicotinate (47.8 g, 0.233 mol) in MeOH (500 ml) was added PtO₂ (1.59 g, 6.99 mmol), followed by conc. HCl (21.3 ml, 0.256 mol) into a Parr Shaker. The mixture was degassed with hydrogen, and the reaction mixture was shaken overnight at room temperature under a 55 psi hydrogen atmosphere. The mixture was filtered, and the filtrate was concentrated to afford the HCl salt of methyl 6-(trifluoromethyl)piperidine-3-carboxylate (53 g, 91.9%) as a white solid, which was used in the next step directly.

(b) 1-benzyl 3-methyl 6-(trifluoromethyl)piperidine-1,3-dicarboxylate

To a mixture of 6-(trifluoromethyl)piperidine-3-carboxylate (5 g, 20.2 mmol) and K₂CO₃ (11.1 g, 80.7 mmol) in THF (50 ml) and H₂O (25 ml) was added benzyl chloroformate (4.12 g, 24.2 mmol) at room temperature. The mixture was stirred overnight, then treated with water and extracted with EtOAc three times. The combined organic layers were washed with brine, dried over anhydrous Na₂SO₄ and concentrated under reduced pressure. The residue was purified by silica gel column chromatography (petroleum ether/ethyl acetate=5/1 v/v %) to afford 1-benzyl 3-methyl 6-(trifluoromethyl)piperidine-1,3-dicarboxylate (5 g). MS-ESI (m/z): 346 (M+1)⁺ (Acq Method: 10-80AB_2 min; Rt: 1.20 min).

(c) 1-(benzyloxycarbonyl)-6-(trifluoromethyl)piperidine-3-carboxylic acid

To a mixture of 1-benzyl 3-methyl 6-(trifluoromethyl)piperidine-1,3-dicarboxylate (5 g, 14.5 mmol) in MeOH (25 ml) and water (25 ml) was added LiOH·H₂O (1.22 g, 30 mmol) at room temperature, and the mixture was stirred for 2 h. The mixture was diluted with water and extracted with EtOAc three times. The combined organic layers were washed with brine, dried over anhydrous Na$_2$SO$_4$, and concentrated in vacuo. The residue was purified by silica gel column chromatography (petroleum ether/ethyl acetate=2/1 v/v %) to afford 1-(benzyloxycarbonyl)-6-(trifluoromethyl)piperidine-3-carboxylic acid (3.16 g, 66.0%).

$^1$H NMR (400 MHz, CHLOROFORM-d) δ 7.34 (s, 5H), 5.20-4.66 (m, 2H), 4.88-4.84 (m, 1H), 4.54-4.36 (dd, J$_1$=5.5 Hz, J$_2$-5.5 Hz, 1H), 3.15-3.00 (m, 1H), 2.48-2.46 (d, J=10.8 Hz, 1H), 2.13-2.06 (m, 2H), 1.84-1.77 (m, 2H).

Intermediate 23I

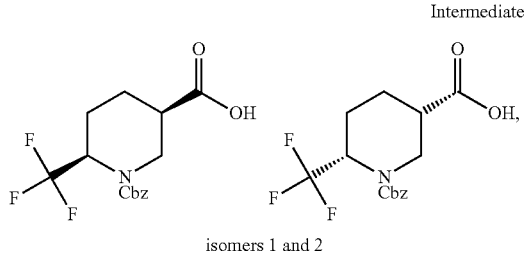

isomers 1 and 2

(a) methyl 6-(trifluoromethyl)-1,4,5,6-tetrahydropyridine-3-carboxylate

To a solution of methyl 6-(trifluoromethyl)nicotinate (30 g, 0.15 mol) containing 10% Pd—C(30 g) in anhydrous methanol (300 ml) was added dry ammonium formate (99 g, 1.5 mol) under an atmosphere of nitrogen. The reaction of the mixture was allowed to stir for 16 h at room temperature. The mixture was filtered, and the filtrate was evaporated under reduced pressure. The residue was purified by column chromatography with silica gel eluted by 0~80% ethyl acetate in petroleum ether (60-90 fraction) to afford methyl 6-(trifluoromethyl)-1,4,5,6-tetrahydropyridine-3-carboxylate (30 g, 96.8%).

MS-ESI (m/z): 206 (M+1)$^+$ (Acq Method: 10-80AB_2 min; Rt: 1.03 min)

(b) Methyl 6-(trifluoromethyl)piperidine-3-carboxylate

To a solution of 6-(trifluoromethyl)-1,4,5,6-tetrahydropyridine-3-carboxylate (20 g, 92 mmol) in TFA (150 ml) was added Et$_3$SiH (13.2 g, 102 mmol) at room temperature, and the resulting mixture was stirred at room temperature for 30 min. The volatiles were concentrated in vacuo, and the crude methyl 6-(trifluoromethyl)piperidine-3-carboxylate was used in the next step without further purification.

(c) 1-benzyl 3-methyl 6-(trifluoromethyl)piperidine-1,3-dicarboxylate

To a solution of methyl 6-(trifluoromethyl)piperidine-3-carboxylate (20 g, 92 mmol) in THF (40 ml) and water (10 ml) was added K$_2$CO$_3$ (25 g, 184 mmol) and benzyl chloroformate (19 g, 184 mmol) at 0° C. under ice-water bath. The resulting mixture was stirred for 1 h at room temperature. The mixture was diluted with water and extracted with ethyl acetate three times. The combined organic layers was washed with brine, dried over anhydrous sodium sulfate, and evaporated under reduced pressure. The residue was purified by column chromatography on silica gel (petroleum ether/ethyl acetate=5/1 v/v %) to give 1-benzyl 3-methyl 6-(trifluoromethyl)piperidine-1,3-dicarboxylate (19 g, 61.3%) as yellow oil. $^1$H-NMR (400 MHz, MeOD) δ 7.32-7.24 (m, 5H), 5.21-5.09 (m, 2H), 4.85-4.69 (m, 2H), 3.67-3.54 (m, 3H), 3.24-2.72 (m, 2H), 2.13-1.94 (m, 4H).

(d) 1-(benzyloxycarbonyl)-6-(trifluoromethyl)piperidine-3-carboxylic acid

To a mixture of 1-benzyl 3-methyl 6-(trifluoromethyl)piperidine-1,3-dicarboxylate (3.5 g, 0.01 mol) in CH$_3$OH (30 ml) and water (6 ml) was added LiOH.H$_2$O (0.84 g, 0.02 mol), and the mixture was stirred for 2 h at room temperature. The mixture was diluted with water and extracted with ethyl acetate three times. The combined organic layers were washed with brine, dried over anhydrous Na$_2$SO$_4$ and concentrated in vacuo. The residue was purified by column chromatography on silica gel to afford the title compound (3.1 g) as a mixture of four enantiomers. MS-ESI (m/z): 332 (M+1)$^+$ (Acq Method: 10-80AB_2 min; Rt: 1.13 min). $^1$H-NMR (400 MHz, MeOD) δ 7.32-7.24 (m, 5H), 5.21-5.09 (m, 2H), 4.85-4.69 (m, 2H), 3.24-2.72 (m, 2H), 2.13-1.94 (m, 4H).

The two cis enantiomers were separated by SFC (Column: Chiralpak AD-H 250×4.6 mm I.D., 5 μm Mobile phase: methanol (0.05% DEA) in CO$_2$ from 5% to 40% Flow rate: 2.35 mL/min Wavelength: 220 nm). E1: (3R,6R)-1-(benzyloxycarbonyl)-6-(trifluoromethyl)piperidine-3-carboxylic acid (Rt=4.02 Min.). E2: (3S,6S)-1-(benzyloxycarbonyl)-6-(trifluoromethyl)piperidine-3-carboxylic acid (Rt=3.19 Min.)

Intermediate 23J

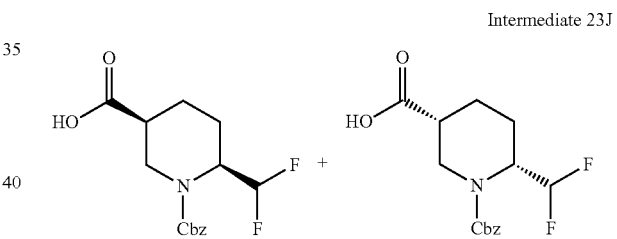

(3S,6S)-1-benzyl 3-methyl 6-(difluoromethyl)piperidine-1,3-dicarboxylate and (3R,6R)-1-benzyl 3-methyl 6-(difluoromethyl)piperidine-1,3-dicarboxylate

(a) methyl 6-(hydroxymethyl)nicotinate

To a solution of methyl 6-(acetoxymethyl)nicotinate (50 g, 0.24 mol) in methanol (500 ml), was added conc. HCl (40 ml), then heated to 70° C. for 1.5 h. The reaction mixture was concentrated in vacuo and the residue was dissolved in DCM and 5% NaHCO$_3$, and the resultant mixture was washed with brine, dried over sodium sulfate and concentrated in vacuo to give the title compound (30 g). $^1$HNMR (400 MHz, DMSO) δ=8.99 (d, J=1.6 Hz, 1H), 8.31 (dd, J$_1$=8 Hz, J$_2$=2 Hz, 1H), 7.63 (m, 1H), 5.63 (t, J=7 Hz, 1H), 4.64 (d, J=7 Hz, 2H), 3.88 (s, 3H).

(b) methyl 6-formylnicotinate

To a solution of methyl 6-(hydroxymethyl)nicotinate (30 g, 0.18 mol) in DCM (500 ml) was added manganese dioxide (150 g, 1.72 mol) portionwise. The resulting mixture was stirred at room temperature for 4 h. The solid was filtered and the filtrate was concentrated in vacuo to give methyl 6-formylnicotinate (20 g). $^1$HNMR (400 MHz, DMSO) δ=10.03 (s, 1H), 9.26 (d, J=1.6 Hz, 1H), 8.50 (dd, $J_1$=4 Hz, $J_2$=1.6 Hz, 1H), 8.03 (d, J=8 Hz, 1H), 3.92 (s, 3H).

(c) Methyl 6-(difluoromethyl)nicotinate

To a solution of methyl 6-formylnicotinate (20 g, 0.121 mol) in DCM (500 ml) was added diethylaminosulfur trifluoride (33 ml, 0.25 mol) dropwise at −60° C. The resulting mixture was allowed to reach room temperature, then stirred for 12 h. The reaction solution was quenched with saturated NaHCO$_3$ at 0° C. and diluted with water (500 ml). The organic layer was washed with brine, dried over sodium sulfate and concentrated to give a crude product which was purified by column chromatography with silica gel eluted by 0~30% ethyl acetate in petroleum ether (60-90 fraction) to give methyl 6-(difluoromethyl)nicotinate (13 g). 1H NMR (400 MHz, chloroform-d) δ=9.24 (d, J=1.00 Hz, 1H), 8.45 (dd, J=2.01, 8.28 Hz, 1H), 7.74 (d, J=8.03 Hz, 1H), 6.49-6.89 (m, 1H), 3.99 (s, 3H).

(d) (racemic)-1-benzyl 3-methyl 6-(difluoromethyl)piperidine-1,3-dicarboxylate

To a solution of methyl 6-(difluoromethyl)nicotinate (13 g, 0.0695 mol) in methanol (200 ml) and HCl (7 ml, 12M) was added PtO$_2$ (1.3 g). The resulting solution was stirred under a 55 psi hydrogen atmosphere overnight. The mixture was filtered and the filtrate was concentrated under reduced pressure to afford methyl 6-(difluoromethyl)piperidine-3-carboxylate hydrochloride (14.7 g, 100%) as a crude product. The product was dissolved in saturated NaHCO$_3$ (400 ml) and carbobenzoxy chloride (20 g, 0.12 mol) was added at 0° C. in portions and the mixture was stirred at room temperature over 10 h. The mixture was separated and the organic layer was washed with brine, dried over sodium sulfate, filtered and concentrated to afford the crude product, which was purified by silica gel column chromatography (0 to 30% ethyl acetate in hexanes) to give the title compound. $^1$HNMR (400 MHz, MeOD) δ=7.38 (s, 5H), 5.92-6.21 (m, 1H), 5.15 (s, 2H), 4.40 (br, 2H), 3.68 (s, 3H), 2.95-3.06 (m, 1H), 2.47-2.54 (m, 1H), 1.98-2.01 (m, 2H), 1.72-1.77 (m, 2H).

(e) (3S,6S)-1-benzyl 3-methyl 6-(difluoromethyl)piperidine-1,3-dicarboxylate and (3R,6R)-1-benzyl 3-methyl 6-(difluoromethyl)piperidine-1,3-dicarboxylate These intermediates were prepared by chiral separation (Instrument: Thar 200; Column: AD 250 mm*50 mm, 5 um; Mobile phase: A: Supercritical CO$_2$, B: MeOH, A:B=85:15 at 160 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to obtain the title compound E1: ((3S,6S)-1-benzyl 3-methyl 6-(difluoromethyl)piperidine-1,3-dicarboxylate (Rt=4.34 min), 5.5 g, 22% and E2: ((3R,6R)-1-benzyl 3-methyl 6-(difluoromethyl)piperidine-1,3-dicarboxylate (Rt=4.12 min), 6.3 g, 25%.

(f) (3S,6S)-1-((benzyloxy)carbonyl)-6-(difluoromethyl)piperidine-3-carboxylic acid To a solution of (3S,6S)-1-benzyl 3-methyl 6-(difluoromethyl)piperidine-1,3-dicarboxylate (5.5 g, 0.0167 mol) in THF/H$_2$O/MeOH (1:1:1, 75 ml) was added LiOH.H$_2$O (1.8 g, 0.0501 mol) in portions. The resulting solution was stirred at room temperature overnight. The solvent was removed and the residue was dissolved in water (50 ml), the aqueous layer was acidified to pH 5 with citric acid monohydrate, then extracted with ethyl acetate (3×50 mL). The combined organic layer were washed with brine, dried over sodium sulfate, filtered and concentrated to give (3S,6S)-1-((benzyloxy)carbonyl)-6-(difluoromethyl)piperidine-3-carboxylic acid (4.5 g, 86.5%).

$^1$HNMR (400 MHz, DMSO) δ=12.54 (br, 1H), 7.31-7.37 (m, 5H), 6.21-6.49 (m, 1H), 5.12 (s, 2H), 4.23-4.36 (m, 2H), 2.86-3.02 (m, 1H), 2.41(s, 1H), 1.88-1.91 (m, 2H), 1.61-1.67 (m, 2H).

(g) (3R,6R)-1-((benzyloxy)carbonyl)-6-(difluoromethyl)piperidine-3-carboxylic acid In the same way as step (f), (3R,6R)-1-benzyl 3-methyl 6-(difluoromethyl)piperidine-1,3-dicarboxylate was hydrolyzed to (3R,6R)-1-((benzyloxy)carbonyl)-6-(difluoromethyl)piperidine-3-carboxylic acid.

Intermediate 23K

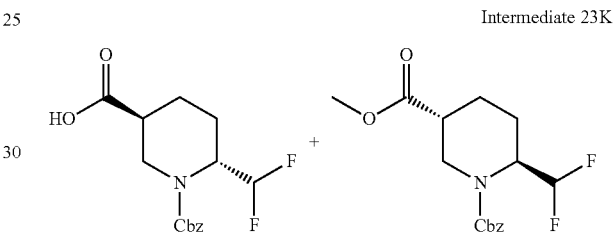

(a) (trans)-1-benzyl 3-methyl 6-(difluoromethyl)piperidine-1,3-dicarboxylate

To a solution of methyl 6-(difluoromethyl)nicotinate (10 g, 0.053 mol) in acetic acid (100 mL) was added NaBH$_3$CN (15 g, 0.23 mol) in portions, keeping the reaction temperature below 20° C. The resulting solution was stirred at 20° C. for 2 hours, then at 40° C. for 1.5 hours. The solvent was removed under reduced pressure to afford 14.7 g of crude product, which was dissolved in saturated NaHCO$_3$ (400 ml). Carbobenzoxy chloride (15 ml, 0.073 mol) was added at 0° C. in portions and the mixture was stirred at room temperature over 10 h. The mixture was separated and the organic layer was washed with brine, dried over sodium sulfate, filtered and concentrated to afford the crude product, which was purified by column chromatography with silica gel eluted by 0~30% ethyl acetate in petroleum ether (60-90 fraction) to give the title compound (11.0 g) as a racemic mixture. MS (ESI): M/Z (M+1): 328. These intermediates were prepared by chiral separation (Instrument: Thar 200; Column: AD 250 mm*50 mm, 5 um; Mobile phase: A: Supercritical CO$_2$, B: MeOH, A:B=85:15 at 160 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to obtain the title compounds E1: (3S,6R)-1-benzyl 3-methyl 6-(difluoromethyl)piperidine-1,3-dicarboxylate, 3.8 g, 34.5%. 1H NMR (400 MHz, METHANOL-d4) δ=7.44-7.26 (m, 5H), 6.23-5.92 (m, 1H), 5.24-5.05 (m, 2H), 4.55 (d, J=14.1 Hz, 1H), 4.46-4.34 (m, 1H), 3.58 (br. s., 3H), 3.24 (d, J=13.1 Hz, 1H), 2.73 (br. s., 1H), 2.10-1.99 (m, 1H), 1.96-1.77 (m, 3H). MS (ESI): M/Z (M+1): 328.

E2: (3R,6S)-1-benzyl 3-methyl 6-(difluoromethyl)piperidine-1,3-dicarboxylate, 2.2 g, 20.0%). ¹H NMR (400 MHz, MeOH-d4) δ=7.43-7.27 (m, 5H), 6.23-5.91 (m, 1H), 5.23-5.05 (m, 2H), 4.54 (d, J=14.1 Hz, 1H), 4.46-4.33 (m, 1H), 3.77-3.51 (m, 3H), 3.23 (d, J=12.5 Hz, 1H), 2.73 (br. s., 1H), 2.09-1.97 (m, 1H), 1.96-1.76 (m, 3H). MS (ESI): M/Z (M+1): 328.

(c) (3S,6R)-1-((benzyloxy)carbonyl)-6-(difluoromethyl)piperidine-3-carboxylic acid To a solution of (3S,6R)-1-benzyl 3-methyl 6-(difluoromethyl)piperidine-1,3-dicarboxylate (3.27 g, 0.01 mol) in THF/H₂O/MeOH (1:1:1, 50 ml) was added LiOH.H₂O (1.2 g, 0.03 mol) in portions. The resulting solution was stirred at room temperature overnight. The solvent was removed and the residue was dissolved in water (50 ml), the aqueous layer was acidified to pH 5-6 with citric acid monohydrate and extracted with ethyl acetate (3×50 mL). The combined organic layer was washed with brine, dried over sodium sulfate, filtered and concentrated to give compound (3S,6R)-1-((benzyloxy)carbonyl)-6-(difluoromethyl)piperidine-3-carboxylic acid (3.26 g, 100%). ¹H NMR (400 MHz, DMSO-d6) δ=12.49 (br. s., 1H), 7.44-7.24 (m, 5H), 6.50-6.16 (m, 1H), 5.16-5.02 (m, 2H), 4.47-4.27 (m, 2H), 3.16 (d, J=11.0 Hz, 1H), 2.67 (br. s., 1H), 1.96-1.85 (m, 1H), 1.83-1.60 (m, 3H). MS (ESI): M/Z (M+1): 314.

Intermediate 23L

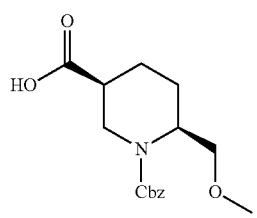

(a) (3S,6S)-1-benzyl 3-methyl 6-(methoxymethyl)piperidine-1,3-dicarboxylate

To a solution of (3S,6S)-1-benzyl 3-methyl 6-(hydroxymethyl)piperidine-1,3-dicarboxylate (0.62 g, 2.0 mmol) in 6 mL of DCM was added 40% aqueous tetrafluoroboric acid (1.1 g, 5.0 mmol) and then a solution of trimethylsilyldiazomethane (2.0 M hexanes, 2.5 mL, 5.0 mmol) dropwise at 0° C. The reaction mixture was stirred at 0° C. for 0.5 h then at 25° C. for 2 h. The mixture was poured into aq. NaHCO₃, and then extracted with DCM. The organic layer was dried over Na₂SO₄, concentrated in vacuo, then purified by column chromatography with silica gel eluted by 0~30% ethyl acetate in petroleum ether to give the title compound (0.4 g). ¹HNMR (400 MHz, CDCl3): δ=7.31~7.37 (m, 5 H), 5.15 (s, 2 H), 4.25~4.53 (m, 2 H), 3.68 (s, 3 H), 3.44~3.50 (m, 2 H), 3.35 (s, 3 H), 2.92~2.99 (m, 1 H), 2.36~2.44 (m, 1 H), 1.84~1.95 (m, 2 H), 1.66~1.75 (m, 2 H).

(b) (3S,6S)-1-((benzyloxy)carbonyl)-6-(methoxymethyl)piperidine-3-carboxylic acid To a mixture of compound (3S,6S)-1-benzyl 3-methyl 6-(methoxymethyl)piperidine-1,3-dicarboxylate (0.4 g, 1.24 mmol) in MeOH/H₂O (4 mL/2 mL) was added lithium hydroxide monohydrate (105 mg, 2.49 mmol). The reaction mixture was stirred at 25° C. overnight, concentrated in vacuo, and adjusted to pH 5~6 with 1N HCl. The reaction was extracted with EtOAc and the organic layer was washed with brine, dried over Na₂SO₄, concentrated in vacuo to give the title compound (0.37 g, yield: 96.8%). MS (ESI): M/Z (M+1): 307.8.

Intermediate 23M

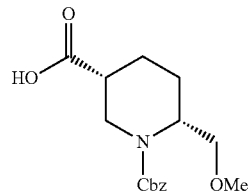

(3R,6R)-1-((benzyloxy)carbonyl)-6-(methoxymethyl)piperidine-3-carboxylic acid

The title compound was made using procedures analogous for synthesis of Intermediate 23L, starting with (3R, 6R)-1-benzyl 3-methyl 6-(hydroxymethyl)-piperidine-1,3-dicarboxylate.

Intermediate 24a and 24b

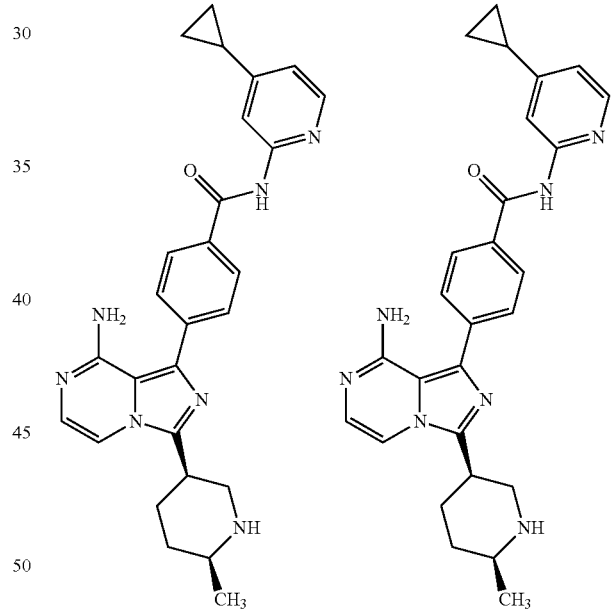

4-(8-amino-3-((cis)-6-methylpiperidin-3-yl)imidazo[1,5-a]pyrazin-1-yl)-N-(4-cyclopropylpyridin-2-yl)benzamide and 4-(8-amino-3-((trans)-6-methylpiperidin-3-yl)imidazo[1,5-a]pyrazin-1-yl)-N-(4-cyclopropylpyridin-2-yl)benzamide These intermediates were prepared, in an analogous manner as described for Intermediate 8, from Intermediate 23a or Intermediate 23b to obtain (cis)-benzyl 5-(8-amino-1-bromoimidazo[1,5-a]pyrazin-3-yl)-2-methylpiperidine-1-carboxylate and (trans)-benzyl 5-(8-amino-1-bromoimidazo pyrazin-3-yl)-2-methylpiperidine-1-carboxylate. Subsequent reaction with N-(pyridin-2-yl)-4-(4,4,5,5-tetramethyl- 1,3,2-dioxaborolan-2-yl)benzamide and deprotection with 33% HBr/HOAc as described for intermediate 9 afforded the title compounds 4-(8-amino-3-((cis)-6-methylpiperidin-3-yl)imidazo[1,5-a]pyrazin-1-yl)-N-(4-cyclopropylpyridin-2-yl)benzamide (Intermediate 24a, 800 mg, 80%) and 4-(8-amino-3-((trans)-6-methylpiperidin-3-yl)imidazo[1,5-a]pyrazin-1-yl)-N-(pyridin-2-yl)benzamide (Intermediate 246, 800 mg, 80%)

Intermediate 24C

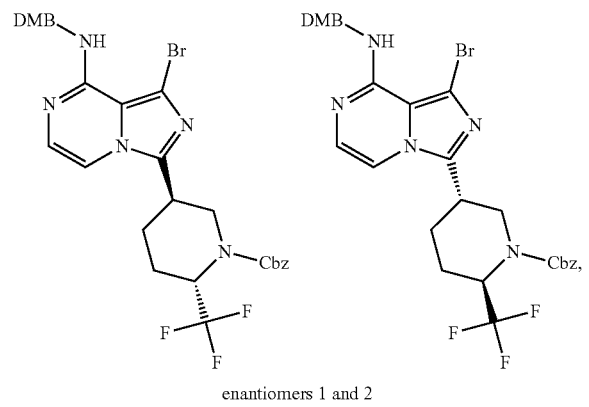

enantiomers 1 and 2

(2S,5R)-benzyl-5-(8-(2,4-dimethoxybenzylamino)-1-bromoimidazo[1,5-a]pyrazin-3-yl)-2-(trifluoromethyl)piperidine-1-carboxylate and (2R,5S)-benzyl-5-(8-(2,4-dimethoxybenzylamino)-1-bromoimidazo[1,5-a]pyrazin-3-yl)-2-(trifluoromethyl)piperidine-1-carboxylate (a) benzyl-5-(((3-chloropyrazin-2-yl)methyl)carbamoyl)-2-(trifluoromethyl)piperidine-1-carboxylate To a mixture of 1-(benzyloxycarbonyl)-6-(trifluoromethyl)piperidine-3-carboxylic acid (3.16 g, 9.55 mmol) and Et$_3$N (2.89 g, 28.6 mmol) in DCM (30 mL) was added (3-chloropyrazin-2-yl)methanamine (1.71 g, 9.55 mmol), followed by the addition of HATU (3.81 g, 10.0 mmol) under ice-bath, and the mixture was stirred for further 1 h at 0° C. The mixture was diluted with water and extracted with ethyl acetate three times. The combined organic layers were washed with brine, dried over anhydrous Na$_2$SO$_4$, and concentrated in vacuo. The residue was purified by silica gel column chromatography (petroleum ether/ethyl acetate=4/1 v/v %) to afford benzyl 5-(((3-chloropyrazin-2-yl)methyl)carbamoyl)-2-(trifluoromethyl)piperidine-1-carboxylate (4.35 g, yield 100%). MS-ESI (m/z): 457 (M+1)$^+$ (Acq Method: 10-80AB_2 min; Rt: 1.12 min).

(b) benzyl 5-(8-chloroimidazo[1,5-a]pyrazin-3-yl)-2-(trifluoromethyl)piperidine-1-carboxylate To a mixture of benzyl 5-(((3-chloropyrazin-2-yl)methyl)carbamoyl)-2-(trifluoromethyl) piperidine-1-carboxylate (2 g, 4.39 mmol) in CH$_3$CN (15 mL) was added POCl$_3$ (1.01 g, 4.39 mmol) dropwise, followed by 5 drops of DMF, the mixture was heated to 55~60° C. and stirred for 2 h at this temperature. After cooling, the mixture was quenched with ice-water and extracted with DCM three times. The combined organic layers were washed with brine, dried over anhydrous Na$_2$SO$_4$ and concentrated in vacuo. The residue was purified by silica gel column chromatography (petroleum ether/ethyl acetate=3/1 v/v %) to afford benzyl 5-(8-chloroimidazo[1,5-a]pyrazin-3-yl)-2-(trifluoromethyl)piperidine-1-carboxylate (1.1 g, 57.3%). MS-ESI (m/z): 439 (M+1)$^+$ (Acq Method: 10-80AB_2 min; Rt: 1.26 min).

(c) benzyl-5-(1-bromo-8-chloroimidazo[1,5-a]pyrazin-3-yl)-2-(trifluoromethyl)piperidine-1-carboxylate To a solution of benzyl 5-(8-chloroimidazo[1,5-a]pyrazin-3-yl)-2-(trifluoromethyl)piperidine-1-carboxylate (2.5 g, 5.71 mmol) in DMF (15 ml) was added a solution of NBS (1.01 g, 5.71 mmol) in DMF (5 ml) dropwise under ice bath. The mixture was stirred for 1 h at room temperature, diluted with water and extracted with ethyl acetate three times. The combined organic layer was washed with brine, dried over anhydrous Na$_2$SO$_4$ and concentrated under reduced pressure. The residue was purified by silica gel column chromatography (petroleum ether/ethyl acetate=3/1 v/v %) to afford benzyl 5-(1-bromo-8-chloroimidazo[1,5-a]pyrazin-3-yl)-2-(trifluoromethyl)piperidine-1-carboxylate (2.96 g, 100%).

MS-ESI (m/z): 519 (M+1)$^+$ (Acq Method: 10-80AB_2 min; Rt: 1.34 min).

(d) benzyl-5-(8-(2,4-dimethoxybenzylamino)-1-bromoimidazo[1,5-a]pyrazin-3-yl)-2-(trifluoromethyl)piperidine-1-carboxylate A mixture of benzyl 5-(1-bromo-8-chloroimidazo[1,5-a]pyrazin-3-yl)-2-(trifluoromethyl) piperidine-1-carboxylate (2.96 g, 5.71 mmol), (2,4-dimethoxyphenyl)methanamine (1.15 g, 6.85 mmol) and K$_2$CO$_3$ (1.58 g, 11.4 mmol) in DMF (20 ml) was heated to 110° C. and stirred for 2 h. After cooling the mixture was diluted with water and extracted with DCM three times. The combined organic layers were washed with brine, dried over anhydrous Na$_2$SO$_4$ and concentrated in vacuo. The residue was purified by silica gel column chromatography (petroleum ether/ethyl acetate=2/1 v/v %) to afford benzyl 5-(8-(2,4-dimethoxybenzylamino)-1-bromoimidazo[1,5-a]pyrazin-3-yl)-2-(trifluoromethyl)piperidine-1-carboxylate (2.78 g, 74.9%). MS-ESI (m/z): 648 (M+1)$^+$ (Acq Method: 10-80AB_2 min; Rt: 1.19 min)

Separation by SFC (Column: Chiralcel OJ-3 50*4.6 mm I.D., 3 um Mobile phase: methanol (0.05% DEA) in CO$_2$ from 5% to 40% Flow rate: 4 mL/min Wavelength: 220 nm) afforded enantiomer 1: (2S,5R)-benzyl-5-(8-(2,4-dimethoxybenzylamino)-1-bromoimidazo[1,5-a]pyrazin-3-yl)-2-(trifluoromethyl)piperidine-1-carboxylate (R.T.: 1.74 Min.) and enantiomer 2: (2R,5S)-benzyl-5-(8-(2,4-dimethoxybenzylamino)-1-bromoimidazo[1,5-a]pyrazin-3-yl)-2-(trifluoromethyl)piperidine-1-carboxylate (R.T.: 2.01 Min.)

Intermediate 24D

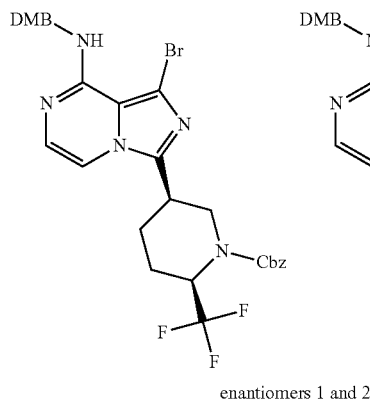

enantiomers 1 and 2

(2R,5R)-benzyl-5-(8-(2,4-dimethoxybenzylamino)-1-bromoimidazo[1,5-a]pyrazin-3-yl)-2-(trifluoromethyl)piperidine-1-carboxylate The title compound was prepared using analogous procedures as for Intermediate 24C, steps a-d, starting from (3R,6R)-1-(benzyloxycarbonyl)-6-(trifluoromethyl)piperidine-3-carboxylic acid. MS-ESI (m/z): 648 (M+1)$^+$ (Acq Method: 10-80AB_2 min; Rt: 1.15 min). This intermediate was separated by SFC (Column: Chiralcel OJ-3 50*4.6 mm I.D., 3 um Mobile phase: methanol (0.05% DEA) in CO$_2$ from 5% to 40% Flow rate: 4 mL/min Wavelength: 220 nm) to afford the enantiomer 1: (2S,5R)-benzyl-5-(8-(2,4-dimethoxybenzylamino)-1-bromoimidazo[1,5-a]pyrazin-3-yl)-2-(trifluoromethyl)piperidine-1-carboxylate (R.T.: 1.74 Min.) and enantiomer 2: (2R,5S)-benzyl-5-(8-(2,4-dimethoxybenzylamino)-1-bromoimidazo[1,5-a]pyrazin-3-yl)-2-(trifluoromethyl)piperidine-1-carboxylate (R.T.: 2.01 Min.).

Intermediate 24E

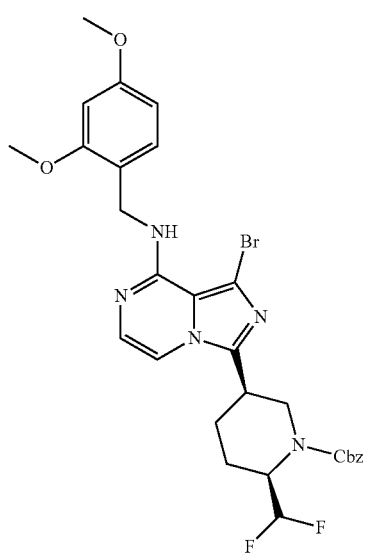

(2S,5S)-benzyl 5-(1-bromo-8-((2,4-dimethoxybenzyl)amino)imidazo[1,5-a]pyrazin-3-yl)-2-(difluoromethyl)piperidine-1-carboxylate The title compound was prepared using analogous procedures as described for intermediate 24C, steps a-d, starting from (3R,6R)-1-benzyl 3-methyl 6-(difluoromethyl)piperidine-1,3-dicarboxylate.

(2R,5R)-benzyl 5-(1-bromo-8-((2,4-dimethoxybenzyl)amino)imidazo[1,5-a]pyrazin-3-yl)-2-(difluoromethyl)piperidine-1-carboxylate (3S,6S)-1-((benzyloxy)carbonyl)-6-(difluoromethyl)piperidine-3-carboxylic acid (4.5 g, 0.014 mmol) was converted to the title compound (2.0 g) using procedures analogous to those described for Intermediate 24C, steps a-d. $^1$HNMR (400 MHz, DMSO) δ=7.52~7.60 (m, 1H), 7.30~7.37 (m, 5H), 7.10~7.14 (m, 1H), 6.78~6.98 (m, 1H), 6.53~6.57 (m, 1H), 6.39~6.44 (m, 1H), 6.25~6.29 (m, 2H), 5.06~5.15 (m, 2H), 4.43~4.55 (m, 2H), 4.17~4.22 (m, 2H), 3.83 (s, 3H), 3.72 (s, 3H), 3.21~3.30 (m, 2H), 1.81~1.97 (m, 4H).

Intermediate 24F

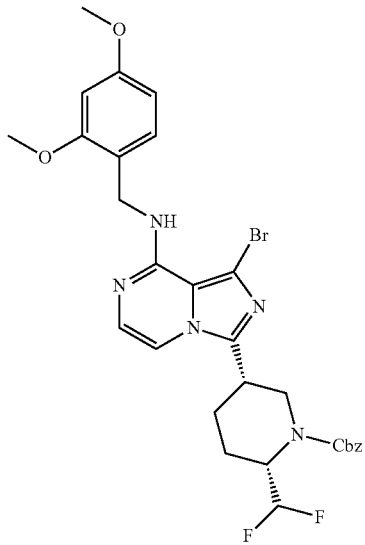

Intermediate 24G

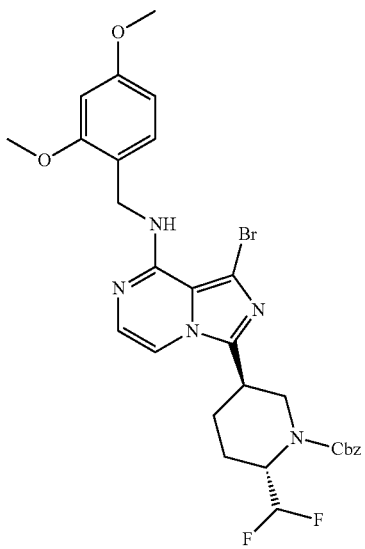

(2S,5R)-benzyl 5-(1-bromo-8-((2,4-dimethoxybenzyl)amino)imidazo[1,5-a]pyrazin-3-yl)-2-(difluoromethyl)piperidine-1-carboxylate (3S,6R)-1-((benzyloxy)carbonyl)-6-(difluoromethyl)piperidine-3-carboxylic acid (3.26 g, 0.01 mol), was converted to the title compound (3.7 g) using procedures analogous to Intermediate 24C, steps a-c. 1H NMR (400 MHz, CDCl3) δ=7.25 (s, 3H), 7.19-7.08 (m, 2H), 7.03 (d, J=5.0 Hz, 1H), 6.91 (d, J=4.8 Hz, 1H), 6.72 (t, J=5.4 Hz, 1H), 6.49 (d, J=2.3 Hz, 1H), 6.46-6.41 (m, J=2.4, 8.2 Hz, 1H), 6.19-5.83 (m, 1H), 5.00 (s, 2H), 4.66 (d, J=5.5 Hz, 2H), 4.47-4.34 (m, 1H), 4.16 (d, J=14.1 Hz, 1H), 3.87 (s, 3H), 3.79 (s, 3H), 3.53 (dd, J=3.6, 13.7 Hz, 1H), 3.21 (br. s., 1H), 2.32 (d, J=5.8 Hz, 1H), 2.24-2.09 (m, 2H), 1.95-1.84 (m, 1H). MS (ESI): M/Z (M/M+2=1/1) 630/632.

Intermediate 24H

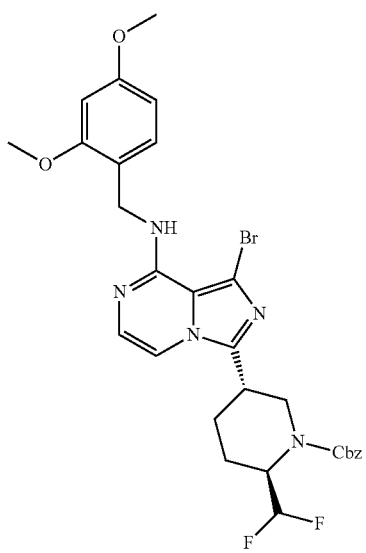

(2R,5S)-benzyl 5-(1-bromo-8-((2,4-dimethoxybenzyl)amino)imidazo[1,5-a]pyrazin-3-yl)-2-(difluoromethyl)piperidine-1-carboxylate The title compound (2.7 g) was prepared in an analogous manner as described for intermediate 24C, steps a-d, from (3R,6S)-1-benzyl 3-methyl 6-(difluoromethyl)piperidine-1,3-dicarboxylate. 1H NMR (400 MHz, CHLOROFORM-d) δ=7.38-7.22 (m, 5H), 7.20-7.09 (m, 2H), 7.04 (d, J=5.0 Hz, 1H), 6.92 (d, J=5.0 Hz, 1H), 6.73 (t, J=5.5 Hz, 1H), 6.52-6.41 (m, 2H), 6.19-5.85 (m, 1H), 5.01 (s, 2H), 4.67 (d, J=5.5 Hz, 2H), 4.49-4.34 (m, 1H), 4.17 (d, J=14.1 Hz, 1H), 3.89 (s, 3H), 3.80 (s, 3H), 3.54 (dd, J=3.9, 13.9 Hz, 1H), 3.22 (br. s., 1H), 2.40-2.27 (m, 1H), 2.25-2.10 (m, 2H), 1.95-1.84 (m, 1H). MS (ESI): M/Z (M/M+2=1/1) 499/501.

Intermediate 24I

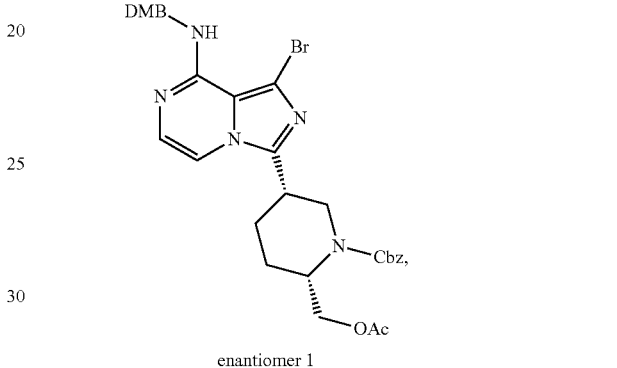

enantiomer 1

(2 S,5S)-benzyl 2-(acetoxymethyl)-5-(1-bromo-8-((2,4-dimethoxybenzyl)amino)-imidazo[1,5-a]pyrazin-3-yl)piperidine-1-carboxylate (a) trans-1-benzyl 3-methyl 6-(acetoxymethyl)piperidine-1,3-dicarboxylate To a solution of methyl 6-(acetoxymethyl)nicotinate (75 g, 358.5 mmol) in AcOH (1000 ml) was added NaBH3CN (45.2 g, 717 mmol) portionwise at r.t. The solution was stirred for overnight. The reaction mixture was concentrated under reduced pressure and the residue was dissolved in H2O (770 ml) and the pH was adjusted to 8 with aqueous NaHCO3. Then the solution was cooled to 0° C. and Cbz-Cl (122 g, 716 mmol) was added dropwise. The mixture was stirred at r.t overnight. The reaction mixture was extracted with DCM (2×500 mL). The organic layer was dried over Na2SO4 and concentrated in vacuo and the residue was purified by column chromatography with silica gel eluted by 5~30% ethyl acetate in petroleum ether, then preparative HPLC to give to trans-1-benzyl 3-methyl 6-(acetoxymethyl)piperidine-1,3-dicarboxylate (42 g, 33.6%) LCMS: Acq Method: D: \METHOD\UFLC\10-80AB_2 min.lcm, MS: M/Z (M+1): 349.9. RetTime: 1.053.

(b) trans-1-benzyl 3-methyl 6-(hydroxymethyl)piperidine-1,3-dicarboxylate

To a solution of trans-1-benzyl 3-methyl 6-(acetoxymethyl)piperidine-1,3-dicarboxylate (8.8 g, 25.2 mmol) in MeOH (88 ml) was added HCl (2.2 ml, 12M). The solution was stirred at reflux overnight, cooled to r.t and concentrated in vacuo. The residue was purified by chromatography to give 4.3 g of trans-1-benzyl 3-methyl 6-(hydroxymethyl) piperidine-1,3-dicarboxylate. 1H NMR (400 MHz, methanol-d4) δ=7.39 (s, 5H), 5.15 (s, 2H), 4.38-4.26 (m, 2H), 3.73-3.67 (m, 4H), 3.66-3.58 (m, 1H), 2.97 (br. s., 1H), 2.48 (tt, J=4.1, 11.8 Hz, 1H), 1.98-1.84 (m, 1H), 1.78-1.57 (m, 1H).

(c) (3S,6S)-1-benzyl 3-methyl 6-(hydroxymethyl) piperidine-1,3-dicarboxylate & (3R,6R)-1-benzyl 3-methyl 6-(hydroxymethyl)piperidine-1,3-dicarboxylate The racemic trans-1-benzyl 3-methyl 6-(hydroxymethyl) piperidine-1,3-dicarboxylate (4.3 g) was resolved with chiral HPLC to give two enantiomers. (Instrument: Thar 200; Column: AD 250 mm*50 mm, 5 um; Mobile phase: A: Supercritical $CO_2$, B: MeOH, A:B=85:15 at 160 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm) 1.3 g of (3S,6S)-1-benzyl 3-methyl 6-(hydroxymethyl)-piperidine-1,3-dicarboxylate and 1.1 g of (3R,6R)-1-benzyl 3-methyl 6-(hydroxymethyl)piperidine-1,3-dicarboxylate were obtained.

(d) (3S,6S)-1-((benzyloxy)carbonyl)-6-(hydroxymethyl)piperidine-3-carboxylic acid To a mixture of (3S,6S)-1-benzyl 3-methyl 6-(hydroxymethyl)piperidine-1,3-dicarboxylate (1.0 g, 3.25 mmol) in MeOH/$H_2O$ (6 mL/3 mL) was added lithium hydroxide monohydrate (273 mg, 6.5 mmol). The reaction mixture was stirred at 25° C. overnight. The mixture was concentrated in vacuo, added 1N HCl (pH 5~6), and then extracted with EA. The organic layer was washed with brine, dried over $Na_2SO_4$, concentrated in vacuo to give (3S,6S)-1-((benzyloxy)carbonyl)-6-(hydroxymethyl)piperidine-3-carboxylic acid (780 mg, yield: 81.8%). $^1$HNMR (400 MHz, $CD_3OD$): δ=7.32~7.40 (m, 5 H), 5.16 (s, 2 H), 4.30~4.36 (m, 2 H), 3.60~3.73 (m, 2 H), 2.93~3.02 (m, 1 H), 2.39~2.46 (m, 1 H), 1.89~1.97 (m, 2 H), 1.59~1.77 (m, 2 H).

(e) (2S,5R)-benzyl 5-((3-chloropyrazin-2-yl)methyl) carbamoyl)-2-(hydroxymethyl)piperidine-1-carboxylate To a solution of (3S,6S)-1-((benzyloxy)carbonyl)-6-(hydroxymethyl)piperidine-3-carboxylic acid (0.78 g, 2.66 mmol) in 20 mL of DMF was added HATU (1.21 g, 3.2 mmol). After stirring for 30 min under $N_2$, (3-Chloropyrazin-2-yl) methanamine hydrochloride (0.48 g, 2.66 mol) and $Et_3N$ (0.8 g, 7.98 nmol) were added. The reaction mixture was stirred at room temperature for 12 h under $N_2$. The mixture was partitioned between EtOAc and water. The organic layer was washed with 1 N HCl and water, dried over sodium sulfate, filtered and concentrated in vacuum. The residue was purified by silica gel column chromatography to afford (2S,5R)-benzyl 5-(((3-chloropyrazin-2-yl) methyl)carbamoyl)-2-(hydroxymethyl) piperidine-1-carboxylate (0.7 g, yield: 63.0%). $^1$HNMR (400 MHz, $CD_3OD$): δ=8.50~8.54 (m, 1 H), 8.35 (d, J=2.4 Hz, 1 H), 7.31~7.41 (m, 5 H), 5.16 (s, 2 H), 4.63 (s, 2 H), 4.34~4.38 (m, 1 H), 4.21~4.25 (m, 1 H), 3.72~3.77 (m, 1 H), 3.63~3.67 (m, 1 H), 3.01~3.07 (m, 1 H), 2.46~2.54 (m, 1 H), 1.80~1.93 (m, 3 H), 1.61~1.71 (m, 1 H). MS (ESI): M/Z (M+1): 419.1.

(f) (2S,5R)-benzyl 2-(acetoxymethyl)-5-(((3-chloropyrazin-2-yl)methyl)-carbamoyl)piperidine-1-carboxylate To a mixture of (2S,5R)-benzyl 5-(((3-chloropyrazin-2-yl)methyl)carbamoyl)-2-(hydroxymethyl) piperidine-1-carboxylate (500 mg, 1.2 mmol) in 4 mL of DCM was added acetyl chloride (141 mg, 1.8 mmol) and pyridine (190 mg, 2.4 mmol). The reaction mixture was stirred at 25° C. overnight. The mixture was poured into aq. $NH_4Cl$, and then extracted with DCM. The organic layer was dried over $Na_2SO_4$, concentrated in vacuo and purified by flash chromatography to give (2S,5R)-benzyl 2-(acetoxymethyl)-5-(((3-chloropyrazin-2-yl)methyl)carbamoyl) piperidine-1-carboxylate (240 mg, yield: 43.6%). $^1$HNMR (400 MHz, $CD_3OD$): δ=8.31~8.50 (m, 2 H), 7.29~7.36 (m, 5 H), 5.10~5.15 (m, 2 H), 4.55~4.61 (m, 3 H), 4.12~4.38 (m, 3 H), 3.04~3.14 (m, 1 H), 2.46~2.54 (m, 1 H), 1.66~1.86 (m, 7 H). MS (ESI): M/Z (M+1): 461.0.

(g) (2R,5R)-benzyl 2-(acetoxymethyl)-5-(1-bromo-8-((2,4-dimethoxybenzyl)amino)imidazo[1,5-a] pyrazin-3-yl)piperidine-1-carboxylate (2S,5R)-benzyl 2-(acetoxymethyl)-5-(((3-chloropyrazin-2-yl)methyl)-carbamoyl)piperidine-1-carboxylate (100 mg, 0.22 mmol) was converted to the title compound (90 mg) using procedures analogous to those described for synthesis of Intermediate 24C, steps b-d. $^1$HNMR (400 MHz, CDCl3): δ=7.34~7.38 (m, 5 H), 7.10~7.14 (m, 1 H), 6.90~6.99 (m, 1 H), 6.74~6.76 (m, 1 H), 6.43~6.50 (m, 2 H), 5.11~5.23 (m, 2 H), 4.65~4.71 (m, 3 H), 4.18~4.39 (m, 3 H), 3.88 (s, 3 H), 3.80 (s, 3 H), 2.98~3.24 (m, 2 H), 1.81~1.98 (m, 7 H). MS (ESI): M/Z (M/M+2=1/1) 652.1/654.1.

Intermediate 24I

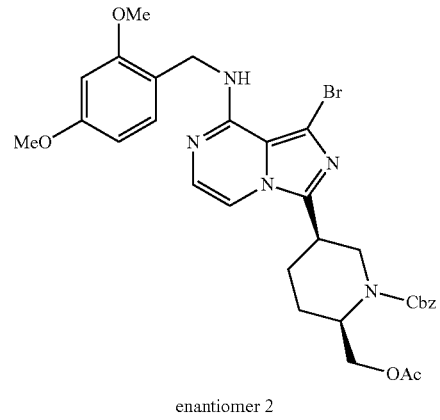

enantiomer 2

(2R,5R)-benzyl 2-(acetoxymethyl)-5-(1-bromo-8-((2,4-dimethoxybenzyl)amino)-imidazo[1,5-a] pyrazin-3-yl)piperidine-1-carboxylate The title compound (90 mg) was prepared using analogous procedures as Intermediate 24I_a. $^1$HNMR (400 MHz, CDCl3): δ=7.34~7.38 (m, 5 H), 7.10~7.14 (m, 1 H), 6.90~6.99 (m, 1 H), 6.74~6.76 (m, 1 H), 6.43~6.50 (m, 2 H), 5.11~5.23 (m, 2 H), 4.65~4.71 (m, 3 H), 4.18~4.39 (m, 3 H), 3.88 (s, 3 H), 3.80 (s, 3 H), 2.98~3.24 (m, 2 H), 1.81~1.98 (m, 7 H). MS (ESI): M/Z (M/M+2=1/1) 652.1/654.1.

Intermediate 24J_E1

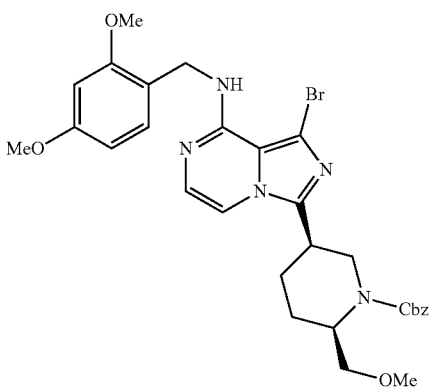

trans-benzyl 5-(1-bromo-8-((2,4-dimethoxybenzyl)amino)imidazo[1,5-a]pyrazin-3-yl)-2-(methoxymethyl)piperidine-1-carboxylate (a) (2R,5R)-benzyl 5-(((3-chloropyrazin-2-yl)methyl)carbamoyl)-2-(methoxymethyl)piperidine-1-carboxylate To a solution of compound (3R,6R)-1-((benzyloxy)carbonyl)-6-(methoxymethyl)piperidine-3-carboxylic acid (Intermediate 23M, 0.37 g, 1.2 mmol) in 4 mL of DMF was added HATU (0.55 g, 1.44 mmol). After stirring for 30 min under N2, (3-Chloro-pyrazin-2-yl)-methanamine hydrochloride (0.22 g, 1.2 mol) and Et3N (0.36 g, 3.6 nmol) was added. The reaction mixture was stirred at room temperature for 12 h under $N_2$. The mixture was partitioned between EtOAc and water. The organic layer was washed with 1 N HCl and water, dried over sodium sulfate, filtered and concentrated in vacuo. The residue was purified by silica gel column chromatography (eluent) to afford the title compound (0.4 g). $^1$HNMR (400 MHz, CDCl3): δ=8.43 (d, J=2.4 Hz, 1 H), 8.33 (d, J=2.4 Hz, 1 H), 7.30~7.38 (m, 5 H), 6.86 (s, 1 H), 5.16 (s, 2 H), 4.68 (d, J=4.4 Hz, 2 H), 4.30~4.52 (m, 2 H), 3.47~3.57 (m, 2 H), 3.34 (s, 3 H), 3.03~3.10 (m, 1 H), 2.37~2.42 (m, 1 H), 1.84~1.87 (m, 2 H), 1.59~1.67 (m, 2 H). MS (ESI): M/Z (M+1): 433.0.

(b) (2R,5R)-benzyl 5-(8-chloroimidazo[1,5-a]pyrazin-3-yl)-2-(methoxymethyl)-piperidine-1-carboxylate To a solution of compound (2S,5S)-benzyl 5-(((3-chloropyrazin-2-yl)methyl)carbamoyl)-2-(methoxymethyl)piperidine-1-carboxylate (390 mg, 0.9 mmol) in 4 mL of anhydrous acetonitrile was added POCl3 (0.69 g, 4.5 mmol) at an ice-water bath. DMF (0.2 mL) was then added and the resulting mixture was stirred at room temperature under N2 overnight. The mixture was poured into aq. NaHCO3 slowly, then extracted with DCM. The organic layer was washed with brine, dried over $Na_2SO_4$, concentrated in vacuo, and purified by flash chromatography to give the title compound (350 mg). $^1$HNMR (400 MHz, CDCl3): δ=7.78 (d, J=12.8 Hz, 1 H), 7.72 (d, J=4.8 Hz, 0.5 H), 7.33~7.44 (m, 6 H), 7.17 (d, J=4.8 Hz, 0.5 H), 5.12~5.24 (m, 2 H), 4.53~4.68 (m, 1 H), 4.22~4.39 (m, 1 H), 3.52~3.76 (m, 3 H), 3.39 (s, 3 H), 2.13~2.27 (m, 1 H), 1.84~2.00 (m, 4 H). MS (ESI): M/Z (M+1): 414.9.

(c) (2R,5R)-benzyl 5-(1-bromo-8-((2,4-dimethoxybenzyl)amino)imidazo[1,5-a]pyrazin-3-yl)-2-(methoxymethyl)piperidine-1-carboxylate The title compound (395 mg) was prepared using analogous procedures as described for Intermediate 24C, steps a-d, starting from (2R,5R)-benzyl 5-(8-chloroimidazo[1,5-a]pyrazin-3-yl)-2-(methoxymethyl)piperidine-1-carboxylate (350 mg, 0.84 mmol). $^1$HNMR (400 MHz, DMSO-d6): δ=7.51~7.62 (m, 1 H), 7.30~7.38 (m, 5 H), 6.98~7.16 (m, 2 H), 6.80 (s, 1 H), 6.60 (s, 1 H), 6.46 (d, J=8.4 Hz, 1 H), 5.05~5.16 (m, 2 H), 4.57 (s, 2 H), 4.43 (s, 1 H), 4.04~4.13 (m, 1 H), 3.86 (s, 3 H), 3.74 (s, 3 H), 3.44~3.62 (m, 3 H), 3.05~3.28 (m, 4 H), 1.75~1.78 (m, 4 H). MS (ESI): M/Z (M/M+2=1/1) 624.1/626.1.

Intermediate 24J_E2

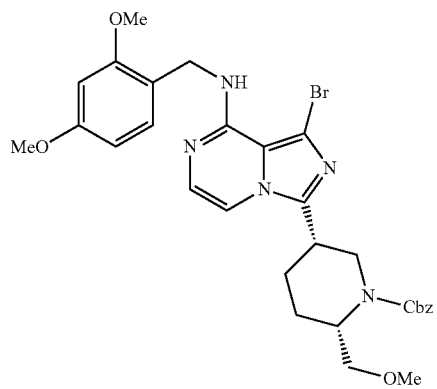

(2S,5S)-benzyl 5-(1-bromo-8-((2,4-dimethoxybenzyl)amino)imidazo[1,5-a]pyrazin-3-yl)-2-(methoxymethyl)piperidine-1-carboxylate The title compound was made from (3S,6S)-1-((benzyloxy)carbonyl)-6-(methoxymethyl)piperidine-3-carboxylic acid (Intermediate 23L) following the same procedure of intermediate 24J_EL. $^1$HNMR (400 MHz, DMSO-d6): δ=11.38 (s, 1 H), 8.70 (d, J=5.2 Hz, 1 H), 8.59 (s, 1 H), 8.17 (d, J=4.8 Hz, 2 H), 7.56~7.74 (m, 4 H), 7.33~7.40 (m, 5 H), 7.09~7.18 (m, 2 H), 6.50 (s, 1 H), 6.43 (d, J=8.0 Hz, 1 H), 5.85 (s, 1 H), 5.07~5.18 (m, 2 H), 4.50 (s, 3 H), 4.14~4.23 (m, 1 H), 3.71 (s, 3 H), 3.48~3.61 (m, 6 H), 3.18~3.29 (m, 4 H), 1.74~1.93 (m, 4 H). MS (ESI): M/Z (M+1): 810.4.

Intermediate 24K

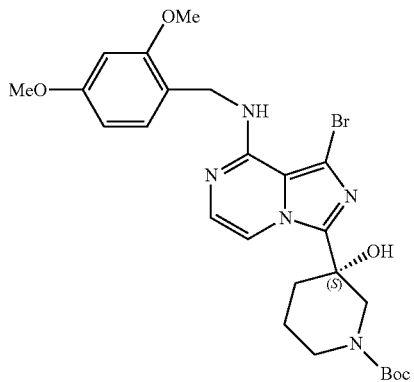

(a) N-((3-chloropyrazin-2-yl)methyl)formamide

To a solution of compound (3-chloropyrazin-2-yl)methanamine hydrochloride (45 g, 0.25 mol) in HC(OMe)$_3$ (350 mL) was stirred at 110° C. under N$_2$ for 12 h. The reaction was concentrated, then taken up in DCM. The organic phase was washed with H$_2$O and brine, dried over Na$_2$SO$_4$, and concentrated under reduced pressure to give compound N-((3-chloropyrazin-2-yl)methyl)formamide (38 g, yield 88.4%). $^1$HNMR (400 MHz, DMSO-d6): δ=8.64 (d, J=2.4 Hz, 1 H), 8.45 (d, J=2.4 Hz, 1 H), 8.18 (s, 1 H), 4.57 (d, J=5.6 Hz, 2 H).

(b) 8-chloroimidazo[1,5-a]pyrazine

POCl$_3$ (170 g, 1.11 mol) was added to a solution of compound N-((3-chloropyrazin-2-yl)methyl)formamide (38 g, 0.22 mol) in ACN (400 mL) at 0° C., NBS (12 g, 67.1 mmol) was added dropwise for 5 min. The reaction mixture was stirred at r.t. for 4 h. The mixture was filtered, and the filtrate was washed by NaHCO$_3$. The crude product was purified by column chromatography on silica gel eluted with petroleum ether/EtOAc to give compound 8-chloroimidazo[1,5-a]pyrazine (18 g, yield 52.9%). $^1$HNMR (400 MHz, DMSO-d6): δ=8.69 (s, 1 H), 8.39 (d, J=5.2 Hz, 1H), 7.85 (s, 1 H), 7.41 (d, J=5.2 Hz, 1 H).

(c) tert-butyl 3-(8-chloroimidazo[1,5-a]pyrazin-3-yl)-3-hydroxypiperidine-1-carboxylate A mixture of compound 8-chloroimidazo[1,5-a]pyrazine (5 g, 32.56 mmol) in tetrahydrofuran (150 mL) was added n-BuLi (18 mL, 39.07 mmol) dropwise at −78° C. The mixture was stirred at −78° C. over 30 min. Then the reaction mixture was added a solution of 3-oxo-piperidine-1-carboxylic acid tert-butyl ester (12.97 g, 65.12 mmol) in tetrahydrofuran dropwise. Then the reaction mixture was warmed to room temperature over a period of 1 h. The reaction mixture was quenched with saturated NaHCO$_3$, extracted with ethyl acetate (3×250 mL). The combined organic layers were washed with brine, dried over sodium sulfate, filtered and concentrated to afford the crude product, which was purified on silica gel column chromatography to give the title compound (8.0 g, 70% yield). $^1$HNMR (400 MHz, CDCl$_3$) d=8.46 (d, J=4.8 Hz, 1H), 7.74 (d, J=0.8 Hz, 1H), 7.26 (s, 1H), 4.27 (br. s., 1H), 4.06 (d, J=13.6 Hz, 1H), 3.57 (d, J=11.0 Hz, 1H), 3.01-2.89 (m, 1H), 2.22-2.06 (m, 2H), 2.03-1.89 (m, 1H), 1.83-1.68 (m, 2H), 1.52-1.35 (m, 9H). MS (EI): M/Z (M+1): 353.1.

(d) tert-butyl 3-(1-bromo-8-chloroimidazo[1,5-a]pyrazin-3-yl)-3-hydroxypiperidine-1-carboxylate To a solution of compound tert-butyl 3-(8-chloroimidazo[1,5-a]pyrazin-3-yl)-3-hydroxypiperidine-1-carboxylate (5 g, 14.17 mmol) in N,N-dimethyl-formamide (50 mL) was added 1-bromo-pyrrolidine-2,5-dione (2.77 g, 15.587 mmol). The resulting mixture was stirred at room temperature for 2 h. The reaction mixture was quenched with saturated sodium bicarbonate and extracted with ethyl acetate. The combined organic layer was washed with brine 3 times, dried over anhydrous sodium sulfate and evaporated to give compound tert-butyl 3-(1-bromo-8-chloroimidazo[1,5-a]pyrazin-3-yl)-3-hydroxypiperidine-1-carboxylate (4.6 g, yield 75%). MS (EI): M/Z (M+1): 431.0

(e) (S)-tert-butyl 3-(1-bromo-8-((2,4-dimethoxybenzyl)amino)imidazo[1,5-a]pyrazin-3-yl)-3-hydroxypiperidine-1-carboxylate A mixture of tert-butyl 3-(1-bromo-8-chloroimidazo[1,5-a]pyrazin-3-yl)-3-hydroxypiperidine-1-carboxylate (4.6 g, 10.65 mmol) 2,4-dimethoxy-benzylamine and K$_2$CO$_3$ (5.34 g, 31.95 mmol) in DMF (50 mL) was stirred at 90° C. for 15 h. The mixture was extracted with ethyl acetate. The combined organic layer was dried over sodium sulfate, filtered and concentrated in vacuum. The residue was purified by silica gel column chromatography to give title compound (3.8 g). MS (EI): M/Z (M+1): 562.1. The enantiomers were purified by SFC chiral separation (AD column) to obtain (S)-tert-butyl 3-(1-bromo-8-((2,4-dimethoxybenzyl)amino)imidazo[1,5-a]pyrazin-3-yl)-3-hydroxypiperidine-1-carboxylate. Then it was purified by SFC separation (Instrument: Thar 200; Column AD 250 mm*50 mm, 20 um; Mobile phase: A: Supercritical CO$_2$, B: EtOH (0.05% NH$_3$H$_2$O), A:B=65:35 at 200 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to give (S)-tert-butyl 3-(1-bromo-8-((2,4-dimethoxybenzyl)amino)imidazo[1,5-a]pyrazin-3-yl)-3-hydroxypiperidine-1-carboxylate.

Intermediate 24L

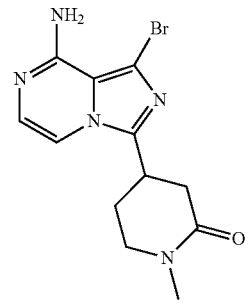

4-(8-amino-1-bromoimidazo[1,5-a]pyrazin-3-yl)-1-methylpiperidin-2-one

(a) methyl 2-oxopiperidine-4-carboxylate

To a solution of 2-oxopiperidine-4-carboxylic acid (10.0 g, 69.9 mmol) and potassium carbonate (29.0 g, 209.6 mmol) in acetonitrile (200 ml) was added iodomethane (29.7 g, 209.6 mmol) under nitrogen protection. The mixture was heated to 70° C. for 12 h, then allowed to cool to room temperature. The mixture was filtered, and the filtrate was diluted with water and extracted with dichloromethane (4×150 mL). The organic layer was washed with brine, dried over sodium sulfate, filtered and concentrated in vacuo to afford methyl 2-oxopiperidine-4-carboxylate (7.0 g) as a white solid. $^1$HNMR (CDCl3 400 MHz): δ 6.40 (s, 1 H), 3.73 (s, 3 H), 3.40-3.32 (m, 2 H), 2.88-2.81 (m, 1 H), 2.60-2.58 (m, 2 H), 2.15-2.11 (m, 1 H), 1.96-1.89 (m, 1 H).

(b) methyl 1-methyl-2-oxopiperidine-4-carboxylate

To 2-oxopiperidine-4-carboxylic acid (1.0 g, 6.36 mmol) in DMF (20 ml) was added NaH (508 mg, 12.7 mmol) portionwise, the mixture was stirred at 0° C. for one h. Iodomethane (1.8 g, 12.73 mmol) was added, and the mixture was stirred at room temperature for 10 h. The mixture was quenched with saturated ammonium chloride, the resulting solution was extracted with dichloromethane (4×50 mL). The organic layer was washed with brine, dried over sodium sulfate, filtered and concentrated in vacuo under reduced pressure to afford methyl 1-methyl-2-oxopiperidine-4-carboxylate (1.0 g) as a yellow oil. $^1$HNMR (CDCl$_3$ 400 MHz): δ 3.71 (s, 3 H), 3.46-3.30 (m, 2 H), 2.94 (s, 3 H), 2.87-2.77 (m, 1 H), 2.68-2.50 (m, 2 H), 2.17-2.11 (m, 1 H), 2.01-1.88 (m, 1 H).

(c) 1-methyl-2-oxopiperidine-4-carboxylic acid

A mixture of methyl 1-methyl-2-oxopiperidine-4-carboxylate (1.0 g, 5.84 mmol), sodium hydroxide (467 mg, 11.7 mmol), methanol (15 ml) and water (10 ml) was stirred at 60° C. for 3 h. The mixture was concentrated in vacuo, then acidified with 2M HCl and then concentrated under reduced pressure. The residue was taken up with THF and stirred at room temperature for one h, filtered and the filtrate was concentrated to give 1-methyl-2-oxopiperidine-4-carboxylic acid (450 mg). $^1$HNMR (DMSO-d6 400 MHz): δ 12.46 (br, 1H), 3.28-3.20 (m, 2 H), 2.79-2.73 (m, 4 H), 2.34-2.31 (m, 1 H), 1.82-1.76 (m, 1 H).

(d) 1-Methyl-2-oxo-piperidine-4-carboxylic acid (3-chloro-pyrazin-2-ylmethyl)amide To a solution of 1-methyl-2-oxopiperidine-4-carboxylic acid (450 mg, 2.86 mmol) in anhydrous dichloromethane (5 ml) was added isobutyl-chloroformate (469 mg, 3.44 mmol) and triethylamine (579 mg, 5.73 mmol) at 0° C. The mixture was stirred at 0° C. and brought to room temperature over one h. Then c-(3-chloro-pyrazin-2-yl)-methylamine (567 mg, 3.15 mmol) and triethylamine (435 mg, 4.30 mmol) were added and the mixture was stirred at room temperature over 3 h, then concentrated. Purification by column chromatography with silica gel eluted by 0~70% ethyl acetate in petroleum ether provided the title compound (400 mg) as a yellow solid. $^1$HNMR (400 MHz, CDCl$_3$): δ=8.47 (d, J=2.4 Hz, 1H), 8.30 (d, J=2.4 Hz, 1 H), 7.76 (s, 1 H), 4.71 (d, J=4.8 Hz, 2 H), 3.41-3.30 (m, 2 H), 2.97-2.81 (m, 5 H), 2.49-2.43 (m, 1 H), 2.40-2.32 (m, 1 H), 1.88-1.78 (m, 1 H). MS (APCI): M/Z (M+1): 283.1

(e) 4-(8-Chloro-imidazo[1,5-a]pyrazin-3-yl)-1-methyl-piperidin-2-one

To a solution of 1-methyl-2-oxo-piperidine-4-carboxylic acid (3-chloro-pyrazin-2-ylmethyl)-amide (1.0 g, 3.54 mmol) and DMF (0.1 ml) in anhydrous acetonitrile (10 ml) was added phosphorusoxychloride (2.71 g, 17.9 mmol) portionwise at an ice-water bath. The resulting mixture was stirred at room temperature for 12 h. The mixture was poured to an ice-water mixture, neutralized with powered sodium bicarbonate, extracted with dichloromethane. The combined organic layer was dried over sodium sulfate, filtered and concentrated in vacuum. The residue was purified by silica gel column chromatography to give 4-(8-Chloro-imidazo[1,5-a]pyrazin-3-yl)-1-methyl-piperidin-2-one (200 mg, yield 21%) as a yellow solid. $^1$HNMR (400 MHz, CDCl3): δ=7.91 (d, J=5.2 Hz, 1 H), 7.82 (s, 1 H), 7.38 (d, J=5.2 Hz, 1 H), 3.50-3.45 (m, 2 H), 3.37-3.17 (m, 3 H), 3.07-3.03 (m, 1 H), 2.81 (s, 3 H), 2.43-2.36 (m, 1 H), 2.01-1.91 (m, 1 H). MS (APCI): M/Z (M+1): 265.1

(f) 4-(1-Bromo-8-chloro-imidazo[1,5-a]pyrazin-3-yl)-1-methyl-piperidin-2-one

To a solution of 4-(8-chloro-imidazo[1,5-a]pyrazin-3-yl)-1-methyl-piperidin-2-one (135 mg, 0.51 mmol) in acetonitrile (5 ml) was added N-bromosuccinimide (108 mg, 0.61 mmol). The resulting mixture was stirred at room temperature for 1 h. The mixture was diluted with water, extracted with dichloromethane (3×30 mL). The combined organic layers were washed with brine, dried, filtered and concentrated to give 4-(1-Bromo-8-chloro-imidazo[1,5-a]pyrazin-3-yl)-1-methyl-piperidin-2-one (130 mg). 1H NMR (400 MHz, CDCl3) δ=7.90 (d, J=5.0 Hz, 1H), 7.32 (d, J=5.0 Hz, 1H), 3.72 (d, J=7.0 Hz, 1H), 3.42-3.38 (m, 1H), 3.34 (d, J=8.3 Hz, 1H), 3.27-3.22 (m, 1H), 3.19-3.14 (m, 1H), 2.82 (s, 3H), 2.44-2.33 (m, 1H), 2.02-1.92 (m, 2H). MS (EI): M/Z (M+1): 342.0/344.0

(g) 4-(8-Amino-1-bromo-imidazo[1,5-a]pyrazin-3-yl)-1-methyl-piperidin-2-one

A mixture of 4-(1-Bromo-8-chloro-imidazo[1,5-a]pyrazin-3-yl)-1-methyl-piperidin-2-one (100 mg, 0.29 mmol) in 2-propanol (3 ml) and ammonium hydroxide (3 ml) was stirred in a sealed tube at 100° C. for 10 h. The reaction was brought to room temperature, the mixture was concentrated and purified by column chromatography with silica gel eluted by 10~40% ethyl acetate in petroleum ether give 4-(8-Amino-1-bromo-imidazo[1,5-a]pyrazin-3-yl)-1-methyl-piperidin-2-one (70 mg) as a yellow solid. UPLC(C) R$_t$: 0.78 min; m/z 325.6 (M+H)$^+$.

Intermediate 24M

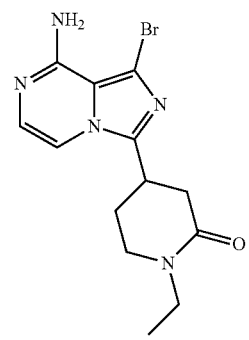

4-(8-amino-1-bromoimidazo[1,5-a]pyrazin-3-yl)-1-ethylpiperidin-2-one 100 mg of 4-(8-amino-1-bromoimidazo[1,5-a]pyrazin-3-yl)-1-ethylpiperidin-2-one was prepared using same procedure of Intermediate 24L. UPLC(C) R$_t$: 0.83 min; m/z 339 (M+H)$^+$.

The following Examples were synthesized following the methods described for Intermediate 24a and 24b and examples 46-49.

| Example | Structure | Name | LC-MS [M + H]+ | Retention time |
|---|---|---|---|---|
| 182 | 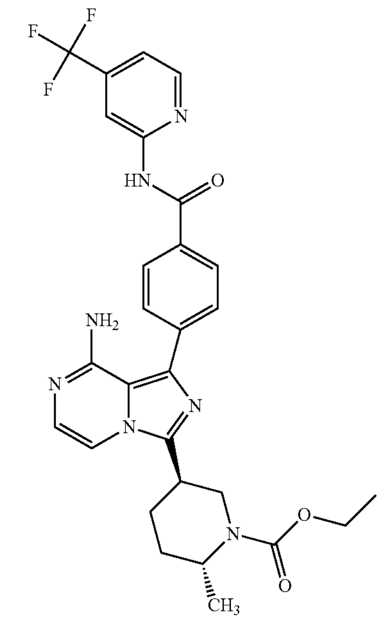 [SMILES: CCOC(=O)N1C[C@H](c2nc(-c3ccc(C(=O)Nc4cc(C(F)(F)F)ccn4)cc3)c3c(N)nccn23)CC[C@H]1C] | (trans)-ethyl 5-(8-amino-1-(4-(4-(trifluoromethyl)pyridin-2-ylcarbamoyl)phenyl)imidazo[1,5-a]pyrazin-3-yl)-2-methylpiperidine-1-carboxylate, TFA salt | 568.2 | 2.78 min |
| 183 | 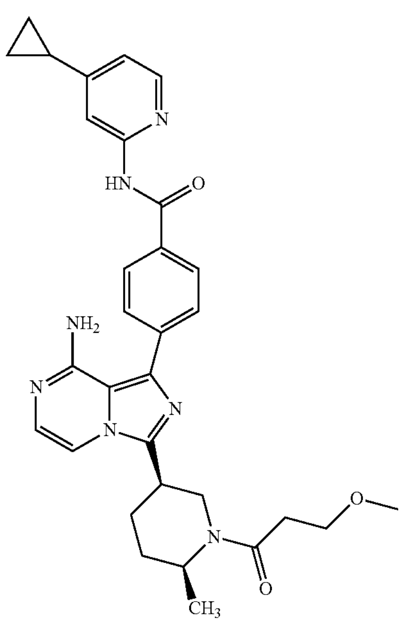 [SMILES: COCCC(=O)N1C[C@H](c2nc(-c3ccc(C(=O)Nc4cc(C5CC5)ccn4)cc3)c3c(N)nccn23)CC[C@@H]1C] | 4-(8-amino-3-((cis)-1-(3-methoxypropanoyl)-6-methylpiperidin-3-yl)imidazo[1,5-a]pyrazin-1-yl)-N-(4-cyclopropylpyridin-2-yl)benzamide, TFA salt | 554.3 | 2.30 min |

| Example | Structure | Name | LC-MS [M + H]+ | Retention time |
|---|---|---|---|---|
| 184 | 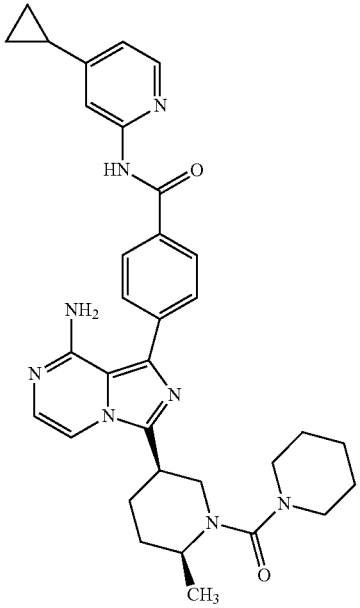 [SMILES: C[C@H]1CC[C@@H](c2nc(-c3ccc(C(=O)Nc4cc(C5CC5)ccn4)cc3)c3c(N)nccn23)CN1C(=O)N1CCCCC1] | 4-(8-amino-3-((cis)-6-methyl-1-(piperidine-1-carbonyl)piperidin-3-yl)imidazo[1,5-a]pyrazin-1-yl)-N-(4-cyclopropylpyridin-2-yl)benzamide, TFA salt | 579.2 | 2.02 min |
| 185 | 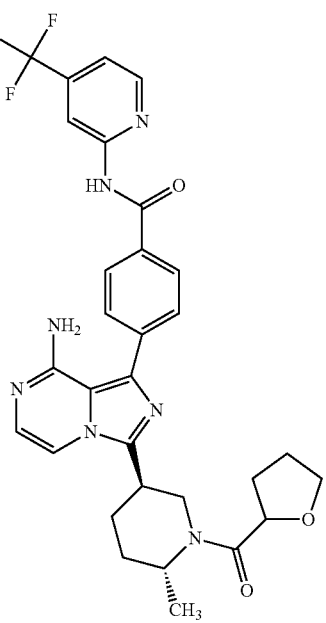 | 4-(8-amino-3-((trans)-6-methyl-1-(tetrahydrofuran-2-carbonyl)piperidin-3-yl)imidazo[1,5-a]pyrazin-1-yl)-N-(4-(trifluoromethyl)pyridin-2-yl)benzamide, TFA salt | 594.2 | 2.59 min |

| Example | Structure | Name | LC-MS [M + H]+ | Retention time |
|---------|-----------|------|----------------|----------------|
| 186 | 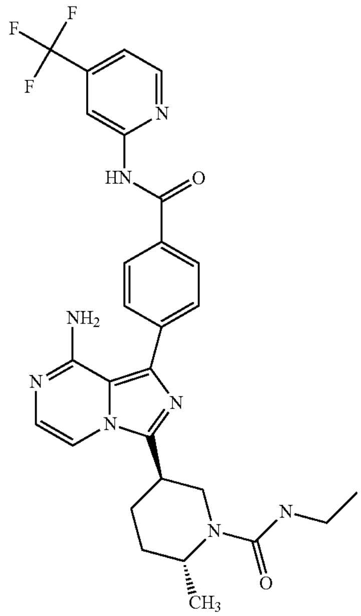 [SMILES: CCNC(=O)N1C[C@H](c2nc(-c3ccc(C(=O)Nc4cc(C(F)(F)F)ccn4)cc3)c3c(N)nccn23)CC[C@H]1C] | (trans)-5-(8-amino-1-(4-(4-(trifluoromethyl)pyridin-2-ylcarbamoyl)phenyl)imidazo[1,5-a]pyrazin-3-yl)-N-ethyl-2-methylpiperidine-1-carboxamide, TFA salt | 567.2 | 2.55 min |
| 187 | 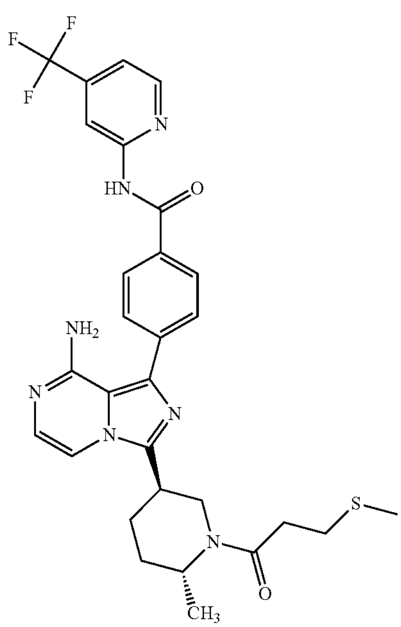 [SMILES: CSCCC(=O)N1C[C@H](c2nc(-c3ccc(C(=O)Nc4cc(C(F)(F)F)ccn4)cc3)c3c(N)nccn23)CC[C@H]1C] | 4-(8-amino-3-((trans)-6-methyl-1-(3-(methylthio)propanoyl)piperidin-3-yl)imidazo[1,5-a]pyrazin-1-yl)-N-(4-(trifluoromethyl)pyridin-2-yl)benzamide, TFA salt | 598.2 | 2.69 min |

-continued

| Example | Structure | Name | LC-MS [M + H]+ | Retention time |
|---|---|---|---|---|
| 188 | 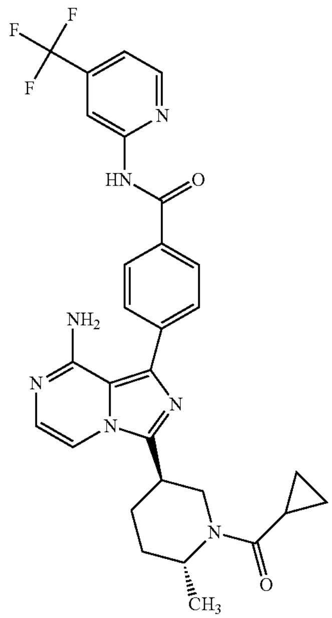 [SMILES: C[C@@H]1CC[C@@H](c2nc(-c3ccc(C(=O)Nc4cc(C(F)(F)F)ccn4)cc3)c3c(N)nccn23)CN1C(=O)C1CC1] | 4-(8-amino-3-((trans)-1-(cyclopropanecarbonyl)-6-methylpiperidin-3-yl)imidazo[1,5-a]pyrazin-1-yl)-N-(4-(trifluoromethyl)pyridin-2-yl)benzamide, TFA salt | 564.3 | 2.82 min |
| 189 | 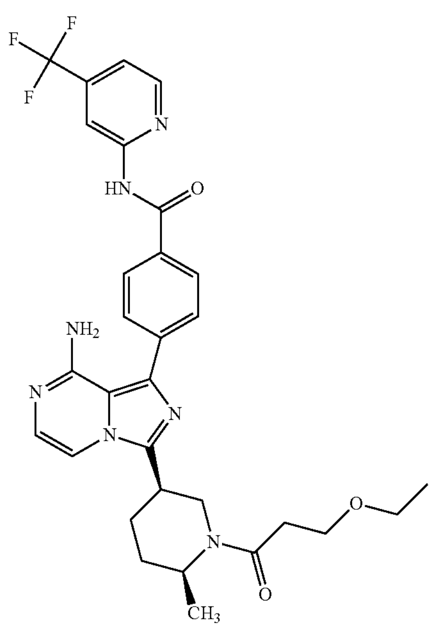 [SMILES: CCOCCC(=O)N1C[C@H](c2nc(-c3ccc(C(=O)Nc4cc(C(F)(F)F)ccn4)cc3)c3c(N)nccn23)CC[C@@H]1C] | 4-(8-amino-3-((cis)-1-(3-ethoxypropanoyl)-6-methylpiperidin-3-yl)imidazo[1,5-a]pyrazin-1-yl)-N-(4-(trifluoromethyl)pyridin-2-yl)benzamide, TFA salt | 596.2 | 2.48 min |

| Example | Structure | Name | LC-MS [M + H]+ | Retention time |
|---|---|---|---|---|
| 190 | 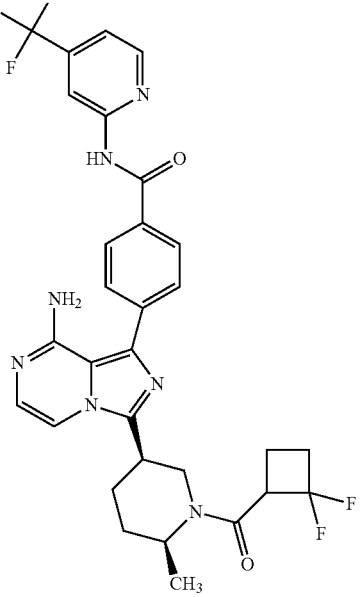 | 4-(8-amino-3-((cis)-1-(2,2-difluorocyclobutanecarbonyl)-6-methylpiperidin-3-yl)imidazo[1,5-a]pyrazin-1-yl)-N-(4-(trifluoromethyl)pyridin-2-yl)benzamide, TFA salt | 614.2 | 2.77 min |
| 191 | 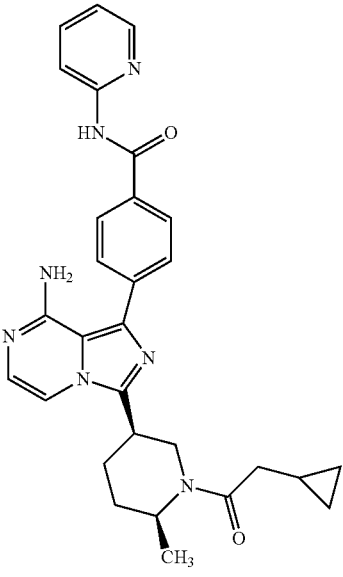 [SMILES: C[C@H]1CC[C@@H](c2nc(-c3ccc(C(=O)Nc4ccccn4)cc3)c3c(N)nccn23)CN1C(=O)CC1CC1] | 4-(8-amino-3-((cis)-1-(2-cyclopropylacetyl)-6-methylpiperidin-3-yl)imidazo[1,5-a]pyrazin-1-yl)-N-(pyridin-2-yl)benzamide, TFA salt | 510.2 | 2.36 min |

| Example | Structure | Name | LC-MS [M + H]+ | Retention time |
|---|---|---|---|---|
| 192 | 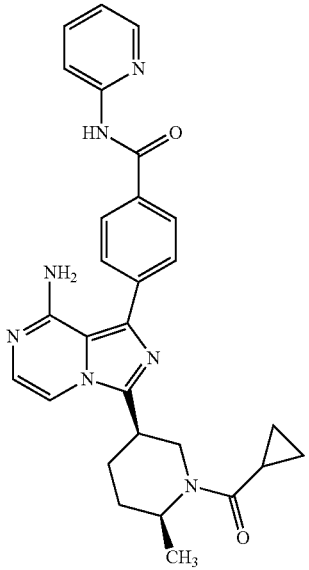 [SMILES: C[C@H]1CC[C@@H](c2nc(-c3ccc(C(=O)Nc4ccccn4)cc3)c3c(N)nccn23)CN1C(=O)C1CC1] | 4-(8-amino-3-((cis)-1-(cyclopropanecarbonyl)-6-methylpiperidin-3-yl)imidazo[1,5-a]pyrazin-1-yl)-N-(pyridin-2-yl)benzamide, TFA salt | 496.2 | 2.76 min |
| 193 | 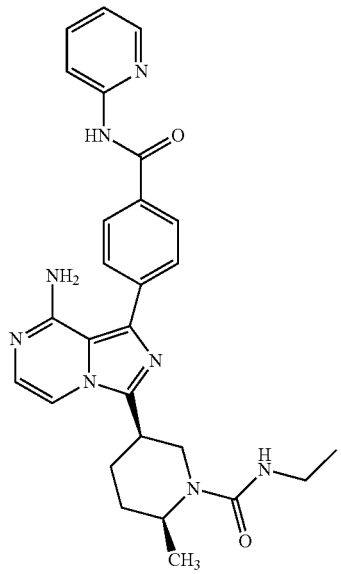 [SMILES: CCNC(=O)N1C[C@H](c2nc(-c3ccc(C(=O)Nc4ccccn4)cc3)c3c(N)nccn23)CC[C@@H]1C] | (cis)-5-(8-amino-1-(4-(pyridin-2-ylcarbamoyl)phenyl)imidazo[1,5-a]pyrazin-3-yl)-N-ethyl-2-methylpiperidine-1-carboxamide, TFA salt | 499.3 | 2.21 min |

| Example | Structure | Name | LC-MS [M + H]⁺ | Retention time |
|---|---|---|---|---|
| 194 | 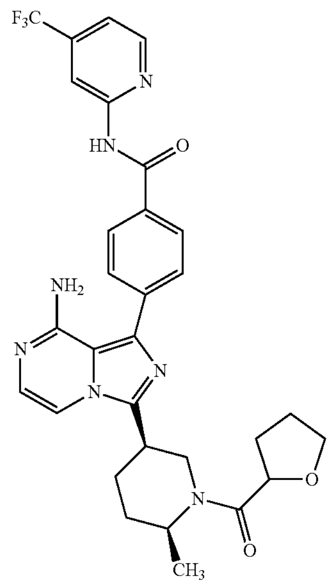 [SMILES: C[C@H]1CC[C@@H](c2nc(-c3ccc(C(=O)Nc4cc(C(F)(F)F)ccn4)cc3)c3c(N)nccn23)CN1C(=O)C1CCCO1] | 4-(8-amino-3-((cis)-6-methyl-1-(tetrahydrofuran-2-carbonyl)piperidin-3-yl)imidazo[1,5-a]pyrazin-1-yl)-N-(4-(trifluoromethyl)pyridin-2-yl)benzamide, TFA salt | 594.2 | 2.43 min |
| 195 | 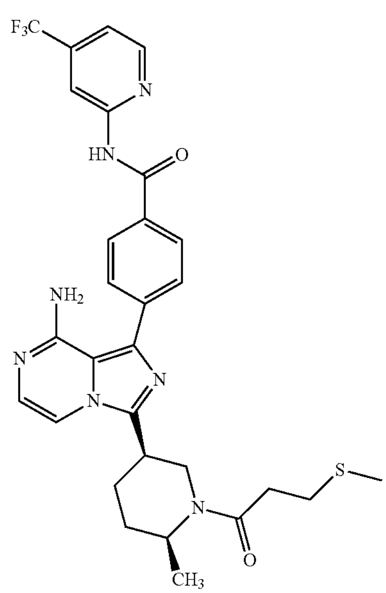 [SMILES: CSCCC(=O)N1C[C@H](c2nc(-c3ccc(C(=O)Nc4cc(C(F)(F)F)ccn4)cc3)c3c(N)nccn23)CC[C@@H]1C] | 4-(8-amino-3-((cis)-6-methyl-1-(3-(methylthio)propanoyl)piperidin-3-yl)imidazo[1,5-a]pyrazin-1-yl)-N-(4-(trifluoromethyl)pyridin-2-yl)benzamide, TFA salt | 598.2 | 2.67 min |

-continued

| Example | Structure | Name | LC-MS [M + H]⁺ | Retention time |
|---|---|---|---|---|
| 196 | 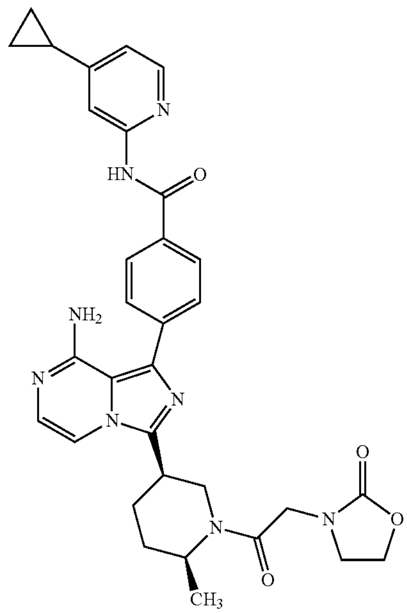 [SMILES: C[C@H]1CC[C@@H](c2nc(-c3ccc(C(=O)Nc4cc(C5CC5)ccn4)cc3)c3c(N)nccn23)CN1C(=O)CN1CCOC1=O] | 4-(8-amino-3-((cis)-6-methyl-1-(2-(2-oxooxazolidin-3-yl)acetyl)piperidin-3-yl)imidazo[1,5-a]pyrazin-1-yl)-N-(4-cyclopropylpyridin-2-yl)benzamide, TFA salt | 595.3 | 2.24 min |
| 197 | 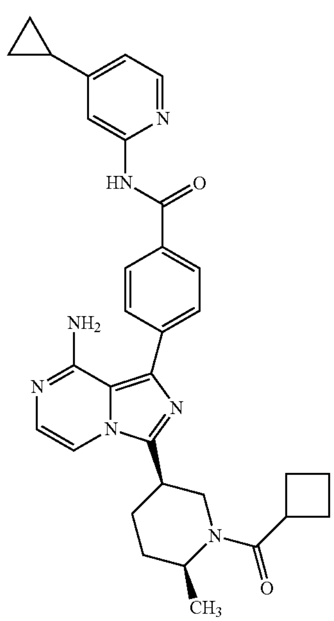 [SMILES: C[C@H]1CC[C@@H](c2nc(-c3ccc(C(=O)Nc4cc(C5CC5)ccn4)cc3)c3c(N)nccn23)CN1C(=O)C1CCC1] | 4-(8-amino-3-((cis)-1-(cyclobutanecarbonyl)-6-methylpiperidin-3-yl)imidazo[1,5-a]pyrazin-1-yl)-N-(4-cyclopropylpyridin-2-yl)benzamide, TFA salt | 550.2 | 2.26 min |

| Example | Structure | Name | LC-MS [M + H]+ | Retention time |
|---|---|---|---|---|
| 198 | 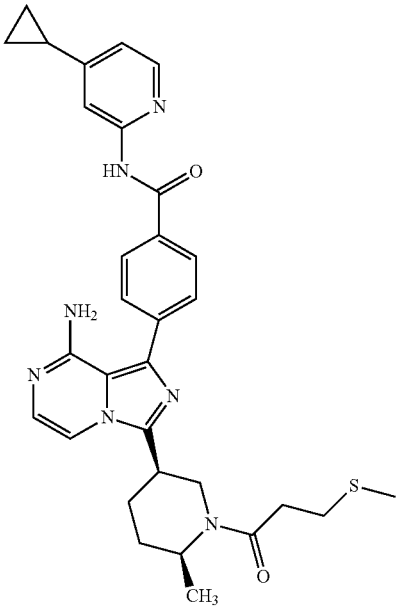 | 4-(8-amino-3-((cis)-6-methyl-1-(3-(methylthio)propanoyl)-piperidin-3-yl)imidazo[1,5-a]pyrazin-1-yl)-N-(4-cyclopropylpyridin-2-yl)benzamide, TFA salt | 570.2 | 1.70 min |
| 199 | 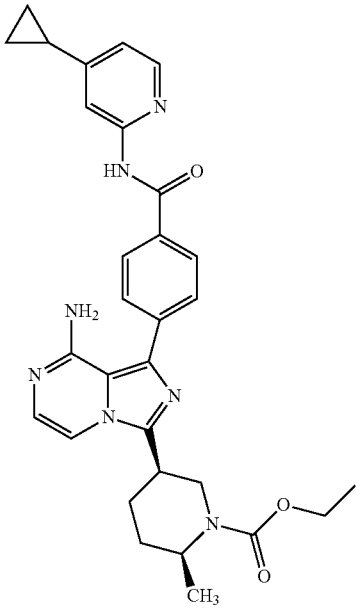 [SMILES: CCOC(=O)N1C[C@H](c2nc(-c3ccc(C(=O)Nc4cc(C5CC5)ccn4)cc3)c3c(N)nccn23)CC[C@@H]1C] | (cis)-ethyl 5-(8-amino-1-(4-(4-cyclopropylpyridin-2-ylcarbamoyl)phenyl)imidazo[1,5-a]pyrazin-3-yl)-2-methylpiperidine-1-carboxylate, TFA salt | 540.3 | 2.19 min |

| Example | Structure | Name | LC-MS [M + H]+ | Retention time |
|---|---|---|---|---|
| 200 | 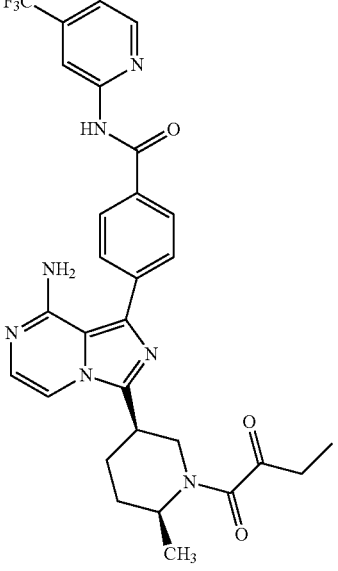 | 4-(8-amino-3-((cis)-6-methyl-1-(2-oxobutanoyl)piperidin-3-yl)imidazo[1,5-a]pyrazin-1-yl)-N-(4-(trifluoromethyl)-pyridin-2-yl)benzamide, TFA salt | 580.2 | 2.55 min |
| 201 | 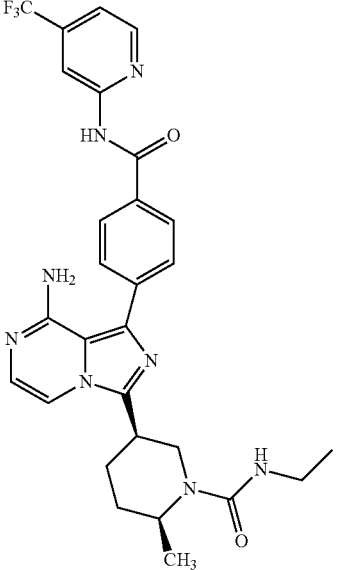 [SMILES: CCNC(=O)N1C[C@H](c2nc(-c3ccc(C(=O)Nc4cc(C(F)(F)F)ccn4)cc3)c3c(N)nccn23)CC[C@@H]1C] | (cis)-5-(8-amino-1-(4-(4-(trifluoromethyl)pyridin-2-ylcarbamoyl)phenyl)imidazo[1,5-a]pyrazin-3-yl)-N-ethyl-2-methylpiperidine-1-carboxamide, TFA salt | 567.2 | 2.54 min |

-continued

| Example | Structure | Name | LC-MS [M + H]+ | Retention time |
|---|---|---|---|---|
| 202 | 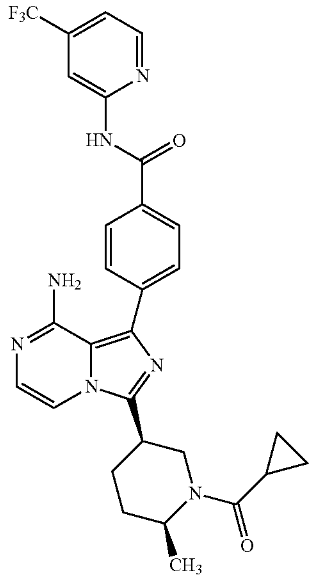 [SMILES: C[C@H]1CC[C@@H](c2nc(-c3ccc(C(=O)Nc4cc(C(F)(F)F)ccn4)cc3)c3c(N)nccn23)CN1C(=O)C1CC1] | 4-(8-amino-3-((cis)-1-(cyclopropanecarbonyl)-6-methylpiperidin-3-yl)imidazo[1,5-a]pyrazin-1-yl)-N-(4-(trifluoromethyl)pyridin-2-yl)benzamide, TFA salt | 564.2 | 2.82 min |
| 203 | 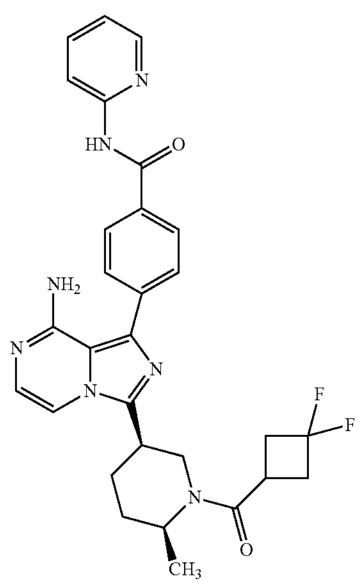 [SMILES: C[C@H]1CC[C@@H](c2nc(-c3ccc(C(=O)Nc4ccccn4)cc3)c3c(N)nccn23)CN1C(=O)C1CC(F)(F)C1] | 4-(8-amino-3-((cis)-1-(3,3-difluorocyclobutanecarbonyl)-6-methylpiperidin-3-yl)imidazo[1,5-a]pyrazin-1-yl)-N-(pyridin-2-yl)benzamide, TFA salt | 546.2 | 2.93 min |

| Example | Structure | Name | LC-MS [M + H]+ | Retention time |
|---------|-----------|------|----------------|----------------|
| 204 | 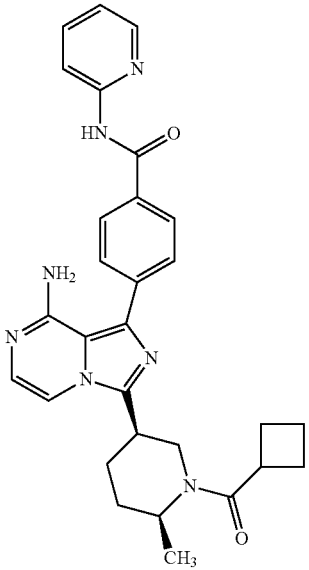 [SMILES: C[C@H]1CC[C@@H](c2nc(-c3ccc(C(=O)Nc4ccccn4)cc3)c3c(N)nccn23)CN1C(=O)C1CCC1] | 4-(8-amino-3-((cis)-1-(cyclobutanecarbonyl)-6-methylpiperidin-3-yl)imidazo[1,5-a]pyrazin-1-yl)-N-(pyridin-2-yl)benzamide, TFA salt | 510.2 | 2.40 min |
| 205 | 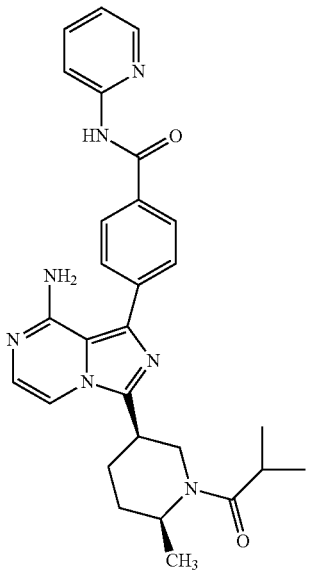 [SMILES: CC(C)C(=O)N1C[C@H](c2nc(-c3ccc(C(=O)Nc4ccccn4)cc3)c3c(N)nccn23)CC[C@@H]1C] | 4-(8-amino-3-((cis)-1-isobutyryl-6-methylpiperidin-3-yl)imidazo[1,5-a]pyrazin-1-yl)-N-(pyridin-2-yl)benzamide, TFA salt | 498.2 | 2.36 min |

-continued

| Example | Structure | Name | LC-MS [M + H]+ | Retention time |
|---------|-----------|------|----------------|----------------|
| 206 | 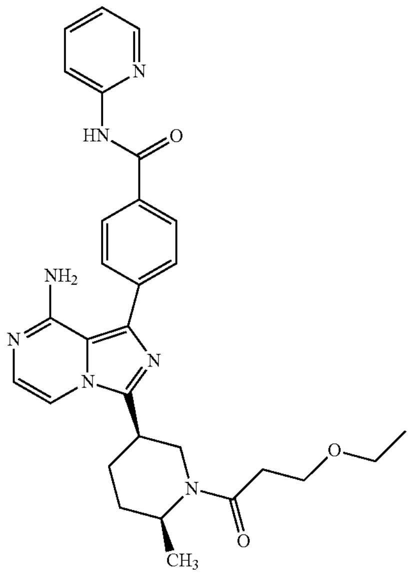 [SMILES: CCOCCC(=O)N1C[C@H](c2nc(-c3ccc(C(=O)Nc4ccccn4)cc3)c3c(N)nccn23)CC[C@@H]1C] | 4-(8-amino-3-((cis)-1-(3-ethoxypropanoyl)-6-methylpiperidin-3-yl)imidazo[1,5-a]pyrazin-1-yl)-N-(pyridin-2-yl)benzamide, TFA salt | 528.2 | 2.30 min |
| 207 | 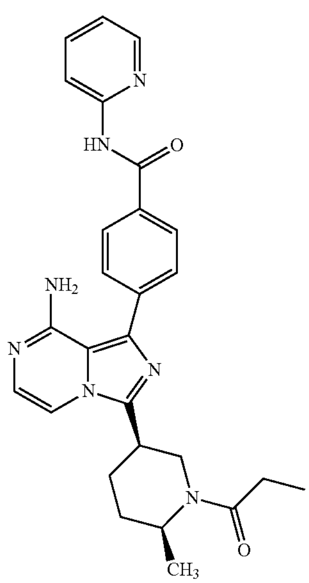 [SMILES: CCC(=O)N1C[C@H](c2nc(-c3ccc(C(=O)Nc4ccccn4)cc3)c3c(N)nccn23)CC[C@@H]1C] | 4-(8-amino-3-((cis)-6-methyl-1-propionylpiperidin-3-yl)imidazo[1,5-a]pyrazin-1-yl)-N-(pyridin-2-yl)benzamide, TFA salt | 484.2 | 2.74 min |

Intermediate 25

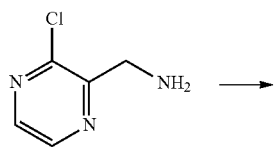

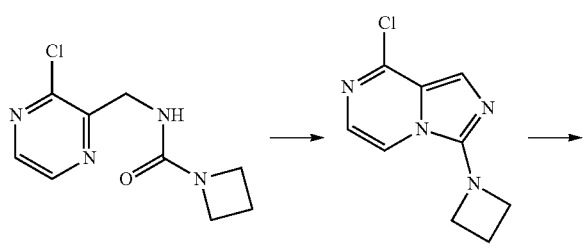

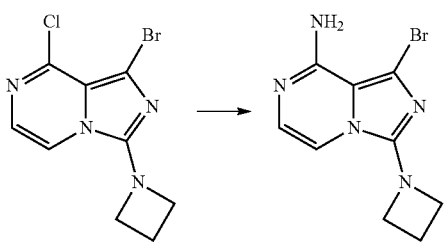

3-(azetidin-1-yl)-1-bromoimidazo[1,5-a]pyrazin-8-amine (a) N-((3-chloropyrazin-2-yl)methyl)azetidine-1-carboxamide A stirred solution of trichloromethyl chloroformate (105 mmol, 12.68 mL) in tetrahydrofuran (100 mL) was cooled to 0° C. and a solution of azetidine (88 mmol, 5 g) and N,N-diisopropylethylamine (193 mmol, 33.6 mL) in tetrahydrofuran (100 mL) was added slowly in 25 minutes. After stirring at 0° C. for one hour the solids were removed by filtration and the filtrate was concentrated at 50 mbar (50° C. bath temperature). The residue was added to a solution of 2-aminomethyl-3-chloropyrazine hydrochloride (66.7 mmol, 12 g) and triethylamine (200 mmol, 27.9 mL) in dichloromethane (200 mL) and the reaction mixture was stirred for three hours. The solids were removed by filtration and the filtrate was concentrated in vacuo. Purification using column chromatography (silica gel; gradient dichloromethane/methanol 100:0 to 95:5) yielded 9.5 g of N-((3-chloropyrazin-2-yl)methyl)azetidine-1-carboxamide.

(b) 3-(azetidin-1-yl)-8-chloroimidazo[1,5-a]pyrazine

To a stirred solution of N-((3-chloropyrazin-2-yl)methyl)azetidine-1-carboxamide (41.9 mmol, 9.5 g) in acetonitrile (130 mL) were added N,N-dimethylformamide (7.12 mmol, 0.55 mL), pyridine (419 mmol, 33.8 mL) and finally phosphorous oxychloride (210 mmol, 19.5 mL). After 7 minutes the reaction mixture was quenched by adding it to a cooled (0° C.) mixture of anhydrous 7N ammonia in methanol (150 mL) and acetonitrile (200 mL) and subsequently concentrated in vacuo. The residue was dissolved in dichloromethane, water (150 mL) and saturated aqueous sodium hydrogencarbonate (150 mL) were added and this mixture extracted six times with dichloromethane (100 mL). The combined organic extracts were dried (sodium sulfate) and concentrated in vacuo. Purification by column chromatography (silica gel; dichloromethane/methanol) gave 4.5 g of the title compound.

(c) 3-(azetidin-1-yl)-1-bromo-8-chloroimidazo[1,5-a]pyrazine

N-Bromosuccinimide (712 mg, 4 mmol) was added to a stirred solution of 3-(azetidin-1-yl)-8-chloroimidazo[1,5-a]pyrazine (4 mmol, 835 mg) in DMF (5 mL). The reaction was stirred 6 h at rt. The reaction was quenched with sat. NaHCO$_3$ (aq) and subsequently extracted with ethyl acetate (3×). The combined organic layers were washed with brine, dried over sodium sulfate, filtered and evaporated to give 2 g crude product. The crude product was purified using gel chromatography (dichloromethane+TEA) to give 3-(azetidin-1-yl)-1-bromo-8-chloroimidazo[1,5-a]pyrazine (350 mg, 30.4%).

(d) 3-(azetidin-1-yl)-1-bromoimidazo[1,5-a]pyrazin-8-amine

2-Propanol (15 ml) was cooled to −70° C. in a pre-weighed flask (with stopper and stirring bar) and ammonia gas was lead through for 30 minutes. The resulting solution was transferred to a pressure vessel after warming to room temperature and 3-(azetidin-1-yl)-1-bromo-8-chloroimidazo[1,5-a]pyrazine (1.217 mmol, 350 mg) was added. The reaction mixture was heated to 110° C. which resulted in an increased pressure to 8 bar. The reaction mixture was stirred at 110° C., overnight. The reaction mixture was concentrated in vacuum, the residue was suspended in ethyl acetate and subsequent washed with water. The layers were separated and the aqueous layer was extracted with ethyl acetate. The combined organic layers were washed with water, saturated sodium chloride solution, dried over sodium sulfate and concentrated to give 278 mg of 3-(azetidin-1-yl)-1-bromoimidazo[1,5-a]pyrazin-8-amine (85%).

Example 208

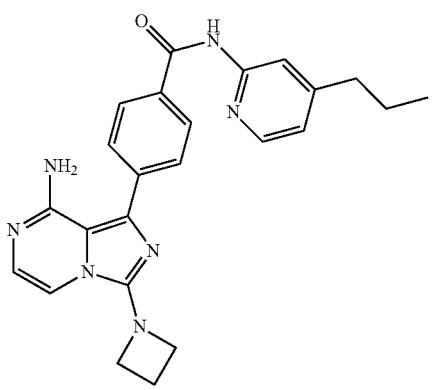 [SMILES: CCCc1ccnc(NC(=O)c2ccc(-c3nc(N4CCC4)n4ccnc(N)c34)cc2)c1]

4-(8-amino-3-(azetidin-1-yl)imidazo[1,5-a]pyrazin-1-yl)-N-(4-propylpyridin-2-yl)benzamide This compound was prepared in an analogous manner as described in Example 1, from Intermediate 25 and Intermediate C, to afford the title compound (8 mg, 12.54%). Data: UPLC(C) $R_t$: 1.66 min; m/z 428.0 (M+H)$^+$.

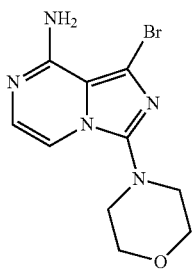

Intermediate 26

1-bromo-3-morpholinoimidazo[1,5-a]pyrazin-8-amine

This intermediate was prepared in an analogous manner as described for intermediate 25, from morpholine to obtain the title compound (679 mg, 105%).

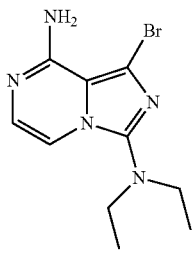

Intermediate 27

1-bromo-N3,N3-diethylimidazo[1,5-a]pyrazine-3,8-diamine

This intermediate was prepared, in an analogous manner as described for intermediate 25 from diethylamine to obtain the title compound (640 mg, 114%).

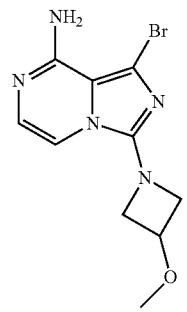

Intermediate 28

1-bromo-3-(3-methoxyazetidin-1-yl)imidazo[1,5-a]pyrazin-8-amine

This intermediate was prepared in an analogous manner as described for intermediate 25, from 3-methoxyazetidine to obtain the title compound (90 mg, 168%).

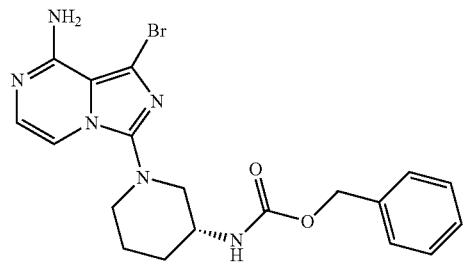

Intermediate 29

(R)-benzyl 1-(8-amino-1-bromoimidazo[1,5-a]pyrazin-3-yl)piperidin-3-ylcarbamate

This intermediate was prepared in an analogous manner as described for intermediate 25, from (R)-benzyl piperidin-3-ylcarbamate to obtain the title compound (403 mg, 85%).

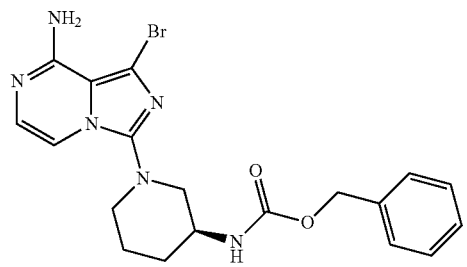

Intermediate 30

(S)-benzyl 1-(8-amino-1-bromoimidazo[1,5-a]pyrazin-3-yl)piperidin-3-ylcarbamate

This intermediate was prepared in an analogous manner as described for intermediate 25, from (S)-benzyl piperidin-3-ylcarbamate to obtain the title compound (462 mg, 83%).

The following Examples were synthesized following the methods described for example 1-49.

| Example | Structure | Name | LC-MS [M + H]+ | Retention time |
|---|---|---|---|---|
| 209 | 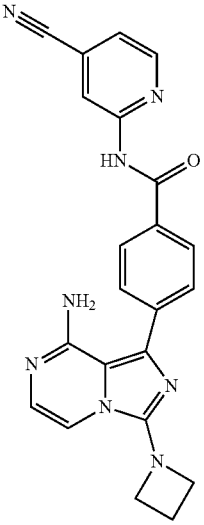 [SMILES: N#Cc1ccnc(NC(=O)c2ccc(-c3nc(N4CCC4)n4ccnc(N)c34)cc2)c1] | 4-(8-amino-3-(azetidin-1-yl)imidazo[1,5-a]pyrazin-1-yl)-N-(4-cyanopyridin-2-yl)benzamide | 411.2 | 1.78 min |
| 210 | 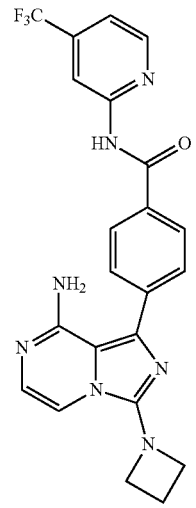 | 4-(8-amino-3-(azetidin-1-yl)imidazo[1,5-a]pyrazin-1-yl)-N-(4-(trifluoromethyl)pyridin-2-yl)benzamide | 454.2 | 2.30 min |
| 211 | 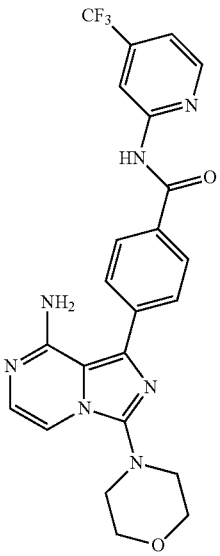 [SMILES: Nc1nccn2c(N3CCOCC3)nc(-c3ccc(C(=O)Nc4cc(C(F)(F)F)ccn4)cc3)c12] | 4-(8-amino-3-morpholinoimidazo[1,5-a]pyrazin-1-yl)-N-(4-(trifluoromethyl)pyridin-2-yl)benzamide | 484.2 | 2.25 min |

-continued
| Example | Structure | Name | LC-MS [M + H]+ | Retention time |
|---|---|---|---|---|
| 212 | 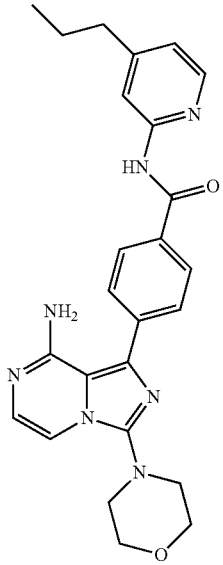 | 4-(8-amino-3-morpholinoimidazo[1,5-a]pyrazin-1-yl)-N-(4-propylpyridin-2-yl)benzamide | 458.2 | 1.63 min |
| 213 | 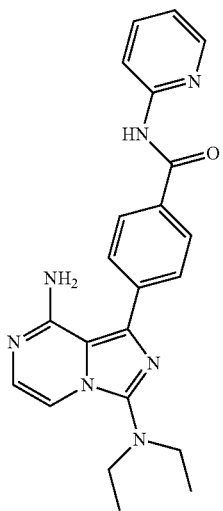 [SMILES: CCN(CC)c1nc(-c2ccc(C(=O)Nc3ccccn3)cc2)c2c(N)nccn12] | 4-(8-amino-3-(diethylamino)imidazo[1,5-a]pyrazin-1-yl)-N-(pyridin-2-yl)benzamide | 402.2 | 1.69 min |

-continued

| Example | Structure | Name | LC-MS [M + H]+ | Retention time |
|---------|-----------|------|----------------|----------------|
| 214 | 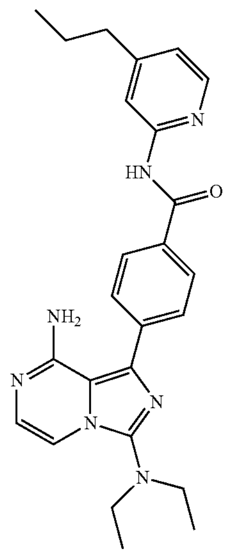 [SMILES: CCCc1ccnc(NC(=O)c2ccc(-c3nc(N(CC)CC)n4ccnc(N)c34)cc2)c1] | 4-(8-amino-3-(diethylamino)imidazo[1,5-a]pyrazin-1-yl)-N-(4-propylpyridin-2-yl)benzamide | 444.3 | 1.96 min |
| 215 | 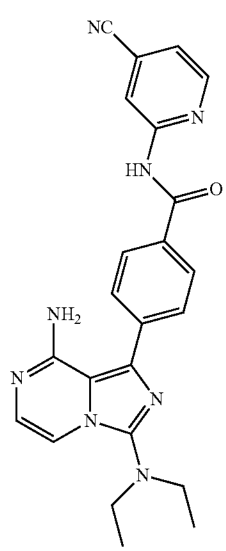 [SMILES: CCN(CC)c1nc(-c2ccc(C(=O)Nc3cc(C#N)ccn3)cc2)c2c(N)nccn12] | 4-(8-amino-3-(diethylamino)imidazo[1,5-a]pyrazin-1-yl)-N-(4-cyanopyridin-2-yl)benzamide | 427.2 | 2.15 min |

| Example | Structure | Name | LC-MS [M + H]+ | Retention time |
|---|---|---|---|---|
| 216 | 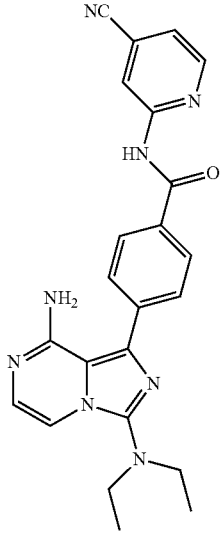 [SMILES: CCN(CC)c1nc(-c2ccc(C(=O)Nc3cc(C#N)ccn3)cc2)c2c(N)nccn12] | 4-(8-amino-3-(diethylamino)imidazo[1,5-a]pyrazin-1-yl)-N-(4-(trifluoromethyl)pyridin-2-yl)benzamide | 470.2 | 2.74 min |
| 217 | 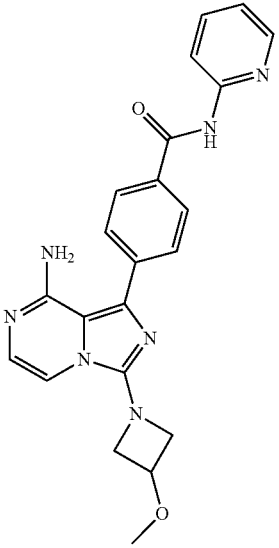 [SMILES: COC1CN(c2nc(-c3ccc(C(=O)Nc4ccccn4)cc3)c3c(N)nccn23)C1] | 4-(8-amino-3-(3-methoxyazetidin-1-yl)imidazo[1,5-a]pyrazin-1-yl)-N-(pyridin-2-yl)benzamide | 416.2 | 1.19 min |

| Example | Structure | Name | LC-MS [M + H]+ | Retention time |
|---|---|---|---|---|
| 218 | 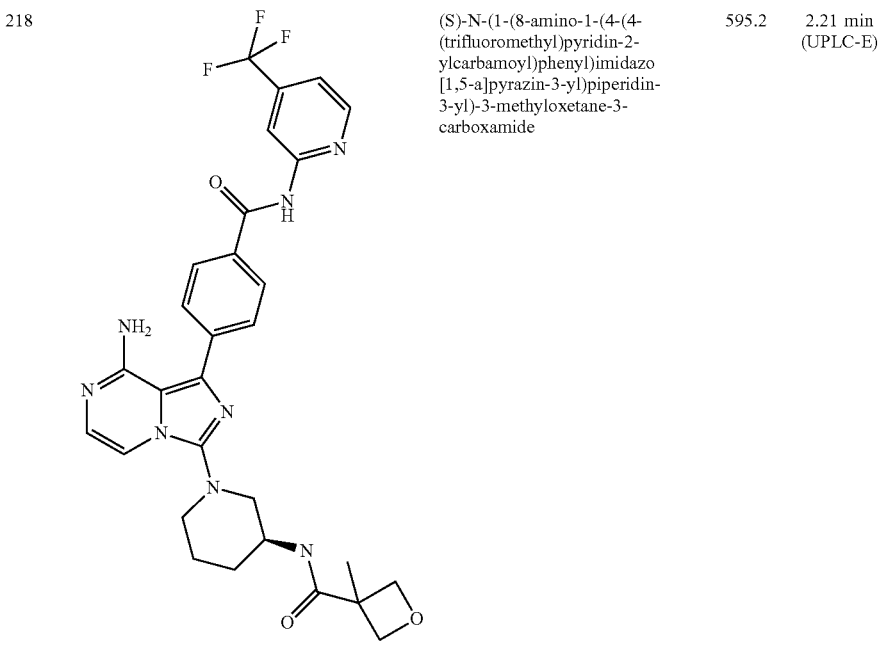 | (S)-N-(1-(8-amino-1-(4-(4-(trifluoromethyl)pyridin-2-ylcarbamoyl)phenyl)imidazo[1,5-a]pyrazin-3-yl)piperidin-3-yl)-3-methyloxetane-3-carboxamide | 595.2 | 2.21 min (UPLC-E) |
| 219 | 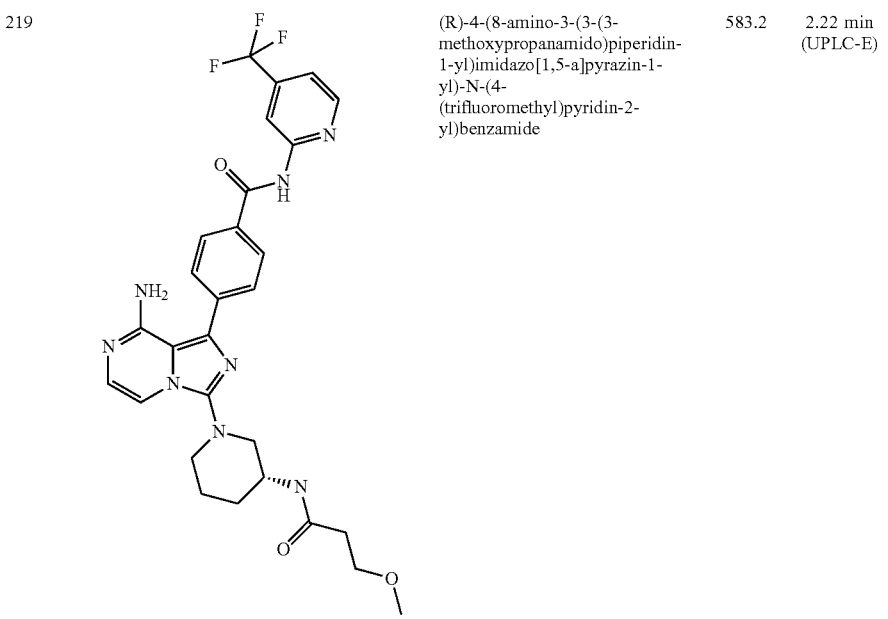 | (R)-4-(8-amino-3-(3-(3-methoxypropanamido)piperidin-1-yl)imidazo[1,5-a]pyrazin-1-yl)-N-(4-(trifluoromethyl)pyridin-2-yl)benzamide | 583.2 | 2.22 min (UPLC-E) |

| Example | Structure | Name | LC-MS [M + H]+ | Retention time |
|---|---|---|---|---|
| 220 | 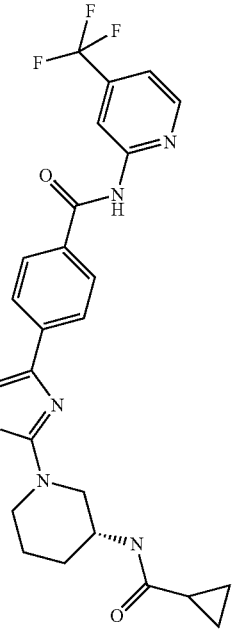 | (R)-4-(8-amino-3-(3-(cyclopropanecarboxamido)piperidin-1-yl)imidazo[1,5-a]pyrazin-1-yl)-N-(4-(trifluoromethyl)pyridin-2-yl)benzamide | 565.2 | 2.36 min (UPLC-E) |
| 221 | 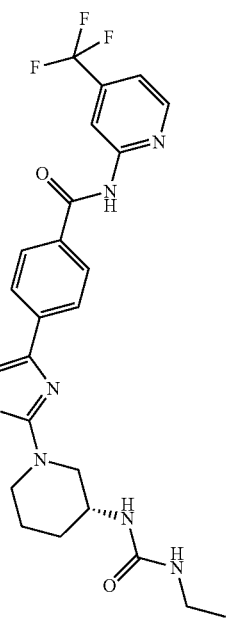 | (R)-4-(8-amino-3-(3-(3-ethylureido)piperidin-1-yl)imidazo[1,5-a]pyrazin-1-yl)-N-(4-(trifluoromethyl)pyridin-2-yl)benzamide | 568.2 | 2.25 min (UPLC-E) |

| Example | Structure | Name | LC-MS [M + H]+ | Retention time |
|---|---|---|---|---|
| 222 | 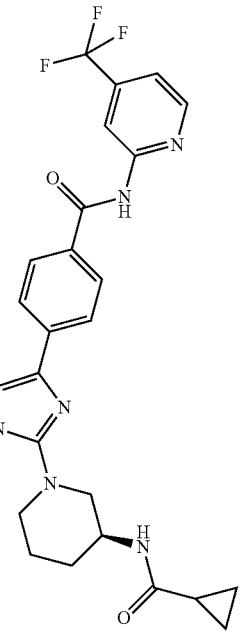 | (S)-4-(8-amino-3-(3-(cyclopropanecarboxamido)piperidin-1-yl)imidazo[1,5-a]pyrazin-1-yl)-N-(4-(trifluoromethyl)pyridin-2-yl)benzamide | 565.2 | 2.40 min (UPLC-E) |
| 223 | 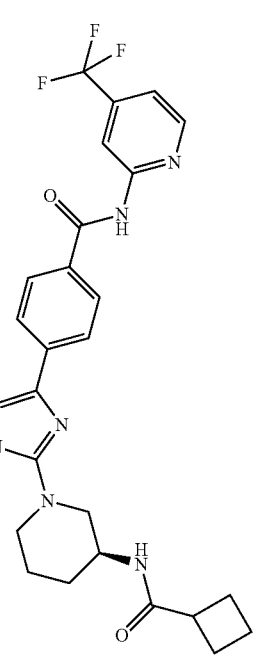 | (S)-4-(8-amino-3-(3-(cyclobutanecarboxamido)piperidin-1-yl)imidazo[1,5-a]pyrazin-1-yl)-N-(4-(trifluoromethyl)pyridin-2-yl)benzamide | 579.2 | 2.56 min (UPLC-E) |

Intermediate 31

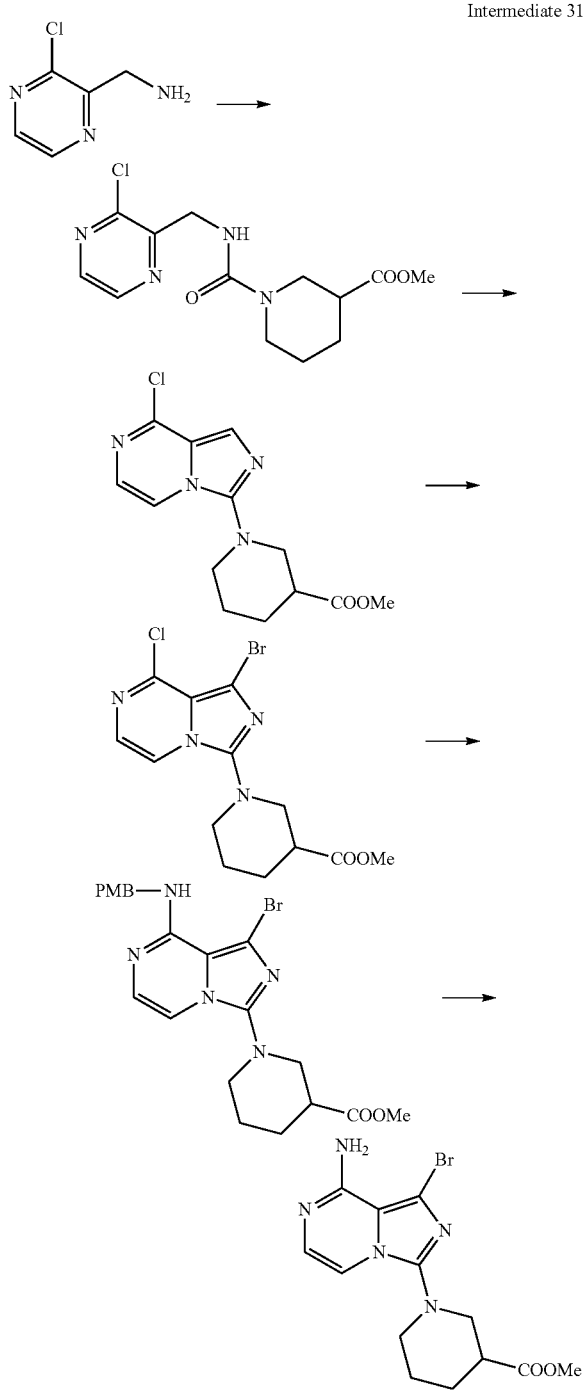

methyl 1-(8-amino-1-bromoimidazo[1,5-a]pyrazin-3-yl)piperidine-3-carboxylate (a) methyl 1-((3-chloropyrazin-2-yl)methylcarbamoyl)piperidine-3-carboxylate To a solution of 2-aminomethyl-3-chloropyrazine (40 g, 0.22 mol) in DCM (400 mL) was added CDI (35.1 g, 0.22 mol) and DIPEA (85.1 g, 0.22 mol). The mixture was stirred at 40° C. for 3 h. Then methyl piperidine-3-carboxylate (31.8 g, 0.22 mol) was added, the mixture was stirred at 40° C. for another 8 h. Then the mixture was evaporated to dryness, extracted with EtOAc (3×500 mL). The combined organic layers were washed with brine (2×300 mL), dried over anhydrous MgSO$_4$, filtered, and concentrated in vacuum. The residue was purified by silica gel column chromatography (PE: EtOAc=100:1 to 1:1 v/v %) to afford methyl 1-((3-chloropyrazin-2-yl)methylcarbamoyl)piperidine-3-carboxylate (25 g, yield 36.3%).

(b) methyl 1-(8-chloroimidazo[1,5-a]pyrazin-3-yl)piperidine-3-carboxylate

To a solution of methyl 1-((3-chloropyrazin-2-yl)methylcarbamoyl)piperidine-3-carboxylate (25 g, 0.08 mol) in acetonitril (250 mL) was added DMI (50 mL) and POCl$_3$ (50 mL) under N$_2$ protection. The mixture was stirred at 90° C. for 3 h. Then the reaction was quenched with ice water and NaHCO$_3$ solution, extracted with EtOAc (3×300 mL). The combined organic layers were washed with brine (2×200 mL), dried over anhydrous MgSO$_4$, filtered, and concentrated in vacuum. The residue was purified by column chromatography on silica gel (PE: EtOAc=100:1 to 2:1 v/v %) to afford methyl 1-(8-chloroimidazo[1,5-a]pyrazin-3-yl)piperidine-3-carboxylate (15 g, yield 36.3%).

(c) methyl 1-(1-bromo-8-chloroimidazo[1,5-a]pyrazin-3-yl)piperidine-3-carboxylate To a solution of methyl 1-(8-chloroimidazo[1,5-a]pyrazin-3-yl)piperidine-3-carboxylate (20 g, 7 mmol) in acetonitril (200 mL) was added NBS (13 g, 7.7 mmol) in portions. The mixture was stirred at room temperature for 1 h. Then the mixture was extracted with EtOAc (3×200 mL). The combined organic layers were washed with brine (2×300 mL), dried over anhydrous MgSO$_4$, filtered, and concentrated in vacuum. The residue was purified by column chromatography on silica gel (PE: EtOAc=100:1 to 1:1 v/v %) to afford methyl 1-(1-bromo-8-chloroimidazo[1,5-a]pyrazin-3-yl)piperidine-3-carboxylate (14 g, yield 53.8%).

(d) methyl 1-(1-bromo-8-(4-methoxybenzylamino)imidazo[1,5-a]pyrazin-3-yl)piperidine-3-carboxylate To a solution of methyl 1-(1-bromo-8-chloroimidazo[1,5-a]pyrazin-3-yl)piperidine-3-carboxylate (14 g, 37.5 mmol) in i-PrOH (140 mL) was added paramethoxybenzyl amine (6.2 g, 45 mmol) and TEA (11.4 g, 112.5 mmol). The mixture was reacted at 110° C. for 16 h. Then the mixture was evaporated in vacuo, extracted with DCM (3×200 mL). The combined organic layers were washed with brine (2×100 mL), dried over anhydrous MgSO$_4$, filtered, and concentrated in vacuum to give methyl 1-(1-bromo-8-(4-methoxybenzylamino)imidazo[1,5-a]pyrazin-3-yl)piperidine-3-carboxylate (11 g, yield 62.0%) without further purification.

(e) methyl 1-(8-amino-1-bromoimidazo[1,5-a]pyrazin-3-yl)piperidine-3-carboxylate A solution of methyl 1-(1-bromo-8-(4-methoxybenzylamino)imidazo[1,5-a]pyrazin-3-yl)piperidine-3-carboxylate (11 g, 23.3 mmol) in TFA (100 mL) was reacted at 100° C. for 12 h. Then the mixture was evaporated in vacuo, extracted with DCM (3×200 mL). The combined organic layers were washed with brine (2×100 mL), dried over anhydrous MgSO$_4$, filtered, and concentrated in vacuum to afford methyl 1-(8-amino-1-bromoimidazo[1,5-a]pyrazin-3-yl)piperidine-3-carboxylate (11 g, yield 100%).

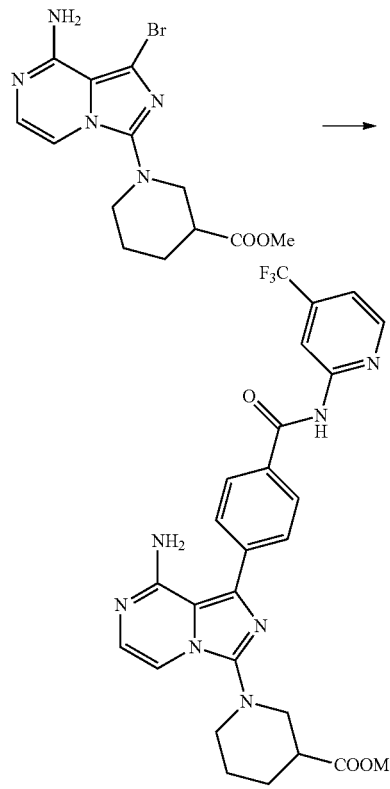

Intermediate 32

2-dioxaborolan-2-yl)-N-(4-(trifluoromethyl)pyridin-2-yl)benzamide (Intermediate D) (3.26 g, 8.3 mmol), $K_2CO_3$ (18.75 mL, 37.5 mmol) and $Pd(dppf)Cl_2$ (585 mg, 0.8 mmol) under $N_2$ protection. The reaction mixture was stirred at 120° C. for 2 h. The resulting suspension was concentrated in vacuo, and then poured into 30 mL of water. The aqueous layer was extracted with EtOAc (3×40 mL). The combined organic layers were washed with brine (2×300 mL), dried over anhydrous $MgSO_4$, filtered, and concentrated in vacuo. The residue was purified by column chromatography on silica gel (PE: EtOAc=10:1 to 0:1 v/v %) to afford 2.2 g methyl 1-(8-amino-1-(4-(4-(trifluoromethyl)pyridin-2-ylcarbamoyl)phenyl)imidazo[1,5-a]pyrazin-3-yl)piperidine-3-carboxylate (2.2 g, yield 54.3%).

(b) 1-(8-amino-1-(4-(4-(trifluoromethyl)pyridin-2-ylcarbamoyl)phenyl)imidazo[1,5-a]pyrazin-3-yl)piperidine-3-carboxylic acid To a solution of methyl 1-(8-amino-1-(4-(4-(trifluoromethyl)pyridin-2-ylcarbamoyl)phenyl)imidazo[1,5-a]pyrazin-3-yl)piperidine-3-carboxylate (2.2 g, 4 mmol) in THF (22 mL) and water (22 mL) was added LiOH (0.34 g, 8 mmol). The reaction mixture was stirred at room temperature for 12 h. Then the mixture was washed with EtOAc (2×20 mL), and the aqueous layer was acidified with glacial citric solution to pH=5~6, after which the product precipitated from solution. After filtration and washing, the solid was collected to give 1-(8-amino-1-(4-(4-(trifluoromethyl)pyridin-2-ylcarbamoyl)phenyl)-imidazo[1,5-a]pyrazin-3-yl)piperidine-3-carboxylic acid (1.3 g, yield 61.9%).

Example 224

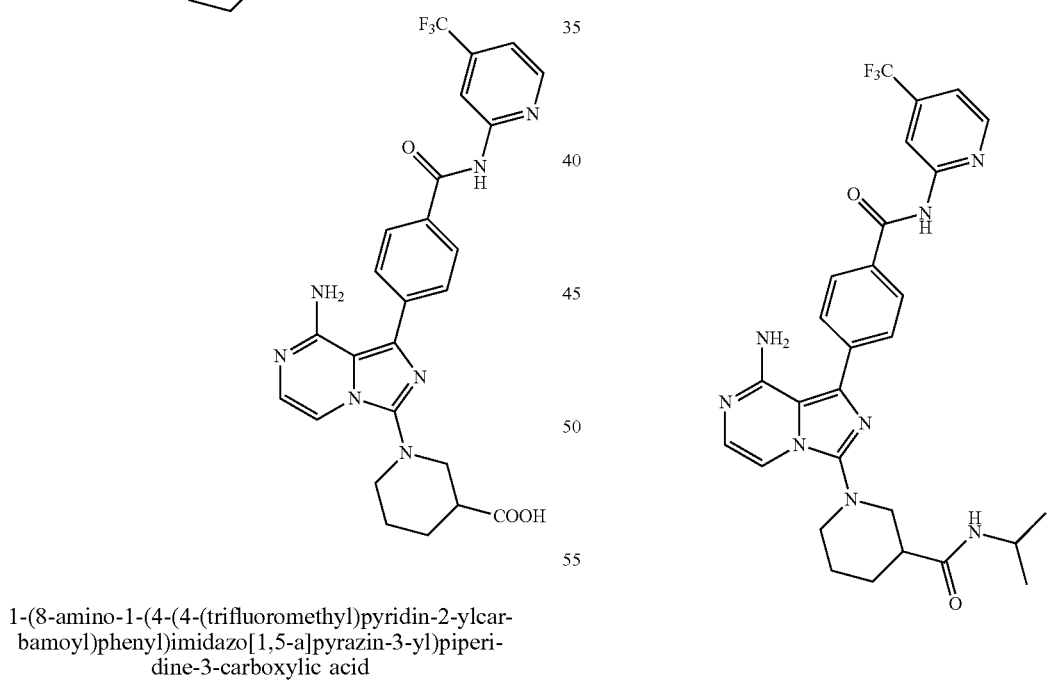

1-(8-amino-1-(4-(4-(trifluoromethyl)pyridin-2-ylcarbamoyl)phenyl)imidazo[1,5-a]pyrazin-3-yl)piperidine-3-carboxylic acid (a) methyl 1-(8-amino-1-(4-(4-(trifluoromethyl)pyridin-2-ylcarbamoyl)phenyl)imidazo[1,5-a]pyrazin-3-yl)piperidine-3-carboxylate To a solution of methyl 1-(8-amino-1-bromoimidazo[1,5-a]pyrazin-3-yl)piperidine-3-carboxylate (2.66 g, 7.5 mmol) in dioxane (30 mL) was added 4-(4,4,5,5-Tetramethyl-1,3, 1-(8-amino-1-(4-(4-(trifluoromethyl)pyridin-2-ylcarbamoyl)phenyl)imidazo[1,5-a]pyrazin-3-yl)-N-isopropylpiperidine-3-carboxamide To a solution of 1-(8-amino-1-(4-(4-(trifluoromethyl)pyridin-2-ylcarbamoyl)phenyl)imidazo[1,5-a]pyrazin-3-yl)piperidine-3-carboxylic acid (50 mg, 0.095 mmol) in DMF (2 mL) was added isopropylamine (6.74 mg, 0.114 mmol), HATU (72.2 mg, 0.19 mmol), and TEA (28.79 mg, 0.285 mmol), which was stirred at 25° C. for 16 h. The mixture was purified by preparative HPLC. Fractions containing product were collected and lyophilized to afford 10.8 mg of 1-(8-amino-1-(4-(4-(trifluoromethyl)pyridin-2-ylcarbamoyl)phenyl)imidazo[1,5-a]pyrazin-3-yl)-N-isopropylpiperidine-3-carboxamide (20% yield). Data: UPLC (F) R$_t$: 2.73 min; m/z 567.2 (M+H)$^+$.

The following Examples were synthesized following the methods described for example 224.

| Example | Structure | Name | LC-MS {M + H}$^+$ | Retention time |
|---------|-----------|------|-------------------|----------------|
| 225 | 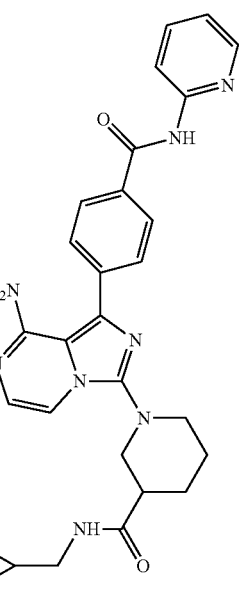 mix | 1-(8-amino-1-(4-(pyridin-2-ylcarbamoyl)phenyl)imidazo[1,5-a]pyrazin-3-yl)-N-(cyclopropylmethyl)-piperidine-3-carboxamide, TFA sat | 511.3 | 2.41 min |
| 226 | 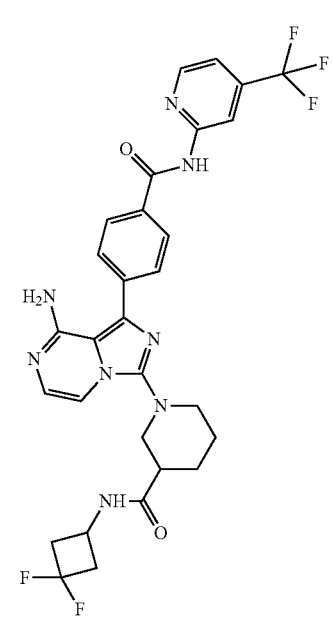 mix | 1-(8-amino-1-(4-(4-(trifluoromethyl)pyridin-2-ylcarbamoyl)phenyl)imidazo[1,5-a]pyrazin-3-yl)-N-(3,3-difluorocyclobutyl)piperidine-3-carboxamide, TFA salt | 615.2 | 2.83 min |

-continued
| Example | Structure | Name | LC-MS {M + H}+ | Retention time |
|---|---|---|---|---|
| 227 | 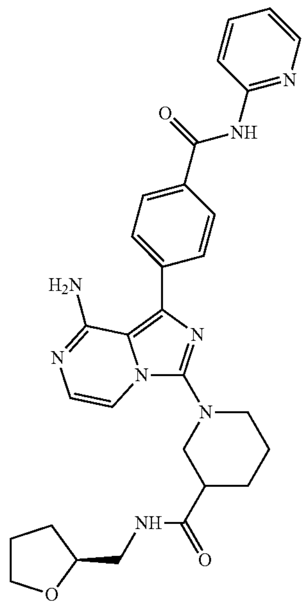 [SMILES: Nc1nccn2c(N3CCCC(C(=O)NC[C@@H]4CCCO4)C3)nc(-c3ccc(C(=O)Nc4ccccn4)cc3)c12] | 1-(8-amino-1-(4-(pyridin-2-ylcarbamoyl)phenyl)imidazo[1,5-a]pyrazin-3-yl)-N-(((S)-tetrahydrofuran-2-yl)methyl)piperidine-3-carboxamide, TFA salt | 541.3 | 2.27 min |
| 228 | 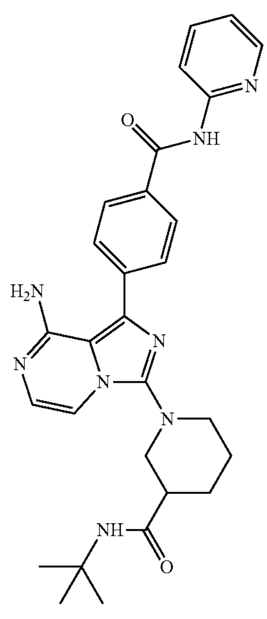 [SMILES: CC(C)(C)NC(=O)C1CCCN(c2nc(-c3ccc(C(=O)Nc4ccccn4)cc3)c3c(N)nccn23)C1] | 1-(8-amino-1-(4-(pyridin-2-ylcarbamoyl)phenyl)imidazo[1,5-a]pyrazin-3-yl)-N-tert-butylpiperidine-3-carboxamide, TFA salt | 513.3 | 2.65 min |

| Example | Structure | Name | LC-MS {M + H}+ | Retention time |
|---|---|---|---|---|
| 229 | 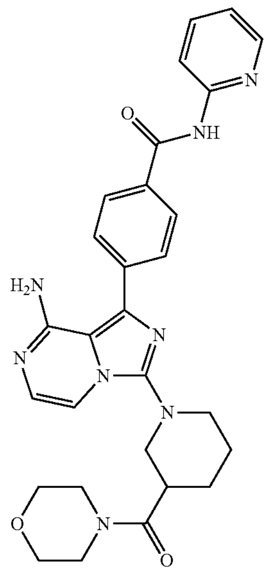 [SMILES: Nc1nccn2c(N3CCCC(C(=O)N4CCOCC4)C3)nc(-c3ccc(C(=O)Nc4ccccn4)cc3)c12] | 4-(8-amino-3-(3-(morpholine-4-carbonyl)piperidin-1-yl)imidazo[1,5-a]pyrazin-1-yl)-N-(pyridin-2-yl)benzamide, TFA salt | 527.2 | 2.20 min |
| 230 | 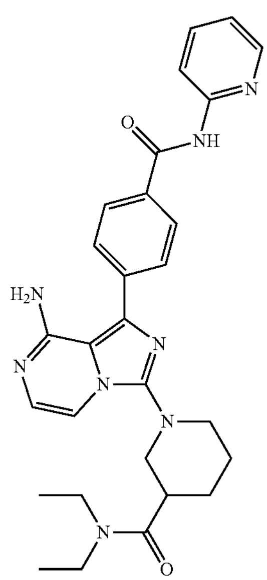 [SMILES: CCN(CC)C(=O)C1CCCN(c2nc(-c3ccc(C(=O)Nc4ccccn4)cc3)c3c(N)nccn23)C1] | 1-(8-amino-1-(4-(pyridin-2-ylcarbamoyl)phenyl)imidazo[1,5-a]pyrazin-3-yl)-N,N-diethylpiperidine-3-carboxamide, TFA salt | 513.2 | 2.06 min |

-continued

| Example | Structure | Name | LC-MS {M + H}+ | Retention time |
|---------|-----------|------|----------------|----------------|
| 231 | 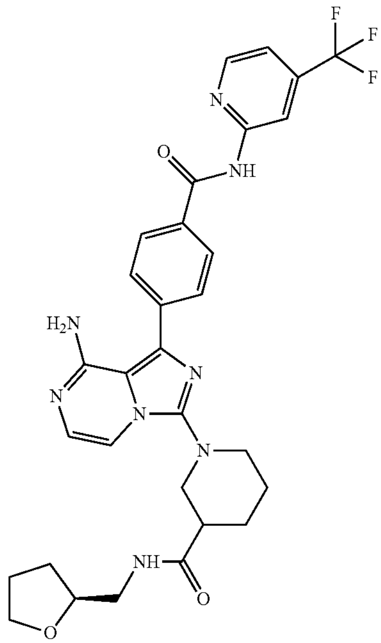 [SMILES: Nc1nccn2c(N3CCCC(C(=O)NC[C@@H]4CCCO4)C3)nc(-c3ccc(C(=O)Nc4cc(C(F)(F)F)ccn4)cc3)c12] | 1-(8-amino-1-(4-(4-(trifluoromethyl)pyridin-2-ylcarbamoyl)phenyl)imidazo[1,5-a]pyrazin-3-yl)-N-(((S)-tetrahydrofuran-2-yl)methyl)piperidine-3-carboxamide, TFA salt | 609.3 | 2.64 min |
| 232 | 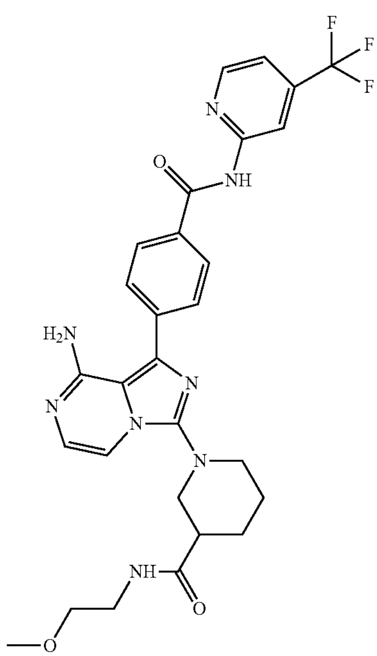 [SMILES: COCCNC(=O)C1CCCN(c2nc(-c3ccc(C(=O)Nc4cc(C(F)(F)F)ccn4)cc3)c3c(N)nccn23)C1] | 1-(8-amino-1-(4-(4-(trifluoromethyl)pyridin-2-ylcarbamoyl)phenyl)imidazo[1,5-a]pyrazin-3-yl)-N-(2-methoxyethyl)piperidine-3-carboxamide, TFA salt | 583.2 | 2.45 min |

| Example | Structure | Name | LC-MS {M + H}+ | Retention time |
|---|---|---|---|---|
| 233 | 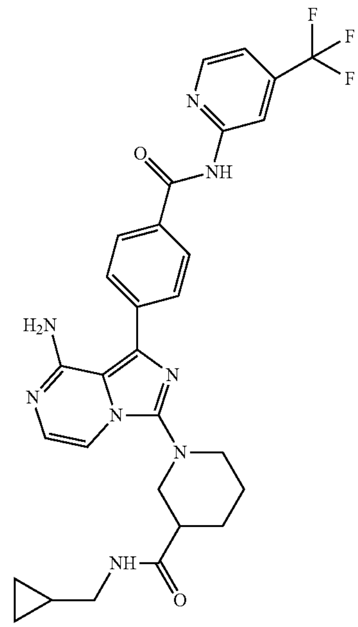 [SMILES: Nc1nccn2c(N3CCCC(C(=O)NCC4CC4)C3)nc(-c3ccc(C(=O)Nc4cc(C(F)(F)F)ccn4)cc3)c12] | 1-(8-amino-1-(4-(4-(trifluoromethyl)pyridin-2-ylcarbamoyl)phenyl)imidazo[1,5-a]pyrazin-3-yl)-N-(cyclopropylmethyl)piperidine-3-carboxamide, TFA salt | 579.2 | 2.62 min |
| 234 | 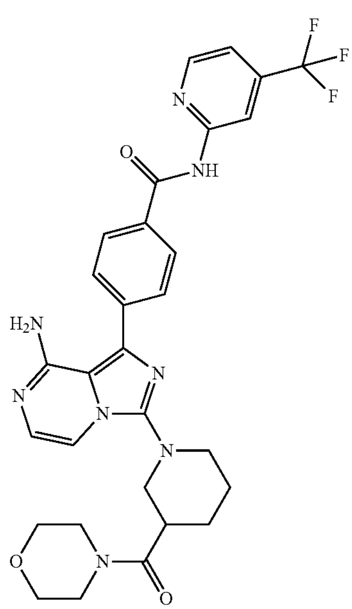 [SMILES: Nc1nccn2c(N3CCCC(C(=O)N4CCOCC4)C3)nc(-c3ccc(C(=O)Nc4cc(C(F)(F)F)ccn4)cc3)c12] | 4-(8-amino-3-(3-(morpholine-4-carbonyl)piperidin-1-yl)imidazo[1,5-a]pyrazin-1-yl)-N-(4-(trifluoromethyl)pyridin-2-yl)benzamide, TFA salt | 595.2 | 2.51 min |

-continued

| Example | Structure | Name | LC-MS {M + H}+ | Retention time |
|---|---|---|---|---|
| 235 | 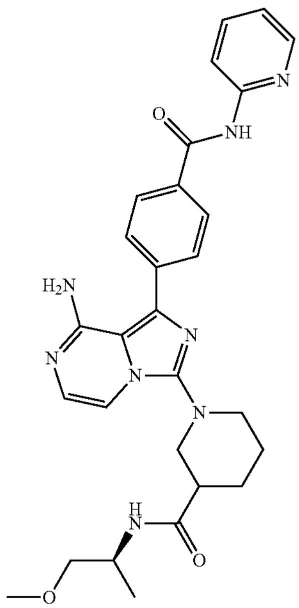 [SMILES: COC[C@H](C)NC(=O)C1CCCN(c2nc(-c3ccc(C(=O)Nc4ccccn4)cc3)c3c(N)nccn23)C1] | 1-(8-amino-1-(4-(pyridin-2-ylcarbamoyl)phenyl)imidazo[1,5-a]pyrazin-3-yl)-N-((S)-1-methoxypropan-2-yl)piperidine-3-carboxamide, TFA salt | 529.2 | 2.21 min |
| 236 | mix | 1-(8-amino-1-(4-(4-(trifluoromethyl)pyridin-2-ylcarbamoyl)phenyl)imidazo[1,5-a]pyrazin-3-yl)-N-ethylpiperidine-3-carboxamide, TFA salt | 553.2 | 2.46 min |

| Example | Structure | Name | LC-MS {M + H}+ | Retention time |
|---|---|---|---|---|
| 237 | 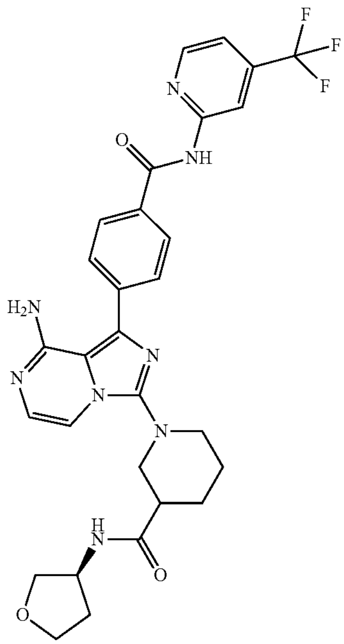 [SMILES: Nc1nccn2c(N3CCCC(C(=O)N[C@H]4CCOC4)C3)nc(-c3ccc(C(=O)Nc4cc(C(F)(F)F)ccn4)cc3)c12] | 1-(8-amino-1-(4-(4-(trifluoromethyl)pyridin-2-ylcarbamoyl)phenyl)imidazo[1,5-a]pyrazin-3-yl)-N-((S)-tetrahydrofuran-3-yl)piperidine-3-carboxamide, TFA salt | 595.2 | 2.44 min |
| 238 | 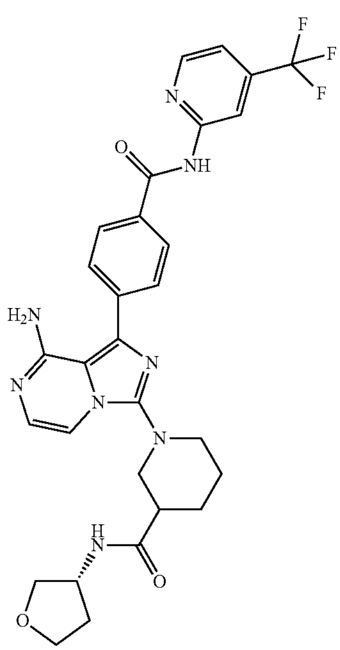 [SMILES: Nc1nccn2c(N3CCCC(C(=O)N[C@@H]4CCOC4)C3)nc(-c3ccc(C(=O)Nc4cc(C(F)(F)F)ccn4)cc3)c12] | 1-(8-amino-1-(4-(4-(trifluoromethyl)pyridin-2-ylcarbamoyl)phenyl)imidazo[1,5-a]pyrazin-3-yl)-N-((R)-tetrahydrofuran-3-yl)piperidine-3-carboxamide, TFA salt | 595.2 | 2.45 min |

| Example | Structure | Name | LC-MS {M + H}+ | Retention time |
|---|---|---|---|---|
| 239 | 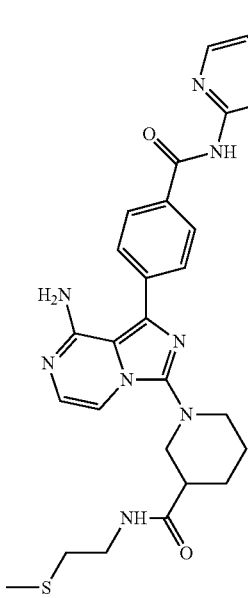 mix | 1-(8-amino-1-(4-(4-(trifluoromethyl)pyridin-2-ylcarbamoyl)phenyl)imidazo[1,5-a]pyrazin-3-yl)-N-(2-(methylthio)ethyl)piperidine-3-carboxamide, TFA salt | 599.2 | 2.57 min |
| 240 | 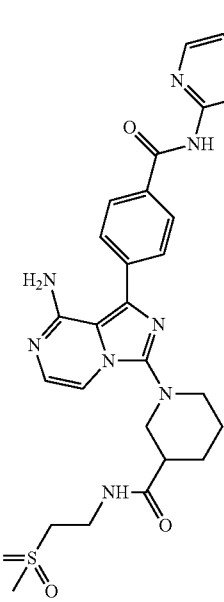 mix | 1-(8-amino-1-(4-(4-(trifluoromethyl)pyridin-2-ylcarbamoyl)phenyl)imidazo[1,5-a]pyrazin-3-yl)-N-(2-(methylsulfonyl)ethyl)piperidine-3-carboxamide, TFA salt | 631.2 | 2.61 min |

| Example | Structure | Name | LC-MS {M + H}+ | Retention time |
|---|---|---|---|---|
| 241 | 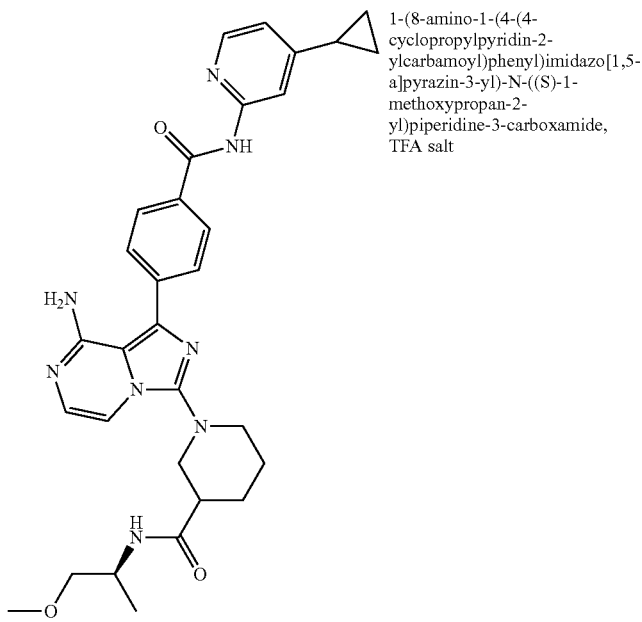 | 1-(8-amino-1-(4-(4-cyclopropylpyridin-2-ylcarbamoyl)phenyl)imidazo[1,5-a]pyrazin-3-yl)-N-((S)-1-methoxypropan-2-yl)piperidine-3-carboxamide, TFA salt | 569.2 | 1.96 min |
| 242 | 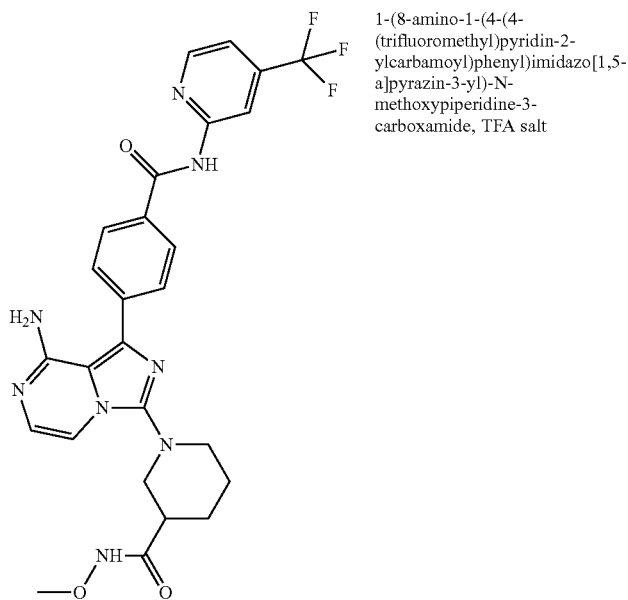<br>mix | 1-(8-amino-1-(4-(4-(trifluoromethyl)pyridin-2-ylcarbamoyl)phenyl)imidazo[1,5-a]pyrazin-3-yl)-N-methoxypiperidine-3-carboxamide, TFA salt | 555.1 | 2.29 min |

| Example | Structure | Name | LC-MS {M + H}+ | Retention time |
|---|---|---|---|---|
| 243 | mix | 4-(8-amino-3-(3-(3,3-difluoropiperidine-1-carbonyl)piperidin-1-yl)imidazo[1,5-a]pyrazin-1-yl)-N-(4-(trifluoromethyl)pyridin-2-yl)benzamide, TFA salt | 629.2 | 2.76 min |
| 244 | mix | 1-(8-amino-1-(4-(4-cyclopropylpyridin-2-ylcarbamoyl)phenyl)imidazo[1,5-a]pyrazin-3-yl)-N-methoxypiperidine-3-carboxamide, TFA salt | 527.2 | 1.85 min |

-continued
| Example | Structure | Name | LC-MS {M + H}+ | Retention time |
|---|---|---|---|---|
| 245 | 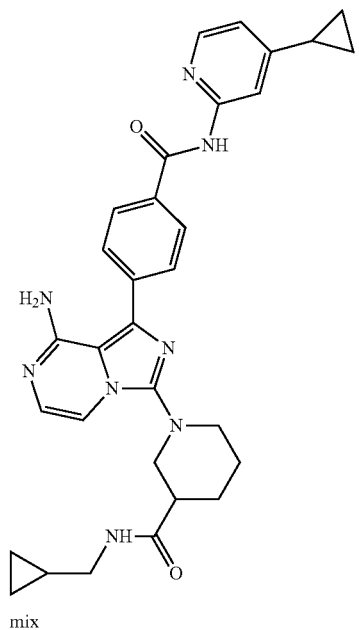 [SMILES: Nc1nccn2c(N3CCCC(C(=O)NCC4CC4)C3)nc(-c3ccc(C(=O)Nc4cc(C5CC5)ccn4)cc3)c12] mix | 1-(8-amino-1-(4-(4-cyclopropylpyridin-2-ylcarbamoyl)phenyl)imidazo[1,5-a]pyrazin-3-yl)-N-(cyclopropylmethyl)piperidine-3-carboxamide, TFA salt | 551.2 | 2.02 min |
| 246 | 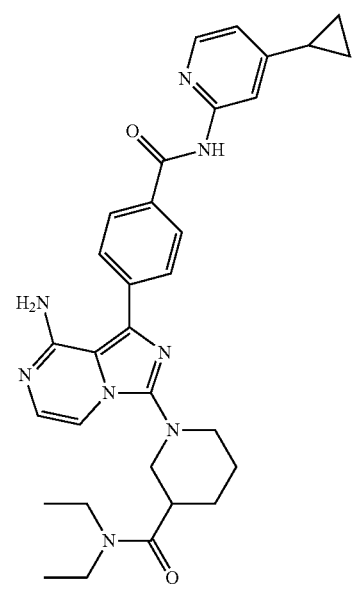 mix | 1-(8-amino-1-(4-(4-cyclopropylpyridin-2-ylcarbamoyl)phenyl)imidazo[1,5-a]pyrazin-3-yl)-N,N-diethylpiperidine-3-carboxamide, TFA salt | 553.2 | 2.08 min |

| Example | Structure | Name | LC-MS {M + H}+ | Retention time |
|---|---|---|---|---|
| 247 | mix | 4-(8-amino-3-(3-(pyrrolidine-1-carbonyl)piperidin-1-yl)imidazo[1,5-a]pyrazin-1-yl)-N-(4-cyclopropylpyridin-2-yl)benzamide, TFA salt | 551.2 | 2.83 min |

Intermediate 33

3-cyclopropyl-4,5,6,7-tetrahydro-1H-indazole-5-carboxylic acid (a) methyl 4-morpholinocyclohex-3-enecarboxylic acid The solution of methyl 4-oxocyclohexanecarboxylic acid (172.0 g, 1.01 mol), morpholine (97.0 g, 1.11 mol) and p-toluenesulfonic acid (200 mg) in toluene (500 mL) was stirred 18 h at reflux. The reaction mixture was concentrated in vacuum to give 235 g methyl 4-morpholinocyclohex-3-enecarboxylic acid. The compound was used in the next reaction without further purification.

(b) methyl 3-(cyclopropanecarbonyl)-4-oxocyclohexanecarboxylic acid

The crude compound methyl 4-morpholinocyclohex-3-enecarboxylic acid (134.0 g, 0.56 mol) was dissolved in anhydrous DCM (1.0 L) in the presence of Et$_3$N (89.0 g, 0.88 mol). Cyclopropanecarbonyl chloride (73.0 g, 0.70 mol) was added dropwise at 0° C. The reaction mixture was stirred 18 h at rt. The reaction mixture was acidified with 5% HCl solution to pH=3 at 10° C. After stirring for 30 min at room temperature, the organic layer was separated. The aqueous layer was extracted by EtOAc (3×70 mL). The organic phase was washed with brine, dried (Na$_2$SO$_4$) and concentrated. The crude product was purified using gel chromatography (petroleum ether/EtOAc 6/1) to give 36.0 g methyl 3-(cyclopropanecarbonyl)-4-oxocyclohexanecarboxylic acid (27% yield for 2 steps).

(c) methyl 3-cyclopropyl-4,5,6,7-tetrahydro-1H-indazole-5-carboxylate

To a solution of compound 3-(cyclopropanecarbonyl)-4-oxocyclohexanecarboxylic acid (36.0 g, 0.15 mol) in EtOH

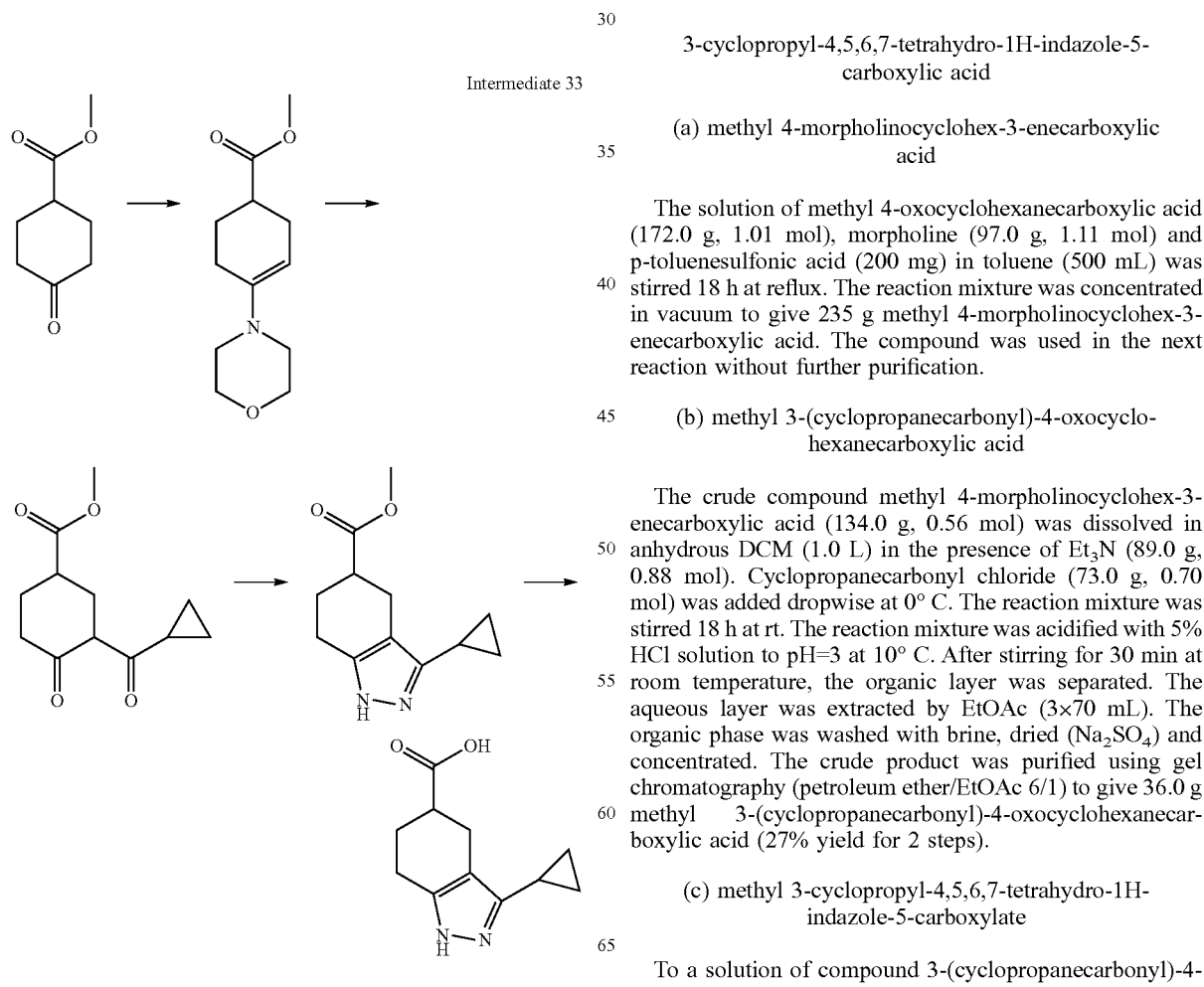

(95%, 300 mL) was added hydrazine hydrate (23.0 g, 0.39 mol) at 0° C. The reaction mixture was stirred 18 h at rt. The solvent was concentrated in vacuo to give methyl 3-cyclopropyl-4,5,6,7-tetrahydro-1H-indazole-5-carboxylate (35.0 g). The compound was used in the next reaction without further purification.

(d) 3-cyclopropyl-4,5,6,7-tetrahydro-1H-indazole-5-carboxylic acid

To a solution methyl 3-cyclopropyl-4,5,6,7-tetrahydro-1H-indazole-5-carboxylate (35.0 g) in MeOH (300 mL) was added a solution of LiOH.H₂O (10.8 g, 0.26 mol) in H₂O (200 mL) at 0° C. After stirring 18 h at rt the solvent was removed in vacuo. To the residue water (200 mL) was added and aqueous solution was acidified to pH=4~5 with 10% HCl. The precipitate was collected by filtration to give 3-cyclopropyl-4,5,6,7-tetrahydro-1H-indazole-5-carboxylic acid (25.0 g, 80% yield for 2 steps).

Intermediate 34

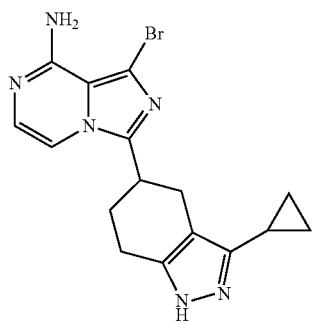

1-bromo-3-(3-cyclopropyl-4,5,6,7-tetrahydro-1H-indazol-5-yl)imidazo[1,5-a]pyrazin-8-amine This intermediate was prepared, in an analogous manner as described for intermediate 1, from 3-cyclopropyl-4,5,6,7-tetrahydro-1H-indazole-5-carboxylic acid (Intermediate 33) to obtain the title compound (235 mg, 66.3%).

Intermediate 35

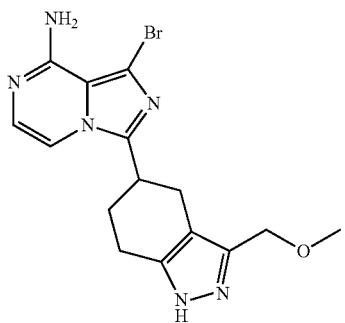

1-bromo-3-(3-(methoxymethyl)-4,5,6,7-tetrahydro-1H-indazol-5-yl)imidazo[1,5-a]pyrazin-8-amine This intermediate was prepared, in an analogous manner as described for intermediate 34, from 3-(methoxymethyl)-4,5,6,7-tetrahydro-1H-indazole-5-carboxylic acid to obtain the title compound (140 mg, 44.8%).

Intermediate 35B

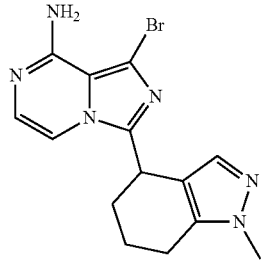

1-bromo-3-(1-methyl-4,5,6,7-tetrahydro-1H-indazol-4-yl)imidazo[1,5-a]pyrazin-8-amine (a) 2-((dimethylamino)methylene)cyclohexane-1,3-dione A mixture of cyclohexane-1,3-dione (33.6 g, 300 mmol) in DMF-DMA (120 ml) was heated to 100° C. and stirred for 1 h under nitrogen atmosphere. The volatiles were concentrated under reduced pressure. The red solid (55 g crude) was used in the next step directly.

(b) 1-methyl-6,7-dihydro-1H-indazol-4(5H)-one

To a solution of 2-((dimethylamino)methylene)cyclohexane-1,3-dione (55 g crude, 300 mmol) in t-BuOH (400 ml) was added methylhydrazine solution (35 g, 40% aqueous solution, 304 mmol) and AcOH (20 ml) at room temperature. The resulting mixture was heated to reflux for 3 h under nitrogen protection. After cooling the mixture was concentrated in vacuo and the residue was purified by column chromatography on silica gel (petroleum ether/ethyl acetate=1/1 v/v %) to give 1-methyl-6,7-dihydro-1H-indazol-4(5H)-one (20 g, two steps: 44%). MS-ESI (m/z): 151 (M+1)⁺ (Acq Method: 0-60AB_2 min; Rt: 0.90 min)

(c) 1-methyl-6,7-dihydro-1H-indazol-4-yl trifluoromethanesulfonate

To a solution of 1-methyl-6,7-dihydro-1H-indazol-4(5H)-one (10 g, 66.6 mmol) in anhydrous THF (250 ml) was added N-phenylbis(trifluoromethanesulfonimide) (26 g, 66.6 mmol), the mixture was cooled to −78° C., followed by the addition of KHMDS (140 ml, 0.5 M in THF, 70 mmol). After the addition was completed, the mixture was allowed to warm to room temperature and stirred for 16 h. The mixture was quenched by water and extracted with ethyl acetate three times. The combined organic layers were washed with water and brine, dried over Na₂SO₄ and concentrated in vacuo. The residue was purified by column chromatography on silica gel (petroleum ether/ethyl acetate=3/1 v/v %) to afford 1-methyl-6,7-dihydro-1H-indazol-4-yl trifluoromethanesulfonate (12 g, 64%). MS-ESI (m/z): 283 (M+1)⁺ (Acq Method: 10-80AB_2 min; Rt: 1.05 min)

(d) methyl 1-methyl-6,7-dihydro-1H-indazole-4-carboxylate

To a mixture of 1-methyl-6,7-dihydro-1H-indazol-4-yl trifluoromethanesulfonate (12 g, 42.5 mmol) in DMF (150 ml) and MeOH (15 ml) was added Pd(OAc)₂ (1 g, 4.25 mmol). The mixture was degassed with carbon monoxide, heated to 70° C. and stirred for 4 h under a carbon monoxide atmosphere. After cooling the mixture was filtered, the filtrate was diluted with water and extracted with ethyl acetate three times. The combined organic layers were washed with brine, dried over Na$_2$SO$_4$, and the solvent was removed under reduced pressure. The residue was purified by column chromatography on silica gel (petroleum ether/ ethyl acetate=5/1 v/v %) to afford methyl 1-methyl-6,7-dihydro-1H-indazole-4-carboxylate (7.5 g, 91%). MS-ESI (m/z): 193 (M+1)$^+$ (Acq Method: 10-80AB_2 min; Rt: 0.83 min)

(e) methyl 1-methyl-4,5,6,7-tetrahydro-1H-indazole-4-carboxylate

To a mixture of methyl 1-methyl-6,7-dihydro-1H-indazole-4-carboxylate (7.5 g, 38.7 mmol) and nickel chloride hexahydrate (9.2 g, 38.7 mmol) in MeOH (250 ml) was added NaBH$_4$ (14.6 g, 387 mmol) portions at 0° C. After the addition was completed the mixture was stirred at room temperature for 1 h. The mixture was partitioned between water and ethyl acetate. The organic layer was washed with water and brine, dried over Na$_2$SO$_4$, and concentrated in vacuo. The residue was purified by column chromatography on silica gel (petroleum ether/ethyl acetate=5/1 v/v %) to afford methyl 1-methyl-4,5,6,7-tetrahydro-1H-indazole-4-carboxylate (7 g, 94%). MS-ESI (m/z): 195 (M+1)$^+$ (Acq Method: 10-80AB_2 min; Rt: 0.20 min)

(f) 1-methyl-4,5,6,7-tetrahydro-1H-indazole-4-carboxylic acid

To a solution of methyl 1-methyl-4,5,6,7-tetrahydro-1H-indazole-4-carboxylate (7 g, 36 mmol) in methanol (100 ml), THF (50 ml) and H$_2$O (50 ml) was added LiOH.H$_2$O (4.5 g, 108 mmol). The reaction mixture was stirred at room temperature for 2 h. The mixture was acidified with 1N HCl solution, and extracted with ethyl acetate three times. The combined organic layers were washed with brine, dried over Na$_2$SO$_4$ and concentrated in vacuo to give 1-methyl-4,5,6,7-tetrahydro-1H-indazole-4-carboxylic acid (6 g, 94%). MS-ESI (m/z): 181 (M+1)$^+$ (Acq Method: 0-60AB_2 min; Rt: 0.89 min)

(g) 1-bromo-8-chloro-3-(1-methyl-3a,4,5,6,7,7a-hexahydro-1H-indazol-4-yl)imidazo[1,5-a]pyrazine This compound was prepared in an analogous manner as described in Intermediate 24C from step d to step f, starting from 1-methyl-4,5,6,7-tetrahydro-1H-indazole-4-carboxylic acid, to afford 1-bromo-8-chloro-3-(1-methyl-3a,4,5,6,7,7a-hexahydro-1H-indazol-4-yl)imidazo[1,5-a]pyrazine. MS-ESI (m/z): 366 (M+1)$^+$ (Acq Method: 10-80AB_2 min; Rt: 1.04 min)

(h) 1-bromo-3-(1-methyl-4,5,6,7-tetrahydro-1H-indazol-4-yl)imidazo[1,5-a]pyrazin-8-amine A solution of 1-bromo-8-chloro-3-(1-methyl-3a,4,5,6,7,7a-hexahydro-1H-indazol-4-yl)imidazo[1,5-a]pyrazine (200 mg, 0.5 mmol) in NH$_3$/i-PrOH (5 ml) was added in a sealed tube, then heated to 120° C. and stirred overnight. After cooling the mixture was filtered, and the filtrate was evaporated under reduce pressure. The residue was purified by preparative TLC to give 1-bromo-3-(1-methyl-4,5,6,7-tetrahydro-1H-indazol-4-yl)imidazo[1,5-a]pyrazin-8-amine (150 mg, 87%). MS-ESI (m/z): 347 (M+1)$^+$ (Acq Method: 0-60AB_2 min; Rt: 0.98 min).

Intermediate 35C

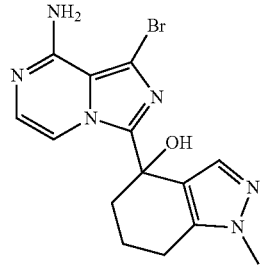

4-(8-amino-1-bromoimidazo[1,5-a]pyrazin-3-yl)-1-methyl-4,5,6,7-tetrahydro-1H-indazol-4-ol (a) 4-(8-chloroimidazo[1,5-a]pyrazin-3-yl)-1-methyl-4,5,6,7-tetrahydro-1H-indazol-4-ol To a solution of 1-methyl-6,7-dihydro-1H-indazol-4(5H)-one (770 mg, 5 mmol) in anhydrous THF (10 ml) was added n-BuLi (2.5 M, 2 ml, 5 mmol) dropwise at −78° C. under nitrogen protection. After the addition was completed, the mixture was stirred at −78° C. for further 15 min, then another solution of 8-chloroimidazo[1,5-a]pyrazine (710 mg, 4.75 mmol) in anhydrous THF (5 ml) was added slowly. The reaction mixture was allowed to warm to room temperature and for 1 h. The mixture was diluted with water and extracted with ethyl acetate three times. The combined organic layers were dried over Na$_2$SO$_4$ and concentrated in vacuo. The residue was purified by column chromatography on silica gel (MeOH/DCM=1/50 to 1/15 v/v %) to give 4-(8-chloroimidazo[1,5-a]pyrazin-3-yl)-1-methyl-4,5,6,7-tetrahydro-1H-indazol-4-ol (1 g, 70%). MS-ESI (m/z): 304 (M+1)$^+$ (Acq Method: 0-60AB_2 min; Rt: 1.07 min)

(b) 4-(1-bromo-8-chloroimidazo[1,5-a]pyrazin-3-yl)-1-methyl-4,5,6,7-tetrahydro-1H-indazol-4-ol To a solution of 4-(8-chloroimidazo[1,5-a]pyrazin-3-yl)-1-methyl-4,5,6,7-tetrahydro-1H-indazol-4-ol (1 g, 3.3 mmol) in DMF (8 ml) was added NBS (584 mg, 3.3 mmol) portionwise at 0° C. After the addition was complete, the reaction mixture was stirred at 0° C. for 30 minutes. The mixture was diluted with water and extracted with ethyl acetate three times. The combined organic layers were washed with brine, dried over Na$_2$SO$_4$ and concentrated in vacuo. The residue was purified by preparative TLC to give 4-(1-bromo-8-chloroimidazo[1,5-a]pyrazin-3-yl)-1-methyl-4,5,6,7-tetrahydro-1H-indazol-4-ol (860 mg, 68%). MS-ESI (m/z): 382 (M+1)$^+$ (Acq Method: 10-80AB_2 min; Rt: 1.01 min).

(c) 4-(8-amino-1-bromoimidazo[1,5-a]pyrazin-3-yl)-1-methyl-4,5,6,7-tetrahydro-1H-indazol-4-ol A mixture of 4-(1-bromo-8-chloroimidazo[1,5-a]pyrazin-3-yl)-1-methyl-4,5,6,7-tetrahydro-1H-indazol-4-ol (860 mg, 2.26 mmol) in NH$_3$/i-PrOH (25 ml) was added in a sealed tube, and then stirred at 120° C. overnight. After cooling to room temperature, the mixture was filtered and the filtrate was evaporated under reduce pressure. The residue was re-dissolved in DCM, washed with water and brine, dried over MgSO$_4$ and concentrated in vacuo to give 4-(8-amino- 1-bromoimidazo[1,5-a]pyrazin-3-yl)-1-methyl-4,5,6,7-tetrahydro-1H-indazol-4-ol (720 mg, 88%). MS-ESI (m/z): 363 (M+1)+ (Acq Method: 0-60AB_2 min; Rt: 0.98 min).

The following Examples were synthesized following the methods described for Examples 1-23 starting with Intermediates 34 and 35.

| Example | Structure | Name | LC-MS [M + H]+ | Retention time |
|---|---|---|---|---|
| 248 | 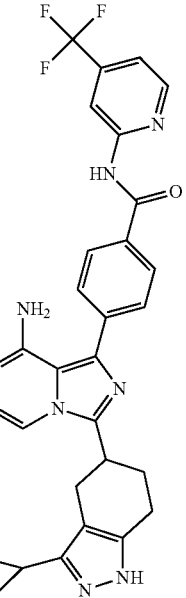 mix | 4-(8-amino-3-(3-cyclopropyl-4,5,6,7-tetrahydro-1H-indazol-5-yl)imidazo[1,5-a]pyrazin-1-yl)-N-(4-(trifluoromethyl)pyridin-2-yl)benzamide | 559.3 | 2.22 min |
| 249 | 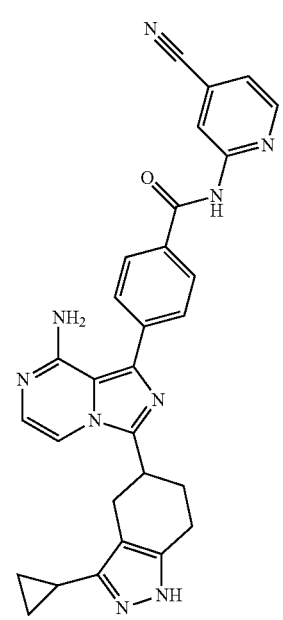 mix | 4-(8-amino-3-(3-cyclopropyl-4,5,6,7-tetrahydro-1H-indazol-5-yl)imidazo[1,5-a]pyrazin-1-yl)-N-(4-cyanopyridin-2-yl)benzamide, TFA salt | 516.3 | 1.63 min |

-continued
| Example | Structure | Name | LC-MS [M + H]+ | Retention time |
|---|---|---|---|---|
| 250 | mix | 4-(8-amino-3-(3-(methoxymethyl)-4,5,6,7-tetrahydro-1H-indazol-5-yl)imidazo[1,5-a]pyrazin-1-yl)-N-(4-(trifluoromethyl)pyridin-2-yl)benzamide | 563.3 | 2.15 min |
Intermediate 36
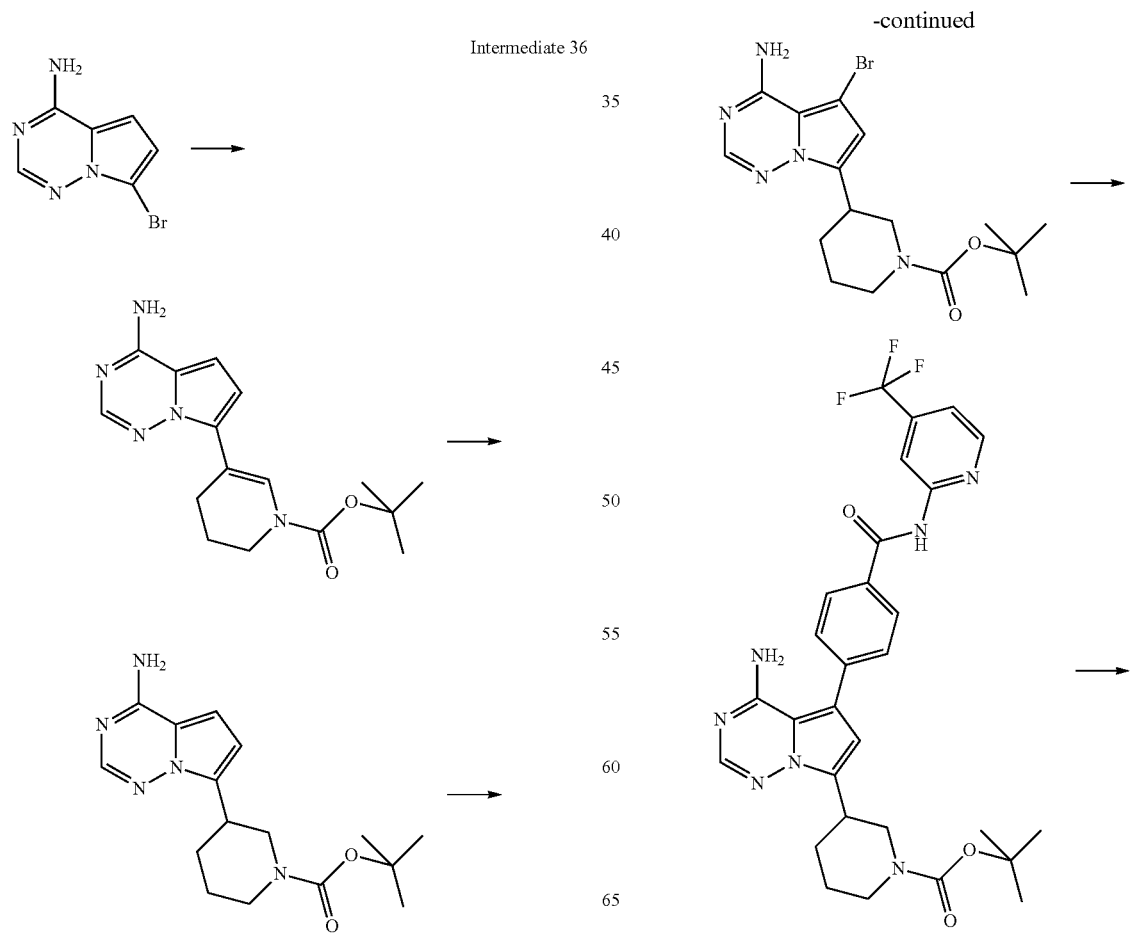

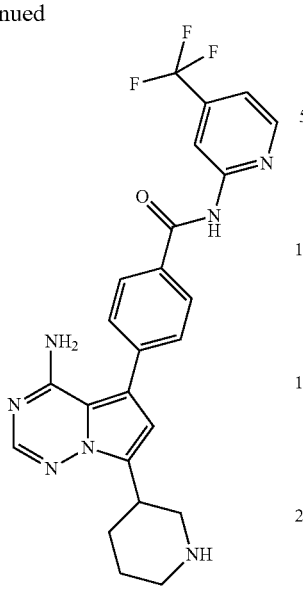

4-(4-amino-7-(piperidin-3-yl)pyrrolo[1,2-f][1,2,4]triazin-5-yl)-N-(4-(trifluoromethyl)-pyridin-2-yl)-benzamide (a) tert-Butyl 3-(4-aminopyrrolo[1,2-f][1,2,4]triazin-7-yl)-5,6-dihydropyridine-1(2H)-carboxylate 7-Bromopyrrolo[1,2-f][1,2,4]triazin-4-amine (2.264 mmol, 482 mg) and tert-butyl 5-(4,4,5,5-tetramethyl-1,3,2-dioxaborolan-2-yl)-3,4-dihydropyridine-1(2H)carboxylate (2.264 mmol, 700 mg) were dissolved in dioxane (15 mL). 2 M-solution of potassium carbonate (5.66 mmol, 2.83 ml) in water was added. The resulting solution was purged with $N_2$ 5 minutes at 30° C. Tetrakis(triphenyl-phosphine)palladium(0) (0.113 mmol, 131 mg) was added and the resulting solution was purged another 5 minutes at 30° C. with $N_2$. The reaction was heated 6 h at reflux. The reaction mixture was cooled to rt and water and EtOAc were added. The resulting suspension was filtered over decalite. The filtrate was extracted with EtOAc (2x). The combined organic layers were dried ($Na_2SO_4$), filtered and concentrated. The product was purified using silica gel chromatography (dichloromethane/methanol=100/0 to 9/1 (v/v %) to give 250 mg of tert-Butyl 3-(4-aminopyrrolo[1,2-f][1,2,4]triazin-7-yl)-5,6-dihydropyridine-1(2H)-carboxylate (35%).

(b) tert-Butyl 3-(4-aminopyrrolo[1,2-f][1,2,4]triazin-7-yl)piperidine-1-carboxylate tert-Butyl 3-(4-aminopyrrolo[1,2-f][1,2,4]triazin-7-yl)-5,6-dihydropyridine-1(2H)-carboxylate (1.490 mmol, 470 mg) was dissolved in ethanol (60 mL). 2 Drops of HOAc were added and the reaction mixture was filtered over an HPLC-filter. The filtrate was eluted over 10% Pd/C cartridge in the H-cube at 50 bar pressure and 35° C., $H_2$-flow, twice. The reaction mixture was concentrated to give 210 mg of tert-butyl 3-(4-aminopyrrolo[1,2-f][1,2,4]triazin-7-yl)piperidine-1-carboxylate (44%). The crude product was used directly in the next step.

(c) tert-butyl 3-(4-amino-5-bromopyrrolo[1,2-f][1,2,4]triazin-7-yl)piperidine-1-carboxylate A suspension of tert-butyl 3-(4-aminopyrrolo[1,2-f][1,2,4]triazin-7-yl)piperidine-1-carboxylate (0.662 mmol, 210 mg) in DMF (5 mL) was cooled to −50° C. 1,3-Dibromo-5,5-dimethylimidazolidine-2,4-dione (0.331 mmol, 95 mg) was added. The reaction mixture was stirred 1.5 h at 0° C. The reaction mixture was quenched in water and extracted with EtOAc (2x). The combined organic layers were washed with water and brine, filtered over phase-separation filter and concentrated to give 262 mg of tert-butyl 3-(4-amino-5-bromopyrrolo[1,2-f][1,2,4]triazin-7-yl)piperidine-1-carboxylate (100%). The crude product was used directly in the next step.

(d) tert-Butyl 3-(4-amino-5-(4-(4-(trifluoromethyl)pyridin-2-ylcarbamoyl)phenyl)pyrrolo[1,2-f][1,2,4]triazin-7-yl)piperidine-1-carboxylate A 2 M solution of potassium carbonate (2.62 mmol, 1.312 ml) was added to a suspension of tert-butyl 3-(4-amino-5-bromopyrrolo[1,2-f][1,2,4]triazin-7-yl)piperidine-1-carboxylate (0.656 mmol, 260 mg) and 4-(4,4,5,5-tetramethyl-1,3,2-dioxaborolan-2-yl)-N-(4-(trifluoromethyl)pyridin-2-yl)benzamide (0.722 mmol, 283 mg) in dioxane (6 mL). The resulting solution was purged with $N_2$ for 5 min at 30° C. 1,1'-Bis(diphenylphosphino)ferrocene Palladium (II) Chloride (0.0330 mmol, 26.5 mg) was added and the resulting solution was purged another 5 min at 30° C. with $N_2$. The reaction was heated for 6 h at reflux. The reaction was cooled and water and EtOAc were added. The suspension was filtered over decalite. The filtrate was extracted with EtOAc. The combined organic layers were combined, dried ($Na_2SO_4$), filtered and concentrated. The product was purified using silica gel chromatography (dichloromethane/methanol=100/0 to 9/1 (v/v %) to give 141 mg of tert-Butyl 3-(4-amino-5-(4-(4-(trifluoromethyl)pyridin-2-ylcarbamoyl)phenyl)pyrrolo[1,2-f][1,2,4]triazin-7-yl)piperidine-1-carboxylate (37%).

(e) 4-(4-amino-7-(piperidin-3-yl)pyrrolo[1,2-f][1,2,4]triazin-5-yl)-N-(4-(trifluoromethyl)pyridin-2-yl)benzamide tert-Butyl 3-(4-amino-5-(4-(4-(trifluoromethyl)pyridin-2-ylcarbamoyl)phenyl)pyrrolo[1,2-f][1,2,4]triazin-7-yl)piperidine-1-carboxylate (0.241 mmol, 140 mg) in hydrogen chloride (4.81 mmol, 1204 µL) (4M solution in dioxane) was stirred 1.5 h at rt. The reaction mixture was concentrated and water and $NaHCO_3$ (aq) were added. The waterlayer was extracted with DCM (2x). The combined organic layers were dried ($Na_2SO_4$), filtered and concentrated to give 69 mg of 4-(4-amino-7-(piperidin-3-yl)pyrrolo[1,2-f][1,2,4]triazin-5-yl)-N-(4-(trifluoromethyl)pyridin-2-yl)benzamide (59%).

The following Examples were synthesized following the methods described for Examples 46-49 starting with Intermediate 36.

| Example | Structure | Name | LC-MS [M + H]+ | Retention time |
|---|---|---|---|---|
| 251 | mix | ethyl 3-(4-amino-5-(4-(4-(trifluoromethyl)pyridin-2-ylcarbamoyl)phenyl)pyrrolo[1,2-f][1,2,4]triazin-7-yl)piperidine-1-carboxylate | 555.2 | 3.71 min |
| 252 | mix | 3-(4-amino-5-(4-(4-(trifluoromethyl)pyridin-2-ylcarbamoyl)phenyl)pyrrolo[1,2-f][1,2,4]triazin-7-yl)-N-ethylpiperidine-1-carboxamide | 553.2 | 3.02 min |

-continued
| Example | Structure | Name | LC-MS [M + H]+ | Retention time |
|---|---|---|---|---|
| 253 | 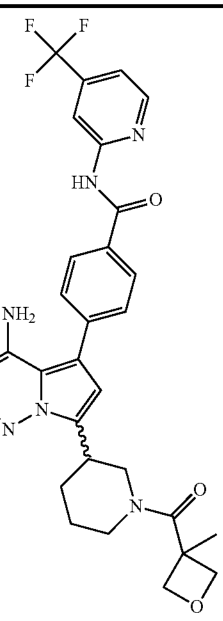 | 4-(4-amino-7-(1-(3-methyloxetane-3-carbonyl)piperidin-3-yl)pyrrolo[1,2-f][1,2,4]triazin-5-yl)-N-(4-(trifluoromethyl)pyridin-2-yl)benzamide | 581.2 | 3.06 min |
mix
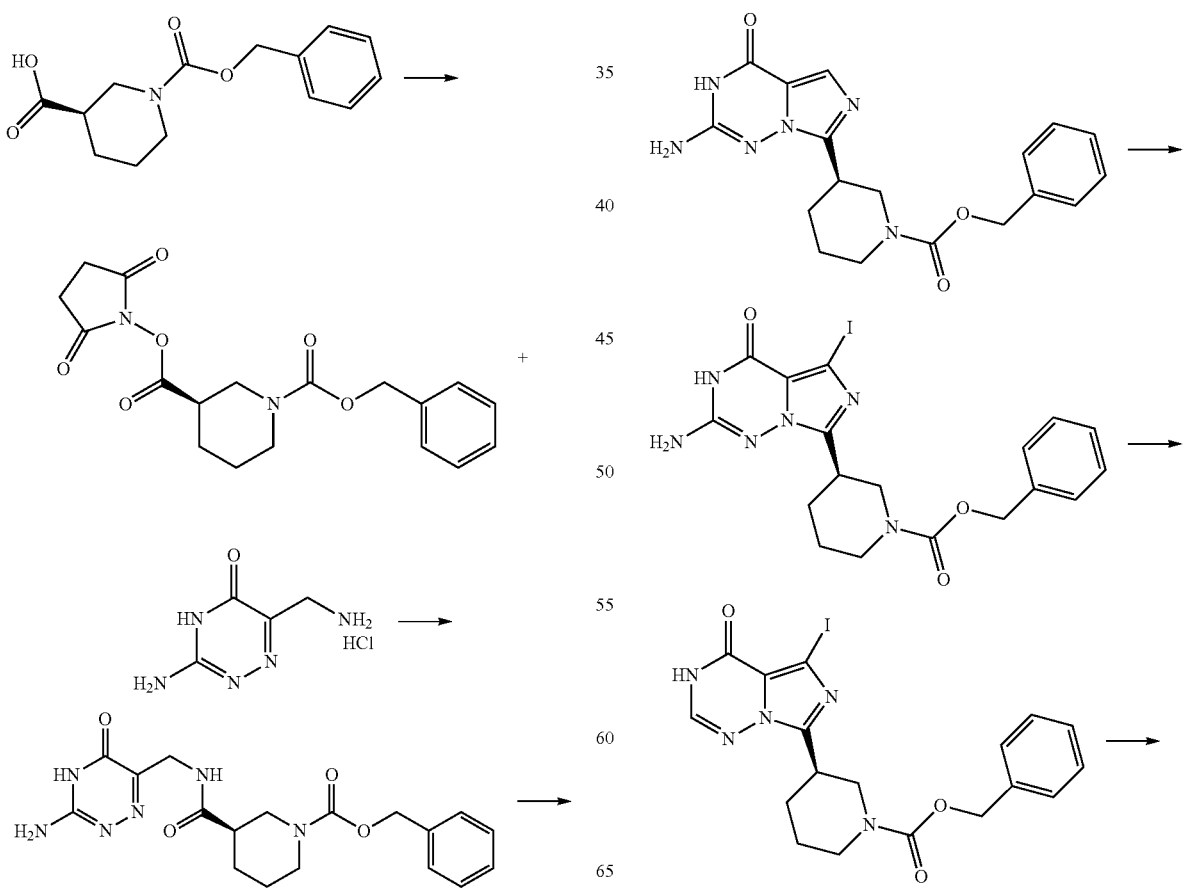

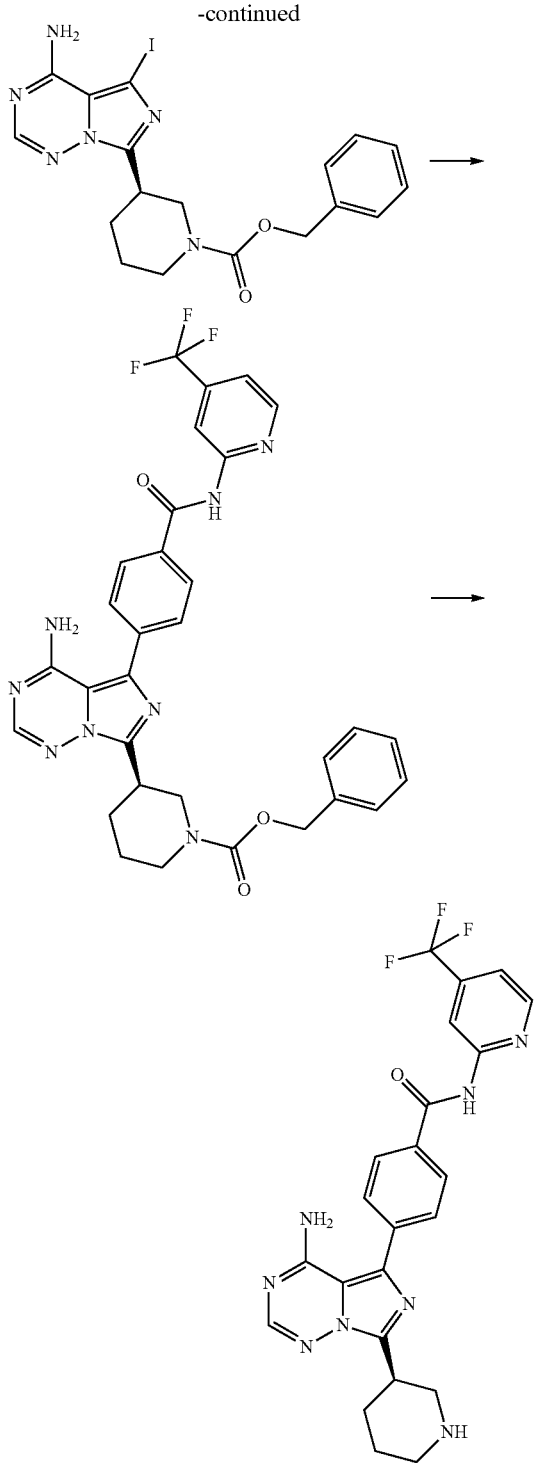

(R)-4-(4-amino-7-(piperidin-3-yl)imidazo[1,5-f][1,2,4]triazin-5-yl)-N-(4-(trifluoromethyl)pyridin-2-yl)benzamide (a) (R)-1-benzyl 3-(2,5-dioxopyrrolidin-1-yl) piperidine-1,3-dicarboxylate 1,3-Dicyclohexylcarbodiimide (36.1 mmol, 7.45 g) was added as a solid to a rapidly stirred turbid solution of (R)-piperidine-1,3-dicarboxylic acid 1-benzyl ester (36.1 mmol, 9.50 g) and N-hydroxysuccinimide (36.1 mmol, 4.15 g) in dioxane (180 mL). The reaction was stirred overnight at rt. The solids were removed by filtration and the filtrate was concentrated. The residue was subjected to high vacuum to give 15.0 g (R)-1-benzyl 3-(2,5-dioxopyrrolidin-1-yl) piperidine-1,3-dicarboxylate (100%). The crude product was used directly in the next reaction.

(b) (R)-benzyl 3-((3-amino-5-oxo-4,5-dihydro-1,2,4-triazin-6-yl)methyl-carbamoyl)piperidine-1-carboxylate Sodium hydrogen carbonate (72.2 mmol, 6.06 g) in water (45 mL) was added to a vigorously stirred solution of 3-amino-6-(aminomethyl)-1,2,4-triazin-5(4H)-one hydrochloride (36.1 mmol, 6.41 g) [Mitchel, W. L. et al, *J. Heterocycl. Chem.* 21, (1984), pp 697] in water (120 mL) at 0° C. After addition the resulting light brown suspension was allowed to come to rt. (R)-1-benzyl 3-(2,5-dioxopyrrolidin-1-yl) piperidine-1,3-dicarboxylate (36.1 mmol, 13.01 g) in a mixture of acetonitrile (40 mL), THF (40 mL) was added dropwise. After completion of addition the suspension was stirred 18 h at rt. The reaction mixture was filtered and the residue was washed with 2×20 mL water followed by 2×20 mL Et$_2$O to give 11.2 g (R)-benzyl 3-((3-amino-5-oxo-4,5-dihydro-1,2,4-triazin-6-yl)methylcarbamoyl) piperidine-1-carboxylate (81%).

(c) (R)-benzyl 3-(2-amino-4-oxo-3,4-dihydroimidazo[1,5-f][1,2,4]triazin-7-yl)piperidine-1-carboxylate Phosphorous oxychloride (50.7 mmol, 4.73 mL, 7.77 g) was added to a vigorously stirred suspension of (R)-benzyl 3-((3-amino-5-oxo-4,5-dihydro-1,2,4-triazin-6-yl)methylcarbamoyl)piperidine-1-carboxylate (24.15 mmol, 9.33 g) in acetonitrile (200 mL). The reaction was heated 18 h at reflux. The reaction was cooled to 0° C. and ammonia (362 mmol, 13.95 mL, 12.69 g) was added dropwise, maintaining the temperature below 10° C. until pH~7. The resulting solids were stirred 1 h at it and concentrated. The residue was co-evaporated with EtOH (2×10 mL) to remove water. The residue was refluxed in 200 mL MeCN for 2 h, cooled to 60° C. and filtered. The filtrate was concentrated to give 4.95 g red/brown oil. The residue was refluxed again in 200 mL MeOH 1 h, cooled to 60° C. and filtered. The filtrates were combined and concentrated and purified using silica gel chromatography (dichloromethane/methanol: 100/0 to 90/10 (v/v %)) to give 3.22 g of (R)-benzyl 3-(2-amino-4-oxo-3,4-dihydroimidazo[1,5-f][1,2,4]triazin-7-yl)piperidine-1-carboxylate (36%).

(d) (R)-benzyl 3-(2-amino-5-iodo-4-oxo-3,4-dihydroimidazo[1,5-f][1,2,4]triazin-7-yl)piperidine-1-carboxylate N-Iodosuccinimide (13.11 mmol, 2.95 g) was added to a stirred light yellow/orange solution of (R)-benzyl 3-(2- amino-4-oxo-3,4-dihydroimidazo[1,5-f][1,2,4]triazin-7-yl)piperidine-1-carboxylate (8.74 mmol, 3.22 g) in DMF (50 mL). The resulting light brown/orange solution was stirred 18 h at rt. The reaction mixture was poured in a 1/1/1 (v/v %) mixture of EtOAc/water/brine (500 mL). The water layer was extracted with EtOAc (2×50 mL). The combined organic layers were washed with 100 mL 5% $Na_2S_2O_4$ solution, water (2×500 mL), brine (100 mL), dried ($Na_2SO_4$), filtered and concentrated to give 4.00 g of (R)-benzyl 3-(2-amino-5-iodo-4-oxo-3,4-dihydroimidazo[1,5-f][1,2,4]triazin-7-yl)piperidine-1-carboxylate (93%). The crude product was used directly in the next step.

(e) (R)-benzyl 3-(5-iodo-4-oxo-3,4-dihydroimidazo[1,5-f][1,2,4]triazin-7-yl)piperidine-1-carboxylate Tert-butylnitrite (40.5 mmol, 4.85 mL, 4.17 g) was added to a stirred solution of (R)-benzyl 3-(2-amino-5-iodo-4-oxo-3,4-dihydroimidazo[1,5-f][1,2,4]triazin-7-yl)piperidine-1-carboxylate (8.09 mmol, 4.00 g) in THF (125 mL), DMF (25 mL) at rt. The reaction was stirred 6 h at rt. The reaction mixture was poured in 500 mL EtOAc/water/brine (1/1/1) (v/v %) and the waterlayer was extracted with 2×50 mL EtOAc. The combined organic layers were washed with 2×500 mL water, brine (100 mL), dried ($Na_2SO_4$), filtered and concentrated to give 4.02 g brown foam. The foam was stirred in 50 mL EtOAc and 110 mL heptane was added dropwise via a funnel. A yellowish solid precipitated. The mixture was concentrated to remove EtOAc and heptane, which resulted in the formation of an off-white powder. The solid was stirred 2 h in 50 mL EtOAc and filtered to give 2.00 g of (R)-benzyl 3-(5-iodo-4-oxo-3,4-dihydroimidazo[1,5-f][1,2,4]triazin-7-yl)piperidine-1-carboxylate (52%). The filtrate was purified using silica gel chromatography (dichloromethane/methanol=100/0 to 90/10 (v/v %)) to give an additional amount of 1.03 g (R)-benzyl 3-(5-iodo-4-oxo-3,4-dihydroimidazo[1,5-f][1,2,4]triazin-7-yl)piperidine-1-carboxylate (27%).

(f) (R)-benzyl 3-(4-amino-5-iodoimidazo[1,5-f][1,2,4]triazin-7-yl)piperidine-1-carboxylate Phosphorous oxychloride (6.57 mmol, 0.613 mL, 1.00 g) was added to a stirred suspension of 1H-1,2,4-triazole (19.7 mmol, 1.36 g) in pyridine (10 mL). The resulting fine white suspension was stirred 15 minutes at rt. (R)-benzyl 3-(5-iodo-4-oxo-3,4-dihydroimidazo[1,5-f][1,2,4]triazin-7-yl)piperidine-1-carboxylate (2.19 mmol, 1.05 g) in pyridine (20 mL) was added dropwise. The resulting dark orange reaction mixture, still containing a fine white precipitate, was stirred 2 h at rt. The reaction mixture was slowly added dropwise to a vigorously stirred mixture of ammonia (263 mmol, 40.5 mL) in ice (400 g) keeping the temperature below 0° C. The mixture was stirred 15 minutes after which the waterlayer was extracted with 3×50 mL EtOAc. The combined organic layers were washed with water (2×50 mL), brine (50 mL), dried ($Na_2SO_4$) filtered and concentrated. The product was purified using silica gel chromatography (dichloromethane/methanol=98/2 to 96/4 (v/v %)+TEA) to give 810 mg of (R)-benzyl 3-(4-amino-5-iodoimidazo[1,5-f][1,2,4]triazin-7-yl)piperidine-1-carboxylate (77%).

(g) (R)-benzyl 3-(4-amino-5-(4-(4-(trifluoromethyl)pyridin-2-ylcarbamoyl)phenyl)imidazo[1,5-f][1,2,4]triazin-7-yl)piperidine-1-carboxylate Potassium carbonate (10.87 mmol, 5.44 mL) was added (as a 2 N solution in water) to a stirred solution of (R)-benzyl 3-(4-amino-5-iodoimidazo[1,5-f][1,2,4]triazin-7-yl)piperidine-1-carboxylate (2.17 mmol, 1.04 g) and 4-(4,4,5,5-tetramethyl-1,3,2-dioxaborolan-2-yl)-N-(trifluoromethyl)pyridine-2-yl)benzamide (3.26 mmol, 1.279 g) in dioxane (11 mL). The resulting solution was purged with $N_2$ 5 minutes at 30° C. 1,1'-Bis(diphenylphosphino)ferrocene Palladium (II) Chloride (1.04 mmol, 88 mg) was added and the resulting orange solution was purged another 5 minutes at 30° C. with $N_2$. The reaction was heated 4 h at reflux. The reaction mixture was diluted with water (20 mL) and EtOAc (50 mL) and filtered over decalite. The phases were separated and the waterlayer was extracted with EtOAc (50 mL). The combined organic layers were washed with water (150 mL), brine (100 mL), dried ($Na_2SO_4$) filtered and concentrated to give 2.16 g of crude (R)-benzyl 3-(4-amino-5-(4-(4-(trifluoromethyl)pyridin-2-ylcarbamoyl)phenyl)imidazo[1,5-f][1,2,4]triazin-7-yl)piperidine-1-carboxylate (100%). The crude product was used directly in the next step.

(h) (R)-4-(4-amino-7-(piperidin-3-yl)imidazo[1,5-f][1,2,4]triazin-5-yl)-N-(4-(trifluoromethyl)pyridin-2-yl)benzamide Hydrobromic acid (87 mmol, 15.0 mL) was added to (R)-benzyl 3-(4-amino-5-(4-(4-(trifluoromethyl)pyridin-2-ylcarbamoyl)phenyl)imidazo[1,5-f][1,2,4]triazin-7-yl)piperidine-1-carboxylate (2.17 mmol, 1.34 g). The reaction was stirred 2 h at rt and turned slowly into a brown solution. The reaction mixture was cooled to 0° C. and water (100 mL) was added dropwise. The mixture was extracted with 4×100 mL DCM. The water layer was added dropwise to 250 mL 4N NaOH keeping the temperature below 10° C. The resulting yellow suspension was stirred 1 h and extracted with 4×100 DCM/2-BuOH (3/1 (v/v %)). The combined organic layers were dried ($Na_2SO_4$), filtered and concentrated and subjected to high vacuum to give 846 mg of (R)-4-(4-amino-7-(piperidin-3-yl)imidazo[1,5-f][1,2,4]triazin-5-yl)-N-(4-(trifluoromethyl)-pyridin-2-yl)benzamide (81%, 2 steps).

The following Examples were synthesized following the methods described for Examples 46-49 starting with Intermediate 37.

| Example | Structure | Name | LC-MS [M + H]+ | Retention time |
|---|---|---|---|---|
| 254 | 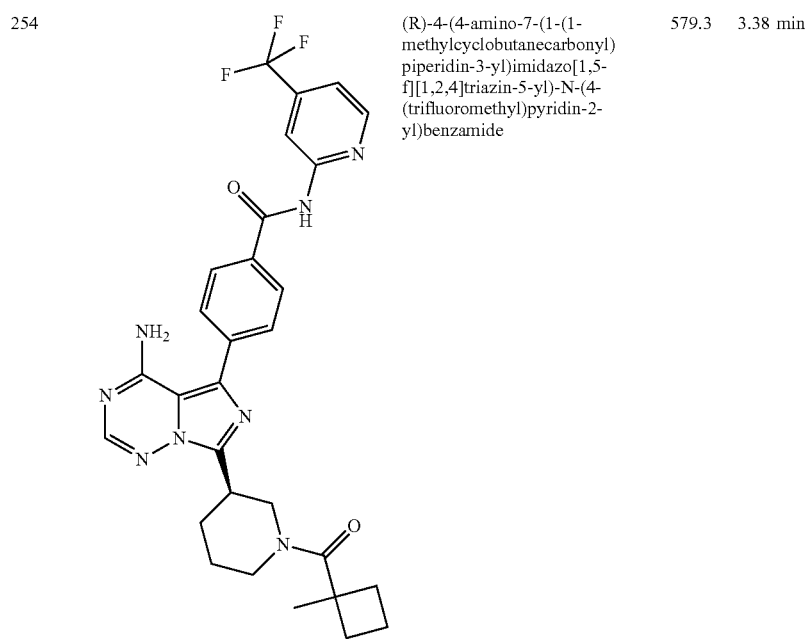 | (R)-4-(4-amino-7-(1-(1-methylcyclobutanecarbonyl)piperidin-3-yl)imidazo[1,5-f][1,2,4]triazin-5-yl)-N-(4-(trifluoromethyl)pyridin-2-yl)benzamide | 579.3 | 3.38 min |
| 255 | 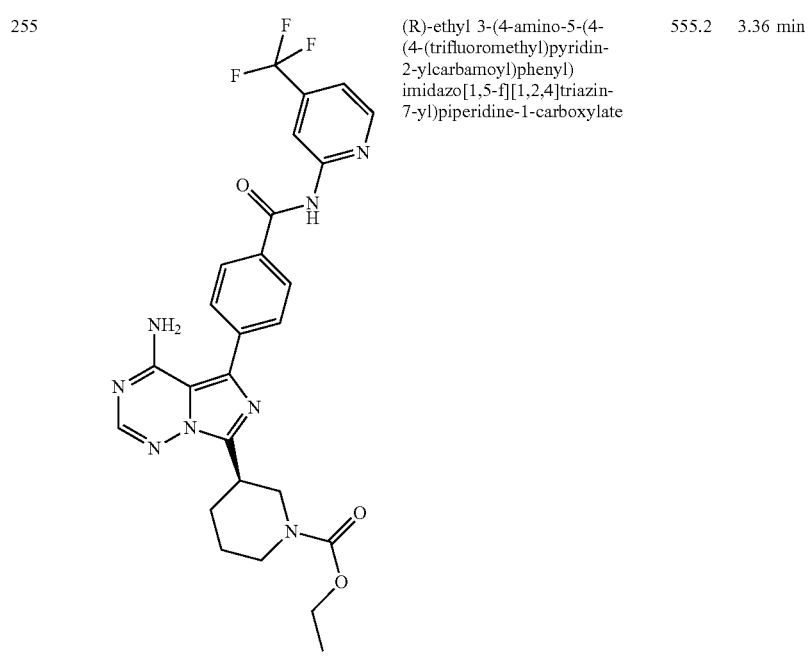 | (R)-ethyl 3-(4-amino-5-(4-(4-(trifluoromethyl)pyridin-2-ylcarbamoyl)phenyl)imidazo[1,5-f][1,2,4]triazin-7-yl)piperidine-1-carboxylate | 555.2 | 3.36 min |

| Example | Structure | Name | LC-MS [M + H]+ | Retention time |
|---|---|---|---|---|
| 256 | 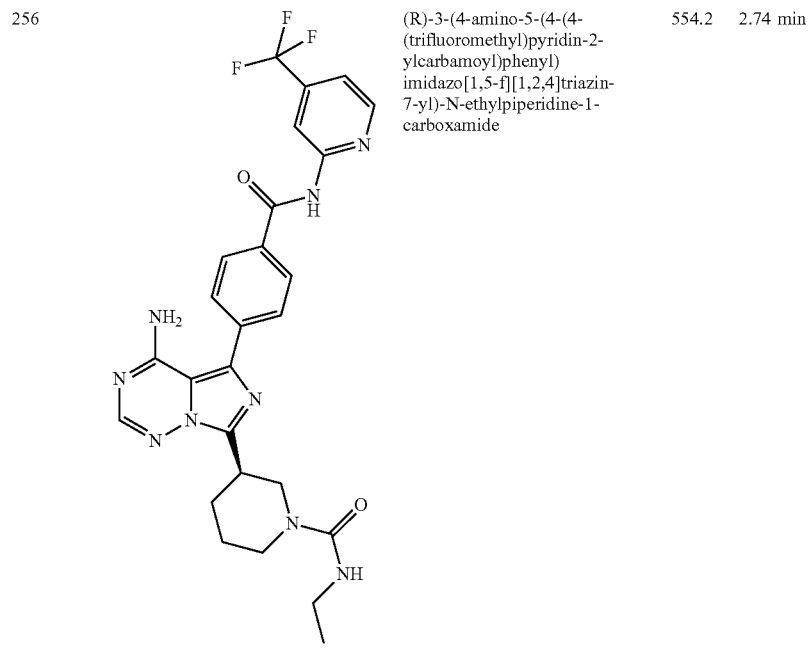 | (R)-3-(4-amino-5-(4-(4-(trifluoromethyl)pyridin-2-ylcarbamoyl)phenyl)imidazo[1,5-f][1,2,4]triazin-7-yl)-N-ethylpiperidine-1-carboxamide | 554.2 | 2.74 min |
| 257 | 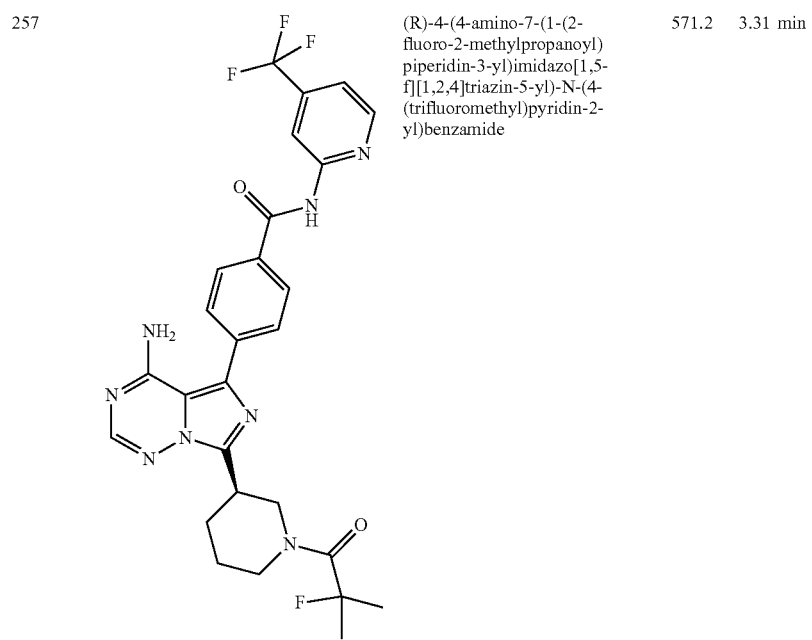 | (R)-4-(4-amino-7-(1-(2-fluoro-2-methylpropanoyl)piperidin-3-yl)imidazo[1,5-f][1,2,4]triazin-5-yl)-N-(4-(trifluoromethyl)pyridin-2-yl)benzamide | 571.2 | 3.31 min |

| Example | Structure | Name | LC-MS [M + H]+ | Retention time |
|---|---|---|---|---|
| 258 | 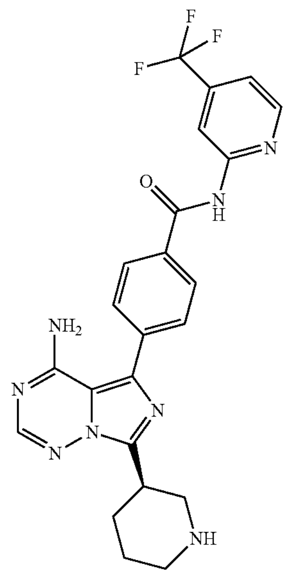 [SMILES: Nc1ncnn2c([C@@H]3CCCNC3)nc(-c3ccc(C(=O)Nc4cc(C(F)(F)F)ccn4)cc3)c12] | (R)-4-(4-amino-7-(piperidin-3-yl)imidazo[1,5-f][1,2,4]triazin-5-yl)-N-(4-(trifluoromethyl)pyridin-2-yl)benzamide | 482.9 | 1.55 min (LCMS-B) |
| 259 | 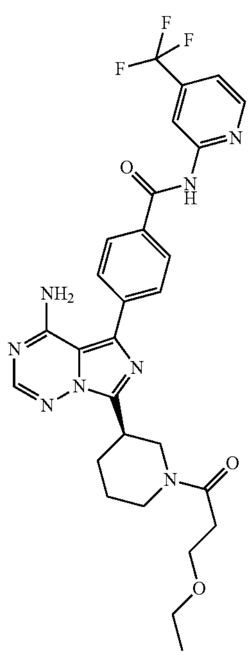 [SMILES: CCOCCC(=O)N1CCC[C@@H](c2nc(-c3ccc(C(=O)Nc4cc(C(F)(F)F)ccn4)cc3)c3c(N)ncnn23)C1] | (R)-4-(4-amino-7-(1-(3-ethoxypropanoyl)piperidin-3-yl)imidazo[1,5-f][1,2,4]triazin-5-yl)-N-(4-(trifluoromethyl)pyridin-2-yl)benzamide | 583.2 | 2.95 min |

-continued
| Example | Structure | Name | LC-MS [M + H]+ | Retention time |
|---|---|---|---|---|
| 260 | 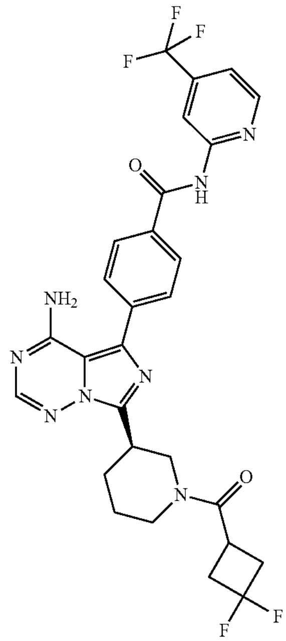 [SMILES: Nc1ncnn2c([C@@H]3CCCN(C(=O)C4CC(F)(F)C4)C3)nc(-c3ccc(C(=O)Nc4cc(C(F)(F)F)ccn4)cc3)c12] | (R)-4-(4-amino-7-(1-(3,3-difluorocyclobutanecarbonyl)piperidin-3-yl)imidazo[1,5-f][1,2,4]triazin-5-yl)-N-(4-(trifluoromethyl)pyridin-2-yl)benzamide | 601.2 | 3.28 min |
| 261 | 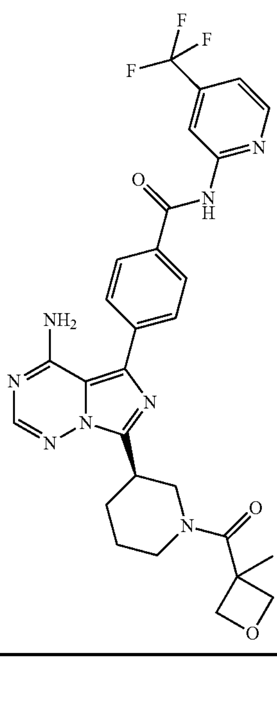 | (R)-4-(4-amino-7-(1-(3-methyloxetane-3-carbonyl)piperidin-3-yl)imidazo[1,5-f][1,2,4]triazin-5-yl)-N-(4-(trifluoromethyl)pyridin-2-yl)benzamide | 581.2 | 2.87 min |
Intermediate 38
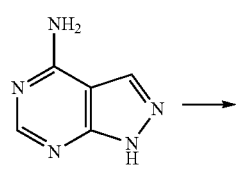
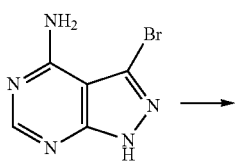

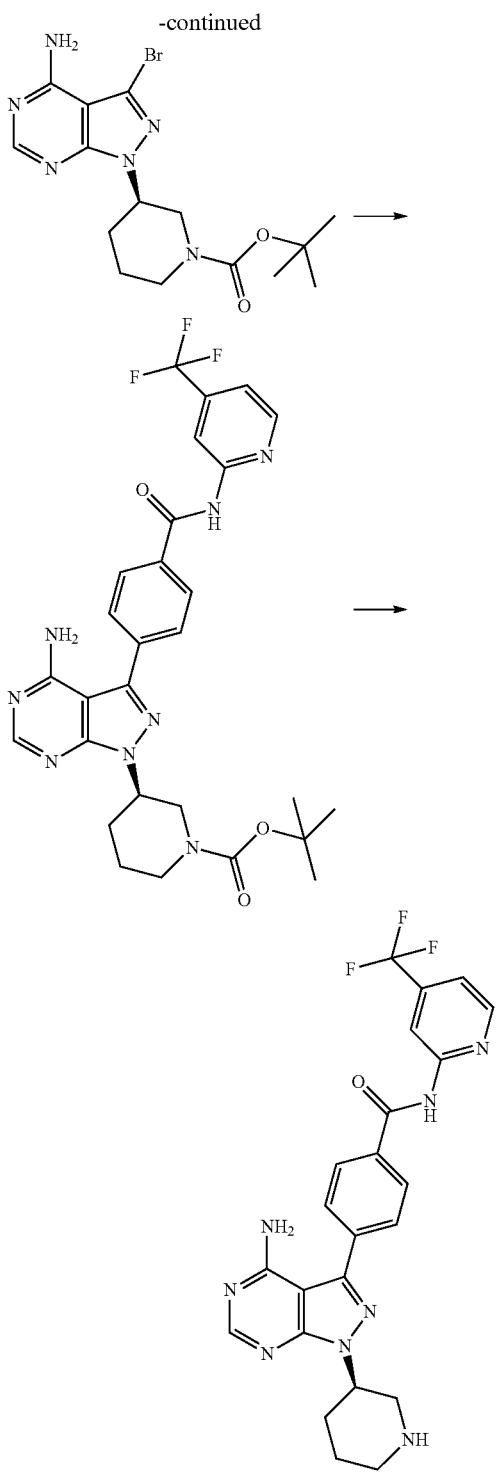

(R)-4-(4-amino-1-(piperidin-3-yl)-1H-pyrazolo[3,4-d]pyrimidin-3-yl)-N-(4-(trifluoromethyl)pyridin-2-yl)benzamide (a) 3-Bromo-1H-pyrazolo[3,4-d]pyrimidin-4-amine N-Bromosuccinimide (37.0 mmol, 6.59 g) was added to a stirred suspension of 1H-pyrazolo[3,4-d]pyrimidin-4-amine (37.0 mmol, 5.00 g) in 50 mL DMF and heated to 60° C. for 4 h. The reaction mixture was concentrated in vacuum. The residual brown solid was stirred in di-ethylether and filtered to give 11.9 g of 3-bromo-1H-pyrazolo-[3,4-d]pyrimidin-4-amine (100%). The crude product was used directly in the next step.

(b) (R)-tert-butyl 3-(4-amino-3-bromo-1H-pyrazolo[3,4-d]pyrimidin-1-yl)piperidine-1-carboxylate A suspension of 3-bromo-1H-pyrazolo[3,4-d]pyrimidin-4-amine (37.0 mmol, 7.92 g), (S)-tert-butyl 3-hydroxypiperidine-1-carboxylate (62.9 mmol, 12.7 g) and triphenylphosphine (62.9 mmol, 16.5 g) in dry THF (150 mL) was cooled to −10° C. DEAD (62.9 mmol, 28.8 mL, 40% solution in toluene) was added dropwise. The reaction mixture was allowed to warm to rt and was stirred 3 h. EtOAc was added and extracted with 10% aq. NaCl. The organic layer was dried (Na$_2$SO$_4$), filtered and concentrated. The product was purified using silica gel chromatography (dichloromethane/methanol=97/3 (v/v %)+TEA to give 16.5 g of (R)-tert-butyl 3-(4-amino-3-bromo-1H-pyrazolo[3,4-d]pyrimidin-1-yl)piperidine-1-carboxylate (100%).

(c) (R)-tert-butyl 3-(4-amino-3-(4-(4-(trifluoromethyl)pyridin-2-ylcarbamoyl)phenyl)-1H-pyrazolo[3,4-d]pyrimidin-1-yl)piperidine-1-carboxylate Potassium carbonate (36.2 mmol, 18.12 mL) was added as a 2N solution in H$_2$O to a stirred suspension of (R)-tert-butyl 3-(4-amino-3-bromo-1H-pyrazolo[3,4-d]pyrimidin-1-yl)piperidine-1-carboxylate (7.25 mmol, 2.28 g) and 4-(4,4,5,5-tetramethyl-1,3,2-dioxaborolan-2-yl)-N-(trifluoromethyl)pyridine-2-yl)benzamide (10.87 mmol, 4.26 g) in dioxane (36 mL). 1,1'-Bis(diphenylphosphino)ferrocene Palladium (II) Chloride (0.362 mmol, 293 mg) was added and the reaction mixture was purged 5 minutes with N$_2$. The reaction was heated 4 h at reflux. EtOAc was added and the solution was filtered. The filtrate was washed with 10% NaCl-sol., dried (Na$_2$SO$_4$), filtered and concentrated. The product was purified using silica gel chromatography (dichloromethane/methanol=95/5 (v/v %) to give 3.66 g of (R)-tert-butyl 3-(4-amino-3-(4-(4-(trifluoromethyl)pyridin-2-ylcarbamoyl)phenyl)-1H-pyrazolo[3,4-d]pyrimidin-1-yl)piperidine-1-carboxylate (87%).

(d) (R)-4-(4-amino-1-(piperidin-3-yl)-1H-pyrazolo[3,4-d]pyrimidin-3-yl)-N-(4-(trifluoromethyl)-pyridin-2-yl)benzamide HCl/dioxane 4N was added to (R)-tert-butyl 3-(4-amino-3-(4-(4-(trifluoromethyl)pyridin-2-ylcarbamoyl)phenyl)-1H-pyrazolo[3,4-d]pyrimidin-1-yl)piperidine-1-carboxylate and the reaction was stirred 1 hr at rt. The reaction mixture was diluted with 50 mL water, and washed with DCM (3×50 mL). The waterlayer was added drop wise to 100 mL NaOH 4N solution, and extracted with DCM (3×50 mL). The combined organic layers were dried (Na$_2$SO$_4$), filtered and concentrated to give 0.792 mg of (R)-4-(4-amino-1-(piperidin-3-yl)-1H-pyrazolo[3,4-d]pyrimidin-3-yl)-N-(4-(trifluoromethyl)pyridin-2-yl)benzamide (26%).

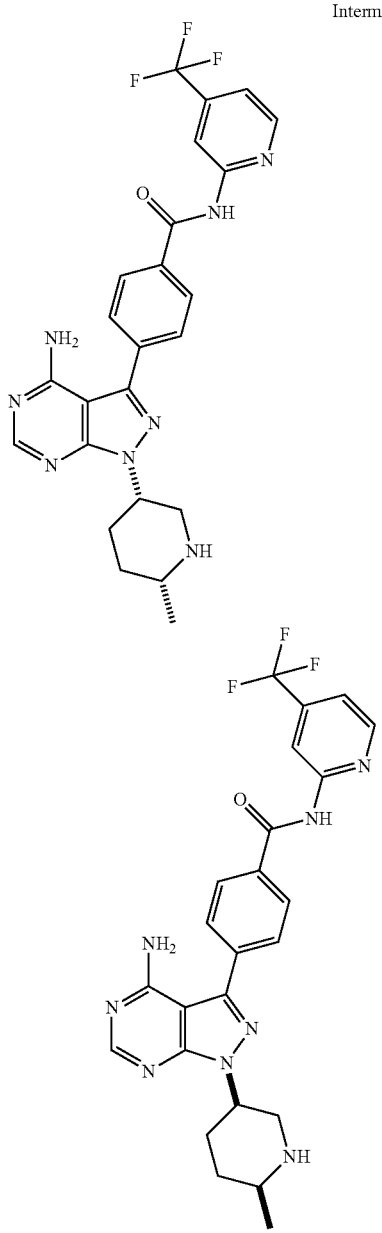

Intermediates 38b and 38c (a) Tert-butyl 5-hydroxy-2-methylpiperidine-1-carboxylate To a stirred suspension of 6-methylpiperidin-3-ol (cis-trans mixture, 1.0 g, 8.68 mmol) in $CH_2Cl_2$ (20.00 ml) at r.t. was added triethylamine (3.03 ml, 21.71 mmol) and clear mixture was cooled in ice bath. $(Boc)_2O$ (2.369 g, 10.85 mmol) was added and the resultant cloudy mixture was stirred at 0° C. for ½ hr and at r. t. overnight. The mixture was washed with saturated $NaHCO_3$, dried over $MgSO_4$ and evaporated to dryness. The crude was purified on RediSep 120 g cartridge and eluted with 1 1 Hexane, 1 1 15% EtOAc/hexane and 1 1 30% EtOAc/hexane to give the product as a white solid (0.44 g, 23%)

(b) Tert-butyl 5-(4-amino-3-bromo-1H-pyrazolo[3,4-d]pyrimidin-1-yl)-2-methylpiperidine-1-carboxylate To a stirred suspension of 3-bromo-1H-pyrazolo[3,4-d]pyrimidin-4-amine (3.14 g, 14.66 mmol) in 75 ml of THF at r.t. under nitrogen atmosphere was added, tert-butyl 5-hydroxy-2-methylpiperidine-1-carboxylate (2.870 g, 13.33 mmol) and triphenylphosphine (3.50 g, 13.33 mmol). The suspension was cooled to ° C. in ice bath and DIAD (2.64 ml, 13.33 mmol) was added dropwise at 0° C. The suspension became clear, and the solution was stirred at 0° C. for 0.5 hr. and at r. t. overnight. The mixture was evaporated to dryness and residue was triturated with $CH_2Cl_2$, the suspension was filtered and washed with $CH_2Cl_2$. The filtrate was concentrated to small volume and purified on RediSep 120 g cartridge. The column was eluted with 1 1 $CH_2Cl_2$, 2 1 1.5% MeOH-2M $NH_3/CH_2Cl_2$ and 2 l 3% MeOH-2M $NH_3/CH_2Cl_2$ to isolate the product as gummy solid (3.9 g, 72%).

(c) Tert-butyl 5-(4-amino-3-(4-((4-(trifluoromethyl)pyridin-2-yl)carbamoyl)-phenyl)-1H-pyrazolo[3,4-d]pyrimidin-1-yl)-2-methylpiperidine-1-carboxylate To a solution of tert-butyl 5-(4-amino-3-bromo-1H-pyrazolo[3,4-d]pyrimidin-1-yl)-2-methylpiperidine-1-carboxylate (3.700 g, 9.00 mmol) in a mixture of 1,4-dioxane (60.00 ml) and water (15.00 ml), 4-(4,4,5,5-tetramethyl-1,3,2-dioxaborolan-2-yl)-N-(trifluoromethyl)pyridine-2-yl)benzamide (4.41 g, 11.24 mmol), $K_3PO_4$ (4.77 g, 22.49 mmol) and 1,1'-bis(diphenylphosphino)ferrocene Palladium (II) Chloride (0.735 g, 0.900 mmol) were added under nitrogen atmosphere. The contents were degassed 3 times with $N_2$ and mixture was stirred at 80° C. overnight. The mixture was concentrated to small volume and partitioned between 150 ml EtOAc and 100 ml $H_2O$. The suspension was filtered through microfiber filter and solid was washed with EtOAc. The contents were transferred to separatory funnel, the organic phase was separated, dried over $MgSO_4$ and evaporated to dryness gave brown gum. The solid on microfiber filter was stirred with 150 ml $CH_2Cl_2$+75 ml $H_2O$. The organic phase was separated, dried over $MgSO_4$, evaporated to dryness and this crude was combined with crude from EtOAc work up. The combined crude was purified on RediSep 120 g cartridge. The column was eluted with 500 ml $CH_2Cl_2$, 2 lt 1.5% MeOH-2M $NH_3/CH_2Cl_2$ and 2 lt 3% MeOH-2M $NH_3/CH_2Cl_2$ gave brown solid (4.2 g, 78%).

(d) Cis-racemic-4-(4-amino-1-(6-methylpiperidin-3-yl)-1H-pyrazolo[3,4-d]pyrimidin-3-yl)-N-(4-(trifluoromethyl)pyridin-2-yl)benzamide To a stirred solution of tert-butyl 5-(4-amino-3-(4-((4-(trifluoromethyl)pyridin-2-yl)carbamoyl)phenyl)-1H-pyrazolo[3,4-d]pyrimidin-1-yl)-2-methylpiperidine-1-carboxylate (4.180 g, 7.01 mmol) in $CH_2Cl_2$ (50.00 ml) at r. t. was added TFA (10 ml, 135 mmol). The reaction was stirred at r. t. overnight. The solvent was evaporated to dryness and azeotroped with toluene. The crude was purified on RediSep 80 g cartridge and eluted with 1 1 2.5% MeOH-2M NH2/$CH_2Cl_2$, 3 l 5% MeOH-2M $NH_3/CH_2Cl_2$ to give the product as a brown solid (3.0 g, 87%). Purification on chiral AD SFC column provided the enantiomers.

Fast moving Intermediate 38b 1 $[\alpha]_D^{25}$=+15.958
Slow moving Intermediate 38c $[\alpha]_D^{25}$=−15.973

The following Examples were synthesized following the methods described for Examples 46-49 starting with Intermediate 38.

| Example | Structure | Name | LC-MS [M + H]+ | Retention time |
|---|---|---|---|---|
| 262 | 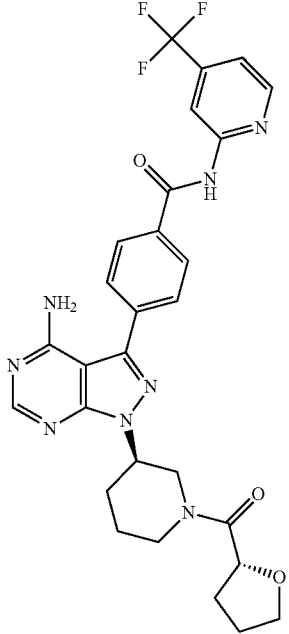 [SMILES: Nc1ncnc2c1c(-c1ccc(C(=O)Nc3cc(C(F)(F)F)ccn3)cc1)nn2[C@@H]1CCCN(C(=O)[C@H]2CCCO2)C1] | 4-(4-amino-1-((R)-1-((R)-tetrahydrofuran-2-carbonyl)piperidin-3-yl)-1H-pyrazolo[3,4-d]pyrimidin-3-yl)-N-(4-(trifluoromethyl)pyridin-2-yl)benzamide | 581.2 | 2.81 min |
| 263 | 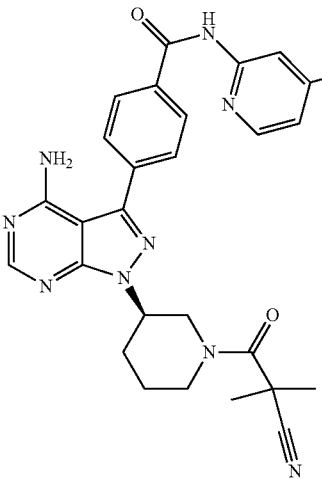 | (R)-4-(4-amino-1-(1-(2-cyano-2-methylpropanoyl)piperidin-3-yl)-1H-pyrazolo[3,4-d]pyrimidin-3-yl)-N-(4-(trifluoromethyl)pyridin-2-yl)benzamide | 578.2 | 3.27 min |

-continued

| Example | Structure | Name | LC-MS [M + H]+ | Retention time |
|---|---|---|---|---|
| 264 | 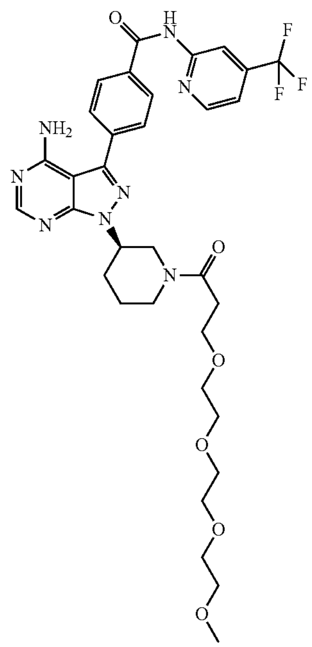 [SMILES: COCCOCCOCCOCCC(=O)N1CCC[C@@H](n2nc(-c3ccc(C(=O)Nc4cc(C(F)(F)F)ccn4)cc3)c3c(N)ncnc32)C1] | (R)-4-(1-(1-2,5,8,11-tetraoxatetradecanepiperidin-3-yl)-4-amino-1H-pyrazolo[3,4-d]pyrimidin-3-yl)-N-(4-(trifluoromethyl)pyridin-2-yl)benzamide | 701.3 | 2.92 min |
| 265 | 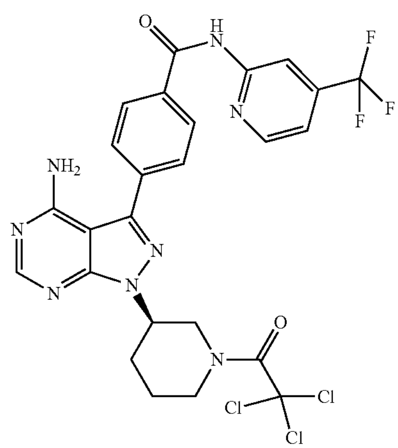 [SMILES: Nc1ncnc2c1c(-c1ccc(C(=O)Nc3cc(C(F)(F)F)ccn3)cc1)nn2[C@@H]1CCCN(C(=O)C(Cl)(Cl)Cl)C1] | (R)-4-(4-amino-1-(1-(2,2,2-trichloroacetyl)piperidin-3-yl)-1H-pyrazolo[3,4-d]pyrimidin-3-yl)-N-(4-(trifluoromethyl)pyridin-2-yl)benzamide | 629.0 | 3.97 min |
| 266 | 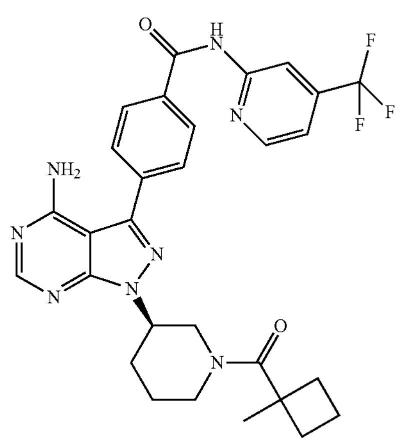 [SMILES: CC1(C(=O)N2CCC[C@@H](n3nc(-c4ccc(C(=O)Nc5cc(C(F)(F)F)ccn5)cc4)c4c(N)ncnc43)C2)CCC1] | (R)-4-(4-amino-1-(1-(1-methylcyclobutanecarbonyl)piperidin-3-yl)-1H-pyrazolo[3,4-d]pyrimidin-3-yl)-N-(4-(trifluoromethyl)pyridin-2-yl)benzamide | 580.2 | 3.50 min |

| Example | Structure | Name | LC-MS [M + H]+ | Retention time |
|---------|-----------|------|----------------|----------------|
| 267 | 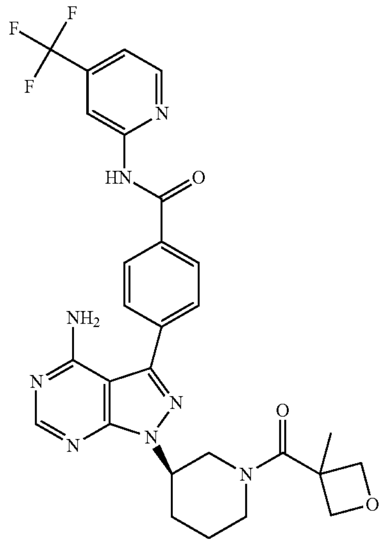 [SMILES: CC1(C(=O)N2CCC[C@@H](n3nc(-c4ccc(C(=O)Nc5cc(C(F)(F)F)ccn5)cc4)c4c(N)ncnc43)C2)COC1] | (R)-4-(4-amino-1-(1-(3-methyloxetane-3-carbonyl)piperidin-3-yl)-1H-pyrazolo[3,4-d]pyrimidin-3-yl)-N-(4-(trifluoromethyl)pyridin-2-yl)benzamide | 581.2 | 2.72 min |
| 268 | 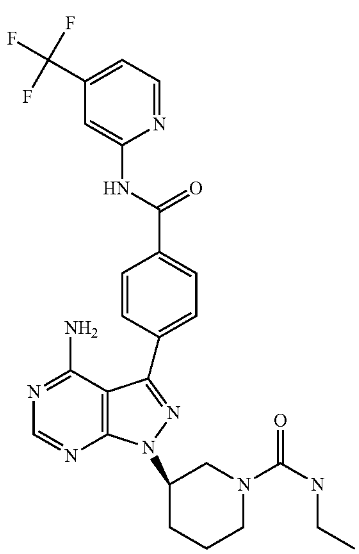 [SMILES: CCNC(=O)N1CCC[C@@H](n2nc(-c3ccc(C(=O)Nc4cc(C(F)(F)F)ccn4)cc3)c3c(N)ncnc32)C1] | (R)-3-(4-amino-3-(4-(4-(trifluoromethyl)pyridin-2-ylcarbamoyl)phenyl)-1H-pyrazolo[3,4-d]pyrimidin-1-yl)-N-ethylpiperidine-1-carboxamide | 555.2 | 2.74 min |

| Example | Structure | Name | LC-MS [M + H]+ | Retention time |
|---|---|---|---|---|
| 269 | 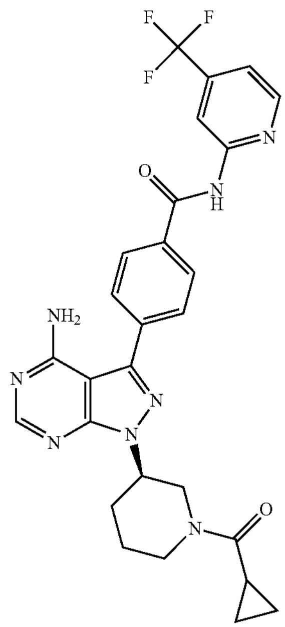 [SMILES: Nc1ncnc2c1c(-c1ccc(C(=O)Nc3cc(C(F)(F)F)ccn3)cc1)nn2[C@@H]1CCCN(C(=O)C2CC2)C1] | (R)-4-(4-amino-1-(1-(cyclopropanecarbonyl)piperidin-3-yl)-1H-pyrazolo[3,4-d]pyrimidin-3-yl)-N-(4-(trifluoromethyl)pyridin-2-yl)benzamide | 551.2 | 2.98 min |
| 270 | 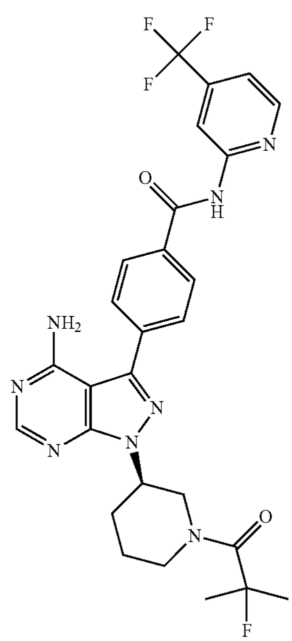 [SMILES: CC(C)(F)C(=O)N1CCC[C@@H](n2nc(-c3ccc(C(=O)Nc4cc(C(F)(F)F)ccn4)cc3)c3c(N)ncnc32)C1] | (R)-4-(4-amino-1-(1-(2-fluoro-2-methylpropanoyl)piperidin-3-yl)-1H-pyrazolo[3,4-d]pyrimidin-3-yl)-N-(4-(trifluoromethyl)pyridin-2-yl)benzamide | 572.2 | 3.30 min |

| Example | Structure | Name | LC-MS [M + H]⁺ | Retention time |
|---------|-----------|------|----------------|----------------|
| 271 | 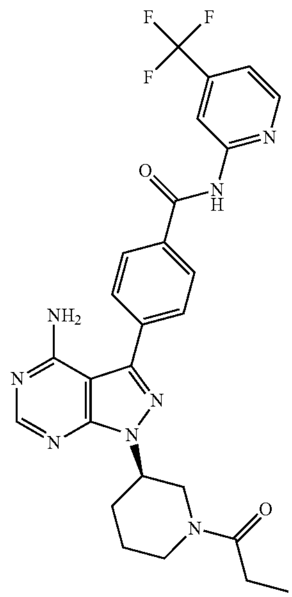 [SMILES: CCC(=O)N1CCC[C@@H](n2nc(-c3ccc(C(=O)Nc4cc(C(F)(F)F)ccn4)cc3)c3c(N)ncnc32)C1] | (R)-4-(4-amino-1-(1-propionylpiperidin-3-yl)-1H-pyrazolo[3,4-d]pyrimidin-3-yl)-N-(4-(trifluoromethyl)pyridin-2-yl)benzamide | 539.2 | 2.89 min |
| 272 | 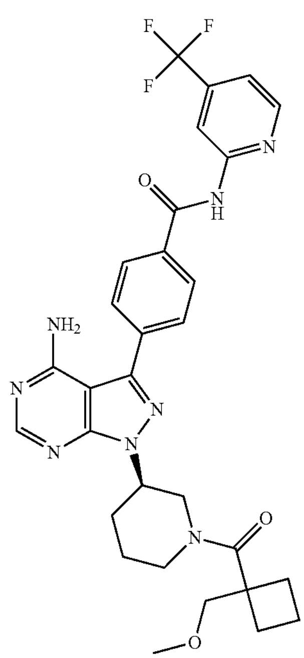 [SMILES: COCC1(C(=O)N2CCC[C@@H](n3nc(-c4ccc(C(=O)Nc5cc(C(F)(F)F)ccn5)cc4)c4c(N)ncnc43)C2)CCC1] | (R)-4-(4-amino-1-(1-(1-(methoxymethyl)cyclobutanecarbonyl)piperidin-3-yl)-1H-pyrazolo[3,4-d]pyrimidin-3-yl)-N-(4-(trifluoromethyl)pyridin-2-yl)benzamide | 610.2 | 3.32 min |

| Example | Structure | Name | LC-MS [M + H]+ | Retention time |
|---|---|---|---|---|
| 273 | 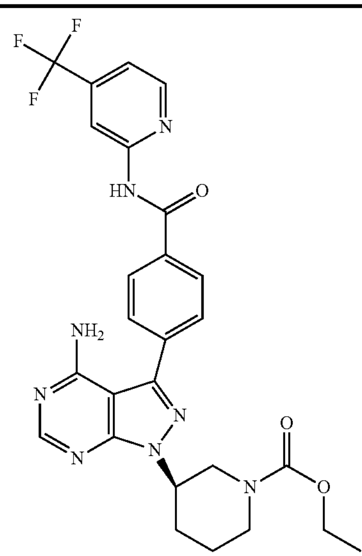 | (R)-ethyl 3-(4-amino-3-(4-(4-(trifluoromethyl)pyridin-2-ylcarbamoyl)phenyl)-1H-pyrazolo[3,4-d]pyrimidin-1-yl)piperidine-1-carboxylate | 555.0 | 3.33 min |
| 274 | 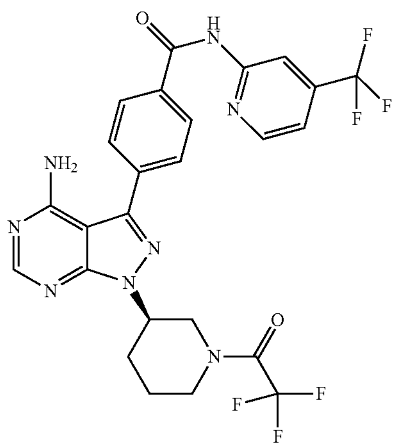 [SMILES: Nc1ncnc2c1c(-c1ccc(C(=O)Nc3cc(C(F)(F)F)ccn3)cc1)nn2[C@@H]1CCCN(C(=O)C(F)(F)F)C1] | (R)-4-(4-amino-1-(1-(2,2,2-trifluoroacetyl)piperidin-3-yl)-1H-pyrazolo[3,4-d]pyrimidin-3-yl)-N-(4-(trifluoromethyl)pyridin-2-yl)benzamide | 579.0 | 3.54 min |
| 275 | 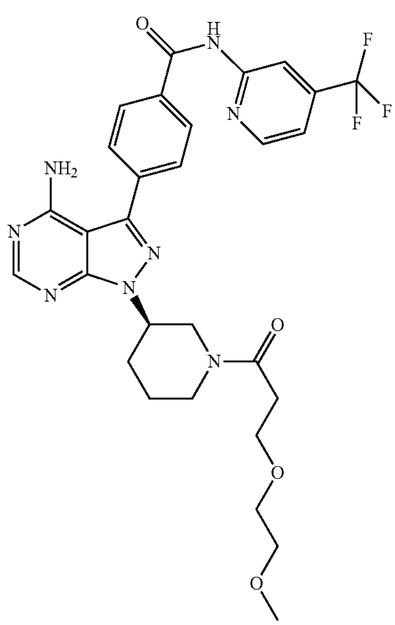 [SMILES: COCCOCCC(=O)N1CCC[C@@H](n2nc(-c3ccc(C(=O)Nc4cc(C(F)(F)F)ccn4)cc3)c3c(N)ncnc32)C1] | (R)-4-(4-amino-1-(1-(3-(2-methoxyethoxy)propanoyl)piperidin-3-yl)-1H-pyrazolo[3,4-d]pyrimidin-3-yl)-N-(4-(trifluoromethyl)pyridin-2-yl)benzamide | 613.2 | 2.89 min |

| Example | Structure | Name | LC-MS [M + H]+ | Retention time |
|---|---|---|---|---|
| 276 | 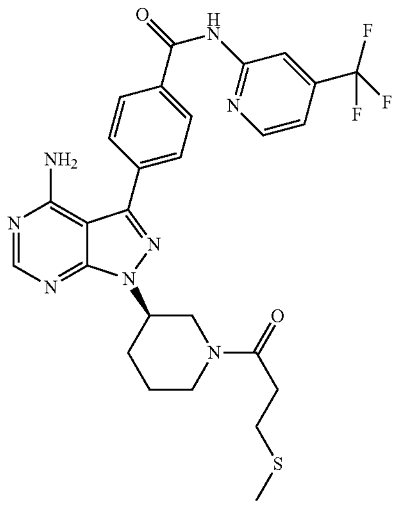 [SMILES: CSCCC(=O)N1CCC[C@@H](n2nc(-c3ccc(C(=O)Nc4cc(C(F)(F)F)ccn4)cc3)c3c(N)ncnc32)C1] | (R)-4-(4-amino-1-(1-(3-(methylthio)propanoyl)piperidin-3-yl)-1H-pyrazolo[3,4-d]pyrimidin-3-yl)-N-(4-(trifluoromethyl)pyridin-2-yl)benzamide | 586.2 | 3.20 min |
| 277 | 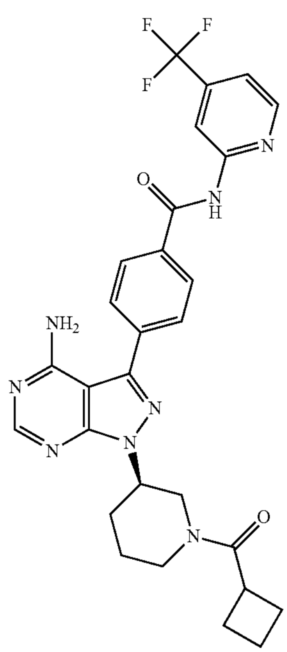 [SMILES: Nc1ncnc2c1c(-c1ccc(C(=O)Nc3cc(C(F)(F)F)ccn3)cc1)nn2[C@@H]1CCCN(C(=O)C2CCC2)C1] | (R)-4-(4-amino-1-(1-(cyclobutanecarbonyl)piperidin-3-yl)-1H-pyrazolo[3,4-d]pyrimidin-3-yl)-N-(4-(trifluoromethyl)pyridin-2-yl)benzamide | 565.2 | 3.24 min |

| Example | Structure | Name | LC-MS [M + H]+ | Retention time |
|---------|-----------|------|----------------|----------------|
| 278 | 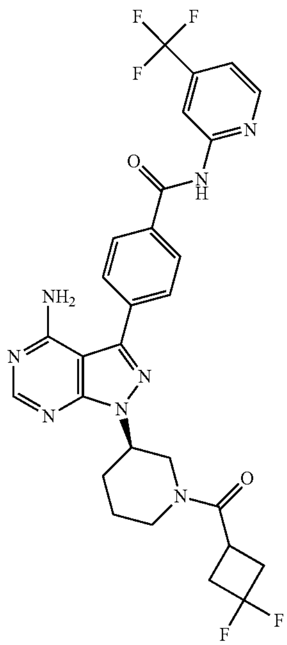 [SMILES: Nc1ncnc2c1c(-c1ccc(C(=O)Nc3cc(C(F)(F)F)ccn3)cc1)nn2[C@@H]1CCCN(C(=O)C2CC(F)(F)C2)C1] | (R)-4-(4-amino-1-(1-(3,3-difluorocyclobutanecarbonyl)piperidin-3-yl)-1H-pyrazolo[3,4-d]pyrimidin-3-yl)-N-(4-(trifluoromethyl)pyridin-2-yl)benzamide | 602.2 | 3.24 min |
| 279 | 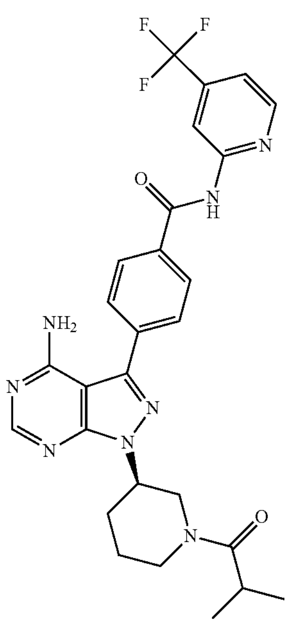 [SMILES: CC(C)C(=O)N1CCC[C@@H](n2nc(-c3ccc(C(=O)Nc4cc(C(F)(F)F)ccn4)cc3)c3c(N)ncnc32)C1] | (R)-4-(4-amino-1-(1-isobutyrylpiperidin-3-yl)-1H-pyrazolo[3,4-d]pyrimidin-3-yl)-N-(4-(trifluoromethyl)pyridin-2-yl)benzamide | 553.2 | 3.10 min |

-continued

| Example | Structure | Name | LC-MS [M + H]+ | Retention time |
|---------|-----------|------|----------------|----------------|
| 280 | 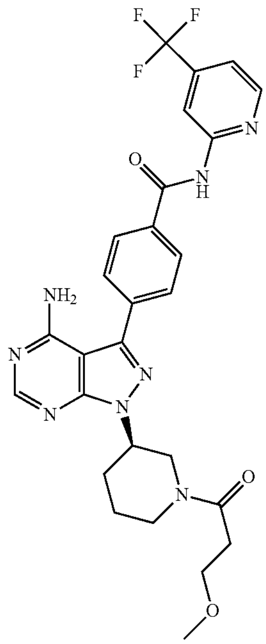 [SMILES: COCCC(=O)N1CCC[C@@H](n2nc(-c3ccc(C(=O)Nc4cc(C(F)(F)F)ccn4)cc3)c3c(N)ncnc32)C1] | (R)-4-(4-amino-1-(1-(3-methoxypropanoyl)piperidin-3-yl)-1H-pyrazolo[3,4-d]pyrimidin-3-yl)-N-(4-(trifluoromethyl)pyridin-2-yl)benzamide | 569.2 | 2.76 min |
| 281 | 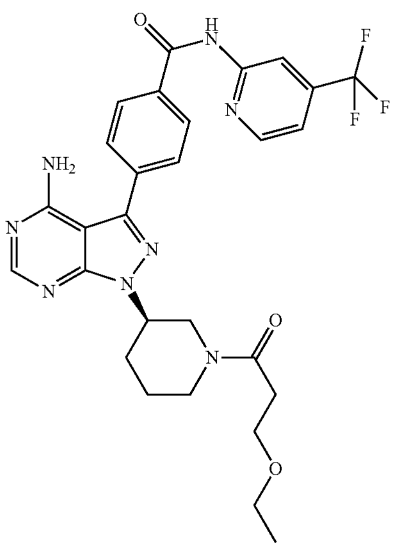 [SMILES: CCOCCC(=O)N1CCC[C@@H](n2nc(-c3ccc(C(=O)Nc4cc(C(F)(F)F)ccn4)cc3)c3c(N)ncnc32)C1] | (R)-4-(4-amino-1-(1-(3-ethoxypropanoyl)piperidin-3-yl)-1H-pyrazolo[3,4-d]pyrimidin-3-yl)-N-(4-(trifluoromethyl)pyridin-2-yl)benzamide | 583.2 | 3.05 min |

The following Examples were synthesized following the methods described for Examples 1-281 using appropriate intermediates.

| Example | Structure | Name | LC-MS [M + H]+ | Retention time |
|---|---|---|---|---|
| 282 | 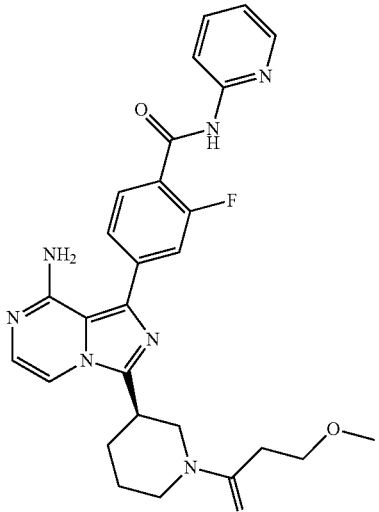 | (R)-4-(8-amino-3-(1-(3-methoxypropanoyl)piperidin-3-yl)imidazo[1,5-a]pyrazin-1-yl)-2-fluoro-N-(pyridin-2-yl)benzamide, TFA salt | 518.2 | 2.48 min |
| 283 | 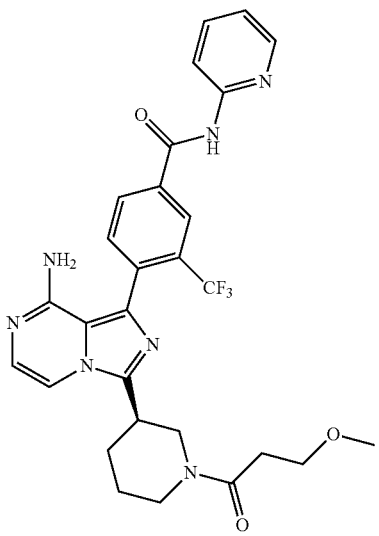 [SMILES: COCCC(=O)N1CCC[C@@H](c2nc(-c3ccc(C(=O)Nc4ccccn4)cc3C(F)(F)F)c3c(N)nccn23)C1] | 4-(8-amino-3-((R)-1-(3-methoxypropanoyl)piperidin-3-yl)imidazo[1,5-a]pyrazin-1-yl)-N-(pyridin-2-yl)-3-(trifluoromethyl)benzamide, TFA salt | 568.2 | 2.17 min |

-continued

| Example | Structure | Name | LC-MS [M + H]+ | Retention time |
|---|---|---|---|---|
| 284 | 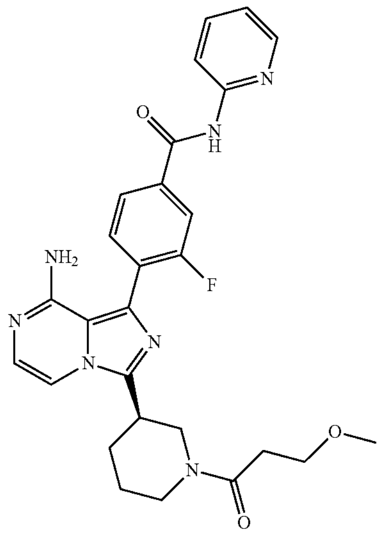 [SMILES: COCCC(=O)N1CCC[C@@H](c2nc(-c3ccc(C(=O)Nc4ccccn4)cc3F)c3c(N)nccn23)C1] | 4-(8-amino-3-((R)-1-(3-methoxypropanoyl)piperidin-3-yl)imidazo[1,5-a]pyrazin-1-yl)-3-fluoro-N-(pyridin-2-yl)benzamide, TFA salt | 518.2 | 2.20 min |
| 285 | 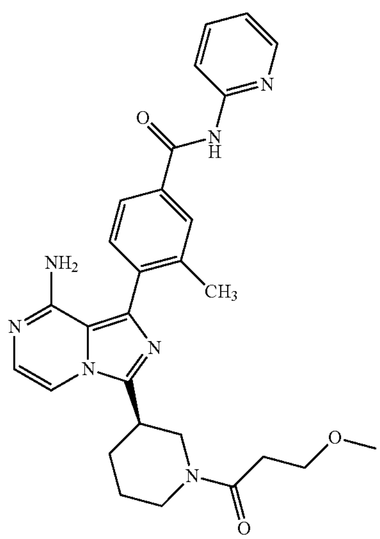 [SMILES: COCCC(=O)N1CCC[C@@H](c2nc(-c3ccc(C(=O)Nc4ccccn4)cc3C)c3c(N)nccn23)C1] | 4-(8-amino-3-((R)-1-(3-methoxypropanoyl)piperidin-3-yl)imidazo[1,5-a]pyrazin-1-yl)-3-methyl-N-(pyridin-2-yl)benzamide, TFA salt | 514.2 | 2.39 min |
| 286 | 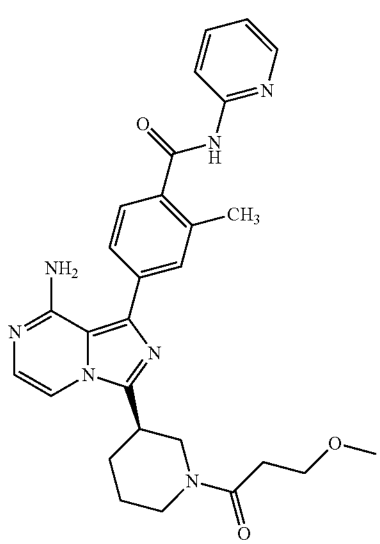 [SMILES: COCCC(=O)N1CCC[C@@H](c2nc(-c3ccc(C(=O)Nc4ccccn4)c(C)c3)c3c(N)nccn23)C1] | (R)-4-(8-amino-3-(1-(3-methoxypropanoyl)piperidin-3-yl)imidazo[1,5-a]pyrazin-1-yl)-2-methyl-N-(pyridin-2-yl)benzamide, TFA salt | 514.2 | 2.65 min |

| Example | Structure | Name | LC-MS [M + H]+ | Retention time |
|---|---|---|---|---|
| 287 | 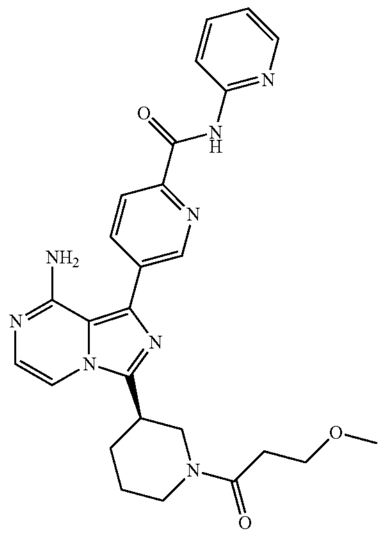 | (R)-5-(8-amino-3-(1-(3-methoxypropanoyl)piperidin-3-yl)imidazo[1,5-a]pyrazin-1-yl)-N-(pyridin-2-yl)picolinamide, TFA salt | 501.2 | 2.05 min |
| 288 | 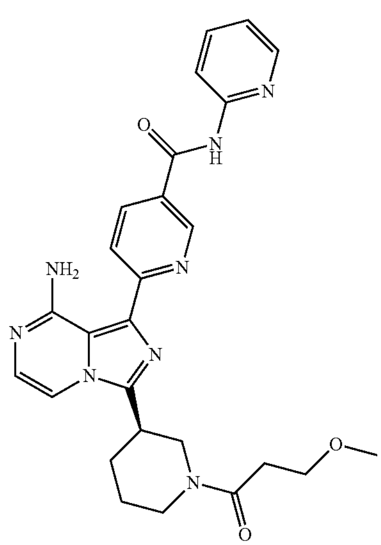 | (R)-6-(8-amino-3-(1-(3-methoxypropanoyl)piperidin-3-yl)imidazo[1,5-a]pyrazin-1-yl)-N-(pyridin-2-yl)nicotinamide | 501.2 | 2.35 min |

| Example | Structure | Name | LC-MS [M + H]+ | Retention time |
|---------|-----------|------|----------------|----------------|
| 289 | 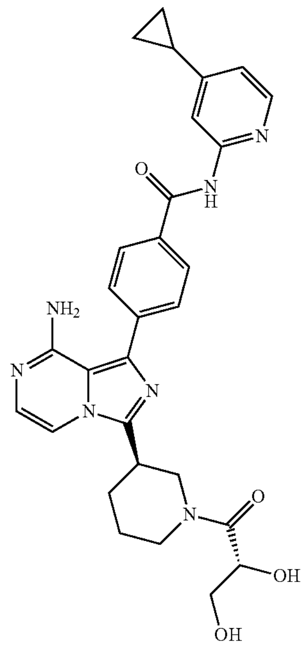 [SMILES: Nc1nccn2c([C@@H]3CCCN(C(=O)[C@H](O)CO)C3)nc(-c3ccc(C(=O)Nc4cc(C5CC5)ccn4)cc3)c12] | 4-(8-amino-3-((R)-1-((R)-2,3-dihydroxypropanoyl)piperidin-3-yl)imidazo[1,5-a]pyrazin-1-yl)-N-(4-cyclopropylpyridin-2-yl)benzamide | 542.3 | 1.33 min (UPLC-E) |
| 290 | 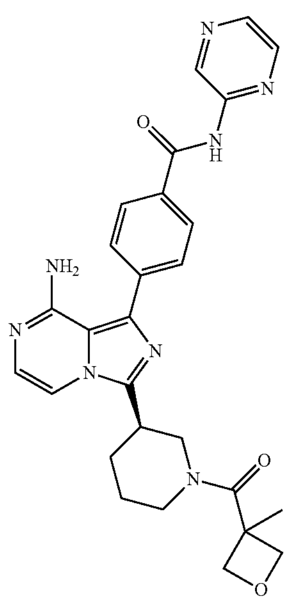 [SMILES: CC1(C(=O)N2CCC[C@@H](c3nc(-c4ccc(C(=O)Nc5cnccn5)cc4)c4c(N)nccn34)C2)COC1] | (R)-4-(8-amino-3-(1-(3-methyloxetane-3-carbonyl)piperidin-3-yl)imidazo[1,5-a]pyrazin-1-yl)-N-(pyrazin-2-yl)benzamide | 513.0 (LCMS-A) | 1.37 min (UPLC-E) |

Intermediate 39

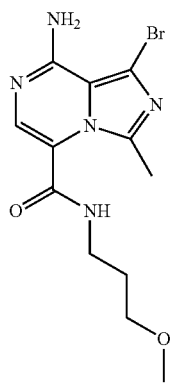

8-amino-1-bromo-N-(3-methoxypropyl)-3-methyl-imidazo[1,5-a]pyrazine-5-carboxamide (a) N-((3-chloropyrazin-2-yl)methyl)acetamide To a cooled (0° C.) suspension of (3-chloropyrazin-2-yl) methanamine.hydrochloride (5 g, 27.8 mmol) and triethylamine (11.61 mL, 83 mmol) in dichloromethane (80 mL) was added acetic anhydride (2.63 mL, 27.8 mmol) and the reaction mixture was stirred at 0° C. for 30 min. The mixture was filtered and the filtrate concentrated in vacuo. The product was purified using silica gel chromatography (ethylacetate/ethanol=5/1 v/v %) to give 4.45 g of N-((3-chloropyrazin-2-yl)methyl)acetamide (88%).

(b) 8-chloro-3-methylimidazo[1,5-a]pyrazine

N-((3-chloropyrazin-2-yl)methyl)acetamide (4.45 g, 24.51 mmol) was dissolved in acetonitrile (40 ml). Phosphorus oxychloride (9.14 ml, 1.226 mol) was added and the mixture was stirred at 80° C. for 1 h. The mixture was concentrated, dissolved in dichloromethane and quenched with an excess of 7M ammonia in MeOH (50 ml). The mixture was added dropwise to 25% aq. ammonia (47.2 mL) in 1000 mL crushed ice keeping the temperature below 0° C. The resulting suspension was stirred another 15 min after which it was extracted with dichloromethane (3×). The combined organic layers were washed with water, brine, dried over sodium sulfate and concentrated in vacuo to give 4 g of 8-chloro-3-methylimidazo[1,5-a]pyrazine (97%). Product was used directly in the next step.

(c) 8-chloro-3-methylimidazo[1,5-a]pyrazine-5-carboxylic acid n-Butyllithium (2.5M in hexane, 13.6 mmol, 5.44 mL) was added dropwise to a stirred solution of 8-chloro-3-methylimidazo[1,5-a]pyrazine (2.28 g, 13.6 mmol) in THF (75 mL) at −78° C. After addition the reaction mixture was stirred at −78° C. for 5 min. Crushed $CO_2$ was added and the dark coloured reaction turned into a light brown solution. Methanol (75 mL) was added and the resulting clear solution was concentrated. The residue was triturated with ethyl acetate and the solid formed was filtered of and dried to give 2.3 g of 8-chloro-3-methylimidazo[1,5-a]pyrazine-5-carboxylic acid (80.8%).

(d) 8-chloro-N-(3-methoxypropyl)-3-methylimidazo[1,5-a]pyrazine-5-carboxamide

Oxalyl chloride (2.60 mmol, 0.223 mL) was added to a stirred suspension of 8-chloro-3-methylimidazo[1,5-a]pyrazine-5-carboxylic acid (500 mg, 2.63 mmol) and 1,3-dimethyl-2-imidazolidinone (0.236 mmol, 26 µL) at 0° C. in THF (20 mL). The reaction mixture was stirred for 30 min at 0° C. and allowed to warm to room temperature. 3-Methoxypropylamine (232 mg, 0.266 mL) and triethylamine (4.73 mmol, 0.659 mL) were added and the reaction mixture was stirred for 1 h at room temperature. The reaction mixture was concentrated and the crude product was purified using silica gel chromatography (dichloromethane/methanol=9/1 v/v %) to give 600 mg of 8-chloro-N-(3-methoxypropyl)-3-methylimidazo[1,5-a]pyrazine-5-carboxamide (90%).

(e) 1-bromo-8-chloro-N-(3-methoxypropyl)-3-methylimidazo[1,5-a]pyrazine-5-carboxamide N-Bromosuccinimide (340 mg, 1.91 mmol) was added to a stirred solution of 8-chloro-N-(3-methoxypropyl)-3-methylimidazo[1,5-a]pyrazine-5-carboxamide (2.122 mmol, 600 mg) in DMF (120 mL). The reaction was stirred 2 h at room temperature. The reaction was quenched with brine/water/ethyl acetate=1/1/1 (150 mL). The aqueous layer was extracted with ethyl acetate. The combined organic layers were washed with water, brine, dried over sodium sulfate, filtered and evaporated to give 576 mg of 1-bromo-8-chloro-N-(3-methoxypropyl)-3-methylimidazo[1,5-a]pyrazine-5-carboxamide (75%).

(f) 8-amino-1-bromo-N-(3-methoxypropyl)-3-methylimidazo[1,5-a]pyrazine-5-carboxamide 1-bromo-8-chloro-N-(3-methoxypropyl)-3-methylimidazo[1,5-a]pyrazine-5-carboxamide (576 mg, 1.568 mmol) was dissolved in 2M $NH_3$/i-PrOH (31.4 mmol, 15.68 mL). The reaction mixture was heated at 120° C. in a microwave (5 bar). The reaction mixture was concentrated, the residue dissolved in dichloromethane and washed with water. The combined organic layers were filtered over a PS-filter and concentrated to give 500 mg crude product. The crude product was purified using silica gel chromatography (dichloromethane/methanol=9/1 v/v %) to give 276 mg of 8-amino-1-bromo-N-(3-methoxypropyl)-3-methylimidazo[1,5-a]pyrazine-5-carboxamide (51.4%).

Example 291

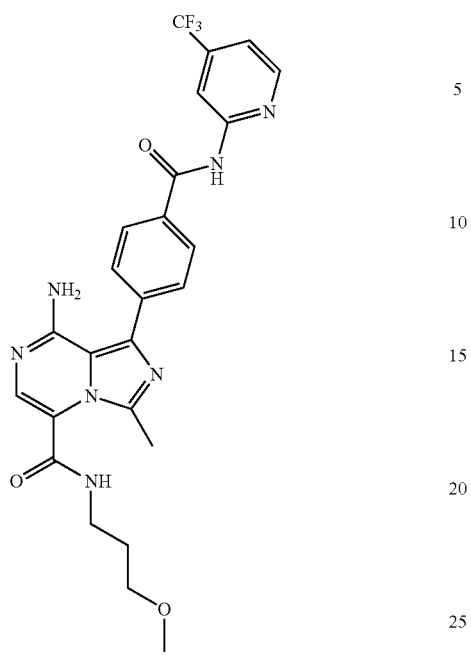

8-amino-N-(3-methoxypropyl)-3-methyl-1-(4-(4-(trifluoromethyl)pyridin-2-ylcarbamoyl)phenyl)imidazo[1,5-a]pyrazine-5-carboxamide This compound was prepared, in an analogous manner as described in Example 1, from Intermediate 39 and Intermediate D, to afford the title compound (10.9 mg, 20.2%). Data: UPLC(C) $R_t$: 2.14 min; m/z 528.2 $(M+H)^+$.

The following Examples were synthesized following the methods described for intermediate 39 and Example 1.

| Example | Structure | Name | LC-MS [M + H]$^+$ | Retention time |
|---|---|---|---|---|
| 292 | (structure) | 8-amino-N-benzyl-3-methyl-1-(4-(4-(trifluoromethyl)pyridin-2-ylcarbamoyl)phenyl)imidazo[1,5-a]pyrazine-5-carboxamide | 546.1 | 2.57 min |

| Example | Structure | Name | LC-MS [M + H]+ | Retention time |
|---|---|---|---|---|
| 293 | 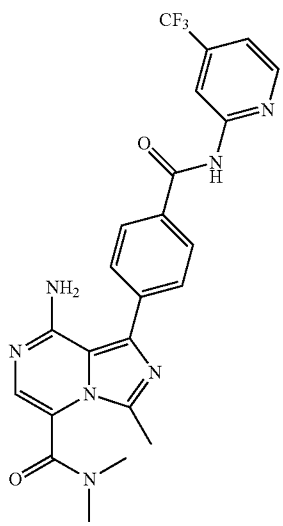 [SMILES: Cc1nc(-c2ccc(C(=O)Nc3cc(C(F)(F)F)ccn3)cc2)c2c(N)ncc(C(=O)N(C)C)n12] | 8-amino-N,N,3-trimethyl-1-(4-(4-(trifluoromethyl)pyridin-2-ylcarbamoyl)phenyl)imidazo[1,5-a]pyrazine-5-carboxamide | 484.1 | 2.06 min |
| 294 | 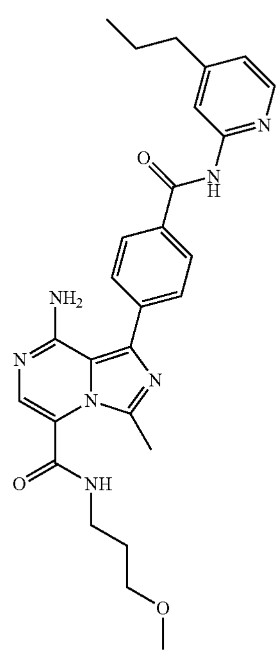 [SMILES: CCCc1ccnc(NC(=O)c2ccc(-c3nc(C)n4c(C(=O)NCCCOC)cnc(N)c34)cc2)c1] | 8-amino-N-(3-methoxypropyl)-3-methyl-1-(4-(4-propylpyridin-2-ylcarbamoyl)phenyl)imidazo[1,5-a]pyrazine-5-carboxamide | 502.2 | 1.53 min |

-continued
| Example | Structure | Name | LC-MS [M + H]+ | Retention time |
|---|---|---|---|---|
| 295 | 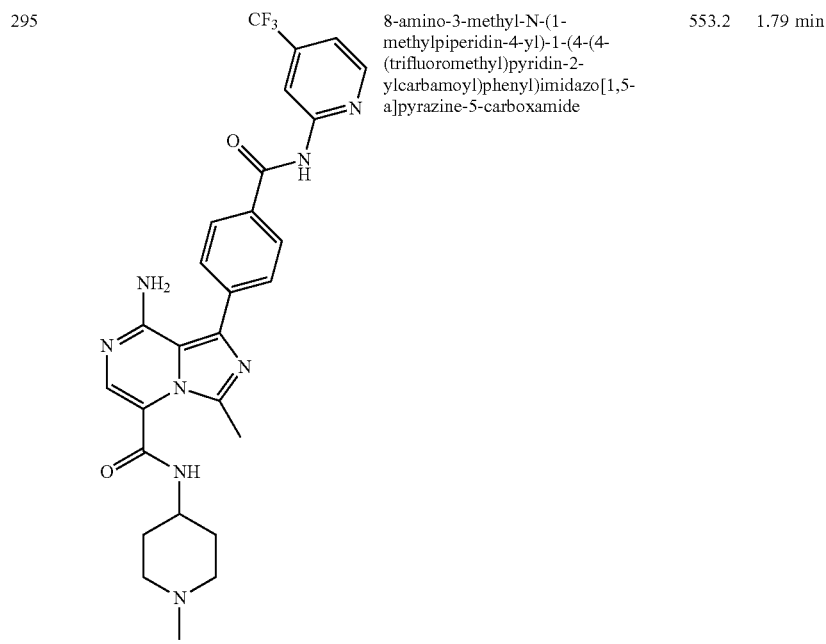 | 8-amino-3-methyl-N-(1-methylpiperidin-4-yl)-1-(4-(4-(trifluoromethyl)pyridin-2-ylcarbamoyl)phenyl)imidazo[1,5-a]pyrazine-5-carboxamide | 553.2 | 1.79 min |
| 296 | 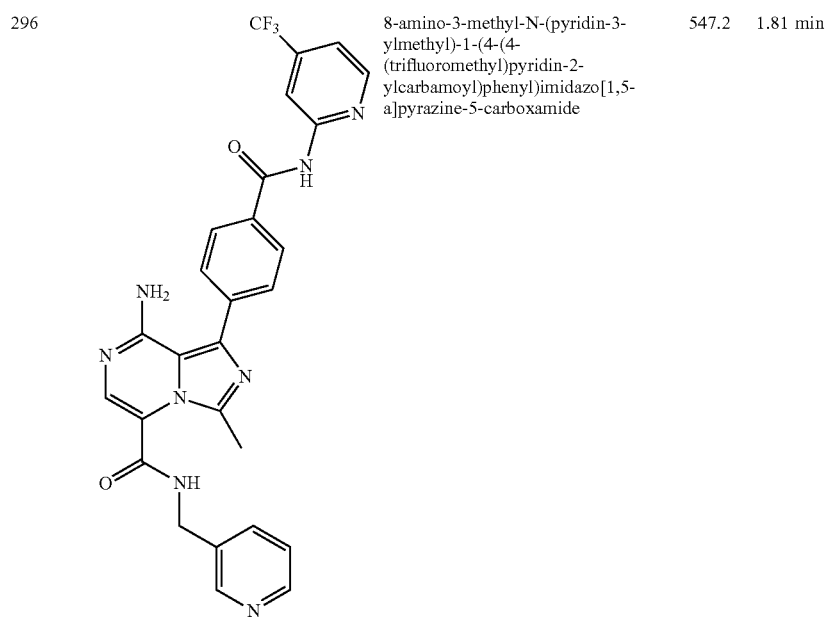 | 8-amino-3-methyl-N-(pyridin-3-ylmethyl)-1-(4-(4-(trifluoromethyl)pyridin-2-ylcarbamoyl)phenyl)imidazo[1,5-a]pyrazine-5-carboxamide | 547.2 | 1.81 min |

| Example | Structure | Name | LC-MS [M + H]+ | Retention time |
|---|---|---|---|---|
| 297 | 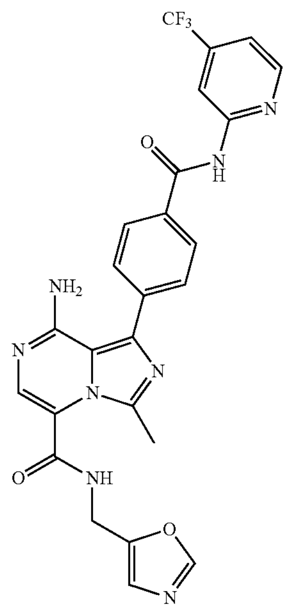 [SMILES: Cc1nc(-c2ccc(C(=O)Nc3cc(C(F)(F)F)ccn3)cc2)c2c(N)ncc(C(=O)NCc3cnco3)n12] | 8-amino-3-methyl-N-(oxazol-5-ylmethyl)-1-(4-(4-(trifluoromethyl)pyridin-2-ylcarbamoyl)phenyl)imidazo[1,5-a]pyrazine-5-carboxamide | 537.1 | 2.06 min |

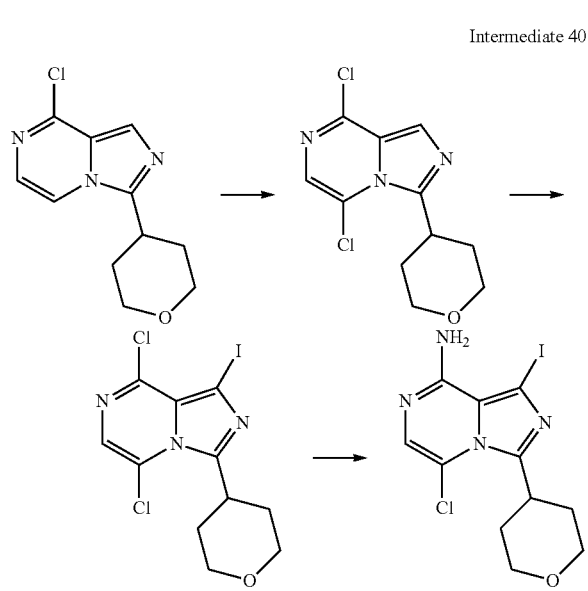

Intermediate 40

5-chloro-1-iodo-3-(tetrahydro-2H-pyran-4-yl)imidazo[1,5-a]pyrazin-8-amine (a) 5,8-dichloro-3-(tetrahydro-2H-pyran-4-yl)imidazo[1,5-a]pyrazine n-Butyllithium (1.6M in hexane, 198 μL, 0.495 mmol) was added to a stirred solution of 8-chloro-3-(tetrahydro-2H-pyran-4-yl)imidazo[1,5-a]pyrazine (0.450 mmol, 107 mg) in THF (3 ml) at −78° C. After 10 min hexachloroethane (0.540 mmol, 128 mg) in THF (1 ml) was added. Upon addition the color changed from brownish yellow into dark brown. After addition the reaction mixture was allowed to warm to room temperature. After 20 minutes the reaction was quenched with NH₄Cl (aq) and extracted with ethyl acetate three times. The combined organic extracts were dried (Na₂SO₄) and concentrated in vacuo. The crude product was purified using silica gel chromatography (heptanes/ethyl acetate gradient of 3/1 to 1/1) to give 104 mg of 5,8-dichloro-3-(tetrahydro-2H-pyran-4-yl)imidazo[1,5-a]pyrazine (85%).

(b) 5,8-dichloro-1-iodo-3-(tetrahydro-2H-pyran-4-yl)imidazo[1,5-a]pyrazine

To a solution of 5,8-dichloro-3-(tetrahydro-2H-pyran-4-yl)imidazo[1,5-a]pyrazine (0.382 mmol, 104 mg) in N-methyl-2-pyrrolidinone (1 ml), acetonitrile (1 mL) and dichloromethane (1 mL) was added N-iodosuccinimide (0.418 mmol, 94 mg) and the reaction mixture heated at 95° C. for 8 h. Water (25 mL) was added and the resulting mixture extracted with ethylacetate/heptanes 3/1 (three times 20 mL). The combined organic extracts were dried (Na₂SO₄) and concentrated in vacuo. The crude product was purified using silica gel chromatography (ethyl acetate/heptanes=1/3 v/v %) to give 101 mg of 5,8-dichloro-1-iodo-3-(tetrahydro-2H-pyran-4-yl)imidazo[1,5-a]pyrazine (66.4%).

(c) 5-chloro-1-iodo-3-(tetrahydro-2H-pyran-4-yl)imidazo[1,5-a]pyrazin-8-amine 5,8-dichloro-1-iodo-3-(tetrahydro-2H-pyran-4-yl)imidazo[1,5-a]pyrazine (100 mg, 0.251 mmol) was dissolved in 2M NH₃/i-PrOH (10 mmol, 5 mL). The reaction mixture was heated at 120° C. in a microwave (7 bar). The product crystallized after standing overnight. Crystals were filtered, washed and dried to give 40 mg of 5-chloro-1-iodo-3-(tetrahydro-2H-pyran-4-yl)imidazo[1,5-a]pyrazin-8-amine (42.1%).

Example 298

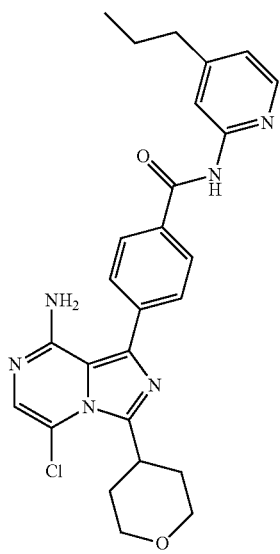 [SMILES: CCCc1ccnc(NC(=O)c2ccc(-c3nc(C4CCOCC4)n4c(Cl)cnc(N)c34)cc2)c1]

4-(8-amino-5-chloro-3-(tetrahydro-2H-pyran-4-yl)imidazo[1,5-a]pyrazin-1-yl)-N-(4-propylpyridin-2-yl)benzamide This compound was prepared, in an analogous manner as described in Example 1, from Intermediate 40 and Intermediate C, to afford the title compound (13 mg, 47.7%). Data: UPLC(C) $R_t$: 1.83 min; m/z 491.2 (M+H)$^+$.

Intermediate 41

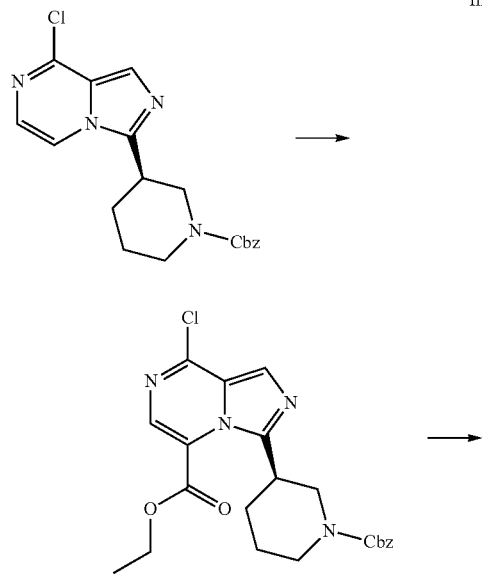

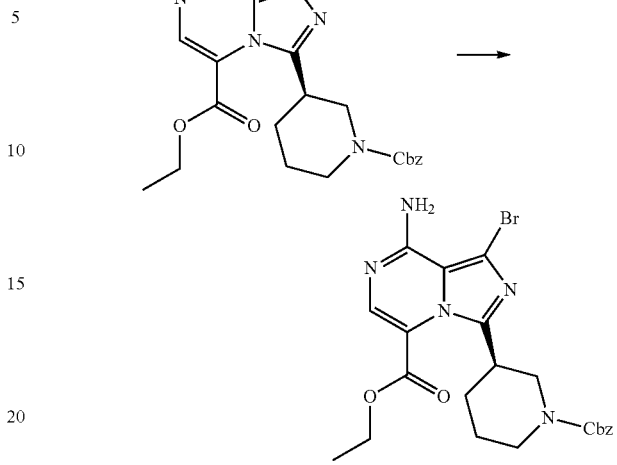

(R)-benzyl 3-(8-amino-1-bromo-5-chloroimidazo[1,5-a]pyrazin-3-yl)piperidine-1-carboxylate (a) (R)-ethyl 3-(1-(benzyloxycarbonyl)piperidin-3-yl)-8-chloroimidazo[1,5-a]pyrazine-5-carboxylate n-Butyllithium (2.5M in hexane, 2 mL, 5 mmol) was added dropwise via a syringe in 15 min to a stirred solution of (R)-benzyl 3-(8-chloroimidazo[1,5-a]pyrazin-3-yl)piperidine-1-carboxylate (1.5 g, 4.04 mmol) in THF (fresh dried) (15 ml) keeping the temperature below −70° C. The resulting dark brown solution was stirred 10 min followed by addition of ethyl chloroformate (0.66 g, 6.07 mmol) in THF (fresh dried) (5 ml) via a syringe in 10 min keeping the temperature below −70° C. After 2 h at −78° C., the reaction was allowed to warm to room temperature and stirred for an additional 20 min. The reaction was quenched with sat. NH$_4$Cl, extracted with EtOAc, washed with brine and dried over sodium sulfate. After removal of solvent, the residue was purified by column chromatography on silica gel, eluting with hexane/ethyl acetate (4/1 to 2/1 v/v %) to get the title compound as a yellow foam (482 mg, 27%).

(b) (R)-ethyl 3-(1-(benzyloxycarbonyl)piperidin-3-yl)-1-bromo-8-chloroimidazo[1,5-a]pyrazine-5-carboxylate NBS (199 mg, 1.1 mmol) was added to a DMF solution (10 mL) of (R)-ethyl 3-(1-(benzyloxycarbonyl)piperidin-3-yl)-8-chloroimidazo[1,5-a]pyrazine-5-carboxylate (450 mg, 1.0 mmol) at room temperature. The reaction was stirred overnight and LCMS showed clear conversion to (R)-ethyl 3-(1-(benzyloxycarbonyl)piperidin-3-yl)-1-bromo-8-chloroimidazo[1,5-a]pyrazine-5-carboxylate. Sat. NaHCO$_3$ (10 mL) was added followed by ethyl acetate (20 mL). The mixture was stirred for 20 min and the organic layer was separated, dried (Na$_2$SO$_4$), filtered and concentrated to get an oil. The crude was used directly for next reaction.

(c) (R)-ethyl 8-amino-3-(1-(benzyloxycarbonyl)piperidin-3-yl)-1-bromoimidazo[1,5-a]pyrazine-5-carboxylate (R)-Ethyl 3-(1-(benzyloxycarbonyl)piperidin-3-yl)-1-bromo-8-chloroimidazo-[1,5-a]pyrazine-5-carboxylate (700 mg, 1.3 mmol) was suspended in 2N NH₃/IPA (15 mL, 30 mmol) and heated at 120° C. for 2 h. The reaction mixture was concentrated to dryness and purified on silica gel eluting with 2% to 3% MeOH(NH₃)/DCM to isolate a yellow solid (658 mg, 98%).

Intermediate 41B

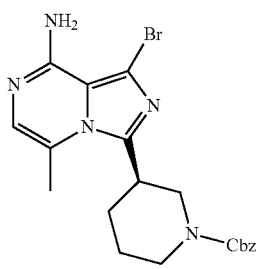

(R)-benzyl 3-(8-amino-1-bromo-5-methylimidazo[1,5-a]pyrazin-3-yl)piperidine-1-carboxylate (a) (R)-benzyl 3-(8-chloro-5-methylimidazo[1,5-a]pyrazin-3-yl)piperidine-1-carboxylate N-butyllithium (4.04 ml, 40.4 mmol, 1.5 equiv) was added dropwise in 10 min to a stirred solution of (R)-benzyl 3-(8-chloroimidazo[1,5-a]pyrazin-3-yl)piperidine-1-carboxylate (10 g, 27.0 mmol, 1.0 equiv) in THF (100 ml) at −78° C. The reaction was stirred for 10 min followed by dropwise addition of iodomethane (3.36 ml, 53.9 mmol, 2.0 equiv) in THF (30 mL) over 30 min. The reaction mixture was stirred for 30 min at −78° C. The reaction was quenched with saturated ammonium chloride (13.60 ml, 270 mmol, 10 equiv) dropwise at −78° C., stirred to room temperature, extracted with EtOAc, washed with brine, dried over MgSO₄, filtered and concentrated in vacuo. The crude product was purified on 220 gr Redi Sep Rf filter column on CombiFlash with 0-60% hexane/EtOAc to provide product (R)-benzyl 3-(8-chloro-5-methylimidazo[1,5-a]pyrazin-3-yl)piperidine-1-carboxylate LC-MS (ES, m/z) $C_{20}H_{21}ClN_4O_2$: 384. Found 385 [M+H]⁺.

(b) (R)-benzyl 3-(1-bromo-8-chloro-5-methylimidazo[1,5-a]pyrazin-3-yl)piperidine-1-carboxylate NBS (2.6 g, 14.61 mmol, 1.1 equiv) was added to a stirred solution of (R)-benzyl 3-(8-chloro-5-methylimidazo[1,5-a]pyrazin-3-yl)piperidine-1-carboxylate (5.11 g, 13.28 mmol, 1.0 equiv) in DMF (50 mL, 0.266M). The resulting mixture was stirred for 35 min at room temperature. The mixture was quenched with aq NaHCO₃ and extracted with EtOAc dried over MgSO₄, filtered and concentrated in vacuo to provide product (R)-benzyl 3-(1-bromo-8-chloro-5-methylimidazo[1,5-a]pyrazin-3-yl)piperidine-1-carboxylate LC-MS (ES, m/z) $C_{20}H_{20}BrClN_4O_2$: 462. Found 465[M+H]⁺.

(c) (R)-benzyl 3-(8-amino-1-bromo-5-methylimidazo[1,5-a]pyrazin-3-yl)piperidine-1-carboxylate (R)-benzyl 3-(1-bromo-8-chloro-5-methylimidazo[1,5-a]pyrazin-3-yl)piperidine-1-carboxylate (6.0 g, 12.94 mmol, 1.0 equiv) suspended in 2M ammonia in IPA (240 mL, 480 mmol, 37 equiv) was heated in a sealed tube at 120° C. for 36 h. Solvent was concentrated in vacuo and the residue was purified on 120 gr Redi Sep Rf filter column on CombiFlash with 20-100% Hexane/EtOAc to provide product (R)-benzyl 3-(8-amino-1-bromo-5-methylimidazo[1,5-a]pyrazin-3-yl)piperidine-1-carboxylate LC-MS (ES, m/z) $C_{20}H_{22}BrN_5O_2$: 443. Found 446[M+H]⁺.

Intermediate 41C

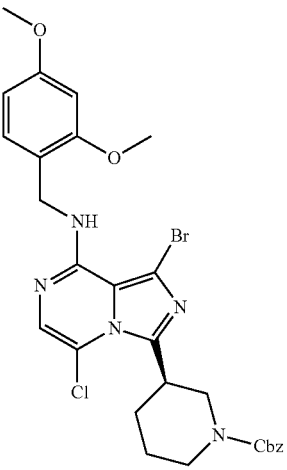

(R)-benzyl 3-(1-bromo-5-chloro-8-((2,4-dimethoxybenzyl)amino)imidazo[1,5-a]pyrazin-3-yl)piperidine-1-carboxylate (a) (R)-benzyl 3-(5,8-dichloroimidazo[1,5-a]pyrazin-3-yl)piperidine-1-carboxylate n-BuLi (39.4 ml, 63.1 mmol) was added dropwise in 10 min to a −78° C. solution of (R)-benzyl 3-(8-chloroimidazo[1,5-a]pyrazin-3-yl)piperidine-1-carboxylate (18 g, 48.5 mmol) in anhydrous THF (200 ml). The reaction was stirred for 10 min and a solution of perchloroethane (18.39 g, 78 mmol) in anhydrous THF (200 ml) was added dropwise. The reaction was stirred for 10 min at −78° C. and quenched w/sat. NH₄Cl. The reaction was extracted with EtOAc, dried (NaSO₄), and purified by flash chromatography on silica gel, eluting with 30% EtOAc/hexanes) to give (R)-benzyl 3-(5,8-dichloroimidazo[1,5-a]pyrazin-3-yl)piperidine-1-carboxylate (14.8 g, 36.5 mmol, 75% yield). LCMS (m/z): 405 (M+H).

(b) (R)-benzyl 3-(1-bromo-5,8-dichloroimidazo[1,5-a]pyrazin-3-yl)piperidine-1-carboxylate In the same procedure as step (c) for the bromination for the synthesis of intermediate 8, (R)-benzyl 3-(5,8-dichloroimidazo[1,5-a]pyrazin-3-yl)piperidine-1-carboxylate was converted to (R)-benzyl 3-(1-bromo-5,8-dichloroimidazo[1,5-a]pyrazin-3-yl)piperidine-1-carboxylate. LCMS (m/z): 485 (M+H).

(c) (R)-benzyl 3-(1-bromo-5-chloro-8-((2,4-dimethoxybenzyl)amino)imidazo-[1,5-a]pyrazin-3-yl)piperidine-1-carboxylate (2,4-dimethoxyphenyl)methanamine (8.81 g, 52.7 mmol) was added to a mixture of (R)-benzyl 3-(1-bromo-5,8-dichloroimidazo[1,5-a]pyrazin-3-yl)piperidine-1-carboxylate (17 g, 35.1 mmol) and N-ethyl-N-isopropylpropan-2-amine (6.81 g, 52.7 mmol) in 1,4-Dioxane (200 ml) and the reaction was stirred at rt for 3 h. LCMS showed completion, at M+H=616. The reaction was washed with 5% KH2PO4, extracted with EtOAc, dried (Na₂SO₄) and evaporated to dryness to give (R)-benzyl 3-(1-bromo-5-chloro-8-((2,4-dimethoxybenzyl)amino)imidazo[1,5-a]pyrazin-3-yl)piperidine-1-carboxylate (21.7 g, 35.3 mmol, 101% yield), which was used in the next step without further purification LCMS (m/z): 616 (M+H).

Intermediate 41D

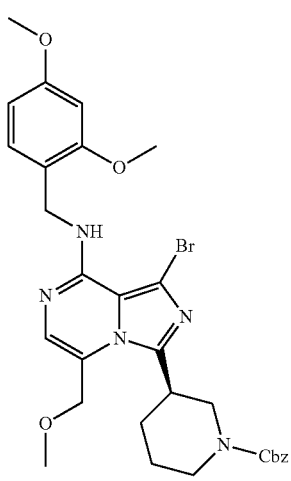

(R)-benzyl3-(8-amino-1-bromo-5-(methoxymethyl) imidazo[1,5-a]pyrazin-3-yl)piperidine-1-carboxylate (a) (R)-benzyl 3-(8-chloro-5-(methoxymethyl)imidazo[1,5-a]pyrazin-3-yl)piperidine-1-carboxylate n-BuLi (5.06 ml, 8.09 mmol) was added dropwise, in 10 min to a −78° C. solution of (R)-benzyl 3-(8-chloroimidazo[1,5-a]pyrazin-3-yl)piperidine-1-carboxylate (2.0 g, 5.39 mmol) in THF (20 ml), stirred for 10 min and iodomethyl methyl ether (0.914 ml, 10.79 mmol) in THF (5 ml) was added dropwise. The reaction was stirred for 10 min at −78° C. and quenched w/sat. NH₄Cl, extracted with EtOAc and dried. The residue was purified on silica gel (50% EtOAc/hexanes) to give (R)-benzyl3-(1-bromo-8-chloro-5-(methoxymethyl)imidazo[1,5-a]pyrazin-3-yl)piperidine-1-carboxylate (1.8 g, 4.34 mmol, 80% yield). LCMS (m/z): 415 (M+H).

(b) (R)-benzyl3-(1-bromo-8-chloro-5-(methoxymethyl)imidazo[1,5-a]pyrazin-3-yl)piperidine-1-carboxylate In the same procedure as step (c) for the bromination for the synthesis of intermediate 8, (R)-benzyl 3-(8-chloro-5-(methoxymethyl)imidazo[1,5-a]pyrazin-3-yl)piperidine-1-carboxylate was converted to (R)-benzyl3-(1-bromo-8-chloro-5-(methoxymethyl)imidazo[1,5-a]pyrazin-3-yl) piperidine-1-carboxylate, LCMS showed M+H at 495 (2.42 min on 4 min run).

(c) (R)-benzyl 3-(1-bromo-8-((2,4-dimethoxybenzyl)amino)-5-(methoxy-methyl)imidazo[1,5-a] pyrazin-3-yl)piperidine-1-carboxylate 2,4-dimethoxyphenyl)methanamine (2.130 ml, 14.18 mmol) was added to a mixture of (R)-benzyl 3-(1-bromo-8-chloro-5-(methoxymethyl)imidazo[1,5-a]pyrazin-3-yl)piperidine-1-carboxylate (2.0 g, 4.05 mmol) and N-ethyl-N-isopropylpropan-2-amine (2.476 ml, 14.18 mmol) in acetonitrile (80 ml). The reaction was stirred overnight at rt. The reaction was heated at 55° C. for 2 h, washed with 5% KH2PO4, extracted with EtOAc, washed with brine, dried (Na₂SO₄) and evaporated to dryness to give (R)-benzyl 3-(1-bromo-8-((2,4-dimethoxybenzyl)amino)-5-(methoxymethyl)imidazo[1,5-a]pyrazin-3-yl)piperidine-1-carboxylate (2.4 g, 3.84 mmol, 95% yield), which was used in the next step for further purification. LCMS (m/z): 626 (M+H).

Intermediate 41E

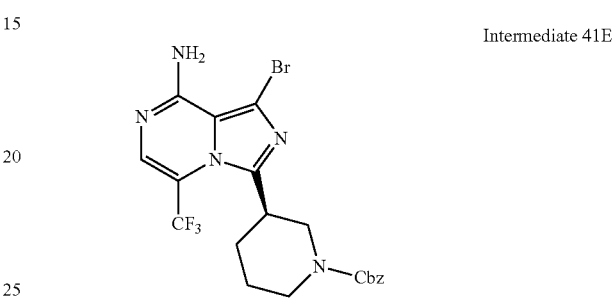

(R)-benzyl 3-(8-amino-1-bromo-5-(trifluoromethyl) imidazo[1,5-a]pyrazin-3-yl)piperidine-1-carboxylate A mixture of (R)-benzyl 3-(8-amino-1-bromoimidazo[1,5-a]pyrazin-3-yl)piperidine-1-carboxylate (52.9 mg, 0.160 mmol), 3,3-dimethyl-1-(trifluoromethyl)-1,2-benziodoxole (46 mg, 0.107 mmol) and chlorotris(trimethylsilyl)silane (30.3 mg, 0.107 mmol) in acetonitrile (2 ml) was stirred at 80° C. for 2 h and concentrated in vacuo. The residue was purified by column chromatography on silica gel, eluting with DCM/MeOH (50/1) to give (R)-benzyl 3-(8-amino-1-bromo-5-(trifluoromethyl)-imidazo[1,5-a]pyrazin-3-yl)piperidine-1-carboxylate (12 mg, 0.024 mmol, 22.53% yield) as a colorless oil. LCMS Data: $R_t$ 1.99 min; m/z 498.0 and 500.0 $(M+H)^+$.

Intermediate 41F

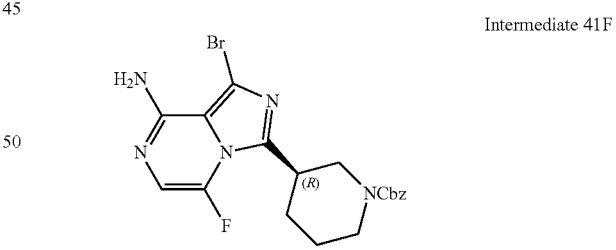

(a) (R)-benzyl 3-(8-chloro-5-fluoroimidazo[1,5-a] pyrazin-3-yl)piperidine-1-carboxylate To (R)-benzyl 3-(8-chloroimidazo[1,5-a]pyrazin-3-yl)piperidine-1-carboxylate (5 g, 13.48 mmol) in THF (100 ml) at −78° C., was slowly added 1.6 M n-BuLi in hexane (18.54 ml, 29.7 mmol) slowly and stirred for 30 min. N-fluoro-N-(phenylsulfonyl)benzenesulfonamide (5.53 g, 17.53 mmol) dissolved in 6 mL of THF was added maintaining the temp at −78° C., stirred for another 30 min. Formation of the product was checked by LCMS, quenched with sat. NH₄Cl (aq) (100 mL), extracted with EtOAc (3×100 mL), dried with Na$_2$SO$_4$, concentrated to dryness and subjected to column chromatography to give (R)-benzyl 3-(8-chloro-5-fluoroimidazo[1,5-a]pyrazin-3-yl)piperidine-1-carboxylate (3.8 g, 72.5%). LCMS: [M+H]$^+$: 389.2, Rt=2.21 min, 3.5 min, KW).

(b) (R)-benzyl 3-(1-bromo-8-chloro-5-fluoroimidazo[1,5-a]pyrazin-3-yl)piperidine-1-carboxylate To (R)-benzyl 3-(8-chloro-5-fluoroimidazo[1,5-a]pyrazin-3-yl)piperidine-1-carboxylate (3.5 g, 9.0 mmol) in 40 mL DMF at 0° C., was added N-bromosuccinimide (1.92 g, 10.8 mmol) and stirred for 1 h at rt. The reaction was quenched with sat. NaHCO$_3$ (100 mL) and extracted with EtOAc (3×100 mL). The organic phase was washed with sat. NaCl dried with Na$_2$SO$_4$, concentrated to dryness to give crude (R)-benzyl 3-(1-bromo-8-chloro-5-fluoroimidazo[1,5-a]pyrazin-3-yl)piperidine-1-carboxylate (4.15 g, 99%), which was used as such with out further purification. LCMS: [M+H]$^+$: 469.0; Rt=2.35 min, 3.5 min).

(c) (R)-benzyl 3-(8-amino-1-bromo-5-fluoroimidazo[1,5-a]pyrazin-3-yl)piperidine-1-carboxylate (R)-benzyl 3-(1-bromo-8-chloro-5-fluoroimidazo[1,5-a]pyrazin-3-yl)piperidine-1-carboxylate (1 g, 2.138 mmol) was dissolved in 2M NH$_3$ in isopropanol (25 mL, 150 mmol) and stirred at 120° C. for 2 h. The reaction mixture was concentrated to dryness and purified on silica gel eluting with hexanes:EtOAc (30-60%) to give (R)-benzyl 3-(8-amino-1-bromo-5-fluoroimidazo[1,5-a]pyrazin-3-yl)piperidine-1-carboxylate (0.44 g, 46%). LCMS: [M+Na]$^+$: 470.0; Rt=1.90 min, 3.5 min).

Intermediate 41G

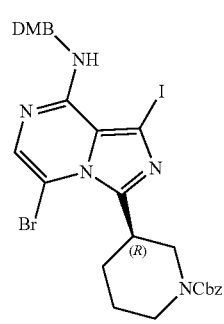

(R)-benzyl 3-(8-amino-5-bromo-1-iodoimidazo[1,5-a]pyrazin-3-yl)piperidine-1-carboxylate (a) (R)-benzyl 3-(5-bromo-8-chloroimidazo[1,5-a]pyrazin-3-yl)piperidine-1-carboxylate (R)-benzyl 3-(8-chloroimidazo[1,5-a]pyrazin-3-yl)piperidine-1-carboxylate (2.0 g, 5.39 mmol) in THF (100 ml) at −78° C., was added 1.6 M n-BuLi in hexane (4.04 ml, 6.47 mmol) slowly and stirred for 10 min. CBr$_4$ (1.789 g, 5.39 mmol) dissolved in 5 mL of THF was added maintaining the temp at −78° C., stirred for another 10 min. Formation of the product was checked by LCMS, quenched with sat. NH$_4$Cl (aq) (10 mL), extracted with EtOAc (3×50 mL), dried with Na$_2$SO$_4$, concentrated to dryness and purified on silica gel eluting with hexanes: EtOAc (30% to 80%) to give (R)-benzyl 3-(5-bromo-8-chloroimidazo[1,5-a]pyrazin-3-yl)piperidine-1-carboxylate (1.3 g). LCMS: [M+H]$^+$: 451.0, Rt=2.106 min, 3.5 min).

(b) (R)-benzyl 3-(5-bromo-8-chloro-1-iodoimidazo[1,5-a]pyrazin-3-yl)piperidine-1-carboxylate To (R)-benzyl 3-(5-bromo-8-chloroimidazo[1,5-a]pyrazin-3-yl)piperidine-1-carboxylate (3.2 g, 7.12 mmol) in DMF (100 ml) at 0° C., was added NIS (1.761 g, 7.83 mmol) and stirred at 60° C. for 16 h. The reaction was quenched with 1M Na$_2$S$_2$O$_2$ (aq) (100 mL), aq. brine (100 mL), extracted with DCM (3×100 mL), dried with Na$_2$SO$_4$, concentrated to dryness, and purified on silica gel using hexane: EtOAc (30% to 80%) to give (R)-benzyl 3-(5-bromo-8-chloro-1-iodoimidazo[1,5-a]pyrazin-3-yl)piperidine-1-carboxylate (2.81 g). LCMS: [M+H]$^+$: 577.0, Rt=2.332 min, 3.5 min).

(c) (R)-benzyl 3-(5-bromo-8-((2,4-dimethoxybenzyl)amino)-1-iodoimidazo[1,5-a]pyrazin-3-yl)piperidine-1-carboxylate (R)-benzyl 3-(5-bromo-8-chloro-1-iodoimidazo[1,5-a]pyrazin-3-yl)piperidine-1-carboxylate (0.5 g, 0.87 g mmol), (2,4-dimethoxyphenyl)methanamine (0.51 g, 3.04 mmol) and N-ethyl-N-isopropylpropan-2-amine (0.52 g, 3.04 mmol) were dissolved in 1,4-dioxane (10 mL) stirred at r.t for 1 overnight. The reaction was concentrated in vacuo to give (R)-benzyl 3-(5-bromo-8-((2,4-dimethoxybenzyl)amino)-1-iodoimidazo[1,5-a]pyrazin-3-yl)piperidine-1-carboxylate (0.58 g), which was used directly in the next step. LCMS: [M+H]$^+$: 708.0, Rt=2.349 min, 3.5 min).

Example 299

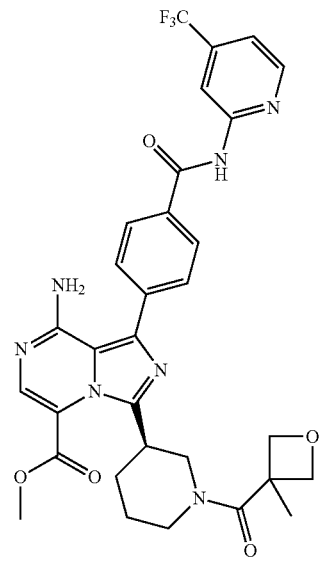 [SMILES: COC(=O)c1cnc(N)c2c(-c3ccc(C(=O)Nc4cc(C(F)(F)F)ccn4)cc3)nc([C@@H]3CCCN(C(=O)C4(C)COC4)C3)n12]

485

(R)-ethyl 8-amino-3-(1-(3-methyloxetane-3-carbonyl)piperidin-3-yl)-1-(4-(4-(trifluoromethyl)pyridine-2-ylcarbamoyl)phenyl)imidazo[1,5-a]pyrazine-5-carboxylate This compound was prepared in an analogous manner as described in Example 46, from Intermediate 41 to afford the title compound (60 mg, 36%). Data: UPLC(G) $R_t$: 2.02 min; m/z 652.2 (M+H)$^+$.

Example 300

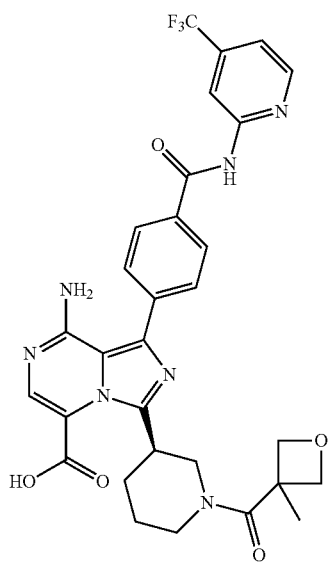 [SMILES: CC1(C(=O)N2CCC[C@@H](c3nc(-c4ccc(C(=O)Nc5cc(C(F)(F)F)ccn5)cc4)c4c(N)ncc(C(=O)O)n34)C2)COC1]

(R)-8-amino-3-(1-(3-methyloxetane-3-carbonyl)piperidin-3-yl)-1-(4-(4-(trifluoromethyl)pyridin-2-ylcarbamoyl)phenyl)imidazo[1,5-a]pyrazine-5-carboxylic acid (R)-ethyl 8-amino-3-(1-(3-methyloxetane-3-carbonyl)piperidin-3-yl)-1-(4-(4-(trifluoromethyl)pyridine-2-ylcarbamoyl)phenyl)imidazo[1,5-a]pyrazine-5-carboxylate (48 mg, 0.07 mmol) was suspended in THF/MeOH. To this was added 0.2 mL LiOH (1 N). Reaction was gently heated at 35° C. for 1 h before it was quenched with 1N HCl (0.3 mL). It was concentrated in vacuo and the residue was purified using preparative HPLC to isolate the title compound (3.4 mg, 6%). Data: UPLC(G) $R_t$: 1.91 min; m/z 624.2 (M+H)$^+$.

486

Example 301

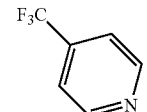

(R)-4-(8-amino-5-chloro-3-(1-(3-methyloxetane-3-carbonyl)piperidin-3-yl)imidazo[1,5-a]pyrazin-1-yl)-N-(4-(trifluoromethyl)pyridin-2-yl)benzamide This compound was prepared in an analogous manner as described for Example 46 and Intermediate 40, to afford the title compound (12.7 mg, 29.6%). Data: UPLC(E) $R_t$: 2.75 min; m/z 614.3 (M+H)$^+$.

Example 302

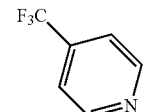

(R)-4-(8-amino-3-(1-(3-methyloxetane-3-carbonyl)piperidin-3-yl)-5-vinylimidazo[1,5-a]pyrazin-1-yl)-N-(4-(trifluoromethyl)pyridin-2-yl)benzamide (R)-4-(8-amino-5-chloro-3-(1-(3-methyloxetane-3-carbonyl)piperidin-3-yl)imidazo[1,5-a]pyrazin-1-yl)-N-(4-(trifluoromethyl)pyridin-2-yl)benzamide (60 mg, 0.1 mmol), vinylboronic acid pinacol ester (45 mg, 0.3 mmol), K$_2$CO$_3$ (27 mg, 0.2 mmol) and Pd(dppf)Cl$_2$ (8 mg, 0.01 mmol) were mixed in dioxane/H$_2$O (2 mL/0.5 mL) in a microwave reaction vial. It was crimped and subjected to microwave (normal absorption, 140° C.) for 1 hr. The mixture was concentrated to dryness. The residue was purified using silica gel chromatography (dichloromethane/methanol (NH$_3$)=98/2 (v/v %) to give 6.6 mg of (R)-4-(8-amino-3-(1-(3-methyloxetane-3-carbonyl)piperidin-3-yl)-5-vinylimidazo[1,5-a]pyrazin-1-yl)-N-(4-(trifluoromethyl)pyridin-2-yl)benzamide (11%). Data: UPLC(G) R$_t$: 1.98 min; m/z 606.2 (M+H)$^+$.

The following Examples were synthesized following the methods described for Examples 291-302 using appropriate electrophiles (CH$_3$I, CD$_3$OD, CD$_3$I, aldehydes, CBr$_4$, n-fluorobenzenesulfonimide, boronic acid, boronic pinacol esters etc.) for the introduction of substituent R$^{11}$.

| Example | Structure | Name | LC-MS [M + H]$^+$ | Retention time |
|---|---|---|---|---|
| 303 | 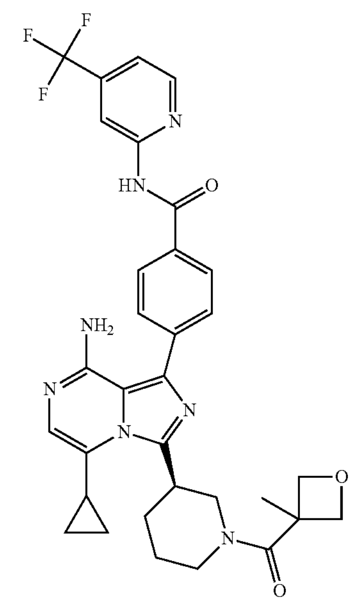 [SMILES: CC1(C(=O)N2CCC[C@@H](c3nc(-c4ccc(C(=O)Nc5cc(C(F)(F)F)ccn5)cc4)c4c(N)ncc(C5CC5)n34)C2)COC1] | (R)-4-(8-amino-5-cyclopropyl-3-(1-(3-methyloxetane-3-carbonyl)piperidin-3-yl)imidazo[1,5-a]pyrazin-1-yl)-N-(4-(trifluoromethyl)pyridin-2-yl)benzamide | 620.2 | 1.96 min |
| 304 | 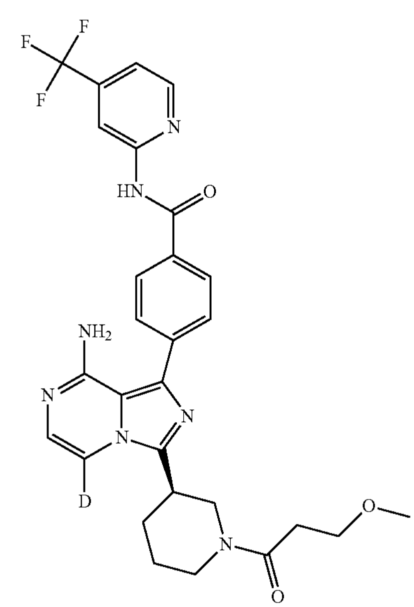 [SMILES: [2H]c1cnc(N)c2c(-c3ccc(C(=O)Nc4cc(C(F)(F)F)ccn4)cc3)nc([C@@H]3CCCN(C(=O)CCOC)C3)n12] | (R)-4-(8-amino-5-deutero-3-(1-(3-methoxypropanoyl)piperidin-3-yl)imidazo[1,5-a]pyrazin-1-yl)-N-(4-(trifluoromethyl)pyridin-2-yl)benzamide | 569.2 | 2.78 min (UPLC-D) |

-continued

| Example | Structure | Name | LC-MS [M + H]+ | Retention time |
|---|---|---|---|---|
| 305 | 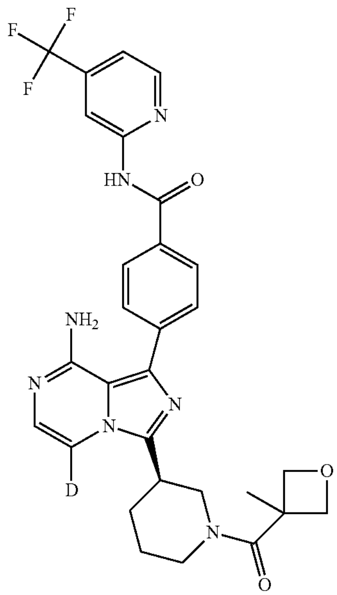 [SMILES: [2H]c1cnc(N)c2c(-c3ccc(C(=O)Nc4cc(C(F)(F)F)ccn4)cc3)nc([C@@H]3CCCN(C(=O)C4(C)COC4)C3)n12] | (R)-4-(8-amino-5-deutero-3-(1-(3-methyloxetane-3-carbonyl)piperidin-3-yl)imidazo[1,5-a]pyrazin-1-yl)-N-(4-(trifluoromethyl)pyridin-2-yl)benzamide | 581.2 | 2.75 min (UPLC-D) |
| 306 | 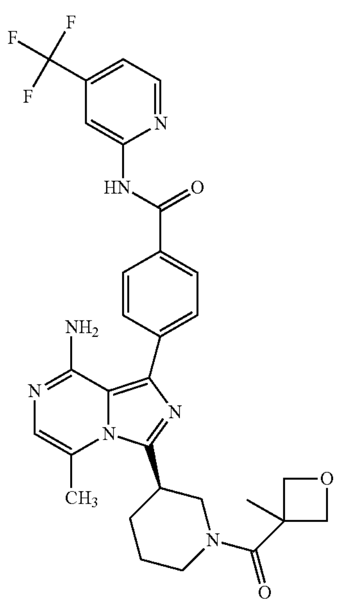 [SMILES: Cc1cnc(N)c2c(-c3ccc(C(=O)Nc4cc(C(F)(F)F)ccn4)cc3)nc([C@@H]3CCCN(C(=O)C4(C)COC4)C3)n12] | (R)-4-(8-amino-5-methyl-3-(1-(3-methyloxetane-3-carbonyl)piperidin-3-yl)imidazo[1,5-a]pyrazin-1-yl)-N-(4-(trifluoromethyl)pyridin-2-yl)benzamide | 594.2 | 2.90 min (UPLC-D) |

| Example | Structure | Name | LC-MS [M + H]+ | Retention time |
|---|---|---|---|---|
| 307 | 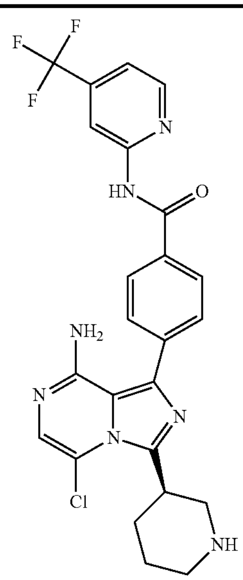 | (R)-4-(8-amino-3-(piperidin-3-yl)imidazo[1,5-a]pyrazin-1-yl)-N-(4-(trifluoromethyl)pyridin-2-yl)benzamide | 516.3 | 2.03 min (UPLC-E) |
| 308 | 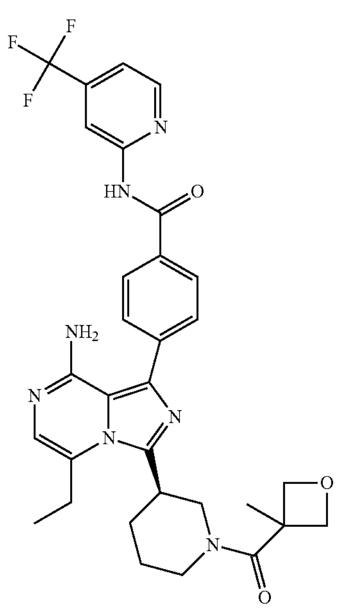 [SMILES: CCc1cnc(N)c2c(-c3ccc(C(=O)Nc4cc(C(F)(F)F)ccn4)cc3)nc([C@@H]3CCCN(C(=O)C4(C)COC4)C3)n12] | (R)-4-(8-amino-5-ethyl-3-(1-(3-methyloxetane-3-carbonyl)piperidin-3-yl)imidazo[1,5-a]pyrazin-1-yl)-N-(4-(trifluoromethyl)pyridin-2-yl)benzamide | 608.2 | 1.98 min |

| Example | Structure | Name | LC-MS [M + H]+ | Retention time |
|---------|-----------|------|----------------|----------------|
| 309 | 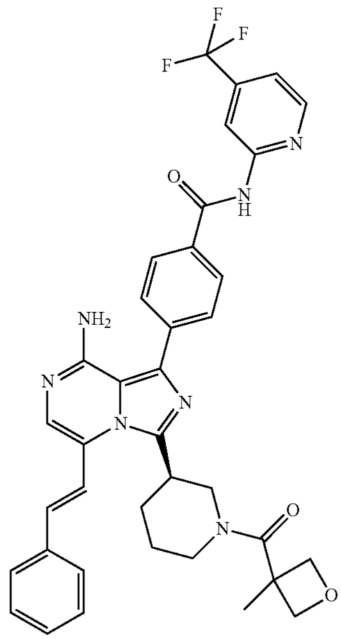 [SMILES: CC1(C(=O)N2CCC[C@@H](c3nc(-c4ccc(C(=O)Nc5cc(C(F)(F)F)ccn5)cc4)c4c(N)ncc(/C=C/c5ccccc5)n34)C2)COC1] | (R,E)-4-(8-amino-3-(1-(3-methyloxetane-3-carbonyl)piperidin-3-yl)-5-styrylimidazo[1,5-a]pyrazin-1-yl)-N-(4-(trifluoromethyl)pyridin-2-yl)benzamide | 682.3 | 3.02 min (UPLC-E) |
| 310 | 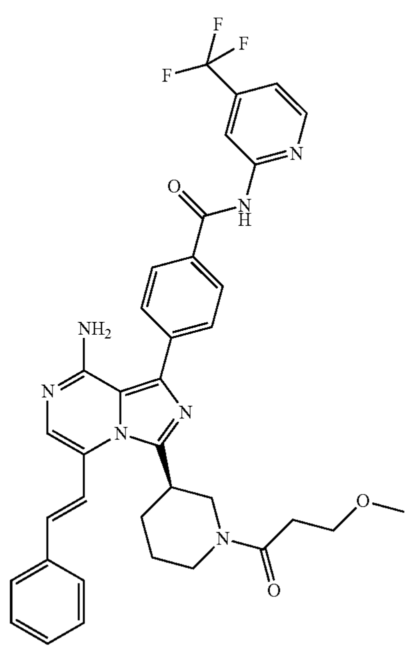 [SMILES: COCCC(=O)N1CCC[C@@H](c2nc(-c3ccc(C(=O)Nc4cc(C(F)(F)F)ccn4)cc3)c3c(N)ncc(/C=C/c4ccccc4)n23)C1] | (R,E)-4-(8-amino-3-(1-(3-methoxypropanoyl)piperidin-3-yl)-5-styrylimidazo[1,5-a]pyrazin-1-yl)-N-(4-(trifluoromethyl)pyridin-2-yl)benzamide | 670.3 | 3.03 min (UPLC-E) |

| Example | Structure | Name | LC-MS [M + H]+ | Retention time |
|---|---|---|---|---|
| 311 | 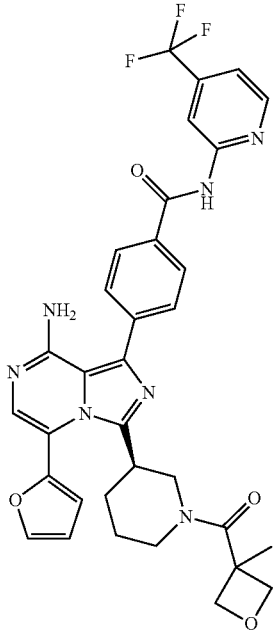 [SMILES: CC1(C(=O)N2CCC[C@@H](c3nc(-c4ccc(C(=O)Nc5cc(C(F)(F)F)ccn5)cc4)c4c(N)ncc(-c5ccco5)n34)C2)COC1] | (R)-4-(8-amino-5-(furan-2-yl)-3-(1-(3-methyloxetane-3-carbonyl)piperidin-3-yl)imidazo[1,5-a]pyrazin-1-yl)-N-(4-(trifluoromethyl)pyridin-2-yl)benzamide | 646.2 | 2.65 min (UPLC-E) |
| 312 | 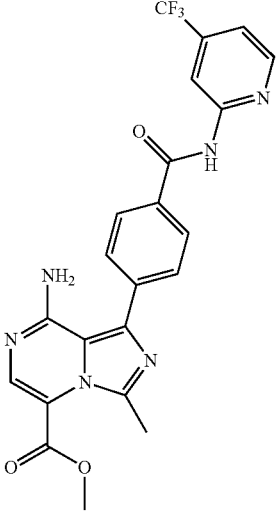 [SMILES: COC(=O)c1cnc(N)c2c(-c3ccc(C(=O)Nc4cc(C(F)(F)F)ccn4)cc3)nc(C)n12] | methyl 8-amino-3-methyl-1-(4-(4-(trifluoromethyl)pyridin-2-ylcarbamoyl)phenyl)imidazo[1,5-a]pyrazine-5-carboxylate | 471.2 | 2.28 min (UPLC-C) |

| Example | Structure | Name | LC-MS [M + H]+ | Retention time |
|---|---|---|---|---|
| 313 | 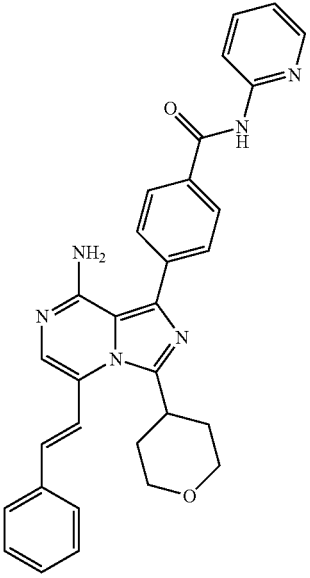 [SMILES: Nc1ncc(/C=C/c2ccccc2)n2c(C3CCOCC3)nc(-c3ccc(C(=O)Nc4ccccn4)cc3)c12] | (E)-4-(8-amino-5-styryl-3-(tetrahydro-2H-pyran-4-yl)imidazo[1,5-a]pyrazin-1-yl)-N-(pyridin-2-yl)benzamide | 517.3 | 2.00 min (UPLC-C) |
| 314 | 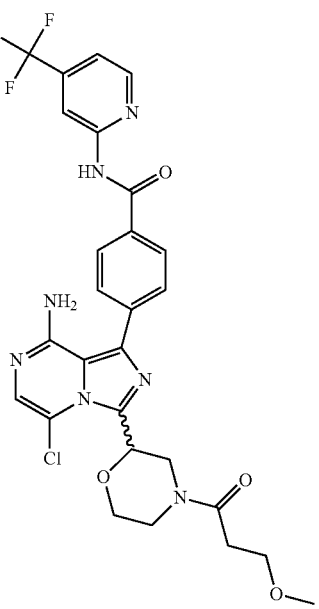 mix | 4-(8-amino-5-chloro-3-(4-(3-methoxypropanoyl)morpholin-2-yl)imidazo[1,5-a]pyrazin-1-yl)-N-(4-(trifluoromethyl)pyridin-2-yl)benzamide | 603.9 (LCMS-A) | 2.70 min (UPLC-C) |

-continued
| Example | Structure | Name | LC-MS [M + H]+ | Retention time |
|---|---|---|---|---|
| 315 | 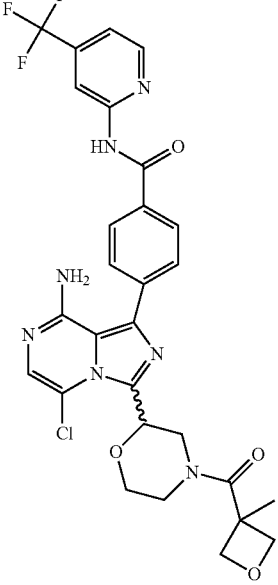 mix | 4-(8-amino-5-chloro-3-(4-(3-methyloxetane-3-carbonyl)morpholin-2-yl)imidazo[1,5-a]pyrazin-1-yl)-N-(4-(trifluoromethyl)pyridin-2-yl)benzamide | 616.1 | 2.58 min (UPLC-E) |
| 316 | 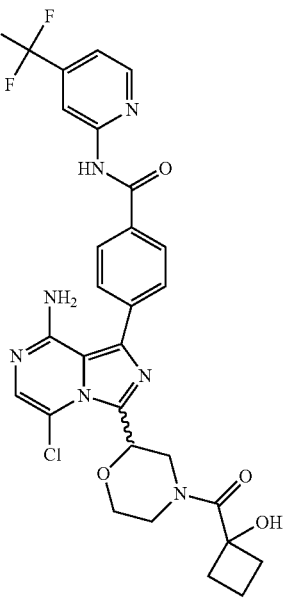 mix | 4-(8-amino-5-chloro-3-(4-(1-hydroxycyclobutanecarbonyl)morpholin-2-yl)imidazo[1,5-a]pyrazin-1-yl)-N-(4-(trifluoromethyl)pyridin-2-yl)benzamide | 616.1 | 2.72 min (UPLC-E) |

-continued

| Example | Structure | Name | LC-MS [M + H]+ | Retention time |
|---|---|---|---|---|
| 317 | 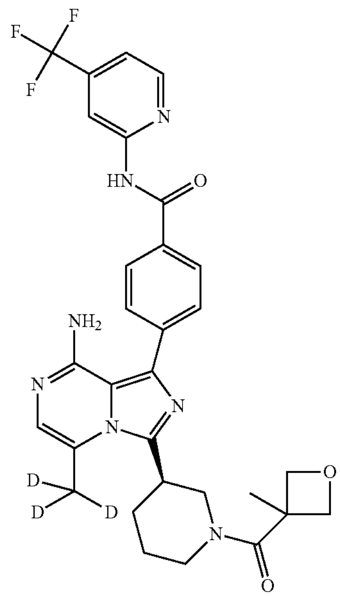 [SMILES: [2H]C([2H])([2H])c1cnc(N)c2c(-c3ccc(C(=O)Nc4cc(C(F)(F)F)ccn4)cc3)nc([C@@H]3CCCN(C(=O)C4(C)COC4)C3)n12] | (R)-4-(8-amino-5-deuteromethyl-3-(1-(3-methyloxetane-3-carbonyl)piperidin-3-yl)imidazo[1,5-a]pyrazin-1-yl)-N-(4-(trifluoromethyl)pyridin-2-yl)benzamide | 597.2 | 1.94 min |
| 318 | 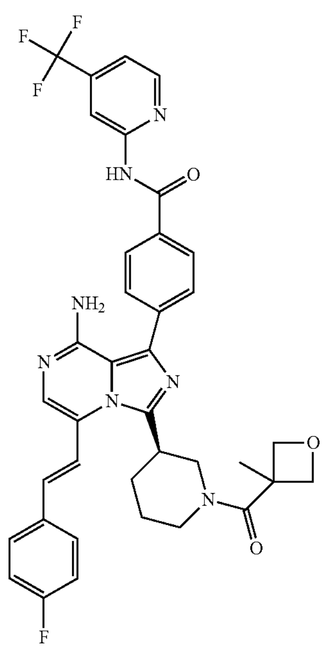 [SMILES: CC1(C(=O)N2CCC[C@@H](c3nc(-c4ccc(C(=O)Nc5cc(C(F)(F)F)ccn5)cc4)c4c(N)ncc(/C=C/c5ccc(F)cc5)n34)C2)COC1] | (R,E)-4-(8-amino-5-(4-fluorostyryl)-3-(1-(3-methyloxetane-3-carbonyl)piperidin-3-yl)imidazo[1,5-a]pyrazin-1-yl)-N-(4-(trifluoromethyl)pyridin-2-yl)benzamide | 700.2 | 2.08 min |

-continued

| Example | Structure | Name | LC-MS [M + H]+ | Retention time |
|---|---|---|---|---|
| 319 | 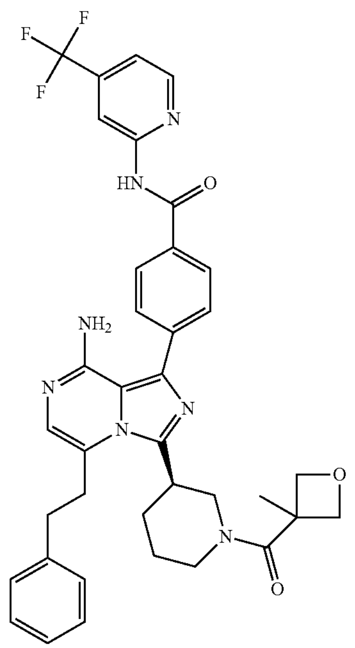 [SMILES: CC1(C(=O)N2CCC[C@@H](c3nc(-c4ccc(C(=O)Nc5cc(C(F)(F)F)ccn5)cc4)c4c(N)ncc(CCc5ccccc5)n34)C2)COC1] | (R)-4-(8-amino-3-(1-(3-methyloxetane-3-carbonyl)piperidin-3-yl)-5-phenethylimidazo[1,5-a]pyrazin-1-yl)-N-(4-(trifluoromethyl)pyridin-2-yl)benzamide | 684.2 | 2.06 min |
| 320 | 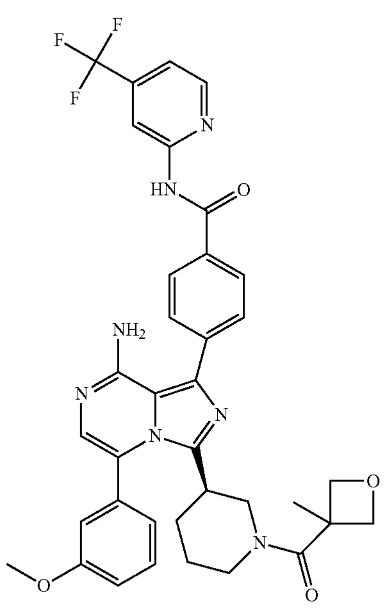 [SMILES: COc1cccc(-c2cnc(N)c3c(-c4ccc(C(=O)Nc5cc(C(F)(F)F)ccn5)cc4)nc([C@@H]4CCCN(C(=O)C5(C)COC5)C4)n23)c1] | (R)-4-(8-amino-5-(3-methoxyphenyl)-3-(1-(3-methyloxetane-3-carbonyl)piperidin-3-yl)imidazo[1,5-a]pyrazin-1-yl)-N-(4-(trifluoromethyl)pyridin-2-yl)benzamide | 686.2 | 2.01 min |

-continued

| Example | Structure | Name | LC-MS [M + H]+ | Retention time |
|---|---|---|---|---|
| 321 | 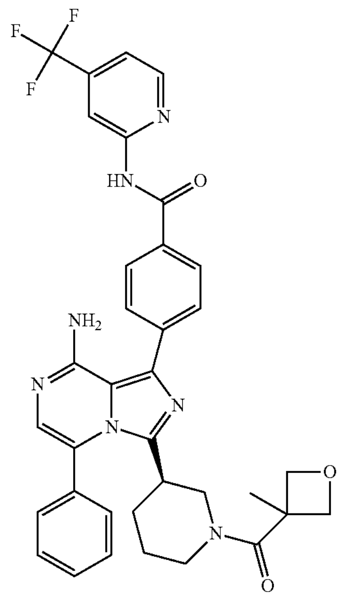 [SMILES: CC1(C(=O)N2CCC[C@@H](c3nc(-c4ccc(C(=O)Nc5cc(C(F)(F)F)ccn5)cc4)c4c(N)ncc(-c5ccccc5)n34)C2)COC1] | (R)-4-(8-amino-3-(1-(3-methyloxetane-3-carbonyl)piperidin-3-yl)-5-phenylimidazo[1,5-a]pyrazin-1-yl)-N-(4-(trifluoromethyl)pyridin-2-yl)benzamide | 656.2 | 2.04 min |
| 322 | 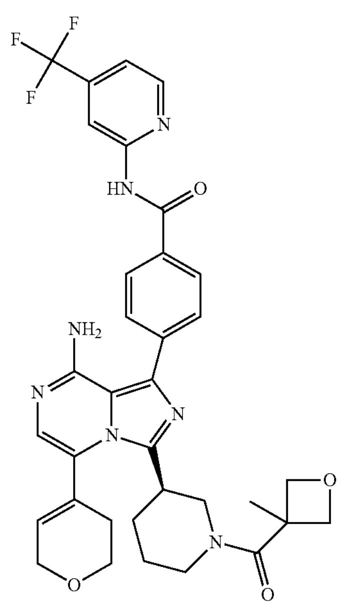 [SMILES: CC1(C(=O)N2CCC[C@@H](c3nc(-c4ccc(C(=O)Nc5cc(C(F)(F)F)ccn5)cc4)c4c(N)ncc(C5=CCOCC5)n34)C2)COC1] | (R)-4-(8-amino-5-(3,6-dihydro-2H-pyran-4-yl)-3-(1-(3-methyloxetane-3-carbonyl)piperidin-3-yl)imidazo[1,5-a]pyrazin-1-yl)-N-(4-(trifluoromethyl)pyridin-2-yl)benzamide | 662.2 | 1.96 min |

-continued

| Example | Structure | Name | LC-MS [M + H]+ | Retention time |
|---|---|---|---|---|
| 323 | mix | 4-(8-amino-5-(1-hydroxy-3-methylbutyl)-3-methylimidazo[1,5-a]pyrazin-1-yl)-N-(4-(trifluoromethyl)pyridin-2-yl)benzamide | 499.2 | 2.67 min (UPLC-C) |

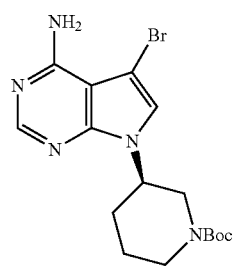

Intermediate 42

(R)-tert-butyl 3-(4-amino-5-bromo-7H-pyrrolo[2,3-d]pyrimidin-7-yl)piperidine-1-carboxylate (a) (R)-tert-butyl 3-(5-bromo-4-chloro-7H-pyrrolo[2,3-d]pyrimidin-7-yl)piperidine-1-carboxylate DEAD (5.43 ml, 34.3 mmol) was added dropwise to a stirred, cooled 0° C. mixture of (S)-1-Boc-3-hydroxypiperidine (6.90 g, 34.3 mmol), 5-bromo-4-chloro-7H-pyrrolo[2,3-d]pyrimidine (4 g, 17.13 mmol) and triphenylphosphine (8.99 g, 34.3 mmol) in THF (50 ml) and the mixture was stirred at 0° C. for 10 min. and warmed to rt. After stirring at rt for overnight and concentrated in vacuo. The residue was diluted with EtOAc, washed with water, dried and concentrated in vacuo. The residue was purified by column chromatography on silica gel, eluting with hexane/EtOAc (4/1) to give (R)-tert-butyl 3-(5-bromo-4-chloro-7H-pyrrolo[2,3-d]pyrimidin-7-yl)piperidine-1-carboxylate (3.3 g, 7.92 mmol, 46.2% yield) as a white foam. R$_t$ 2.396 min; m/z 416.00 and 418.00 (M+H)+.

(b) (R)-tert-butyl 3-(4-amino-5-bromo-7H-pyrrolo[2,3-d]pyrimidin-7-yl)piperidine-1-carboxylate A mixture of (R)-tert-butyl 3-(5-bromo-4-chloro-7H-pyrrolo[2,3-d]pyrimidin-7-yl)piperidine-1-carboxylate (1.67 g, 4.01 mmol) in 2N NH$_3$ in 2-propanol was stirred at 120° C. in a sealed tube for 4 h and concentrated. The residue was purified by column chromatography on silica gel, eluting with hexane/EtOAc (4/1) to give (R)-tert-butyl 3-(4-amino-5-bromo-7H-pyrrolo[2,3-d]pyrimidin-7-yl)piperidine-1-carboxylate (1.6 g, 4.03 mmol, 100% yield) as a white foam. R$_t$ 1.875 min; m/z 397.2 and 399.2 (M+H)+.

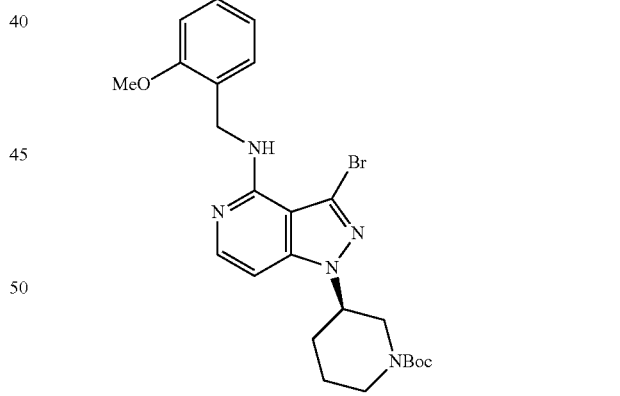

Intermediate 43

(R)-tert-butyl 3-(3-bromo-4-((2,4-dimethoxybenzyl)amino)-1H-pyrazolo[4,3-c]pyridin-1-yl)piperidine-1-carboxylate (a) 3-Bromo-4-chloro-1H-pyrazolo[4,3-c]pyridine A mixture of 4-chloro-1H-pyrazolo[4,3-c]pyridine (380 mg, 2.474 mmol) and NBS (484 mg, 2.72 mmol) in acetonitrile was reacted under microwave conditions (20 min, 120° C.) and concentrated. The residue was purified by column chromatography on silica gel, eluting with (DCM/2N NH$_3$ in MeOH, 50/1 to 20/1) to give 3-bromo-4-chloro-1H-pyrazolo[4,3-c]pyridine (725 mg, 2.495 mmol, 100% yield) as a white solid. LCMS Data: R$_t$ 1.02 min; m/z 231.8 and 233.8 (M+H)$^+$.

(b) (R)-tert-butyl 3-(3-bromo-4-chloro-1H-pyrazolo[4,3-c]pyridin-1-yl)piperidine-1-carboxylate 'DIAD (1.361 ml, 6.87 mmol) was added dropwise to a stirred, cooled (0° C.) mixture of 3-bromo-4-chloro-1H-pyrazolo[4,3-c]pyridine (1.33 g, 5.72 mmol)), (S)-tert-butyl 3-hydroxypiperidine-1-carboxylate (1.382 g, 6.87 mmol)) and Ph$_3$P (1.801 g, 6.87 mmol) in tetrahydrofuran (50 ml) and the mixture was stirred at 0° C. to rt overnight, then concentrated in vacuo. The residue was purified by column chromatography on silica gel, eluting with EtOAc/isohexane (10/1 to 5/1) to give (R)-tert-butyl 3-(3-bromo-4-chloro-1H-pyrazolo[4,3-c]pyridin-1-yl)piperidine-1-carboxylate (2.1 g, 3.03 mmol, 53.0% yield). LCMS Data: R$_t$ 1.21 min; m/z 415.0 and 417.0 (M+H)$^+$.

(c) (R)-tert-butyl 3-(3-bromo-4-((2,4-dimethoxybenzyl)amino)-1H-pyrazolo[4,3-c]pyridin-1-yl)piperidine-1-carboxylate 2,4-Dimethoxybenzylamine (1.602 ml, 10.54 mmol) was added to a stirred mixture of (R)-tert-butyl 3-(3-bromo-4-chloro-1H-pyrazolo[4,3-c]pyridin-1-yl)piperidine-1-carboxylate (1.46 g, 2.107 mmol) and DIPEA (1.840 ml, 10.54 mmol) in acetonitrile (25 ml) and the mixture was stirred at 80° C. for 48 h. and concentrated in vacuo. The residue was purified by column chromatography on silica gel (gold, 80 g), eluting with EtOAc/isohexane (3/1 to 2/1) to give (R)-tert-butyl 3-(3-bromo-4-((2,4-dimethoxybenzyl)amino)-1H-pyrazolo[4,3-c]pyridin-1-yl)piperidine-1-carboxylate (480 mg, 0.878 mmol, 41.7% yield) as a colorless oil. LCMS Data: R$_t$ 2.05 min; m/z 545.9 and 547.9 (M+H)$^+$.

Intermediate 43A

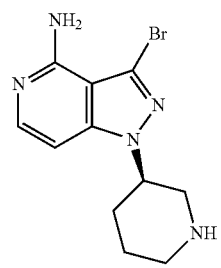

(R)-3-bromo-1-(piperidin-3-yl)-1H-pyrazolo[4,3-c]pyridin-4-amine (R)-tert-butyl 3-(3-bromo-4-((2,4-dimethoxybenzyl)amino)-1H-pyrazolo[4,3-c]pyridin-1-yl)-piperidine-1-carboxylate in TFA (5 mL, 64.9 mmol) and triethylsilane (0.2 mL, 1.252 mmol) was stirred at 80° C. for 2 h and concentrated in vacuo. The residue was purified by column chromatography on silica gel (gold, 40 g), eluting with (DCM/2N NH$_3$ in MeOH, 20/1) to give (R)-3-bromo-1-(piperidin-3-yl)-1H-pyrazolo[4,3-c]pyridin-4-amine (164 mg, 0.554 mmol, 92% yield) as a white solid. LCMS Data: R$_t$ 0.10 and 0.16 min; m/z 296.00 and 298.00 (M+H)$^+$. $^1$HNMR (CDCl$_3$, 500 Hz): 7.73 (d, J=6.5 Hz), 6.63 (d, J=6.5 Hz), 4.33 (m, 1), 3.22 (m, 1), 3.04-3.12 (m, 2), 2.67 (dd, J=11.5, 10 Hz), 2.06-2.18 (m, 2), 1.85 (m, 1) 1.60-1.69 (m, 1).

Intermediate 44

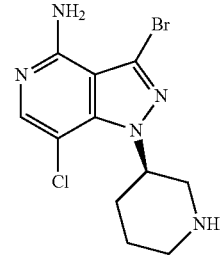

(R)-3-bromo-7-chloro-1-(piperidin-3-yl)-1H-pyrazolo[4,3-c]pyridin-4-amine

NCS (28.9 mg, 0.216 mmol) was added to a stirred 70° C. mixture of (R)-3-bromo-1-(piperidin-3-yl)-1H-pyrazolo[4,3-c]pyridin-4-amine (64 mg, 0.216 mmol) in acetonitrile (10 ml) and the mixture was stirred at 70° C. overnight and concentrated in vacuo. The residue was purified by column chromatography on silica gel (gold, 40 g), eluting with (DCM/2N NH$_3$ in MeOH 50/1 to 20/1) to give (R)-3-bromo-7-chloro-1-(piperidin-3-yl)-1H-pyrazolo[4,3-c]pyridin-4-amine (17.8 mg, 0.060 mmol, 27.8% yield) as a yellow solid. LCMS Data: R$_t$ 0.18 and 0.16 min; m/z 331.93 (M+H)$^+$. NMR (CDCl$_3$, 500 Hz): 7.76 (s, 1),3.90-4.22 (m, 1), 3.39-3.48 (m, 1), 3.10-3.34 (m, 2), 2.81(m, 1), 2.22 (m, 2), 1.93 (m, 1) 1.77 (m, 1).

Example 324

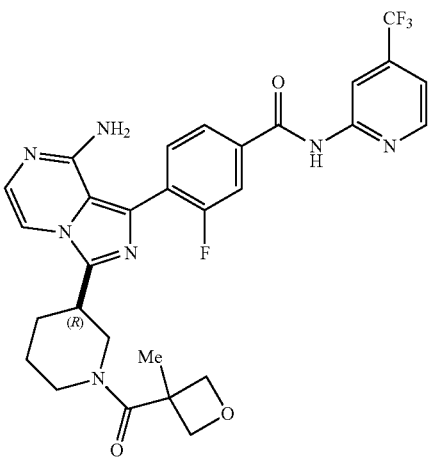

(R)-4-(8-amino-3-(1-(3-methyloxetane-3-carbonyl)piperidin-3-yl)imidazo[1,5-a]pyrazin-1-yl)-3-fluoro-N-(4-(trifluoromethyl)pyridin-2-yl)benzamide The PdCl$_2$(dppf)-CH$_2$Cl$_2$ adduct (0.895 g, 1.096 mmol) was added to a stirred, cooled room temperature mixture of 3-fluoro-4-(4,4,5,5-tetramethyl-1,3,2-dioxaborolan-2-yl)-N-(4-(trifluoromethyl)pyridin-2-yl)benzamide (23.41 g, 45.7 mmol) and (R)-(3-(8-amino-1-bromoimidazo[1,5-a]pyrazin-3-yl)piperidin-1-yl)(3-methyloxetan-3-yl)methanone (14.4 g, 36.5 mmol) in dioxane (250 ml) and potassium carbonate (73.0 ml, 146 mmol) in dioxane (250 m). The mixture was degassed then stirred at 80° C. for 2 h under nitrogen. An additional amount of (R)-(3-(8-amino-1-bromoimidazo[1,5-a]pyrazin-3-yl)piperidin-1-yl)(3-methyloxetan-3-yl) methanone (1.440 g, 3.65 mmol) was then added to drive reaction to completion after one more h at 80° C. After cooling to room temperature, the mixture was partitioned between ethyl acetate and water. The organic layer was separated and the aqueous layer was extracted. The combined organic phase was washed with water and brine, then dried and concentrated. The crude product was purified on two 330 g Isco silica gel columns eluting with 1-10% MeOH/EtOAc to give white solid (R)-4-(8-amino-3-(1-(3-methyloxetane-3-carbonyl)piperidin-3-yl)imidazo[1,5-a]pyrazin-1-yl)-3-fluoro-N-(4-(trifluoromethyl)-pyridin-2-yl)benzamide (17.46 g, 29.2 mmol, 80% yield). LC-MS, [M+H]$^+$: 598.5. $^1$HNMR (400 MHz, CD$_3$Cl, δ, ppm): 8.85 (s, 1H), 8.73 (s, 1H), 8.51 (d, 1H), 7.89 (d,2H), 7.75 (t, 1H), 7.46 (d, 1H), 7.37 (dd, 1H), 5.04 (m, 4H), 4.82 (m, 1H), 4.41 (m, 2H), 3.15 (m, 3H), 2.98 (t, 1H), 2.25 (m, 2H), 1.96 (m, 3H), 1.67 (s, 3H).

Example 325

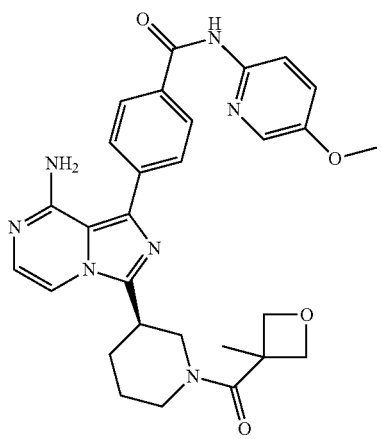 [SMILES: COc1ccc(NC(=O)c2ccc(-c3nc([C@@H]4CCCN(C(=O)C5(C)COC5)C4)n4ccnc(N)c34)cc2)nc1]

(R)-4-(8-amino-3-(1-(3-methyloxetane-3-carbonyl) piperidin-3-yl)imidazo[1,5-a]pyrazin-1-yl)-N-(5-methoxypyridin-2-yl)benzamide To a solution of (R)-4-(8-((2,4-dimethoxybenzyl)amino)-3-(1-(3-methyloxetane-3-carbonyl)piperidin-3-yl)imidazo [1,5-a]pyrazin-1-yl)benzamide in tert-butanol (1000 uL), was added chloro(2-dicyclohexylphosphino-2',6'-di-i-propoxy-1,1'-biphenyl)[2-(2-aminoethyl)phenyl)]palladium (II) (5 mg, 0.005 mmol), chloro[2-(dicyclohexylphosphino)-3,6-dimethoxy-2',4',6'-triisopropyl-1,1'-biphenyl][2-(2-aminoethyl)phenyl]palladium(II) (0.05 mol) 2-chloro-5-methoxypyridine (25 mg, 0.174 mmol) and finally potassium phosphate (30 mg, 0.141 mmol). The reaction mixture was heated at 100° C. for 15 h then cooled to ambient temperature of 21° C., water (500 uL) was added followed by ethyl acetate (2×1000 uL). The organic layers were separated and then concentrated in vacuo via a Genevac. The residue (R)-4-(8-((2,4-dimethoxybenzyl)amino)-3-(1-(3-methyloxetane-3-carbonyl)piperidin-3-yl)imidazo[1,5-a]pyrazin-1-yl)-N-(5-methoxypyridin-2-yl)benzamide thus collected was then dissolved in trifluoroacetic acid (300 uL, 3.89 mmol) and heated to 100° C. for 30 min. The reaction was then diluted with DMSO (1000 uL) and was purified by reverse phase semi prep HPLC Waters XBridge (CH$_3$CN/H$_2$O/NH4OH, C18, 5u, 19×100 mm system) to yield the title compound as a solid. LC/MS=542 [M+1].

Example 326

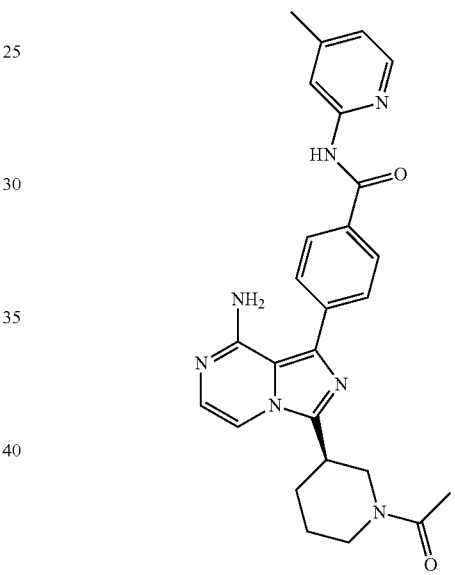

4-{8-amino-3-[(3R)-1-acetylpiperidin-3-yl]imidazo [1,5-a]pyrazin-1-yl}-N-(4-methylpyridin-2-yl)benzamide To (R)-4-(8-amino-3-(piperidin-3-yl)imidazo[1,5-a] pyrazin-1-yl)-N-(4-methylpyridin-2-yl)benzamide (20 mg, 0.047 mmol), in DMF (1000 μL) was added 2,4,6-tripropyl-1,3,5,2,4,6-trioxatriphosphorinane-2,4,6-trioxide (100 μL, 0.162 mmol), acetic acid and triethylamine (50 μL, 0.359 mmol). The reactions were shaken at 21° C. for 30 min and then diluted with 500 μL of MeOH as a quench and then filtered via a 0.4 uM hydrophobic plug. The reaction was then diluted with DMSO (1000 μL) and was purified by reverse phase semi prep HPLC Waters XBridge (CH$_3$CN/H$_2$O/NH$_4$OH, C18, 5u, 19×100 mm system) to yield the title compound as a solid. LC/MS=570.2 [M+1].

Example 327

4-(8-amino-3-{(3R)-1-[(3-methyloxetan-3-yl)carbonyl]piperidin-3-yl}imidazo[1,5-a]pyrazin-1-yl)-N-(5-cyanopyridin-2-yl)benzamide

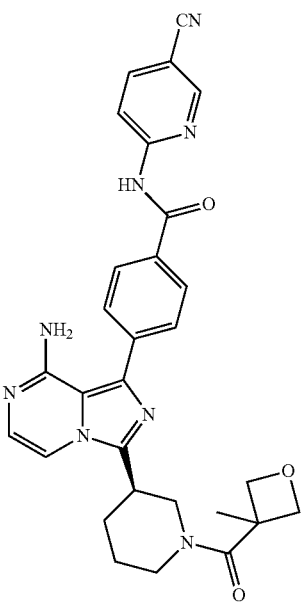 [SMILES: CC1(C(=O)N2CCC[C@@H](c3nc(-c4ccc(C(=O)Nc5ccc(C#N)cn5)cc4)c4c(N)nccn34)C2)COC1]

To the stirred solution of (R)-4-(8-((2,4-dimethoxybenzyl)amino)-3-(1-(3-methyloxetane-3-carbonyl)piperidin-3-yl)imidazo[1,5-a]pyrazin-1-yl)benzoic acid (25 mg, 0.043 mmol) in DCE (1 ml) was added 1-chloro-N,N,2-trimethylprop-1-en-1-amine (8.56 mg, 0.064 mmol). The reaction mixture was stirred at rt for 30 min, then added 4-cyano-2-aminopyridine (6 mg, 2 equiv.) and N,N-dimethylpyridin-4-amine (13.04 mg, 0.107 mmol). The reaction mixture was stirred at 45° C. overnight, cooled to room temperature, then treated with 1 mL of TFA and 0.1 mL of triethylsilane. The reaction was stirred at 80° C. for 3.5 h. The reaction mixture was concentrated in vacuo, redissolved in 1 mL of DMSO, filtered, and purified by reverse phase semi prep HPLC Waters XBridge (CH$_3$CN/H$_2$O/NH4OH, C18, 5u, 19×100 mm system) to yield the title compound as a solid. LC/MS=537.2 [M+1].

The examples in the following table were prepared following the same procedure described in Examples 325 and 326:

| Example | Structure | Name | Exact Mass [M + H]$^+$ | Retention time (min) |
|---|---|---|---|---|
| 328 | ![structure] | 4-(8-amino-3-{(3R)-1-[(3,5-dimethylisoxazol-4-yl)carbonyl]piperidin-3-yl}imidazo[1,5-a]pyrazin-1-yl)-N-[4-trifluoromethyl)pyridin-2-yl]benzamide | Calc'd 605.2, found 605.2 | 1.914 (Method O) |

| Example | Structure | Name | Exact Mass [M + H]⁺ | Retention time (min) |
|---|---|---|---|---|
| 329 | 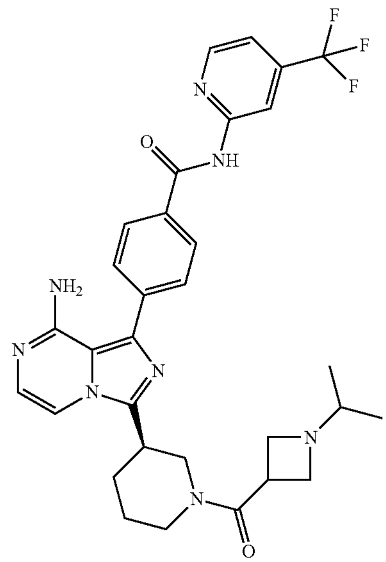 [SMILES: CC(C)N1CC(C(=O)N2CCC[C@@H](c3nc(-c4ccc(C(=O)Nc5cc(C(F)(F)F)ccn5)cc4)c4c(N)nccn34)C2)C1] | 4-{8-amino-3-[(3R)-1-{[1-(1-methylethyl)azetidin-3-yl]carbonyl}piperidin-3-yl]imidazo[1,5-a]pyrazin-1-yl}-N-[4-(trifluoromethyl)pyridin-2-yl]benzamide | Calc'd 607.3, found 607.2 | 1.784 (Method M) |
| 330 | 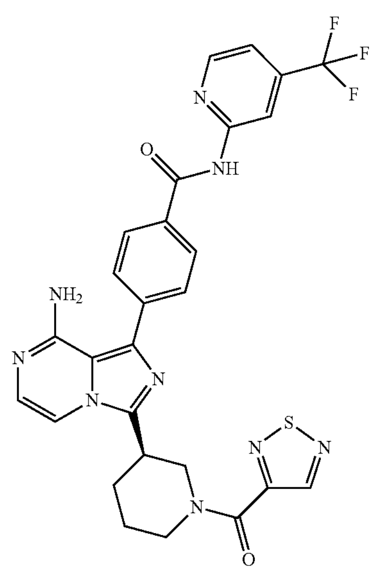 [SMILES: Nc1nccn2c([C@@H]3CCCN(C(=O)c4cnsn4)C3)nc(-c3ccc(C(=O)Nc4cc(C(F)(F)F)ccn4)cc3)c12] | 4-{8-amino-3-[(3R)-1-(1,2,5-thiadiazol-3-ylcarbonyl)piperidin-3-yl]imidazo[1,5-a]pyrazin-1-yl}-N-[4-(trifluoromethyl)pyridin-2-yl]benzamide | Calc'd 594.2, found 594.2 | 1.961 (Method M) |

-continued

| Example | Structure | Name | Exact Mass [M + H]+ | Retention time (min) |
|---|---|---|---|---|
| 331 | 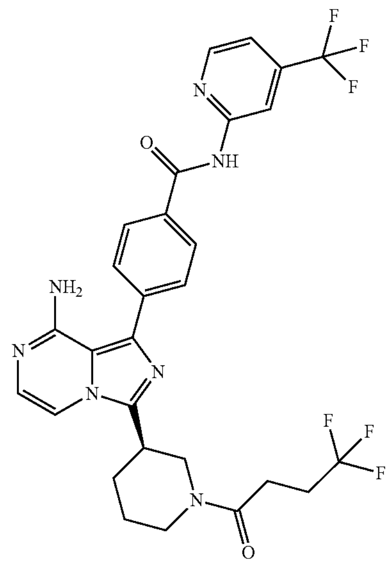 [SMILES: Nc1nccn2c([C@@H]3CCCN(C(=O)CCC(F)(F)F)C3)nc(-c3ccc(C(=O)Nc4cc(C(F)(F)F)ccn4)cc3)c12] | 4-{8-amino-3-[(3R)-1-(4,4,4-trifluorobutanoyl)piperidin-3-yl]imidazo[1,5-a]pyrazin-1-yl}-N-[4-(trifluoromethyl)pyridin-2-yl]benzamide | Calc'd 606.2, found 606.2 | 2.015 (Method M) |
| 332 | 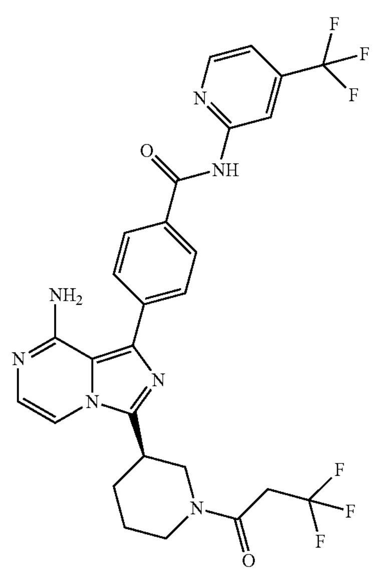 [SMILES: Nc1nccn2c([C@@H]3CCCN(C(=O)CC(F)(F)F)C3)nc(-c3ccc(C(=O)Nc4cc(C(F)(F)F)ccn4)cc3)c12] | 4-{8-amino-3-[(3R)-1-(3,3,3-trifluoropropanoyl)piperidin-3-yl]imidazo[1,5-a]pyrazin-1-yl}-N-[4-(trifluoromethyl)pyridin-2-yl]benzamide | Calc'd 592.2, found 592.2 | 1.015* (Method N) |

| Example | Structure | Name | Exact Mass [M + H]+ | Retention time (min) |
|---|---|---|---|---|
| 333 | 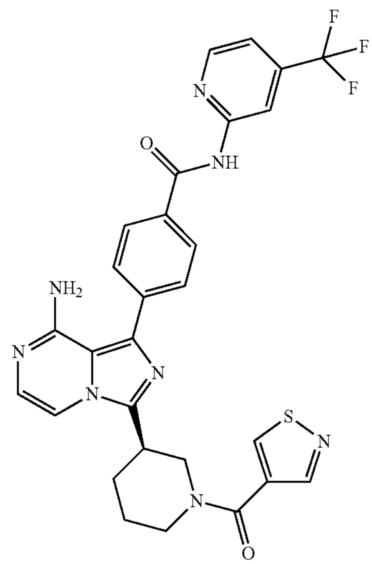 [SMILES: Nc1nccn2c([C@@H]3CCCN(C(=O)c4cnsc4)C3)nc(-c3ccc(C(=O)Nc4cc(C(F)(F)F)ccn4)cc3)c12] | 4-{8-amino-3-[(3R)-1-(isothiazol-4-ylcarbonyl)piperidin-3-yl]imidazo[1,5-a]pyrazin-1-yl}-N-[4-(trifluoromethyl)pyridin-2-yl]benzamide | Calc'd 593.2, found 593.2 | 0.973* (Method N) |
| 334 | 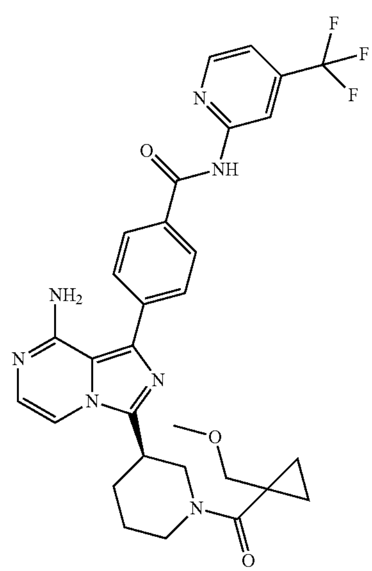 [SMILES: COCC1(C(=O)N2CCC[C@@H](c3nc(-c4ccc(C(=O)Nc5cc(C(F)(F)F)ccn5)cc4)c4c(N)nccn34)C2)CC1] | 4-{8-amino-3-[(3R)-1-{[1-(methoxymethyl)cyclopropyl]carbonyl}piperidin-3-yl]imidazo[1,5-a]pyrazin-1-yl}-N-[4-(trifluoromethyl)pyridin-2-yl]benzamide | Calc'd 594.2, found 594.2 | 0.995* (Method N) |

| Example | Structure | Name | Exact Mass [M + H]+ | Retention time (min) |
|---|---|---|---|---|
| 335 | 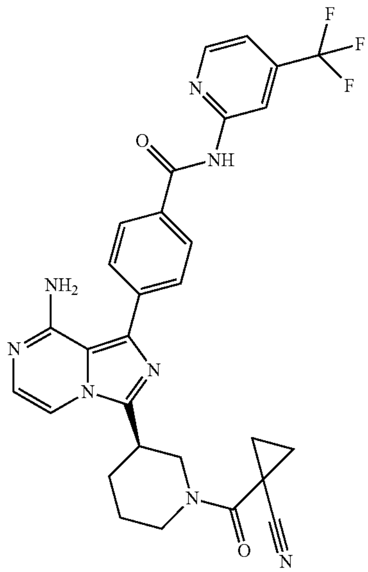 [SMILES: N#CC1(C(=O)N2CCC[C@@H](c3nc(-c4ccc(C(=O)Nc5cc(C(F)(F)F)ccn5)cc4)c4c(N)nccn34)C2)CC1] | 4-(8-amino-3-{(3R)-1-[(1-cyanocyclopropyl)carbonyl]piperidin-3-yl}imidazo[1,5-a]pyrazin-1-yl)-N-[4-(trifluoromethyl)pyridin-2-yl]benzamide, TFA salt | Calc'd 575.2, found 575.2 | 1.979 (Method M) |
| 336 | 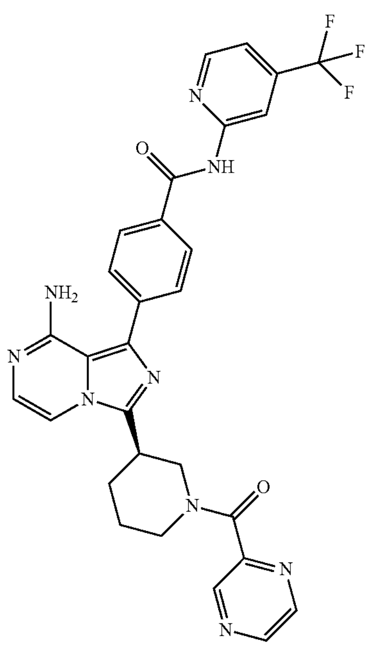 [SMILES: Nc1nccn2c([C@@H]3CCCN(C(=O)c4cnccn4)C3)nc(-c3ccc(C(=O)Nc4cc(C(F)(F)F)ccn4)cc3)c12] | 4-{8-amino-3-[(3R)-1-(pyrazin-2-ylcarbonyl)piperidin-3-yl]imidazo[1,5-a]pyrazin-1-yl}-N-[4-(trifluoromethyl)pyridin-2-yl]benzamide | Calc'd 588.2, found 588.3 | 0.66 (Method Q) |

-continued

| Example | Structure | Name | Exact Mass [M + H]+ | Retention time (min) |
|---|---|---|---|---|
| 337 | 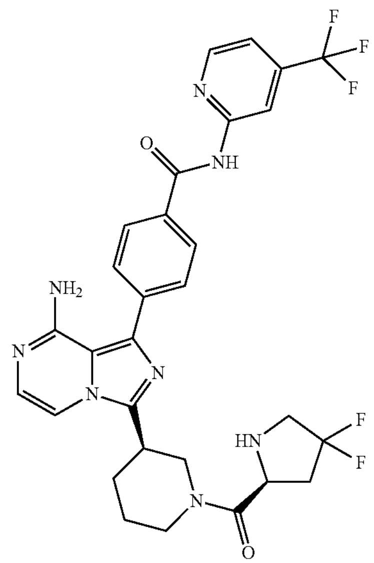 [SMILES: Nc1nccn2c([C@@H]3CCCN(C(=O)[C@@H]4CC(F)(F)CN4)C3)nc(-c3ccc(C(=O)Nc4cc(C(F)(F)F)ccn4)cc3)c12] | 4-{8-amino-3-[(3R)-1-(4,4-difluoro-L-prolyl)piperidin-3-yl]imidazo[1,5-a]pyrazin-1-yl}-N-[4-(trifluoromethyl)pyridin-2-yl]benzamide | Calc'd 615.2, found 615.0 | 1.795 (Method M) |
| 338 | 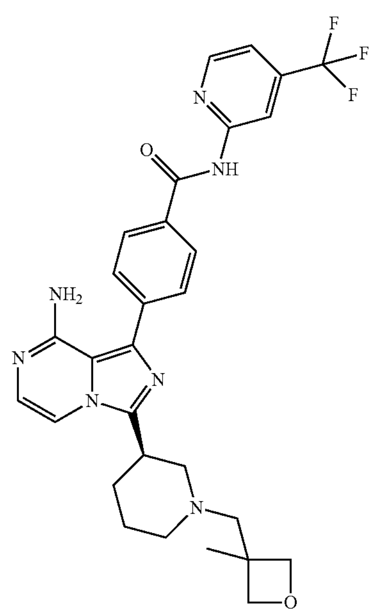 [SMILES: CC1(CN2CCC[C@@H](c3nc(-c4ccc(C(=O)Nc5cc(C(F)(F)F)ccn5)cc4)c4c(N)nccn34)C2)COC1] | 4-(8-amino-3-{(3R)-[(3-methyloxetan-3-yl)methyl]piperidin-3-yl}imidazo[1,5-a]pyrazin-1-yl)-N-[4-(trifluoromethyl)pyridin-2-yl]benzamide, TFA salt | Calc'd 566.2, found 566.0 | 1.706 (Method M) |

| Example | Structure | Name | Exact Mass [M + H]+ | Retention time (min) |
|---|---|---|---|---|
| 339 | 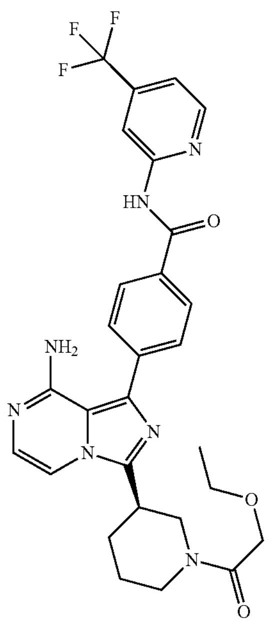 [SMILES: CCOCC(=O)N1CCC[C@@H](c2nc(-c3ccc(C(=O)Nc4cc(C(F)(F)F)ccn4)cc3)c3c(N)nccn23)C1] | 4-{8-amino-3-[(3R)-1-(ethoxyacetyl)piperidin-3-yl]imidazo[1,5-a]pyrazin-1-yl}-N-[4-(trifluoromethyl)pyridin-2-yl]benzamide | Calc'd 568.2, found 568.2 | 1.09 (Method P) |
| 340 | 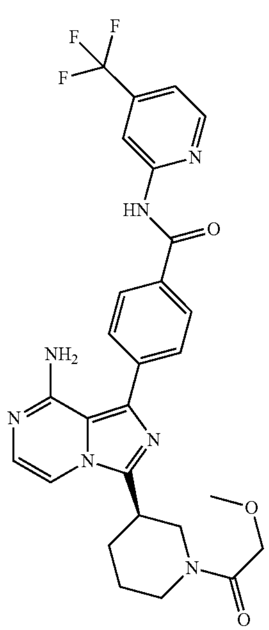 [SMILES: COCC(=O)N1CCC[C@@H](c2nc(-c3ccc(C(=O)Nc4cc(C(F)(F)F)ccn4)cc3)c3c(N)nccn23)C1] | 4-{8-amino-3-[(3R)-1-(methoxyacetyl)piperidin-3-yl]imidazo[1,5-a]pyrazin-1-yl}-N-[4-(trifluoromethyl)pyridin-2-yl]benzamide | Calc'd 554.2, found 554.2 | 1.07 (Method P) |

| Example | Structure | Name | Exact Mass [M + H]+ | Retention time (min) |
|---|---|---|---|---|
| 341 | 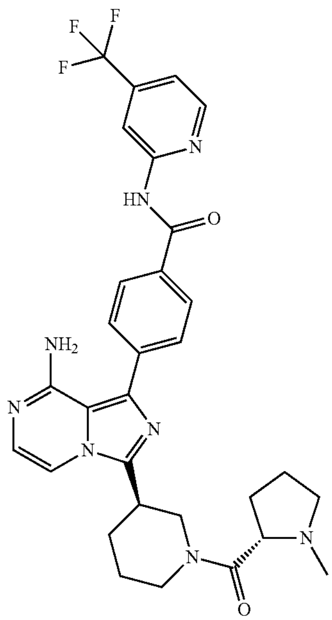 [SMILES: CN1CCC[C@H]1C(=O)N1CCC[C@@H](c2nc(-c3ccc(C(=O)Nc4cc(C(F)(F)F)ccn4)cc3)c3c(N)nccn23)C1] | 4-{8-amino-3-[(3R)-1-(1-methyl-L-prolyl)piperidin-3-yl]imidazo[1,5-a]pyrazin-1-yl}-N-[4-(trifluoromethyl)pyridin-2-yl]benzamide | Calc'd 593.3, found 593.25 | 0.98 (Method Q) |
| 342 | 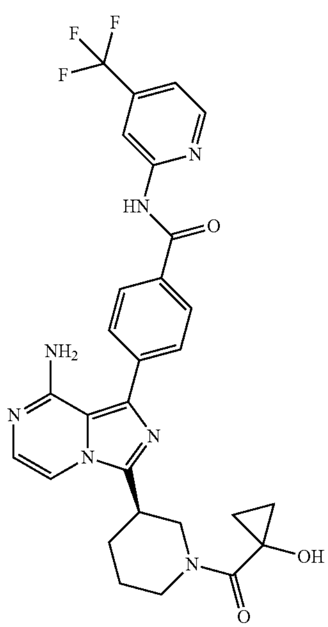 [SMILES: Nc1nccn2c([C@@H]3CCCN(C(=O)C4(O)CC4)C3)nc(-c3ccc(C(=O)Nc4cc(C(F)(F)F)ccn4)cc3)c12] | 4-(8-amino-3-{(3R)-1-[(1-hydroxycyclopropyl)carbonyl]piperidin-3-yl}imidazo[1,5-a]pyrazin-1-yl)-N-[4-(trifluoromethyl)pyridin-2-yl]benzamide | Calc'd 566.2, found 566.21 | 0.92 (Method Q) |

-continued

| Example | Structure | Name | Exact Mass [M + H]+ | Retention time (min) |
|---|---|---|---|---|
| 343 | 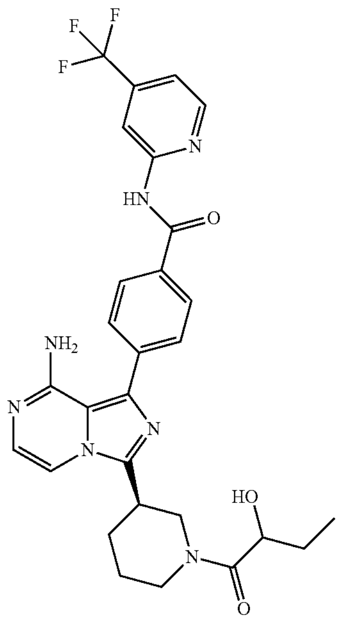 [SMILES: CCC(O)C(=O)N1CCC[C@@H](c2nc(-c3ccc(C(=O)Nc4cc(C(F)(F)F)ccn4)cc3)c3c(N)nccn23)C1] | 4-{8-amino-3-[(3R)-1-(2-hydroxybutanoyl)piperidin-3-yl]imidazo[1,5-a]pyrazin-1-yl}-N-[4-(trifluoromethyl)pyridin-2-yl]benzamide | Calc'd 568.2, found 568.22 | 0.96 (Method Q) |
| 344 | 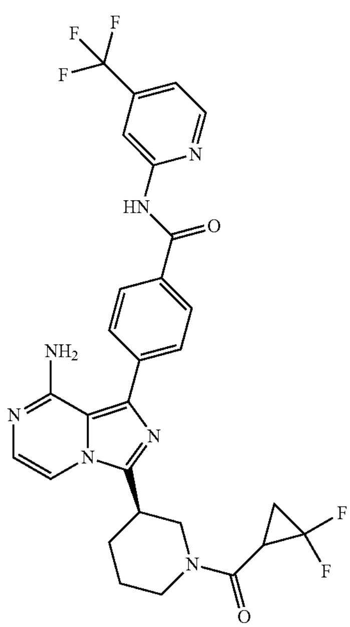 [SMILES: Nc1nccn2c([C@@H]3CCCN(C(=O)C4CC4(F)F)C3)nc(-c3ccc(C(=O)Nc4cc(C(F)(F)F)ccn4)cc3)c12] | 4-(8-amino-3-{(3R)-1-[(2,2-difluorocyclopropyl)carbonyl]piperidin-3-yl}imidazo[1,5-a]pyrazin-1-yl)-N-[4-(trifluoromethyl)pyridin-2-yl]benzamide | Calc'd 586.2, found 586.19 | 1.00 (Method Q) |

-continued

| Example | Structure | Name | Exact Mass [M + H]⁺ | Retention time (min) |
|---|---|---|---|---|
| 345 | 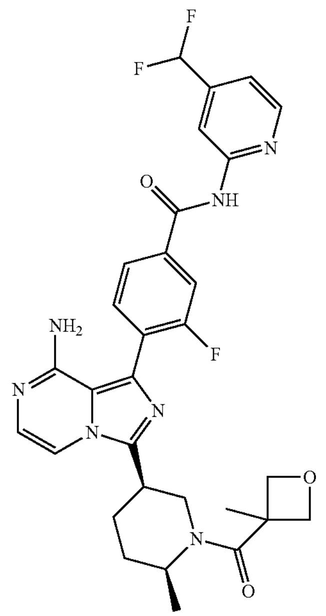 [SMILES: C[C@H]1CC[C@@H](c2nc(-c3ccc(C(=O)Nc4cc(C(F)F)ccn4)cc3F)c3c(N)nccn23)CN1C(=O)C1(C)COC1] | 4-(8-amino-3-{(3R)-1-[(2S)-2-hydroxypropanoyl]piperidin-3-yl}imidazo[1,5-a]pyrazin-1-yl)-N-[4-(trifluoromethyl)pyridin-2-yl]benzamide | Calc'd 554.2, found 554.21 | 0.85 (Method Q) |
| 346 | 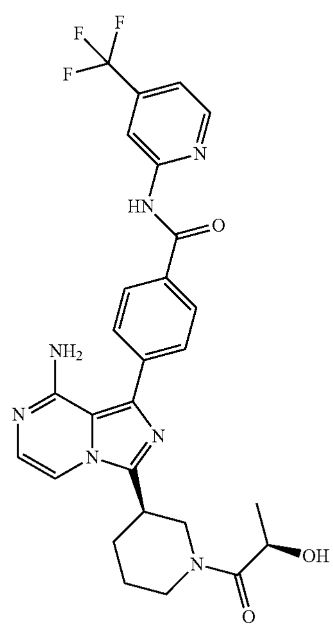 [SMILES: C[C@@H](O)C(=O)N1CCC[C@@H](c2nc(-c3ccc(C(=O)Nc4cc(C(F)(F)F)ccn4)cc3)c3c(N)nccn23)C1] | 4-(8-amino-3-{(3R)-1-[(2R)-2-hydroxypropanoyl]piperidin-3-yl}imidazo[1,5-a]pyrazin-1-yl)-N-[4-(trifluoromethyl)pyridin-2-yl]benzamide | Calc'd 554.2, found 554.21 | 0.85 (Method Q) |

| Example | Structure | Name | Exact Mass [M + H]+ | Retention time (min) |
|---|---|---|---|---|
| 347 | 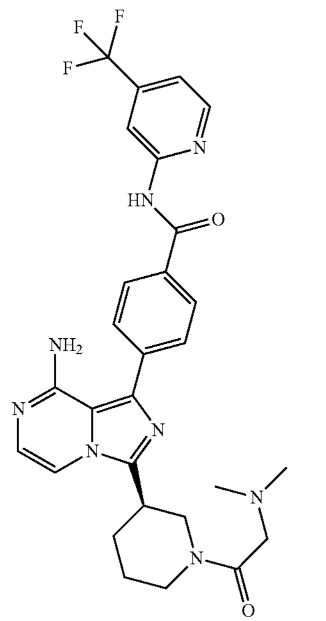 [SMILES: CN(C)CC(=O)N1CCC[C@@H](c2nc(-c3ccc(C(=O)Nc4cc(C(F)(F)F)ccn4)cc3)c3c(N)nccn23)C1] | 4-{8-amino-3-[(3R)-1-(N,N-dimethylglycyl)piperidin-3-yl]imidazo[1,5-a]pyrazin-1-yl}-N-[4-(trifluoromethyl)pyridin-2-yl]benzamide | Calc'd 567.2, found 567.24 | 0.92 (Method Q) |
| 348 | 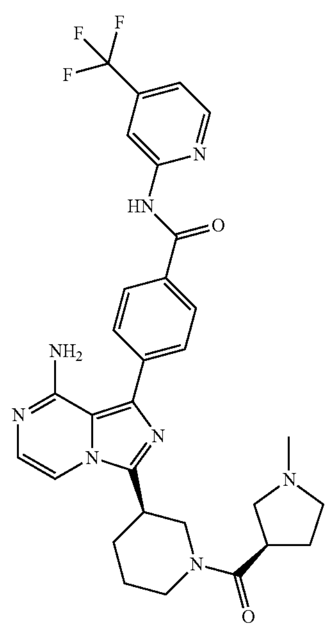 [SMILES: CN1CC[C@@H](C(=O)N2CCC[C@@H](c3nc(-c4ccc(C(=O)Nc5cc(C(F)(F)F)ccn5)cc4)c4c(N)nccn34)C2)C1] | 4-(8-amino-3-[(3R)-1-{[(3R)-1-methylpyrrolidin-3-yl]carbonyl}piperidin-3-yl]imidazo[1,5-a]pyrazin-1-yl}-N-[4-(trifluoromethyl)pyridin-2-yl]benzamide | Calc'd 593.3, found 593.25 | 0.93 (Method Q) |

-continued

| Example | Structure | Name | Exact Mass [M + H]+ | Retention time (min) |
|---|---|---|---|---|
| 349 | 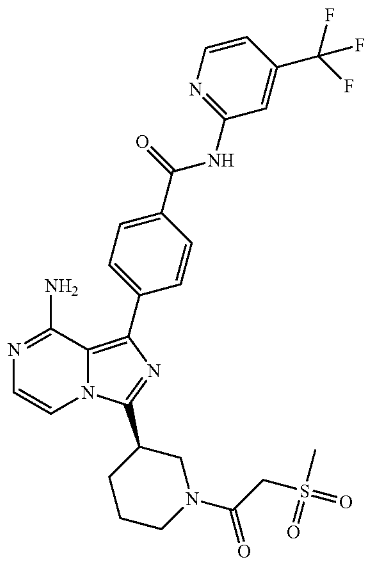 [SMILES: CS(=O)(=O)CC(=O)N1CCC[C@@H](c2nc(-c3ccc(C(=O)Nc4cc(C(F)(F)F)ccn4)cc3)c3c(N)nccn23)C1] | 4-(8-amino-3-{(3R)-1-[(methylsulfonyl)acetyl]piperidin-3-yl}imidazo[1,5-a]pyrazin-1-yl)-N-[4-(trifluoromethyl)pyridin-2-yl]benzamide, TFA salt | Calc'd 602.2, found 602.1 | 1.10 (Method P) |
| 350 | 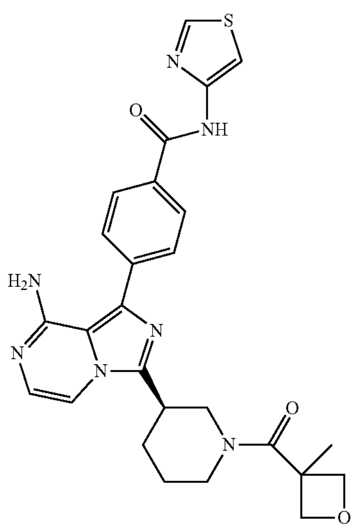 [SMILES: CC1(C(=O)N2CCC[C@@H](c3nc(-c4ccc(C(=O)Nc5cscn5)cc4)c4c(N)nccn34)C2)COC1] | 4-(8-amino-3-{(3R)-1-[(3-methyloxetan-3-yl)carbonyl]piperidin-3-yl}imidazo[1,5-a]pyrazin-1-yl)-N-1,3-thiazol-4-ylbenzamide | Calc'd 518.2, found 519.2 | 0.69 min (Method Q) |
| 351 | 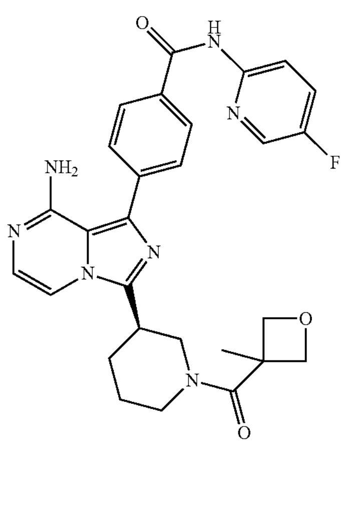 [SMILES: CC1(C(=O)N2CCC[C@@H](c3nc(-c4ccc(C(=O)Nc5ccc(F)cn5)cc4)c4c(N)nccn34)C2)COC1] | 4-(8-amino-3-{(3R)-1-[(3-methyloxetan-3-yl)carbonyl]piperidin-3-yl}imidazo[1,5-a]pyrazin-1-yl)-N-(5-fluoropyridin-2-yl)benzamide | Calc'd 530.2, found 530.2 | 0.75 min (Method Q) |

-continued

| Example | Structure | Name | Exact Mass [M + H]+ | Retention time (min) |
|---|---|---|---|---|
| 352 | 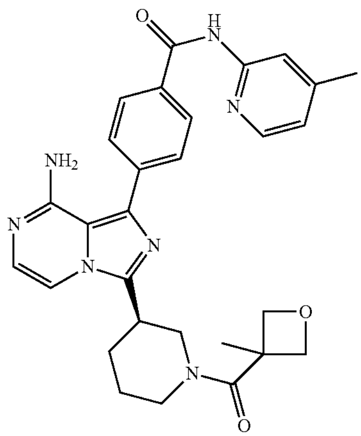 [SMILES: Cc1ccnc(NC(=O)c2ccc(-c3nc([C@@H]4CCCN(C(=O)C5(C)COC5)C4)n4ccnc(N)c34)cc2)c1] | 4-(8-amino-3-{(3R)-1-[(3-methyloxetan-3-yl)carbonyl]piperidin-3-yl}imidazo[1,5-a]pyrazin-1-yl)-N-(4-methylpyridin-2-yl)benzamide | Calc'd 526.3, found 526.3 | 0.76 min (Method Q) |
| 353 | 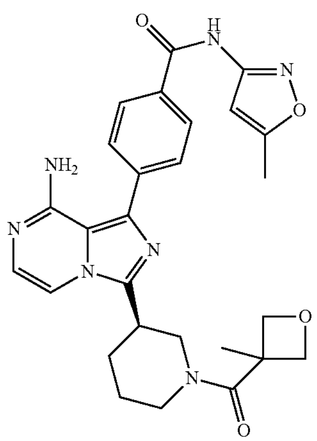 [SMILES: Cc1cc(NC(=O)c2ccc(-c3nc([C@@H]4CCCN(C(=O)C5(C)COC5)C4)n4ccnc(N)c34)cc2)no1] | 4-(8-amino-3-{(3R)-1-[(3-methyloxetan-3-yl)carbonyl]piperidin-3-yl}imidazo[1,5-a]pyrazin-1-yl)-N-(5-methylisoxazol-3-yl)benzamide | Calc'd 516.2, found 516.2 | 0.69 min (Method Q) |
| 354 | 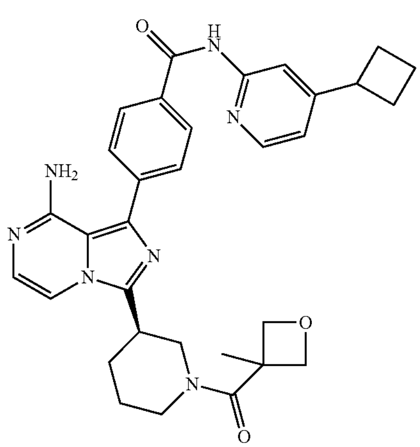 [SMILES: CC1(C(=O)N2CCC[C@@H](c3nc(-c4ccc(C(=O)Nc5cc(C6CCC6)ccn5)cc4)c4c(N)nccn34)C2)COC1] | 4-(8-amino-3-{(3R)-1-[(3-methyloxetan-3-yl)carbonyl]piperidin-3-yl}imidazo[1,5-a]pyrazin-1-yl)-N-(4-cyclobutylpyridin-2-yl)benzamide | Calc'd 566.3, found 566.3 | 0.92 min (Method Q) |

-continued

| Example | Structure | Name | Exact Mass [M + H]+ | Retention time (min) |
|---|---|---|---|---|
| 355 | 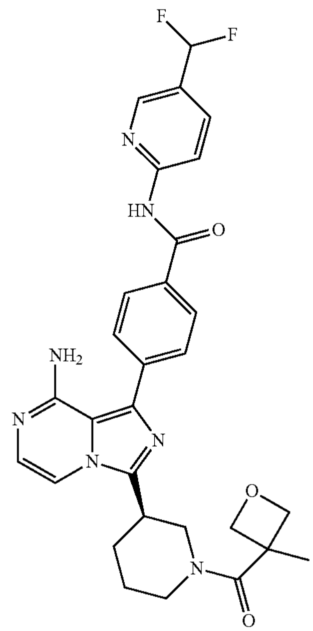 [SMILES: CC1(C(=O)N2CCC[C@@H](c3nc(-c4ccc(C(=O)Nc5ccc(C(F)F)cn5)cc4)c4c(N)nccn34)C2)COC1] | 4-(8-amino-3-{(3R)-1-[(3-methyloxetan-3-yl)carbonyl]piperidin-3-yl}imidazo[1,5-a]pyrazin-1-yl)-N-[5-(difluoromethyl)pyridin-2-yl]benzamide, TFA salt | Calc'd 562.2, found 562.22 | 0.68 (Method Q) |
| 356 | 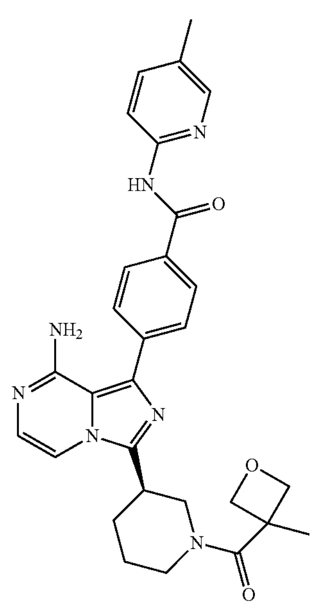 [SMILES: Cc1ccc(NC(=O)c2ccc(-c3nc([C@@H]4CCCN(C(=O)C5(C)COC5)C4)n4ccnc(N)c34)cc2)nc1] | 4-(8-amino-3-{(3R)-1-[(3-methyloxetan-3-yl)carbonyl]piperidin-3-yl}imidazo[1,5-a]pyrazin-1-yl)-N-(5-methylpyridin-2-yl)benzamide, TFA salt | Calc'd 526.3, found 526.1 | 0.49 (Method Q) |

| Example | Structure | Name | Exact Mass [M + H]+ | Retention time (min) |
|---------|-----------|------|---------------------|----------------------|
| 357 | 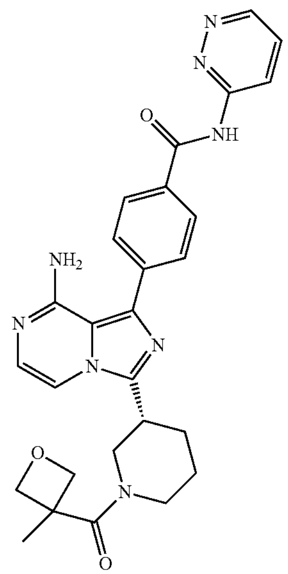 [SMILES: CC1(C(=O)N2CCC[C@@H](c3nc(-c4ccc(C(=O)Nc5cccnn5)cc4)c4c(N)nccn34)C2)COC1] | 4-(8-amino-3-{(3R)-1-[(3-methyloxetan-3-yl)carbonyl]piperidin-3-yl}imidazo[1,5-a]pyrazin-1-yl)-N-pyridazin-3-ylbenzamide | Calc'd 513.2, found 513.23 | 0.62 (Method Q) |
| 358 | 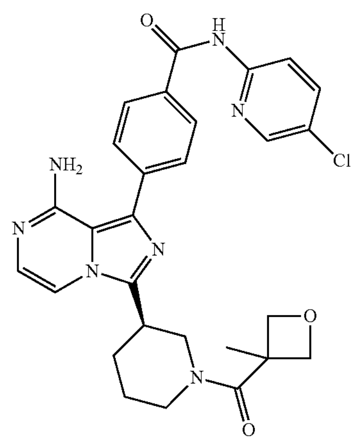 [SMILES: CC1(C(=O)N2CCC[C@@H](c3nc(-c4ccc(C(=O)Nc5ccc(Cl)cn5)cc4)c4c(N)nccn34)C2)COC1] | 4-(8-amino-3-{(3R)-1-[(3-methyloxetan-3-yl)carbonyl]piperidin-3-yl}imidazo[1,5-a]pyrazin-1-yl)-N-(5-chloropyridin-2-yl)benzamide | Calc'd 546.2, found 546.2 | 0.79 min (Method Q) |
| 359 | 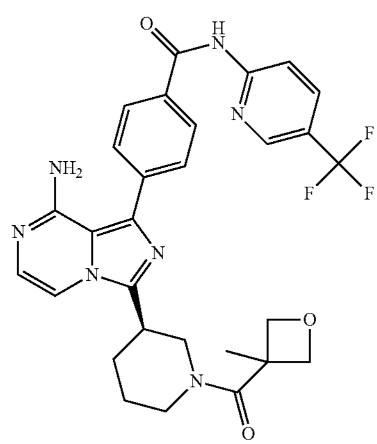 [SMILES: CC1(C(=O)N2CCC[C@@H](c3nc(-c4ccc(C(=O)Nc5ccc(C(F)(F)F)cn5)cc4)c4c(N)nccn34)C2)COC1] | 4-(8-amino-3-{(3R)-1-[(3-methyloxetan-3-yl)carbonyl]piperidin-3-yl}imidazo[1,5-a]pyrazin-1-yl)-N-[5-(trifluoromethyl)pyridin-2-yl]benzamide | Calc'd 580.2, found 580.2 | 0.85 min (Method Q) |

-continued

| Example | Structure | Name | Exact Mass [M + H]+ | Retention time (min) |
|---|---|---|---|---|
| 360 | 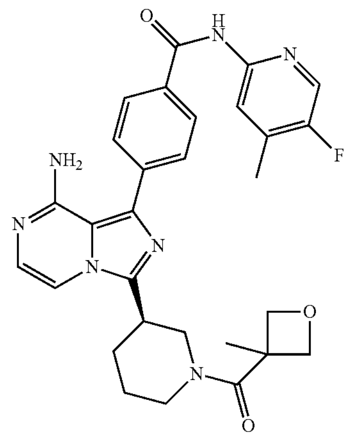 [SMILES: Cc1cc(NC(=O)c2ccc(-c3nc([C@@H]4CCCN(C(=O)C5(C)COC5)C4)n4ccnc(N)c34)cc2)ncc1F] | 4-(8-amino-3-{(3R)-1-[(3-methyloxetan-3-yl)carbonyl]piperidin-3-yl}imidazo[1,5-a]pyrazin-1-yl)-N-(5-fluoro-4-methylpyridin-2-yl)benzamide | Calc'd 544.2, found 544.2 | 0.77 min (Method Q) |
| 361 | 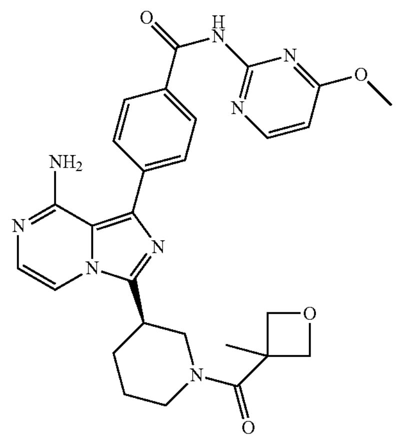 [SMILES: COc1ccnc(NC(=O)c2ccc(-c3nc([C@@H]4CCCN(C(=O)C5(C)COC5)C4)n4ccnc(N)c34)cc2)n1] | 4-(8-amino-3-{(3R)-1-[(3-methyloxetan-3-yl)carbonyl]piperidin-3-yl}imidazo[1,5-a]pyrazin-1-yl)-N-(4-methoxypyrimidin-2-yl)benzamide | Calc'd 543.2, found 543.2 | 0.61 min (Method Q) |
| 362 | 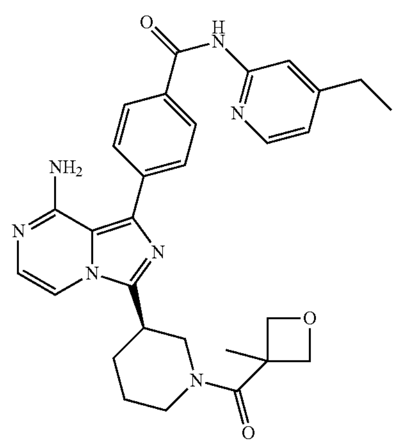 [SMILES: CCc1ccnc(NC(=O)c2ccc(-c3nc([C@@H]4CCCN(C(=O)C5(C)COC5)C4)n4ccnc(N)c34)cc2)c1] | 4-(8-amino-3-{(3R)-1-[(3-methyloxetan-3-yl)carbonyl]piperidin-3-yl}imidazo[1,5-a]pyrazin-1-yl)-N-(4-ethylpyridin-2-yl)benzamide | Calc'd 540.3, found 540.3 | 0.79 min (Method Q) |

-continued

| Example | Structure | Name | Exact Mass [M + H]⁺ | Retention time (min) |
|---|---|---|---|---|
| 363 | 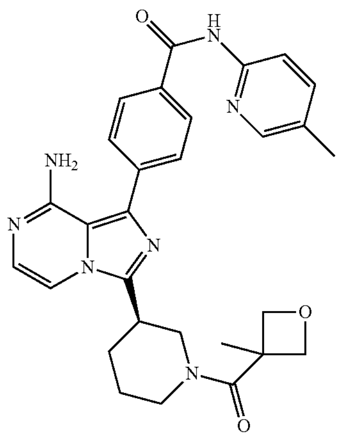 [SMILES: Cc1ccc(NC(=O)c2ccc(-c3nc([C@@H]4CCCN(C(=O)C5(C)COC5)C4)n4ccnc(N)c34)cc2)nc1] | 4-(8-amino-3-{(3R)-1-[(3-methyloxetan-3-yl)carbonyl]piperidin-3-yl}imidazo[1,5-a]pyrazin-1-yl)-N-(5-methylpyridin-2-yl)benzamide | Calc'd 526.3, found 526.3 | 0.73 min (Method Q) |
| 364 | 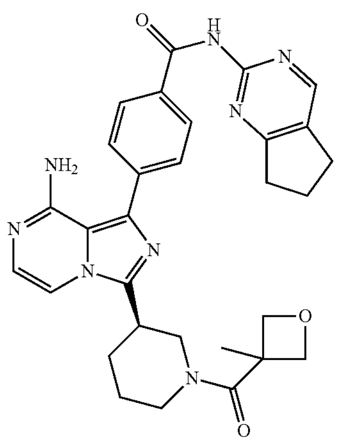 [SMILES: CC1(C(=O)N2CCC[C@@H](c3nc(-c4ccc(C(=O)Nc5ncc6c(n5)CCC6)cc4)c4c(N)nccn34)C2)COC1] | 4-(8-amino-3-{(3R)-1-[(3-methyloxetan-3-yl)carbonyl]piperidin-3-yl}imidazo[1,5-a]pyrazin-1-yl)-N-(6,7-dihydro-5H-cyclopenta[d]pyrimidin-2-yl)benzamide | Calc'd 553.3, found 553.3 | 0.62 min (Method Q) |
| 365 | 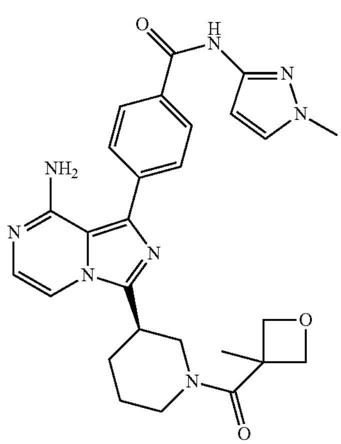 [SMILES: Cn1ccc(NC(=O)c2ccc(-c3nc([C@@H]4CCCN(C(=O)C5(C)COC5)C4)n4ccnc(N)c34)cc2)n1] | 4-(8-amino-3-{(3R)-1-[(3-methyloxetan-3-yl)carbonyl]piperidin-3-yl}imidazo[1,5-a]pyrazin-1-yl)-N-(1-methyl-1H-pyrazol-3-yl)benzamide | Calc'd 515.3, found 515.24 | 0.59 min (Method Q) |

| Example | Structure | Name | Exact Mass [M + H]⁺ | Retention time (min) |
|---|---|---|---|---|
| 366 | 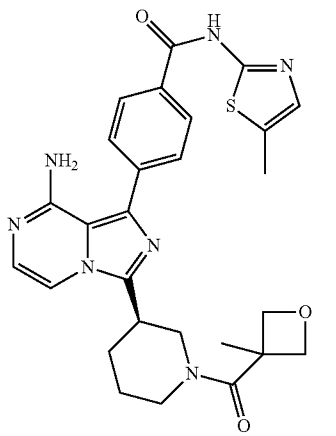 [SMILES: Cc1cnc(NC(=O)c2ccc(-c3nc([C@@H]4CCCN(C(=O)C5(C)COC5)C4)n4ccnc(N)c34)cc2)s1] | 4-(8-amino-3-{(3R)-1-[(3-methyloxetan-3-yl)carbonyl]piperidin-3-yl}imidazo[1,5-a]pyrazin-1-yl)-N-(5-methyl-1,3-thiazol-2-yl)benzamide | Calc'd 532.2, found 532.2 | 0.69 min (Method Q) |
| 367 | 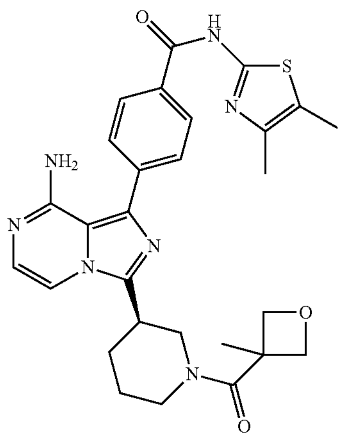 [SMILES: Cc1nc(NC(=O)c2ccc(-c3nc([C@@H]4CCCN(C(=O)C5(C)COC5)C4)n4ccnc(N)c34)cc2)sc1C] | 4-(8-amino-3-{(3R)-1-[(3-methyloxetan-3-yl)carbonyl]piperidin-3-yl}imidazo[1,5-a]pyrazin-1-yl)-N-(4,5-dimethyl-1,3-thiazol-2-yl)benzamide | Calc'd 546.2, found 546.2 | 0.75 min (Method Q) |
| 368 | 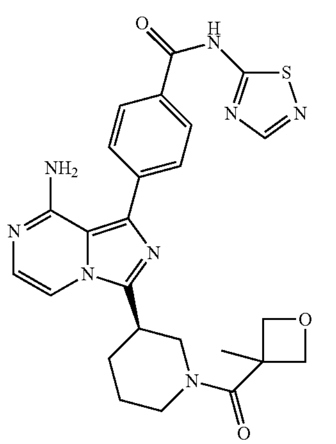 [SMILES: CC1(C(=O)N2CCC[C@@H](c3nc(-c4ccc(C(=O)Nc5ncns5)cc4)c4c(N)nccn34)C2)COC1] | 4-(8-amino-3-{(3R)-1-[(3-methyloxetan-3-yl)carbonyl]piperidin-3-yl}imidazo[1,5-a]pyrazin-1-yl)-N-1,2,4-thiadiazol-5-ylbenzamide | Calc'd 519.2, found 519.2 | 0.44 min (Method Q) |

| Example | Structure | Name | Exact Mass [M + H]+ | Retention time (min) |
|---|---|---|---|---|
| 369 | 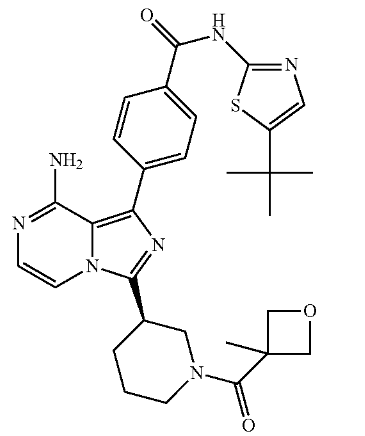 [SMILES: CC1(C(=O)N2CCC[C@@H](c3nc(-c4ccc(C(=O)Nc5ncc(C(C)(C)C)s5)cc4)c4c(N)nccn34)C2)COC1] | 4-(8-amino-3-{(3R)-1-[(3-methyloxetan-3-yl)carbonyl]piperidin-3-yl}imidazo[1,5-a]pyrazin-1-yl)-N-(5-tert-butyl-1,3-thiazol-2-yl)benzamide | Calc'd 574.3, found 574.3 | 0.87 min (Method Q) |
| 370 | 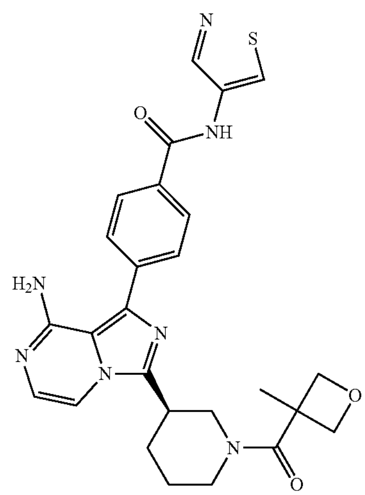 [SMILES: CC1(C(=O)N2CCC[C@@H](c3nc(-c4ccc(C(=O)N/C(C=N)=C/S)cc4)c4c(N)nccn34)C2)COC1] | 4-(8-amino-3-{(3R)-1-[(3-methyloxetan-3-yl)carbonyl]piperidin-3-yl}imidazo[1,5-a]pyrazin-1-yl)-N-isothiazol-4-ylbenzamide, TFA salt | Calc'd 518.2, found 518.3 | 2.22 (Method H) |
| 371 | 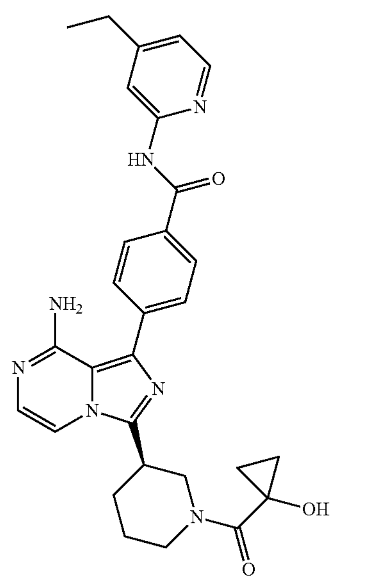 [SMILES: CCc1ccnc(NC(=O)c2ccc(-c3nc([C@@H]4CCCN(C(=O)C5(O)CC5)C4)n4ccnc(N)c34)cc2)c1] | 4-(8-amino-3-{(3R)-1-[(1-hydroxycyclopropyl)carbonyl]piperidin-3-yl}imidazo[1,5-a]pyrazin-1-yl)-N-(4-ethylpyridin-2-yl)benzamide | Calc'd 526.3, found 526.25 | 0.81 (Method Q) |

| Example | Structure | Name | Exact Mass [M + H]$^+$ | Retention time (min) |
|---|---|---|---|---|
| 372 | 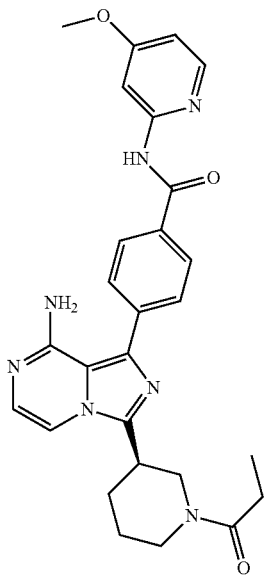 [SMILES: CCC(=O)N1CCC[C@@H](c2nc(-c3ccc(C(=O)Nc4cc(OC)ccn4)cc3)c3c(N)nccn23)C1] | 4-{8-amino-3-[(3R)-1-propanoylpiperidin-3-yl]imidazo[1,5-a]pyrazin-1-yl}-N-(4-methoxypyridin-2-yl)benzamide | Calc'd 500.2, found 500.23 | 0.77 (Method Q) |

Example 373

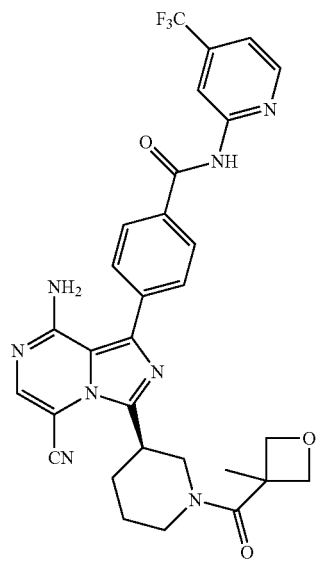 [SMILES: CC1(C(=O)N2CCC[C@@H](c3nc(-c4ccc(C(=O)Nc5cc(C(F)(F)F)ccn5)cc4)c4c(N)ncc(C#N)n34)C2)COC1]

(R)-4-(8-amino-5-cyano-3-(1-(3-methyloxetane-3-carbonyl)piperidin-3-yl)imidazo[1,5-a]pyrazin-1-yl)-N-(4-(trifluoromethyl)pyridin-2-yl)benzamide NaCN (63.9 mg, 1.303 mmol) and tetrabutylammonium bromide (420 mg, 1.303 mmol) were added to a stirred mixture of (R)-4-(8-amino-5-chloro-3-(1-(3-methyloxetane-3-carbonyl)piperidin-3-yl)imidazo[1,5-a]pyrazin-1-yl)-N-(4-(trifluoromethyl)pyridin-2-yl)benzamide (Example 301, 80 mg, 0.130 mmol) in toluene (4 mL) and water (1 mL) and the mixture was stirred at 120° C. for 3 h under microwave condition. The organic layer was separated and concentrated in vacuo. The residue was purified by column chromatography on silica gel (gold 80 g), eluting with DCM/MeOH (20/1) to give (R)-4-(8-amino-5-cyano-3-(1-(3-methyloxetane-3-carbonyl)piperidin-3-yl)imidazo[1,5-a]pyrazin-1-yl)-N-(4-(trifluoromethyl)pyridin-2-yl)benzamide (18 mg, 0.030 mmol, 22.85% yield). LCMS Data: R$_t$ 0.18 and 1.16 min; m/z 605.07 (M+H)$^+$. NMR (CDCl$_3$, 500 Hz): 8.71 (s, 1), 8.49 (d, 1, J=5.5 Hz), 8.12 (d, 2, J=8.5 Hz), 7.79 (d, 2, J=8.5 Hz), 7.32 (d, 1, J=5.5 Hz), 4.99-5.01 (m, 2), 4.66 (d, 1, J J=12), 4.38 (t, 2, J=5.5 Hz), 3.05-3.20 (m, 4), 1.99-2.21 (m, 4), 1.70 (s, 3).

The following compounds in the table were prepared using the intermediate 23.

| Example Number | Structure | Name | Exact Mass [M + H]+ | Retention time (min) |
|---|---|---|---|---|
| 374 | 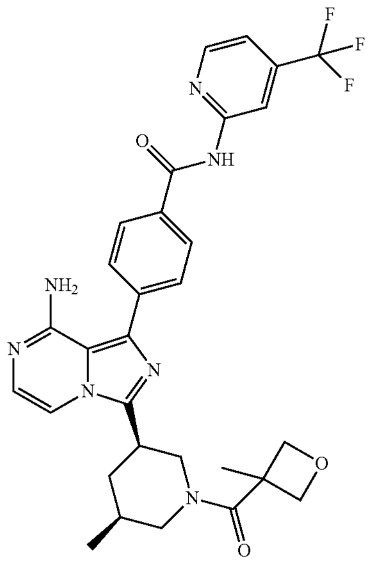 [SMILES: C[C@H]1C[C@@H](c2nc(-c3ccc(C(=O)Nc4cc(C(F)(F)F)ccn4)cc3)c3c(N)nccn23)CN(C(=O)C2(C)COC2)C1] | 4-(8-amino-3-{(3R,5S)-5-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide | Calc'd 594.2, found 594.2 | 1.973 (Method M) |
| 375 | 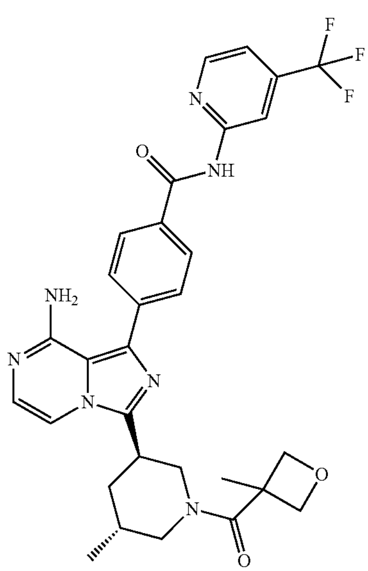 [SMILES: C[C@@H]1C[C@@H](c2nc(-c3ccc(C(=O)Nc4cc(C(F)(F)F)ccn4)cc3)c3c(N)nccn23)CN(C(=O)C2(C)COC2)C1] | 4-(8-amino-3-{(3R,5R)-5-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide | Calc'd 594.2, found 594.1 | 2.111 (Method Q) |

| Example Number | Structure | Name | Exact Mass [M + H]⁺ | Retention time (min) |
|---|---|---|---|---|
| 376 | 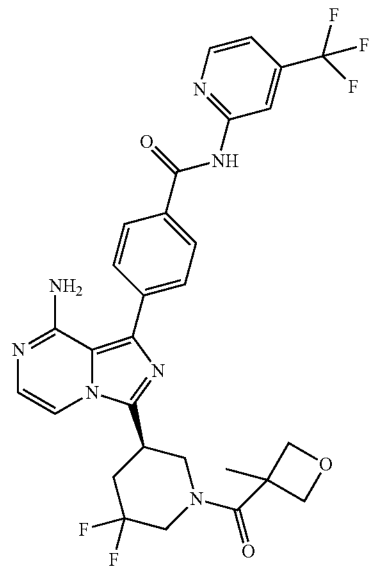 [SMILES: CC1(C(=O)N2C[C@H](c3nc(-c4ccc(C(=O)Nc5cc(C(F)(F)F)ccn5)cc4)c4c(N)nccn34)CC(F)(F)C2)COC1] | 4-(8-amino-3-{5,5-difluoro-1-[(3-methyloxetan-3-yl)carbonyl]piperidin-3-yl}imidazo[1,5-a]pyrazin-1-yl)-N-[4-(trifluoromethyl)pyridin-2-yl]benzamide | Calc'd 616.2, found 615.8 | 0.906 (Method N) |
| 377 | 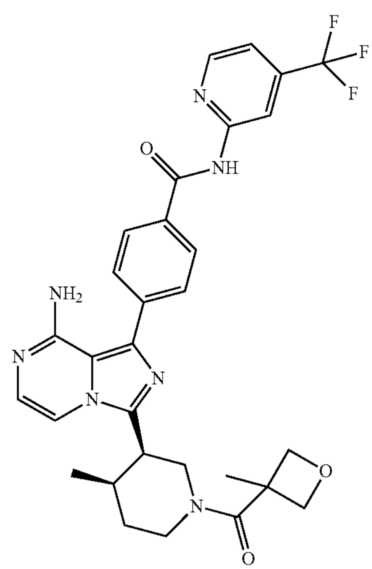 [SMILES: C[C@@H]1CCN(C(=O)C2(C)COC2)C[C@@H]1c1nc(-c2ccc(C(=O)Nc3cc(C(F)(F)F)ccn3)cc2)c2c(N)nccn12] | 4-(8-amino-3-{(3R,4R)-4-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide | Calc'd 594.2, found 594.2 | 0.907 (Method N) |

| Example Number | Structure | Name | Exact Mass [M + H]⁺ | Retention time (min) |
|---|---|---|---|---|
| 378 | 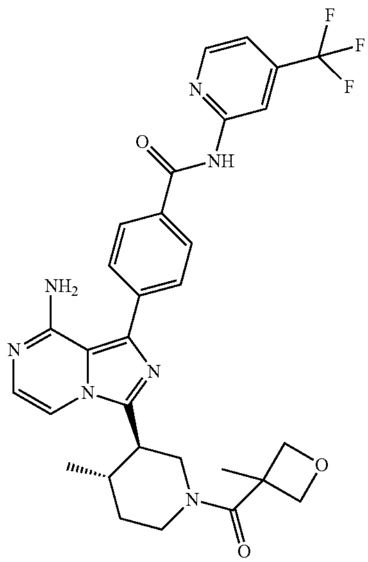 [SMILES: C[C@H]1CCN(C(=O)C2(C)COC2)C[C@@H]1c1nc(-c2ccc(C(=O)Nc3cc(C(F)(F)F)ccn3)cc2)c2c(N)nccn12] | 4-(8-amino-3-{(3R,4S)-4-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide | Calc'd 594.2, found 594.2 | 0.892 (Method N) |
| 379 | 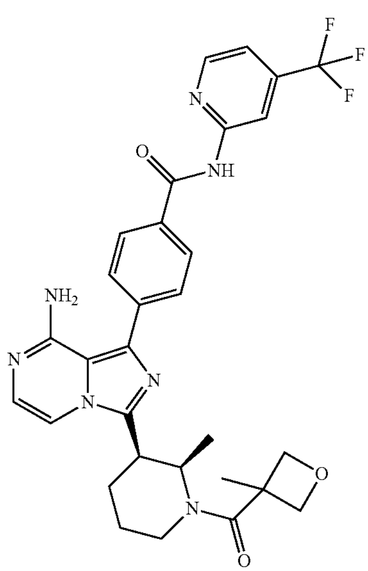 [SMILES: C[C@@H]1[C@H](c2nc(-c3ccc(C(=O)Nc4cc(C(F)(F)F)ccn4)cc3)c3c(N)nccn23)CCCN1C(=O)C1(C)COC1] | 4-(8-amino-3-{(2R,3R)-2-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide | Calc'd 594.2, found 593.8 | 0.896 (Method N) |

-continued

| Example Number | Structure | Name | Exact Mass [M + H]+ | Retention time (min) |
|---|---|---|---|---|
| 380 | 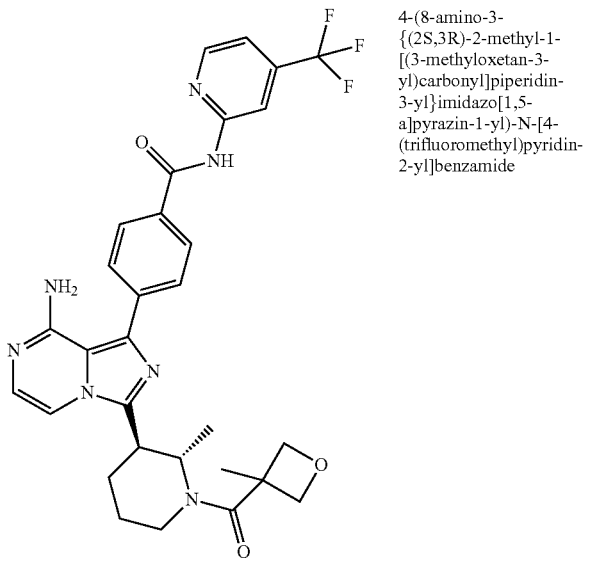 | 4-(8-amino-3-{(2S,3R)-2-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide | Calc'd 594.2, found 594.2 | 2.085 (Method M) |

The compounds in the following tables were prepared using the intermediates and procedures described above.

| Example | Structure | Name | Exact Mass [M + H]+ | Retention time (min) |
|---|---|---|---|---|
| 381 | 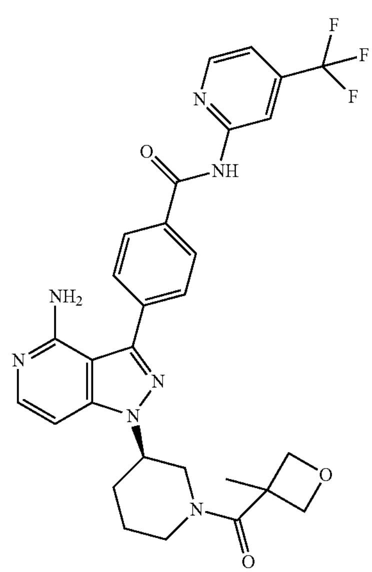 [SMILES: CC1(C(=O)N2CCC[C@@H](n3nc(-c4ccc(C(=O)Nc5cc(C(F)(F)F)ccn5)cc4)c4c(N)nccc43)C2)COC1] | 4-(4-amino-1-{(3R)-1-[(3-methyloxetan-3-yl)carbonyl]piperidin-3-yl}-1H-pyrazolo[4,3-c]pyridin-3-yl)-N-[4-(trifluoromethyl)pyridin-2-yl]benzamide | Calc'd 580.2, found 580.0 | 1.89 (Method M) |

-continued

| Example | Structure | Name | Exact Mass [M + H]+ | Retention time (min) |
|---|---|---|---|---|
| 382 | 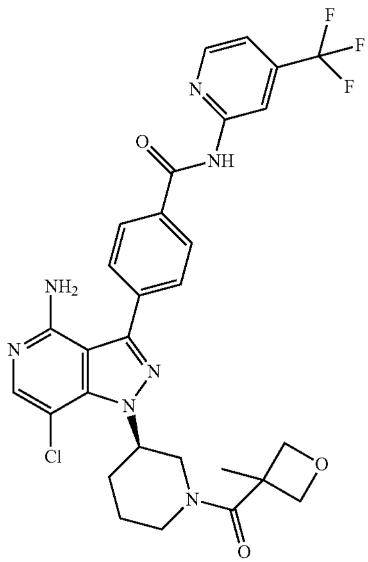 [SMILES: CC1(C(=O)N2CCC[C@@H](n3nc(-c4ccc(C(=O)Nc5cc(C(F)(F)F)ccn5)cc4)c4c(N)ncc(Cl)c43)C2)COC1] | 4-(4-amino-7-chloro-1-{(3R)-1-[(3-methyloxetan-3-yl)carbonyl]piperidin-3-yl}-1H-pyrazolo[4,3-c]pyridin-3-yl)-N-[4-(trifluoromethyl)pyridin-2-yl]benzamide | Calc'd 614.2, found 614.3 | 1.12 (Method P) |
| 383 | 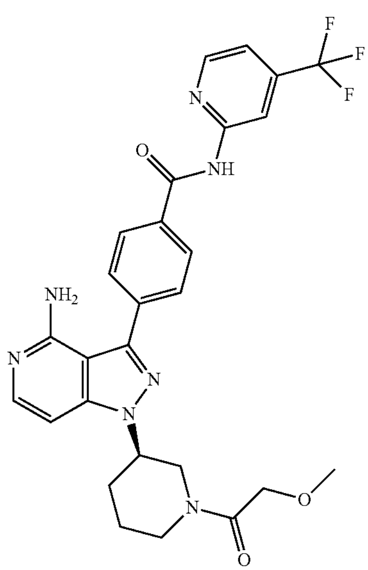 [SMILES: COCC(=O)N1CCC[C@@H](n2nc(-c3ccc(C(=O)Nc4cc(C(F)(F)F)ccn4)cc3)c3c(N)nccc32)C1] | 4-{4-amino-1-[(3R)-1-(methoxyacetyl)piperidin-3-yl]-1H-pyrazolo[4,3-c]pyridin-3-yl}-N-[4-(trifluoromethyl)pyridin-2-yl]benzamide, TFA salt | Calc'd 554.2, found 554.0 | 1.82 (Method O) |

| Example | Structure | Name | Exact Mass [M + H]+ | Retention time (min) |
|---|---|---|---|---|
| 384 | 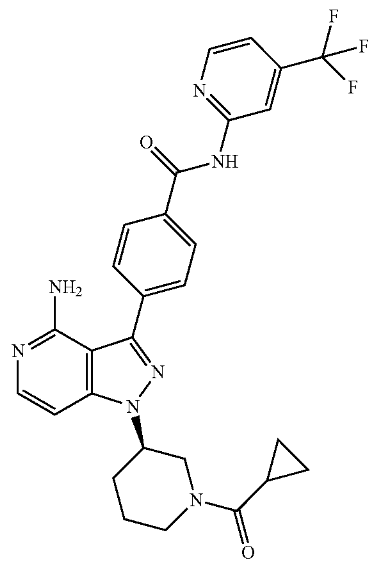 [SMILES: Nc1nccc2c1c(-c1ccc(C(=O)Nc3cc(C(F)(F)F)ccn3)cc1)nn2[C@@H]1CCCN(C(=O)C2CC2)C1] | 4-{4-amino-1-[(3R)-1-(cyclopropylcarbonyl)piperidin-3-yl]-1H-pyrazolo[4,3-c]pyridin-3-yl}-N-[4-(trifluoromethyl)pyridin-2-yl]benzamide, TFA salt | Calc'd 550.2, found 550.0 | 2.14 (Method O) |
| 385 | 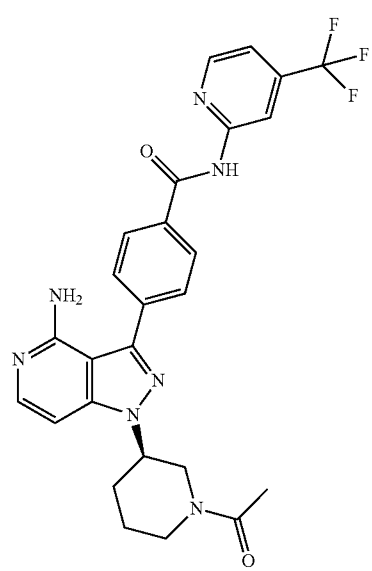 [SMILES: CC(=O)N1CCC[C@@H](n2nc(-c3ccc(C(=O)Nc4cc(C(F)(F)F)ccn4)cc3)c3c(N)nccc32)C1] | 4-{1-[(3R)-1-acetylpiperidin-3-yl]-4-amino-1H-pyrazolo[4,3-c]pyridin-3-yl}-N-[4-(trifluoromethyl)pyridin-2-yl]benzamide, TFA salt | Calc'd 524.2, found 524.0 | 1.81 (Method O) |

| Example | Structure | Name | Exact Mass [M + H]+ | Retention time (min) |
|---|---|---|---|---|
| 386 | 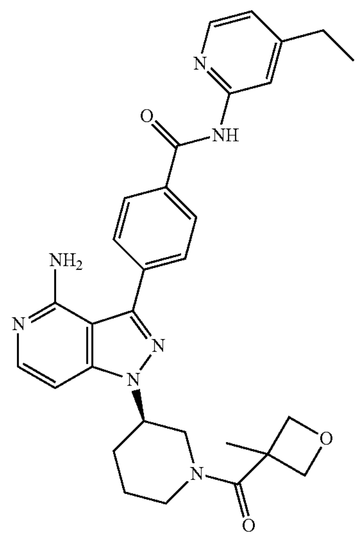 [SMILES: CCc1ccnc(NC(=O)c2ccc(-c3nn([C@@H]4CCCN(C(=O)C5(C)COC5)C4)c4ccnc(N)c34)cc2)c1] | 4-(4-amino-1-{(3R)-1-[(3-methyloxetan-3-yl)carbonyl]piperidin-3-yl}-1H-pyrazolo[4,3-c]pyridin-3-yl)-N-(4-ethylpyridin-2-yl)benzamide, TFA salt | Calc'd 540.3, found 540.3 | 1.01 (Method P) |
| 387 | 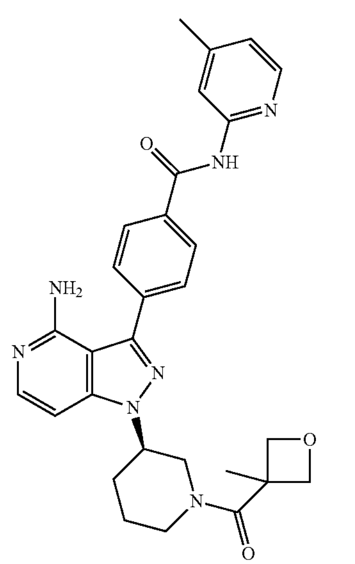 [SMILES: Cc1ccnc(NC(=O)c2ccc(-c3nn([C@@H]4CCCN(C(=O)C5(C)COC5)C4)c4ccnc(N)c34)cc2)c1] | 4-(4-amino-1-{(3R)-1-[(3-methyloxetan-3-yl)carbonyl]piperidin-3-yl}-1H-pyrazolo[4,3-c]pyridin-3-yl)-N-(4-methylpyridin-2-yl)benzamide, TFA salt | Calc'd 526.3, found 526.2 | 1.02 (Method P) |

-continued

| Example | Structure | Name | Exact Mass [M + H]+ | Retention time (min) |
|---|---|---|---|---|
| 388 | 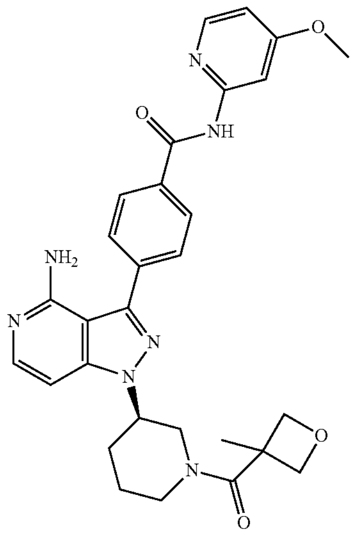 [SMILES: COc1ccnc(NC(=O)c2ccc(-c3nn([C@@H]4CCCN(C(=O)C5(C)COC5)C4)c4ccnc(N)c34)cc2)c1] | 4-(4-amino-1-{(3R)-1-[(3-methyloxetan-3-yl)carbonyl]piperidin-3-yl}-1H-pyrazolo[4,3-c]pyridin-3-yl)-N-(4-methoxypyridin-2-yl)benzamide, TFA salt | Calc'd 542.3, found 542.3 | 0.99 (Method P) |
| 389 | 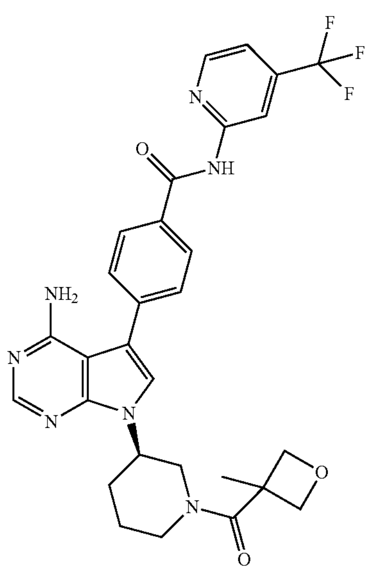 [SMILES: CC1(C(=O)N2CCC[C@@H](n3cc(-c4ccc(C(=O)Nc5cc(C(F)(F)F)ccn5)cc4)c4c(N)ncnc43)C2)COC1] | 4-(4-amino-7-{(3R)-1-[(3-methyloxetan-3-yl)carbonyl]piperidin-3-yl}-7H-pyrrolo[2,3-d]pyrimidin-5-yl)-N-[4-(trifluoromethyl)pyridin-2-yl]benzamide | Calc'd 580.2, found 580.2 | 1.949 (Method M) |

| Example | Structure | Name | Exact Mass [M + H]+ | Retention time (min) |
|---|---|---|---|---|
| 390 | 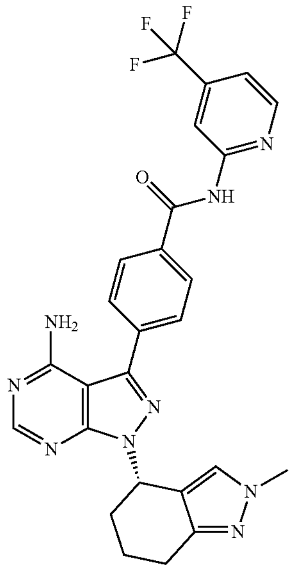 [SMILES: Cn1cc2c(n1)CCC[C@@H]2n1nc(-c2ccc(C(=O)Nc3cc(C(F)(F)F)ccn3)cc2)c2c(N)ncnc21] | 4-(4-amino-7-{(3R)-1-[(3-methyloxetan-3-yl)carbonyl]piperidin-3-yl}-7H-pyrrolo[2,3-d]pyrimidin-5-yl)-N-(4-cyanopyridin-2-yl)benzamide | Calc'd 537.2, found 537.2 | 1.746 (Method M) |
| 391 | 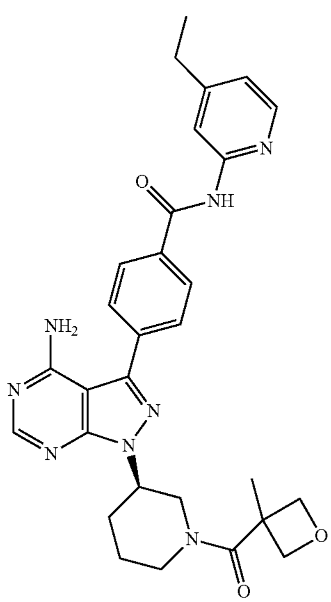 [SMILES: CCc1ccnc(NC(=O)c2ccc(-c3nn([C@@H]4CCCN(C(=O)C5(C)COC5)C4)c4ncnc(N)c34)cc2)c1] | 4-(4-amino-7-{(3R)-1-[(3-methyloxetan-3-yl)carbonyl]piperidin-3-yl}-7H-pyrrolo[2,3-d]pyrimidin-5-yl)-N-(4-ethylpyridin-2-yl)benzamide | Calc'd 540.3, found | 1.634 min (Method M) |

-continued

| Example | Structure | Name | Exact Mass [M + H]+ | Retention time (min) |
|---|---|---|---|---|
| 392 | 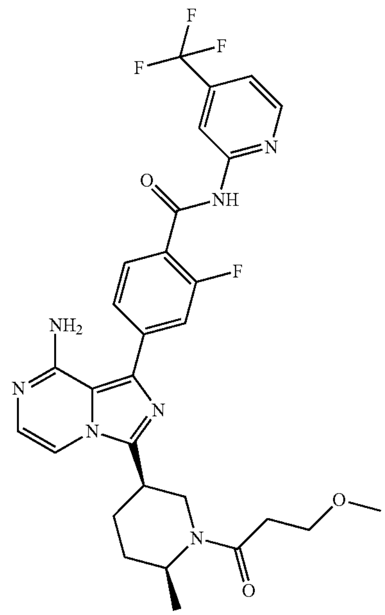 [SMILES: COCCC(=O)N1C[C@H](c2nc(-c3ccc(C(=O)Nc4cc(C(F)(F)F)ccn4)c(F)c3)c3c(N)nccn23)CC[C@@H]1C] | 4-{8-amino-3-[(3R,6S)-1-(3-methoxypropanoyl)-6-methylpiperidin-3-yl]imidazo[1,5-a]pyrazin-1-yl}-2-fluoro-N-[4-(trifluoromethyl)pyridin-2-yl]benzamide | Calc'd 600.2, found 600.2 | 2.60 (Method H) |
| 393 | 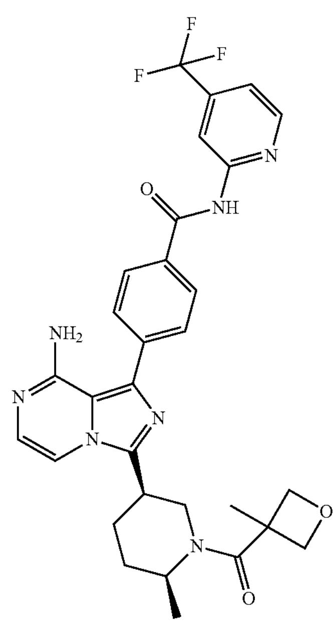 [SMILES: C[C@H]1CC[C@@H](c2nc(-c3ccc(C(=O)Nc4cc(C(F)(F)F)ccn4)cc3)c3c(N)nccn23)CN1C(=O)C1(C)COC1] | 4-(8-amino-3-{(3R,6S)-6-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide | Calc'd 594.2, found 594.2 | 2.50 (Method H) |

-continued

| Example | Structure | Name | Exact Mass [M + H]+ | Retention time (min) |
|---|---|---|---|---|
| 394 | 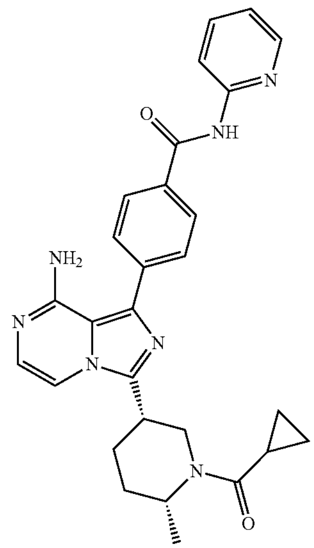 [SMILES: C[C@@H]1CC[C@H](c2nc(-c3ccc(C(=O)Nc4ccccn4)cc3)c3c(N)nccn23)CN1C(=O)C1CC1] | 4-{8-amino-3-[(3R,6S)-1-(cyclopropylcarbonyl)-6-methylpiperidin-3-yl]imidazo[1,5-a]pyrazin-1-yl}-N-pyridin-2-ylbenzamide | Calc'd 496.2, found 496.3 | 2.58 (Method H) |
| 395 | 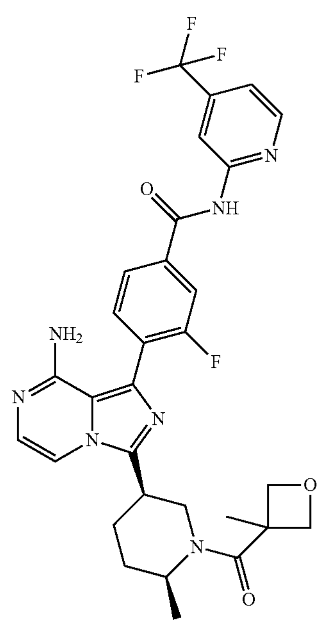 [SMILES: C[C@H]1CC[C@@H](c2nc(-c3ccc(C(=O)Nc4cc(C(F)(F)F)ccn4)cc3F)c3c(N)nccn23)CN1C(=O)C1(C)COC1] | 4-(8-amino-3-{(3R,6S)-6-methyl-1-[(3-methyloxetan-3-yl)carbonyl]piperidin-3-yl}imidazo[1,5-a]pyrazin-1-yl)-3-fluoro-N-[4-(trifluoromethyl)pyridin-2-yl]benzamide, TFA salt | Calc'd 612.2, found 612.2 | 2.28 (Method H) |

| Example | Structure | Name | Exact Mass [M + H]+ | Retention time (min) |
|---------|-----------|------|---------------------|----------------------|
| 396 | 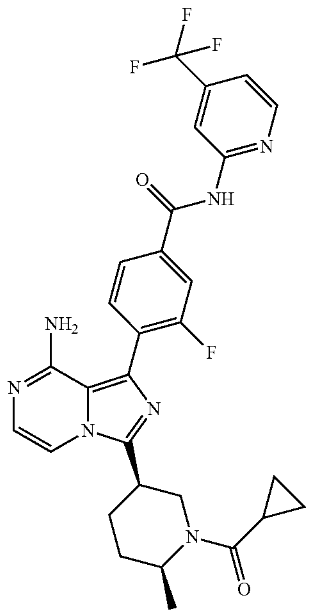 [SMILES: C[C@H]1CC[C@@H](c2nc(-c3ccc(C(=O)Nc4cc(C(F)(F)F)ccn4)cc3F)c3c(N)nccn23)CN1C(=O)C1CC1] | 4-{8-amino-3-[(3R,6S)-1-(cyclopropylcarbonyl)-6-methylpiperidin-3-yl]imidazo[1,5-a]pyrazin-1-yl}-3-fluoro-N-[4-(trifluoromethyl)pyridin-2-yl]benzamide, TFA salt | Calc'd 582.2, found 582.2 | 2.70 (Method H) |
| 397 | 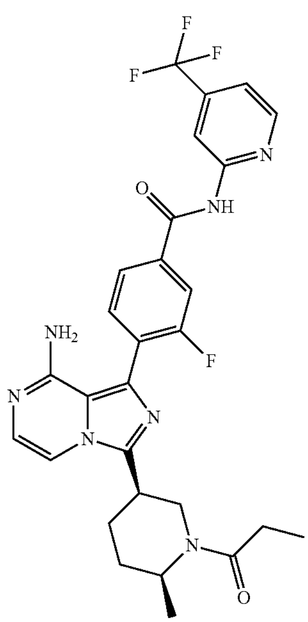 [SMILES: CCC(=O)N1C[C@H](c2nc(-c3ccc(C(=O)Nc4cc(C(F)(F)F)ccn4)cc3F)c3c(N)nccn23)CC[C@@H]1C] | 4-{8-amino-3-[(3R,6S)-6-methyl-1-propanoylpiperidin-3-yl]imidazo[1,5-a]pyrazin-1-yl}-3-fluoro-N-[4-(trifluoromethyl)pyridin-2-yl]benzamide, TFA salt | Calc'd 570.2, found 570.2 | 2.64 (Method H) |

| Example | Structure | Name | Exact Mass [M + H]+ | Retention time (min) |
|---|---|---|---|---|
| 398 | 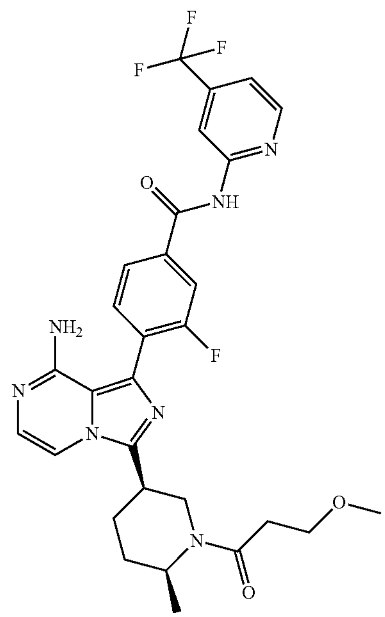 [SMILES: COCCC(=O)N1C[C@H](c2nc(-c3ccc(C(=O)Nc4cc(C(F)(F)F)ccn4)cc3F)c3c(N)nccn23)CC[C@@H]1C] | 4-{8-amino-3-[(3R,6S)-1-(3-methoxypropanoyl)-6-methylpiperidin-3-yl]imidazo[1,5-a]pyrazin-1-yl}-3-fluoro-N-[4-(trifluoromethyl)pyridin-2-yl]benzamide, TFA salt | Calc'd 600.2, found 600.2 | 2.28 (Method H) |
| 399 | 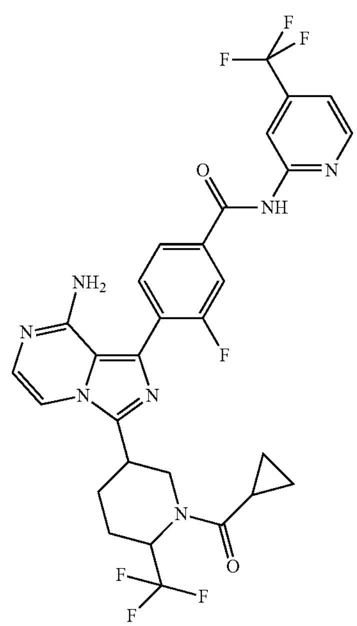 [SMILES: Nc1nccn2c(C3CCC(C(F)(F)F)N(C(=O)C4CC4)C3)nc(-c3ccc(C(=O)Nc4cc(C(F)(F)F)ccn4)cc3F)c12] | 4-{8-amino-3-[1-(cyclopropylcarbonyl)-6-(trifluoromethyl)piperidin-3-yl]imidazo[1,5-a]pyrazin-1-yl}-3-fluoro-N-[4-(trifluoromethyl)pyridin-2-yl]benzamide, TFA salt | Calc'd 636.2, found 636.2 | 3.02 (Method H) |

-continued

| Example | Structure | Name | Exact Mass [M + H]+ | Retention time (min) |
|---|---|---|---|---|
| 400 | 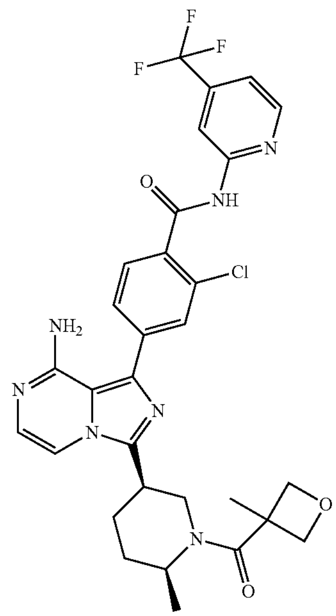 [SMILES: C[C@H]1CC[C@@H](c2nc(-c3ccc(C(=O)Nc4cc(C(F)(F)F)ccn4)c(Cl)c3)c3c(N)nccn23)CN1C(=O)C1(C)COC1] | 4-(8-amino-3-{(3R,6S)-6-methyl-1-[(3-methyloxetan-3-yl)carbonyl]piperidin-3-yl}imidazo[1,5-a]pyrazin-1-yl)-2-chloro-N-[4-(trifluoromethyl)pyridin-2-yl]benzamide, TFA salt | Calc'd 628.2, found 628.2 | 2.32 (Method H) |
| 401 | 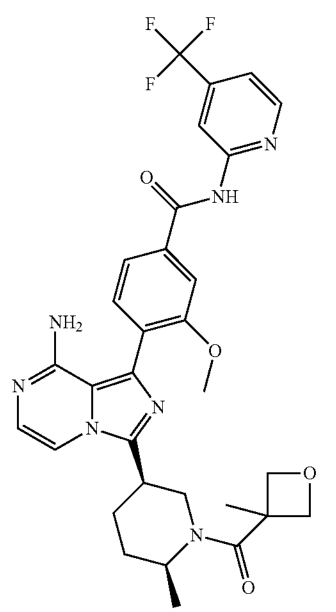 [SMILES: COc1cc(C(=O)Nc2cc(C(F)(F)F)ccn2)ccc1-c1nc([C@@H]2CC[C@H](C)N(C(=O)C3(C)COC3)C2)n2ccnc(N)c12] | 4-(8-amino-3-{(3R,6S)-6-methyl-1-[(3-methyloxetan-3-yl)carbonyl]piperidin-3-yl}imidazo[1,5-a]pyrazin-1-yl)-3-methoxy-N-[4-(trifluoromethyl)pyridin-2-yl]benzamide, TFA salt | Calc'd 624.3, found 624.3 | 2.43 (Method H) |

| Example | Structure | Name | Exact Mass [M + H]+ | Retention time (min) |
|---|---|---|---|---|
| 402 | 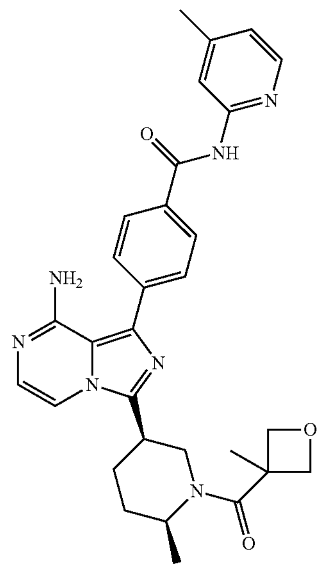 [SMILES: Cc1ccnc(NC(=O)c2ccc(-c3nc([C@@H]4CC[C@H](C)N(C(=O)C5(C)COC5)C4)n4ccnc(N)c34)cc2)c1] | 4-(8-amino-3-{(3R,6S)-6-methyl-1-[(3-methyloxetan-3-yl)carbonyl]piperidin-3-yl}imidazo[1,5-a]pyrazin-1-yl)-N-(4-methylpyridin-2-yl)benzamide, TFA salt | Calc'd 540.3, found 540.3 | 1.89 (Method H) |
| 403 | 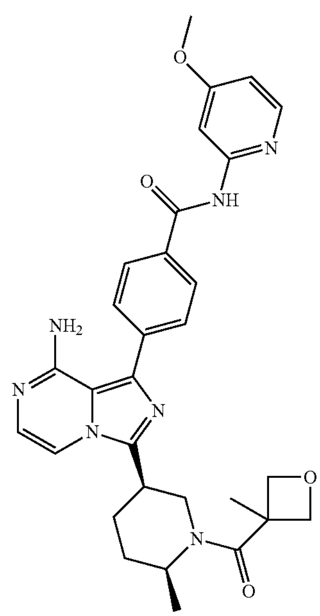 [SMILES: COc1ccnc(NC(=O)c2ccc(-c3nc([C@@H]4CC[C@H](C)N(C(=O)C5(C)COC5)C4)n4ccnc(N)c34)cc2)c1] | 4-(8-amino-3-{(3R,6S)-6-methyl-1-[(3-methyloxetan-3-yl)carbonyl]piperidin-3-yl}imidazo[1,5-a]pyrazin-1-yl)-N-(4-methoxypyridin-2-yl)benzamide, TFA salt | Calc'd 556.3, found 556.3 | 1.86 (Method H) |

| Example | Structure | Name | Exact Mass [M + H]+ | Retention time (min) |
|---|---|---|---|---|
| 404 | 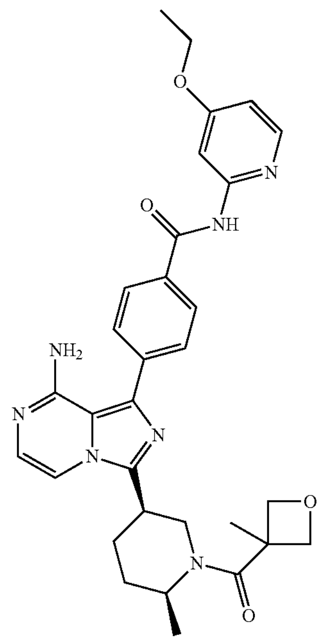 [SMILES: CCOc1ccnc(NC(=O)c2ccc(-c3nc([C@@H]4CC[C@H](C)N(C(=O)C5(C)COC5)C4)n4ccnc(N)c34)cc2)c1] | 4-(8-amino-3-{(3R,6S)-6-methyl-1-[(3-methyloxetan-3-yl)carbonyl]piperidin-3-yl}imidazo[1,5-a]pyrazin-1-yl)-N-(4-ethoxypyridin-2-yl)benzamide, TFA salt | Calc'd 5703, found 570.3 | 1.73 (Method H) |
| 405 | 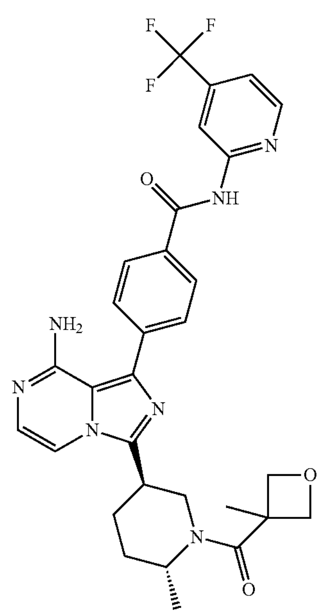 [SMILES: C[C@@H]1CC[C@@H](c2nc(-c3ccc(C(=O)Nc4cc(C(F)(F)F)ccn4)cc3)c3c(N)nccn23)CN1C(=O)C1(C)COC1] | 4-(8-amino-3-{(3R,6R)-6-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide, TFA salt | Calc'd 594.2, found 594.2 | 2.22 (Method H) |

-continued

| Example | Structure | Name | Exact Mass [M + H]+ | Retention time (min) |
|---|---|---|---|---|
| 406 | 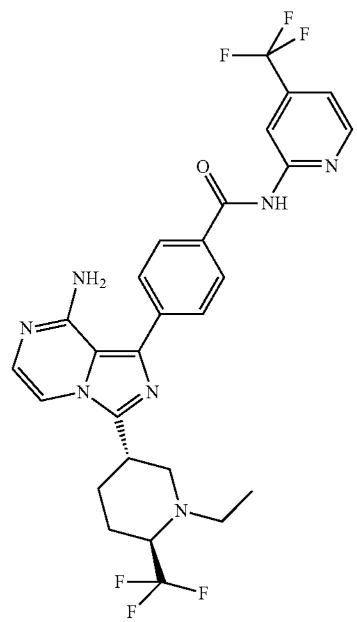 [SMILES: CCN1C[C@@H](c2nc(-c3ccc(C(=O)Nc4cc(C(F)(F)F)ccn4)cc3)c3c(N)nccn23)CC[C@@H]1C(F)(F)F] | 4-{8-amino-3-[(3S,6R)-1-ethyl-6-(trifluoromethyl)piperidin-3-yl]imidazo[1,5-a]pyrazin-1-yl}-N-[4-(trifluoromethyl)pyridin-2-yl]benzamide, TFA salt | Calc'd 578.2, found 578.2 | 2.58 (Method H) |
| 407 | 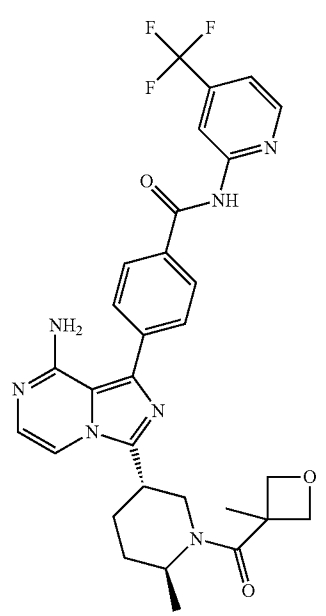 [SMILES: C[C@H]1CC[C@H](c2nc(-c3ccc(C(=O)Nc4cc(C(F)(F)F)ccn4)cc3)c3c(N)nccn23)CN1C(=O)C1(C)COC1] | 4-(8-amino-3-{(3S,6S)-6-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide, TFA salt | Calc'd 594.2, found 594.2 | 2.44 (Method H) |

| Example | Structure | Name | Exact Mass [M + H]+ | Retention time (min) |
|---|---|---|---|---|
| 408 | 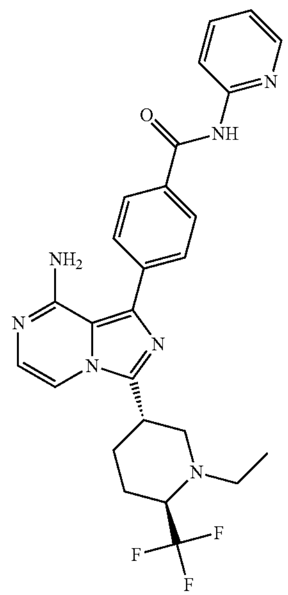 [SMILES: CCN1C[C@@H](c2nc(-c3ccc(C(=O)Nc4ccccn4)cc3)c3c(N)nccn23)CC[C@@H]1C(F)(F)F] | 4-{8-amino-3-[(3S,6R)-1-ethyl-6-(trifluoromethyl)piperidin-3-yl]imidazo[1,5-a]pyrazin-1-yl}-N-pyridin-2-ylbenzamide, TFA salt | Calc'd 510.2, found 510.2 | 2.07 (Method H) |
| 409 | 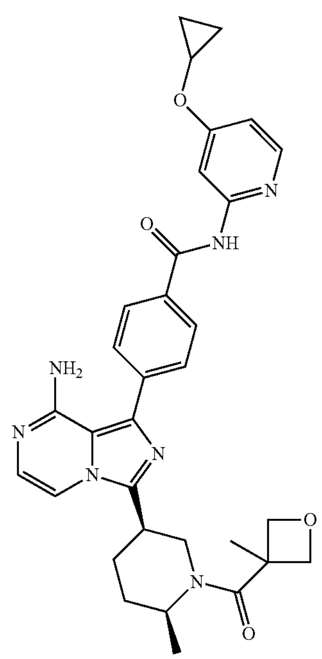 [SMILES: C[C@H]1CC[C@@H](c2nc(-c3ccc(C(=O)Nc4cc(OC5CC5)ccn4)cc3)c3c(N)nccn23)CN1C(=O)C1(C)COC1] | 4-(8-amino-3-{(3R,6S)-6-methyl-1-[(3-methyloxetan-3-yl)carbonyl]piperidin-3-yl}imidazo[1,5-a]pyrazin-1-yl)-N-[4-(cyclopropyloxy)pyridin-2-yl]benzamide, TFA salt | Calc'd 582.3, found 582.3 | 1.99 (Method H) |

| Example | Structure | Name | Exact Mass [M + H]+ | Retention time (min) |
|---|---|---|---|---|
| 410 | 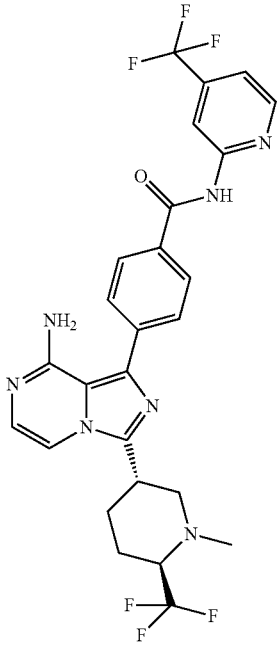 [SMILES: CN1C[C@@H](c2nc(-c3ccc(C(=O)Nc4cc(C(F)(F)F)ccn4)cc3F)c3c(N)nccn23)CC[C@@H]1C(F)(F)F] | 4-{8-amino-3-[(3S,6R)-1-methyl-6-(trifluoromethyl)piperidin-3-yl]imidazo[1,5-a]pyrazin-1-yl}-N-[4-(trifluoromethyl)pyridin-2-yl]benzamide, TFA salt | Calc'd 564.2, found 564.2 | 2.48 (Method H) |
| 411 | 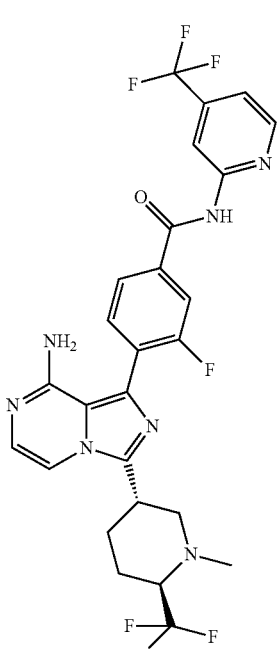 | 4-{8-amino-3-[(3S,6R)-1-methyl-6-(trifluoromethyl)piperidin-3-yl]imidazo[1,5-a]pyrazin-1-yl}-3-fluoro-N-[4-(trifluoromethyl)pyridin-2-yl]benzamide, TFA salt | Calc'd 582.2, found 582.2 | 2.53 (Method H) |

-continued

| Example | Structure | Name | Exact Mass [M + H]+ | Retention time (min) |
|---|---|---|---|---|
| 412 | 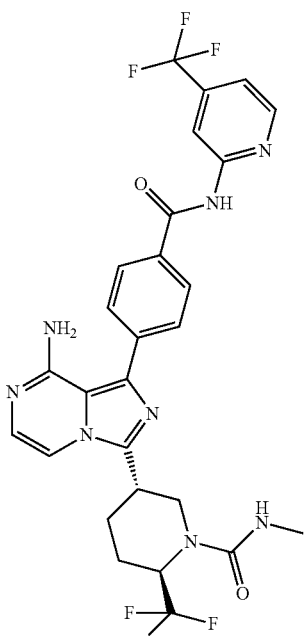 | (2R,5S)-5-[8-amino-1-(4-{[4-(trifluoromethyl)pyridin-2-yl]carbamoyl}phenyl)imidazo[1,5-a]pyrazin-3-yl]-N-methyl-2-(trifluoromethyl)piperidine-1-carboxamide, TFA salt | Calc'd 607.2, found 607.2 | 2.38 (Method H) |
| 413 | 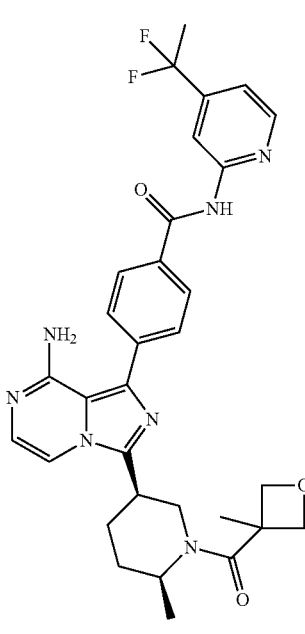 | 4-(8-amino-3-{(3R,6S)-6-methyl-1-[(3-methyloxetan-3-yl)carbonyl]piperidin-3-yl}imidazo[1,5-a]pyrazin-1-yl)-N-[4-(1,1-difluoroethyl)pyridin-2-yl]benzamide, TFA salt | Calc'd 590.3, found 590.3 | 2.10 (Method H) |

| Example | Structure | Name | Exact Mass [M + H]+ | Retention time (min) |
|---|---|---|---|---|
| 414 | 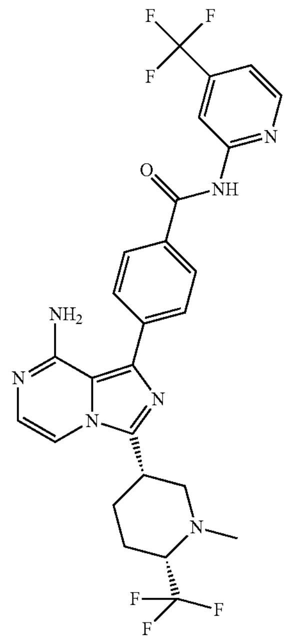 [SMILES: CN1C[C@@H](c2nc(-c3ccc(C(=O)Nc4cc(C(F)(F)F)ccn4)cc3)c3c(N)nccn23)CC[C@H]1C(F)(F)F] | 4-{8-amino-3-[(3S,6S)-1-methyl-6-(trifluoromethyl)piperidin-3-yl]imidazo[1,5-a]pyrazin-1-yl}-N-[4-(trifluoromethyl)pyridin-2-yl]benzamide, TFA salt | Calc'd 564.2, found 564.2 | 2.36 (Method H) |
| 415 | 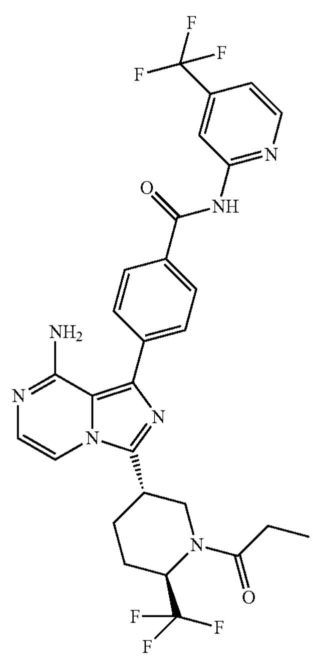 [SMILES: CCC(=O)N1C[C@@H](c2nc(-c3ccc(C(=O)Nc4cc(C(F)(F)F)ccn4)cc3)c3c(N)nccn23)CC[C@@H]1C(F)(F)F] | 4-{8-amino-3-[(3S,6R)-1-propanoyl-6-(trifluoromethyl)piperidin-3-yl]imidazo[1,5-a]pyrazin-1-yl}-N-[4-(trifluoromethyl)pyridin-2-yl]benzamide, TFA salt | Calc'd 606.2, found 606.2 | 2.74 (Method H) |

-continued

| Example | Structure | Name | Exact Mass [M + H]⁺ | Retention time (min) |
|---|---|---|---|---|
| 416 | 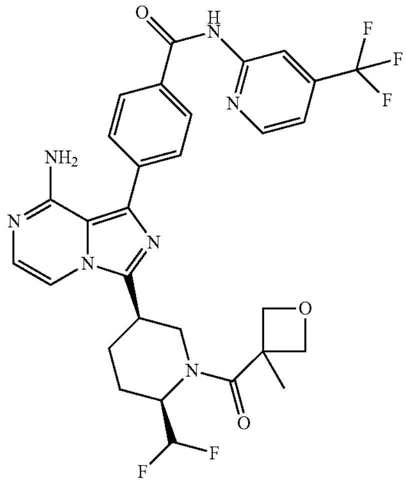 [SMILES: CC1(C(=O)N2C[C@H](c3nc(-c4ccc(C(=O)Nc5cc(C(F)(F)F)ccn5)cc4)c4c(N)nccn34)CC[C@@H]2C(F)F)COC1] | 4-(8-amino-3-{(3R,6R)-6-(difluoromethyl)-1-[(3-methyloxetan-3-yl)carbonyl]piperidin-3-yl}imidazo[1,5-a]pyrazin-1-yl)-N-[4-(trifluoromethyl)pyridin-2-yl]benzamide, TFA salt | Calc'd 630.2, found 630.2 | 2.32 (Method H) |
| 417 | 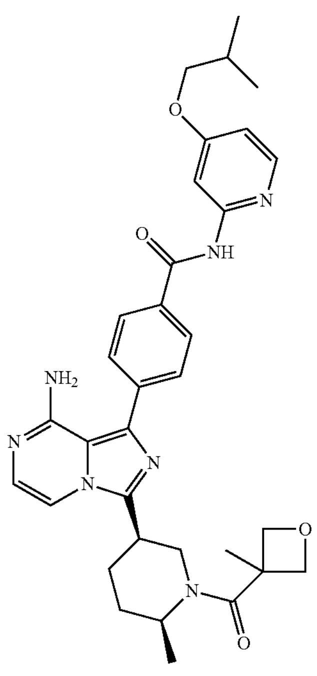 [SMILES: CC(C)COc1ccnc(NC(=O)c2ccc(-c3nc([C@@H]4CC[C@H](C)N(C(=O)C5(C)COC5)C4)n4ccnc(N)c34)cc2)c1] | 4-(8-amino-3-{(3R,6S)-6-methyl-1-[(3-methyloxetan-3-yl)carbonyl]piperidin-3-yl}imidazo[1,5-a]pyrazin-1-yl)-N-[4-(2-methylpropoxy)pyridin-2-yl]benzamide, TFA salt | Calc'd 598.3, found 598.3 | 2.19 (Method H) |

-continued

| Example | Structure | Name | Exact Mass [M + H]⁺ | Retention time (min) |
|---|---|---|---|---|
| 418 | 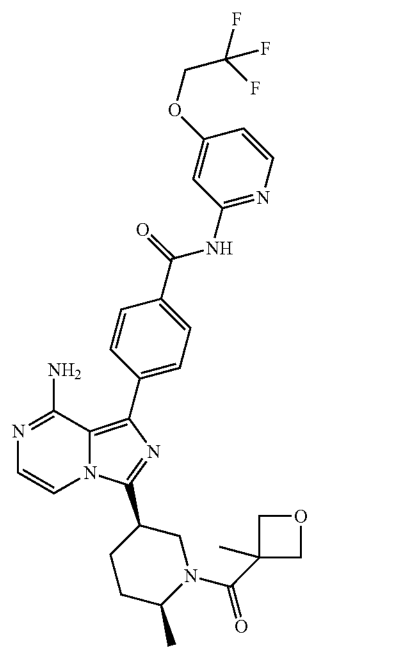 [SMILES: C[C@H]1CC[C@@H](c2nc(-c3ccc(C(=O)Nc4cc(OCC(F)(F)F)ccn4)cc3)c3c(N)nccn23)CN1C(=O)C1(C)COC1] | 4-(8-amino-3-{(3R,6S)-6-methyl-1-[(3-methyloxetan-3-yl)carbonyl]piperidin-3-yl}imidazo[1,5-a]pyrazin-1-yl)-N-[4-(2,2,2-trifluoroethoxy)pyridin-2-yl]benzamide, TFA salt | Calc'd 624.3, found 624.3 | 2.22 (Method H) |
| 419 | 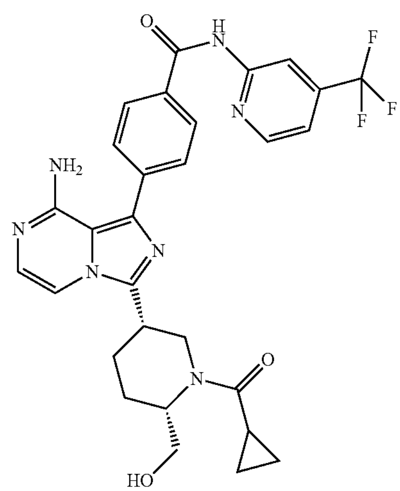 [SMILES: Nc1nccn2c([C@H]3CC[C@@H](CO)N(C(=O)C4CC4)C3)nc(-c3ccc(C(=O)Nc4cc(C(F)(F)F)ccn4)cc3)c12] | 4-{8-amino-3-[(3S,6S)-1-(cyclopropylcarbonyl)-6-(hydroxymethyl)piperidin-3-yl]imidazo[1,5-a]pyrazin-1-yl}-N-[4-(trifluoromethyl)pyridin-2-yl]benzamide, TFA salt | Calc'd 580.2, found 580.2 | 2.40 (Method H) |
| 420 | | omitted | | |
| 421 | | omitted | | |
| 422 | | omitted | | |
| 423 | | omitted | | |

-continued

| Example | Structure | Name | Exact Mass [M + H]+ | Retention time (min) |
|---|---|---|---|---|
| 424 | 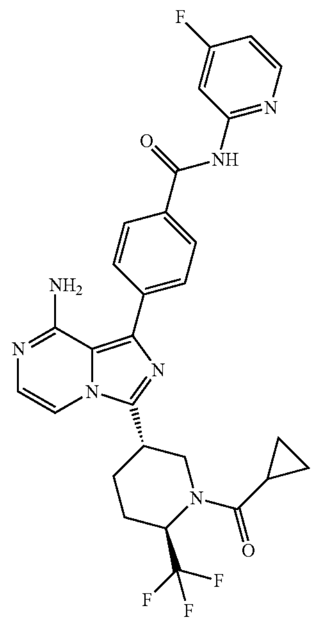 [SMILES: Nc1nccn2c([C@H]3CC[C@H](C(F)(F)F)N(C(=O)C4CC4)C3)nc(-c3ccc(C(=O)Nc4cc(F)ccn4)cc3)c12] | 4-{8-amino-3-[(3S,6R)-1-(cyclopropylcarbonyl)-6-(trifluoromethyl)piperidin-3-yl]imidazo[1,5-a]pyrazin-1-yl}-N-(4-fluoropyridin-2-yl)benzamide, TFA salt | Calc'd 568.2, found 568.2 | 3.37 (Method H) |
| 425 | 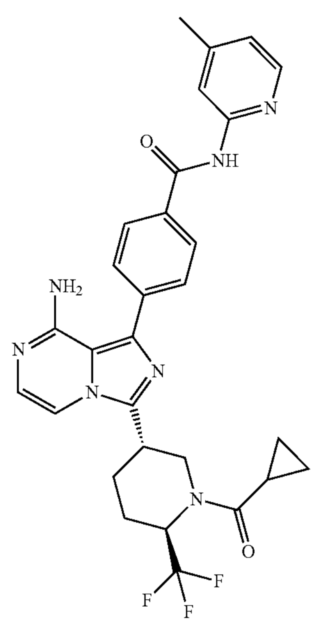 [SMILES: Cc1ccnc(NC(=O)c2ccc(-c3nc([C@H]4CC[C@H](C(F)(F)F)N(C(=O)C5CC5)C4)n4ccnc(N)c34)cc2)c1] | 4-{8-amino-3-[(3S,6R)-1-(cyclopropylcarbonyl)-6-(trifluoromethyl)piperidin-3-yl]imidazo[1,5-a]pyrazin-1-yl}-N-(4-methylpyridin-2-yl)benzamide, TFA salt | Calc'd 564.2, found 564.2 | 2.47 (Method H) |

-continued

| Example | Structure | Name | Exact Mass [M + H]+ | Retention time (min) |
|---|---|---|---|---|
| 426 | 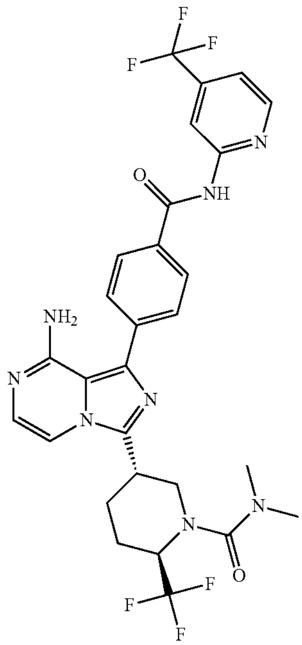 [SMILES: CN(C)C(=O)N1C[C@@H](c2nc(-c3ccc(C(=O)Nc4cc(C(F)(F)F)ccn4)cc3)c3c(N)nccn23)CC[C@@H]1C(F)(F)F] | (2R,5S)-5-[8-amino-1-(4-{[4-(trifluoromethyl)pyridin-2-yl]carbamoyl}phenyl)imidazo[1,5-a]pyrazin-3-yl]-N,N-dimethyl-2-(trifluoromethyl)piperidine-1-carboxamide, TFA salt | Calc'd 621.2, found 621.2 | 2.62 (Method H) |
| 427 | 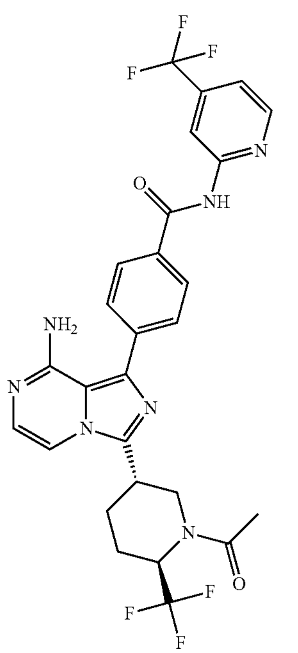 [SMILES: CC(=O)N1C[C@@H](c2nc(-c3ccc(C(=O)Nc4cc(C(F)(F)F)ccn4)cc3)c3c(N)nccn23)CC[C@@H]1C(F)(F)F] | 4-{3-[(3S,6R)-1-acetyl-6-(trifluoromethyl)piperidin-3-yl]-8-aminoimidazo[1,5-a]pyrazin-1-yl}-N-[4-(trifluoromethyl)pyridin-2-yl]benzamide, TFA salt | Calc'd 592.2, found 592.2 | 2.68 (Method H) |

-continued

| Example | Structure | Name | Exact Mass [M + H]+ | Retention time (min) |
|---|---|---|---|---|
| 428 | 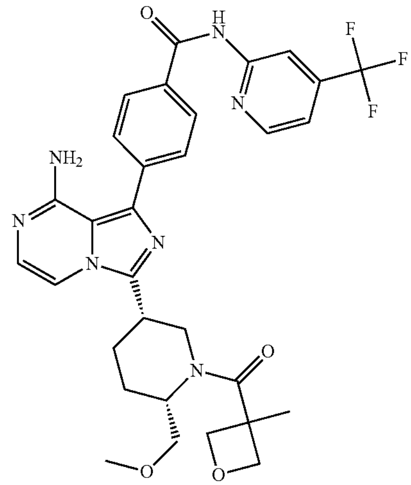 [SMILES: COC[C@@H]1CC[C@H](c2nc(-c3ccc(C(=O)Nc4cc(C(F)(F)F)ccn4)cc3)c3c(N)nccn23)CN1C(=O)C1(C)COC1] | 4-(8-amino-3-{(3S,6S)-6-(methoxymethyl)-1-[(3-methyloxetan-3-yl)carbonyl]piperidin-3-yl}imidazo[1,5-a]pyrazin-1-yl)-N-[4-(trifluoromethyl)pyridin-2-yl]benzamide, TFA salt | Calc'd 624.3, found 624.3 | 2.29 (Method H) |
| 429 | 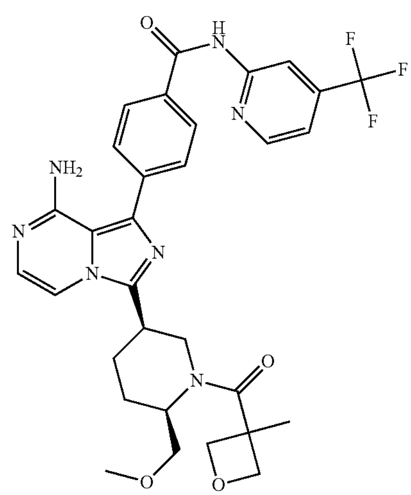 [SMILES: COC[C@H]1CC[C@@H](c2nc(-c3ccc(C(=O)Nc4cc(C(F)(F)F)ccn4)cc3)c3c(N)nccn23)CN1C(=O)C1(C)COC1] | 4-(8-amino-3-{(3R,6R)-6-(methoxymethyl)-1-[(3-methyloxetan-3-yl)carbonyl]piperidin-3-yl}imidazo[1,5-a]pyrazin-1-yl)-N-[4-(trifluoromethyl)pyridin-2-yl]benzamide, TFA salt | Calc'd 624.3, found 624.3 | 2.27 (Method H) |

-continued

| Example | Structure | Name | Exact Mass [M + H]+ | Retention time (min) |
|---|---|---|---|---|
| 430 | 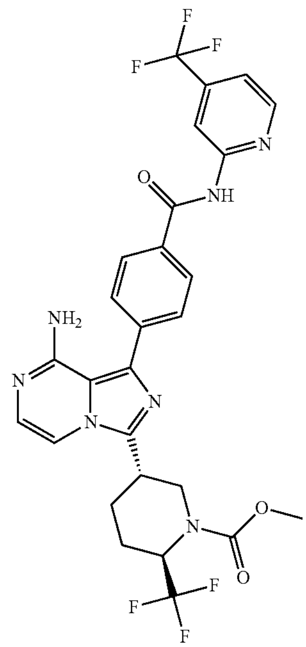 [SMILES: COC(=O)N1C[C@@H](c2nc(-c3ccc(C(=O)Nc4cc(C(F)(F)F)ccn4)cc3)c3c(N)nccn23)CC[C@@H]1C(F)(F)F] | methyl (2R,5S)-5-[8-amino-1-(4-{[4-(trifluoromethyl)pyridin-2-yl]carbamoyl}phenyl)imidazo[1,5-a]pyrazin-3-yl]-2-(trifluoromethyl)piperidine-1-carboxylate | Calc'd 608.2, found 608.2 | 2.47 (Method H) |
| 431 | | omitted | | |
| 432 | | omitted | | |
| 433 | | omitted | | |
| 434 | 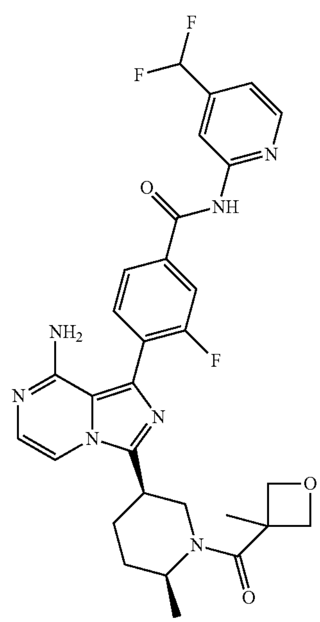 [SMILES: C[C@H]1CC[C@@H](c2nc(-c3ccc(C(=O)Nc4cc(C(F)F)ccn4)cc3F)c3c(N)nccn23)CN1C(=O)C1(C)COC1] | 4-(8-amino-3-{(3R,6S)-6-methyl-1-[(3-methyl-oxetan-3-yl)carbonyl]-piperidin-3-yl}imidazo-[1,5-a]pyrazin-1-yl)-N-[4-(difluoromethyl)pyridin-2-yl]-3-fluorobenzamide, TFA salt | Calc'd 594.2, found 594.2 | 2.14 (Method H) |

-continued

| Example | Structure | Name | Exact Mass [M + H]+ | Retention time (min) |
|---|---|---|---|---|
| 435 | 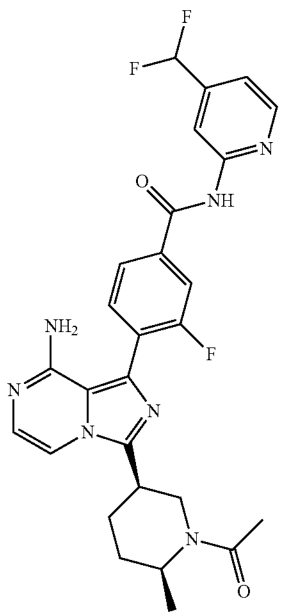 | 4-{3-[(3R,6S)-1-acetyl-6-methylpiperidin-3-yl]-8-aminoimidazo[1,5-a]pyrazin-1-yl}-N-[4-(difluoromethyl)pyridin-2-yl]-3-fluorobenzamide, TFA salt | Calc'd 538.2, found 538.2 | 2.40 (Method H) |
| 436 | 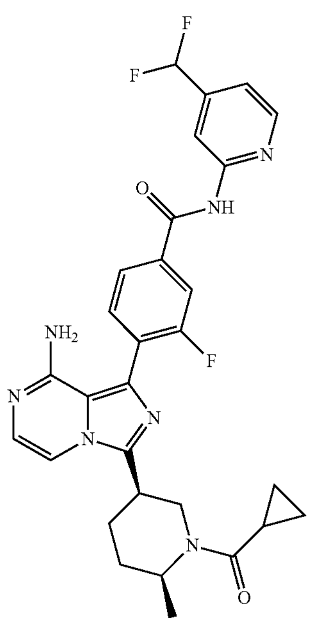 [SMILES: C[C@H]1CC[C@@H](c2nc(-c3ccc(C(=O)Nc4cc(C(F)F)ccn4)cc3F)c3c(N)nccn23)CN1C(=O)C1CC1] | 4-{8-amino-3-[(3R,6S)-1-(cyclopropylcarbonyl)-6-methylpiperidin-3-yl]imidazo[1,5-a]pyrazin-1-yl}-N-[4-(difluoromethyl)pyridin-2-yl]-3-fluorobenzamide, TFA salt | Calc'd 564.2, found 564.2 | 2.50 (Method H) |

-continued

| Example | Structure | Name | Exact Mass [M + H]+ | Retention time (min) |
|---|---|---|---|---|
| 437 | 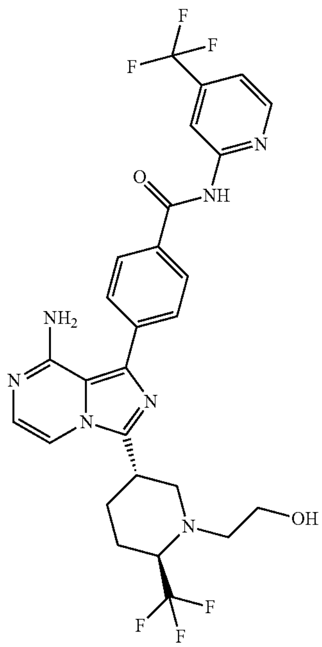 [SMILES: Nc1nccn2c([C@H]3CC[C@H](C(F)(F)F)N(CCO)C3)nc(-c3ccc(C(=O)Nc4cc(C(F)(F)F)ccn4)cc3)c12] | 4-{8-amino-3-[(3S,6R)-1-(2-hydroxyethyl)-6-(trifluoromethyl)piperidin-3-yl]imidazo[1,5-a]pyrazin-1-yl}-N-[4-(trifluoromethyl)pyridin-2-yl]benzamide, TFA salt | Calc'd 594.2, found 594.2 | 2.56 (Method H) |
| 438 | 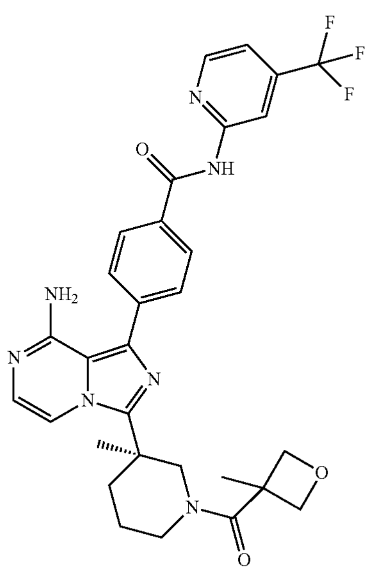 [SMILES: CC1(C(=O)N2CCC[C@@](C)(c3nc(-c4ccc(C(=O)Nc5cc(C(F)(F)F)ccn5)cc4)c4c(N)nccn34)C2)COC1] | 4-(8-amino-3-{(3R)-3-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide, TFA salt | Calc'd 594.2, found 594.2 | 1.12 (Method P) |

| Example | Structure | Name | Exact Mass [M + H]+ | Retention time (min) |
|---|---|---|---|---|
| 439 | 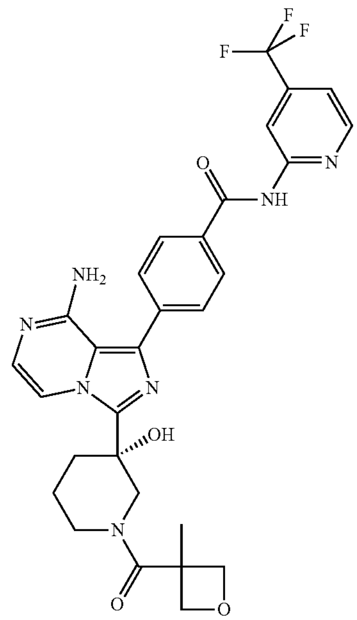 [SMILES: CC1(C(=O)N2CCC[C@@](O)(c3nc(-c4ccc(C(=O)Nc5cc(C(F)(F)F)ccn5)cc4)c4c(N)nccn34)C2)COC1] | 4-(8-amino-3-{(3S)-3-hydroxy-1-[(3-methyloxetan-3-yl)carbonyl]piperidin-3-yl}imidazo[1,5-a]pyrazin-1-yl)-N-[4-(trifluoromethyl)pyridin-2-yl]benzamide, TFA salt | Calc'd 596.2, found 596.3 | 2.19 (Method H) |
| 440 | 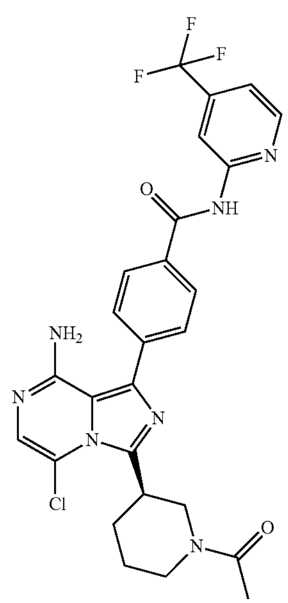 [SMILES: CC(=O)N1CCC[C@@H](c2nc(-c3ccc(C(=O)Nc4cc(C(F)(F)F)ccn4)cc3)c3c(N)ncc(Cl)n23)C1] | 4-{3-[(3R)-1-acetylpiperidin-3-yl]-8-amino-5-chloroimidazo[1,5-a]pyrazin-1-yl}-N-[4-(trifluoromethyl)pyridin-2-yl]benzamide | Calc'd 558.2, found | 1.79 min (Method O) |

| Example | Structure | Name | Exact Mass [M + H]+ | Retention time (min) |
|---|---|---|---|---|
| 441 | 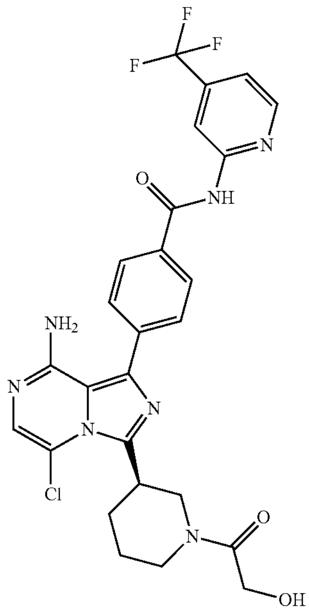 [SMILES: Nc1ncc(Cl)n2c([C@@H]3CCCN(C(=O)CO)C3)nc(-c3ccc(C(=O)Nc4cc(C(F)(F)F)ccn4)cc3)c12] | 4-{8-amino-5-chloro-3-[(3R)-1-(hydroxyacetyl)piperidin-3-yl]imidazo[1,5-a]pyrazin-1-yl}-N-[4-(trifluoromethyl)pyridin-2-yl]benzamide | Calc'd 574.2, found | 1.80 min (Method O) |
| 442 | 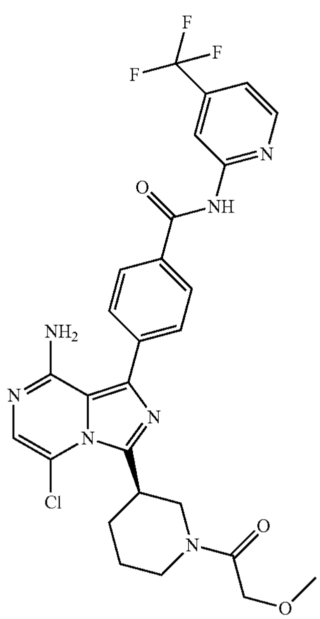 [SMILES: COCC(=O)N1CCC[C@@H](c2nc(-c3ccc(C(=O)Nc4cc(C(F)(F)F)ccn4)cc3)c3c(N)ncc(Cl)n23)C1] | 4-{8-amino-5-chloro-3-[(3R)-1-(methoxyacetyl)piperidin-3-yl]imidazo[1,5-a]pyrazin-1-yl}-N-[4-(trifluoromethyl)pyridin-2-yl]benzamide | Calc'd 588.2, found | 1.78 min (Method O) |

| Example | Structure | Name | Exact Mass [M + H]+ | Retention time (min) |
|---|---|---|---|---|
| 443 | 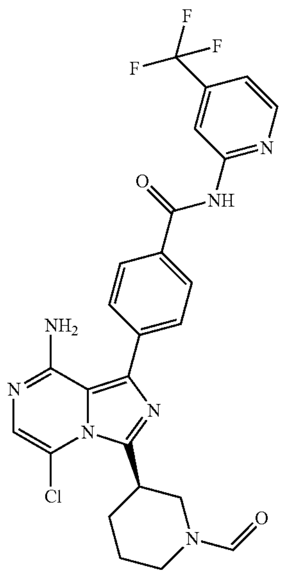 [SMILES: Nc1ncc(Cl)n2c([C@@H]3CCCN(C=O)C3)nc(-c3ccc(C(=O)Nc4cc(C(F)(F)F)ccn4)cc3)c12] | 4-{8-amino-5-chloro-3-[(3R)-1-formylpiperidin-3-yl]imidazo[1,5-a]pyrazin-1-yl}-N-[4-(trifluoromethyl)pyridin-2-yl]benzamide | Calc'd 544.1, found | 1.73 min (Method O) |
| 444 | 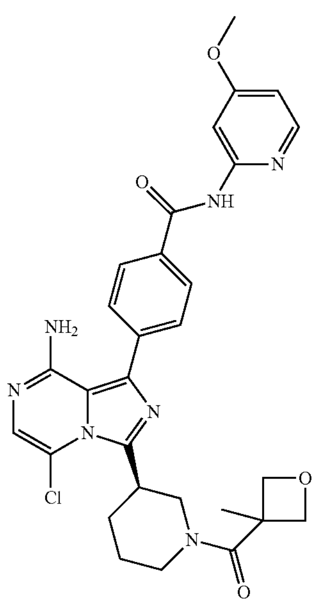 [SMILES: COc1ccnc(NC(=O)c2ccc(-c3nc([C@@H]4CCCN(C(=O)C5(C)COC5)C4)n4c(Cl)cnc(N)c34)cc2)c1] | 4-(8-amino-5-chloro-3-{(3R)-1-[(3-methyloxetan-3-yl)carbonyl]piperidin-3-yl}imidazo[1,5-a]pyrazin-1-yl)-N-(4-methoxypyridin-2-yl)benzamide | Calc'd 576.2, found 576.2 | 0.81 min (Method Q) |

-continued

| Example | Structure | Name | Exact Mass [M + H]+ | Retention time (min) |
|---|---|---|---|---|
| 445 | 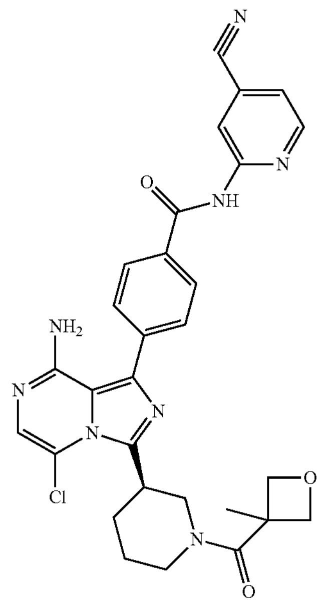 [SMILES: CC1(C(=O)N2CCC[C@@H](c3nc(-c4ccc(C(=O)Nc5cc(C#N)ccn5)cc4)c4c(N)ncc(Cl)n34)C2)COC1] | 4-(8-amino-5-chloro-3-{(3R)-1-[(3-methyloxetan-3-yl)carbonyl]piperidin-3-yl}imidazo[1,5-a]pyrazin-1-yl)-N-(4-cyanopyridin-2-yl)benzamide | Calc'd 571.2, found 571.2 | 0.82 min (Method Q) |
| 446 | 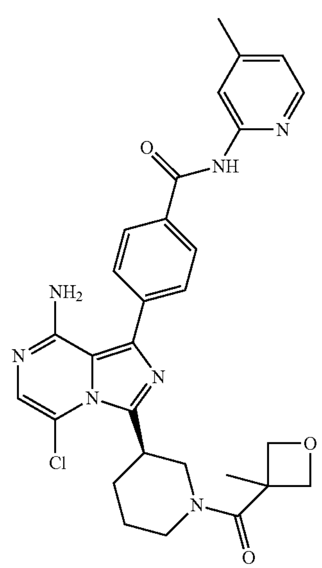 [SMILES: Cc1ccnc(NC(=O)c2ccc(-c3nc([C@@H]4CCCN(C(=O)C5(C)COC5)C4)n4c(Cl)cnc(N)c34)cc2)c1] | 4-(8-amino-5-chloro-3-{(3R)-1-[(3-methyloxetan-3-yl)carbonyl]piperidin-3-yl}imidazo[1,5-a]pyrazin-1-yl)-N-(4-methylpyridin-2-yl)benzamide | Calc'd 560.2, found 560.2 | 0.84 min (Method Q) |

| Example | Structure | Name | Exact Mass [M + H]+ | Retention time (min) |
|---|---|---|---|---|
| 447 | 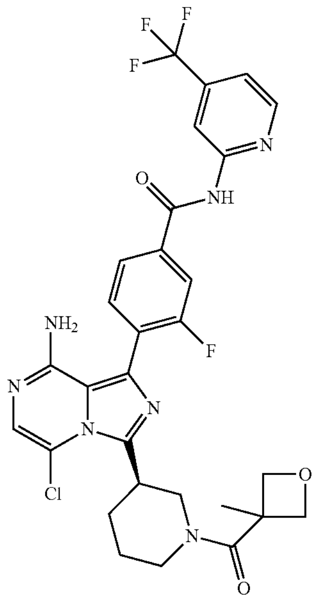 [SMILES: CC1(C(=O)N2CCC[C@@H](c3nc(-c4ccc(C(=O)Nc5cc(C(F)(F)F)ccn5)cc4F)c4c(N)ncc(Cl)n34)C2)COC1] | 4-(8-amino-5-chloro-3-{(3R)-1-[(3-methyloxetan-3-yl)carbonyl]piperidin-3-yl}imidazo[1,5-a]pyrazin-1-yl)-3-fluoro-N-[4-(trifluoromethyl)pyridin-2-yl]benzamide, TFA salt | Calc'd 632.2, found 632.2 | 2.38 (Method H) |
| 448 | 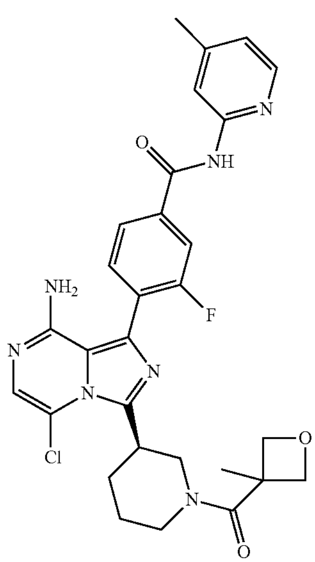 [SMILES: Cc1ccnc(NC(=O)c2ccc(-c3nc([C@@H]4CCCN(C(=O)C5(C)COC5)C4)n4c(Cl)cnc(N)c34)c(F)c2)c1] | 4-(8-amino-5-chloro-3-{(3R)-1-[(3-methyloxetan-3-yl)carbonyl]piperidin-3-yl}imidazo[1,5-a]pyrazin-1-yl)-3-fluoro-N-(4-methylpyridin-2-yl)benzamide | Calc'd 578.2, found | 1.93 (Method H) |

| Example | Structure | Name | Exact Mass [M + H]+ | Retention time (min) |
|---|---|---|---|---|
| 449 | 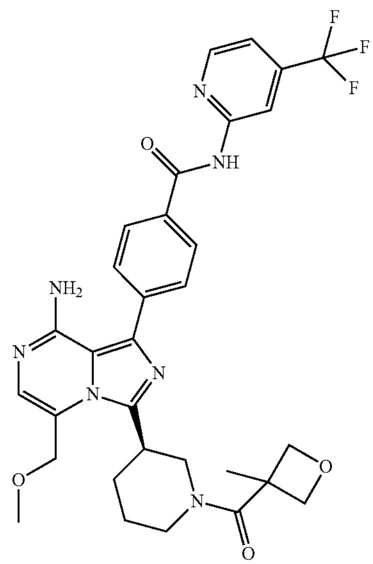 [SMILES: COCc1cnc(N)c2c(-c3ccc(C(=O)Nc4cc(C(F)(F)F)ccn4)cc3)nc([C@@H]3CCCN(C(=O)C4(C)COC4)C3)n12] | 4-[8-amino-5-(methoxymethyl)-3-{(3R)-1-[(3-methyloxetan-3-yl)carbonyl]piperidin-3-yl}imidazo[1,5-a]pyrazin-1-yl]-N-[4-(trifluoromethyl)pyridin-2-yl]benzamide | Calc'd 624.3, found 624.2 | 1.840 (Method M) |
| 450 | 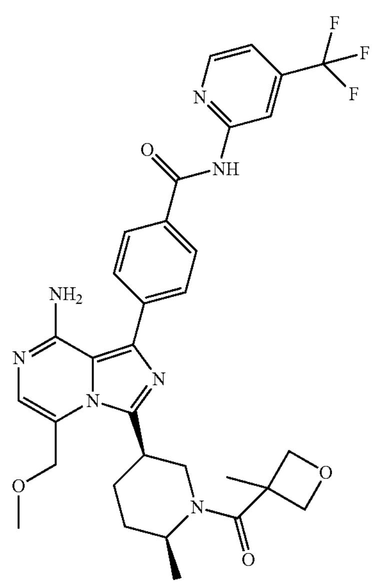 [SMILES: COCc1cnc(N)c2c(-c3ccc(C(=O)Nc4cc(C(F)(F)F)ccn4)cc3)nc([C@@H]3CC[C@H](C)N(C(=O)C4(C)COC4)C3)n12] | 4-[8-amino-5-(methoxymethyl)-3-{(3R,6S)-6-methyl-1-[(3-methyloxetan-3-yl)carbonyl]piperidin-3-yl}imidazo[1,5-a]pyrazin-1-yl]-N-[4-(trifluoromethyl)pyridin-2-yl]benzamide | Calc'd 638.3, found 638.0 | 1.911 (Method M) |

| Example | Structure | Name | Exact Mass [M + H]+ | Retention time (min) |
|---|---|---|---|---|
| 451 | 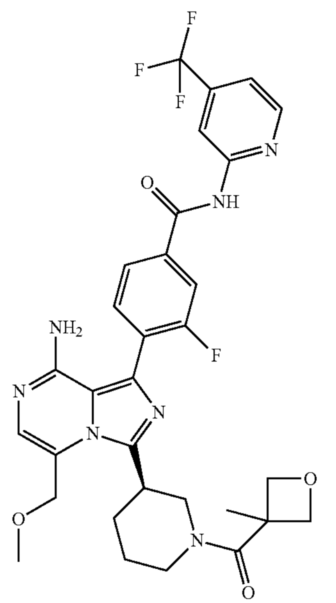 [SMILES: COCc1cnc(N)c2c(-c3ccc(C(=O)Nc4cc(C(F)(F)F)ccn4)cc3F)nc([C@@H]3CCCN(C(=O)C4(C)COC4)C3)n12] | 4-[8-amino-5-(methoxymethyl)-3-{(3R)-1-[(3-methyloxetan-3-yl)carbonyl]piperidin-3-yl}imidazo[1,5-a]pyrazin-1-yl]-3-fluoro-N-[4-(trifluoromethyl)pyridin-2-yl]benzamide, TFA salt | Calc'd 642.2, found 642.2 | 2.77 (Method H) |
| 452 | 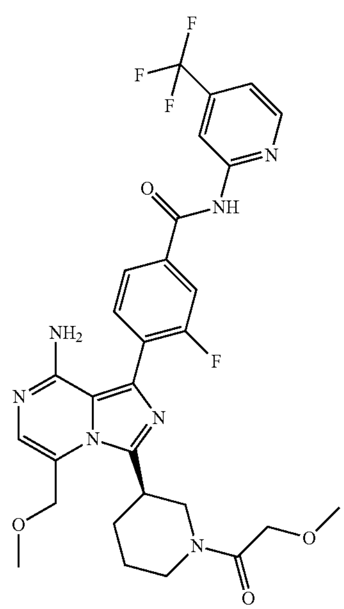 [SMILES: COCC(=O)N1CCC[C@@H](c2nc(-c3ccc(C(=O)Nc4cc(C(F)(F)F)ccn4)cc3F)c3c(N)ncc(COC)n23)C1] | 4-{8-amino-3-[(3R)-1-(methoxyacetyl)piperidin-3-yl]-5-(methoxymethyl)-imidazo[1,5-a]pyrazin-1-yl}-3-fluoro-N-[4-(trifluoromethyl)pyridin-2-yl]benzamide, TFA salt | Calc'd 616.2, found 616.2 | 2.70 (Method H) |

-continued

| Example | Structure | Name | Exact Mass [M + H]+ | Retention time (min) |
|---|---|---|---|---|
| 453 | 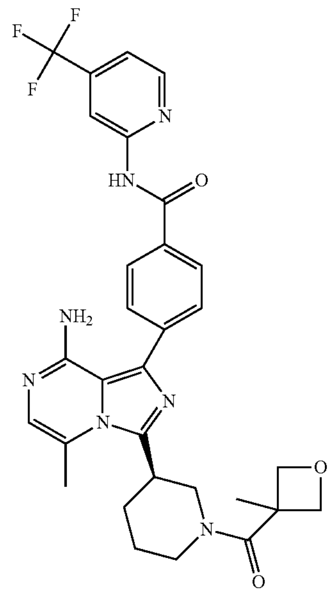 [SMILES: Cc1cnc(N)c2c(-c3ccc(C(=O)Nc4cc(C(F)(F)F)ccn4)cc3)nc([C@@H]3CCCN(C(=O)C4(C)COC4)C3)n12] | 4-(8-amino-5-methyl-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide, TFA salt | Calc'd 593, found 594+ | 1.05 min (Method P) |
| 454 | 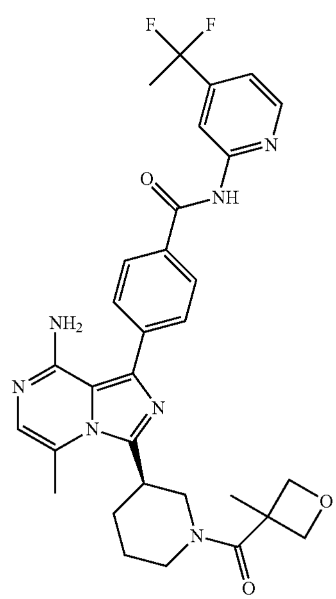 [SMILES: Cc1cnc(N)c2c(-c3ccc(C(=O)Nc4cc(C(C)(F)F)ccn4)cc3)nc([C@@H]3CCCN(C(=O)C4(C)COC4)C3)n12] | 4-(8-amino-5-methyl-3-{(3R)-1-[(3-methyloxetan-3-yl)carbonyl]piperidin-3-yl}imidazo[1,5-a]pyrazin-1-yl)-N-[4-(1,1-difluoroethyl)pyridin-2-yl]benzamide, TFA salt | Calc'd 590.3, found 590.3 | 2.35 (Method H) |

-continued

| Example | Structure | Name | Exact Mass [M + H]+ | Retention time (min) |
|---|---|---|---|---|
| 455 | 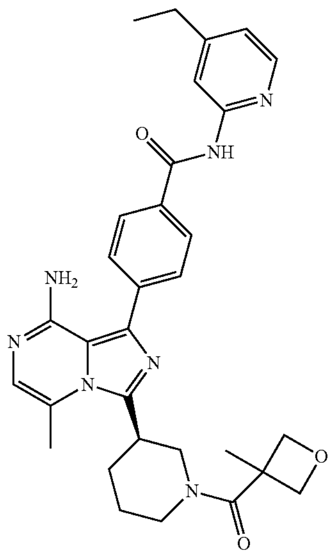 [SMILES: CCc1ccnc(NC(=O)c2ccc(-c3nc([C@@H]4CCCN(C(=O)C5(C)COC5)C4)n4c(C)cnc(N)c34)cc2)c1] | 4-(8-amino-5-methyl-3-{(3R)-1-[(3-methyloxetan-3-yl)carbonyl]piperidin-3-yl}imidazo[1,5-a]pyrazin-1-yl)-N-(4-ethylpyridin-2-yl)benzamide, TFA salt | Calc'd 554.3, found 554.3 | 1.75 (Method H) |
| 456 | 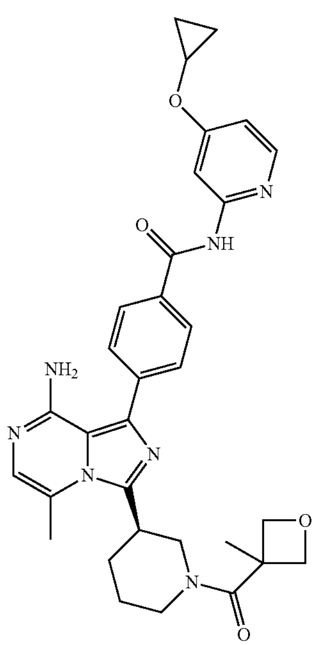 [SMILES: Cc1cnc(N)c2c(-c3ccc(C(=O)Nc4cc(OC5CC5)ccn4)cc3)nc([C@@H]3CCCN(C(=O)C4(C)COC4)C3)n12] | 4-(8-amino-5-methyl-3-{(3R)-1-[(3-methyloxetan-3-yl)carbonyl]piperidin-3-yl}imidazo[1,5-a]pyrazin-1-yl)-N-[4-(cyclopropyloxy)pyridin-2-yl]benzamide, TFA salt | Calc'd 582.3, found 582.3 | 1.74 (Method H) |

-continued

| Example | Structure | Name | Exact Mass [M + H]+ | Retention time (min) |
|---|---|---|---|---|
| 457 | 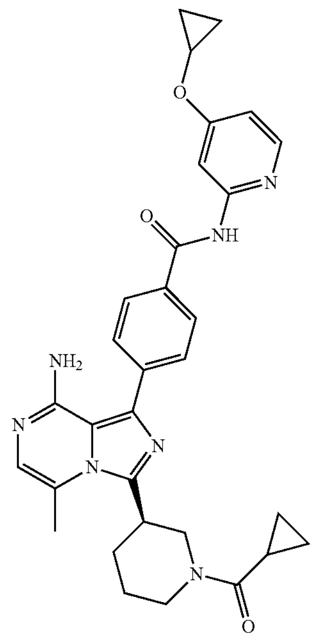 [SMILES: Cc1cnc(N)c2c(-c3ccc(C(=O)Nc4cc(OC5CC5)ccn4)cc3)nc([C@@H]3CCCN(C(=O)C4CC4)C3)n12] | 4-{8-amino-3-[(3R)-1-(cyclopropylcarbonyl)piperidin-3-yl]-5-methylimidazo[1,5-a]pyrazin-1-yl}-N-[4-(cyclopropyloxy)pyridin-2-yl]benzamide, TFA salt | Calc'd 552.3, found 552.3 | 2.42 (Method H) |
| 458 | 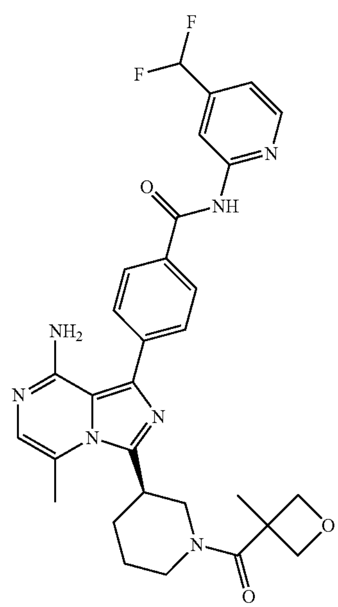 [SMILES: Cc1cnc(N)c2c(-c3ccc(C(=O)Nc4cc(C(F)F)ccn4)cc3)nc([C@@H]3CCCN(C(=O)C4(C)COC4)C3)n12] | 4-(8-amino-5-methyl-3-{(3R)-1-[(3-methyloxetan-3-yl)carbonyl]piperidin-3-yl}imidazo[1,5-a]pyrazin-1-yl)-N-[4-(difluoromethyl)pyridin-2-yl]benzamide, TFA salt | Calc'd 576.3, found 576.3 | 2.60 (Method H) |

-continued

| Example | Structure | Name | Exact Mass [M + H]+ | Retention time (min) |
|---|---|---|---|---|
| 459 | 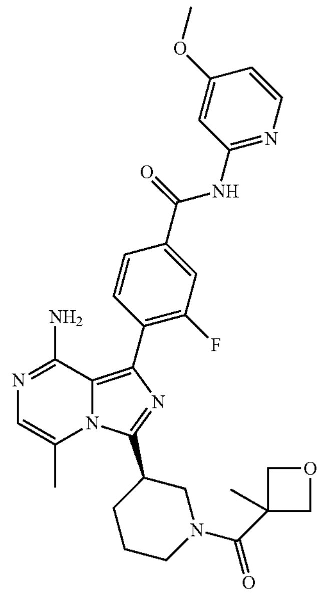 [SMILES: COc1ccnc(NC(=O)c2ccc(-c3nc([C@@H]4CCCN(C(=O)C5(C)COC5)C4)n4c(C)cnc(N)c34)c(F)c2)c1] | 4-(8-amino-5-methyl-3-{(3R)-1-[(3-methyloxetan-3-yl)carbonyl]piperidin-3-yl}imidazo[1,5-a]pyrazin-1-yl)-N-(4-methoxypyridin-2-yl)benzamide, TFA salt | Calc'd 555, found 556 | 0.9 min (Method P) |
| 460 | 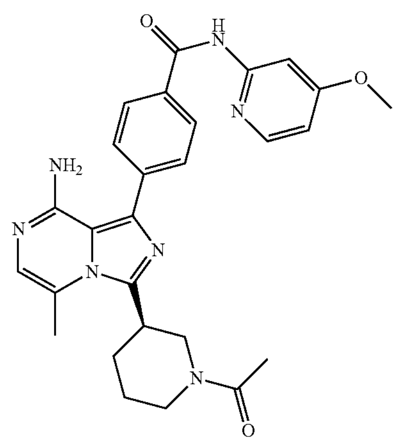 [SMILES: COc1ccnc(NC(=O)c2ccc(-c3nc([C@@H]4CCCN(C(C)=O)C4)n4c(C)cnc(N)c34)cc2)c1] | 4-{3-[(3R)-1-acetylpiperidin-3-yl]-8-amino-5-methylimidazo[1,5-a]pyrazin-1-yl}-N-(4-methoxypyridin-2-yl)benzamide, TFA salt | Calc'd 499, found 500 | 0.91 min (Method P) |

-continued

| Example | Structure | Name | Exact Mass [M + H]+ | Retention time (min) |
|---------|-----------|------|---------------------|----------------------|
| 461 | 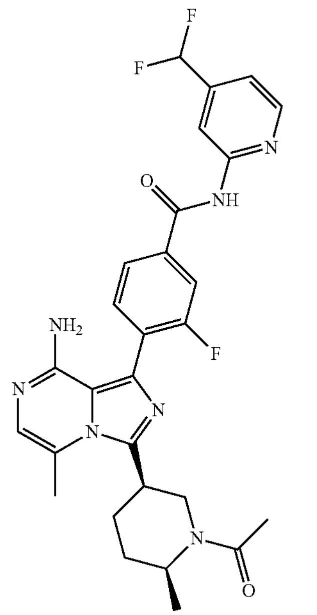 [SMILES: CC(=O)N1C[C@H](c2nc(-c3ccc(C(=O)Nc4cc(C(F)F)ccn4)cc3F)c3c(N)ncc(C)n23)CC[C@@H]1C] | 4-{3-[(3R,6S)-1-acetyl-6-methylpiperidin-3-yl]-8-amino-5-methylimidazo[1,5-a]pyrazin-1-yl}-N-[4-(difluoromethyl)pyridin-2-yl]-3-fluorobenzamide, TFA salt | Calc'd 552.2, found 552.2 | 2.44 (Method H) |
| 462 | 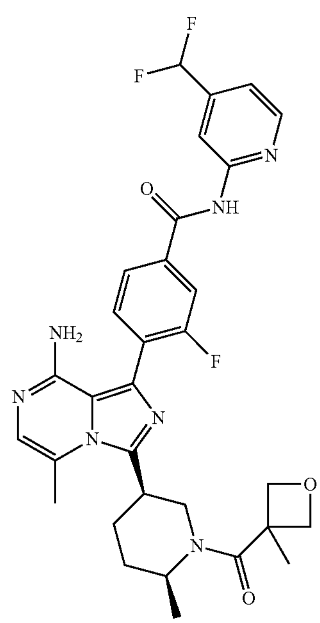 [SMILES: Cc1cnc(N)c2c(-c3ccc(C(=O)Nc4cc(C(F)F)ccn4)cc3F)nc([C@@H]3CC[C@H](C)N(C(=O)C4(C)COC4)C3)n12] | 4-(8-amino-5-methyl-3-{(3R,6S)-6-methyl-1-[(3-methyloxetan-3-yl)carbonyl]piperidin-3-yl}imidazo[1,5-a]pyrazin-1-yl)-N-[4-(difluoromethyl)pyridin-2-yl]-3-fluorobenzamide, TFA salt | Calc'd 608.3, found 608.3 | 2.21 (Method H) |

-continued

| Example | Structure | Name | Exact Mass [M + H]+ | Retention time (min) |
|---|---|---|---|---|
| 463 | 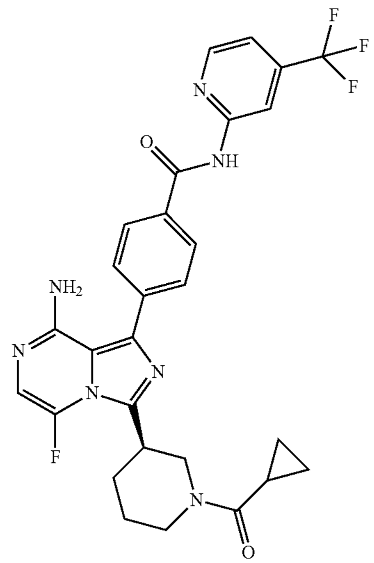 [SMILES: Nc1ncc(F)n2c([C@@H]3CCCN(C(=O)C4CC4)C3)nc(-c3ccc(C(=O)Nc4cc(C(F)(F)F)ccn4)cc3)c12] | 4-{8-amino-3-[(3R)-1-(cyclopropylcarbonyl)piperidin-3-yl]-5-fluoroimidazo[1,5-a]pyrazin-1-yl}-N-[4-(trifluoromethyl)pyridin-2-yl]benzamide | Calc'd 568.2, found 568.2 | 1.961 (Method M) |
| 464 | 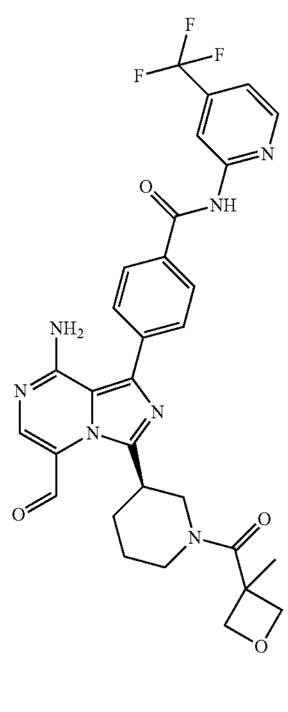 [SMILES: CC1(C(=O)N2CCC[C@@H](c3nc(-c4ccc(C(=O)Nc5cc(C(F)(F)F)ccn5)cc4)c4c(N)ncc(C=O)n34)C2)COC1] | 4-(8-amino-5-formyl-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide | Calc'd 608.2, found 608.3 | 2.44 (Method H) |

| Example | Structure | Name | Exact Mass [M + H]+ | Retention time (min) |
|---|---|---|---|---|
| 465 | 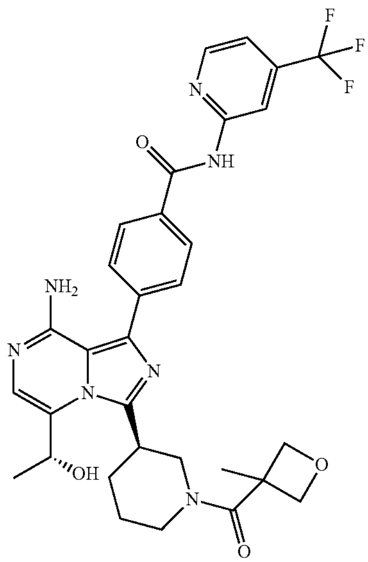 [SMILES: C[C@@H](O)c1cnc(N)c2c(-c3ccc(C(=O)Nc4cc(C(F)(F)F)ccn4)cc3)nc([C@@H]3CCCN(C(=O)C4(C)COC4)C3)n12] | 4-(8-amino-5-[(1R)-1-hydroxyethyl]-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide | Calc'd 624.3, found 624.2 | 1.09 (Method P) |
| 466 | 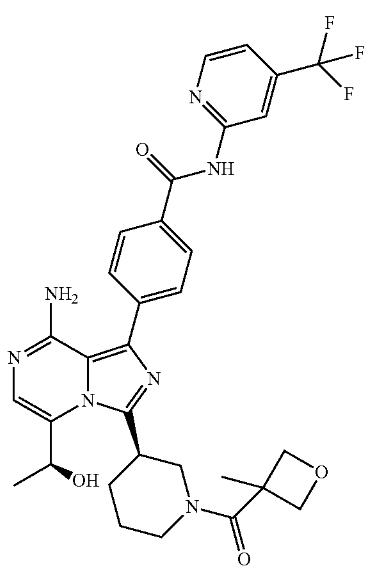 [SMILES: C[C@H](O)c1cnc(N)c2c(-c3ccc(C(=O)Nc4cc(C(F)(F)F)ccn4)cc3)nc([C@@H]3CCCN(C(=O)C4(C)COC4)C3)n12] | 4-(8-amino-5-[(1S)-1-hydroxyethyl]-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide | Calc'd 624.3, found 624.2 | 1.09 (Method P) |

| Example | Structure | Name | Exact Mass [M + H]+ | Retention time (min) |
|---|---|---|---|---|
| 467 | 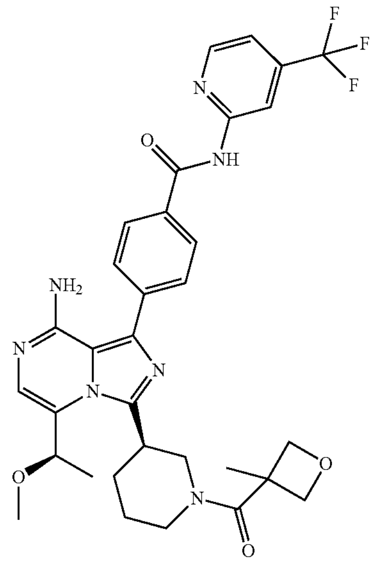 [SMILES: CO[C@H](C)c1cnc(N)c2c(-c3ccc(C(=O)Nc4cc(C(F)(F)F)ccn4)cc3)nc([C@@H]3CCCN(C(=O)C4(C)COC4)C3)n12] | 4-(8-amino-5-[(1R)-1-methoxyethyl]-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide | Calc'd 638.3, found 638.2 | 1.11 (Method P) |
| 468 | 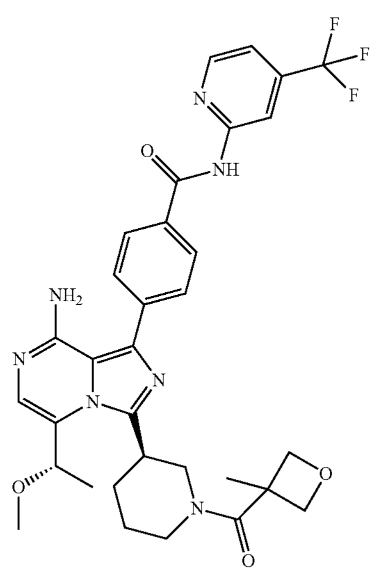 [SMILES: CO[C@@H](C)c1cnc(N)c2c(-c3ccc(C(=O)Nc4cc(C(F)(F)F)ccn4)cc3)nc([C@@H]3CCCN(C(=O)C4(C)COC4)C3)n12] | 4-(8-amino-5-[(1S)-1-methoxyethyl]-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide | Calc'd 638.3, found 638.2 | 1.11 (Method P) |

| Example | Structure | Name | Exact Mass [M + H]+ | Retention time (min) |
|---|---|---|---|---|
| 469 | 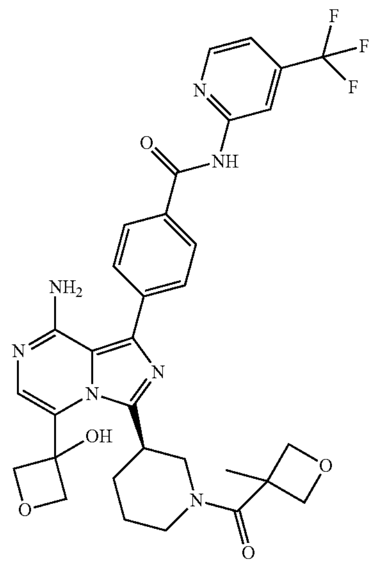 [SMILES: CC1(C(=O)N2CCC[C@@H](c3nc(-c4ccc(C(=O)Nc5cc(C(F)(F)F)ccn5)cc4)c4c(N)ncc(C5(O)COC5)n34)C2)COC1] | 4-[8-amino-5-(3-hydroxyoxetan-3-yl)-3-{(3R)-1-[(3-methyloxetan-3-yl)carbonyl]piperidin-3-yl}imidazo[1,5-a]pyrazin-1-yl]-N-[4-(trifluoromethyl)pyridin-2-yl]benzamide | Calc'd 652.2, found 652.0 | 1.68 (Method O) |
| 470 | 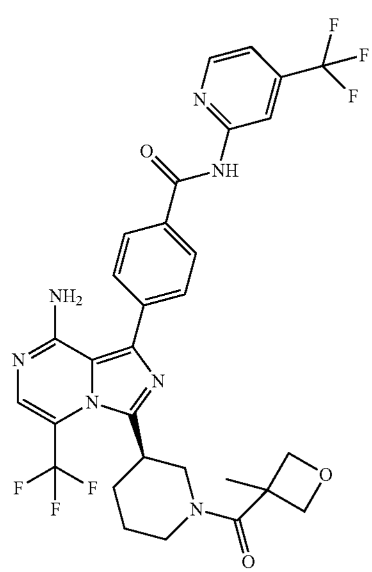 [SMILES: CC1(C(=O)N2CCC[C@@H](c3nc(-c4ccc(C(=O)Nc5cc(C(F)(F)F)ccn5)cc4)c4c(N)ncc(C(F)(F)F)n34)C2)COC1] | 4-[8-amino-3-{(3R)-1-[(3-methyloxetan-3-yl)carbonyl]piperidin-3-yl}-5-(trifluoromethyl)imidazo[1,5-a]pyrazin-1-yl]-N-[4-(trifluoromethyl)pyridin-2-yl]benzamide | Calc'd 648.2, found 648.2 | 1.976 (Method M) |

| Example | Structure | Name | Exact Mass [M + H]+ | Retention time (min) |
|---|---|---|---|---|
| 471 | 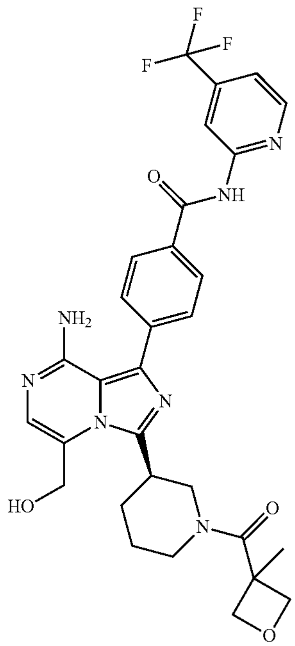 [SMILES: CC1(C(=O)N2CCC[C@@H](c3nc(-c4ccc(C(=O)Nc5cc(C(F)(F)F)ccn5)cc4)c4c(N)ncc(CO)n34)C2)COC1] | 4-[8-amino-5-(hydroxymethyl)-3-{(3R)-1-[(3-methyloxetan-3-yl)carbonyl]piperidin-3-yl}imidazo[1,5-a]pyrazin-1-yl]-N-[4-(trifluoromethyl)pyridin-2-yl]benzamide, TFA salt | Calc'd 610.2, found 610.3 | 2.46 (Method H) |
| 472 | 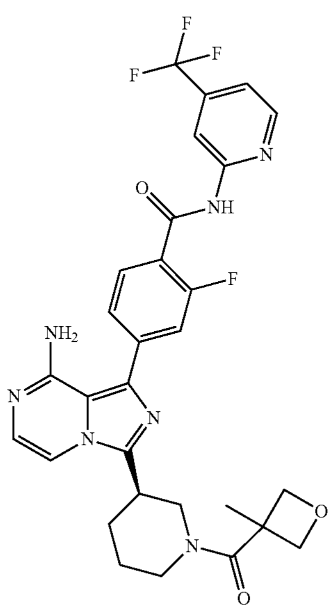 [SMILES: CC1(C(=O)N2CCC[C@@H](c3nc(-c4ccc(C(=O)Nc5cc(C(F)(F)F)ccn5)c(F)c4)c4c(N)nccn34)C2)COC1] | 4-(8-amino-3-{(3R)-1-[(3-methyloxetan-3-yl)carbonyl]piperidin-3-yl}imidazo[1,5-a]pyrazin-1-yl)-2-fluoro-N-[4-(trifluoromethyl)pyridin-2-yl]benzamide, TFA salt | Calc'd 598.2, found 598.2 | 2.49 (Method H) |

| Example | Structure | Name | Exact Mass [M + H]+ | Retention time (min) |
|---|---|---|---|---|
| 473 | 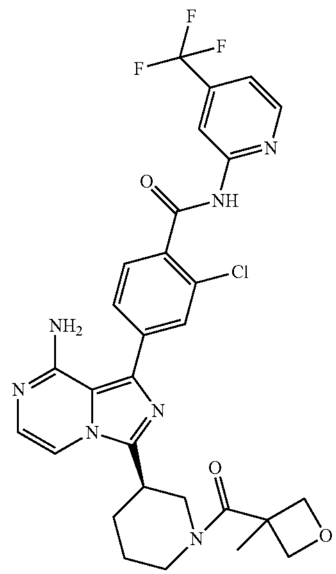 [SMILES: CC1(C(=O)N2CCC[C@@H](c3nc(-c4ccc(C(=O)Nc5cc(C(F)(F)F)ccn5)c(Cl)c4)c4c(N)nccn34)C2)COC1] | 4-(8-amino-3-{(3R)-1-[(3-methyloxetan-3-yl)carbonyl]piperidin-3-yl}imidazo[1,5-a]pyrazin-1-yl)-2-chloro-N-[4-(trifluoromethyl)pyridin-2-yl]benzamide, TFA salt | Calc'd 614.2, found 614.2 | 2.43 (Method H) |
| 474 | 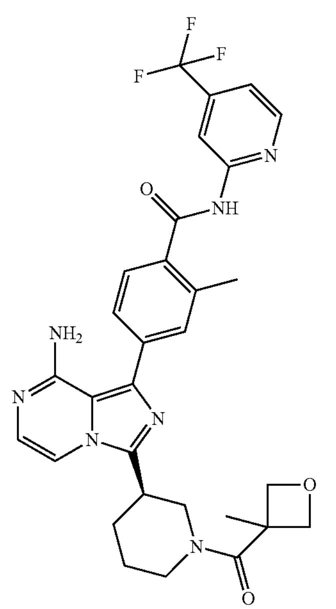 [SMILES: Cc1cc(-c2nc([C@@H]3CCCN(C(=O)C4(C)COC4)C3)n3ccnc(N)c23)ccc1C(=O)Nc1cc(C(F)(F)F)ccn1] | 4-(8-amino-3-{(3R)-1-[(3-methyloxetan-3-yl)carbonyl]piperidin-3-yl}imidazo[1,5-a]pyrazin-1-yl)-2-methyl-N-[4-(trifluoromethyl)pyridin-2-yl]benzamide, TFA salt | Calc'd 594.2, found 594.2 | 2.19 (Method H) |

-continued

| Example | Structure | Name | Exact Mass [M + H]+ | Retention time (min) |
|---|---|---|---|---|
| 475 | 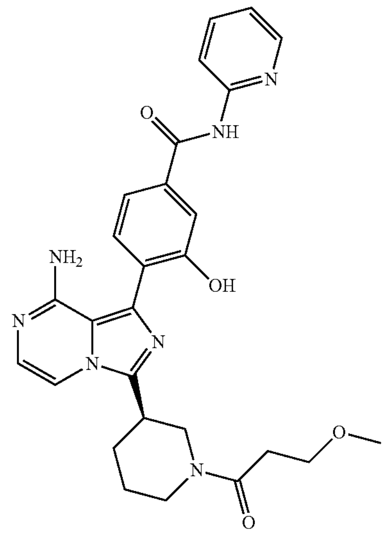 [SMILES: COCCC(=O)N1CCC[C@@H](c2nc(-c3ccc(C(=O)Nc4ccccn4)cc3O)c3c(N)nccn23)C1] | 4-{8-amino-3-[(3R)-1-(3-methoxypropanoyl)piperidin-3-yl]imidazo[1,5-a]pyrazin-1-yl}-3-hydroxy-N-pyridin-2-ylbenzamide, TFA salt | Calc'd 516.2, found 516.2 | 1.93 (Method H) |
| 476 | 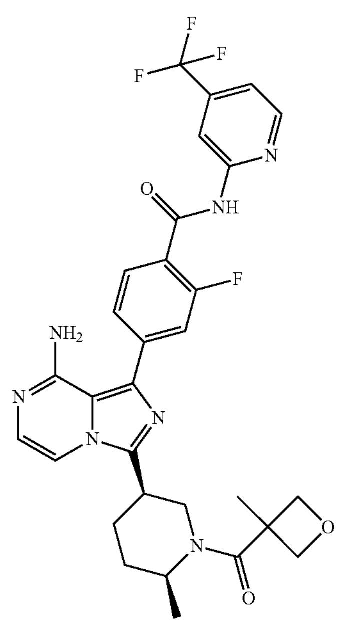 [SMILES: C[C@H]1CC[C@@H](c2nc(-c3ccc(C(=O)Nc4cc(C(F)(F)F)ccn4)c(F)c3)c3c(N)nccn23)CN1C(=O)C1(C)COC1] | 4-(8-amino-3-{(3R,6S)-6-methyl-1-[(3-methyloxetan-3-yl)carbonyl]piperidin-3-yl}imidazo[1,5-a]pyrazin-1-yl)-2-fluoro-N-[4-(trifluoromethyl)pyridin-2-yl]benzamide | Calc'd 612.2, found 612.2 | 2.48 (Method H) |

-continued

| Example | Structure | Name | Exact Mass [M + H]+ | Retention time (min) |
|---|---|---|---|---|
| 477 | 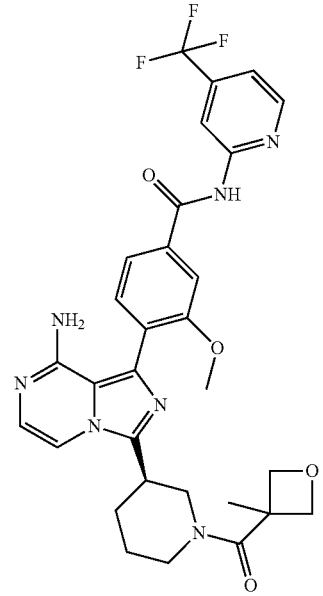 [SMILES: COc1cc(C(=O)Nc2cc(C(F)(F)F)ccn2)ccc1-c1nc([C@@H]2CCCN(C(=O)C3(C)COC3)C2)n2ccnc(N)c12] | 4-(8-amino-3-{(3R)-1-[(3-methyloxetan-3-yl)carbonyl]piperidin-3-yl}imidazo[1,5-a]pyrazin-1-yl)-3-methoxy-N-[4-(trifluoromethyl)pyridin-2-yl]benzamide, TFA salt | Calc'd 610.2, found 610.2 | 2.69 (Method H) |
| 478 | 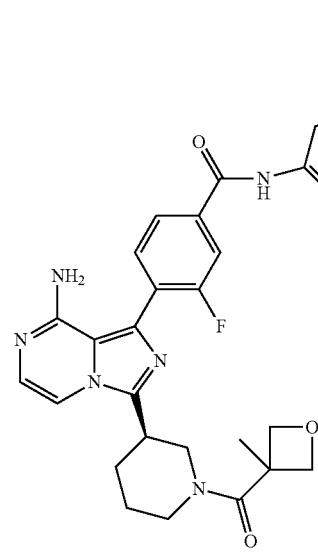 | 4-(8-amino-3-{(3R)-1-[(3-methyloxetan-3-yl)carbonyl]piperidin-3-yl}imidazo[1,5-a]pyrazin-1-yl)-N-[4-(difluoromethoxy)pyridin-2-yl]-3-fluorobenzamide, TFA salt | Calc'd 596.2, found 596.2 | 2.00 (Method H) |

-continued

| Example | Structure | Name | Exact Mass [M + H]+ | Retention time (min) |
|---|---|---|---|---|
| 479 | 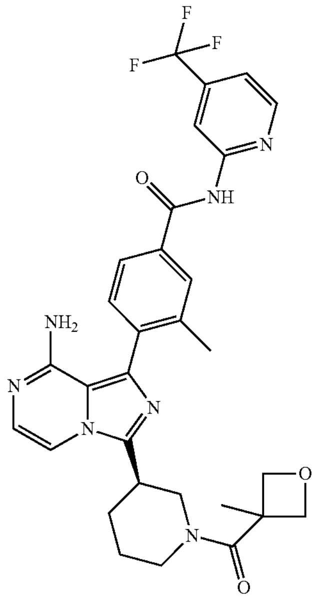 [SMILES: Cc1cc(C(=O)Nc2cc(C(F)(F)F)ccn2)ccc1-c1nc([C@@H]2CCCN(C(=O)C3(C)COC3)C2)n2ccnc(N)c12] | 4-(8-amino-3-{(3R)-1-[(3-methyloxetan-3-yl)carbonyl]piperidin-3-yl}imidazo[1,5-a]pyrazin-1-yl)-3-methyl-N-[4-(trifluoromethyl)pyridin-2-yl]benzamide, TFA salt | Calc'd 594.2, found 594.2 | 2.40 (Method H) |
| 480 | 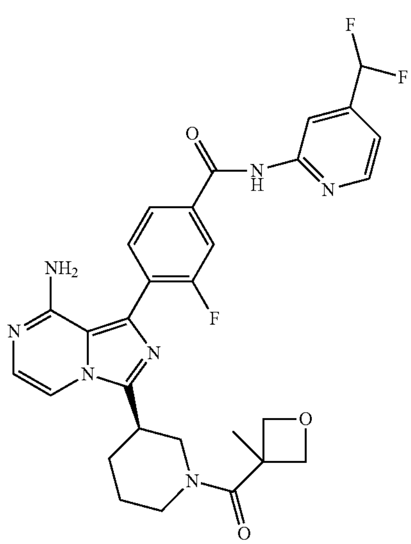 [SMILES: CC1(C(=O)N2CCC[C@@H](c3nc(-c4ccc(C(=O)Nc5cc(C(F)F)ccn5)cc4F)c4c(N)nccn34)C2)COC1] | 4-(8-amino-3-{(3R)-1-[(3-methyloxetan-3-yl)carbonyl]piperidin-3-yl}imidazo[1,5-a]pyrazin-1-yl)-N-[4-(difluoromethyl)pyridin-2-yl]-3-fluorobenzamide, TFA salt | Calc'd 580.2, found 580.2 | 2.55 (Method H) |

| Example | Structure | Name | Exact Mass [M + H]+ | Retention time (min) |
|---|---|---|---|---|
| 481 | 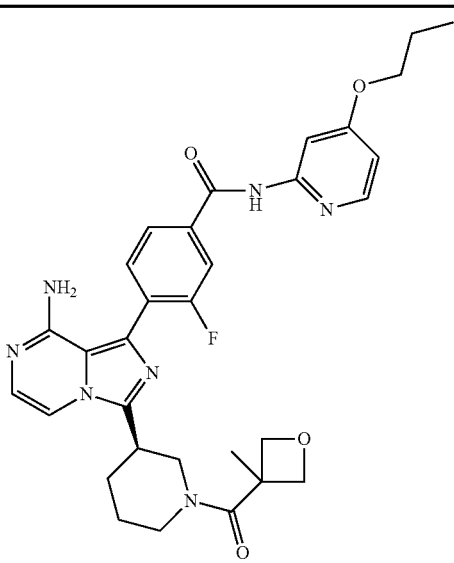 | 4-(8-amino-3-{(3R)-1-[(3-methyloxetan-3-yl)carbonyl]piperidin-3-yl}imidazo[1,5-a]pyrazin-1-yl)-3-fluoro-N-(4-propoxypyridin-2-yl)benzamide, TFA salt | Calc'd 588.3, found 588.3 | 1.78 (Method H) |
| 482 | 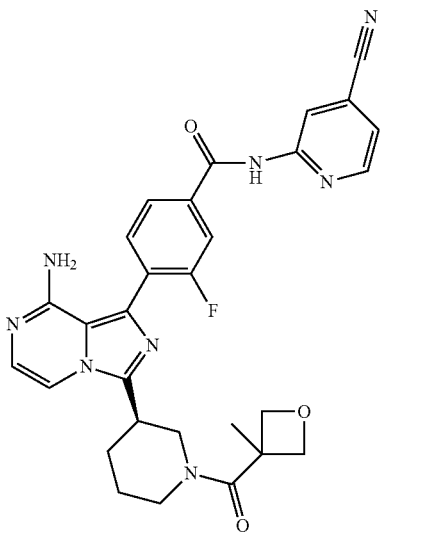 [SMILES: CC1(C(=O)N2CCC[C@@H](c3nc(-c4ccc(C(=O)Nc5cc(C#N)ccn5)cc4F)c4c(N)nccn34)C2)COC1] | 4-(8-amino-3-{(3R)-1-[(3-methyloxetan-3-yl)carbonyl]piperidin-3-yl}imidazo[1,5-a]pyrazin-1-yl)-N-(4-cyanopyridin-2-yl)-3-fluorobenzamide, TFA salt | Calc'd 555.2, found 555.2 | 2.98 (Method H) |

| Example | Structure | Name | Exact Mass [M + H]+ | Retention time (min) |
|---|---|---|---|---|
| 483 | 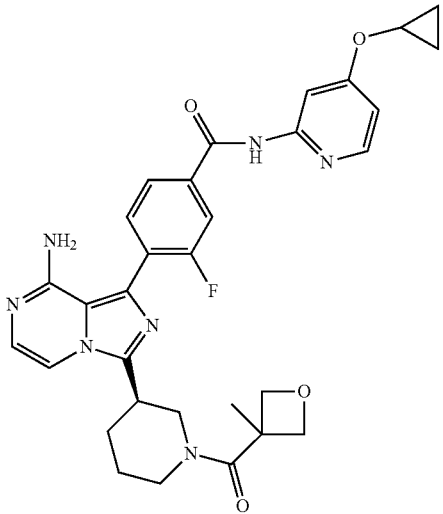 [SMILES: CC1(C(=O)N2CCC[C@@H](c3nc(-c4ccc(C(=O)Nc5cc(OC6CC6)ccn5)cc4F)c4c(N)nccn34)C2)COC1] | 4-(8-amino-3-{(3R)-1-[(3-methyloxetan-3-yl)carbonyl]piperidin-3-yl}imidazo[1,5-a]pyrazin-1-yl)-N-[4-(cyclopropyloxy)pyridin-2-yl]-3-fluorobenzamide, TFA salt | Calc'd 586.3, found 586.3 | 1.98 (Method H) |
| 484 | 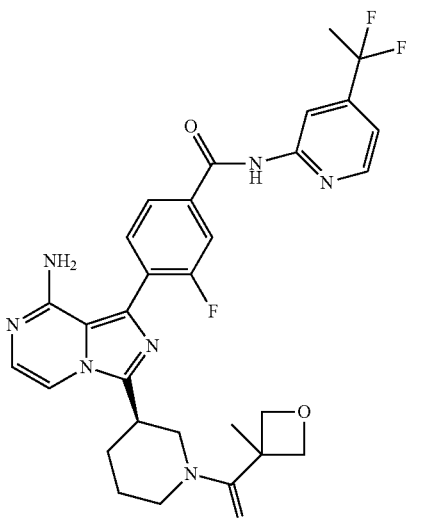 | 4-(8-amino-3-{(3R)-1-[(3-methyloxetan-3-yl)carbonyl]piperidin-3-yl}imidazo[1,5-a]pyrazin-1-yl)-N-[4-(1,1-difluoroethyl)pyridin-2-yl]-3-fluorobenzamide, TFA salt | Calc'd 594.2, found 594.2 | 2.07 (Method H) |

-continued
| Example | Structure | Name | Exact Mass [M + H]+ | Retention time (min) |
|---|---|---|---|---|
| 485 | 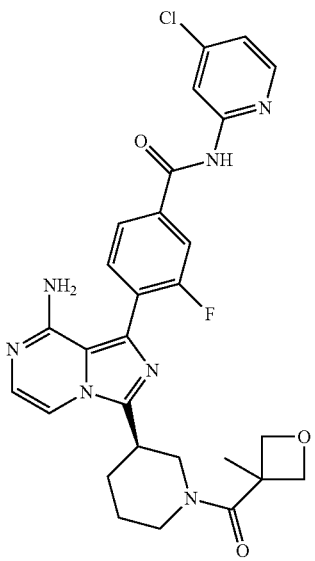 [SMILES: CC1(C(=O)N2CCC[C@@H](c3nc(-c4ccc(C(=O)Nc5cc(Cl)ccn5)cc4F)c4c(N)nccn34)C2)COC1] | 4-(8-amino-3-{(3R)-1-[(3-methyloxetan-3-yl)carbonyl]piperidin-3-yl}imidazo[1,5-a]pyrazin-1-yl)-N-(4-chloropyridin-2-yl)-3-fluorobenzamide, TFA salt | Calc'd 564.2, found 564.2 | 2.31 (Method H) |
| 486 | 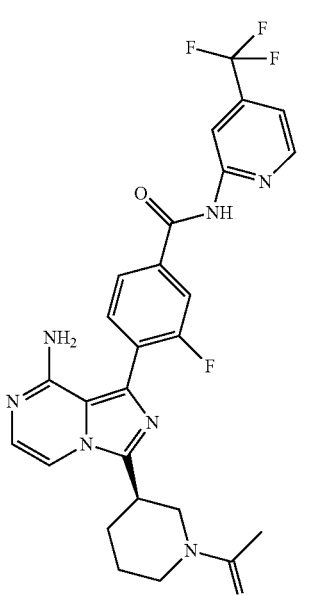 | 4-{3-[(3R)-1-acetylpiperidin-3-yl]-8-aminoimidazo[1,5-a]pyrazin-1-yl}-3-fluoro-N-[4-(trifluoromethyl)pyridin-2-yl]benzamide, TFA salt | Calc'd 542.2, found 542.2 | 2.90 (Method H) |

| Example | Structure | Name | Exact Mass [M + H]+ | Retention time (min) |
|---|---|---|---|---|
| 487 | 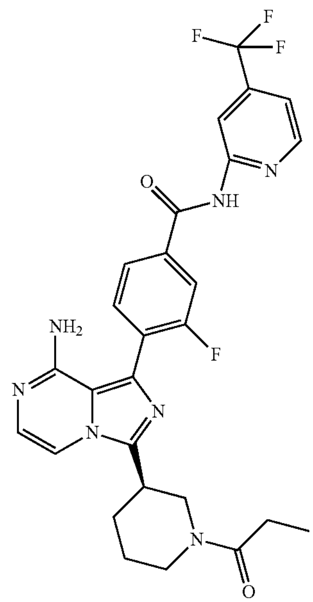 [SMILES: CCC(=O)N1CCC[C@@H](c2nc(-c3ccc(C(=O)Nc4cc(C(F)(F)F)ccn4)cc3F)c3c(N)nccn23)C1] | 4-{8-amino-3-[(3R)-1-propanoylpiperidin-3-yl]imidazo[1,5-a]pyrazin-1-yl}-3-fluoro-N-[4-(trifluoromethyl)pyridin-2-yl]benzamide, TFA salt | Calc'd 556.2, found 556.2 | 2.77 (Method H) |
| 488 | 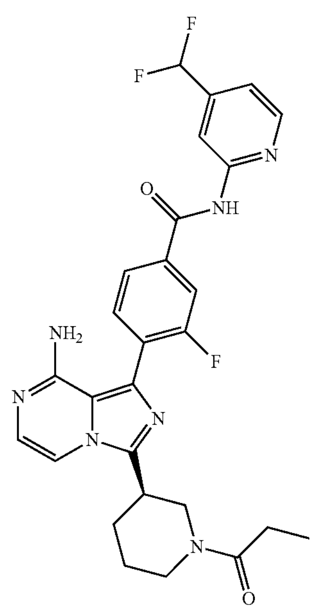 [SMILES: CCC(=O)N1CCC[C@@H](c2nc(-c3ccc(C(=O)Nc4cc(C(F)F)ccn4)cc3F)c3c(N)nccn23)C1] | 4-{8-amino-3-[(3R)-1-propanoylpiperidin-3-yl]imidazo[1,5-a]pyrazin-1-yl}-N-[4-(difluoromethyl)pyridin-2-yl]-3-fluorobenzamide, TFA salt | Calc'd 538.2, found 538.2 | 2.41 (Method H) |

-continued

| Example | Structure | Name | Exact Mass [M + H]⁺ | Retention time (min) |
|---|---|---|---|---|
| 489 | 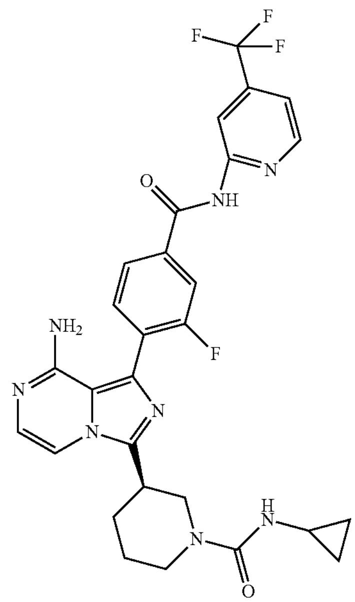 [SMILES: Nc1nccn2c([C@@H]3CCCN(C(=O)NC4CC4)C3)nc(-c3ccc(C(=O)Nc4cc(C(F)(F)F)ccn4)cc3F)c12] | (3R)-3-[8-amino-1-(2-fluoro-4-{[4-(trifluoromethyl)pyridin-2-yl]carbamoyl}phenyl)imidazo[1,5-a]pyrazin-3-yl]-N-cyclopropylpiperidine-1-carboxamide, TFA salt | Calc'd 583.2, found | 2.52 (Method H) |
| 490 | 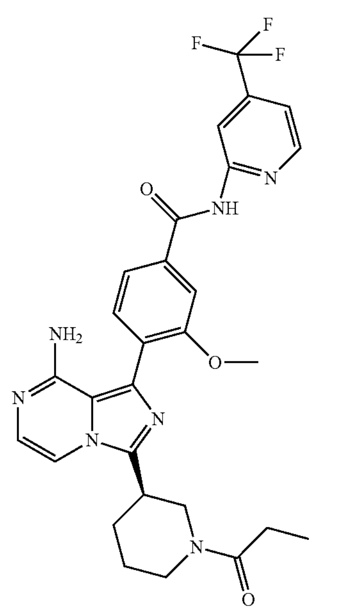 [SMILES: CCC(=O)N1CCC[C@@H](c2nc(-c3ccc(C(=O)Nc4cc(C(F)(F)F)ccn4)cc3OC)c3c(N)nccn23)C1] | 4-{8-amino-3-[(3R)-1-propanoylpiperidin-3-yl]imidazo[1,5-a]pyrazin-1-yl}-3-methoxy-N-[4-(trifluoromethyl)pyridin-2-yl]benzamide, TFA salt | Calc'd 568.2, found 568.2 | 3.30 (Method H) |

Example 491 and 492

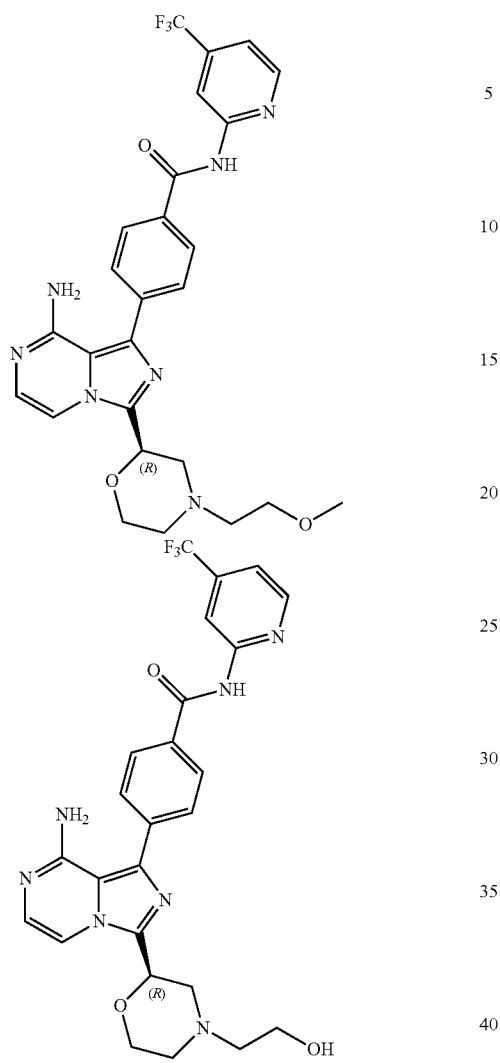

(R)-4-(8-amino-3-(4-(2-methoxyethyl)morpholin-2-yl)imidazo[1,5-a]pyrazin-1-yl)-N-(4-(trifluoromethyl)pyridin-2-yl)benzamide and (R)-4-(8-amino-3-(4-(2-hydroxyethyl)morpholin-2-yl)imidazo[1,5-a]pyrazin-1-yl)-N-(4-(trifluoromethyl)pyridin-2-yl)benzamide (R)-4-(8-amino-3-(morpholin-2-yl)imidazo[1,5-a]pyrazin-1-yl)-N-(4-(trifluoromethyl)pyridin-2-yl)benzamide (50 mg, 0.103 mmol) was dissolved in 2 mL of THF, 1-bromo-2-methoxyethane (43.1 mg, 0.310 mmol) was then added followed by N-ethyl-N-isopropylpropan-2-amine (40.1 mg, 0.310 mmol). The reaction mixture was stirred at 50° C. overnight. The mixture was concentrated to dryness and purified by reverse phase chromatography (CH$_3$CN:TFA:H$_2$O) to give (R)-4-(8-amino-3-(4-(2-methoxyethyl)morpholin-2-yl)imidazo[1,5-a]pyrazin-1-yl)-N-(4-(trifluoromethyl)pyridin-2-yl)benzamide (11 mg) (LC-MS (ESI), [M+H]$^+$: calc 542.2, found 542.2) and (R)-4-(8-amino-3-(4-(2-hydroxyethyl)morpholin-2-yl)imidazo[1,5-a]pyrazin-1-yl)-N-(4-(trifluoromethyl)pyridin-2-yl)benzamide (10 mg) (LC-MS (ESI), [M+H]$^+$: calc 528.2, 528.2) as white solids in their TFA salt forms.

| Example | Structure | Name | Exact Mass [M + H]+ | Retention time (min) |
|---|---|---|---|---|
| 493 | 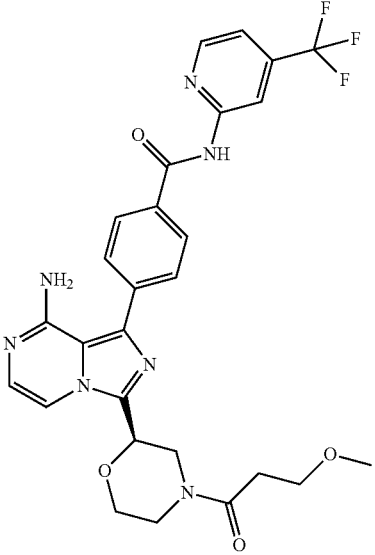 [SMILES: COCCC(=O)N1CCO[C@@H](c2nc(-c3ccc(C(=O)Nc4cc(C(F)(F)F)ccn4)cc3)c3c(N)nccn23)C1] | 4-{8-amino-3-[(2R)-4-(3-methoxypropanoyl)morpholin-2-yl]imidazo[1,5-a]pyrazin-1-yl}-N-[4-(trifluoromethyl)pyridin-2-yl]benzamide | Calc'd 570.2, found 570.0 | 2.016 (Method M) |
| 494 | 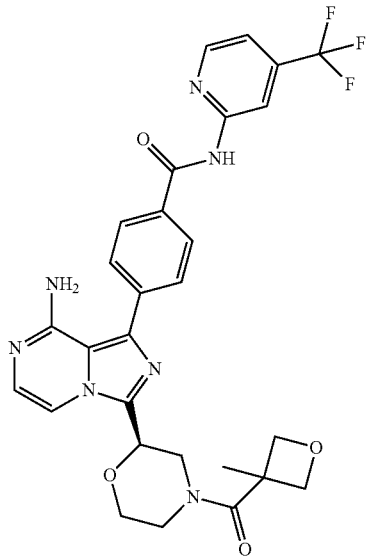 [SMILES: CC1(C(=O)N2CCO[C@@H](c3nc(-c4ccc(C(=O)Nc5cc(C(F)(F)F)ccn5)cc4)c4c(N)nccn34)C2)COC1] | 4-(8-amino-3-{(2R)-4-[(3-methyloxetan-3-yl)carbonyl]morpholin-2-yl}imidazo[1,5-a]pyrazin-1-yl)-N-[4-(trifluoromethyl)pyridin-2-yl]benzamide | Calc'd 582.2, found 582.0 | 1.804 (Method M) |

| Example | Structure | Name | Exact Mass [M + H]+ | Retention time (min) |
|---|---|---|---|---|
| 495 | 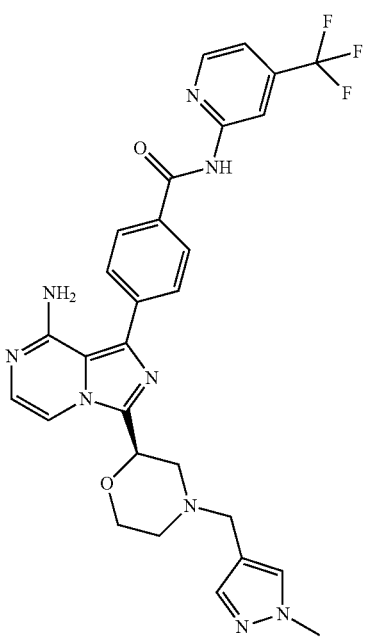 [SMILES: Cn1cc(CN2CCO[C@@H](c3nc(-c4ccc(C(=O)Nc5cc(C(F)(F)F)ccn5)cc4)c4c(N)nccn34)C2)cn1] | 4-(8-amino-3-{(2R)-4-[(1-methyl-1H-pyrazol-4-yl)methyl]morpholin-2-yl}imidazo[1,5-a]pyrazin-1-yl)-N-[4-(trifluoromethyl)pyridin-2-yl]benzamide | Calc'd 578.2, found 578.0 | 1.690 (Method M) |
| 496 | 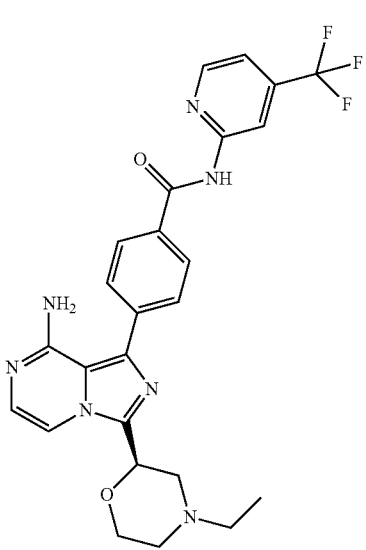 [SMILES: CCN1CCO[C@@H](c2nc(-c3ccc(C(=O)Nc4cc(C(F)(F)F)ccn4)cc3)c3c(N)nccn23)C1] | 4-{8-amino-3-[(2R)-4-ethylmorpholin-2-yl]imidazo[1,5-a]pyrazin-1-yl}-N-[4-(trifluoromethyl)pyridin-2-yl]benzamide | Calc'd 512.2, found 512.2 | 1.714 (Method M) |

| Example | Structure | Name | Exact Mass [M + H]+ | Retention time (min) |
|---|---|---|---|---|
| 497 | 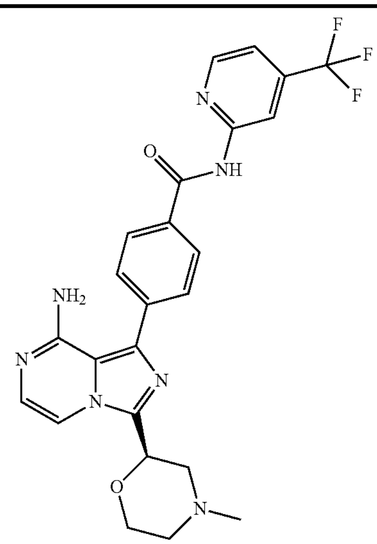 | 4-{8-amino-3-[(2R)-4-methylmorpholin-2-yl]imidazo[1,5-a]pyrazin-1-yl}-N-[4-(trifluoromethyl)pyridin-2-yl]benzamide | Calc'd 498.2, found 498.0 | 1.645 (Method M) |
| 498 | 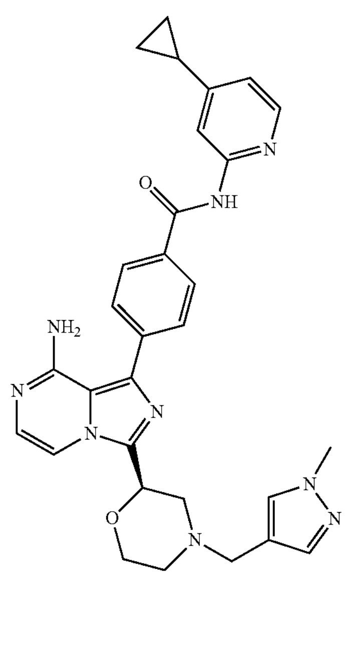 [SMILES: Cn1cc(CN2CCO[C@@H](c3nc(-c4ccc(C(=O)Nc5cc(C6CC6)ccn5)cc4)c4c(N)nccn34)C2)cn1] | 4-(8-amino-3-{(2R)-4-[(1-methyl-1H-pyrazol-4-yl)methyl]morpholin-2-yl}imidazo[1,5-a]pyrazin-1-yl)-N-(4-cyclopropylpyridin-2-yl)benzamide | Calc'd 550.3, found 550.0 | 1.368 (Method M) |

| Example | Structure | Name | Exact Mass [M + H]+ | Retention time (min) |
|---|---|---|---|---|
| 499 | 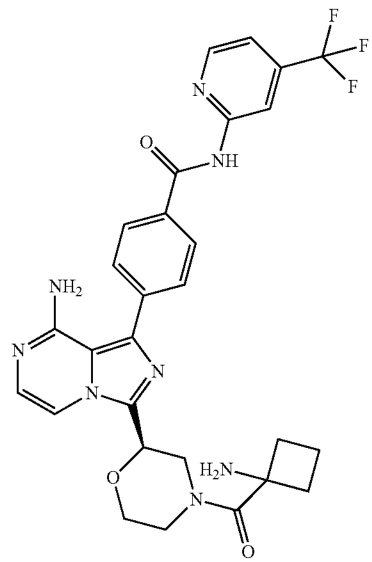 [SMILES: Nc1nccn2c([C@H]3CN(C(=O)C4(N)CCC4)CCO3)nc(-c3ccc(C(=O)Nc4cc(C(F)(F)F)ccn4)cc3)c12] | 4-(8-amino-3-{(2R)-4-[(1-aminocyclobutyl)carbonyl]morpholin-2-yl}imidazo[1,5-a]pyrazin-1-yl)-N-[4-(trifluoromethyl)pyridin-2-yl]benzamide | Calc'd 581.2, found 581.0 | 1.667 (Method M) |
| 500 | 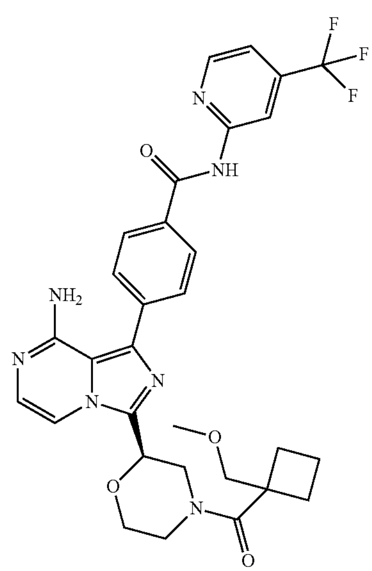 [SMILES: COCC1(C(=O)N2CCO[C@@H](c3nc(-c4ccc(C(=O)Nc5cc(C(F)(F)F)ccn5)cc4)c4c(N)nccn34)C2)CCC1] | 4-{8-amino-3-[(2R)-4-{[1-(methoxymethyl)cyclobutyl]carbonyl}morpholin-2-yl]imidazo[1,5-a]pyrazin-1-yl}-N-[4-(trifluoromethyl)pyridin-2-yl]benzamide | Calc'd 610.2, found 610.0 | 1.936 (Method M) |

-continued

| Example | Structure | Name | Exact Mass [M + H]+ | Retention time (min) |
|---|---|---|---|---|
| 501 | 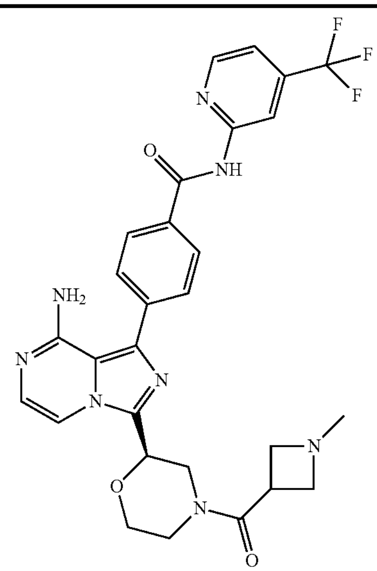 | 4-(8-amino-3-{(2R)-4-[(1-methylazetidin-3-yl)carbonyl]morpholin-2-yl}imidazo[1,5-a]pyrazin-1-yl)-N-[4-(trifluoromethyl)pyridin-2-yl]benzamide | Calc'd 581.2, found 581.0 | 1.672 (Method M) |
| 502 | 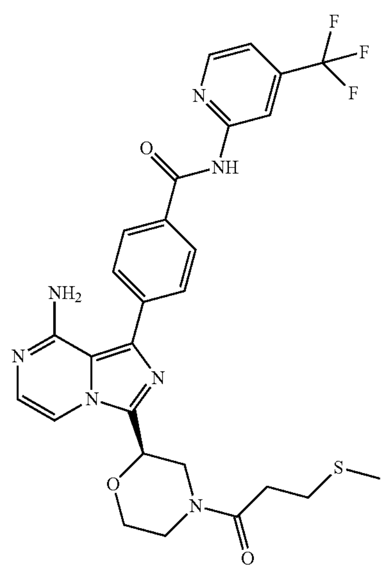 [SMILES: CSCCC(=O)N1CCO[C@@H](c2nc(-c3ccc(C(=O)Nc4cc(C(F)(F)F)ccn4)cc3)c3c(N)nccn23)C1] | 4-(8-amino-3-{(2R)-4-[3-(methylsulfanyl)propanoyl]morpholin-2-yl}imidazo[1,5-a]pyrazin-1-yl)-N-[4-(trifluoromethyl)pyridin-2-yl]benzamide | Calc'd 586.2, found 586.0 | 1.886 (Method M) |
| 503 | 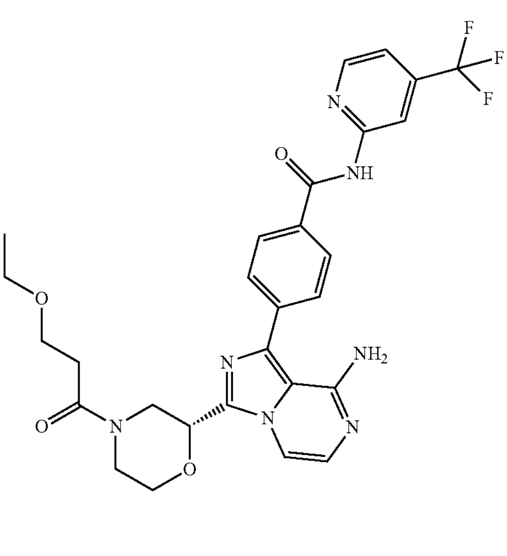 [SMILES: CCOCCC(=O)N1CCO[C@@H](c2nc(-c3ccc(C(=O)Nc4cc(C(F)(F)F)ccn4)cc3)c3c(N)nccn23)C1] | 4-{8-amino-3-[(2R)-4-(3-ethoxypropanoyl)morpholin-2-yl]imidazo[1,5-a]pyrazin-1-yl}-N-[4-(trifluoromethyl)pyridin-2-yl]benzamide | Calc'd 584.2, found 584.0 | 1.862 (Method M) |

| Example | Structure | Name | Exact Mass [M + H]+ | Retention time (min) |
|---|---|---|---|---|
| 504 | 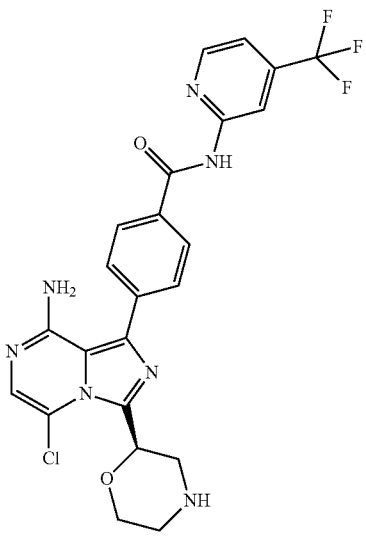 [SMILES: Nc1ncc(Cl)n2c([C@H]3CNCCO3)nc(-c3ccc(C(=O)Nc4cc(C(F)(F)F)ccn4)cc3)c12] | 4-{8-amino-5-chloro-3-[(2R)-morpholin-2-yl]imidazo[1,5-a]pyrazin-1-yl}-N-[4-(trifluoromethyl)pyridin-2-yl]benzamide | Calc'd 518.1, found 518.0 | 1.689 (Method M) |
| 505 | 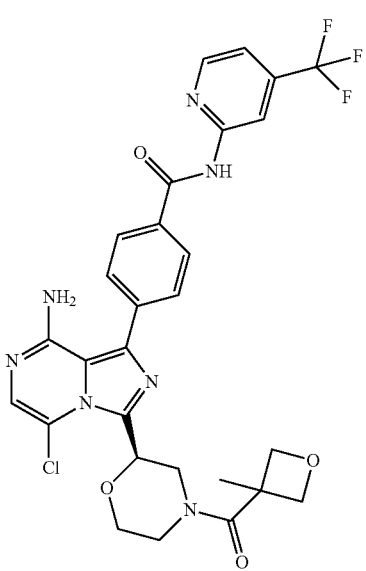 [SMILES: Cc1cnc(N)c2c(-c3ccc(C(=O)Nc4cc(C(F)(F)F)ccn4)cc3)nc([C@H]3CN(C(=O)C4(C)COC4)CCO3)n12] | 4-(8-amino-5-chloro-3-{(2R)-4-[(3-methyloxetan-3-yl)carbonyl]morpholin-2-yl}imidazo[1,5-a]pyrazin-1-yl)-N-[4-(trifluoromethyl)pyridin-2-yl]benzamide | Calc'd 616.2, found 616.0 | 1.853 (Method M) |

-continued

| Example | Structure | Name | Exact Mass [M + H]+ | Retention time (min) |
|---|---|---|---|---|
| 506 | 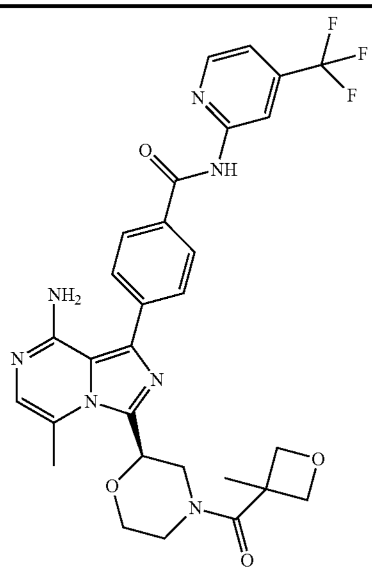 | 4-(8-amino-5-methyl-3-{(2R)-4-[(3-methyloxetan-3-yl)carbonyl]morpholin-2-yl}imidazo[1,5-a]pyrazin-1-yl)-N-[4-(trifluoromethyl)pyridin-2-yl]benzamide | Calc'd 596.2, found 596.0 | 1.837 (Method M) |
| 507 | 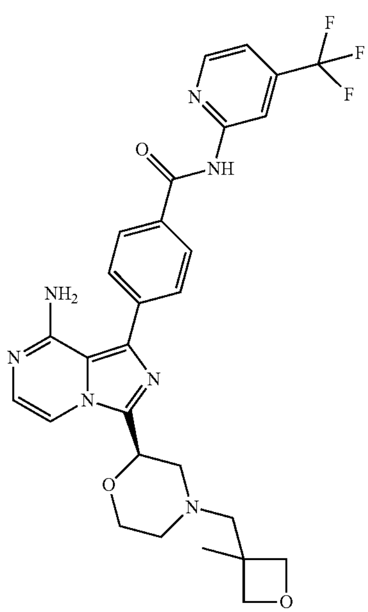 [SMILES: CC1(CN2CCO[C@@H](c3nc(-c4ccc(C(=O)Nc5cc(C(F)(F)F)ccn5)cc4)c4c(N)nccn34)C2)COC1] | 4-(8-amino-3-{(2R)-4-[(3-methyloxetan-3-yl)methyl]morpholin-2-yl}imidazo[1,5-a]pyrazin-1-yl)-N-[4-(trifluoromethyl)pyridin-2-yl]benzamide | Calc'd 568.2, found 568.0 | 1.703 (Method M) |

-continued
| Example | Structure | Name | Exact Mass [M + H]+ | Retention time (min) |
|---|---|---|---|---|
| 508 | 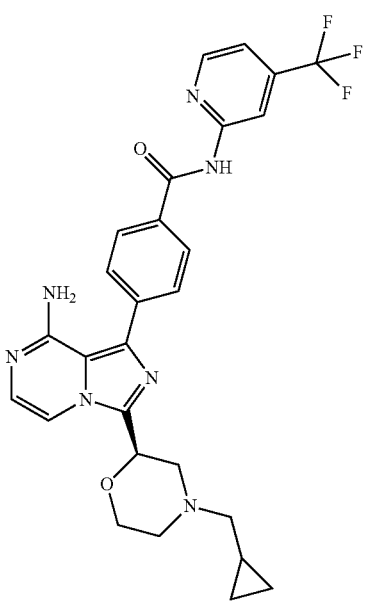 [SMILES: Nc1nccn2c([C@H]3CN(CC4CC4)CCO3)nc(-c3ccc(C(=O)Nc4cc(C(F)(F)F)ccn4)cc3)c12] | 4-{8-amino-3-[(2R)-4-(cyclopropylmethyl)morpholin-2-yl]imidazo[1,5-a]pyrazin-1-yl}-N-[4-(trifluoromethyl)pyridin-2-yl]benzamide | Calc'd 538.2, found 538.0 | 1.740 (Method M) |
| 509 | 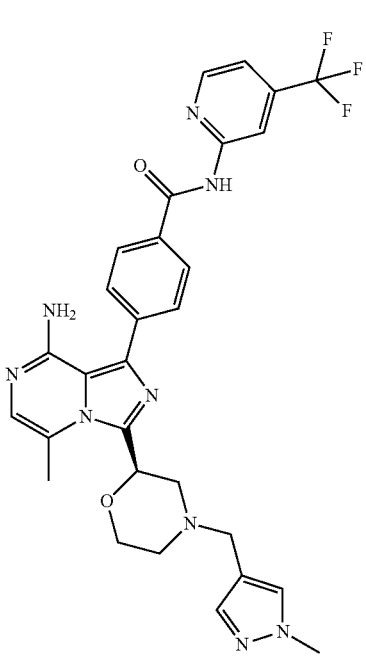 [SMILES: Cc1cnc(N)c2c(-c3ccc(C(=O)Nc4cc(C(F)(F)F)ccn4)cc3)nc([C@H]3CN(Cc4cnn(C)c4)CCO3)n12] | 4-(8-amino-5-methyl-3-{(2R)-4-[(1-methyl-1H-pyrazol-4-yl)methyl]morpholin-2-yl}imidazo[1,5-a]pyrazin-1-yl)-N-[4-(trifluoromethyl)pyridin-2-yl]benzamide | Calc'd 592.2, found 592.0 | 1.714 (Method M) |

| Example | Structure | Name | Exact Mass [M + H]+ | Retention time (min) |
|---|---|---|---|---|
| 510 | 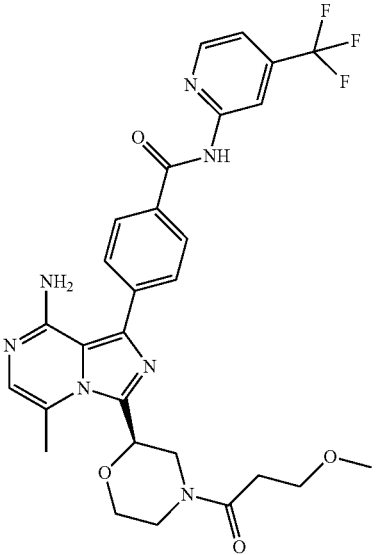 [SMILES: COCCC(=O)N1CCO[C@@H](c2nc(-c3ccc(C(=O)Nc4cc(C(F)(F)F)ccn4)cc3)c3c(N)ncc(C)n23)C1] | 4-{8-amino-3-[(2R)-4-(3-methoxypropanoyl)morpholin-2-yl]-5-methylimidazo[1,5-a]pyrazin-1-yl}-N-[4-(trifluoromethyl)pyridin-2-yl]benzamide | Calc'd 584.2, found 584.0 | 1.849 (Method M) |
| 511 | 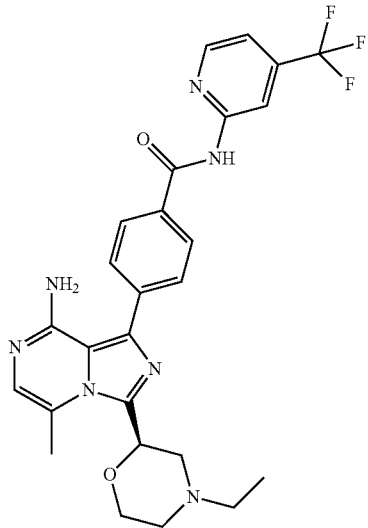 [SMILES: CCN1CCO[C@@H](c2nc(-c3ccc(C(=O)Nc4cc(C(F)(F)F)ccn4)cc3)c3c(N)ncc(C)n23)C1] | 4-{8-amino-3-[(2R)-4-ethylmorpholin-2-yl]-5-methylimidazo[1,5-a]pyrazin-1-yl}-N-[4-(trifluoromethyl)pyridin-2-yl]benzamide | Calc'd 526.2, found 526.2 | 1.772 (Method M) |

-continued

| Example | Structure | Name | Exact Mass [M + H]⁺ | Retention time (min) |
|---|---|---|---|---|
| 512 | 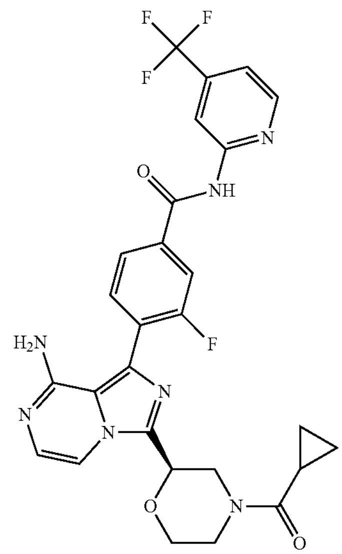 [SMILES: Nc1nccn2c([C@H]3CN(C(=O)C4CC4)CCO3)nc(-c3ccc(C(=O)Nc4cc(C(F)(F)F)ccn4)cc3F)c12] | 4-{8-amino-3-[(2R)-4-(cyclopropylcarbonyl)morpholin-2-yl]imidazo[1,5-a]pyrazin-1-yl}-3-fluoro-N-[4-(trifluoromethyl)pyridin-2-yl]benzamide, TFA salt | Calc'd 570.2, found 570.2 | 0.90 min (Method Q) |
| 513 | 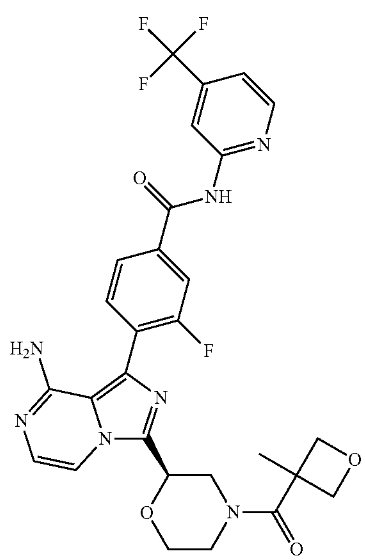 [SMILES: CC1(C(=O)N2CCO[C@@H](c3nc(-c4ccc(C(=O)Nc5cc(C(F)(F)F)ccn5)cc4F)c4c(N)nccn34)C2)COC1] | 4-(8-amino-3-{(2R)-4-[(3-methyloxetan-3-yl)carbonyl]morpholin-2-yl}imidazo[1,5-a]pyrazin-1-yl)-3-fluoro-N-[4-(trifluoromethyl)pyridin-2-yl]benzamide, TFA salt | Calc'd 600.2, found 600.2 | 2.43 (Method H) |

-continued

| Example | Structure | Name | Exact Mass [M + H]+ | Retention time (min) |
|---|---|---|---|---|
| 514 | 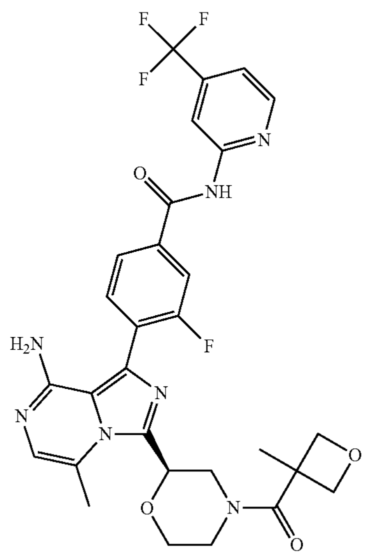 [SMILES: Cc1cnc(N)c2c(-c3ccc(C(=O)Nc4cc(C(F)(F)F)ccn4)cc3F)nc([C@H]3CN(C(=O)C4(C)COC4)CCO3)n12] | 4-(8-amino-5-methyl-3-{(2R)-4-[(3-methyloxetan-3-yl)carbonyl]morpholin-2-yl}imidazo[1,5-a]pyrazin-1-yl)-3-fluoro-N-[4-(trifluoromethyl)pyridin-2-yl]benzamide | Calc'd 614.2, found 614.3 | 2.25 (Method H) |
| 515 | 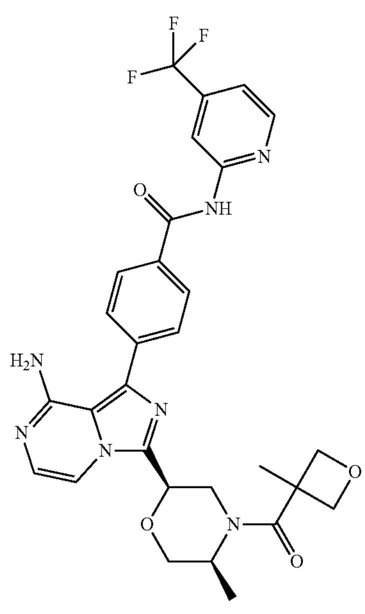 [SMILES: C[C@H]1CO[C@@H](c2nc(-c3ccc(C(=O)Nc4cc(C(F)(F)F)ccn4)cc3)c3c(N)nccn23)CN1C(=O)C1(C)COC1] | 4-(8-amino-3-{(2R,5S)-5-methyl-4-[(3-methyloxetan-3-yl)carbonyl]morpholin-2-yl}imidazo[1,5-a]pyrazin-1-yl)-N-[4-(trifluoromethyl)pyridin-2-yl]benzamide, TFA salt | Calc'd 596.2, found 596.3 | 2.24 (Method H) |

| Example | Structure | Name | Exact Mass [M + H]+ | Retention time (min) |
|---|---|---|---|---|
| 516 | 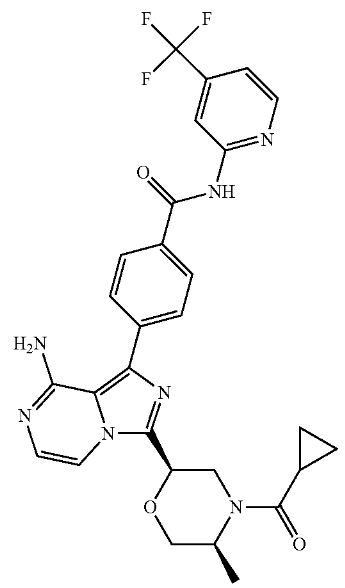 [SMILES: C[C@H]1CO[C@@H](c2nc(-c3ccc(C(=O)Nc4cc(C(F)(F)F)ccn4)cc3)c3c(N)nccn23)CN1C(=O)C1CC1] | 4-{8-amino-3-[(2R,5S)-4-(cyclopropylcarbonyl)-5-methylmorpholin-2-yl]imidazo[1,5-a]pyrazin-1-yl}-N-[4-(trifluoromethyl)pyridin-2-yl]benzamide, TFA salt | Calc'd 566.2, found 566.3 | 2.57 (Method H) |
| 517 | 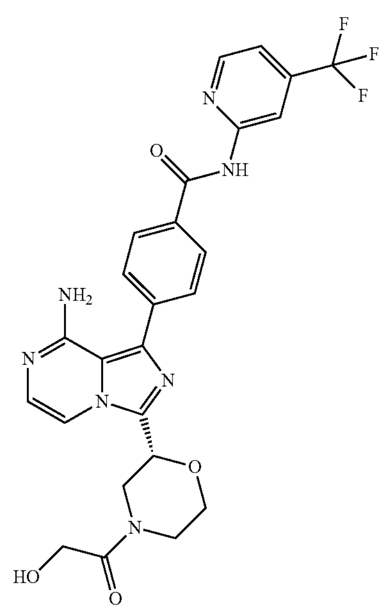 [SMILES: Nc1nccn2c([C@H]3CN(C(=O)CO)CCO3)nc(-c3ccc(C(=O)Nc4cc(C(F)(F)F)ccn4)cc3)c12] | 4-{8-amino-3-[(2R)-4-(hydroxyacetyl)morpholin-2-yl]imidazo[1,5-a]pyrazin-1-yl}-N-[4-(trifluoromethyl)pyridin-2-yl]benzamide | Calc'd 542.2, found 542.17 | 0.79 (Method Q) |

| Example | Structure | Name | Exact Mass [M + H]+ | Retention time (min) |
|---------|-----------|------|---------------------|----------------------|
| 518 | 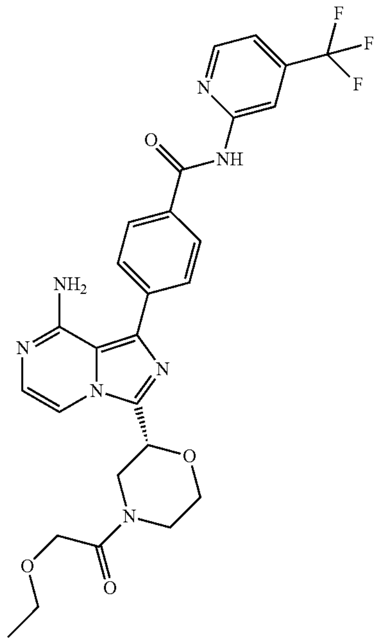 [SMILES: CCOCC(=O)N1CCO[C@@H](c2nc(-c3ccc(C(=O)Nc4cc(C(F)(F)F)ccn4)cc3)c3c(N)nccn23)C1] | 4-{8-amino-3-[(2R)-4-(ethoxyacetyl)morpholin-2-yl]imidazo[1,5-a]pyrazin-1-yl}-N-[4-(trifluoromethyl)pyridin-2-yl]benzamide | Calc'd 570.2, found 570.2 | 0.88 (Method Q) |
| 519 | 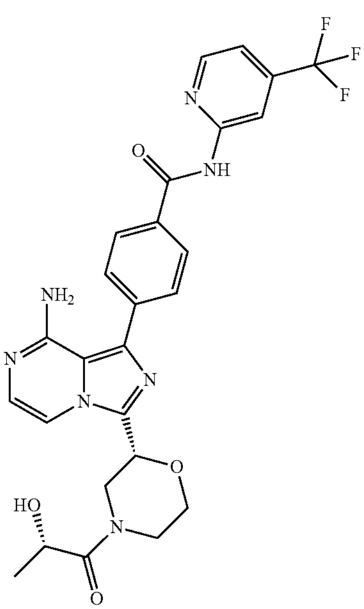 [SMILES: C[C@H](O)C(=O)N1CCO[C@@H](c2nc(-c3ccc(C(=O)Nc4cc(C(F)(F)F)ccn4)cc3)c3c(N)nccn23)C1] | 4-(8-amino-3-{(2R)-4-[(2S)-2-hydroxypropanoyl]morpholin-2-yl}imidazo[1,5-a]pyrazin-1-yl)-N-[4-(trifluoromethyl)pyridin-2-yl]benzamide | Calc'd 556.2, found 556.18 | 0.81 (Method Q) |

| Example | Structure | Name | Exact Mass [M + H]+ | Retention time (min) |
|---|---|---|---|---|
| 520 | 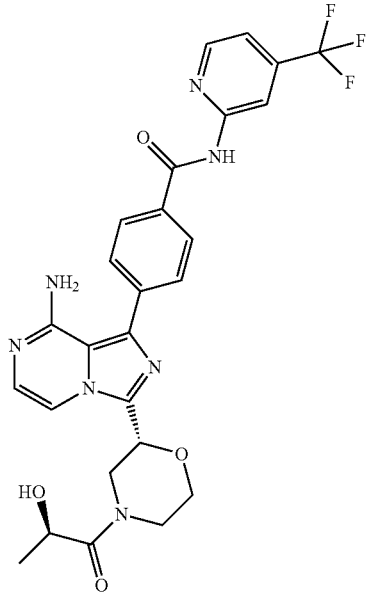 [SMILES: C[C@@H](O)C(=O)N1CCO[C@@H](c2nc(-c3ccc(C(=O)Nc4cc(C(F)(F)F)ccn4)cc3)c3c(N)nccn23)C1] | 4-(8-amino-3-{(2R)-4-[(2R)-2-hydroxypropanoyl]morpholin-2-yl}imidazo[1,5-a]pyrazin-1-yl)-N-[4-(trifluoromethyl)pyridin-2-yl]benzamide | Calc'd 556.2, found 556.18 | 0.81 (Method Q) |
| 521 | 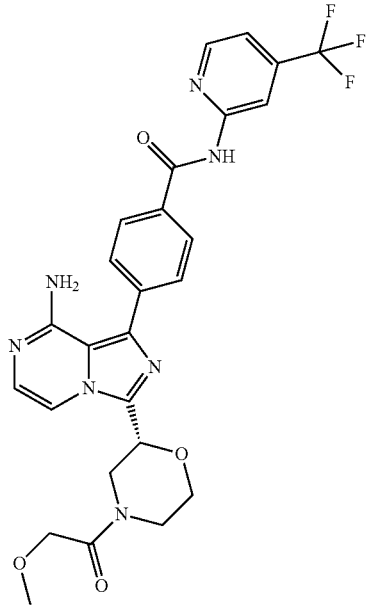 [SMILES: COCC(=O)N1CCO[C@@H](c2nc(-c3ccc(C(=O)Nc4cc(C(F)(F)F)ccn4)cc3)c3c(N)nccn23)C1] | 4-{8-amino-3-[(2R)-4-(methoxyacetyl)morpholin-2-yl]imidazo[1,5-a]pyrazin-1-yl}-N-[4-(trifluoromethyl)pyridin-2-yl]benzamide | Calc'd 556.2, found 556.18 | 0.81 (Method Q) |

-continued
| Example | Structure | Name | Exact Mass [M + H]+ | Retention time (min) |
|---|---|---|---|---|
| 522 | 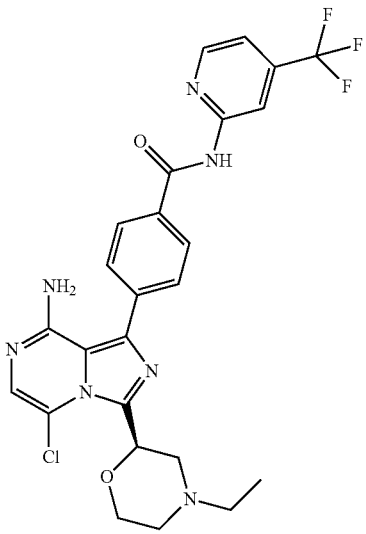 [SMILES: CCN1CCO[C@@H](c2nc(-c3ccc(C(=O)Nc4cc(C(F)(F)F)ccn4)cc3)c3c(N)ncc(Cl)n23)C1] | 4-{8-amino-5-chloro-3-[(2R)-4-ethylmorpholin-2-yl]imidazo[1,5-a]pyrazin-1-yl}-N-[4-(trifluoromethyl)pyridin-2-yl]benzamide | Calc'd 546.2, found 546.1 | 1.04 (Method P) |
| 523 | 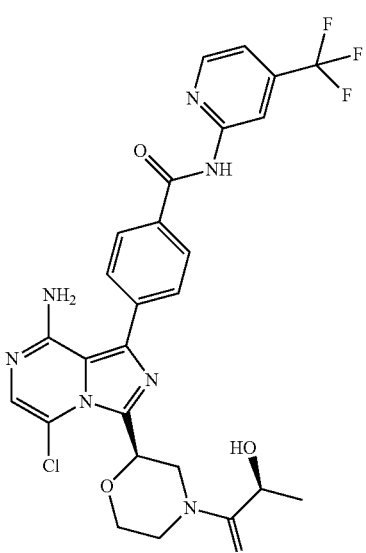 | 4-(8-amino-5-chloro-3-{(2R)-4-[(2S)-2-hydroxypropanoyl]morpholin-2-yl}imidazo[1,5-a]pyrazin-1-yl)-N-[4-(trifluoromethyl)pyridin-2-yl]benzamide | Calc'd 590.2, found 590.1 | 1.07 (Method P) |

-continued
| Example | Structure | Name | Exact Mass [M + H]⁺ | Retention time (min) |
|---------|-----------|------|---------------------|----------------------|
| 524 | 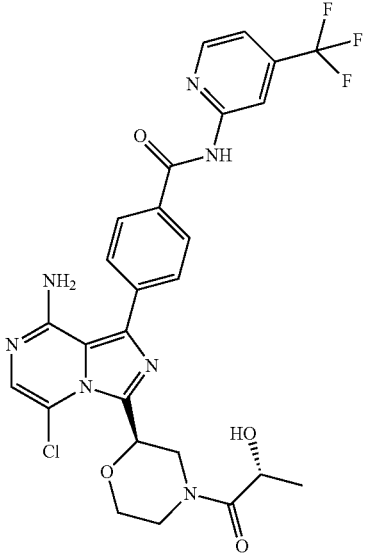 [SMILES: C[C@@H](O)C(=O)N1CCO[C@@H](c2nc(-c3ccc(C(=O)Nc4cc(C(F)(F)F)ccn4)cc3)c3c(N)ncc(Cl)n23)C1] | 4-(8-amino-5-chloro-3-{(2R)-4-[(2R)-2-hydroxypropanoyl]morpholin-2-yl}imidazo[1,5-a]pyrazin-1-yl)-N-[4-(trifluoromethyl)pyridin-2-yl]benzamide | Calc'd 590.2, found 590.1 | 1.16 (Method P) |
| 525 | 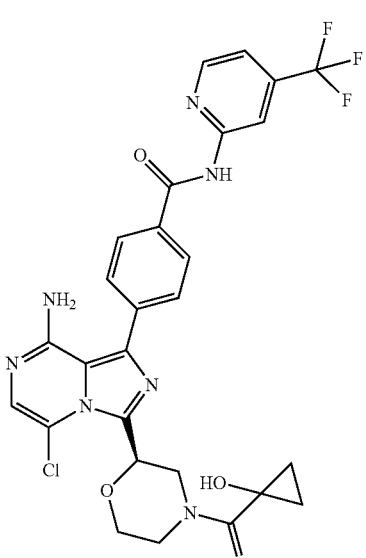 | 4-(8-amino-5-chloro-3-{(2R)-4-[(1-hydroxycyclopropyl)carbonyl]morpholin-2-yl}imidazo[1,5-a]pyrazin-1-yl)-N-[4-(trifluoromethyl)pyridin-2-yl]benzamide | Calc'd 602.2, found 602.1 | 1.09 (Method P) |

-continued
| Example | Structure | Name | Exact Mass [M + H]+ | Retention time (min) |
|---|---|---|---|---|
| 526 | 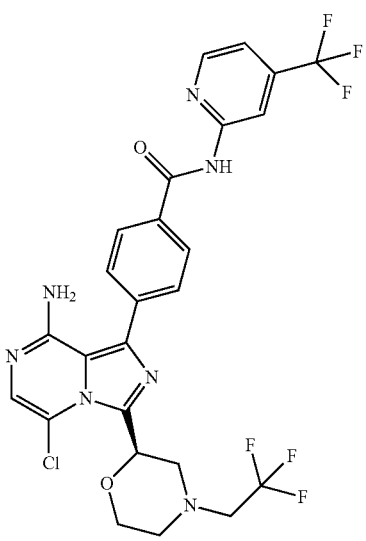 [SMILES: Nc1ncc(Cl)n2c([C@H]3CN(CC(F)(F)F)CCO3)nc(-c3ccc(C(=O)Nc4cc(C(F)(F)F)ccn4)cc3)c12] | 4-{8-amino-5-chloro-3-[(2R)-4-(2,2,2-trifluoroethyl)morpholin-2-yl]imidazo[1,5-a]pyrazin-1-yl}-N-[4-(trifluoromethyl)pyridin-2-yl]benzamide | Calc'd 600.1, found 600.2 | 1.16 (Method P) |
| 527 | 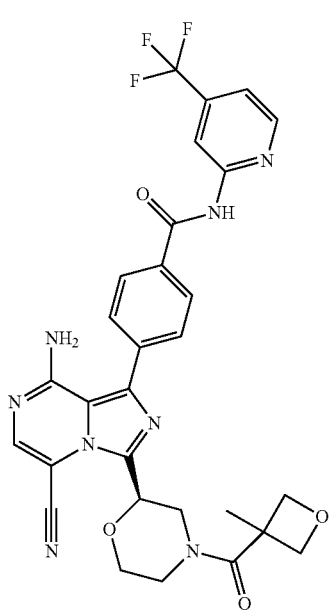 [SMILES: CC1(C(=O)N2CCO[C@@H](c3nc(-c4ccc(C(=O)Nc5cc(C(F)(F)F)ccn5)cc4)c4c(N)ncc(C#N)n34)C2)COC1] | 4-(8-amino-5-cyano-3-{(2R)-4-[(3-methyloxetan-3-yl)carbonyl]morpholin-2-yl}imidazo[1,5-a]pyrazin-1-yl)-N-[4-(trifluoromethyl)pyridin-2-yl]benzamide | Calc'd 607.2, found 607.2 | 2.78 (Method H) |

-continued
| Example | Structure | Name | Exact Mass [M + H]+ | Retention time (min) |
|---|---|---|---|---|
| 528 | 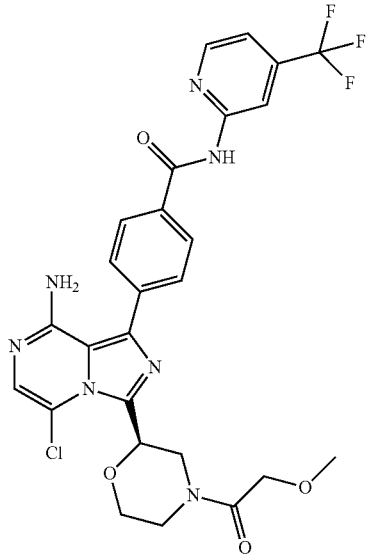 [SMILES: COCC(=O)N1CCO[C@@H](c2nc(-c3ccc(C(=O)Nc4cc(C(F)(F)F)ccn4)cc3)c3c(N)ncc(Cl)n23)C1] | 4-{8-amino-5-chloro-3-[(2R)-4-(methoxyacetyl)morpholin-2-yl]imidazo[1,5-a]pyrazin-1-yl}-N-[4-(trifluoromethyl)pyridin-2-yl]benzamide | Calc'd 590.2, found 590.2 | 1.53 (Method O) |
| 529 | 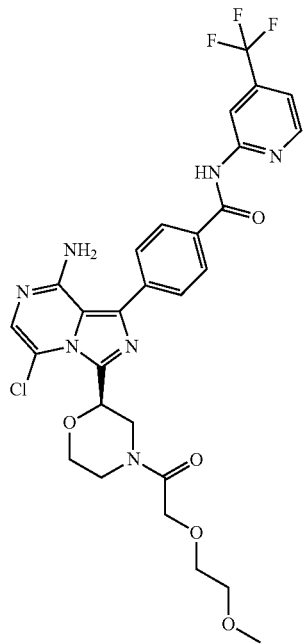 [SMILES: COCCOCC(=O)N1CCO[C@@H](c2nc(-c3ccc(C(=O)Nc4cc(C(F)(F)F)ccn4)cc3)c3c(N)ncc(Cl)n23)C1] | 4-(8-amino-5-chloro-3-{(2R)-4-[(2-methoxyethoxy)acetyl]morpholin-2-yl}imidazo[1,5-a]pyrazin-1-yl)-N-[4-(trifluoromethyl)pyridin-2-yl]benzamide | Calc'd 634.2, found 634.2 | 1.53 (Method O) |

| Example | Structure | Name | Exact Mass [M + H]+ | Retention time (min) |
|---|---|---|---|---|
| 530 | 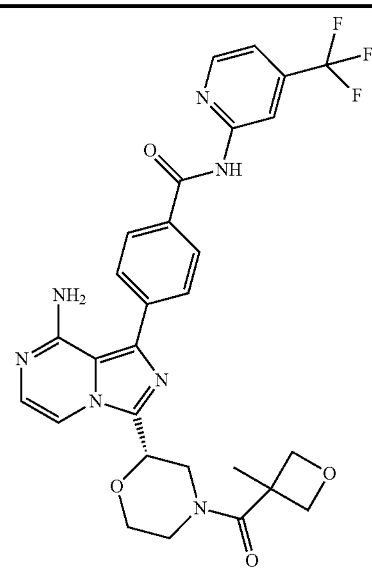 | 4-(8-amino-3-{(2S)-4-[(3-methyloxetan-3-yl)carbonyl]morpholin-2-yl}imidazo[1,5-a]pyrazin-1-yl)-N-[4-(trifluoromethyl)pyridin-2-yl]benzamide | Calc'd 582.2, found 582.1 | 1.04 (Method P) |
| 531 | 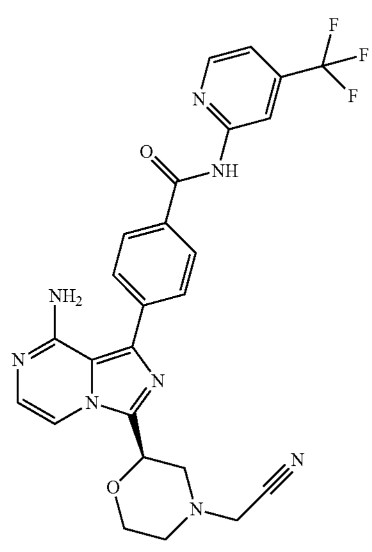 [SMILES: N#CCN1CCO[C@@H](c2nc(-c3ccc(C(=O)Nc4cc(C(F)(F)F)ccn4)cc3)c3c(N)nccn23)C1] | 4-{8-amino-3-[(2R)-4-(cyanomethyl)morpholin-2-yl]imidazo[1,5-a]pyrazin-1-yl}-N-[4-(trifluoromethyl)pyridin-2-yl]benzamide | Calc'd 523.2, found 523.06 | 1.05 (Method P) |

| Example | Structure | Name | Exact Mass [M + H]+ | Retention time (min) |
|---|---|---|---|---|
| 532 | 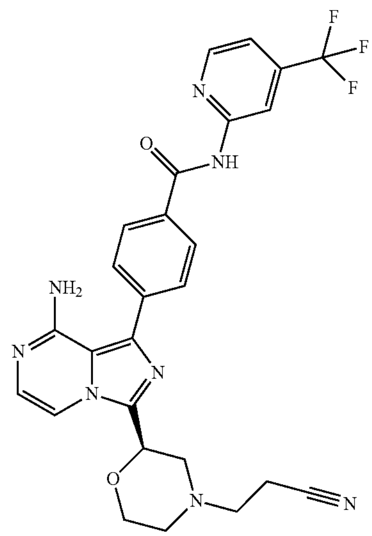 [SMILES: N#CCCN1CCO[C@@H](c2nc(-c3ccc(C(=O)Nc4cc(C(F)(F)F)ccn4)cc3)c3c(N)nccn23)C1] | 4-{8-amino-3-[(2R)-4-(2-cyanoethyl)morpholin-2-yl]imidazo[1,5-a]pyrazin-1-yl}-N-[4-(trifluoromethyl)pyridin-2-yl]benzamide | Calc'd 537.2, found 537.07 | 1.00 (Method P) |
| 533 | 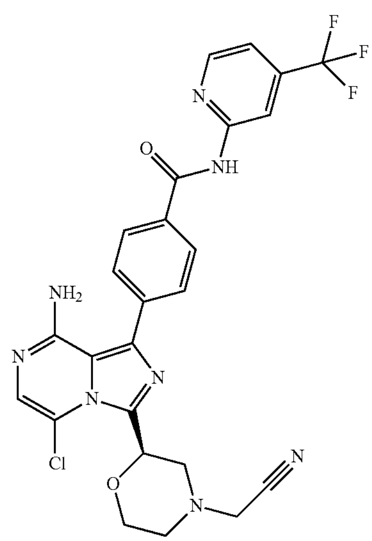 [SMILES: N#CCN1CCO[C@@H](c2nc(-c3ccc(C(=O)Nc4cc(C(F)(F)F)ccn4)cc3)c3c(N)ncc(Cl)n23)C1] | 4-{8-amino-5-chloro-3-[(2R)-4-(cyanomethyl)morpholin-2-yl]imidazo[1,5-a]pyrazin-1-yl}-N-[4-(trifluoromethyl)pyridin-2-yl]benzamide | Calc'd 557.1, found 557.02 | 1.07 (Method P) |
| 534 | 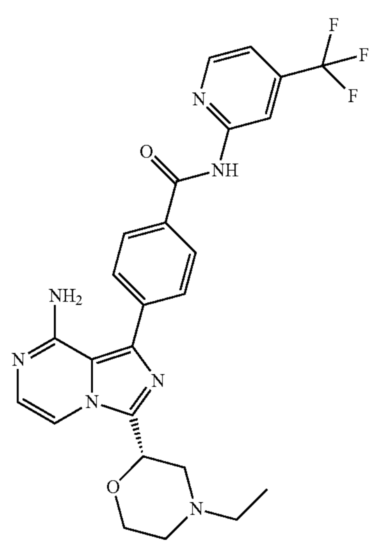 [SMILES: CCN1CCO[C@H](c2nc(-c3ccc(C(=O)Nc4cc(C(F)(F)F)ccn4)cc3)c3c(N)nccn23)C1] | 4-{8-amino-3-[(2S)-4-ethylmorpholin-2-yl]imidazo[1,5-a]pyrazin-1-yl}-N-[4-(trifluoromethyl)pyridin-2-yl]benzamide | Calc'd 512.2, found 512.08 | 0.99 (Method P) |

| Example | Structure | Name | Exact Mass [M + H]+ | Retention time (min) |
|---|---|---|---|---|
| 535 | 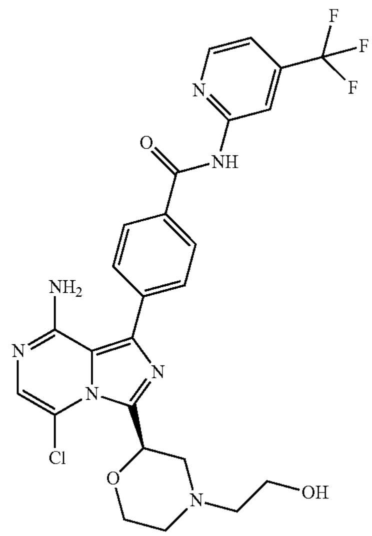 [SMILES: Nc1ncc(Cl)n2c([C@H]3CN(CCO)CCO3)nc(-c3ccc(C(=O)Nc4cc(C(F)(F)F)ccn4)cc3)c12] | 4-{8-amino-5-chloro-3-[(2R)-4-(2-hydroxyethyl)morpholin-2-yl]imidazo[1,5-a]pyrazin-1-yl}-N-[4-(trifluoromethyl)pyridin-2-yl]benzamide, TFA salt | Calc'd 562.2, found 562.0 | 1.00 (Method P) |
| 536 | 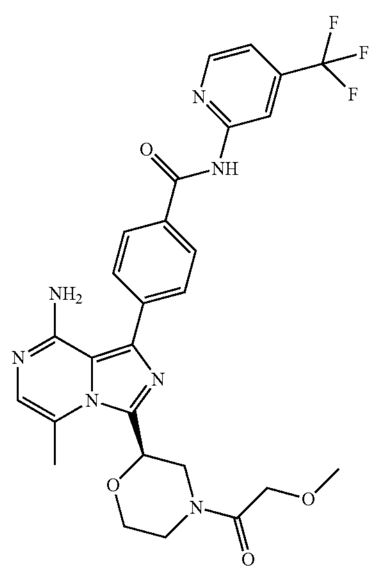 [SMILES: COCC(=O)N1CCO[C@@H](c2nc(-c3ccc(C(=O)Nc4cc(C(F)(F)F)ccn4)cc3)c3c(N)ncc(C)n23)C1] | 4-{8-amino-3-[(2R)-4-(methoxyacetyl)morpholin-2-yl]-5-methylimidazo[1,5-a]pyrazin-1-yl}-N-[4-(trifluoromethyl)pyridin-2-yl]benzamide, TFA salt | Calc'd 570.2, found 570.1 | 1.70 (Method O) |

-continued
| Example | Structure | Name | Exact Mass [M + H]+ | Retention time (min) |
|---|---|---|---|---|
| 537 | 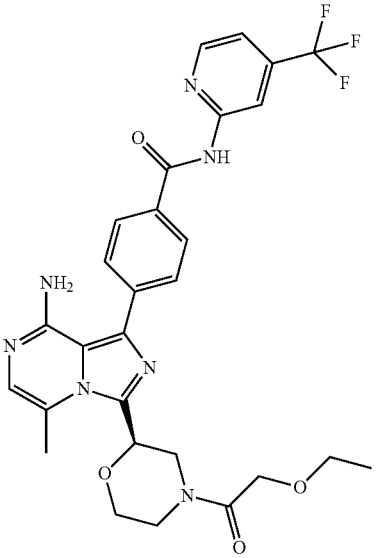 | 4-{8-amino-3-[(2R)-4-(ethoxyacetyl)morpholin-2-yl]-5-methylimidazo[1,5-a]pyrazin-1-yl}-N-[4-(trifluoromethyl)pyridin-2-yl]benzamide, TFA salt | Calc'd 584.2, found 584.1 | 1.10 (Method P) |
| 538 | 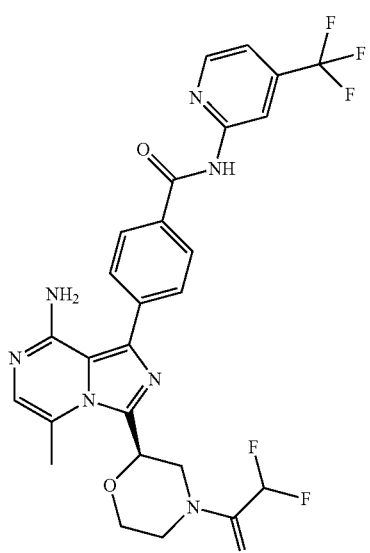 | 4-{8-amino-3-[(2R)-4-(difluoroacetyl)morpholin-2-yl]-5-methylimidazo[1,5-a]pyrazin-1-yl}-N-[4-(trifluoromethyl)pyridin-2-yl]benzamide, TFA salt | Calc'd 576.2, found 576.1 | 1.82 (Method O) |

-continued

| Example | Structure | Name | Exact Mass [M + H]+ | Retention time (min) |
|---|---|---|---|---|
| 539 | 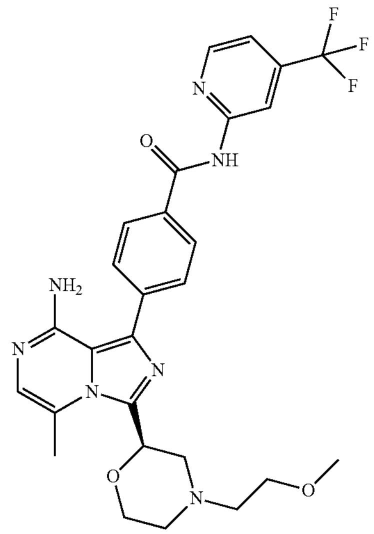 [SMILES: COCCN1CCO[C@@H](c2nc(-c3ccc(C(=O)Nc4cc(C(F)(F)F)ccn4)cc3)c3c(N)ncc(C)n23)C1] | 4-{8-amino-3-[(2R)-4-(2-methoxyethyl)morpholin-2-yl]-5-methylimidazo[1,5-a]pyrazin-1-yl}-N-[4-(trifluoromethyl)pyridin-2-yl]benzamide, TFA salt | Calc'd 556.2, found 556.19 | 1.04 (Method P) |
| 540 | 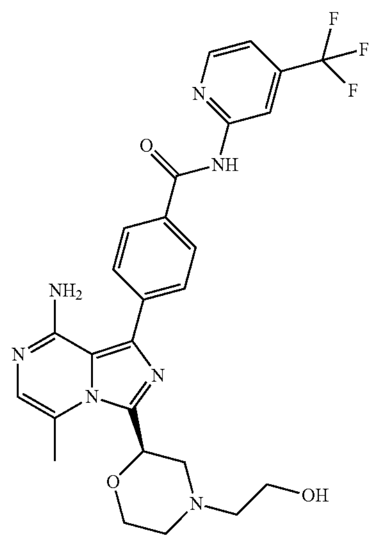 [SMILES: Cc1cnc(N)c2c(-c3ccc(C(=O)Nc4cc(C(F)(F)F)ccn4)cc3)nc([C@H]3CN(CCO)CCO3)n12] | 4-{8-amino-3-[(2R)-4-(2-hydroxyethyl)morpholin-2-yl]-5-methylimidazo[1,5-a]pyrazin-1-yl}-N-[4-(trifluoromethyl)pyridin-2-yl]benzamide, TFA salt | Calc'd 542.2, found 542.18 | 1.02 (Method P) |
| 541 | 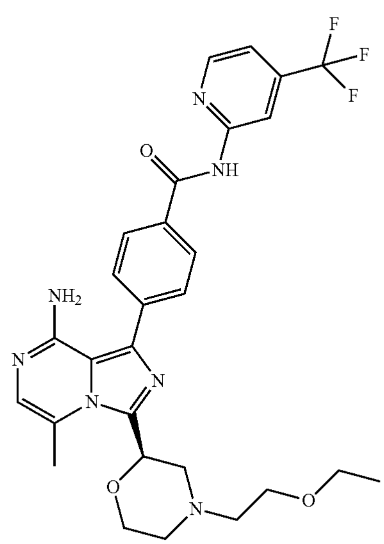 [SMILES: CCOCCN1CCO[C@@H](c2nc(-c3ccc(C(=O)Nc4cc(C(F)(F)F)ccn4)cc3)c3c(N)ncc(C)n23)C1] | 4-{8-amino-3-[(2R)-4-(2-ethoxyethyl)morpholin-2-yl]-5-methylimidazo[1,5-a]pyrazin-1-yl}-N-[4-(trifluoromethyl)pyridin-2-yl]benzamide, TFA salt | Calc'd 570.2, found 570.2 | 1.06 (Method P) |

-continued
| Example | Structure | Name | Exact Mass [M + H]+ | Retention time (min) |
|---|---|---|---|---|
| 542 | 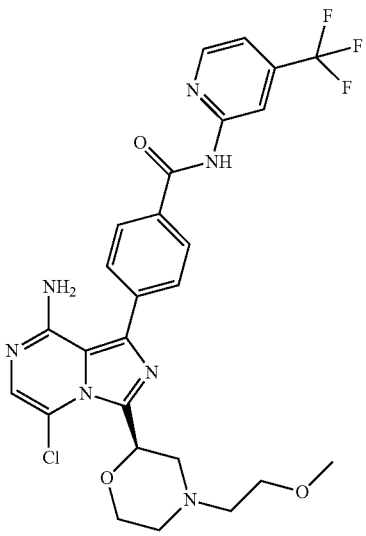 | 4-{8-amino-5-chloro-3-[(2R)-4-(2-methoxyethyl)morpholin-2-yl]imidazo[1,5-a]pyrazin-1-yl}-N-[4-(trifluoromethyl)pyridin-2-yl]benzamide, TFA salt | Calc'd 576.2, found 576.0 | 1.04 (Method P) |
| 543 | 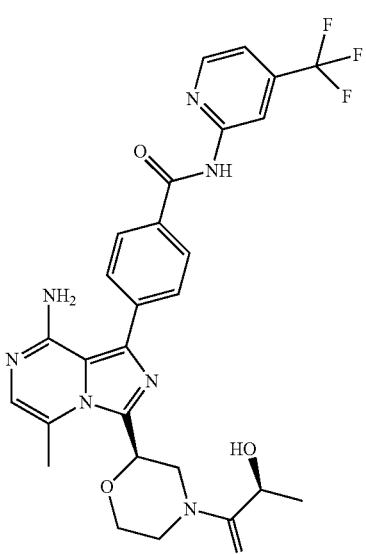 | 4-(8-amino-3-{(2R)-4-[(2S)-2-hydroxypropanoyl]morpholin-2-yl}-5-methylimidazo[1,5-a]pyrazin-1-yl)-N-[4-(trifluoromethyl)pyridin-2-yl]benzamide, TFA salt | Calc'd 570.2, found 570.18 | 1.08 (Method P) |

-continued
| Example | Structure | Name | Exact Mass [M + H]+ | Retention time (min) |
|---|---|---|---|---|
| 544 | 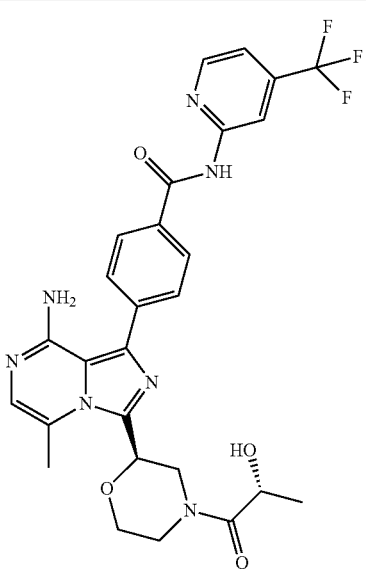 [SMILES: Cc1cnc(N)c2c(-c3ccc(C(=O)Nc4cc(C(F)(F)F)ccn4)cc3)nc([C@H]3CN(C(=O)[C@@H](C)O)CCO3)n12] | 4-(8-amino-3-{(2R)-4-[(2R)-2-hydroxypropanoyl]morpholin-2-yl}-5-methylimidazo[1,5-a]pyrazin-1-yl)-N-[4-(trifluoromethyl)pyridin-2-yl]benzamide | Calc'd 570.2, found 570.18 | 1.07 (Method P) |
| 545 | 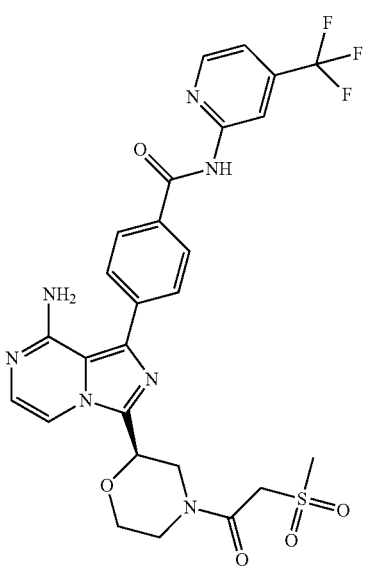 | 4-(8-amino-3-{(2R)-4-[(methylsulfonyl)acetyl]morpholin-2-yl}imidazo[1,5-a]pyrazin-1-yl)-N-[4-(trifluoromethyl)pyridin-2-yl]benzamide | Calc'd 604.2, found 604.09 | 1.08 (Method P) |

-continued
| Example | Structure | Name | Exact Mass [M + H]+ | Retention time (min) |
|---|---|---|---|---|
| 546 | 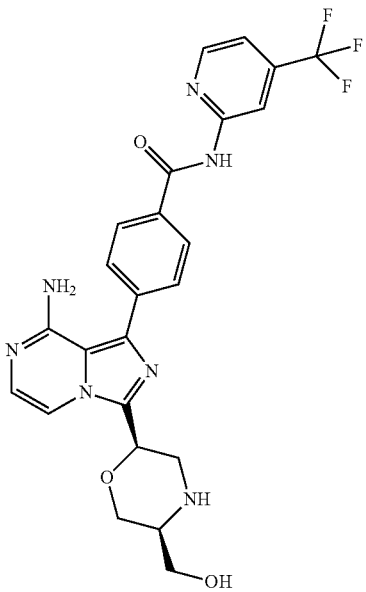 [SMILES: Nc1nccn2c([C@H]3CN[C@@H](CO)CO3)nc(-c3ccc(C(=O)Nc4cc(C(F)(F)F)ccn4)cc3)c12] | 4-{8-amino-3-[(2R,5S)-5-(hydroxymethyl)morpholin-2-yl]imidazo[1,5-a]pyrazin-1-yl}-N-[4-(trifluoromethyl)pyridin-2-yl]benzamide | Calc'd 514.2, found 514.07 | 1.01 (Method P) |
| 547 | 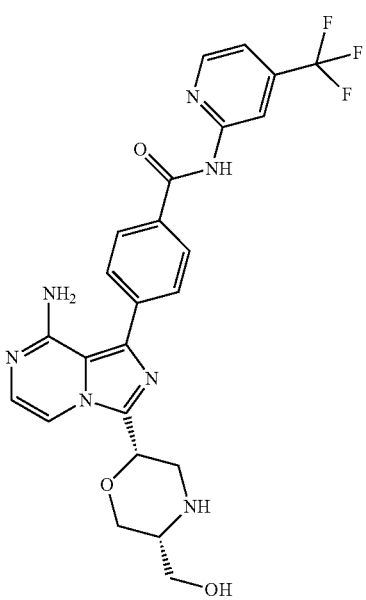 [SMILES: Nc1nccn2c([C@@H]3CN[C@H](CO)CO3)nc(-c3ccc(C(=O)Nc4cc(C(F)(F)F)ccn4)cc3)c12] | 4-{8-amino-3-[(2S,5R)-5-(hydroxymethyl)morpholin-2-yl]imidazo[1,5-a]pyrazin-1-yl}-N-[4-(trifluoromethyl)pyridin-2-yl]benzamide, TFA salt | Calc'd 514.2, found 514.04 | 0.99 (Method P) |

-continued

| Example | Structure | Name | Exact Mass [M + H]+ | Retention time (min) |
|---|---|---|---|---|
| 548 | 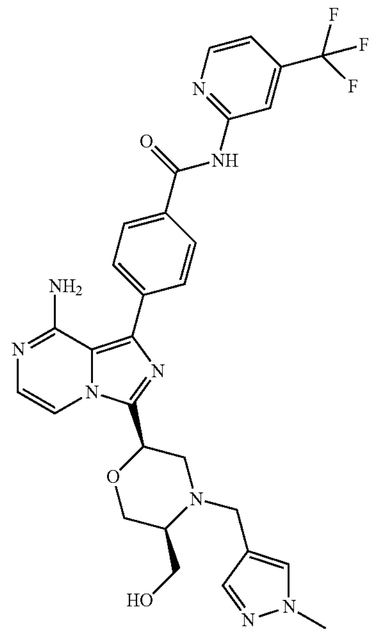 [SMILES: Cn1cc(CN2C[C@H](c3nc(-c4ccc(C(=O)Nc5cc(C(F)(F)F)ccn5)cc4)c4c(N)nccn34)OC[C@@H]2CO)cn1] | 4-(8-amino-3-{(2R,5S)-5-(hydroxymethyl)-4-[(1-methyl-1H-pyrazol-4-yl)methyl]morpholin-2-yl}imidazo[1,5-a]pyrazin-1-yl)-N-[4-(trifluoromethyl)pyridin-2-yl]benzamide, TFA salt | Calc'd 608.2, found 608.18 | 1.00 (Method P) |
| 549 | 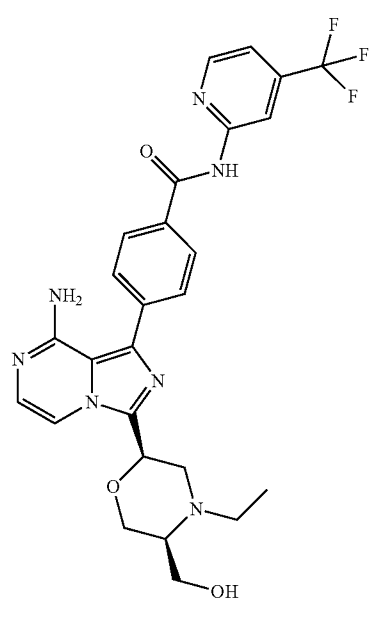 [SMILES: CCN1C[C@H](c2nc(-c3ccc(C(=O)Nc4cc(C(F)(F)F)ccn4)cc3)c3c(N)nccn23)OC[C@@H]1CO] | 4-{8-amino-3-[(2R,5S)-4-ethyl-5-(hydroxymethyl)morpholin-2-yl]imidazo[1,5-a]pyrazin-1-yl}-N-[4-(trifluoromethyl)pyridin-2-yl]benzamide, TFA salt | Calc'd 542.2, found 542.10 | 1.00 (Method P) |

-continued
| Example | Structure | Name | Exact Mass [M + H]⁺ | Retention time (min) |
|---|---|---|---|---|
| 550 | 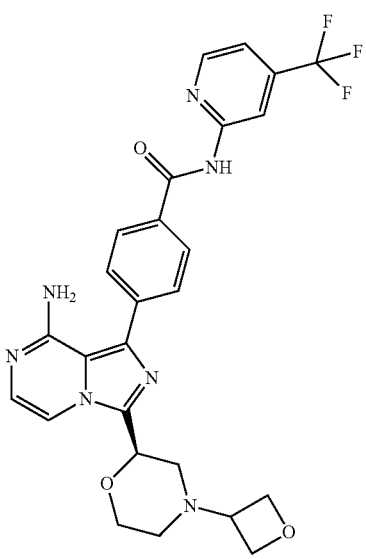 [SMILES: Nc1nccn2c([C@H]3CN(C4COC4)CCO3)nc(-c3ccc(C(=O)Nc4cc(C(F)(F)F)ccn4)cc3)c12] | 4-{8-amino-3-[(2R)-4-oxetan-3-ylmorpholin-2-yl]imidazo[1,5-a]pyrazin-1-yl}-N-[4-(trifluoromethyl)pyridin-2-yl]benzamide, TFA salt | Calc'd 540.2, found 540.14 | 1.00 (Method P) |
| 551 | 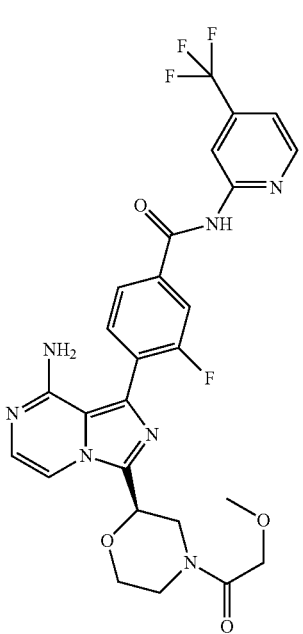 [SMILES: COCC(=O)N1CCO[C@@H](c2nc(-c3ccc(C(=O)Nc4cc(C(F)(F)F)ccn4)cc3F)c3c(N)nccn23)C1] | 4-{8-amino-3-[(2R)-4-(methoxyacetyl)morpholin-2-yl]imidazo[1,5-a]pyrazin-1-yl}-3-fluoro-N-[4-(trifluoromethyl)pyridin-2-yl]benzamide, TFA salt | Calc'd 574.2, found 574.2 | 0.84 min (Method Q) |

| Example | Structure | Name | Exact Mass [M + H]+ | Retention time (min) |
|---------|-----------|------|---------------------|----------------------|
| 552 | 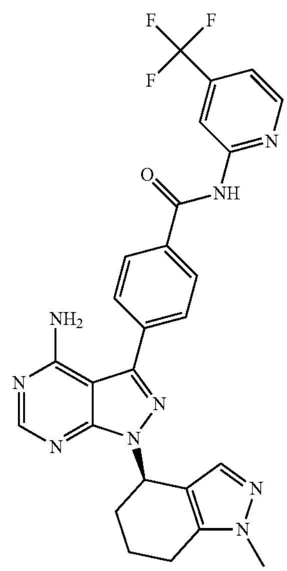 [SMILES: Cn1ncc2c1CCC[C@H]2n1nc(-c2ccc(C(=O)Nc3cc(C(F)(F)F)ccn3)cc2)c2c(N)ncnc21] | 4-{4-amino-1-[(4R)-1-methyl-4,5,6,7-tetrahydro-1H-indazol-4-yl]-1H-pyrazolo[3,4-d]pyrimidin-3-yl}-N-[4-(trifluoromethyl)pyridin-2-yl]benzamide, TFA salt | Calc'd 534.2, found 534.2 | 2.61 (Method H) |
| 553 | 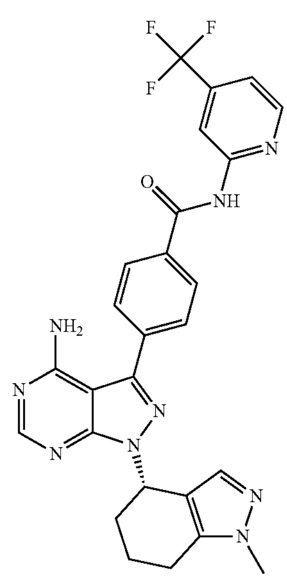 [SMILES: Cn1ncc2c1CCC[C@@H]2n1nc(-c2ccc(C(=O)Nc3cc(C(F)(F)F)ccn3)cc2)c2c(N)ncnc21] | 4-{4-amino-1-[(4S)-1-methyl-4,5,6,7-tetrahydro-1H-indazol-4-yl]-1H-pyrazolo[3,4-d]pyrimidin-3-yl}-N-[4-(trifluoromethyl)pyridin-2-yl]benzamide, TFA salt | Calc'd 534.2, found 534.2 | 2.61 (Method H) |

| Example | Structure | Name | Exact Mass [M + H]+ | Retention time (min) |
|---|---|---|---|---|
| 554 | 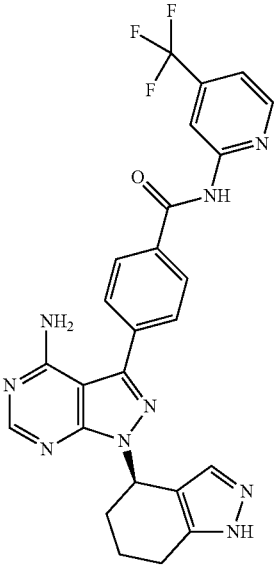 [SMILES: Nc1ncnc2c1c(-c1ccc(C(=O)Nc3cc(C(F)(F)F)ccn3)cc1)nn2[C@@H]1CCCc2[nH]ncc21] | 4-{4-amino-1-[(4R)-4,5,6,7-tetrahydro-1H-indazol-4-yl]-1H-pyrazolo[3,4-d]pyrimidin-3-yl}-N-[4-(trifluoromethyl)pyridin-2-yl]benzamide, TFA salt | Calc'd 520.2, found 520.2 | 2.75 (Method H) |
| 555 | 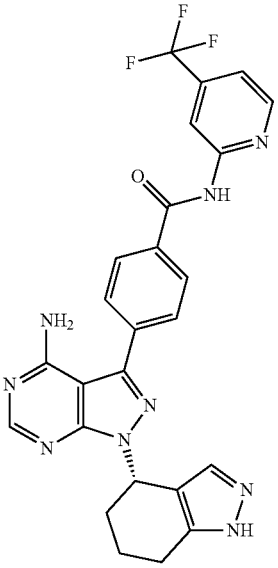 [SMILES: Nc1ncnc2c1c(-c1ccc(C(=O)Nc3cc(C(F)(F)F)ccn3)cc1)nn2[C@H]1CCCc2[nH]ncc21] | 4-{4-amino-1-[(4S)-4,5,6,7-tetrahydro-1H-indazol-4-yl]-1H-pyrazolo[3,4-d]pyrimidin-3-yl}-N-[4-(trifluoromethyl)pyridin-2-yl]benzamide, TFA salt | Calc'd 520.2, found 520.2 | 2.76 (Method H) |

| Example | Structure | Name | Exact Mass [M + H]+ | Retention time (min) |
|---|---|---|---|---|
| 556 | 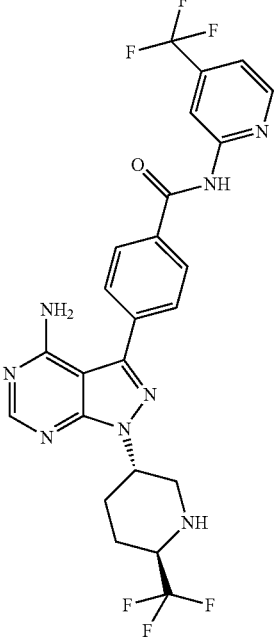 | 4-{4-amino-1-[(3S,6R)-6-(trifluoromethyl)piperidin-3-yl]-1H-pyrazolo[3,4-d]pyrimidin-3-yl}-N-[4-(trifluoromethyl)pyridin-2-yl]benzamide, TFA salt | Calc'd 551.2, found 551.2 | 2.74 (Method H) |
| 557 | 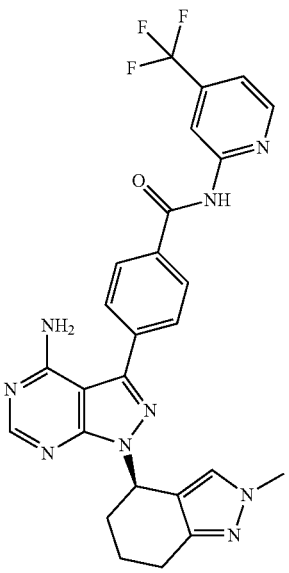 | 4-{4-amino-1-[(4R)-2-methyl-4,5,6,7-tetrahydro-2H-indazol-4-yl]-1H-pyrazolo[3,4-d]pyrimidin-3-yl}-N-[4-(trifluoromethyl)pyridin-2-yl]benzamide, TFA salt | Calc'd 534.2, found 534.2 | 2.85 (Method H) |

| Example | Structure | Name | Exact Mass [M + H]+ | Retention time (min) |
|---|---|---|---|---|
| 558 | 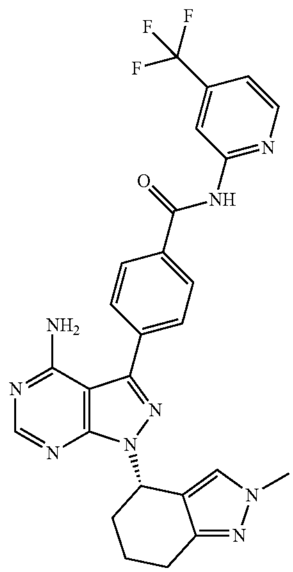 [SMILES: Cn1cc2c(n1)CCC[C@@H]2n1nc(-c2ccc(C(=O)Nc3cc(C(F)(F)F)ccn3)cc2)c2c(N)ncnc21] | 4-{4-amino-1-[(4S)-2-methyl-4,5,6,7-tetrahydro-2H-indazol-4-yl]-1H-pyrazolo[3,4-d]pyrimidin-3-yl}-N-[4-(trifluoromethyl)pyridin-2-yl]benzamide, TFA salt | Calc'd 534.2, found 534.2 | 2.85 (Method H) |
| 559 | 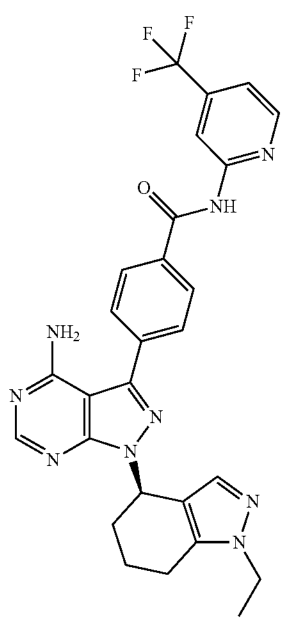 [SMILES: CCn1ncc2c1CCC[C@H]2n1nc(-c2ccc(C(=O)Nc3cc(C(F)(F)F)ccn3)cc2)c2c(N)ncnc21] | 4-{4-amino-1-[(4R)-1-ethyl-4,5,6,7-tetrahydro-1H-indazol-4-yl]-1H-pyrazolo[3,4-d]pyrimidin-3-yl}-N-[4-(trifluoromethyl)pyridin-2-yl]benzamide, TFA salt | Calc'd 548.2, found 548.2 | 3.14 (Method H) |

| Example | Structure | Name | Exact Mass [M + H]+ | Retention time (min) |
|---------|-----------|------|---------------------|----------------------|
| 560 | 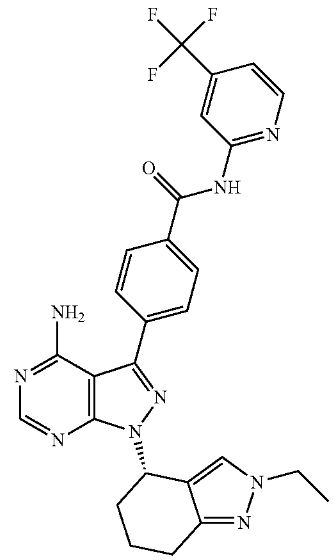 [SMILES: CCn1cc2c(n1)CCC[C@@H]2n1nc(-c2ccc(C(=O)Nc3cc(C(F)(F)F)ccn3)cc2)c2c(N)ncnc21] | 4-{4-amino-1-[(4S)-2-ethyl-4,5,6,7-tetrahydro-2H-indazol-4-yl]-1H-pyrazolo[3,4-d]pyrimidin-3-yl}-N-[4-(trifluoromethyl)pyridin-2-yl]benzamide, TFA salt | Calc'd 548.2, found 548.2 | 2.59 (Method H) |
| 561 | 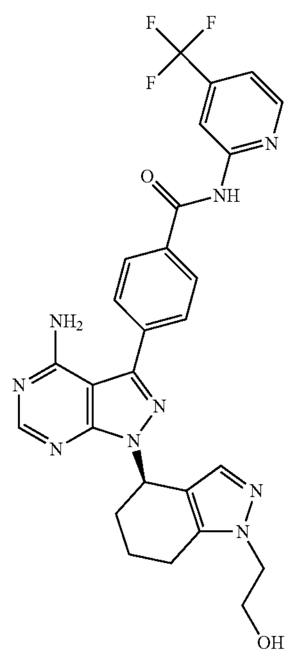 [SMILES: Nc1ncnc2c1c(-c1ccc(C(=O)Nc3cc(C(F)(F)F)ccn3)cc1)nn2[C@@H]1CCCc2c1cnn2CCO] | 4-{4-amino-1-[(4R)-1-(2-hydroxyethyl)-4,5,6,7-tetrahydro-1H-indazol-4-yl]-1H-pyrazolo[3,4-d]pyrimidin-3-yl}-N-[4-(trifluoromethyl)pyridin-2-yl]benzamide, TFA salt | Calc'd 564.2, found 564.2 | 3.25 (Method H) |

-continued

| Example | Structure | Name | Exact Mass [M + H]+ | Retention time (min) |
|---|---|---|---|---|
| 562 | 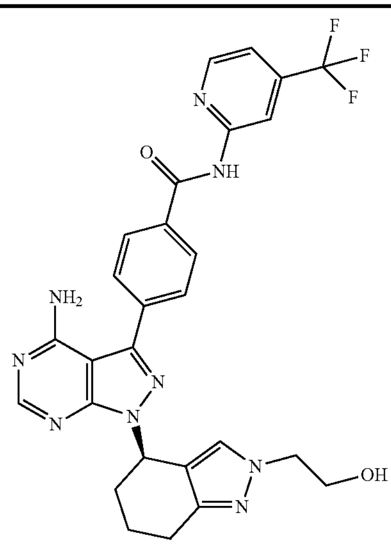 | 4-{4-amino-1-[(4R)-2-(2-hydroxyethyl)-4,5,6,7-tetrahydro-2H-indazol-4-yl]-1H-pyrazolo[3,4-d]pyrimidin-3-yl}-N-[4-(trifluoromethyl)pyridin-2-yl]benzamide, TFA salt | Calc'd 564.2, found 564.2 | 3.27 (Method H) |
| 563 | 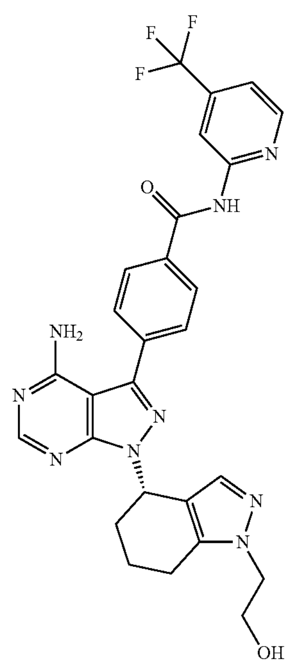 [SMILES: Nc1ncnc2c1c(-c1ccc(C(=O)Nc3cc(C(F)(F)F)ccn3)cc1)nn2[C@H]1CCCc2c1cnn2CCO] | 4-{4-amino-1-[(4S)-1-(2-hydroxyethyl)-4,5,6,7-tetrahydro-1H-indazol-4-yl]-1H-pyrazolo[3,4-d]pyrimidin-3-yl}-N-[4-(trifluoromethyl)pyridin-2-yl]benzamide, TFA salt | Calc'd 564.2, found 564.2 | 3.25 (Method H) |

-continued

| Example | Structure | Name | Exact Mass [M + H]+ | Retention time (min) |
|---|---|---|---|---|
| 564 | 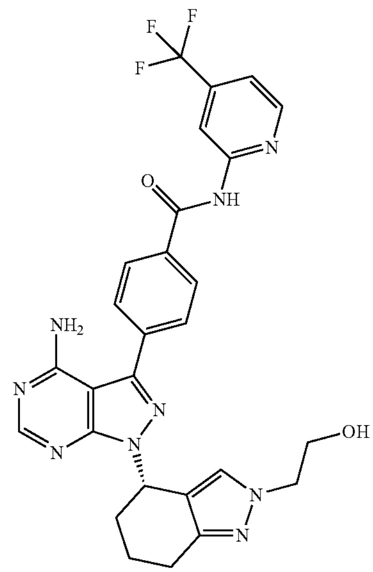 [SMILES: Nc1ncnc2c1c(-c1ccc(C(=O)Nc3cc(C(F)(F)F)ccn3)cc1)nn2[C@H]1CCCc2nn(CCO)cc21] | 4-{4-amino-1-[(4S)-2-(2-hydroxyethyl)-4,5,6,7-tetrahydro-2H-indazol-4-yl]-1H-pyrazolo[3,4-d]pyrimidin-3-yl}-N-[4-(trifluoromethyl)pyridin-2-yl]benzamide, TFA salt | Calc'd 564.2, found 564.2 | 3.27 (Method H) |
| 565 | 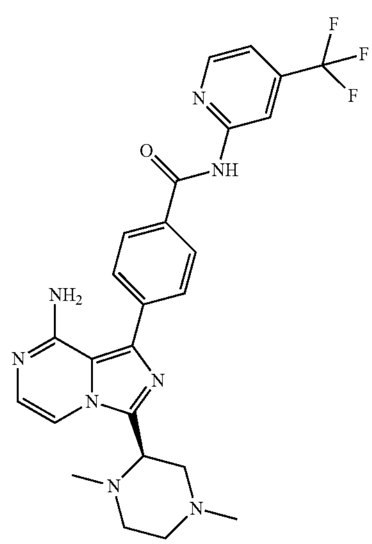 [SMILES: CN1CCN(C)[C@@H](c2nc(-c3ccc(C(=O)Nc4cc(C(F)(F)F)ccn4)cc3)c3c(N)nccn23)C1] | 4-{8-amino-3-[(2R)-1,4-dimethylpiperazin-2-yl]imidazo[1,5-a]pyrazin-1-yl}-N-[4-(trifluoromethyl)pyridin-2-yl]benzamide | Calc'd 511.2, found 511.2 | 1.668 (Method M) |

-continued
| Example | Structure | Name | Exact Mass [M + H]+ | Retention time (min) |
|---|---|---|---|---|
| 566 | 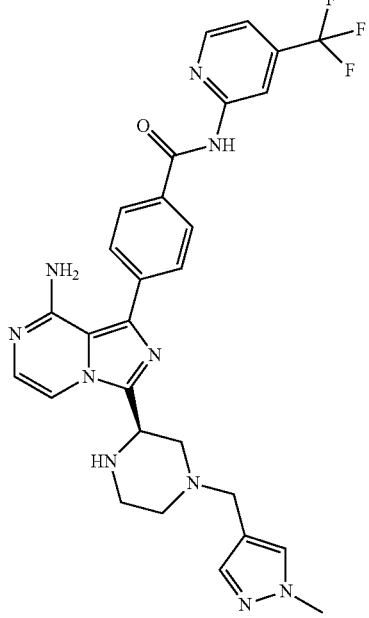 | 4-(8-amino-3-{(2R)-4-[(1-methyl-1H-pyrazol-4-yl)methyl]piperazin-2-yl}imidazo[1,5-a]pyrazin-1-yl)-N-[4-(trifluoromethyl)pyridin-2-yl]benzamide | Calc'd 577.2, found 577.2 | 1.672 (Method M) |
| 567 | 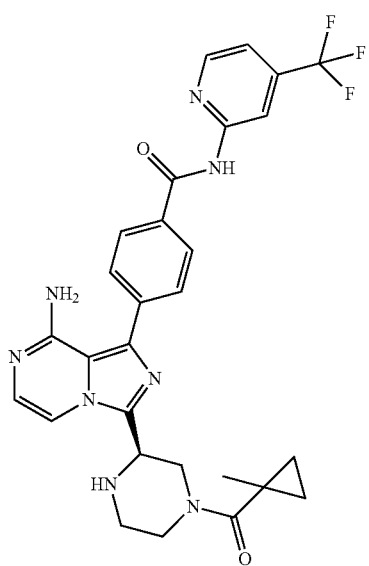 [SMILES: CC1(C(=O)N2CCN[C@@H](c3nc(-c4ccc(C(=O)Nc5cc(C(F)(F)F)ccn5)cc4)c4c(N)nccn34)C2)CC1] | 4-(8-amino-3-{(2R)-4-[(1-methylcyclopropyl)carbonyl]piperazin-2-yl}imidazo[1,5-a]pyrazin-1-yl)-N-[4-(trifluoromethyl)pyridin-2-yl]benzamide | Calc'd 565.2, found 565.2 | 1.710 (Method M) |

-continued

| Example | Structure | Name | Exact Mass [M + H]+ | Retention time (min) |
|---|---|---|---|---|
| 568 | 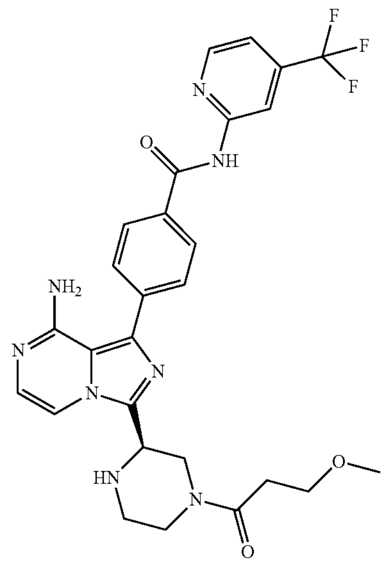 [SMILES: COCCC(=O)N1CCN[C@@H](c2nc(-c3ccc(C(=O)Nc4cc(C(F)(F)F)ccn4)cc3)c3c(N)nccn23)C1] | 4-{8-amino-3-[(2R)-4-(3-methoxypropanoyl)piperazin-2-yl]imidazo[1,5-a]pyrazin-1-yl}-N-[4-(trifluoromethyl)pyridin-2-yl]benzamide | Calc'd 569.2, found 569.0 | 1.885 (Method M) |
| 569 | 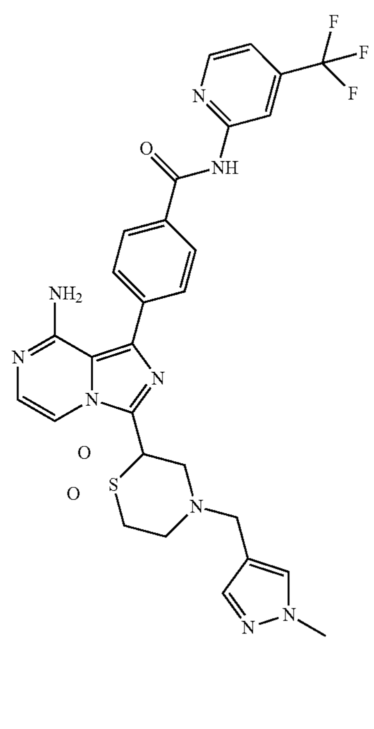 | 4-(8-amino-3-{4-[(1-methyl-1H-pyrazol-4-yl)methyl]-1,1-dioxidothiomorpholin-2-yl}imidazo[1,5-a]pyrazin-1-yl)-N-[4-(trifluoromethyl)pyridin-2-yl]benzamide | Calc'd 626.2, found 626.2 | 1.729 (Method M) |

-continued

| Example | Structure | Name | Exact Mass [M + H]+ | Retention time (min) |
|---|---|---|---|---|
| 570 | 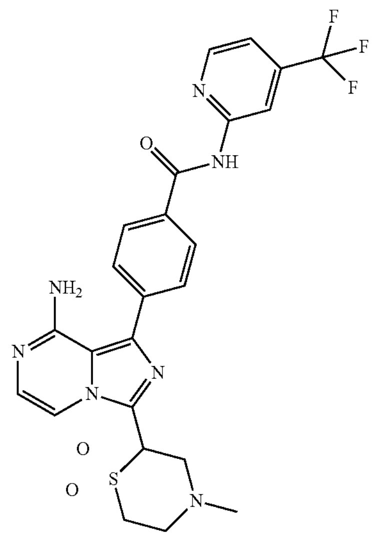 | 4-[8-amino-3-(4-methyl-1,1-dioxidothiomorpholin-2-yl)imidazo[1,5-a]pyrazin-1-yl]-N-[4-(trifluoromethyl)pyridin-2-yl]benzamide | Calc'd 546.2, found 546.2 | 1.686 (Method M) |
| 571 | 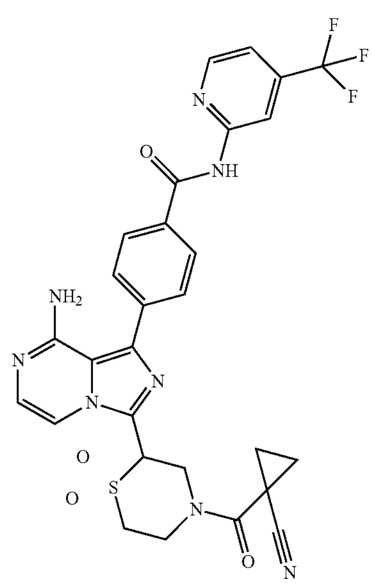 | 4-(8-amino-3-{4-[(1-cyanocyclopropyl)carbonyl]-1,1-dioxidothiomorpholin-2-yl}imidazo[1,5-a]pyrazin-1-yl)-N-[4-(trifluoromethyl)pyridin-2-yl]benzamide | Calc'd 625.2, found 625.2 | 1.880 (Method M) |

| Example | Structure | Name | Exact Mass [M + H]+ | Retention time (min) |
|---|---|---|---|---|
| 572 | 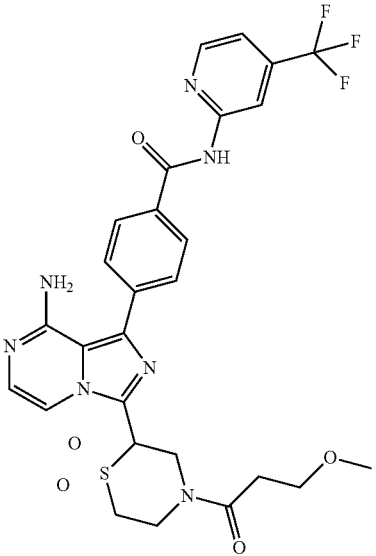 | 4-{8-amino-3-[4-(3-methoxypropanoyl)-1,1-dioxidothiomorpholin-2-yl]imidazo[1,5-a]pyrazin-1-yl}-N-[4-(trifluoromethyl)-pyridin-2-yl]benzamide | Calc'd 618.2, found 618.0 | 2.009 (Method M) |
| 573 | 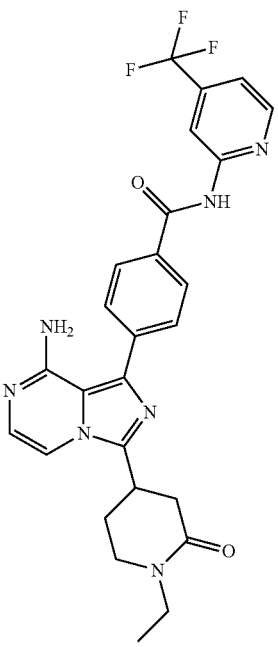 [SMILES: CCN1CCC(c2nc(-c3ccc(C(=O)Nc4cc(C(F)(F)F)ccn4)cc3)c3c(N)nccn23)CC1=O] | 4-[8-amino-3-(1-ethyl-2-oxopiperidin-4-yl)imidazo[1,5-a]pyrazin-1-yl]-N-[4-(trifluoromethyl)-pyridin-2-yl]benzamide, TFA salt | Calc'd 524.2, found 524.2 | 2.49 (Method H) |

| Example | Structure | Name | Exact Mass [M + H]+ | Retention time (min) |
|---------|-----------|------|---------------------|----------------------|
| 574 | 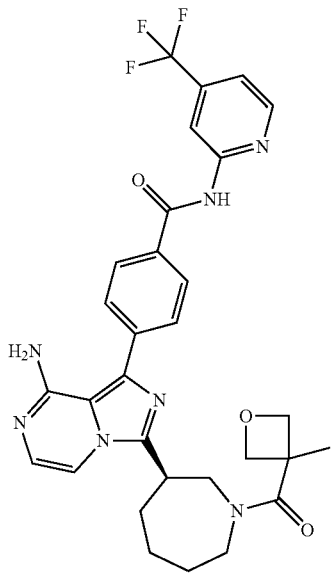 [SMILES: CC1(C(=O)N2CCCC[C@@H](c3nc(-c4ccc(C(=O)Nc5cc(C(F)(F)F)ccn5)cc4)c4c(N)nccn34)C2)COC1] | 4-(8-amino-3-{(3R)-1-[(3-methyloxetan-3-yl)carbonyl]azepan-3-yl}imidazo[1,5-a]pyrazin-1-yl)-N-[4-(trifluoromethyl)pyridin-2-yl]benzamide, TFA salt | Calc'd 594.2, found 594.2 | |
| 575 | 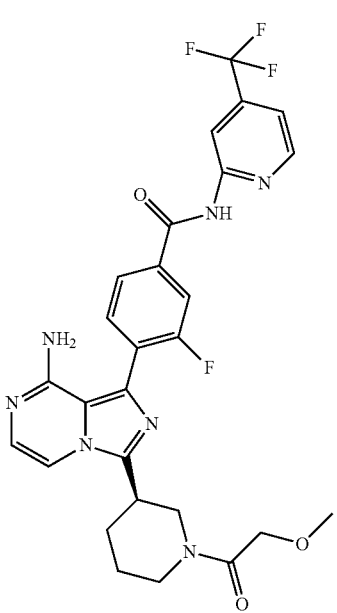 [SMILES: COCC(=O)N1CCC[C@@H](c2nc(-c3ccc(C(=O)Nc4cc(C(F)(F)F)ccn4)cc3F)c3c(N)nccn23)C1] | 4-{8-amino-3-[(3R)-1-(methoxyacetyl)piperidin-3-yl]imidazo[1,5-a]pyrazin-1-yl}-3-fluoro-N-[4-(trifluoromethyl)pyridin-2-yl]benzamide, TFA salt | Calc'd 572.2, found 572.2 | |

| Example | Structure | Name | Exact Mass [M + H]+ | Retention time (min) |
|---|---|---|---|---|
| 576 | 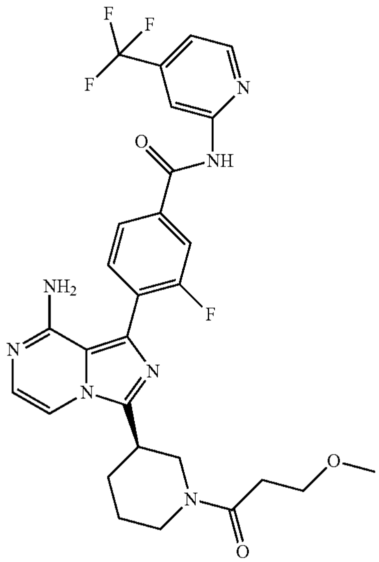 [SMILES: COCCC(=O)N1CCC[C@@H](c2nc(-c3ccc(C(=O)Nc4cc(C(F)(F)F)ccn4)cc3F)c3c(N)nccn23)C1] | 4-{8-amino-3-[(3R)-1-(3-methoxypropanoyl)piperidin-3-yl]imidazo[1,5-a]pyrazin-1-yl}-3-fluoro-N-[4-(trifluoromethyl)pyridin-2-yl]benzamide, TFA salt | Calc'd 586.2, found 586.2 | |
| 577 | 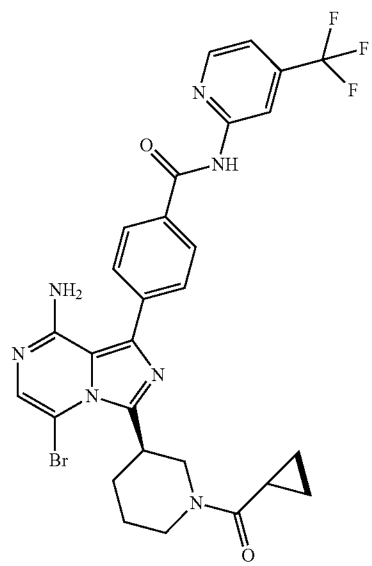 | (R)-4-(8-amino-5-bromo-3-(1-(cyclopropanecarbonyl)piperidin-3-yl)imidazo[1,5-a]pyrazin-1-yl)-N-(4-(trifluoromethyl)pyridin-2-yl)benzamide | Calc'd 628.0, found 628.0 | 1.99 (Method M) |

Example 577

Btk Enzyme Activity Assay Methods (a) Assay Method A

Btk enzyme activity is measured using the IMAP (immobilized metal ion affinity-based fluorescence polarization) assay as outlined below. Btk enzyme (His-Btk (Millipore catalog #14-552), is diluted to 0.4 U/mL in KR buffer (10 mM Tris-HCl, 10 mM MgCl$_2$, 0.01% Tween-20, 0.05% NaN$_3$, 1 mM DTT, 2 mM MnCl$_2$, pH 7.2).

Serial dilution log 10 from 2 mM to 63.2 nM of test compounds are made in 100% DMSO. The dilutions in DMSO are then diluted 50-fold in KR-buffer. Final compound concentration range in the assay from 10 µM to 0.316 nM. 5 µL/well of test compound in KR buffer (final DMSO concentration in the assay is 1%) is mixed with 5 µl/well of 0.4 U/mL Btk enzyme (final concentration in the assay is 0.1 U/mL). Test compounds and Btk enzyme are pre-incubated 60 minutes at room temperature, before adding 5 µL/well of 200 nM Fluorescin labeled substrate peptide (Blk/Lyntide substrate, e.g. #R7188/#R7233, Molecular Devices) in KR-buffer. Final peptide substrate concentration in assay is 50 nM. The kinase assay is started by adding 5 µL/well of 20 µM ATP in KR-buffer (final ATP concentration is 5 µM ATP, Km ATP in Btk IMAP assay). Following incubation for 2 h at room temperature the enzyme reaction is stopped by adding 40 µL/well IMAP Progressive Binding Solution (according to suppliers (Molecular Devices) protocol using 75% 1× buffer A and 25% 1× buffer B with 1:600 Progressive Binding Solution). After 60 min incubation at room temperature in the dark the FP signal is read. Fluorescence at 535 nm is measured using parallel and perpendicular filters to determine differences in rotation due to binding of the phosphorylated substrate peptide to the beads. Values are calculated as percentage of the difference in readout (ΔmPi) of the controls with and without ATP. $EC_{50}$ values are determined by curve fitting of the experimental results using Activity Base.

All examples have an EC50 of 10 μM or lower.

TABLE A

EC50 Btk activity values - Assay Method A

| EC50 | Example |
|---|---|
| ≥1 μM | 17, 283, 293, |
| ≥100 nM-<1 μM | 12, 16, 18, 22, 29, 49, 115, 124, 125, 126, 127, 128, 129, 133, 137, 147, 150, 151, 152, 153, 209, 213, 217, 288, 291, 292, 294, 295, 296, 297, |
| ≥10 nM-<100 nM | 1, 9, 15, 21, 23, 26, 27, 28, 32, 33, 35, 37, 38, 39, 51, 53, 54, 55, 56, 57, 58, 79, 88, 93, 94, 95, 108, 111, 112, 113, 121, 122, 123, 132, 134, 136, 138, 140, 143, 144, 145, 146, 148, 149, 154, 157, 168, 179, 185, 187, 188, 210, 215, 216, 225, 228, 229, 230, 250, 258, 263, 265, 270, 272, 274, 279, 285, 286, 287, 290, 303, 312, 320, 321, 322, 323 |
| <10 nM | 2, 3, 4, 5, 6, 7, 8, 10, 11, 13, 14, 19, 20, 24, 25, 30, 31, 34, 36, 40, 41, 42, 43, 44, 45, 46, 47, 48, 50, 52, 59, 60, 61, 62, 63, 64, 65, 66, 67, 68, 69, 70, 71, 72, 73, 74, 75, 76, 77, 78, 80, 81, 82, 83, 84, 85, 86, 87, 89, 90, 91, 92, 96, 97, 98, 99, 100, 101, 102, 103, 104, 105, 106, 107, 109, 110, 114, 116, 117, 118, 119, 120, 130, 131, 135, 139, 141, 142, 155, 156, 158, 159, 160, 161, 162, 163, 164, 165, 166, 167, 169, 170, 171, 172, 173, 174, 175, 176, 177, 178, 180, 181, 182, 183, 184, 186, 189, 190, 191, 192, 193, 194, 195, 196, 197, 198, 199, 200, 201, 202, 203, 204, 205, 206, 207, 208, 211, 212, 214, 218, 219, 220, 221, 222, 223, 224, 226, 227, 231, 232, 233, 234, 235, 236, 237, 238, 239, 240, 241, 242, 243, 244, 245, 246, 247, 248, 249, 251, 252, 253, 254, 255, 256, 257, 259, 260, 261, 262, 264, 266, 267, 268, 269, 271, 273, 275, 276, 277, 278, 280, 281, 282, 284, 289, 298, 299, 300, 301, 302, 304, 305, 306, 307, 308, 309, 310, 311, 313, 314, 315, 316, 317, 318, 319, |

(b) Assay Method B

BTK enzymatic activity was determined in an IMAP-FP assay (Immobilized Metal ion Affinity-based fluorescence Polarization; Molecular Devices). Using this assay format, the potency ($IC_{50}$) of each compound was determined from a 10 point (1:3 serial dilution, final compound concentration range in assay from 10 μM to 0.508 nM) titration curve using the following outlined procedure. To each well of a black Corning 384-well microplate (Corning Catalog #3575), 200 nL of compound (100 fold dilution in final assay volume of 20 μL) was dispensed, followed by the addition of 10 μL of 1× kinase buffer (10 mM Tris pH 7.2, 10 mM $MgCl_2$, 0.01% Tween 20, 2 mM $MnCl_2$, and 1 mM DTT) containing 0.16 ng/μL (2.1 nM) of BTK enzyme (recombinant protein from baculovirus-transfected Sf9 cells: full-length BTK, 6HIS-tag cleaved). Following a 60 minute compound & enzyme incubation, each reaction was initiated by the addition of 10 μL kinase buffer containing 100 nM "Blk/Lyntide" IMAP substrate peptide (5-carboxyfluorescein-EFPIYDFL-PAKKK-$NH_2$; Molecular Devices Catalog #R7188), and 10 μM ATP. The final reaction in each well of 20 μL consists of 1.05 nM hBTK, 50 nM Blk/Lyntide IMAP substrate, and 5 μM ATP. Phosphorylation reactions were allowed to proceed for 120 minutes and were immediately quenched by the addition of 40 μL IMAP detection beads resuspended in IMAP progressive binding buffer (beads were diluted 1:600 in 75% and 25% progressive binding buffer A and B, respectively; Molecular Devices). Plates were read on Packard microplate reader after 60 minutes binding equilibration using Fluorescence Polarization protocol. Specifically, fluorescence at 535 nm is measured using emission filters oriented both parallel and perpendicular to the polarized excitation filter. This allows detection of changes in Fluorescence Polarization due to binding of the phosphorylated substrate peptide to the beads. Values are calculated as percentage of the difference in readout (ΔmP) of the controls with and without hBTK enzyme. $IC_{50}$ values are determined by curve fitting of the experimental results using Activity Base.

TABLE B

IC50 Btk activity values - Assay Method B

| IC50 | Example |
|---|---|
| ≥1 μM | 567 |
| ≥ 100 nM-<1 μM | 377, 405, 565, 566, 568, 569, 570, 571, 572 |
| ≥ 10 nM-<100 nM | 375, 378, 380, 390, 391, 406, 407, 474, 475, 479, 495, 496, 497, 498, 499, 500 |
| <10 nM | 374, 376, 379, 389, 394, 401, 402, 403, 404, 463, 574, 577 |

(c) Assay Method C

BTK enzymatic activity was determined with the LANCE (Lanthanide Chelate Excite) TR-FRET (Time-resolved fluorescence resonance energy transfer) assay. In this assay, the potency ($IC_{50}$) of each compound was determined from an eleven point (1:3 serial dilution; final compound concentration range in assay from 1 μM to 0.017 nM) titration curve using the following outlined procedure. To each well of a black non-binding surface Corning 384-well microplate (Corning Catalog #3820), 5 nL of compound (2000 fold dilution in final assay volume of 10 μL) was dispensed, followed by the addition of 7.5 μL of 1× kinase buffer (50 mM Hepes 7.5, 10 mM $MgCl_2$, 0.01% Brij-35, 1 mM EGTA, 0.05% BSA & 1 mM DTT) containing 5.09 pg/μL (66.67 pM) of BTK enzyme (recombinant protein from baculovirus-transfected Sf9 cells: full-length BTK, 6HIS-tag cleaved). Following a 60 minute compound & enzyme incubation, each reaction was initiated by the addition of 2.5 μL 1× kinase buffer containing 8 μM biotinylated "A5" peptide (Biotin-EQEDEPEGDYFEWLE-$NH2$), and 100 μM ATP. The final reaction in each well of 10 μL consists of 50 pM hBTK, 2 μM biotin-A5-peptide, and 25 μM ATP. Phosphorylation reactions were allowed to proceed for 120 minutes. Reactions were immediately quenched by the addition of 20 uL of 1× quench buffer (15 mM EDTA, 25 mM Hepes 7.3, and 0.1% Triton X-100) containing detection reagents (0.626 nM of LANCE-Eu-W1024-anti-phospho Tyrosine antibody, PerkinElmer and 86.8 nM of Streptavidin-conjugated Dylight 650, Dyomics/ThermoFisher Scientific). After 60 minutes incubation with detection reagents, reaction plates were read on a PerkinElmer EnVision plate reader using standard TR-FRET protocol. Briefly, excitation of donor molecules (Eu-chelate:anti-phospho-antibody) with a laser light source at 337 nm produces energy that can be transferred to Dylight-650 acceptor molecules if this donor:acceptor pair is within close proximity. Fluorescence intensity at both 665 nm (acceptor) and 615 nm (donor) are measured and a TR-FRET ratio calculated for each well (acceptor intensity/donor intensity). $IC_{50}$ values were determined by 4 parameter robust fit of TR-FRET ratio values vs. ($Log_{10}$) compound concentrations.

TABLE C

| IC50 | Example |
|---|---|
| ≥1 μM | |
| ≥100 nM-<1 μM | 353, 357, 361, 557 |
| ≥10 nM-<100 nM | 325, 350, 351, 359, 364, 365, 368, 370, 423, 428, 464, 469, 506, 530, 534, 547, 554, 560, 573 |
| <10 nM | 324, 326, 327, 328, 329, 330, 331, 332, 333, 334, 335, 336, 337, 338, 339, 340, 341, 342, 343, 344, 345, 346, 347, 348, 349, 352, 354, 355, 356, 358, 360, 362, 363, 366, 367, 369, 371, 372, 373, 381, 382, 383, 384, 385, 386, 387, 388, 392, 393, 395, 396, 397, 398, 399, 400, 408, 409, 410, 411, 412, 413, 414, 415, 416, 417, 418, 419, 420, 421, 422, 424, 425, 426, 427, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 465, 466, 467, 468, 470, 471, 472, 473, 476, 477, 478, 480, 481, 482, 483, 484, 485, 486, 487, 488, 489, 490, 491, 492, 493, 494, 501, 502, 503, 504, 505, 507, 508, 509, 510, 511, 512, 513, 514, 515, 516, 517, 518, 519, 520, 521, 522, 523, 524, 525, 526, 527, 528, 529, 531, 532, 533, 535, 536, 537, 538, 539, 540, 541, 542, 543, 544, 545, 546, 548, 549, 550, 551, 552, 553, 555, 556, 558, 559, 561, 562, 563, 564, 575, 576 |

IC50 Btk activity values - Assay Method C

The following Table D provides specific IC50 values for some of the examples set forth above in Table C. The IC50 values set forth below were determined according to Assay Method C described above.

| Example | IC50 BTK activity value |
|---|---|
| 324 | 0.3215 |
| 345 | 0.4722 |
| 346 | 0.2191 |
| 355 | 1.327 |
| 393 | 0.1666 |
| 395 | 0.1562 |
| 396 | 0.3979 |
| 398 | 0.3561 |
| 400 | 0.9603 |
| 413 | 0.2003 |
| 436 | 0.4795 |
| 449 | 0.6558 |
| 456 | 0.4026 |
| 476 | 0.3215 |
| 477 | 0.6684 |
| 483 | 0.5217 |
| 485 | 0.2536 |
| 528 | 0.8919 |

The invention claimed is:

1. A compound according to Formula Ia, or a pharmaceutically acceptable salt thereof

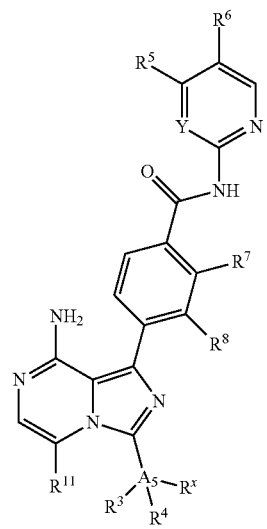

Formula Ia wherein:
$R^{11}$ is independently selected from the group consisting of:
a) H,
b) halogen,
c) $Si(CH_3)_3$,
d) cyano,
e) $C^2H_3$,
f) $CO_2H$,
g) $CO_2$(1-6C)alkyl,
h) CO(1-6C)alkyl,
i) CONH(1-6C)alkoxy,
j) CONH(1-6C)alkyl,
k) CONHdi(1-6C)alkyl,
l) CONHheterocycloalkyl,
m) CONHheteroaryl(1-6C)alkyl,
n) (1-6C)alkyl,
o) (3-7C)cycloalkyl,
p) (6-10C)aryl,
q) (1-5C)heteroaryl,
r) (2-6C)alkenyl,
s) (2-6C)alkynyl,
t) (6-10C)aryl(2-6C)alkenyl,
u) (3-7C)heterocycloalkyl, and
v) (3-7C)heterocycloalkenyl;
$R^{11}$ is optionally substituted with one or more groups selected from: halogen, (1-6C)alkyl, (1-5C)alkoxy, hydroxyl, oxo, (6-10C)aryl, or $R^{16}$(CO);
Y is $C(R^6)$, N, O or S;
$R^7$ is H, halogen, OH, $CF_3$, (1-3C)alkyl, (1-3C)alkoxy or halo(1-3C)alkyl;
$R^8$ is H, halogen, OH, $CF_3$, (1-3C)alkyl, (1-3C)alkoxy or halo(1-3C)alkyl;
$R^5$ is H, halogen, cyano, (1-4C)alkyl, (1-5C)alkoxy, (3-6C)cycloalkyl; (3-6C)cycloalkoxy; any alkyl group of $R^5$ may optionally be substituted with one, two or three halogen; or $R^5$ is (6-10C)aryl, (1-5C)heteroaryl or (2-6C)heterocycloalkyl; the aryl or heterocycloalkyl of which may optionally be substituted with halogen, (1-6C)alkyl, (1-3C)alkoxy;
$R^6$ is H, halogen, (1-3C)alkyl, cyano, (1-6C)alkyl, or (1-6C)alkoxy;
$R^6$ may optionally be substituted with one, two or three halogen or cyano; or $R^5$ and $R^6$ together form a (3-7C)cycloalkenyl or (2-6C) heterocycloalkenyl; each optionally substituted with (1-3C)alkyl or with one or more halogen;
wherein

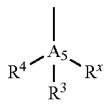

is selected from the group consisting of

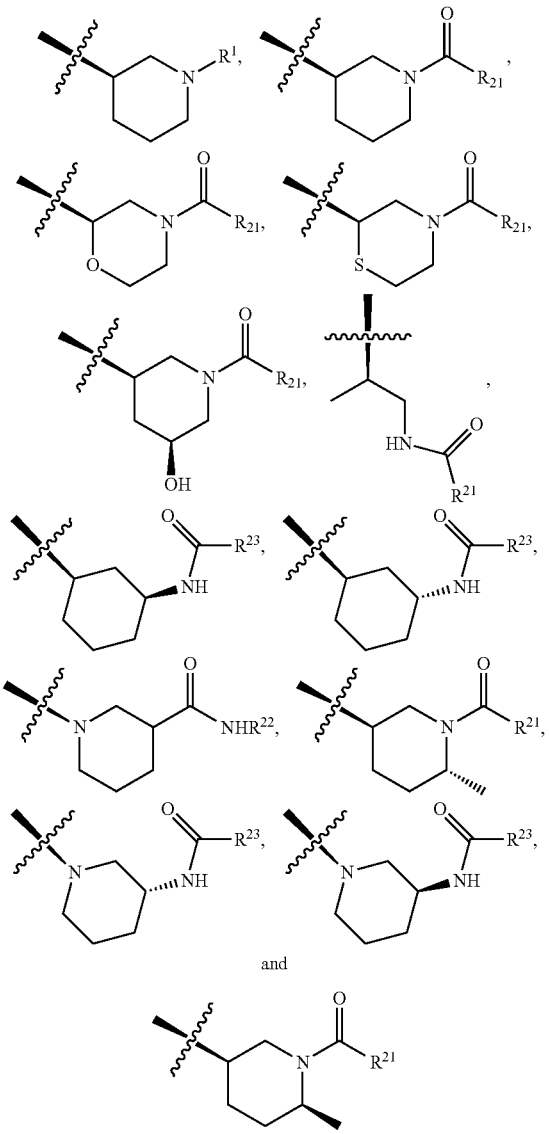

and $R^1$ is
a) $R^{21}$ C(O),
b) $R^{22}$NHC(O),
c) $R^{23}$C(O)NH,
d) $R^{24}$S(O),
e) $R^{25}$SO$_2$,
f) NH$_2$,
g) H,
h) (3-7C)cycloalkyl(1-4C)alkyl,
i) (1-6C)alkoxycarbonyl(3-7C)cycloalkyl(1-4C)alkyl,
j) (6-10C)aryl(1-4C)alkyl,
k) (1-6C)alkyl,
l) (1-5C)heteroaryl(1-4C)alkyl, wherein the (1-5C)heteroaryl is optionally substituted with one or two(1-4C)alkyl, hydroxyl or halogen,
m) (1-5C)heterocycloalkyl(1-4C)alkyl, wherein the (1-5C)heterocycloalkyl is optionally substituted with one or two(1-4C)alkyl, hydroxyl or halogen,
n) cyano(1-6C)alkyl,
o) halo(1-6C)alkyl,
p) hydroxy(1-6C)alkyl,
q) (1-4C)alkoxy(1-6C)alkyl, or
r) (1-6C)alkoxyl;
$R^{21}$ is selected from the group consisting of:
a) H,
b) trifluoromethylcarbonyl,
c) hydroxy(1-6C)alkyl,
d) di[hydroxy](1-6C)alkyl,
e) di[(1-6C)alkyl]amino(1-6C)alkyl,
f) CF$_3$,
g) CCl$_3$,
h) amino(3-7C)cycloalkyl,
i) (6-10C)aryloxy,
j) (6-10C)arylcarbonyl(2-5C)heterocycloalkyl,
k) (6-10C)arylcarbonyl,
l) (6-10C)aryl(1-6C)alkoxy,
m) (3-7C)cycloalkylcarbonyl(1-5C)heterocycloalkyl,
n) (3-7C)cycloalkyl(1-4C)alkyl,
o) (3-7C)cycloalkyl,
p) (3-10C)cycloalkylamino,
q) (3-10C)cycloalkyl,
r) (3-10C)cycloalkylcarbonyl,
s) (4-10C)bicycloalkyl,
t) (1-6C)heterocycloalkyl,
u) (1-6C)alkylsulfonyl(2-5C)heterocycloalkyl,
v) (1-6C)alkylcarbonyl(2-5C)heterocycloalkyl,
w) (1-6C)alkylcarbonyl,
x) (1-6C)alkylaminocarbonyl,
y) (6-10C)arylaminocarbonyl,
z) (1-6C)alkylamino,
aa) (1-6C)alkoxycarbonyl,
bb) (1-6C)alkoxycarbonyl(1-4C)alkylamino(3-7C)cycloalkyl,
cc) (1-6C)alkoxycarbonyl(1-4C)alkyl,
dd) (1-6C)alkoxycarbonyl(3-7C)cycloalkyl(1-4C)alkyl,
ee) (1-6C)alkoxy,
ff) (6-10C)aryl(1-6C)alkoxy,
gg) (1-5C)heteroarylcarbonyl,
hh) (1-5C)heteroaryl(1-4C)alkyl,
ii) (1-5C)heteroaryl(3-7C)cycloalkyl,
jj) (1-5C)heterocycloalkyl,
kk) (1-4C)thioalkyl(1-6C)alkyl,
ll) di[(1-4C)alkyl]aminocarbonyl,
mm) (1-4C)alkylsulfonyl(1-6C)alkyl,
nn) (1-4C)alkylaminocarbonyl,
oo) (1-4C)alkoxy(1-6C)alkyl,
pp) (1-8C)alkoxy(1-16C)alkyl,
qq) cyano(1-6C)alkyl,
rr) amino(1-6C)alkyl,
ss) (6-10C)arylamino,
tt) (3-7C)cycloalkoxy,
uu) (1-6C)alkyl,
vv) (1-5C)heteroaryl,
ww) (1-4C)alkoxy[(2-4C)alkoxy]$_m$(1-6C)alkyl, and
xx) amino(1-4C)alkoxy[(2-4C)alkoxy]$_m$(1-6C)alkyl;

$R^{21}$ may optionally be substituted with one, two or three $R^{211}$ substituents;

m is 1-10;

$R^{22}$ is selected from the group consisting of:
a) (3-7C)cycloalkyl(1-4C)alkyl,
b) (3-7C)cycloalkyl,
c) (4-10C)bicycloalkyl,
d) (3-7C)cycloalkoxy(1-4C)alkyl,
e) (3-6C)cycloalkoxy,
f) (1-5C)heterocycloalkyl,
g) (1-5C)heterocycloalkyl(1-6C)alkyl,
h) (6-10C)aryl,
i) (1-6C)alkyl,
j) (1-6C)alkoxy,
k) (1-4C)thioalkyl(1-6C)alkyl,
l) (1-4C)alkylsulfonyl(1-6C)alkyl, and
m) (1-4C)alkoxy(1-6C)alkyl;

$R^{22}$ may optionally be substituted with one, two or three $R^{221}$ substituents;

$R^{23}$ is selected from the group consisting of:
a) (6-10C)aryl(1-6C)alkoxy,
b) (3-7C)cycloalkyl,
c) (3-7C)cycloalkoxy,
d) (1-6C)alkylamino,
e) (1-6C)alkyl, and
f) (1-4C)alkoxy(1-6C)alkyl;

$R^{23}$ may optionally be substituted with one, two or three $R^{231}$ substituents;

$R^{24}$ is selected from the group consisting of:
a) (3-7C)cycloalkyl,
b) (1-6C)alkyl,
c) (6-10C)aryl, and
d) (2-5C)heteroaryl;

$R^{24}$ may optionally be substituted with one, two or three $R^{241}$ substituents;

$R^{25}$ is independently selected from the group consisting of:
a) (3-7C)cycloalkyl,
b) (1-6C)alkyl,
c) (6-10C)aryl, and
d) (2-5C)heteroaryl;

$R^{25}$ may optionally be substituted with one, two or three $R^{251}$ substituents;

$R^{211}$, $R^{221}$, $R^{231}$, $R^{241}$, and $R^{251}$ are independently selected from the group consisting of:
a) halogen,
b) $CF_3$,
c) $OCF_3$,
d) oxo,
e) hydroxyl,
f) cyano,
g) amino,
h) (1-6C)alkyl,
i) (1-4C)alkoxyl,
j) (3-7C)cycloalkyl,
k) (3-7C)cycloalkoxy,
l) (di[(1-6C)alkyl]amino,
m) (1-4C)akoxy(1-6C)alkyl,
n) (1-5C)heteroaryl, and
o) (2-5C)heterocycloalkyl.

2. The compound of claim 1, wherein $R^5$ is selected from the group consisting of hydrogen, fluorine, chlorine, CN, cyclopropyl, (1-3C)alkyl and(1-2C) alkoxy; the (1-3C)alkyl group of which is optionally substituted with one or more halogen.

3. The compound of claim 2, wherein $R^5$ is selected from the group consisting of hydrogen, fluorine, methyl, ethyl, propyl, cyclopropyl, methoxy and trifluoromethyl.

4. The compound of claim 1, wherein $R^1$ is selected from the group consisting of: $R^{21}C(O)$, $R^{22}NHC(O)$, $R^{23}C(O)$ NH, $R^{25}SO_2$, (3-7C)cycloalkyl(1-4C)alkyl, (6-10C)aryl(1-4C)alkyl, (1-6C)alkyl, (1-5C)heteroaryl(1-4C)alkyl, halo 1-6C)alkyl, hydroxyl(1-6Calkyl, (1-4C)alkoxy(1-6C)alkyl, (1-4C)alkoxy(1-6C)alkyl and(1-6C)alkoxyl.

5. The compound of claim 4, wherein $R^1$ is selected from the group consisting of: $R^{21}C(O)$, $R^{22}NHC(O)$, $R^{23}C(O)$ NH, (6-10C)aryl(1-4C)alkyl, (1-5C)heteroaryl(1-4C)alkyl, halo(1-6C)alkyl, hydroxyl(1-6Calkyl, (1-4C)alkoxy(1-6C) alkyl, (1-4C)alkoxy(1-6C)alkyl and (1-6C)alkoxyl.

6. The compound of claim 5, wherein $R^1$ is selected from the group consisting of $R^{21}C(O)$, $R^{22}NHC(O)$, and $R^{23}C(O)$ NH.

7. The compound of claim 1, wherein
$R^{21}$ is selected from the group consisting of di[hydroxy] (1-6C)alkyl, di[(1-6C)alkyl]amino(1-6C)alkyl, amino (3-7C)cycloalkyl, (6-10C)aryloxy, (6-10C)arylcarbonyl(2-5C)heterocycloalkyl, (3-7C)cycloalkylcarbonyl (1-5C)heterocycloalkyl, (3-7C)cycloalkyl, (3-6C) cycloalkoxy, (3-10C)cycloalkylamino, (3-10C) cycloalkyl, (1-6C)alkylsulfonyl(2-5C) heterocycloalkyl, (1-6C)alkylcarbonyl(2-5C) heterocycloalkyl, (1-6C)alkylamino, (1-6C)alkoxy, (1-5C)heteroarylcarbonyl, (1-5C)heteroaryl(1-4C) alkyl, (1-5C)heterocycloalkyl, (1-4C)thioalkyl(1-6C) alkyldi[(1-4C)alkyl]aminocarbonyl, (1-4C)alkylsulfonyl(1-6C)alkyl, (1-4C)alkylaminocarbonyl, (1-4C) alkoxy(1-6C)alkyl, (1-6C)alkoxy, amino(1-6C)alkyl, (6-10C)arylamino, (3-7C)cycloalkoxy,(2-5C)heterocycloalkyl, (1-6C)cycloalkyl, (1-6C)alkyl, (1-6C)alkoxycarbonyl(1-4C)alkyl, (1-5C)heteroaryl, and (1-4C) alkoxy[(2-4C)alkoxy]$_m$(1-6C)alkyl; amino(1-4C) alkoxy[(2-4C)alkoxy]$_m$(1-6C)alkyl; $R^{21}$ may optionally be substituted with $R^{211}$;
$R^{22}$ is selected from the group consisting of (3-7C) cycloalkyl(1-4C)alkyl, (3-7C)cycloalkyl, (3-7C)cycloalkoxy(1-4C)alkyl, (3-6C)cycloalkoxy, (1-6C)alkyl, (1-6C)alkoxy, (1-4C)thioalkyl(1-6C)alkyl, (1-4C) alkylsulfonyl(1-6C)alkyl, and (1-4C)alkoxy(1-6C) alkyl; and $R^{22}$ may optionally be substituted with $R^{221}$; and
$R^{23}$ is selected from the group consisting of (6-10C)aryl (1-6C)alkoxy, (3-7C)cycloalkyl, (3-7C)cycloalkoxy, (1-6C)alkylamino, (1-6C)alkyl, and (1-4C)alkoxy(1-6C)alkyl; and $R^{23}$ may optionally be substituted with $R^{231}$.

8. The compound of claim 7, wherein
$R^{21}$ is selected from the group consisting of (3-7C) cycloalkylcarbonyl(1-5C)heterocycloalkyl, (3-7C)cycloalkyl, (3-6C)cycloalkoxy, (3-10C)cycloalkylamino, (3-10C)cycloalkyl, (1-6C)alkylsulfonyl(2-5C)heterocycloalkyl, (1-6C)alkylcarbonyl(2-5C)heterocycloalkyl, (1-6C)alkylamino, (1-6C)alkoxy, (1-5C)heteroarylcarbonyl, (1-5C)heteroaryl(1-4C)alkyl, (1-5C) heterocycloalkyl, (1-4C)thioalkyl(1-6C)alkyl, di[(1-4C)alkyl]aminocarbonyl, (1-4C)alkoxy[(2-4C) alkoxy]$_m$(1-6C)alkyl, (1-4C)alkylsulfonyl(1-6C)alkyl, (1-4C)alkylaminocarbonyl, (1-4C)alkoxy(1-6C)alkyl, (1-6C)alkoxy, amino(1-6C)alkyl, (6-10C)arylamino, (3-7C)cycloalkoxy, (2-5C)heterocycloalkyl, (1-6C)cycloalkyl, (1-6C)alkyl, (1-6C)alkoxycarbonyl(1-4C) alkyl, and (1-5C)heteroaryl; $R^{21}$ may optionally be substituted with $R^{211}$.

9. The compound of claim 8, wherein
R$^{21}$ is selected from the group consisting of (3-7C)cycloalkyl, (3-6C)cycloalkoxy, (1-6C)alkylsulfonyl(2-5C)heterocycloalkyl, (1-4C)thioalkyl(1-6C)alkyl, (1-4C)alkylsulfonyl(1-6C)alkyl, (1-4C)alkoxy(1-6C)alkyl, (3-7C)cycloalkoxy, (1-6C)alkyl, and (1-5C)heteroaryl; and R$^{21}$ may optionally be substituted with R$^{211}$;
R$^{22}$ is selected from the group consisting of (3-7C)cycloalkyl, (3-7C)cycloalkoxy(1-4C)alkyl, (3-6C)cycloalkoxy, (1-6C)alkyl, and (1-4C)alkoxy(1-6C)alkyl; and R$^{22}$ may optionally be substituted with R$^{221}$;
R$^{23}$ is selected from the group consisting of (3-7C)cycloalkyl, (3-7C)cycloalkoxy, and (1-4C)alkoxy(1-6C)alkyl; and R$^{23}$ may optionally be substituted with R$^{231}$;
R$^{24}$ is selected from the group consisting of (3-7C)cycloalkyl and (1-6C)alkyl; and R$^{24}$ may optionally be substituted with R$^{241}$; and
R$^{25}$ is selected from the group consisting of (3-7C)cycloalkyl and (1-6C)alkyl and R$^{25}$ may optionally be substituted with R$^{251}$.

10. The compound of claim 1, wherein R$^{11}$ is selected from the group consisting of H, F, Cl, Br, Me, C$^{2}$H$_{3}$, ethyl, cyclopropyl and vinyl.

11. The compound of claim 10, wherein R$^{11}$ is H.

12. A compound of a pharmaceutically acceptable salt thereof selected from the group consisting of:
4-(8-amino-3-((trans)-4-hydroxycyclohexyl)imidazo[1,5-a]pyrazin-1-yl)-N-(pyridin-2-yl)benzamide;
4-(8-amino-3-((trans)-4-hydroxycyclohexyl)imidazo[1,5-a]pyrazin-1-yl)-N-(4-(trifluoromethyl)pyridin-2-yl)benzamide;
4-(8-amino-3-((trans)-4-hydroxycyclohexyl)imidazo[1,5-a]pyrazin-1-yl)-N-(4-propylpyridin-2-yl)benzamide;
4-(8-amino-3-((trans)-4-hydroxycyclohexyl)imidazo[1,5-a]pyrazin-1-yl)-N-(5-ethylthiazol-2-yl)benzamide;
4-(8-amino-3-((trans)-4-hydroxycyclohexyl)imidazo[1,5-a]pyrazin-1-yl)-N-(4-methylpyridin-2-yl)benzamide;
4-(8-amino-3-((trans)-4-hydroxycyclohexyl)imidazo[1,5-a]pyrazin-1-yl)-N-(4-isopropylpyridin-2-yl)benzamide;
4-(8-amino-3-((trans)-4-hydroxycyclohexyl)imidazo[1,5-a]pyrazin-1-yl)-N-(4-cyclopropylpyridin-2-yl)benzamide;
4-(8-amino-3-((trans)-4-hydroxycyclohexyl)imidazo[1,5-a]pyrazin-1-yl)-N-(4,5,6,7-tetrahydrobenzo[d]thiazol-2-yl)benzamide;
4-(8-amino-3-((trans)-4-hydroxycyclohexyl)imidazo[1,5-a]pyrazin-1-yl)-2-methoxy-N-(pyridin-2-yl)benzamide;
4-(8-amino-3-((trans)-4-hydroxycyclohexyl)imidazo[1,5-a]pyrazin-1-yl)-3-methyl-N-(4-propylpyridin-2-yl)benzamide;
4-(8-amino-3-((trans)-4-hydroxycyclohexyl)imidazo[1,5-a]pyrazin-1-yl)-2-methoxy-N-(4-propylpyridin-2-yl)benzamide;
4-(8-amino-3-((trans)-4-hydroxycyclohexyl)imidazo[1,5-a]pyrazin-1-yl)-2-fluoro-N-(pyridin-2-yl)benzamide;
4-(8-amino-3-((trans)-4-hydroxycyclohexyl)imidazo[1,5-a]pyrazin-1-yl)-2-fluoro-N-(4-propylpyridin-2-yl)benzamide;
4-(8-amino-3-((trans)-4-hydroxycyclohexyl)imidazo[1,5-a]pyrazin-1-yl)-N-(6-methyl-4,5,6,7-tetrahydrobenzo[d]thiazol-2-yl)benzamide;
4-(8-amino-3-((trans)-4-hydroxycyclohexyl)imidazo[1,5-a]pyrazin-1-yl)-N-(6,7-dihydro-4H-pyrano[4,3-d]thiazol-2-yl)benzamide;
4-(8-amino-3-((trans)-4-hydroxycyclohexyl)imidazo[1,5-a]pyrazin-1-yl)-3-methyl-N-(pyridin-2-yl)benzamide;
4-(8-amino-3-((trans)-4-hydroxycyclohexyl)imidazo[1,5-a]pyrazin-1-yl)-N-(4,5,6,7-tetrahydrothiazolo[5,4-c]pyridin-2-yl)benzamide;
4-(8-amino-3-((trans)-4-hydroxycyclohexyl)imidazo[1,5-a]pyrazin-1-yl)-N-(5-methyl-4,5,6,7-tetrahydrothiazolo[5,4-c]pyridin-2-yl)benzamide;
4-(8-amino-3-((trans)-4-hydroxycyclohexyl)imidazo[1,5-a]pyrazin-1-yl)-N-(4-ethylpyridin-2-yl)benzamide;
4-(8-amino-3-((trans)-4-hydroxycyclohexyl)imidazo[1,5-a]pyrazin-1-yl)-N-(4-phenylpyridin-2-yl)benzamide;
4-(8-amino-3-((trans)-4-hydroxycyclohexyl)imidazo[1,5-a]pyrazin-1-yl)-N-(4-(pyrrolidin-1-yl)pyridin-2-yl)benzamide;
4-(8-amino-3-((trans)-4-hydroxycyclohexyl)imidazo[1,5-a]pyrazin-1-yl)-N-(pyridin-2-yl)-1-naphthamide;
4-(8-amino-3-((trans)-4-hydroxycyclohexyl)imidazo[1,5-a]pyrazin-1-yl)-2-chloro-N-(pyridin-2-yl)benzamide;
4-(8-amino-3-(tetrahydro-2H-pyran-4-yl)imidazo[1,5-a]pyrazin-1-yl)-N-(4-propylpyridin-2-yl)benzamide;
4-(8-amino-3-(tetrahydro-2H-pyran-4-yl)imidazo[1,5-a]pyrazin-1-yl)-N-(4-(trifluoromethyl)pyridin-2-yl)benzamide;
4-(8-amino-3-(tetrahydro-2H-pyran-4-yl)imidazo[1,5-a]pyrazin-1-yl)-N-(4-cyanopyridin-2-yl)benzamide;
4-(8-amino-3-(tetrahydro-2H-pyran-4-yl)imidazo[1,5-a]pyrazin-1-yl)-N-(pyridin-2-yl)benzamide 4-(8-amino-3-(tetrahydro-2H-pyran-4-yl)imidazo[1,5-a]pyrazin-1-yl)-N-(5-ethylthiazol-2-yl)benzamide;
4-(8-amino-3-(tetrahydro-2H-pyran-4-yl)imidazo[1,5-a]pyrazin-1-yl)-N-(thiazol-2-yl)benzamide
4-(8-amino-3-((1R,5S,6S)-3-oxabicyclo[3.1.0]hexan-6-yl)imidazo[1,5-a]pyrazin-1-yl)-N-(4-propylpyridin-2-yl)benzamide;
4-(8-amino-3-((1R,5S,6S)-3-oxabicyclo[3.1.0]hexan-6-yl)imidazo[1,5-a]pyrazin-1-yl)-N-(4-(trifluoromethyl)pyridin-2-yl)benzamide;
4-(8-amino-3-((1R,5S,6S)-3-oxabicyclo[3.1.0]hexan-6-yl)imidazo[1,5-a]pyrazin-1-yl)-N-(6-methyl-4,5,6,7-tetrahydrobenzo[d]thiazol-2-yl)benzamide;
4-(8-amino-3-(tetrahydrofuran-3-yl)imidazo[1,5-a]pyrazin-1-yl)-N-(4-cyanopyridin-2-yl)benzamide;
4-(8-amino-3-(2,2-dimethyltetrahydro-2H-pyran-4-yl)imidazo[1,5-a]pyrazin-1-yl)-N-(4-(trifluoromethyl)pyridin-2-yl)benzamide;
4-(8-amino-3-(2,2-dimethyltetrahydro-2H-pyran-4-yl)imidazo[1,5-a]pyrazin-1-yl)-N-(pyridin-2-yl)benzamide;
4-(8-amino-3-(2,2-dimethyltetrahydro-2H-pyran-4-yl)imidazo[1,5-a]pyrazin-1-yl)-N-(4-propylpyridin-2-yl)benzamide;
4-(8-amino-3-(2,2-dimethyltetrahydro-2H-pyran-4-yl)imidazo[1,5-a]pyrazin-1-yl)-N-(4-cyanopyridin-2-yl)benzamide;
(trans)-4-(8-amino-1-(4-(5-ethylthiazol-2-ylcarbamoyl)phenyl)imidazo[1,5-a]pyrazin-3-yl)cyclohexyl acetate;
4-(8-amino-3-((cis)-4-methoxycyclohexyl)imidazo[1,5-a]pyrazin-1-yl)-N-(5-ethylthiazol-2-yl)benzamide;
4-(8-amino-3-((cis)-4-methoxycyclohexyl)imidazo[1,5-a]pyrazin-1-yl)-N-(4-(trifluoromethyl)pyridin-2-yl)benzamide;
4-(8-amino-3-((cis)-4-methoxycyclohexyl)imidazo[1,5-a]pyrazin-1-yl)-N-(4-cyanopyridin-2-yl)benzamide;

4-(8-amino-3-((cis)-4-methoxycyclohexyl)imidazo[1,5-a]pyrazin-1-yl)-N-(4-propylpyridin-2-yl)benzamide;

4-(8-amino-3-cyclopentylimidazo[1,5-a]pyrazin-1-yl)-N-(4-(trifluoromethyl)pyridin-2-yl)benzamide;

4-(8-amino-3-cyclopentylimidazo[1,5-a]pyrazin-1-yl)-N-(4-cyanopyridin-2-yl)benzamide;

4-(8-amino-3-cyclopentylimidazo[1,5-a]pyrazin-1-yl)-N-(pyridin-2-yl)benzamide;

(R)-4-(8-amino-3-(1-propionylpiperidin-3-yl)imidazo[1,5-a]pyrazin-1-yl)-N-(pyridin-2-yl)benzamide;

(R)-ethyl 3-(8-amino-1-(4-(pyridin-2-ylcarbamoyl)phenyl)imidazo[1,5-a]pyrazin-3-yl)piperidine-1-carboxylate;

(R)-3-(8-amino-1-(4-(pyridin-2-ylcarbamoyl)phenyl)imidazo[1,5-a]pyrazin-3-yl)-N-ethylpiperidine-1-carboxamide;

(R)-4-(8-amino-3-(1-(methylsulfonyl)piperidin-3-yl)imidazo[1,5-a]pyrazin-1-yl)-N-(pyridin-2-yl)benzamide;

(R)-4-(8-amino-3-(1-(3-methoxypropanoyl)piperidin-3-yl)imidazo[1,5-a]pyrazin-1-yl)-N-(pyridin-2-yl)benzamide;

(R)-4-(8-amino-3-(1-(4-(dimethylamino)butanoyl)piperidin-3-yl)imidazo[1,5-a]pyrazin-1-yl)-N-(pyridin-2-yl)benzamide;

(R)-4-(8-amino-3-(1-(cyclopropanecarbonyl)piperidin-3-yl)imidazo[1,5-a]pyrazin-1-yl)-N-(pyridin-2-yl)benzamide;

(R)-4-(8-amino-3-(1-(2-hydroxyacetyl)piperidin-3-yl)imidazo[1,5-a]pyrazin-1-yl)-N-(pyridin-2-yl)benzamide;

(R)-4-(8-amino-3-(1-(5-aminopentanoyl)piperidin-3-yl)imidazo[1,5-a]pyrazin-1-yl)-N-(pyridin-2-yl)benzamide;

4-(8-amino-3-((R)-1-((trans)-4-aminocyclohexanecarbonyl)piperidin-3-yl)imidazo[1,5-a]pyrazin-1-yl)-N-(pyridin-2-yl)benzamide;

4-(8-amino-3-((3R)-1-(tetrahydrofuran-3-carbonyl)piperidin-3-yl)imidazo[1,5-a]pyrazin-1-yl)-N-(pyridin-2-yl)benzamide;

4-(8-amino-3-((R)-1-((S)-2-methoxypropanoyl)piperidin-3-yl)imidazo[1,5-a]pyrazin-1-yl)-N-(pyridin-2-yl)benzamide;

4-(8-amino-3-((R)-1-((S)-2-methylbutanoyl)piperidin-3-yl)imidazo[1,5-a]pyrazin-1-yl)-N-(pyridin-2-yl)benzamide;

(R)-4-(8-amino-3-(1-(cyclobutanecarbonyl)piperidin-3-yl)imidazo[1,5-a]pyrazin-1-yl)-N-(4-cyclopropylpyridin-2-yl)benzamide;

(R)-4-(8-amino-3-(1-propionylpiperidin-3-yl)imidazo[1,5-a]pyrazin-1-yl)-N-(4-cyclopropylpyridin-2-yl)benzamide;

(R)-4-(8-amino-3-(1-(3-methoxypropanoyl)piperidin-3-yl)imidazo[1,5-a]pyrazin-1-yl)-N-(4-cyclopropylpyridin-2-yl)benzamide;

4-(8-amino-3-((3R)-1-(2-methylcyclopropanecarbonyl)piperidin-3-yl)imidazo[1,5-a]pyrazin-1-yl)-N-(4-cyclopropylpyridin-2-yl)benzamide;

(R)-3-(8-amino-1-(4-(4-cyclopropylpyridin-2-ylcarbamoyl)phenyl)imidazo[1,5-a]pyrazin-3-yl)-N-ethylpiperidine-1-carboxamide;

(R)-4-(8-amino-3-(1-(2-fluoro-2-methylpropanoyl)piperidin-3-yl)imidazo[1,5-a]pyrazin-1-yl)-N-(4-cyclopropylpyridin-2-yl)benzamide;

(R)-4-(8-amino-3-(1-propionylpiperidin-3-yl)imidazo[1,5-a]pyrazin-1-yl)-N-(6-methyl-4,5,6,7-tetrahydrobenzo[d]thiazol-2-yl)benzamide;

(R)-4-(8-amino-3-(1-(1-(methoxymethyl)cyclobutanecarbonyl)piperidin-3-yl)imidazo[1,5-a]pyrazin-1-yl)-N-(4-(trifluoromethyl)pyridin-2-yl)benzamide;

(R)-4-(8-amino-3-(1-(3-methyloxetane-3-carbonyl)piperidin-3-yl)imidazo[1,5-a]pyrazin-1-yl)-N-(4-(trifluoromethyl)pyridin-2-yl)benzamide;

(R)-4-(8-amino-3-(1-(3-(2-methoxyethoxy)propanoyl)piperidin-3-yl)imidazo[1,5-a]pyrazin-1-yl)-N-(4-(trifluoromethyl)pyridin-2-yl)benzamide;

(R)-4-(8-amino-3-(1-(3-(methylthio)propanoyl)piperidin-3-yl)imidazo[1,5-a]pyrazin-1-yl)-N-(4-(trifluoromethyl)pyridin-2-yl)benzamide;

(R)-4-(8-amino-3-(1-(1-methylcyclobutanecarbonyl)piperidin-3-yl)imidazo[1,5-a]pyrazin-1-yl)-N-(4-(trifluoromethyl)pyridin-2-yl)benzamide;

(R)-4-(8-amino-3-(1-(3-hydroxy-3-methylbutanoyl)piperidin-3-yl)imidazo[1,5-a]pyrazin-1-yl)-N-(4-(trifluoromethyl)pyridin-2-yl)benzamide;

(R)-4-(8-amino-3-(1-(2,2,2-trifluoroacetyl)piperidin-3-yl)imidazo[1,5-a]pyrazin-1-yl)-N-(4-(trifluoromethyl)pyridin-2-yl)benzamide;

(R)-4-(8-amino-3-(1-(1-(methylsulfonyl)azetidine-3-carbonyl)piperidin-3-yl)imidazo[1,5-a]pyrazin-1-yl)-N-(4-(trifluoromethyl)pyridin-2-yl)benzamide;

(R)-4-(8-amino-3-(1-(3,5-dimethylisoxazole-4-carbonyl)piperidin-3-yl)imidazo[1,5-a]pyrazin-1-yl)-N-(4-(trifluoromethyl)pyridin-2-yl)benzamide;

(R)-4-(8-amino-3-(1-(cyclopropylsulfonyl)piperidin-3-yl)imidazo[1,5-a]pyrazin-1-yl)-N-(4-(trifluoromethyl)pyridin-2-yl)benzamide;

(R)-4-(8-amino-3-(1-pivaloylpiperidin-3-yl)imidazo[1,5-a]pyrazin-1-yl)-N-(4-(trifluoromethyl)pyridin-2-yl)benzamide;

(R)-4-(8-amino-3-(1-(3-(methylsulfonyl)propanoyl)piperidin-3-yl)imidazo[1,5-a]pyrazin-1-yl)-N-(4-(trifluoromethyl)pyridin-2-yl)benzamide;

(R)-4-(8-amino-3-(1-(3-hydroxy-2,2-dimethylpropanoyl)piperidin-3-yl)imidazo[1,5-a]pyrazin-1-yl)-N-(4-(trifluoromethyl)pyridin-2-yl)benzamide;

(R)-4-(8-amino-3-(1-(1-(dimethylamino)cyclobutanecarbonyl)piperidin-3-yl)imidazo[1,5-a]pyrazin-1-yl)-N-(4-(trifluoromethyl)pyridin-2-yl)benzamide;

(R)-4-(3-(1-2,5,8,11,14,17,20,23-octaoxahexacosanepiperidin-3-yl)-8-aminoimidazo[1,5-a]pyrazin-1-yl)-N-(4-(trifluoromethyl)pyridin-2-yl)benzamide;

(R)-4-(8-amino-3-(1-(1-hydroxycyclobutanecarbonyl)piperidin-3-yl)imidazo[1,5-a]pyrazin-1-yl)-N-(4-(trifluoromethyl)pyridin-2-yl)benzamide;

4-(8-amino-3-((R)-1-((1S,2S)-2-(3-methyl-1,2,4-oxadiazol-5-yl)cyclopropanecarbonyl)piperidin-3-yl)imidazo[1,5-a]pyrazin-1-yl)-N-(4-(trifluoromethyl)pyridin-2-yl)benzamide;

(R)-4-(8-amino-3-(1-(3,3-difluorocyclobutanecarbonyl)piperidin-3-yl)imidazo[1,5-a]pyrazin-1-yl)-N-(4-(trifluoromethyl)pyridin-2-yl)benzamide;

(R)-4-(8-amino-3-(1-(1-benzoylazetidine-3-carbonyl)piperidin-3-yl)imidazo[1,5-a]pyrazin-1-yl)-N-(4-(trifluoromethyl)pyridin-2-yl)benzamide;

(R)-4-(8-amino-3-(1-(1-amino-3,6,9,12-tetraoxapentadecane)piperidin-3-yl)imidazo[1,5-a]pyrazin-1-yl)-N-(4-(trifluoromethyl)pyridin-2-yl)benzamide;

(R)-4-(8-amino-3-(1-(thietane-3-carbonyl)piperidin-3-yl)imidazo[1,5-a]pyrazin-1-yl)-N-(4-(trifluoromethyl)pyridin-2-yl)benzamide;

4-(8-amino-3-((R)-1-((R)-4-oxoazetidine-2-carbonyl)piperidin-3-yl)imidazo[1,5-a]pyrazin-1-yl)-N-(4-(trifluoromethyl)pyridin-2-yl)benzamide;

(R)-4-(8-amino-3-(1-(1-(dimethylamino)cyclopropanecarbonyl)piperidin-3-yl)imidazo[1,5-a]pyrazin-1-yl)-N-(4-(trifluoromethyl)pyridin-2-yl)benzamide;
(R)-4-(8-amino-3-(1-(3-isopropylcyclobutanecarbonyl)piperidin-3-yl)imidazo[1,5-a]pyrazin-1-yl)-N-(4-(trifluoromethyl)pyridin-2-yl)benzamide;
(R)-4-(8-amino-3-(1-(bicyclo[1.1.1]pentane-1-carbonyl)piperidin-3-yl)imidazo[1,5-a]pyrazin-1-yl)-N-(4-(trifluoromethyl)pyridin-2-yl)benzamide;
(R)-4-(8-amino-3-(1-(3-vinyloxetane-3-carbonyl)piperidin-3-yl)imidazo[1,5-a]pyrazin-1-yl)-N-(4-(trifluoromethyl)pyridin-2-yl)benzamide;
(R)-4-(8-amino-3-(1-(2-cyclopropylacetyl)piperidin-3-yl)imidazo[1,5-a]pyrazin-1-yl)-N-(pyridin-2-yl)benzamide;
(R)-4-(8-amino-3-(1-(2,2-difluorobutanoyl)piperidin-3-yl)imidazo[1,5-a]pyrazin-1-yl)-N-(pyridin-2-yl)benzamide;
(R)-4-(8-amino-3-(1-(1-hydroxycyclopropanecarbonyl)piperidin-3-yl)imidazo[1,5-a]pyrazin-1-yl)-N-(pyridin-2-yl)benzamide;
(R)-4-(8-amino-3-(1-formylpiperidin-3-yl)imidazo[1,5-a]pyrazin-1-yl)-N-(pyridin-2-yl)benzamide;
(R)-4-(8-amino-3-(1-propionylpiperidin-3-yl)imidazo[1,5-a]pyrazin-1-yl)-N-(4-cyanopyridin-2-yl)benzamide;
(R)-4-(8-amino-3-(1-(3-methoxypropanoyl)piperidin-3-yl)imidazo[1,5-a]pyrazin-1-yl)-N-(4-cyanopyridin-2-yl)benzamide;
(R)-4-(8-amino-3-(1-(cyclopropanecarbonyl)piperidin-3-yl)imidazo[1,5-a]pyrazin-1-yl)-N-(4-cyanopyridin-2-yl)benzamide;
(R)-4-(8-amino-3-(1-(3-methyloxetane-3-carbonyl)piperidin-3-yl)imidazo[1,5-a]pyrazin-1-yl)-N-(4-cyanopyridin-2-yl)benzamide;
(R)-4-(8-amino-3-(1-isobutyrylpiperidin-3-yl)imidazo[1,5-a]pyrazin-1-yl)-N-(4-cyanopyridin-2-yl)benzamide;
(R)-3-(8-amino-1-(4-(4-cyanopyridin-2-ylcarbamoyl)phenyl)imidazo[1,5-a]pyrazin-3-yl)-N-ethylpiperidine-1-carboxamide;
(R)-4-(8-amino-3-(1-(3-methoxypropanoyl)piperidin-3-yl)imidazo[1,5-a]pyrazin-1-yl)-N-(4-(trifluoromethyl)pyridin-2-yl)benzamide;
(R)-4-(8-amino-3-(1-(cyclopropanecarbonyl)piperidin-3-yl)imidazo[1,5-a]pyrazin-1-yl)-N-(4-(trifluoromethyl)pyridin-2-yl)benzamide;
(R)-4-(8-amino-3-(1-isobutyrylpiperidin-3-yl)imidazo[1,5-a]pyrazin-1-yl)-N-(4-(trifluoromethyl)pyridin-2-yl)benzamide;
(R)-4-(8-amino-3-(1-(3-hydroxy-2-(hydroxymethyl)-2-methylpropanoyl)piperidin-3-yl)imidazo[1,5-a]pyrazin-1-yl)-N-(4-(trifluoromethyl)pyridin-2-yl)benzamide;
(R)-4-(8-amino-3-(piperidin-3-yl)imidazo[1,5-a]pyrazin-1-yl)-N-(4-(trifluoromethyl)pyridin-2-yl)benzamide;
(R)-benzyl 3-(8-amino-1-(4-(4-(trifluoromethyl)pyridin-2-ylcarbamoyl)phenyl)imidazo[1,5-a]pyrazin-3-yl)piperidine-1-carboxylate;
(R)-4-(8-amino-3-(1-(2-cyano-2-methylpropanoyl)piperidin-3-yl)imidazo[1,5-a]pyrazin-1-yl)-N-(pyridin-2-yl)benzamide;
(R)-4-(8-amino-3-(1-(3,3-difluorocyclobutanecarbonyl)piperidin-3-yl)imidazo[1,5-a]pyrazin-1-yl)-N-(4-cyclopropylpyridin-2-yl)benzamide;
(R)-4-(8-amino-3-(1-(2-(2-oxooxazolidin-3-yl)acetyl)piperidin-3-yl)imidazo[1,5-a]pyrazin-1-yl)-N-(4-cyclopropylpyridin-2-yl)benzamide;
(R)-4-(8-amino-3-(1-(2-(dimethylamino)-2-oxoacetyl)piperidin-3-yl)imidazo[1,5-a]pyrazin-1-yl)-N-(4-cyclopropylpyridin-2-yl)benzamide;
(R)-4-(8-amino-3-(1-(2-(isobutylamino)-2-oxoacetyl)piperidin-3-yl)imidazo[1,5-a]pyrazin-1-yl)-N-(4-cyclopropylpyridin-2-yl)benzamide;
(R)-4-(8-amino-3-(1-(2-(3,4-dimethylphenylamino)-2-oxoacetyl)piperidin-3-yl)imidazo[1,5-a]pyrazin-1-yl)-N-(4-cyclopropylpyridin-2-yl)benzamide;
(R)-4-(8-amino-3-(1-(2-oxobutanoyl)piperidin-3-yl)imidazo[1,5-a]pyrazin-1-yl)-N-(4-cyclopropylpyridin-2-yl)benzamide;
(R)-4-(8-amino-3-(1-(3,3,3-trifluoro-2-oxopropanoyl)piperidin-3-yl)imidazo[1,5-a]pyrazin-1-yl)-N-(4-cyclopropylpyridin-2-yl)benzamide;
(R)-4-(8-amino-3-(1-(5-methyl-1,3,4-oxadiazole-2-carbonyl)piperidin-3-yl)imidazo[1,5-a]pyrazin-1-yl)-N-(4-cyclopropylpyridin-2-yl)benzamide;
(R)-4-(8-amino-3-(1-(6-cyanonicotinoyl)piperidin-3-yl)imidazo[1,5-a]pyrazin-1-yl)-N-(4-cyclopropylpyridin-2-yl)benzamide;
(R)-4-(8-amino-3-(1-(4-cyanothiophene-2-carbonyl)piperidin-3-yl)imidazo[1,5-a]pyrazin-1-yl)-N-(4-cyclopropylpyridin-2-yl)benzamide;
(R)-4-(8-amino-3-(1-(pyrrolidine-1-carbonyl)piperidin-3-yl)imidazo[1,5-a]pyrazin-1-yl)-N-(4-cyclopropylpyridin-2-yl)benzamide;
(R)-3-(8-amino-1-(4-(4-cyclopropylpyridin-2-ylcarbamoyl)phenyl)imidazo[1,5-a]pyrazin-3-yl)-N-(2-chlorophenyl)piperidine-1-carboxamide;
(R)-4-(8-amino-3-(1-(adamantyl-1-carbonyl)piperidin-3-yl)imidazo[1,5-a]pyrazin-1-yl)-N-(4-cyclopropylpyridin-2-yl)benzamide;
(R)-phenyl 3-(8-amino-1-(4-(4-cyclopropylpyridin-2-ylcarbamoyl)phenyl)imidazo[1,5-a]pyrazin-3-yl)piperidine-1-carboxylate;
(R)-4-(8-amino-3-(1-(2-(furan-2-yl)-2-oxoacetyl)piperidin-3-yl)imidazo[1,5-a]pyrazin-1-yl)-N-(4-cyclopropylpyridin-2-yl)benzamide;
(R)-4-(8-amino-3-(1-(4-(dimethylamino)butanoyl)pyrrolidin-3-yl)imidazo[1,5-a]pyrazin-1-yl)-N-(pyridin-2-yl)benzamide;
(R)-4-(8-amino-3-(1-(3-methoxypropanoyl)pyrrolidin-3-yl)imidazo[1,5-a]pyrazin-1-yl)-N-(pyridin-2-yl)benzamide;
(R)-4-(8-amino-3-(1-(3-methyloxetane-3-carbonyl)pyrrolidin-3-yl)imidazo[1,5-a]pyrazin-1-yl)-N-(pyridin-2-yl)benzamide;
(R)-4-(8-amino-3-(1-isobutyrylpyrrolidin-3-yl)imidazo[1,5-a]pyrazin-1-yl)-N-(pyridin-2-yl)benzamide;
(R)-4-(8-amino-3-(1-(tetrahydrofuran-3-carbonyl)pyrrolidin-3-yl)imidazo[1,5-a]pyrazin-1-yl)-N-(pyridin-2-yl)benzamide;
4-(8-amino-3-(1-isobutyrylpiperidin-4-yl)imidazo[1,5-a]pyrazin-1-yl)-N-(pyridin-2-yl)benzamide
4-(8-amino-3-(1-propionamidopropan-2-yl)imidazo[1,5-a]pyrazin-1-yl)-N-(4-(trifluoromethyl)pyridin-2-yl)benzamide;
N-(2-(8-amino-1-(4-(4-(trifluoromethyl)pyridin-2-ylcarbamoyl)phenyl)imidazo[1,5-a]pyrazin-3-yl)propyl)-3-methyloxetane-3-carboxamide;
benzyl 2-(8-amino-1-(4-(4-(trifluoromethyl)pyridin-2-ylcarbamoyl)phenyl)imidazo[1,5-a]pyrazin-3-yl)propylcarbamate;
(R)-4-(8-amino-3-(1-benzylpiperidin-3-yl)imidazo[1,5-a]pyrazin-1-yl)-N-(pyridin-2-yl)benzamide (R)-4-(8-amino-3-(1-phenethylpiperidin-3-yl)imidazo[1,5-a]pyrazin-1-yl)-N-(pyridin-2-yl)benzamide;
(R)-4-(8-amino-3-(1-((1-methyl-1H-pyrazol-4-yl)methyl)piperidin-3-yl)imidazo[1,5-a]pyrazin-1-yl)-N-(pyridin-2-yl)benzamide;
(R)-4-(8-amino-3-(1-(3,3,3-trifluoropropyl)piperidin-3-yl)imidazo[1,5-a]pyrazin-1-yl)-N-(pyridin-2-yl)benzamide;
ethyl 2-(((R)-3-(8-amino-1-(4-(pyridin-2-ylcarbamoyl)phenyl)imidazo[1,5-a]pyrazin-3-yl)piperidin-1-yl)methyl)cyclopropanecarboxylate;
(R)-4-(8-amino-3-(1-ethylpiperidin-3-yl)imidazo[1,5-a]pyrazin-1-yl)-N-(4-(trifluoromethyl)pyridin-2-yl)benzamide;
4-(8-amino-3-((3R)-1-(2,3-dihydroxypropyl)piperidin-3-yl)imidazo[1,5-a]pyrazin-1-yl)-N-(4-(trifluoromethyl)pyridin-2-yl)benzamide;
(R)-4-(8-amino-3-(1-(cyclopropylmethyl)piperidin-3-yl)imidazo[1,5-a]pyrazin-1-yl)-N-(4-(trifluoromethyl)pyridin-2-yl)benzamide;
(R)-4-(8-amino-3-(1-(pyridin-4-ylmethyl)piperidin-3-yl)imidazo[1,5-a]pyrazin-1-yl)-N-(4-(trifluoromethyl)pyridin-2-yl)benzamide;
4-(8-amino-3-((3R)-1-((tetrahydrofuran-3-yl)methyl)piperidin-3-yl)imidazo[1,5-a]pyrazin-1-yl)-N-(4-(trifluoromethyl)pyridin-2-yl)benzamide;
(R)-4-(8-amino-3-(1-(cyclopentylmethyl)piperidin-3-yl)imidazo[1,5-a]pyrazin-1-yl)-N-(4-cyclopropylpyridin-2-yl)benzamide;
(R)-4-(3-(1-((1H-pyrrol-2-yl)methyl)piperidin-3-yl)-8-aminoimidazo[1,5-a]pyrazin-1-yl)-N-(4-cyclopropylpyridin-2-yl)benzamide;
4-(8-amino-3-((3R)-1-((tetrahydrofuran-3-yl)methyl)piperidin-3-yl)imidazo[1,5-a]pyrazin-1-yl)-N-(4-cyclopropylpyridin-2-yl)benzamide;
4-(8-amino-3-(7-(tetrahydrofuran-2-carbonyl)-7-azabicyclo[2.2.1]heptan-2-yl)imidazo[1,5-a]pyrazin-1-yl)-N-(pyridin-2-yl)benzamide;
4-(8-amino-3-(7-propionyl-7-azabicyclo[2.2.1]heptan-2-yl)imidazo[1,5-a]pyrazin-1-yl)-N-(pyridin-2-yl)benzamide;
4-(8-amino-3-(7-(3-methoxypropanoyl)-7-azabicyclo[2.2.1]heptan-2-yl)imidazo[1,5-a]pyrazin-1-yl)-N-(pyridin-2-yl)benzamide;
benzyl 2-(8-amino-1-(4-(pyridin-2-ylcarbamoyl)phenyl)imidazo[1,5-a]pyrazin-3-yl)-7-azabicyclo[2.2.1]heptane-7-carboxylate;
4-(8-amino-3-(6-isobutyryl-6-azaspiro[2.5]octan-1-yl)imidazo[1,5-a]pyrazin-1-yl)-N-(pyridin-2-yl)benzamide;
4-(8-amino-3-(6-(3-methoxypropanoyl)-6-azaspiro[2.5]octan-1-yl)imidazo[1,5-a]pyrazin-1-yl)-N-(pyridin-2-yl)benzamide;
4-(8-amino-3-(6-(2-hydroxyacetyl)-6-azaspiro[2.5]octan-1-yl)imidazo[1,5-a]pyrazin-1-yl)-N-(pyridin-2-yl)benzamide;
4-(8-amino-3-(6-propionyl-6-azaspiro[2.5]octan-1-yl)imidazo[1,5-a]pyrazin-1-yl)-N-(pyridin-2-yl)benzamide;
benzyl (cis)-3-(8-amino-1-(4-(4-(trifluoromethyl)pyridin-2-ylcarbamoyl)phenyl)imidazo[1,5-a]pyrazin-3-yl)cyclohexylcarbamate;
4-(8-amino-3-((cis)-3-(3-ethylureido)cyclohexyl)imidazo[1,5-a]pyrazin-1-yl)-N-(4-(trifluoromethyl)pyridin-2-yl)benzamide;
4-(8-amino-3-((cis)-3-(cyclopropanecarboxamido)cyclohexyl)imidazo[1,5-a]pyrazin-1-yl)-N-(4-(trifluoromethyl)pyridin-2-yl)benzamide;
4-(8-amino-3-((cis)-3-aminocyclohexyl)imidazo[1,5-a]pyrazin-1-yl)-N-(4-(trifluoromethyl)pyridin-2-yl)benzamide;
4-(8-amino-3-((cis)-3-(3-methoxypropanamido)cyclohexyl)imidazo[1,5-a]pyrazin-1-yl)-N-(4-(trifluoromethyl)pyridin-2-yl)benzamide;
4-(8-amino-3-((cis)-3-isobutyramidocyclohexyl)imidazo[1,5-a]pyrazin-1-yl)-N-(4-(trifluoromethyl)pyridin-2-yl)benzamide;
N-((cis)-3-(8-amino-1-(4-(4-(trifluoromethyl)pyridin-2-ylcarbamoyl)phenyl)imidazo[1,5-a]pyrazin-3-yl)cyclohexyl)-3-methyloxetane-3-carboxamide;
4-(8-amino-3-((cis)-3-propionamidocyclohexyl)imidazo[1,5-a]pyrazin-1-yl)-N-(4-(trifluoromethyl)pyridin-2-yl)benzamide;
4-(8-amino-3-((trans)-3-(2-cyano-2-methylpropanamido)cyclohexyl)imidazo[1,5-a]pyrazin-1-yl)-N-(4-(trifluoromethyl)pyridin-2-yl)benzamide;
4-(8-amino-3-((trans)-3-(2-fluoro-2-methylpropanamido)cyclohexyl)imidazo[1,5-a]pyrazin-1-yl)-N-(4-(trifluoromethyl)pyridin-2-yl)benzamide;
4-(8-amino-3-((trans)-3-(cyclopropanecarboxamido)cyclohexyl)imidazo[1,5-a]pyrazin-1-yl)-N-(4-(trifluoromethyl)pyridin-2-yl)benzamide;
4-(8-amino-3-((trans)-3-aminocyclohexyl)imidazo[1,5-a]pyrazin-1-yl)-N-(4-(trifluoromethyl)pyridin-2-yl)benzamide;
4-(8-amino-3-((trans)-3-(3-methoxypropanamido)cyclohexyl)imidazo[1,5-a]pyrazin-1-yl)-N-(4-(trifluoromethyl)pyridin-2-yl)benzamide;
4-(8-amino-3-((trans)-3-isobutyramidocyclohexyl)imidazo[1,5-a]pyrazin-1-yl)-N-(4-(trifluoromethyl)pyridin-2-yl)benzamide;
N-((trans)-3-(8-amino-1-(4-(4-(trifluoromethyl)pyridin-2-ylcarbamoyl)phenyl)imidazo[1,5-a]pyrazin-3-yl)cyclohexyl)-3-methyloxetane-3-carboxamide;
N-((trans)-3-(8-amino-1-(4-(4-(trifluoromethyl)pyridin-2-ylcarbamoyl)phenyl)imidazo[1,5-a]pyrazin-3-yl)cyclohexyl)tetrahydrofuran-2-carboxamide;
4-(8-amino-3-((trans)-3-propionamidocyclohexyl)imidazo[1,5-a]pyrazin-1-yl)-N-(4-(trifluoromethyl)pyridin-2-yl)benzamide;
4-(8-amino-3-((trans)-3-(cyclobutanecarboxamido)cyclohexyl)imidazo[1,5-a]pyrazin-1-yl)-N-(4-(trifluoromethyl)pyridin-2-yl)benzamide;
4-(8-amino-3-(4-propionylthiomorpholin-2-yl)imidazo[1,5-a]pyrazin-1-yl)-N-(4-(trifluoromethyl)pyridin-2-yl)benzamide;
4-(8-amino-3-(4-isobutyrylmorpholin-2-yl)imidazo[1,5-a]pyrazin-1-yl)-N-(4-(trifluoromethyl)pyridin-2-yl)benzamide;
4-(8-amino-3-(4-(2-fluoro-2-methylpropanoyl)morpholin-2-yl)imidazo[1,5-a]pyrazin-1-yl)-N-(4-(trifluoromethyl)pyridin-2-yl)benzamide;
4-(8-amino-3-(4-(3-methoxypropanoyl)morpholin-2-yl)imidazo[1,5-a]pyrazin-1-yl)-N-(4-(trifluoromethyl)pyridin-2-yl)benzamide;
4-(8-amino-3-(4-(cyclopropanecarbonyl)morpholin-2-yl)imidazo[1,5-a]pyrazin-1-yl)-N-(4-(trifluoromethyl)pyridin-2-yl)benzamide;
4-(8-amino-3-(4-(3-methyloxetane-3-carbonyl)morpholin-2-yl)imidazo[1,5-a]pyrazin-1-yl)-N-(4-(trifluoromethyl)pyridin-2-yl)benzamide;

2-(8-amino-1-(4-(4-(trifluoromethyl)pyridin-2-ylcarbamoyl)phenyl)imidazo[1,5-a]pyrazin-3-yl)-N-ethylmorpholine-4-carboxamide;

4-(8-amino-3-((cis)-5-hydroxy-1-(3-methyloxetane-3-carbonyl)piperidin-3-yl)imidazo[1,5-a]pyrazin-1-yl)-N-(4-(trifluoromethyl)pyridin-2-yl)benzamide;

4-(8-amino-3-((cis)-1-(cyclopropanecarbonyl)-5-hydroxypiperidin-3-yl)imidazo[1,5-a]pyrazin-1-yl)-N-(4-(trifluoromethyl)pyridin-2-yl)benzamide;

4-(8-amino-3-((cis)-5-hydroxy-1-(3-methoxypropanoyl)piperidin-3-yl)imidazo[1,5-a]pyrazin-1-yl)-N-(4-(trifluoromethyl)pyridin-2-yl)benzamide;

(trans)-ethyl 5-(8-amino-1-(4-(4-(trifluoromethyl)pyridin-2-ylcarbamoyl)phenyl)imidazo[1,5-a]pyrazin-3-yl)-2-methylpiperidine-1-carboxylate;

4-(8-amino-3-((cis)-1-(3-methoxypropanoyl)-6-methylpiperidin-3-yl)imidazo[1,5-a]pyrazin-1-yl)-N-(4-cyclopropylpyridin-2-yl)benzamide;

4-(8-amino-3-((cis)-6-methyl-1-(piperidine-1-carbonyl)piperidin-3-yl)imidazo[1,5-a]pyrazin-1-yl)-N-(4-cyclopropylpyridin-2-yl)benzamide;

4-(8-amino-3-((trans)-6-methyl-1-(tetrahydrofuran-2-carbonyl)piperidin-3-yl)imidazo[1,5-a]pyrazin-1-yl)-N-(4-(trifluoromethyl)pyridin-2-yl)benzamide;

(trans)-5-(8-amino-1-(4-(4-(trifluoromethyl)pyridin-2-ylcarbamoyl)phenyl)imidazo[1,5-a]pyrazin-3-yl)-N-ethyl-2-methylpiperidine-1-carboxamide;

4-(8-amino-3-((trans)-6-methyl-1-(3-(methylthio)propanoyl)piperidin-3-yl)imidazo[1,5-a]pyrazin-1-yl)-N-(4-(trifluoromethyl)pyridin-2-yl)benzamide;

4-(8-amino-3-((trans)-1-(cyclopropanecarbonyl)-6-methylpiperidin-3-yl)imidazo[1,5-a]pyrazin-1-yl)-N-(4-(trifluoromethyl)pyridin-2-yl)benzamide;

4-(8-amino-3-((cis)-1-(3-ethoxypropanoyl)-6-methylpiperidin-3-yl)imidazo[1,5-a]pyrazin-1-yl)-N-(4-(trifluoromethyl)pyridin-2-yl)benzamide;

4-(8-amino-3-((cis)-1-(2,2-difluorocyclobutanecarbonyl)-6-methylpiperidin-3-yl)imidazo[1,5-a]pyrazin-1-yl)-N-(4-(trifluoromethyl)pyridin-2-yl)benzamide;

4-(8-amino-3-((cis)-1-(2-cyclopropylacetyl)-6-methylpiperidin-3-yl)imidazo[1,5-a]pyrazin-1-yl)-N-(pyridin-2-yl)benzamide;

4-(8-amino-3-((cis)-1-(cyclopropanecarbonyl)-6-methylpiperidin-3-yl)imidazo[1,5-a]pyrazin-1-yl)-N-(pyridin-2-yl)benzamide;

(cis)-5-(8-amino-1-(4-(pyridin-2-ylcarbamoyl)phenyl)imidazo[1,5-a]pyrazin-3-yl)-N-ethyl-2-methylpiperidine-1-carboxamide;

4-(8-amino-3-((cis)-6-methyl-1-(tetrahydrofuran-2-carbonyl)piperidin-3-yl)imidazo[1,5-a]pyrazin-1-yl)-N-(4-(trifluoromethyl)pyridin-2-yl)benzamide;

4-(8-amino-3-((cis)-6-methyl-1-(3-(methylthio)propanoyl)piperidin-3-yl)imidazo[1,5-a]pyrazin-1-yl)-N-(4-(trifluoromethyl)pyridin-2-yl)benzamide;

4-(8-amino-3-((cis)-6-methyl-1-(2-(2-oxooxazolidin-3-yl)acetyl)piperidin-3-yl)imidazo[1,5-a]pyrazin-1-yl)-N-(4-cyclopropylpyridin-2-yl)benzamide;

4-(8-amino-3-((cis)-1-(cyclobutanecarbonyl)-6-methylpiperidin-3-yl)imidazo[1,5-a]pyrazin-1-yl)-N-(4-cyclopropylpyridin-2-yl)benzamide;

4-(8-amino-3-((cis)-6-methyl-1-(3-(methylthio)propanoyl)piperidin-3-yl)imidazo[1,5-a]pyrazin-1-yl)-N-(4-cyclopropylpyridin-2-yl)benzamide;

(cis)-ethyl 5-(8-amino-1-(4-(4-cyclopropylpyridin-2-ylcarbamoyl)phenyl)imidazo[1,5-a]pyrazin-3-yl)-2-methylpiperidine-1-carboxylate;

4-(8-amino-3-((cis)-6-methyl-1-(2-oxobutanoyl)piperidin-3-yl)imidazo[1,5-a]pyrazin-1-yl)-N-(4-(trifluoromethyl)pyridin-2-yl)benzamide;

(cis)-5-(8-amino-1-(4-(4-(trifluoromethyl)pyridin-2-ylcarbamoyl)phenyl)imidazo[1,5-a]pyrazin-3-yl)-N-ethyl-2-methylpiperidine-1-carboxamide;

4-(8-amino-3-((cis)-1-(cyclopropanecarbonyl)-6-methylpiperidin-3-yl)imidazo[1,5-a]pyrazin-1-yl)-N-(4-(trifluoromethyl)pyridin-2-yl)benzamide;

4-(8-amino-3-((cis)-1-(3,3-difluorocyclobutanecarbonyl)-6-methylpiperidin-3-yl)imidazo[1,5-a]pyrazin-1-yl)-N-(pyridin-2-yl)benzamide;

4-(8-amino-3-((cis)-1-(cyclobutanecarbonyl)-6-methylpiperidin-3-yl)imidazo[1,5-a]pyrazin-1-yl)-N-(pyridin-2-yl)benzamide;

4-(8-amino-3-((cis)-1-isobutyryl-6-methylpiperidin-3-yl)imidazo[1,5-a]pyrazin-1-yl)-N-(pyridin-2-yl)benzamide;

4-(8-amino-3-((cis)-1-(3-ethoxypropanoyl)-6-methylpiperidin-3-yl)imidazo[1,5-a]pyrazin-1-yl)-N-(pyridin-2-yl)benzamide;

4-(8-amino-3-((cis)-6-methyl-1-propionylpiperidin-3-yl)imidazo[1,5-a]pyrazin-1-yl)-N-(pyridin-2-yl)benzamide;

4-(8-amino-3-(azetidin-1-yl)imidazo[1,5-a]pyrazin-1-yl)-N-(4-propylpyridin-2-yl)benzamide;

4-(8-amino-3-(azetidin-1-yl)imidazo[1,5-a]pyrazin-1-yl)-N-(4-cyanopyridin-2-yl)benzamide;

4-(8-amino-3-(azetidin-1-yl)imidazo[1,5-a]pyrazin-1-yl)-N-(4-(trifluoromethyl)pyridin-2-yl)benzamide;

4-(8-amino-3-morpholinoimidazo[1,5-a]pyrazin-1-yl)-N-(4-(trifluoromethyl)pyridin-2-yl)benzamide;

4-(8-amino-3-morpholinoimidazo[1,5-a]pyrazin-1-yl)-N-(4-propylpyridin-2-yl)benzamide;

4-(8-amino-3-(diethylamino)imidazo[1,5-a]pyrazin-1-yl)-N-(pyridin-2-yl)benzamide;

4-(8-amino-3-(diethylamino)imidazo[1,5-a]pyrazin-1-yl)-N-(4-propylpyridin-2-yl)benzamide;

4-(8-amino-3-(diethylamino)imidazo[1,5-a]pyrazin-1-yl)-N-(4-cyanopyridin-2-yl)benzamide;

4-(8-amino-3-(diethylamino)imidazo[1,5-a]pyrazin-1-yl)-N-(4-(trifluoromethyl)pyridin-2-yl)benzamide;

4-(8-amino-3-(3-methoxyazetidin-1-yl)imidazo[1,5-a]pyrazin-1-yl)-N-(pyridin-2-yl)benzamide;

(S)-N-(1-(8-amino-1-(4-(4-(trifluoromethyl)pyridin-2-ylcarbamoyl)phenyl)imidazo[1,5-a]pyrazin-3-yl)piperidin-3-yl)-3-methyloxetane-3-carboxamide;

(R)-4-(8-amino-3-(3-(3-methoxypropanamido)piperidin-1-yl)imidazo[1,5-a]pyrazin-1-yl)-N-(4-(trifluoromethyl)pyridin-2-yl)benzamide;

(R)-4-(8-amino-3-(3-(cyclopropanecarboxamido)piperidin-1-yl)imidazo[1,5-a]pyrazin-1-yl)-N-(4-(trifluoromethyl)pyridin-2-yl)benzamide;

(R)-4-(8-amino-3-(3-(3-ethylureido)piperidin-1-yl)imidazo[1,5-a]pyrazin-1-yl)-N-(4-(trifluoromethyl)pyridin-2-yl)benzamide;

(S)-4-(8-amino-3-(3-(cyclopropanecarboxamido)piperidin-1-yl)imidazo[1,5-a]pyrazin-1-yl)-N-(4-(trifluoromethyl)pyridin-2-yl)benzamide;

(S)-4-(8-amino-3-(3-(cyclobutanecarboxamido)piperidin-1-yl)imidazo[1,5-a]pyrazin-1-yl)-N-(4-(trifluoromethyl)pyridin-2-yl)benzamide;

1-(8-amino-1-(4-(4-(trifluoromethyl)pyridin-2-ylcarbamoyl)phenyl)imidazo[1,5-a]pyrazin-3-yl)-N-isopropylpiperidine-3-carboxamide;

1-(8-amino-1-(4-(pyridin-2-ylcarbamoyl)phenyl)imidazo[1,5-a]pyrazin-3-yl)-N-(cyclopropylmethyl)piperidine-3-carboxamide;
1-(8-amino-1-(4-(4-(trifluoromethyl)pyridin-2-ylcarbamoyl)phenyl)imidazo[1,5-a]pyrazin-3-yl)-N-(3,3-difluorocyclobutyl)piperidine-3-carboxamide;
1-(8-amino-1-(4-(pyridin-2-ylcarbamoyl)phenyl)imidazo[1,5-a]pyrazin-3-yl)-N-(((S)-tetrahydrofuran-2-yl)methyl)piperidine-3-carboxamide;
1-(8-amino-1-(4-(pyridin-2-ylcarbamoyl)phenyl)imidazo[1,5-a]pyrazin-3-yl)-N-tert-butylpiperidine-3-carboxamide;
4-(8-amino-3-(3-(morpholine-4-carbonyl)piperidin-1-yl)imidazo[1,5-a]pyrazin-1-yl)-N-(pyridin-2-yl)benzamide;
1-(8-amino-1-(4-(pyridin-2-ylcarbamoyl)phenyl)imidazo[1,5-a]pyrazin-3-yl)-N, N-diethylpiperidine-3-carboxamide;
1-(8-amino-1-(4-(4-(trifluoromethyl)pyridin-2-ylcarbamoyl)phenyl)imidazo[1,5-a]pyrazin-3-yl)-N—(((S)-tetrahydrofuran-2-yl)methyl)piperidine-3-carboxamide;
1-(8-amino-1-(4-(4-(trifluoromethyl)pyridin-2-ylcarbamoyl)phenyl)imidazo[1,5-a]pyrazin-3-yl)-N-(2-methoxyethyl)piperidine-3-carboxamide;
1-(8-amino-1-(4-(4-(trifluoromethyl)pyridin-2-ylcarbamoyl)phenyl)imidazo[1,5-a]pyrazin-3-yl)-N-(cyclopropylmethyl)piperidine-3-carboxamide;
4-(8-amino-3-(3-(morpholine-4-carbonyl)piperidin-1-yl)imidazo[1,5-a]pyrazin-1-yl)-N-(4-(trifluoromethyl)pyridin-2-yl)benzamide;
1-(8-amino-1-(4-(pyridin-2-ylcarbamoyl)phenyl)imidazo[1,5-a]pyrazin-3-yl)-N-((S)-1-methoxypropan-2-yl)piperidine-3-carboxamide;
1-(8-amino-1-(4-(4-(trifluoromethyl)pyridin-2-ylcarbamoyl)phenyl)imidazo[1,5-a]pyrazin-3-yl)-N-ethylpiperidine-3-carboxamide;
1-(8-amino-1-(4-(4-(trifluoromethyl)pyridin-2-ylcarbamoyl)phenyl)imidazo[1,5-a]pyrazin-3-yl)-N((S)-tetrahydrofuran-3-yl)piperidine-3-carboxamide;
1-(8-amino-1-(4-(4-(trifluoromethyl)pyridin-2-ylcarbamoyl)phenyl)imidazo[1,5-a]pyrazin-3-yl)-N-((R)-tetrahydrofuran-3-yl)piperidine-3-carboxamide;
1-(8-amino-1-(4-(4-(trifluoromethyl)pyridin-2-ylcarbamoyl)phenyl)imidazo[1,5-a]pyrazin-3-yl)-N-(2-(methylthio)ethyl)piperidine-3-carboxamide;
1-(8-amino-1-(4-(4-(trifluoromethyl)pyridin-2-ylcarbamoyl)phenyl)imidazo[1,5-a]pyrazin-3-yl)-N-(2-(methylsulfonyl)ethyl)piperidine-3-carboxamide;
1-(8-amino-1-(4-(4-cyclopropylpyridin-2-ylcarbamoyl)phenyl)imidazo[1,5-a]pyrazin-3-yl)-N—((S)-1-methoxypropan-2-yl)piperidine-3-carboxamide;
1-(8-amino-1-(4-(4-(trifluoromethyl)pyridin-2-ylcarbamoyl)phenyl)imidazo[1,5-a]pyrazin-3-yl)-N-methoxypiperidine-3-carboxamide;
4-(8-amino-3-(3-(3,3-difluoropiperidine-1-carbonyl)piperidin-1-yl)imidazo[1,5-a]pyrazin-1-yl)-N-(4-(trifluoromethyl)pyridin-2-yl)benzamide;
1-(8-amino-1-(4-(4-cyclopropylpyridin-2-ylcarbamoyl)phenyl)imidazo[1,5-a]pyrazin-3-yl)-N-methoxypiperidine-3-carboxamide;
1-(8-amino-1-(4-(4-cyclopropylpyridin-2-ylcarbamoyl)phenyl)imidazo[1,5-a]pyrazin-3-yl)-N-(cyclopropylmethyl)piperidine-3-carboxamide;
1-(8-amino-1-(4-(4-cyclopropylpyridin-2-ylcarbamoyl)phenyl)imidazo[1,5-a]pyrazin-3-yl)-N,N-diethylpiperidine-3-carboxamide;
4-(8-amino-3-(3-(pyrrolidine-1-carbonyl)piperidin-1-yl)imidazo[1,5-a]pyrazin-1-yl)-N-(4-cyclopropylpyridin-2-yl)benzamide;
4-(8-amino-3-(3-cyclopropyl-4,5,6,7-tetrahydro-1H-indazol-5-yl)imidazo[1,5-a]pyrazin-1-yl)-N-(4-(trifluoromethyl)pyridin-2-yl)benzamide;
4-(8-amino-3-(3-cyclopropyl-4,5,6,7-tetrahydro-1H-indazol-5-yl)imidazo[1,5-a]pyrazin-1-yl)-N-(4-cyanopyridin-2-yl)benzamide;
4-(8-amino-3-(3-(methoxymethyl)-4,5,6,7-tetrahydro-1H-indazol-5-yl)imidazo[1,5-a]pyrazin-1-yl)-N-(4-(trifluoromethyl)pyridin-2-yl)benzamide;
ethyl 3-(4-amino-5-(4-(4-(trifluoromethyl)pyridin-2-ylcarbamoyl)phenyl)pyrrolo[1,2-f][1,2,4]triazin-7-yl)piperidine-1-carboxylate;
3-(4-amino-5-(4-(4-(trifluoromethyl)pyridin-2-ylcarbamoyl)phenyl)pyrrolo[1,2-f][1,2,4]triazin-7-yl)-N-ethylpiperidine-1-carboxamide;
4-(4-amino-7-(1-(3-methyloxetane-3-carbonyl)piperidin-3-yl)pyrrolo[1,2-f][1,2,4]triazin-5-yl)-N-(4-(trifluoromethyl)pyridin-2-yl)benzamide;
(R)-4-(4-amino-7-(1-(1-methylcyclobutanecarbonyl)piperidin-3-yl)imidazo[1,5-f][1,2,4]triazin-5-yl)-N-(4-(trifluoromethyl)pyridin-2-yl)benzamide;
(R)-ethyl 3-(4-amino-5-(4-(4-(trifluoromethyl)pyridin-2-ylcarbamoyl)phenyl)imidazo[1,5-f][1,2,4]triazin-7-yl)piperidine-1-carboxylate;
(R)-3-(4-amino-5-(4-(4-(trifluoromethyl)pyridin-2-ylcarbamoyl)phenyl)imidazo[1,5-f][1,2,4]triazin-7-yl)-N-ethylpiperidine-1-carboxamide;
(R)-4-(4-amino-7-(1-(2-fluoro-2-methylpropanoyl)piperidin-3-yl)imidazo[1,5-f][1,2,4]triazin-5-yl)-N-(4-(trifluoromethyl)pyridin-2-yl)benzamide;
(R)-4-(4-amino-7-(piperidin-3-yl)imidazo[1,5-f][1,2,4]triazin-5-yl)-N-(4-(trifluoromethyl)pyridin-2-yl)benzamide;
(R)-4-(4-amino-7-(1-(3-ethoxypropanoyl)piperidin-3-yl)imidazo[1,5-f][1,2,4]triazin-5-yl)-N-(4-(trifluoromethyl)pyridin-2-yl)benzamide;
(R)-4-(4-amino-7-(1-(3,3-difluorocyclobutanecarbonyl)piperidin-3-yl)imidazo[1,5-f][1,2,4]triazin-5-yl)-N-(4-(trifluoromethyl)pyridin-2-yl)benzamide;
(R)-4-(4-amino-7-(1-(3-methyloxetane-3-carbonyl)piperidin-3-yl)imidazo[1,5-f][1,2,4]triazin-5-yl)-N-(4-(trifluoromethyl)pyridin-2-yl)benzamide;
4-(4-amino-1-((R)-1-((R)-tetrahydrofuran-2-carbonyl)piperidin-3-yl)-1H-pyrazolo[3,4-d]pyrimidin-3-yl)-N-(4-(trifluoromethyl)pyridin-2-yl)benzamide;
(R)-4-(4-amino-1-(1-(2-cyano-2-methylpropanoyl)piperidin-3-yl)-1H-pyrazolo[3,4-d]pyrimidin-3-yl)-N-(4-(trifluoromethyl)pyridin-2-yl)benzamide;
(R)-4-(1-(1-2,5,8,11-tetraoxatetradecanepiperidin-3-yl)-4-amino-1H-pyrazolo[3,4-d]pyrimidin-3-yl)-N-(4-(trifluoromethyl)pyridin-2-yl)benzamide;
(R)-4-(4-amino-1-(1-(2,2,2-trichloroacetyl)piperidin-3-yl)-1H-pyrazolo[3,4-d]pyrimidin-3-yl)-N-(4-(trifluoromethyl)pyridin-2-yl)benzamide;
(R)-4-(4-amino-1-(1-(1-methylcyclobutanecarbonyl)piperidin-3-yl)-1H-pyrazolo[3,4-d]pyrimidin-3-yl)-N-(4-(trifluoromethyl)pyridin-2-yl)benzamide;
(R)-4-(4-amino-1-(1-(3-methyloxetane-3-carbonyl)piperidin-3-yl)-1H-pyrazolo[3,4-d]pyrimidin-3-yl)-N-(4-(trifluoromethyl)pyridin-2-yl)benzamide;
(R)-3-(4-amino-3-(4-(4-(trifluoromethyl)pyridin-2-ylcarbamoyl)phenyl)-1H-pyrazolo[3,4-d]pyrimidin-1-yl)-N-ethylpiperidine-1-carboxamide;

(R)-4-(4-amino-1-(1-(cyclopropanecarbonyl)piperidin-3-yl)-1H-pyrazolo[3,4-d]pyrimidin-3-yl)-N-(4-(trifluoromethyl)pyridin-2-yl)benzamide;

(R)-4-(4-amino-1-(1-(2-fluoro-2-methylpropanoyl)piperidin-3-yl)-1H-pyrazolo[3,4-d]pyrimidin-3-yl)-N-(4-(trifluoromethyl)pyridin-2-yl)benzamide;

(R)-4-(4-amino-1-(1-propionylpiperidin-3-yl)-1H-pyrazolo[3,4-d]pyrimidin-3-yl)-N-(4-(trifluoromethyl)pyridin-2-yl)benzamide;

(R)-4-(4-amino-1-(1-(1-(methoxymethyl)cyclobutanecarbonyl)piperidin-3-yl)-1H-pyrazolo[3,4-d]pyrimidin-3-yl)-N-(4-(trifluoromethyl)pyridin-2-yl)benzamide;

(R)-ethyl 3-(4-amino-3-(4-(4-(trifluoromethyl)pyridin-2-ylcarbamoyl)phenyl)-1H-pyrazolo[3,4-d]pyrimidin-1-yl)piperidine-1-carboxylate;

(R)-4-(4-amino-1-(1-(2,2,2-trifluoroacetyl)piperidin-3-yl)-1H-pyrazolo[3,4-d]pyrimidin-3-yl)-N-(4-(trifluoromethyl)pyridin-2-yl)benzamide;

(R)-4-(4-amino-1-(1-(3-(2-methoxyethoxy)propanoyl)piperidin-3-yl)-1H-pyrazolo[3,4-d]pyrimidin-3-yl)-N-(4-(trifluoromethyl)pyridin-2-yl)benzamide;

(R)-4-(4-amino-1-(1-(3-(methylthio)propanoyl)piperidin-3-yl)-1H-pyrazolo[3,4-d]pyrimidin-3-yl)-N-(4-(trifluoromethyl)pyridin-2-yl)benzamide;

(R)-4-(4-amino-1-(1-(cyclobutanecarbonyl)piperidin-3-yl)-1H-pyrazolo[3,4-d]pyrimidin-3-yl)-N-(4-(trifluoromethyl)pyridin-2-yl)benzamide;

(R)-4-(4-amino-1-(1-(3,3-difluorocyclobutanecarbonyl)piperidin-3-yl)-1H-pyrazolo[3,4-d]pyrimidin-3-yl)-N-(4-(trifluoromethyl)pyridin-2-yl)benzamide (R)-4-(4-amino-1-(1-isobutyrylpiperidin-3-yl)-1H-pyrazolo[3,4-d]pyrimidin-3-yl)-N-(4-(trifluoromethyl)pyridin-2-yl)benzamide;

(R)-4-(4-amino-1-(1-(3-methoxypropanoyl)piperidin-3-yl)-1H-pyrazolo[3,4-d]pyrimidin-3-yl)-N-(4-(trifluoromethyl)pyridin-2-yl)benzamide;

(R)-4-(4-amino-1-(1-(3-ethoxypropanoyl)piperidin-3-yl)-1H-pyrazolo[3,4-d]pyrimidin-3-yl)-N-(4-(trifluoromethyl)pyridin-2-yl)benzamide;

(R)-4-(8-amino-3-(1-(3-methoxypropanoyl)piperidin-3-yl)imidazo[1,5-a]pyrazin-1-yl)-2-fluoro-N-(pyridin-2-yl)benzamide;

4-(8-amino-3-((R)-1-(3-methoxypropanoyl)piperidin-3-yl)imidazo[1,5-a]pyrazin-1-yl)-N-(pyridin-2-yl)-3-(trifluoromethyl)benzamide;

4-(8-amino-3-((R)-1-(3-methoxypropanoyl)piperidin-3-yl)imidazo[1,5-a]pyrazin-1-yl)-3-fluoro-N-(pyridin-2-yl)benzamide;

4-(8-amino-3-((R)-1-(3-methoxypropanoyl)piperidin-3-yl)imidazo[1,5-a]pyrazin-1-yl)-3-methyl-N-(pyridin-2-yl)benzamide;

(R)-4-(8-amino-3-(1-(3-methoxypropanoyl)piperidin-3-yl)imidazo[1,5-a]pyrazin-1-yl)-2-methyl-N-(pyridin-2-yl)benzamide;

(R)-5-(8-amino-3-(1-(3-methoxypropanoyl)piperidin-3-yl)imidazo[1,5-a]pyrazin-1-yl)-N-(pyridin-2-yl)picolinamide;

(R)-6-(8-amino-3-(1-(3-methoxypropanoyl)piperidin-3-yl)imidazo[1,5-a]pyrazin-1-yl)-N-(pyridin-2-yl)nicotinamide;

4-(8-amino-3-((R)-1-((R)-2,3-dihydroxypropanoyl)piperidin-3-yl)imidazo[1,5-a]pyrazin-1-yl)-N-(4-cyclopropylpyridin-2-yl)benzamide;

(R)-4-(8-amino-3-(1-(3-methyloxetane-3-carbonyl)piperidin-3-yl)imidazo[1,5-a]pyrazin-1-yl)-N-(pyrazin-2-yl)benzamide;

8-amino-N-(3-methoxypropyl)-3-methyl-1-(4-(4-(trifluoromethyl)pyridin-2-ylcarbamoyl)phenyl)imidazo[1,5-a]pyrazine-5-carboxamide;

8-amino-N-benzyl-3-methyl-1-(4-(4-(trifluoromethyl)pyridin-2-ylcarbamoyl)phenyl)imidazo[1,5-a]pyrazine-5-carboxamide;

8-amino-N,N,3-trimethyl-1-(4-(4-(trifluoromethyl)pyridin-2-ylcarbamoyl)phenyl)imidazo[1,5-a]pyrazine-5-carboxamide;

8-amino-N-(3-methoxypropyl)-3-methyl-1-(4-(4-propylpyridin-2-ylcarbamoyl)phenyl)imidazo[1,5-a]pyrazine-5-carboxamide;

8-amino-3-methyl-N-(1-methylpiperidin-4-yl)-1-(4-(4-(trifluoromethyl)pyridin-2-ylcarbamoyl)phenyl)imidazo[1,5-a]pyrazine-5-carboxamide;

8-amino-3-methyl-N-(pyridin-3-ylmethyl)-1-(4-(4-(trifluoromethyl)pyridin-2-ylcarbamoyl)phenyl)imidazo[1,5-a]pyrazine-5-carboxamide;

8-amino-3-methyl-N-(oxazol-5-ylmethyl)-1-(4-(4-(trifluoromethyl)pyridin-2-ylcarbamoyl)phenyl)imidazo[1,5-a]pyrazine-5-carboxamide;

4-(8-amino-5-chloro-3-(tetrahydro-2H-pyran-4-yl)imidazo[1,5-a]pyrazin-1-yl)-N-(4-propylpyridin-2-yl)benzamide;

(R)-ethyl 8-amino-3-(1-(3-methyloxetane-3-carbonyl)piperidin-3-yl)-1-(4-(4-(trifluoromethyl)pyridine-2-ylcarbamoyl)phenyl)imidazo[1,5-a]pyrazine-5-carboxylate;

(R)-8-amino-3-(1-(3-methyloxetane-3-carbonyl)piperidin-3-yl)-1-(4-(4-(trifluoromethyl)pyridin-2-ylcarbamoyl)phenyl)imidazo[1,5-a]pyrazine-5-carboxylic acid;

(R)-4-(8-amino-5-chloro-3-(1-(3-methyloxetane-3-carbonyl)piperidin-3-yl)imidazo[1,5-a]pyrazin-1-yl)-N-(4-(trifluoromethyl)pyridin-2-yl)benzamide;

(R)-4-(8-amino-3-(1-(3-methyloxetane-3-carbonyl)piperidin-3-yl)-5-vinylimidazo[1,5-a]pyrazin-1-yl)-N-(4-(trifluoromethyl)pyridin-2-yl)benzamide;

(R)-4-(8-amino-5-cyclopropyl-3-(1-(3-methyloxetane-3-carbonyl)piperidin-3-yl)imidazo[1,5-a]pyrazin-1-yl)-N-(4-(trifluoromethyl)pyridin-2-yl)benzamide;

(R)-4-(8-amino-5-deutero-3-(1-(3-methoxypropanoyl)piperidin-3-yl)imidazo[1,5-a]pyrazin-1-yl)-N-(4-(trifluoromethyl)pyridin-2-yl)benzamide;

(R)-4-(8-amino-5-deutero-3-(1-(3-methyloxetane-3-carbonyl)piperidin-3-yl)imidazo[1,5-a]pyrazin-1-yl)-N-(4-(trifluoromethyl)pyridin-2-yl)benzamide;

(R)-4-(8-amino-5-methyl-3-(1-(3-methyloxetane-3-carbonyl)piperidin-3-yl)imidazo[1,5-a]pyrazin-1-yl)-N-(4-(trifluoromethyl)pyridin-2-yl)benzamide;

(R)-4-(8-amino-3-(piperidin-3-yl)imidazo[1,5-a]pyrazin-1-yl)-N-(4-(trifluoromethyl)pyridin-2-yl)benzamide;

(R)-4-(8-amino-5-ethyl-3-(1-(3-methyloxetane-3-carbonyl)piperidin-3-yl)imidazo[1,5-a]pyrazin-1-yl)-N-(4-(trifluoromethyl)pyridin-2-yl)benzamide;

(R,E)-4-(8-amino-3-(1-(3-methyloxetane-3-carbonyl)piperidin-3-yl)-5-styrylimidazo[1,5-a]pyrazin-1-yl)-N-(4-(trifluoromethyl)pyridin-2-yl)benzamide;

(R,E)-4-(8-amino-3-(1-(3-methoxypropanoyl)piperidin-3-yl)-5-styrylimidazo[1,5-a]pyrazin-1-yl)-N-(4-(trifluoromethyl)pyridin-2-yl)benzamide;

(R)-4-(8-amino-5-(furan-2-yl)-3-(1-(3-methyloxetane-3-carbonyl)piperidin-3-yl)imidazo[1,5-a]pyrazin-1-yl)-N-(4-(trifluoromethyl)pyridin-2-yl)benzamide;

methyl 8-amino-3-methyl-1-(4-(4-(trifluoromethyl)pyridin-2-ylcarbamoyl)phenyl)imidazo[1,5-a]pyrazine-5-carboxylate;

(E)-4-(8-amino-5-styryl-3-(tetrahydro-2H-pyran-4-yl)
imidazo[1,5-a]pyrazin-1-yl)-N-(pyridin-2-yl)benzamide;
4-(8-amino-5-chloro-3-(4-(3-methoxypropanoyl)morpholin-2-yl)imidazo[1,5-a]pyrazin-1-yl)-N-(4-(trifluoromethyl)pyridin-2-yl)benzamide;
4-(8-amino-5-chloro-3-(4-(3-methyloxetane-3-carbonyl)morpholin-2-yl)imidazo[1,5-a]pyrazin-1-yl)-N-(4-(trifluoromethyl)pyridin-2-yl)benzamide;
4-(8-amino-5-chloro-3-(4-(1-hydroxycyclobutanecarbonyl)morpholin-2-yl)imidazo[1,5-a]pyrazin-1-yl)-N-(4-(trifluoromethyl)pyridin-2-yl)benzamide;
(R)-4-(8-amino-5-deuteromethyl-3-(1-(3-methyloxetane-3-carbonyl)piperidin-3-yl)imidazo[1,5-a]pyrazin-1-yl)-N-(4-(trifluoromethyl)pyridin-2-yl)benzamide;
(R,E)-4-(8-amino-5-(4-fluorostyryl)-3-(1-(3-methyloxetane-3-carbonyl)piperidin-3-yl)imidazo[1,5-a]pyrazin-1-yl)-N-(4-(trifluoromethyl)pyridin-2-yl)benzamide;
(R)-4-(8-amino-3-(1-(3-methyloxetane-3-carbonyl)piperidin-3-yl)-5-phenethylimidazo[1,5-a]pyrazin-1-yl)-N-(4-(trifluoromethyl)pyridin-2-yl)benzamide;
(R)-4-(8-amino-5-(3-methoxyphenyl)-3-(1-(3-methyloxetane-3-carbonyl)piperidin-3-yl)imidazo[1,5-a]pyrazin-1-yl)-N-(4-(trifluoromethyl)pyridin-2-yl)benzamide;
(R)-4-(8-amino-3-(1-(3-methyloxetane-3-carbonyl)piperidin-3-yl)-5-phenylimidazo[1,5-a]pyrazin-1-yl)-N-(4-(trifluoromethyl)pyridin-2-yl)benzamide;
4-(8-amino-5-(1-hydroxy-3-methylbutyl)-3-methylimidazo[1,5-a]pyrazin-1-yl)-N-(4-(trifluoromethyl)pyridin-2-yl)benzamide;
(R)-4-(8-amino-5-(3,6-dihydro-2H-pyran-4-yl)-3-(1-(3-methyloxetane-3-carbonyl)piperidin-3-yl)imidazo[1,5-a]pyrazin-1-yl)-N-(4-(trifluoromethyl)pyridin-2-yl)benzamide;
4-(8-amino-3-{(3R)-1-[(3-methyloxetan-3-yl)carbonyl]piperidin-3-yl}imidazo[1,5-a]pyrazin-1-yl)-3-fluoro-N-[4-(trifluoromethyl)pyridin-2-yl]benzamide;
4-(8-amino-3-{(3R)-1-[(3-methyloxetan-3-yl)carbonyl]piperidin-3-yl}imidazo[1,5-a]pyrazin-1-yl)-N-(5-methoxypyridin-2-yl)benzamide;
4-{3-[(3R)-1-acetylpiperidin-3-yl]-8-aminoimidazo[1,5-a]pyrazin-1-yl}-N-(4-methylpyridin-2-yl)benzamide;
4-(8-amino-3-{(3R)-1-[(3-methyloxetan-3-yl)carbonyl]piperidin-3-yl}imidazo[1,5-a]pyrazin-1-yl)-N-(5-cyanopyridin-2-yl)benzamide;
4-(8-amino-3-{(3R)-1-[(3,5-dimethylisoxazol-4-yl)carbonyl]piperidin-3-yl}imidazo[1,5-a]pyrazin-1-yl)-N-[4-(trifluoromethyl)pyridin-2-yl]benzamide;
4-{8-amino-3-[(3R)-1-{[1-(1-methylethyl)azetidin-3-yl]carbonyl}piperidin-3-yl]imidazo[1,5-a]pyrazin-1-yl}-N-[4-(trifluoromethyl)pyridin-2-yl]benzamide;
4-{8-amino-3-[(3R)-1-(1,2,5-thiadiazol-3-ylcarbonyl)piperidin-3-yl]imidazo[1,5-a]pyrazin-1-yl}-N-[4-(trifluoromethyl)pyridin-2-yl]benzamide;
4-{8-amino-3-[(3R)-1-(4,4,4-trifluorobutanoyl)piperidin-3-yl]imidazo[1,5-a]pyrazin-1-yl}-N-[4-(trifluoromethyl)pyridin-2-yl]benzamide;
4-{8-amino-3-[(3R)-1-(3,3,3-trifluoropropanoyl)piperidin-3-yl]imidazo[1,5-a]pyrazin-1-yl}-N-[4-(trifluoromethyl)pyridin-2-yl]benzamide;
4-{8-amino-3-[(3R)-1-(isothiazol-4-ylcarbonyl)piperidin-3-yl]imidazo[1,5-a]pyrazin-1-yl}-N-[4-(trifluoromethyl)pyridin-2-yl]benzamide;
4-{8-amino-3-[(3R)-1-{[1-(methoxymethyl)cyclopropyl]carbonyl}piperidin-3-yl]imidazo[1,5-a]pyrazin-1-yl}-N-[4-(trifluoromethyl)pyridin-2-yl]benzamide;
4-(8-amino-3-{(3R)-1-[(1-cyanocyclopropyl)carbonyl]piperidin-3-yl}imidazo[1,5-a]pyrazin-1-yl)-N-[4-(trifluoromethyl)pyridin-2-yl]benzamide;
4-{8-amino-3-[(3R)-1-(pyrazin-2-ylcarbonyl)piperidin-3-yl]imidazo[1,5-a]pyrazin-1-yl}-N-[4-(trifluoromethyl)pyridin-2-yl]benzamide;
4-{8-amino-3-[(3R)-1-(4,4-difluoro-L-prolyl)piperidin-3-yl]imidazo[1,5-a]pyrazin-1-yl}-N-[4-(trifluoromethyl)pyridin-2-yl]benzamide;
4-(8-amino-3-{(3R)-1-[(3-methyloxetan-3-yl(methyl)piperidin-3-yl}imidazo[1,5-a]pyrazin-1-yl)-N-[4-(trifluoromethyl)pyridin-2-yl]benzamide;
4-{8-amino-3-[(3R)-1-(ethoxyacetyl)piperidin-3-yl]imidazo[1,5-a]pyrazin-1-yl}-N-[4-(trifluoromethyl)pyridin-2-yl]benzamide;
4-{8-amino-3-[(3R)-1-(methoxyacetyl)piperidin-3-yl]imidazo[1,5-a]pyrazin-1-yl}-N-[4-(trifluoromethyl)pyridin-2-yl]benzamide;
4-{8-amino-3-[(3R)-1-(1-methyl-L-prolyl)piperidin-3-yl]imidazo[1,5-a]pyrazin-1-yl}-N-[4-(trifluoromethyl)pyridin-2-yl]benzamide;
4-(8-amino-3-{(3R)-1-[(1-hydroxycyclopropyl)carbonyl]piperidin-3-yl}imidazo[1,5-a]pyrazin-1-yl)-N-[4-(trifluoromethyl)pyridin-2-yl]benzamide;
4-{8-amino-3-[(3R)-1-(2-hydroxybutanoyl)piperidin-3-yl]imidazo[1,5-a]pyrazin-1-yl}-N-[4-(trifluoromethyl)pyridin-2-yl]benzamide;
4-(8-amino-3-{(3R)-1-[(2,2-difluorocyclopropyl)carbonyl]piperidin-3-yl}imidazo[1,5-a]pyrazin-1-yl)-N-[4-(trifluoromethyl)pyridin-2-yl]benzamide;
4-(8-amino-3-{(3R)-1-[(2S)-2-hydroxypropanoyl]piperidin-3-yl}imidazo[1,5-a]pyrazin-1-yl)-N-[4-(trifluoromethyl)pyridin-2-yl]benzamide;
4-(8-amino-3-{(3R)-1-[(2R)-2-hydroxypropanoyl]piperidin-3-yl}imidazo[1,5-a]pyrazin-1-yl)-N-[4-(trifluoromethyl)pyridin-2-yl]benzamide;
4-{8-amino-3-[(3R)-1-(N,N-dimethylglycyl)piperidin-3-yl]imidazo[1,5-a]pyrazin-1-yl}-N-[4-(trifluoromethyl)pyridin-2-yl]benzamide;
4-{8-amino-3-[(3R)-1-{[(3R)-1-methylpyrrolidin-3-yl]carbonyl}piperidin-3-yl]imidazo[1,5-a]pyrazin-1-yl}-N-[4-(trifluoromethyl)pyridin-2-yl]benzamide formate salt;
4-(8-amino-3-{(3R)-1-[(methylsulfonyl)acetyl]piperidin-3-yl}imidazo[1,5-a]pyrazin-1-yl)-N-[4-(trifluoromethyl)pyridin-2-yl]benzamide;
4-(8-amino-3-{(3R)-1-[(3-methyloxetan-3-yl)carbonyl]piperidin-3-yl}imidazo[1,5-a]pyrazin-1-yl)-N-1,3-thiazol-4-ylbenzamide;
4-(8-amino-3-{(3R)-1-[(3-methyloxetan-3-yl)carbonyl]piperidin-3-yl}imidazo[1,5-a]pyrazin-1-yl)-N-(5-fluoropyridin-2-yl)benzamide;
4-(8-amino-3-{(3R)-1-[(3-methyloxetan-3-yl)carbonyl]piperidin-3-yl}imidazo[1,5-a]pyrazin-1-yl)-N-(4-methylpyridin-2-yl)benzamide;
4-(8-amino-3-{(3R)-1-[(3-methyloxetan-3-yl)carbonyl]piperidin-3-yl}imidazo[1,5-a]pyrazin-1-yl)-N-(5-methylisoxazol-3-yl)benzamide;
4-(8-amino-3-{(3R)-1-[(3-methyloxetan-3-yl)carbonyl]piperidin-3-yl}imidazo[1,5-a]pyrazin-1-yl)-N-(4-cyclobutylpyridin-2-yl)benzamide;
4-(8-amino-3-{(3R)-1-[(3-methyloxetan-3-yl)carbonyl]piperidin-3-yl}imidazo[1,5-a]pyrazin-1-yl)-N-(5-(difluoromethyl)pyridin-2-yl)benzamide;
4-(8-amino-3-{(3R)-1-[(3-methyloxetan-3-yl)carbonyl]piperidin-3-yl}imidazo[1,5-a]pyrazin-1-yl)-N-(5-methylpyridin-2-yl)benzamide;

4-(8-amino-3-{(3R)-1-[(3-methyloxetan-3-yl)carbonyl]piperidin-3-yl}imidazo[1,5-a]pyrazin-1-yl)-N-pyridazin-3-ylbenzamide 4-(8-amino-3-{(3R)-1-[(3-methyloxetan-3-yl)carbonyl]piperidin-3-yl}imidazo[1,5-a]pyrazin-1-yl)-N-(5-chloropyridin-2-yl)benzamide;

4-(8-amino-3-{(3R)-1-[(3-methyloxetan-3-yl)carbonyl]piperidin-3-yl}imidazo[1,5-a]pyrazin-1-yl)-N-[5-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-N-(5-fluoro-4-methylpyridin-2-yl)benzamide;

4-(8-amino-3-{(3R)-1-[(3-methyloxetan-3-yl)carbonyl]piperidin-3-yl}imidazo[1,5-a]pyrazin-1-yl)-N-(4-methoxypyrimidin-2-yl)benzamide;

4-(8-amino-3-{(3R)-1-[(3-methyloxetan-3-yl)carbonyl]piperidin-3-yl}imidazo[1,5-a]pyrazin-1-yl)-N-(4-ethylpyridin-2-yl)benzamide;

4-(8-amino-3-{(3R)-1-[(3-methyloxetan-3-yl)carbonyl]piperidin-3-yl}imidazo[1,5-a]pyrazin-1-yl)-N-(5-methylpyridin-2-yl)benzamide;

4-(8-amino-3-{(3R)-1-[(3-methyloxetan-3-yl)carbonyl]piperidin-3-yl}imidazo[1,5-a]pyrazin-1-yl)-N-(6,7-dihydro-5H-cyclopenta[d]pyrimidin-2-yl)benzamide;

4-(8-amino-3-{(3R)-1-[(3-methyloxetan-3-yl)carbonyl]piperidin-3-yl}imidazo[1,5-a]pyrazin-1-yl)-N-(1-methyl-1H-pyrazol-3-yl)benzamide;

4-(8-amino-3-{(3R)-1-[(3-methyloxetan-3-yl)carbonyl]piperidin-3-yl}imidazo[1,5-a]pyrazin-1-yl)-N-(5-methyl-1,3-thiazol-2-yl)benzamide;

4-(8-amino-3-{(3R)-1-[(3-methyloxetan-3-yl)carbonyl]piperidin-3-yl}imidazo[1,5-a]pyrazin-1-yl)-N-(4,5-dimethyl-1,3-thiazol-2-yl)benzamide;

4-(8-amino-3-{(3R)-1-[(3-methyloxetan-3-yl)carbonyl]piperidin-3-yl}imidazo[1,5-a]pyrazin-1-yl)-N-1,2,4-thiadiazol-5-ylbenzamide;

4-(8-amino-3-{(3R)-1-[(3-methyloxetan-3-yl)carbonyl]piperidin-3-yl}imidazo[1,5-a]pyrazin-1-yl)-N-(5-tert-butyl-1,3-thiazol-2-yl)benzamide;

4-(8-amino-3-{(3R)-1-[(3-methyloxetan-3-yl)carbonyl]piperidin-3-yl}imidazo[1,5-a]pyrazin-1-yl)-N-isothiazol-4-ylbenzamide;

4-(8-amino-3-{(3R)-1-[(1-hydroxycyclopropyl)carbonyl]piperidin-3-yl}imidazo[1,5-a]pyrazin-1-yl)-N-(4-ethylpyridin-2-yl)benzamide;

4-{8-amino-3-[(3R)-1-propanoylpiperidin-3-yl]imidazo[1,5-a]pyrazin-1-yl}-N-(4-methoxypyridin-2-yl)benzamide;

4-(8-amino-5-cyano-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(3R,5S)-5-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(3R,5R)-5-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{5,5-difluoro-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(3R,4R)-4-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(3R,4S)-4-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(2R,3R)-2-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(2S,3R)-2-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(4-amino-1-{(3R)-1-[(3-methyloxetan-3-yl)carbonyl]piperidin-3-yl}-1H-pyrazolo[4,3-c]pyridin-3-yl)-N-[4-(trifluoromethyl)pyridin-2-yl]benzamide;

4-(4-amino-7-chloro-1-{(3R)-1-[(3-methyloxetan-3-yl)carbonyl]piperidin-3-yl}-1H-pyrazolo[4,3-c]pyridin-3-yl)-N-[4-(trifluoromethyl)pyridin-2-yl]benzamide;

4-{4-amino-1-[(3R)-1-(methoxyacetyl)piperidin-3-yl]-1H-pyrazolo[4,3-c]pyridin-3-yl}-N-[4-(trifluoromethyl)pyridin-2-yl]benzamide;

4-{4-amino-1-[(3R)-1-(cyclopropylcarbonyl)piperidin-3-yl]-1H-pyrazolo[4,3-c]pyridin-3-yl}-N-[4-(trifluoromethyl)pyridin-2-yl]benzamide;

4-{1-[(3R)-1-acetylpiperidin-3-yl]-4-amino-1H-pyrazolo[4,3-c]pyridin-3-yl}-N-[4-(trifluoromethyl)pyridin-2-yl]benzamide;

4-(4-amino-1-{(3R)-1-[(3-methyloxetan-3-yl)carbonyl]piperidin-3-yl}-1H-pyrazolo[4,3-c]pyridin-3-yl)-N-(4-ethylpyridin-2-yl)benzamide;

4-(4-amino-1-{(3R)-1-[(3-methyloxetan-3-yl)carbonyl]piperidin-3-yl}-1H-pyrazolo[4,3-c]pyridin-3-yl)-N-(4-methylpyridin-2-yl)benzamide;

4-(4-amino-1-{(3R)-1-[(3-methyloxetan-3-yl)carbonyl]piperidin-3-yl}-1H-pyrazolo[4,3-c]pyridin-3-yl)-N-(4-methoxypyridin-2-yl)benzamide;

4-(4-amino-7-{(3R)-1-[(3-methyloxetan-3-yl)carbonyl]piperidin-3-yl}-7H-pyrrolo[2,3-d]pyrimidin-5-yl)-N-[4-(trifluoromethyl)pyridin-2-yl]benzamide;

4-(4-amino-7-{(3R)-1-[(3-methyloxetan-3-yl)carbonyl]piperidin-3-yl}-7H-pyrrolo[2,3-d]pyrimidin-5-yl)-N-(4-cyanopyridin-2-yl)benzamide;

4-(4-amino-7-{(3R)-1-[(3-methyloxetan-3-yl)carbonyl]piperidin-3-yl}-7H-pyrrolo[2,3-d]pyrimidin-5-yl)-N-(4-ethylpyridin-2-yl)benzamide;

4-{8-amino-3-[(3R,6S)-1-(3-methoxypropanoyl)-6-methylpiperidin-3-yl]imidazo[1,5-a]pyrazin-1-yl}-2-fluoro-N-[4-(trifluoromethyl)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-{8-amino-3-[(3R,6S)-1-(cyclopropylcarbonyl)-6-methylpiperidin-3-yl]imidazo[1,5-a]pyrazin-1-yl}-N-pyridin-2-ylbenzamide;

4-(8-amino-3-{(3R,6S)-6-methyl-1-[(3-methyloxetan-3-yl)carbonyl]piperidin-3-yl}imidazo[1,5-a]pyrazin-1-yl)-3-fluoro-N-[4-(trifluoromethyl)pyridin-2-yl]benzamide;

4-{8-amino-3-[(3R,6S)-1-(cyclopropylcarbonyl)-6-methylpiperidin-3-yl]imidazo[1,5-a]pyrazin-1-yl}-3-fluoro-N-[4-(trifluoromethyl)pyridin-2-yl]benzamide;

4-{8-amino-3-[(3R,6S)-6-methyl-1-propanoylpiperidin-3-yl]imidazo[1,5-a]pyrazin-1-yl}-3-fluoro-N-[4-(trifluoromethyl)pyridin-2-yl]benzamide;

4-{8-amino-3-[(3R,6S)-1-(3-methoxypropanoyl)-6-methylpiperidin-3-yl]imidazo[1,5-a]pyrazin-1-yl}-3-fluoro-N-[4-(trifluoromethyl)pyridin-2-yl]benzamide;

4-{8-amino-3-[1-(cyclopropylcarbonyl)-6-(trifluoromethyl)piperidin-3-yl]imidazo[1,5-a]pyrazin-1-yl}-3-fluoro-N-[4-(trifluoromethyl)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-2-chloro-N-[4-(trifluoromethyl)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-3-methoxy-N-[4-(trifluoromethyl)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-N-(4-methylpyridin-2-yl)benzamide;

4-(8-amino-3-{(3R,6S)-6-methyl-1-[(3-methyloxetan-3-yl)carbonyl]piperidin-3-yl}imidazo[1,5-a]pyrazin-1-yl)-N-(4-methoxypyridin-2-yl)benzamide;

4-(8-amino-3-{(3R,6S)-6-methyl-1-[(3-methyloxetan-3-yl)carbonyl]piperidin-3-yl}imidazo[1,5-a]pyrazin-1-yl)-N-(4-ethoxypyridin-2-yl)benzamide;

4-(8-amino-3-{(3R,6R)-6-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-{8-amino-3-[(3S,6R)-1-ethyl-6-(trifluoromethyl)piperidin-3-yl]imidazo[1,5-a]pyrazin-1-yl}-N-[4-(trifluoromethyl)pyridin-2-yl]benzamide;

4-(8-amino-3-{(3S,6S)-6-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-{8-amino-3-[(3S,6R)-1-ethyl-6-(trifluoromethyl)piperidin-3-yl]imidazo[1,5-a]pyrazin-1-yl}-N-pyridin-2-ylbenzamide;

4-(8-amino-3-{(3R,6S)-6-methyl-1-[(3-methyloxetan-3-yl)carbonyl]piperidin-3-yl}imidazo[1,5-a]pyrazin-1-yl)-N-[4-(cyclopropyloxy)pyridin-2-yl]benzamide;

4-{8-amino-3-[(3S,6R)-1-methyl-6-(trifluoromethyl)piperidin-3-yl]imidazo[1,5-a]pyrazin-1-yl}-N-[4-(trifluoromethyl)pyridin-2-yl]benzamide;

4-{8-amino-3-[(3S,6R)-1-methyl-6-(trifluoromethyl)piperidin-3-yl]imidazo[1,5-a]pyrazin-1-yl}-3-fluoro-N-[4-(trifluoromethyl)pyridin-2-yl]benzamide;

(2R,5S)-5-[8-amino-1-(4-{[4-(trifluoromethyl)pyridin-2-yl]carbamoyl}-phenyl)imidazo[1,5-a]pyrazin-3-yl]-N-methyl-2-(trifluoromethyl)piperidine-1-carboxamide;

4-(8-amino-3-{(3R,6S)-6-methyl-1-[(3-methyloxetan-3-yl)carbonyl]piperidin-3-yl}imidazo[1,5-a]pyrazin-1-yl)-N-[4-(1,1-difluoroethyl)pyridin-2-yl]benzamide;

4-{8-amino-3-[(3S,6R)-1-methyl-6-(trifluoromethyl)piperidin-3-yl]imidazo[1,5-a]pyrazin-1-yl}-N-[4-(trifluoromethyl)pyridin-2-yl]benzamide;

4-{8-amino-3-[(3S,6R)-1-propanoyl-6-(trifluoromethyl)piperidin-3-yl]imidazo[1,5-a]pyrazin-1-yl}-N-[4-(trifluoromethyl)pyridin-2-yl]benzamide;

4-(8-amino-3-{(3R,6R)-6-(difluoromethyl)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-N-[4-(2-methylpropoxy)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-N-[4-(2,2,2-trifluoroethoxy)pyridin-2-yl]benzamide;

4-{8-amino-3-[(3S,6S)-1-(cyclopropylcarbonyl)-6-(hydroxymethyl)piperidin-3-yl]imidazo[1,5-a]pyrazin-1-yl}-N-[4-(trifluoromethyl)pyridin-2-yl]benzamide;

4-{8-amino-3-[(3S,6R)-1-(cyclopropylcarbonyl)-6-(trifluoromethyl)piperidin-3-yl]imidazo[1,5-a]pyrazin-1-yl}-N-(4-fluoropyridin-2-yl)benzamide;

4-{8-amino-3-[(3S,6R)-1-(cyclopropylcarbonyl)-6-(trifluoromethyl)piperidin-3-yl]imidazo[1,5-a]pyrazin-1-yl}-N-(4-methylpyridin-2-yl)benzamide;

(2R,5S)-5-[8-amino-1-(4-{[4-(trifluoromethyl)pyridin-2-yl]carbamoyl}-phenyl)imidazo[1,5-a]pyrazin-3-yl]-N,N-dimethyl-2-(trifluoromethyl)piperidine-1-carboxamide;

4-{3-[(3S,6R)-1-acetyl-6-(trifluoromethyl)piperidin-3-yl]-8-aminoimidazo[1,5-a]pyrazin-1-yl}-N-[4-(trifluoromethyl)pyridin-2-yl]benzamide;

4-(8-amino-3-{(3S,6S)-6-(methoxymethyl)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(3R,6R)-6-(methoxymethyl)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

methyl (2R,5S)-5-[8-amino-1-(4-{[4-(trifluoromethyl)pyridin-2-yl]carbamoyl}-phenyl)imidazo[1,5-a]pyrazin-3-yl]-2-(trifluoromethyl)piperidine-1-carboxylate;

4-(8-amino-3-{(3R,6S)-6-methyl-1-[(3-methyloxetan-3-yl)carbonyl]piperidin-3-yl}imidazo[1,5-a]pyrazin-1-yl)-N-[4-(difluoromethyl)pyridin-2-yl]-3-fluorobenzamide;

4-{3-[(3R,6S)-1-acetyl-6-methylpiperidin-3-yl]-8-aminoimidazo[1,5-a]pyrazin-1-yl}-N-[4-(difluoromethyl)pyridin-2-yl]-3-fluorobenzamide;

4-{8-amino-3-[(3R,6S)-1-(cyclopropylcarbonyl)-6-methylpiperidin-3-yl]imidazo[1,5-a]pyrazin-1-yl}-N-[4-(difluoromethyl)pyridin-2-yl]-3-fluorobenzamide;

4-{8-amino-3-[(3S,6R)-1-(2-hydroxyethyl)-6-(trifluoromethyl)piperidin-3-yl]imidazo[1,5-a]pyrazin-1-yl}-N-[4-(trifluoromethyl)pyridin-2-yl]benzamide;

4-(8-amino-3-{(3R)-3-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(3S)-3-hydroxy-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-{3-[(3R)-1-acetylpiperidin-3-yl]-8-amino-5-chloroimidazo[1,5-a]pyrazin-1-yl}-N-[4-(trifluoromethyl)pyridin-2-yl]benzamide;

4-{8-amino-5-chloro-3-[(3R)-1-(hydroxyacetyl)piperidin-3-yl]imidazo[1,5-a]pyrazin-1-yl}-N-[4-(trifluoromethyl)pyridin-2-yl]benzamide;

4-{8-amino-5-chloro-3-[(3R)-1-(methoxyacetyl)piperidin-3-yl]imidazo[1,5-a]pyrazin-1-yl}-N-[4-(trifluoromethyl)pyridin-2-yl]benzamide;

4-{8-amino-5-chloro-3-[(3R)-1-formylpiperidin-3-yl]imidazo[1,5-a]pyrazin-1-yl}-N-[4-(trifluoromethyl)pyridin-2-yl]benzamide;

4-(8-amino-5-chloro-3-{(3R)-1-[(3-methyloxetan-3-yl)carbonyl]piperidin-3-yl}imidazo[1,5-a]pyrazin-1-yl)-N-(4-methoxypyridin-2-yl)benzamide;

4-(8-amino-5-chloro-3-{(3R)-1-[(3-methyloxetan-3-yl)carbonyl]piperidin-3-yl}imidazo[1,5-a]pyrazin-1-yl)-N-(4-cyanopyridin-2-yl)benzamide;

4-(8-amino-5-chloro-3-{(3R)-1-[(3-methyloxetan-3-yl)carbonyl]piperidin-3-yl}imidazo[1,5-a]pyrazin-1-yl)-N-(4-methylpyridin-2-yl)benzamide;

4-(8-amino-5-chloro-3-{(3R)-1-[(3-methyloxetan-3-yl)carbonyl]piperidin-3-yl}imidazo[1,5-a]pyrazin-1-yl)-3-fluoro-N-[4-(trifluoromethyl)pyridin-2-yl]benzamide;

4-(8-amino-5-chloro-3-{(3R)-1-[(3-methyloxetan-3-yl)carbonyl]piperidin-3-yl}imidazo[1,5-a]pyrazin-1-yl)-3-fluoro-N-(4-methylpyridin-2-yl)benzamide;

4-[8-amino-5-(methoxymethyl)-3-{(3R)-1-[(3-methyloxetan-3-yl)carbonyl]piperidin-3-yl}imidazo[1,5-a]pyrazin-1-yl]-N-[4-(trifluoromethyl)pyridin-2-yl]benzamide;

4-[8-amino-5-(methoxymethyl)-3-{(3R,6S)-6-methyl-1-[(3-methyloxetan-3-yl)carbonyl]piperidin-3-yl}imidazo[1,5-a]pyrazin-1-yl]-N-[4-(trifluoromethyl)pyridin-2-yl]benzamide;

4-[8-amino-5-(methoxymethyl)-3-{(3R)-1-[(3-methyloxetan-3-yl)carbonyl]piperidin-3-yl}imidazo[1,5-a]pyrazin-1-yl]-3-fluoro-N-[4-(trifluoromethyl)pyridin-2-yl]benzamide;

4-{8-amino-3-[(3R)-1-(methoxyacetyl)piperidin-3-yl]-5-(methoxymethyl)imidazo[1,5-a]pyrazin-1-yl}-3-fluoro-N-[4-(trifluoromethyl)pyridin-2-yl]benzamide;

4-(8-amino-5-methyl-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-5-methyl-3-{(3R)-1-[(3-methyloxetan-3-yl)carbonyl]piperidin-3-yl}imidazo[1,5-a]pyrazin-1-yl)-N-[4-(1,1-difluoroethyl)pyridin-2-yl]benzamide;

4-(8-amino-5-methyl-3-{(3R)-1-[(3-methyloxetan-3-yl)carbonyl]piperidin-3-yl)imidazo[1,5-a]pyrazin-1-yl}-N-(4-ethylpyridin-2-yl)benzamide;

4-(8-amino-5-methyl-3-{(3R)-1-[(3-methyloxetan-3-yl)carbonyl]piperidin-3-yl}imidazo[1,5-a]pyrazin-1-yl)-N-[4-(cyclopropyloxy)pyridin-2-yl]benzamide;

4-{8-amino-3-[(3R)-1-(cyclopropylcarbonyl)piperidin-3-yl]-5-methylimidazo[1,5-a]pyrazin-1-yl}-N-[4-(cyclopropyloxy)pyridin-2-yl]benzamide;

4-(8-amino-5-methyl-3-{(3R)-1-[(3-methyloxetan-3-yl)carbonyl]piperidin-3-yl}imidazo[1,5-a]pyrazin-1-yl)-N-[4-(difluoromethyl)pyridin-2-yl]benzamide;

4-(8-amino-5-methyl-3-{(3R)-1-[(3-methyloxetan-3-yl)carbonyl]piperidin-3-yl}imidazo[1,5-a]pyrazin-1-yl)-N-(4-methoxypyridin-2-yl)benzamide;

4-{3-[(3R)-1-acetylpiperidin-3-yl]-8-amino-5-methylimidazo[1,5-a]pyrazin-1-yl}-N-(4-methoxypyridin-2-yl)benzamide;

4-(8-amino-5-methyl-3-{(3R,6S)-6-methyl-1-[(3-methyloxetan-3-yl)carbonyl]-piperidin-3-yl}imidazo[1,5-a]pyrazin-1-yl)-N-[4-(difluoromethyl)pyridin-2-yl]-3-fluorobenzamide;

4-{3-[(3R,6S)-1-acetyl-6-methylpiperidin-3-yl]-8-amino-5-methylimidazo[1,5-a]pyrazin-1-yl}-N-[4-(difluoromethyl)pyridin-2-yl]-3-fluorobenzamide;

4-{8-amino-3-[(3R)-1-(cyclopropylcarbonyl)piperidin-3-yl]-5-fluoroimidazo[1,5-a]pyrazin-1-yl}-N-[4-(trifluoromethyl)pyridin-2-yl]benzamide;

4-(8-amino-5-formyl-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-5-[(1R)-1-hydroxyethyl]-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-5-[(1S)-1-hydroxyethyl]-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-5-[(1R)-1-methoxyethyl]-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-5-[(1S)-1-methoxyethyl]-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-[8-amino-5-(3-hydroxyoxetan-3-yl)-3-{(3R)-1-[(3-methyloxetan-3-yl)carbonyl]piperidin-3-yl}imidazo[1,5-a]pyrazin-1-yl]-N-[4-(trifluoromethyl)pyridin-2-yl]benzamide;

4-[8-amino-3-{(3R)-1-[(3-methyloxetan-3-yl)carbonyl]piperidin-3-yl}-5-(trifluoromethyl)imidazo[1,5-a]pyrazin-1-yl]-N-[4-(trifluoromethyl)pyridin-2-yl]benzamide;

4-[8-amino-5-(hydroxymethyl)-3-{(3R)-1-[(3-methyloxetan-3-yl)carbonyl]piperidin-3-yl}imidazo[1,5-a]pyrazin-1-yl]-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-2-fluoro-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-2-chloro-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-2-methyl-N-[4-(trifluoromethyl)pyridin-2-yl]benzamide;

4-{8-amino-3-[(3R)-1-(3-methoxypropanoyl)piperidin-3-yl]imidazo[1,5-a]pyrazin-1-yl}-3-hydroxy-N-pyridin-2-ylbenzamide;

4-(8-amino-3-{(3R,6S)-6-methyl-1-[(3-methyloxetan-3-yl)carbonyl]piperidin-3-yl}imidazo[1,5-a]pyrazin-1-yl)-2-fluoro-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-3-methoxy-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-N-[4-(difluoromethoxy)pyridin-2-yl]-3-fluorobenzamide;

4-(8-amino-3-{(3R)-1-[(3-methyloxetan-3-yl)carbonyl]piperidin-3-yl}imidazo[1,5-a]pyrazin-1-yl)-3-methyl-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-N-[4-(difluoromethyl)pyridin-2-yl]-3-fluorobenzamide;

4-(8-amino-3-{(3R)-1-[(3-methyloxetan-3-yl)carbonyl]piperidin-3-yl}imidazo[1,5-a]pyrazin-1-yl)-3-fluoro-N-(4-propoxypyridin-2-yl)benzamide;

4-(8-amino-3-{(3R)-1-[(3-methyloxetan-3-yl)carbonyl]piperidin-3-yl}imidazo[1,5-a]pyrazin-1-yl)-N-(4-cyanopyridin-2-yl)-3-fluorobenzamide;

4-(8-amino-3-{(3R)-1-[(3-methyloxetan-3-yl)carbonyl]piperidin-3-yl}imidazo[1,5-a]pyrazin-1-yl)-N-[4-(cyclopropyloxy)pyridin-2-yl]-3-fluorobenzamide;

4-(8-amino-3-{(3R)-1-[(3-methyloxetan-3-yl)carbonyl]piperidin-3-yl}imidazo[1,5-a]pyrazin-1-yl)-N-[4-(1,1-difluoroethyl)pyridin-2-yl]-3-fluorobenzamide;

4-(8-amino-3-{(3R)-1-[(3-methyloxetan-3-yl)carbonyl]piperidin-3-yl}imidazo[1,5-a]pyrazin-1-yl)-N-(4-chloropyridin-2-yl)-3-fluorobenzamide;

4-{3-[(3R)-1-acetylpiperidin-3-yl]-8-aminoimidazo[1,5-a]pyrazin-1-yl}-3-fluoro-N-[4-(trifluoromethyl)pyridin-2-yl]benzamide;

4-{8-amino-3-[(3R)-1-propanoylpiperidin-3-yl]imidazo[1,5-a]pyrazin-1-yl}-3-fluoro-N-[4-(trifluoromethyl)pyridin-2-yl]benzamide;

4-{8-amino-3-[(3R)-1-propanoylpiperidin-3-yl]imidazo[1,5-a]pyrazin-1-yl}-N-[4-(difluoromethyl)pyridin-2-yl]-3-fluorobenzamide;

(3R)-3-[8-amino-1-(2-fluoro-4-{[4-(trifluoromethyl)pyridin-2-yl]carbamoyl}phenyl)imidazo[1,5-a]pyrazin-3-yl]-N-cyclopropylpiperidine-1-carboxamide;

4-{8-amino-3-[(3R)-1-propanoylpiperidin-3-yl]imidazo[1,5-a]pyrazin-1-yl}-3-methoxy-N-[4-(trifluoromethyl)pyridin-2-yl]benzamide;

4-{8-amino-3-[(2R)-4-(2-methoxyethyl)morpholin-2-yl]imidazo[1,5-a]pyrazin-1-yl}-N-[4-(trifluoromethyl)pyridin-2-yl]benzamide;

4-{8-amino-3-[(2R)-4-(2-hydroxyethyl)morpholin-2-yl]imidazo[1,5-a]pyrazin-1-yl}-N-[4-(trifluoromethyl)pyridin-2-yl]benzamide;

4-{8-amino-3-[(2R)-4-(3-methoxypropanoyl)morpholin-2-yl]imidazo[1,5-a]pyrazin-1-yl}-N-[4-(trifluoromethyl)pyridin-2-yl]benzamide;

4-(8-amino-3-{(2R)-4-[(3-methyloxetan-3-yl)carbonyl]morpholin-2-yl}imidazo[1,5-a]pyrazin-1-yl)-N-[4-(trifluoromethyl)pyridin-2-yl]benzamide;

4-(8-amino-3-{(2R)-4-[(1-methyl-1H-pyrazol-4-yl)methyl]morpholin-2-yl}imidazo[1,5-a]pyrazin-1-yl)-N-[4-(trifluoromethyl)pyridin-2-yl]benzamide;

4-{8-amino-3-[(2R)-4-ethylmorpholin-2-yl]imidazo[1,5-a]pyrazin-1-yl}-N-[4-(trifluoromethyl)pyridin-2-yl]benzamide;

4-{8-amino-3-[(2R)-4-methylmorpholin-2-yl]imidazo[1,5-a]pyrazin-1-yl}-N-[4-(trifluoromethyl)pyridin-2-yl]benzamide;

4-(8-amino-3-{(2R)-4-[(1-methyl-1H-pyrazol-4-yl)methyl]morpholin-2-yl}imidazo[1,5-a]pyrazin-1-yl)-N-(4-cyclopropylpyridin-2-yl)benzamide;

4-(8-amino-3-{(2R)-4-[(1-aminocyclobutyl)carbonyl]morpholin-2-yl}imidazo[1,5-a]pyrazin-1-yl)-N-[4-(trifluoromethyl)pyridin-2-yl]benzamide;

4-{8-amino-3-[(2R)-4-{[1-(methoxymethyl)cyclobutyl]carbonyl}morpholin-2-yl]imidazo[1,5-a]pyrazin-1-yl}-N-[4-(trifluoromethyl)pyridin-2-yl]benzamide;

4-(8-amino-3-{(2R)-4-[(1-methylazetidin-3-yl)carbonyl]morpholin-2-yl}imidazo[1,5-a]pyrazin-1-yl)-N-[4-(trifluoromethyl)pyridin-2-yl]benzamide;

4-(8-amino-3-{(2R)-4-[3-(methylsulfanyl)propanoyl]morpholin-2-yl}imidazo[1,5-a]pyrazin-1-yl)-N-[4-(trifluoromethyl)pyridin-2-yl]benzamide;

4-{8-amino-3-[(2R)-4-(3-ethoxypropanoyl)morpholin-2-yl]imidazo[1,5-a]pyrazin-1-yl}-N-[4-(trifluoromethyl)pyridin-2-yl]benzamide;

4-{8-amino-5-chloro-3-[(2R)-morpholin-2-yl]imidazo[1,5-a]pyrazin-1-yl}-N-[4-(trifluoromethyl)pyridin-2-yl]benzamide;

4-(8-amino-5-chloro-3-{(2R)-4-[(3-methyloxetan-3-yl)carbonyl]morpholin-2-yl}imidazo[1,5-a]pyrazin-1-yl)-N-[4-(trifluoromethyl)pyridin-2-yl]benzamide;

4-(8-amino-5-methyl-3-{(2R)-4-[(3-methyloxetan-3-yl)carbonyl]morpholin-2-yl}imidazo[1,5-a]pyrazin-1-yl)-N-[4-(trifluoromethyl)pyridin-2-yl]benzamide;

4-(8-amino-3-{(2R)-4-[(3-methyloxetan-3-yl)methyl]morpholin-2-yl}imidazo[1,5-a]pyrazin-1-yl)-N-[4-(trifluoromethyl)pyridin-2-yl]benzamide;

4-{8-amino-3-[(2R)-4-(cyclopropylmethyl)morpholin-2-yl]imidazo[1,5-a]pyrazin-1-yl}-N-[4-(trifluoromethyl)pyridin-2-yl]benzamide;

4-(8-amino-5-methyl-3-{(2R)-4-[(1-methyl-1H-pyrazol-4-yl)methyl]morpholin-2-yl}imidazo[1,5-a]pyrazin-1-yl)-N-[4-(trifluoromethyl)pyridin-2-yl]benzamide;

4-{8-amino-3-[(2R)-4-(3-methoxypropanoyl)morpholin-2-yl]-5-methylimidazo[1,5-a]pyrazin-1-yl}-N-[4-(trifluoromethyl)pyridin-2-yl]benzamide;

4-{8-amino-3-[(2R)-4-ethylmorpholin-2-yl]-5-methylimidazo[1,5-a]pyrazin-1-yl}-N-[4-(trifluoromethyl)pyridin-2-yl]benzamide;

4-{8-amino-3-[(2R)-4-(cyclopropylcarbonyl)morpholin-2-yl]imidazo[1,5-a]pyrazin-1-yl}-3-fluoro-N-[4-(trifluoromethyl)pyridin-2-yl]benzamide;

4-(8-amino-3-{(2R)-4-[(3-methyloxetan-3-yl)carbonyl]morpholin-2-yl}imidazo[1,5-a]pyrazin-1-yl)-3-fluoro-N-[4-(trifluoromethyl)pyridin-2-yl]benzamide;

4-(8-amino-5-methyl-3-{(2R)-4-[(3-methyloxetan-3-yl)carbonyl]morpholin-2-yl}imidazo[1,5-a]pyrazin-1-yl)-3-fluoro-N-[4-(trifluoromethyl)pyridin-2-yl]benzamide;

4-(8-amino-3-{(2R,5S)-5-methyl-4-[(3-methyloxetan-3-yl)carbonyl]morpholin-2-yl}imidazo[1,5-a]pyrazin-1-yl)-N-[4-(trifluoromethyl)pyridin-2-yl]benzamide;

4-{8-amino-3-[(2R,5S)-4-(cyclopropylcarbonyl)-5-methylmorpholin-2-yl]imidazo[1,5-a]pyrazin-1-yl}-N-[4-(trifluoromethyl)pyridin-2-yl]benzamide;

4-{8-amino-3-[(2R)-4-(hydroxyacetyl)morpholin-2-yl]imidazo[1,5-a]pyrazin-1-yl}-N-[4-(trifluoromethyl)pyridin-2-yl]benzamide;

4-{8-amino-3-[(2R)-4-(ethoxyacetyl)morpholin-2-yl]imidazo[1,5-a]pyrazin-1-yl}-N-[4-(trifluoromethyl)pyridin-2-yl]benzamide;

4-(8-amino-3-{(2R)-4-[(2S)-2-hydroxypropanoyl]morpholin-2-yl}imidazo[1,5-a]pyrazin-1-yl)-N-[4-(trifluoromethyl)pyridin-2-yl]benzamide;

4-(8-amino-3-{(2R)-4-[(2R)-2-hydroxypropanoyl]morpholin-2-yl}imidazo[1,5-a]pyrazin-1-yl)-N-[4-(trifluoromethyl)pyridin-2-yl]benzamide;

4-{8-amino-3-[(2R)-4-(methoxyacetyl)morpholin-2-yl]imidazo[1,5-a]pyrazin-1-yl}-N-[4-(trifluoromethyl)pyridin-2-yl]benzamide;

4-{8-amino-5-chloro-3-[(2R)-4-ethylmorpholin-2-yl]imidazo[1,5-a]pyrazin-1-yl}-N-[4-(trifluoromethyl)pyridin-2-yl]benzamide;

4-(8-amino-5-chloro-3-{(2R)-4-[(2S)-2-hydroxypropanoyl]morpholin-2-yl}imidazo[1,5-a]pyrazin-1-yl)-N-[4-(trifluoromethyl)pyridin-2-yl]benzamide;

4-(8-amino-5-chloro-3-{(2R)-4-[(2R)-2-hydroxypropanoyl]morpholin-2-yl}imidazo[1,5-a]pyrazin-1-yl)-N-[4-(trifluoromethyl)pyridin-2-yl]benzamide;

4-(8-amino-5-chloro-3-{(2R)-4-[(1-hydroxycyclopropyl)carbonyl]morpholin-2-yl}imidazo[1,5-a]pyrazin-1-yl)-N-[4-(trifluoromethyl)pyridin-2-yl]benzamide;

4-{8-amino-5-chloro-3-[(2R)-4-(2,2,2-trifluoroethyl)morpholin-2-yl]imidazo[1,5-a]pyrazin-1-yl}-N-[4-(trifluoromethyl)pyridin-2-yl]benzamide;

4-(8-amino-5-cyano-3-{(2R)-4-[(3-methyloxetan-3-yl)carbonyl]morpholin-2-yl}imidazo[1,5-a]pyrazin-1-yl)-N-[4-(trifluoromethyl)pyridin-2-yl]benzamide;

4-{8-amino-5-chloro-3-[(2R)-4-(methoxyacetyl)morpholin-2-yl]imidazo[1,5-a]pyrazin-1-yl}-N-[4-(trifluoromethyl)pyridin-2-yl]benzamide;

4-(8-amino-5-chloro-3-{(2R)-4-[(2-methoxyethoxy)acetyl]morpholin-2-yl}imidazo[1,5-a]pyrazin-1-yl)-N-[4-(trifluoromethyl)pyridin-2-yl]benzamide;

4-(8-amino-3-{(2S)-4-[(3-methyloxetan-3-yl)carbonyl]morpholin-2-yl}imidazo[1,5-a]pyrazin-1-yl)-N-[4-(trifluoromethyl)pyridin-2-yl]benzamide;

4-{8-amino-3-[(2R)-4-(cyanomethyl)morpholin-2-yl]imidazo[1,5-a]pyrazin-1-yl}-N-[4-(trifluoromethyl)pyridin-2-yl]benzamide;

4-{8-amino-3-[(2R)-4-(2-cyanoethyl)morpholin-2-yl]imidazo[1,5-a]pyrazin-1-yl}-N-[4-(trifluoromethyl)pyridin-2-yl]benzamide;

4-{8-amino-5-chloro-3-[(2R)-4-(cyanomethyl)morpholin-2-yl]imidazo[1,5-a]pyrazin-1-yl}-N-[4-(trifluoromethyl)pyridin-2-yl]benzamide;

4-{8-amino-3-[(2S)-4-ethylmorpholin-2-yl]imidazo[1,5-a]pyrazin-1-yl}-N-[4-(trifluoromethyl)pyridin-2-yl]benzamide;

4-{8-amino-5-chloro-3-[(2R)-4-(2-hydroxyethyl)morpholin-2-yl]imidazo[1,5-a]pyrazin-1-yl}-N-[4-(trifluoromethyl)pyridin-2-yl]benzamide;

4-{8-amino-3-[(2R)-4-(methoxyacetyl)morpholin-2-yl]-5-methylimidazo[1,5-a]pyrazin-1-yl}-N-[4-(trifluoromethyl)pyridin-2-yl]benzamide;

4-{8-amino-3-[(2R)-4-(ethoxyacetyl)morpholin-2-yl]-5-methylimidazo[1,5-a]pyrazin-1-yl}-N-[4-(trifluoromethyl)pyridin-2-yl]benzamide;

4-{8-amino-3-[(2R)-4-(difluoroacetyl)morpholin-2-yl]-5-methylimidazo[1,5-a]pyrazin-1-yl}-N-[4-(trifluoromethyl)pyridin-2-yl]benzamide;

4-{8-amino-3-[(2R)-4-(2-methoxyethyl)morpholin-2-yl]-5-methylimidazo[1,5-a]pyrazin-1-yl}-N-[4-(trifluoromethyl)pyridin-2-yl]benzamide;

4-{8-amino-3-[(2R)-4-(2-hydroxyethyl)morpholin-2-yl]-5-methylimidazo[1,5-a]pyrazin-1-yl}-N-[4-(trifluoromethyl)pyridin-2-yl]benzamide;

4-{8-amino-3-[(2R)-4-(2-ethoxyethyl)morpholin-2-yl]-5-methylimidazo[1,5-a]pyrazin-1-yl}-N-[4-(trifluoromethyl)pyridin-2-yl]benzamide;

4-{8-amino-5-chloro-3-[(2R)-4-(2-methoxyethyl)morpholin-2-yl]imidazo[1,5-a]pyrazin-1-yl}-N-[4-(trifluoromethyl)pyridin-2-yl]benzamide;

4-(8-amino-3-{(2R)-4-[(2S)-2-hydroxypropanoyl]morpholin-2-yl}-5-methylimidazo[1,5-a]pyrazin-1-yl)-N-[4-(trifluoromethyl)pyridin-2-yl]benzamide;

4-(8-amino-3-{(2R)-4-[(2R)-2-hydroxypropanoyl]morpholin-2-yl}-5-methylimidazo[1,5-a]pyrazin-1-yl)-N-[4-(trifluoromethyl)pyridin-2-yl]benzamide;

4-(8-amino-3-{(2R)-4-[(methylsulfonyl)acetyl]morpholin-2-yl}imidazo[1,5-a]pyrazin-1-yl)-N-[4-(trifluoromethyl)pyridin-2-yl]benzamide;

4-{8-amino-3-[(2R,5S)-5-(hydroxymethyl)morpholin-2-yl]imidazo[1,5-a]pyrazin-1-yl}-N-[4-(trifluoromethyl)pyridin-2-yl]benzamide;

4-{8-amino-3-[(2S,5R)-5-(hydroxymethyl)morpholin-2-yl]imidazo[1,5-a]pyrazin-1-yl}-N-[4-(trifluoromethyl)pyridin-2-yl]benzamide;

4-(8-amino-3-{(2R,5S)-5-(hydroxymethyl)-4-[(1-methyl-1H-pyrazol-4-yl)methyl]morpholin-2-yl}imidazo[1,5-a]pyrazin-1-yl)-N-[4-(trifluoromethyl)pyridin-2-yl]benzamide;

4-{8-amino-3-[(2R,5S)-4-ethyl-5-(hydroxymethyl)morpholin-2-yl]imidazo[1,5-a]pyrazin-1-yl}-N-[4-(trifluoromethyl)pyridin-2-yl]benzamide;

4-{8-amino-3-[(2R)-4-oxetan-3-ylmorpholin-2-yl]imidazo[1,5-a]pyrazin-1-yl}-N-[4-(trifluoromethyl)pyridin-2-yl]benzamide;

4-{8-amino-3-[(2R)-4-(methoxyacetyl)morpholin-2-yl]imidazo[1,5-a]pyrazin-1-yl}-3-fluoro-N-[4-(trifluoromethyl)pyridin-2-yl]benzamide;

4-{4-amino-1-[(4R)-1-methyl-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4S)-1-methyl-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4R)-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4S)-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(3S,6R)-6-(trifluoromethyl)piperidin-3-yl]-1H-pyrazolo[3,4-d]pyrimidin-3-yl}-N-[4-(trifluoromethyl)pyridin-2-yl]benzamide;

4-{4-amino-1-[(4R)-2-methyl-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{4-amino-1-[(4S)-2-methyl-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{4-amino-1-[(4R)-1-ethyl-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4S)-2-ethyl-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{4-amino-1-[(4R)-1-(2-hydroxyethyl)-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4R)-2-(2-hydroxyethyl)-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{4-amino-1-[(4S)-1-(2-hydroxyethyl)-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4S)-2-(2-hydroxyethyl)-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{8-amino-3-[(2R)-1,4-dimethylpiperazin-2-yl]imidazo[1,5-a]pyrazin-1-yl}-N-[4-(trifluoromethyl)pyridin-2-yl]benzamide;

4-(8-amino-3-{(2R)-4-[(1-methyl-1H-pyrazol-4-yl)methyl]piperazin-2-yl}imidazo[1,5-a]pyrazin-1-yl)-N-[4-(trifluoromethyl)pyridin-2-yl]benzamide;

4-(8-amino-3-{(2R)-4-[(1-methylcyclopropyl)carbonyl]piperazin-2-yl}imidazo[1,5-a]pyrazin-1-yl)-N-[4-(trifluoromethyl)pyridin-2-yl]benzamide;

4-{8-amino-3-[(2R)-4-(3-methoxypropanoyl)piperazin-2-yl]imidazo[1,5-a]pyrazin-1-yl}-N-[4-(trifluoromethyl)pyridin-2-yl]benzamide;

4-(8-amino-3-{4-[(1-methyl-1H-pyrazol-4-yl)methyl]-1,1-dioxidothiomorpholin-2-yl}imidazo[1,5-a]pyrazin-1-yl)-N-[4-(trifluoromethyl)pyridin-2-yl]benzamide;

4-[8-amino-3-(4-methyl-1,1-dioxidothiomorpholin-2-yl)imidazo[1,5-a]pyrazin-1-yl]-N-[4-(trifluoromethyl)pyridin-2-yl]benzamide;

4-(8-amino-3-{4-[(1-cyanocyclopropyl)carbonyl]-1,1-dioxidothiomorpholin-2-yl}imidazo[1,5-a]pyrazin-1-yl)-N-[4-(trifluoromethyl)pyridin-2-yl]benzamide;

4-{8-amino-3-[4-(3-methoxypropanoyl)-1,1-dioxidothiomorpholin-2-yl]imidazo[1,5-a]pyrazin-1-yl}-N-[4-(trifluoromethyl)pyridin-2-yl]benzamide;

4-[8-amino-3-(1-ethyl-2-oxopiperidin-4-yl)imidazo[1,5-a]pyrazin-1-yl]-N-[4-(trifluoromethyl)pyridin-2-yl]benzamide;

4-(8-amino-3-{(3R)-1-[(3-methyloxetan-3-yl)carbonyl]azepan-3-yl}imidazo[1,5-a]pyrazin-1-yl)-N-[4-(trifluoromethyl)pyridin-2-yl]benzamide;

4-{8-amino-3-[(3R)-1-(methoxyacetyl)piperidin-3-yl]imidazo[1,5-a]pyrazin-1-yl}-3-fluoro-N-[4-(trifluoromethyl)pyridin-2-yl]benzamide;

4-{8-amino-3-[(3R)-1-(3-methoxypropanoyl)piperidin-3-yl]imidazo[1,5-a]pyrazin-1-yl}-3-fluoro-N-[4-(trifluoromethyl)pyridin-2-yl]benzamide; and 4-{8-amino-5-bromo-3-[(3R)-1-(cyclopropylcarbonyl)piperidin-3-yl]imidazo[1,5-a]pyrazin-1-yl}-N-[4-(trifluoromethyl)pyridin-2-yl]benzamide.

13. The compound of claim 12 or a pharmaceutically acceptable salt thereof selected from the group consisting of:

4-(8-amino-3-{(3R)-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-3-fluoro-N-[4-(trifluoromethyl)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-N-[4-(trifluoromethyl)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-3-fluoro-N-[4-(trifluoromethyl)pyridin-2-yl]benzamide;

4-{8-amino-3-[(3R,6S)-1-(cyclopropylcarbonyl)-6-methylpiperidin-3-yl]imidazo[1,5-a]pyrazin-1-yl}-3-fluoro-N-[4-(trifluoromethyl)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-2-chloro-N-[4-(trifluoromethyl)pyridin-2-yl]benzamide;

4-[8-amino-5-(methoxymethyl)-3-{(3R)-1-[(3-methyloxetan-3-yl)carbonyl]piperidin-3-yl}imidazo[1,5-a]pyrazin-1-yl]-N-[4-(trifluoromethyl)pyridin-2-yl]benzamide;

4-(8-amino-3-{(3R,6S)-6-methyl-1-[(3-methyloxetan-3-yl)carbonyl]piperidin-3-yl}imidazo[1,5-a]pyrazin-1-yl)-2-fluoro-N-[4-(trifluoromethyl)pyridin-2-yl]benzamide;

4-(8-amino-3-{(3R)-1-[(3-methyloxetan-3-yl)carbonyl]piperidin-3-yl}imidazo[1,5-a]pyrazin-1-yl)-N-(4-chloropyridin-2-yl)-3-fluorobenzamide;

4-{8-amino-3-[(3R)-1-(methoxyacetyl)piperidin-3-yl]imidazo[1,5-a]pyrazin-1-yl}-3-fluoro-N-[4-(trifluoromethyl)pyridin-2-yl]benzamide; and 4-{8-amino-3-[(3R)-1-(3-methoxypropanoyl)piperidin-3-yl]imidazo[1,5-a]pyrazin-1-yl}-3-fluoro-N-[4-(trifluoromethyl)pyridin-2-yl]benzamide.

14. A pharmaceutical composition which comprises the compound of claim 1 or a pharmaceutically acceptable salt thereof and one or more pharmaceutically acceptable excipients.

15. The pharmaceutical composition of claim 14, which further comprises at least one additional therapeutically active agent.

\* \* \* \* \*